United States Patent
Li et al.

(10) Patent No.: US 6,831,175 B2
(45) Date of Patent: Dec. 14, 2004

(54) KINASE INHIBITORS

(75) Inventors: Qun Li, Libertyville, IL (US); Keith W. Woods, Libertyville, IL (US); Gui-Dong Zhu, Gurnee, IL (US); John P. Fischer, Longmont, CO (US); Jianchun Gong, Deerfield, IL (US); Tongmei Li, Waukegan, IL (US); Virajkumar Gandhi, Park City, IL (US); Sheela A. Thomas, Libertyville, IL (US); Garrick K. Packard, San Diego, CA (US); Xiaohong Song, Park City, IL (US); Jason N. Abrams, Des Plaines, IL (US); Robert B. Diebold, Waukegan, IL (US); Jürgen Dinges, Grayslake, IL (US); Charles W. Hutchins, Green Oaks, IL (US); Vincent S. Stoll, Libertyville, IL (US); Saul H. Rosenberg, Grayslake, IL (US); Vincent L. Giranda, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 33 days.

(21) Appl. No.: 10/317,914

(22) Filed: Dec. 12, 2002

(65) Prior Publication Data
US 2003/0199511 A1 Oct. 23, 2003

Related U.S. Application Data
(60) Provisional application No. 60/341,474, filed on Dec. 17, 2001, and provisional application No. 60/341,356, filed on Dec. 13, 2001.

(51) Int. Cl.[7] .................... C07D 211/36; C07D 211/68; C07D 401/00; A61K 31/445

(52) U.S. Cl. ................... 546/187; 546/193; 546/194; 546/199; 546/275.7; 514/316; 514/319; 514/321

(58) Field of Search ............... 546/187, 193, 546/194, 199, 275.7; 514/316, 318, 321

(56) References Cited

U.S. PATENT DOCUMENTS

| | | | |
|---|---|---|---|
| 4,179,563 A | 12/1979 | Butler | |
| 5,629,325 A | 5/1997 | Lin et al. | |
| 5,792,783 A | 8/1998 | Tang et al. | |
| 5,883,116 A | 3/1999 | Tang et al. | |
| 5,935,977 A | 8/1999 | Yamazaki et al. | |
| 6,030,969 A | 2/2000 | Bhagwat et al. | |
| 6,127,386 A | 10/2000 | Lin et al. | |
| 6,147,106 A | 11/2000 | Tang et al. | |
| 6,184,226 B1 * | 2/2001 | Chakravarty et al. | 514/266.22 |
| 6,225,335 B1 | 5/2001 | Tang et al. | |
| 6,277,989 B1 * | 8/2001 | Chakravarty et al. | 544/393 |
| 6,462,036 B1 * | 10/2002 | Doyle et al. | 514/218 |
| 6,476,031 B1 * | 11/2002 | Chakravarty et al. | 514/249 |

FOREIGN PATENT DOCUMENTS

| | | |
|---|---|---|
| DE | 19949209 | 4/2001 |
| EP | 0741707 | 4/1998 |
| WO | 93/10114 | 5/1993 |
| WO | 95/17181 | 6/1995 |
| WO | 96/10012 | 4/1996 |
| WO | 97/30044 | 8/1997 |
| WO | 97/46551 | 12/1997 |
| WO | 98/02434 | 1/1998 |
| WO | 98/38984 | 9/1998 |
| WO | 99/10325 | 3/1999 |
| WO | 99/15500 | 4/1999 |
| WO | 99/31088 | 6/1999 |

(List continued on next page.)

OTHER PUBLICATIONS

Holladay et al., "Structure–activity studies related to ABT–594, a potent nonopioid analgesic agent: effect of pyridine and azetidine ring substitutions on nicotinic acetylcholine receptor affinity and analgesic activity in mice," Bioorganic & Medicinal Chemistry Letters 8:2797–2802 (1998).

Lee, et al., "Synthesis and structure–activity relationship of novel pyridyl ethers for the nicotinic acetylcholine receptor," Bioorganic & medicinal Chemistry Letters 10:1063–1066 (2000).

Lin, et al., "Synthesis and structure–activity relationships of 5–substituted pyridine analogues of 3–[2–((S)–pyrrolidinyl) methoxy]pyridine, A–84543:a potent nicotinic receptor ligand," Bioorgnic & Medicinal Chemistry Letters 11:631–633 (2001).

Kandel et al., "The regulation and activities of the multifunctional serine/threonine kinase Akt/PKB," Experimental Cell Research 253:210–229 (1999).

Scheid et al., "PKB–AKT: Functional Insights from Genetic Models," Nature Review: Molecular Cell Biology 2:760–768 (2001).

* cited by examiner

Primary Examiner—D. Margaret Seaman
(74) Attorney, Agent, or Firm—Johanna M. Corbin; Gregory W. Steele

(57) ABSTRACT

Compounds having the formula

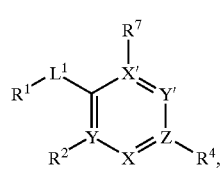

(I)

are useful for inhibiting protein kinases. Also disclosed are compositions which inhibit protein kinases and methods of inhibiting protein kinases in a patient.

21 Claims, No Drawings

FOREIGN PATENT DOCUMENTS

| | | |
|---|---|---|
| WO | 99/58523 | 11/1999 |
| WO | 99/61406 | 12/1999 |
| WO | 99/61422 | 12/1999 |
| WO | 99/65875 | 12/1999 |
| WO | 00/10997 | 3/2000 |
| WO | 00/12084 | 3/2000 |
| WO | 00/18734 | 4/2000 |
| WO | 00/23444 | 4/2000 |
| WO | 00/38519 | 7/2000 |
| WO | 00/49015 | 8/2000 |
| WO | 00/56709 | 9/2000 |
| WO | 00/73264 | 12/2000 |
| WO | 01/16130 | 3/2001 |
| WO | 01/19817 | 3/2001 |
| WO | 01/19829 | 3/2001 |
| WO | 01/27081 | 4/2001 |
| WO | 01/30151 | 5/2001 |
| WO | 01/49287 | 7/2001 |
| WO | 01/55116 | 8/2001 |
| WO | 01/57018 | 8/2001 |
| WO | 01/57040 | 8/2001 |
| WO | 01/60814 | 8/2001 |
| WO | 01/60816 | 8/2001 |
| WO | 01/62251 | 8/2001 |
| WO | 01/62252 | 8/2001 |
| WO | 01/66708 | 9/2001 |
| WO | 01/70687 | 9/2001 |
| WO | 01/81316 | 11/2001 |
| WO | 01/90103 | 11/2001 |
| WO | 01/90104 | 11/2001 |
| WO | 01/94312 | 12/2001 |
| WO | 02/10137 | 2/2002 |
| WO | 02/22601 | 3/2002 |
| WO | 02/50065 | 6/2002 |

KINASE INHIBITORS

CROSS-REFERENCE TO RELATED APPLICATIONS

This application claims priority to U.S. Provisional Patent Application Ser. No. 60/341,474, filed on Dec. 17, 2001, and U.S. Provisional Patent Application Ser. No. 60/341,356, filed on Dec. 13, 2001, which are both hereby incorporated by reference.

TECHNICAL FIELD

The present invention relates to compounds which are useful for inhibiting protein kinases, methods of making the compounds, compositions containing the compounds, and methods of treatment using the compounds.

BACKGROUND OF THE INVENTION

Protein kinases have been clearly shown to be important in the progression of many disease states that are induced by the inappropriate proliferation of cells. These kinases are often found to be up-regulated in many hyperproliferative states such as cancer. These kinases may be important in cell signaling, where their inappropriate activation induces cells to proliferate (e.g. EGFR, ERBB2, VEGFR, FGFR, PDGFR, c-Met, IGF-1R, RET, TIE2). Alternatively, they may be involved in signal transduction within cells (e.g. c-Src, PKC, Akt, PKA, c-Abl, PDK-1). Often these signal transduction genes are recognized proto-oncogenes. Many of these kinases control cell cycle progression near the G1-S transition (e.g. Cdk2, Cdk4), at the G2-M transition (e.g. Wee1, Myt1, Chk1, Cdc2) or at the spindle checkpoint (Plk, Aurora1 or 2, Bub1 or 3). Furthermore, kinases are intimately linked to the DNA damage response (e.g. ATM, ATR, Chk1, Chk2). Disregulation of these cellular functions; cell signaling, signal transduction, cell cycle control, and DNA repair, are all hallmarks of hyperproliferative diseases, particularly cancer. It is therefore likely that pharmacological modulation of one or more kinases would be useful in slowing or stopping disease progression in these diseases.

SUMMARY OF THE INVENTION

In its principle embodiment the present invention provides a compound of formula (I)

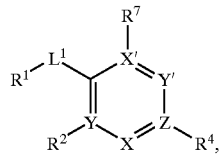

(I)

or a therapeutically acceptable salt thereof, wherein

X is selected from the group consisting of $C(R^8)$ and N; wherein $R^8$ is selected from the group consisting of hydrogen, alkyl, amino, carboxy, cyano, halo, hydroxy, and amido;

X' is selected from the group consisting of C and N;

Y is selected from the group consisting of C and N;

Y' is selected from the group consisting of $C(R^9)$ and N; wherein $R^9$ is selected from the group consisting of hydrogen and $-L^2-L^3(R^3)(R^6)$;

Z is selected from the group consisting of C and N;

provided that 0, 1, or 2 of X, X', Y, Y', and Z are N;

$L^1$ is selected from the group consisting of a bond, —O—, —NR$^5$—, alkenyl, alkynyl, —C(O)—, —S—, —S(O)—, —S(O)$_2$—, —S(O)$_2$N(R$^5$)—, —N(R$^5$)S(O)$_2$—, —C(R$^{12}$)$_2$—, —C(R$^{12}$)$_2$N(R$^5$)—, —N(R$^5$)C(O)—, and —C(O)N(R$^5$)—; wherein each group is drawn with its left end attached to $R^1$ and its right end attached to the aromatic ring;

$L^2$ is selected from the group consisting of a bond, —O—, —C(R$^{12}$)$_2$—, —S—, —N(R$^5$)—, —N(R$^5$)C(O)—, and —C(O)N(R$^5$)—;

$L^3$ is selected from the group consisting of a bond, alkylidene and alkylene, wherein the alkylidene and the alkylene are optionally substituted with one or two substituents independently selected from the group consisting of alkoxy, amino, cyano, and hydroxy;

$R^1$ is selected from the group consisting of aryl, heteroaryl, and heterocycle;

$R^2$ and $R^4$ are independently absent or selected from the group consisting of hydrogen, alkenyl, alkyl, alkynyl, amino, aryl, arylalkynyl, cyano, cyanoalkenyl, halo, heteroaryl, heterocycle, hydroxyalkyl, and nitro; or $R^2$ and $L^1$, together with the carbon atoms to which they are attached, form a ring selected from the group consisting of aryl, heteroaryl, and heterocycle; or $R^4$ and $L^2$, together with the carbon atoms to which they are attached, form a ring selected from the group consisting of aryl, heteroaryl, and heterocycle;

provided that when $L^3$ is alkylidene, $R^4$ and $L^2$, together with the carbon atoms to which they are attached, form a ring selected from the group consisting of aryl, heteroaryl, and heterocycle;

$R^3$ is absent or selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle;

$R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle;

provided that when $L^1$ and $L^2$ are bonds, at least one of $R^3$ and $R^6$ is other than hydrogen;

$R^5$ is selected from the group consisting of hydrogen, alkyl, alkylcarbonyl, alkylsulfonyl, arylcarbonyl, arylsulfonyl, and heteroarylsulfonyl;

$R^7$ is absent or selected from the group consisting of hydrogen, alkyl, cyanoalkenyl, and $-L^2-L^3(R^3)(R^6)$; or $R^7$ and $L^1$, together with the carbon atoms to which they are attached, form a ring selected from the group consisting of aryl, heteroaryl, and heterocycle; and each $R^{12}$ is selected from the group consisting of hydrogen, alkenyl, alkyl, alkynyl, amino, aryl, cyano, halo, heteroaryl, heterocycle, and nitro.

In another embodiment the present invention provides a compound of formula (II)

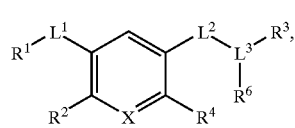

(II)

or a therapeutically acceptable salt thereof, wherein $L^1$ is selected from the group consisting of a bond, —O—, —N(R$^5$)—, alkenyl, alkynyl, —N(R$^5$)C(O)—, and —C(O)N(R$^5$)—;

$L^2$ is selected from the group consisting of a bond, —O—, —N(R$^5$)—, —N(R$^5$)C(O)—, and —C(O)N(R$^5$)—;

$L^3$ is selected from the group consisting of a bond, alkylidene, and alkylene, wherein the alkylidene and the alkylene are optionally substituted with one or two substituents independently selected from the group consisting of amino, cyano, and hydroxy;

$R^1$ is selected from the group consisting of aryl, heteroaryl, and heterocycle;

$R^2$ and $R^4$ are independently selected from the group consisting of hydrogen, alkenyl, alkynyl, arylalkynyl, amino, cyano, cyanoalkenyl, halo, hydroxyalkyl, and heteroaryl; wherein the heteroaryl is selected from the group consisting of furyl, pyrazinyl, thiazolyl, and thienyl; or $R^2$ and $L^1$, together with the carbon atoms to which they are attached, form a ring selected from the group consisting of dihydropyrrolyl, pyrazolyl, and phenyl; or $R^4$ and $L^2$, together with the carbon atoms to which they are attached, form a ring selected from the group consisting of dihydropyrrolyl, phenyl, pyridinyl, and pyrrolyl; wherein the ring can be optionally substituted with oxo; provided that when $L^3$ is alkylidene, $R^4$ and $L^2$, together with the carbon atoms to which they are attached, form a ring selected from the group consisting of dihydropyrrolyl, phenyl, pyridinyl, and pyrrolyl; wherein the ring can be optionally substituted with oxo;

$R^3$ is absent or selected from the group consisting of hydrogen, aryl, arylalkoxy, arylalkylthio, aryloxy, arylthio, cycloalkyl, heteroaryl, heteroarylalkoxy, heteroaryloxy, and heterocycle;

$R^6$ are independently selected from the group consisting of hydrogen, aryl, arylalkoxy, arylalkylthio, aryloxy, arylthio, cycloalkyl, heteroaryl, and heteroarylalkoxy, heteroaryloxy, and heterocycle;

provided that when $L^1$ and $L^2$ are bonds, at least one of $R^3$ and $R^6$ is other than hydrogen;

$R^5$ is selected from the group consisting of hydrogen, alkyl, alkylcarbonyl, alkylsulfonyl, arylcarbonyl, arylsulfonyl, and heteroarylsulfonyl; and X is selected from the group consisting of $C(R^8)$ and N; wherein $R^8$ is selected from the group consisting of hydrogen, amino, carboxy, cyano, and halo.

In another embodiment the present invention provides a compound of formula (III)

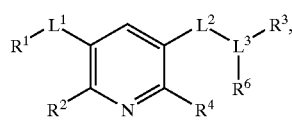

(III)

or a therapeutically acceptable salt thereof, wherein $L^1$ is selected from the group consisting of a bond, —O—, —N($R^5$)—, alkenyl, alkynyl, and —N($R^5$)C(O)—;

$L^2$ is selected from the group consisting of a bond, —O—, —N($R^5$)—, —N($R^5$)C(O)—, and —C(O)N($R^5$)—;

$L^3$ is alkylene, wherein the alkylene is substituted with one or two substituents independently selected from the group consisting of amino and hydroxy;

$R^1$ is selected from the group consisting of aryl, heteroaryl, and heterocycle;

$R^2$ and $R^4$ are independently selected from the group consisting of hydrogen and halo;

$R^3$ and $R^6$ are independently selected from the group consisting of hydrogen, aryl, arylalkoxy, and heteroaryl; provided that when $L^1$ and $L^2$ are bonds, at least one of $R^3$ and $R^6$ is other than hydrogen; and $R^5$ is selected from the group consisting of hydrogen and alkyl.

In another embodiment, the present invention provides a compound of formula (I) wherein X is selected from the group consisting of $C(R^8)$ and N, wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is -$L^2$-$L^3$($R^3$)($R^6$); Z is C; $L^1$ is alkenyl; $L^2$ is selected from the group consisting of a bond, —O—, —C($R^{12})_2$—, —S—, —N($R^5$)—, —N($R^5$)C(O)—, and —C(O)N($R^5$)—; $L^3$ is a bond or selected from the group consisting of alkylidene and alkylene, wherein the alkylidene and the alkylene are optionally substituted with one or two substituents independently selected from the group consisting of alkoxy, amino, cyano, and hydroxy; $R^1$ is selected from the group consisting of aryl, heteroaryl, and heterocycle; $R^2$ and $R^4$ are independently absent or selected from the group consisting of hydrogen, alkenyl, alkyl, alkynyl, amino, aryl, arylalkynyl, cyano, cyanoalkenyl, halo, heteroaryl, heterocycle, hydroxyalkyl, and nitro; $R^3$ is absent or selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^5$ is selected from the group consisting of hydrogen, alkyl, alkylcarbonyl, alkylsulfonyl, arylcarbonyl, arylsulfonyl, and heteroarylsulfonyl; $R^7$ is absent or selected from the group consisting of hydrogen, alkyl, and cyanoalkenyl; and each $R^{12}$ is selected from the group consisting of hydrogen, alkenyl, alkyl, alkynyl, amino, aryl, cyano, halo, heteroaryl, heterocycle, and nitro.

In another embodiment, the present invention provides a compound of formula (I) wherein X is selected from the group consisting of $C(R^8)$ and N, wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is -$L^2$-$L^3$($R^3$)($R^6$); Z is C; $L^1$ is alkenyl; $L^2$ is —O—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; and $R^7$ is absent or selected from the group consisting of hydrogen, alkyl, and cyanoalkenyl.

In another embodiment, the present invention provides a compound of formula (I) wherein X is selected from the group consisting of $C(R^8)$ and N, wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is -$L^2$-$L^3$($R^3$)($R^6$); Z is C; $L^1$ is alkenyl; $L^2$ is —O—; $L^1$ is alkenyl; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; and $R^7$ is absent or selected from the group consisting of hydrogen, alkyl, and cyanoalkenyl.

In another embodiment, the present invention provides a compound of formula (I) wherein X is N; X' is C; Y is C; Y' is C($R^9$), wherein $R^9$ is -$L^2$-$L^3$($R^3$)($R^6$); Z is C; $L^1$ is alkenyl; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is hydrogen.

In another embodiment, the present invention provides a compound of formula (I) wherein X is N; and X' is C; Y is C; Y' is C($R^9$), wherein $R^9$ is -$L^2$-$L^3$($R^3$)($R^6$); Z is C; $L^1$ is alkenyl; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is aryl; and $R^7$ is hydrogen.

In another embodiment, the present invention provides a compound of formula (I) wherein X is selected from the group consisting of C($R^8$) and N, wherein $R^8$ is selected from the group consisting of hydrogen, alkyl, amino, carboxy, cyano, halo, hydroxy, and amido; and X' is selected from the group consisting of C and N; Y is C; Y' is C($R^9$), wherein $R^9$ is -$L^2$-$L^3$($R^3$)($R^6$); Z is C; $L^1$ is alkenyl; $L^2$ is —O—; $L^3$ is a bond; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is absent; $R^6$ is heterocycle; and $R^7$ is absent or selected from the group consisting of hydrogen, alkyl, and cyanoalkenyl.

In another embodiment, the present invention provides a compound of formula (I) wherein X is N; X' is C; Y is C; Y' is C($R^9$), wherein $R^9$ is -$L^2$-$L^3$($R^3$)($R^6$); Z is C; $L^1$ is alkenyl; $L^2$ is —O—; $L^3$ is a bond; $R^1$ is heteroaryl; $R^2$ and $R^4$ are hydrogen; $R^3$ is absent; $R^6$ is heterocycle; and $R^7$ is hydrogen.

In another embodiment, the present invention provides a compound of formula (I) wherein X is selected from the group consisting of C($R^8$) and N, wherein $R^8$ is selected from the group consisting of hydrogen, alkyl, amino, carboxy, cyano, halo, hydroxy, and amido; X' is selected from the group consisting of C and N; Y is C; Y' is C($R^9$), wherein $R^9$ is -$L^2$-$L^3$($R^3$)($R^6$); Z is C; $L^1$ is alkenyl; $L^2$ is —N($R^5$)C(O)—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; and $R^7$ is absent or selected from the group consisting of hydrogen, alkyl, and cyanoalkenyl.

In another embodiment, the present invention provides a compound of formula (I) wherein X is N; and X' is C; Y is C; Y' is C($R^9$), wherein $R^9$ is -$L^2$-$L^3$($R^3$)($R^6$); Z is C; $L^1$ is alkenyl; $L^2$ is —N($R^5$)C(O)—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is hydrogen.

In another embodiment, the present invention provides a compound of formula (I) wherein X is N; X' is C; Y is C; Y' is C($R^9$), wherein $R^9$ is -$L^2$-$L^3$($R^3$)($R^6$); Z is C; $L^1$ is alkenyl; $L^2$ is —N($R^5$)C(O)—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is aryl; and $R^7$ is hydrogen.

In another embodiment, the present invention provides a compound of formula (I) wherein X is selected from the group consisting of C($R^8$) and N, wherein $R^8$ is selected from the group consisting of hydrogen, alkyl, amino, carboxy, cyano, halo, hydroxy, and amido; X' is selected from the group consisting of C and N; Y is C; Y' is C($R^9$), wherein $R^9$ is -$L^2$-$L^3$($R^3$)($R^6$); Z is C; $L^1$ is alkynyl; $L^2$ is selected from the group consisting of a bond, —O—, —C($R^{12}$)$_2$—, —S—, —N($R^5$)—, —N($R^5$)C(O)—, and —C(O)N($R^5$)—; $L^3$ is a bond or selected from the group consisting of alkylidene and alkylene, wherein the alkylidene and the alkylene are optionally substituted with one or two substituents independently selected from the group consisting of alkoxy, amino, cyano, and hydroxy; $R^1$ is selected from the group consisting of aryl, heteroaryl, and heterocycle; $R^2$ and $R^4$ are independently selected from the group consisting of hydrogen, alkenyl, alkyl, alkynyl, amino, aryl, arylalkynyl, cyano, cyanoalkenyl, halo, heteroaryl, heterocycle, hydroxyalkyl, and nitro; $R^3$ is absent or selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^5$ is selected from the group consisting of hydrogen, alkyl, alkylcarbonyl, alkylsulfonyl, arylcarbonyl, arylsulfonyl, and heteroarylsulfonyl; $R^7$ is absent or selected from the group consisting of hydrogen, alkyl, and cyanoalkenyl; and each $R^{12}$ is selected from the group consisting of hydrogen, alkenyl, alkyl, alkynyl, amino, aryl, cyano, halo, heteroaryl, heterocycle, and nitro.

In another embodiment, the present invention provides a compound of formula (I) wherein X is selected from the group consisting of $C(R^8)$ and N, wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is $-L^2-L^3(R^3)(R^6)$; Z is C; $L^1$ is alkynyl; $L^2$ is —O—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; and $R^7$ is absent or selected from the group consisting of hydrogen, alkyl, and cyanoalkenyl.

In another embodiment, the present invention provides a compound of formula (I) wherein X is selected from the group consisting of $C(R^8)$ and N, wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is $-L^2-L^3(R^3)(R^6)$; Z is C; $L^1$ is a bond; $L^2$ is selected from the group consisting of a bond, —O—, $-C(R^{12})_2-$, —S—, $-N(R^5)-$, $-N(R^5)C(O)-$, and $-C(O)N(R^5)-$; $L^3$ is a bond or selected from the group consisting of alkylidene and alkylene, wherein the alkylidene and the alkylene are optionally substituted with one or two substituents independently selected from the group consisting of alkoxy, amino, cyano, and hydroxy; $R^1$ is selected from the group consisting of aryl, heteroaryl, and heterocycle; $R^2$ and $R^4$ are independently selected from the group consisting of hydrogen, alkenyl, alkyl, alkynyl, amino, aryl, arylalkynyl, cyano, cyanoalkenyl, halo, heteroaryl, heterocycle, hydroxyalkyl, and nitro; $R^3$ is absent or selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^5$ is selected from the group consisting of hydrogen, alkyl, alkylcarbonyl, alkylsulfonyl, arylcarbonyl, arylsulfonyl, and heteroarylsulfonyl; $R^7$ is absent or selected from the group consisting of hydrogen, alkyl, and cyanoalkenyl; and each $R^{12}$ is selected from the group consisting of hydrogen, alkenyl, alkyl, alkynyl, amino, aryl, cyano, halo, heteroaryl, heterocycle, and nitro.

In another embodiment, the present invention provides a compound of formula (I) wherein X is selected from the group consisting of $C(R^8)$ and N, wherein $R^8$ is selected from the group consisting of hydrogen, alkyl, amino, carboxy, cyano, halo, hydroxy, and amido; and X' is selected from the group consisting of C and N; Y is C; Y' is $C(R^9)$, wherein $R^9$ is $-L^2-L^3(R^3)(R^6)$; Z is C; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; and $R^7$ is absent or selected from the group consisting of hydrogen, alkyl, and cyanoalkenyl.

In another embodiment, the present invention provides a compound of formula (I) wherein X is N; X' is C; Y is C; Y' is $C(R^9)$, wherein $R^9$ is $-L^2-L^3(R^3)(R^6)$; Z is C; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is aryl; and $R^7$ is hydrogen.

In another embodiment, the present invention provides a compound of formula (I) wherein X is N; X' is C; Y is C; Y' is $C(R^9)$, wherein $R^9$ is $-L^2-L^3(R^3)(R^6)$; Z is C; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is hydrogen.

In another embodiment, the present invention provides a compound of formula (I) wherein X is selected from the group consisting of $C(R^8)$ and N, wherein $R^8$ is hydrogen; X' is N; Y is C; Y' is $C(R^9)$, wherein $R^9$ is $-L^2-L^3(R^3)(R^6)$; Z is C; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is absent.

In another embodiment, the present invention provides a compound of formula (I) wherein X is N; X' is C; Y is N; Y' is $C(R^9)$, wherein $R^9$ is $-L^2-L^3(R^3)(R^6)$; Z is C; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ is absent; $R^4$ is selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is aryl; and $R^7$ is hydrogen.

In another embodiment, the present invention provides a compound of formula (I) wherein X is N; X' is C; Y is N; Y' is $C(R^9)$, wherein $R^9$ is $-L^2-L^3(R^3)(R^6)$; Z is C; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ is absent; $R^4$ is selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is hydrogen.

In another embodiment, the present invention provides a compound of formula (I) wherein X is $C(R^8)$, wherein $R^8$ is hydrogen; X' is C; Y is N; Y' is $C(R^9)$, wherein $R^9$ is $-L^2-L^3(R^3)(R^6)$; Z is C; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ is absent; $R^4$ is selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is aryl; and $R^7$ is hydrogen.

In another embodiment, the present invention provides a compound of formula (I) wherein X is $C(R^8)$, wherein $R^8$ is hydrogen; X' is C; Y is N; Y' is $C(R^9)$, wherein $R^9$ is $-L^2-L^3(R^3)(R^6)$; Z is C; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^2$ is absent; $R^4$ is selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is hydrogen.

In another embodiment, the present invention provides a compound of formula (I) wherein X is $C(R^8)$, wherein $R^8$ is hydrogen; X' is C; Y is N; Y' is $C(R^9)$, wherein $R^9$ is $-L^2-L^3(R^3)(R^6)$; Z is N; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^4$ is absent; $R^2$ is selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is aryl; and $R^7$ is hydrogen.

In another embodiment, the present invention provides a compound of formula (I) wherein X is $C(R^8)$, wherein $R^8$ is hydrogen; X' is C; Y is N; Y' is $C(R^9)$, wherein $R^9$ is $-L^2-L^3(R^3)(R^6)$; Z is N; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^4$ is absent; $R^2$ is selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is hydrogen.

In another embodiment, the present invention provides a compound of formula (I) wherein X is N; X' is C; Y is N; Y' is $C(R^9)$, wherein $R^9$ is $-L^2-L^3(R^3)(R^6)$; Z is N; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^4$ is absent; $R^2$ is selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is aryl; and $R^7$ is hydrogen.

In another embodiment, the present invention provides a compound of formula (I) wherein X is N; X' is C; Y is N; Y' is $C(R^9)$, wherein $R^9$ is $-L^2-L^3(R^3)(R^6)$; Z is N; $L^1$ is a bond; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^4$ is absent; $R^2$ is selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is hydrogen.

In another embodiment, the present invention provides a compound of formula (I) wherein X is selected from the group consisting of $C(R^8)$ and N, wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is $-L^2-L^3(R^3)(R^6)$; Z is —C—; $L^1$ is a bond; $L^2$ is —N($R^5$)—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^5$ is selected from the group consisting of hydrogen, alkyl, alkylcarbonyl, alkylsulfonyl, arylcarbonyl, arylsulfonyl, and heteroarylsulfonyl; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; and $R^7$ is absent or selected from the group consisting of hydrogen, alkyl, and cyanoalkenyl.

In another embodiment, the present invention provides a compound of formula (I) wherein X is N; X' is C; Y is C; Y' is $C(R^9)$, wherein $R^9$ is $-L^2-L^3(R^3)(R^6)$; Z is C; $L^1$ is a bond; $L^2$ is —N($R^5$)—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^5$ is selected from the group consisting of hydrogen, alkyl, alkylcarbonyl, alkylsulfonyl, arylcarbonyl, arylsulfonyl, and heteroarylsulfonyl; $R^6$ is heteroaryl; and $R^7$ is hydrogen.

In another embodiment, the present invention provides a compound of formula (I) wherein X is N; X' is C; Y is C; Y' is $C(R^9)$, wherein $R^9$ is $-L^2-L^3(R^3)(R^6)$; Z is C; $L^1$ is a bond; $L^2$ is —N($R^5$)—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^5$ is selected from the group consisting of hydrogen, alkyl, alkylcarbonyl, alkylsulfonyl, arylcarbonyl, arylsulfonyl, and heteroarylsulfonyl; $R^6$ is aryl; and $R^7$ is hydrogen.

In another embodiment, the present invention provides a compound of formula (I) wherein X is selected from the group consisting of C($R^8$) and N, wherein $R^8$ is selected from the group consisting of hydrogen, alkyl, amino, carboxy, cyano, halo, hydroxy, and amido; X' is selected from the group consisting of C and N; Y is C; Y' is C($R^9$), wherein $R^9$ is -$L^2$-$L^3$($R^3$)($R^6$); Z is C; $L^1$ is a bond; $L^2$ is —N($R^5$)C(O)—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; and $R^7$ is absent or selected from the group consisting of hydrogen, alkyl, and cyanoalkenyl.

In another embodiment, the present invention provides a compound of formula (I) wherein X is N; X' is C; Y is C; Y' is C($R^9$), wherein $R^9$ is -$L^2$-$L^3$($R^3$)($R^6$); Z is C; $L^1$ is a bond; $L^2$ is —N($R^5$)C(O)—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is heteroaryl; and $R^7$ is hydrogen.

In another embodiment, the present invention provides a compound of formula (I) wherein X is N; X' is C; Y is C; Y' is C($R^9$), wherein $R^9$ is -$L^2$-$L^3$($R^3$)($R^6$); Z is C; $L^1$ is a bond; $L^2$ is —N($R^5$)C(O)—; $L^3$ is alkylene, wherein the alkylene is optionally substituted with one substituent selected from the group consisting of alkoxy, amino, cyano, and hydroxy; $R^1$ is heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^6$ is aryl; and $R^7$ is hydrogen.

In another embodiment, the present invention provides a compound of formula (I) wherein X is selected from the group consisting of C($R^8$) and N, wherein $R^8$ is selected from the group consisting of hydrogen, alkyl, amino, carboxy, cyano, halo, hydroxy, and amido; X' is selected from the group consisting of C and N; Y is C; Y' is C($R^9$), wherein $R^9$ is -$L^2$-$L^3$($R^3$)($R^6$); Z is C; $L^1$ is —N($R^5$)—; $L^2$ is selected from the group consisting of a bond, —O—, —C($R^{12}$)$_2$—, —S—, —N($R^5$)—, —N($R^5$)C(O)—, and —C(O)N($R^5$)—; $L^3$ is a bond or selected from the group consisting of alkylidene and alkylene, wherein the alkylidene and the alkylene are optionally substituted with one or two substituents independently selected from the group consisting of alkoxy, amino, cyano, and hydroxy; $R^1$ is selected from the group consisting of aryl, heteroaryl, and heterocycle; $R^2$ and $R^4$ are independently selected from the group consisting of hydrogen, alkenyl, alkyl, alkynyl, amino, aryl, arylalkynyl, cyano, cyanoalkenyl, halo, heteroaryl, heterocycle, hydroxyalkyl, and nitro; $R^3$ is absent or selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^5$ is selected from the group consisting of hydrogen, alkyl, alkylcarbonyl, alkylsulfonyl, arylcarbonyl, arylsulfonyl, and heteroarylsulfonyl; $R^7$ is absent or selected from the group consisting of hydrogen, alkyl, and cyanoalkenyl; and each $R^{12}$ is selected from the group consisting of hydrogen, alkenyl, alkyl, alkynyl, amino, aryl, cyano, halo, heteroaryl, heterocycle, and nitro.

In another embodiment, the present invention provides a compound of formula (I) wherein X is selected from the group consisting of C($R^8$) and N, wherein $R^8$ is selected from the group consisting of hydrogen, alkyl, amino, carboxy, cyano, halo, hydroxy, and amido; X' is selected from the group consisting of C and N; Y is C; Y' is C($R^9$), wherein $R^9$ is -$L^2$-$L^3$($R^3$)($R^6$); Z is C; $L^1$ is —N($R^5$)—; $L^2$ is —O—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^5$ is selected from the group consisting of hydrogen, alkyl, alkylcarbonyl, alkylsulfonyl, arylcarbonyl, arylsulfonyl, and heteroarylsulfonyl; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; and $R^7$ is absent or selected from the group consisting of hydrogen, alkyl, and cyanoalkenyl.

In another embodiment, the present invention provides a compound of formula (I) wherein X is N; X' is C; Y is C; Y' is C($R^9$), wherein $R^9$ is -$L^2$-$L^3$($R^3$)($R^6$); Z is C; $L^1$ is —N($R^5$)—; $L^2$ is —O—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^5$ is selected from the group consisting of hydrogen, alkyl, alkylcarbonyl, alkylsulfonyl, arylcarbonyl, arylsulfonyl, and heteroarylsulfonyl; $R^6$ is heteroaryl; and $R^7$ is hydrogen.

In another embodiment, the present invention provides a compound of formula (I) wherein X is N; X' is C; Y is C; Y' is C($R^9$), wherein $R^9$ is -$L^2$-$L^3$($R^3$)($R^6$); Z is C; $L^1$ is —N($R^5$)—; $L^2$ is —O—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is hydrogen; $R^5$ is selected from the group consisting of hydrogen, alkyl, alkylcarbonyl, alkylsulfonyl, arylcarbonyl, arylsulfonyl, and heteroarylsulfonyl; $R^6$ is aryl; and $R^7$ is hydrogen.

In another embodiment, the present invention provides a compound of formula (I) wherein X is selected from the group consisting of $C(R^8)$ and N, wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is $-L^2-L^3(R^3)(R^6)$; Z is C; $L^1$ is a bond; $L^2$ is a bond; $L^3$ is a bond; $R^2$ and $R^4$ are independently selected from the group consisting of hydrogen, alkenyl, alkynyl, arylalkynyl, amino, cyano, cyanoalkenyl, halo, hydroxyalkyl, and heteroaryl, wherein the heteroaryl is selected from the group consisting of furyl, pyrazinyl, thiazolyl, and thienyl; $R^3$ is absent; $R^6$ is heterocycle; and $R^7$ is absent or selected from the group consisting of hydrogen, alkyl, and cyanoalkenyl.

In another embodiment, the present invention provides a compound of formula (I) wherein X is selected from the group consisting of $C(R^8)$ and N; wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is $-L^2-L^3(R^3)(R^6)$; Z is C; $L^1$ is selected from the group consisting of a bond, —O—, —N($R^5$)—, alkenyl, alkynyl, —C(O)—, —S—, —S(O)—, —S(O)$_2$—, —S(O)$_2$N($R^5$)—, —N($R^5$)S(O)$_2$—, —C($R^{12}$)$_2$—, —C($R^{12}$)$_2$N($R^5$)—, —N($R^5$)C(O)—, and —C(O)N($R^5$)—, wherein each group is drawn with its left end attached to $R^1$ and its right end attached to the aromatic ring; $L^3$ is alkylidene, wherein the alkylidene is optionally substituted with one or two substituents independently selected from the group consisting of alkoxy, amino, cyano, and hydroxy; $R^1$ is selected from the group consisting of aryl, heteroaryl, and heterocycle; $R^4$ and $L^2$, together with the carbon atoms to which they are attached, form a ring selected from the group consisting of aryl, heteroaryl, and heterocycle; $R^3$ is absent or selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^6$ is selected from the group consisting of hydrogen, aryl, arylalkoxy, arylalkylamino, arylalkylthio, aryloxy, arylthio, cycloalkyl, heteroaryl, heteroarylalkoxy, heteroaryloxy, and heterocycle; $R^5$ is selected from the group consisting of hydrogen, alkyl, alkylcarbonyl, alkylsulfonyl, arylcarbonyl, arylsulfonyl, and heteroarylsulfonyl; $R^7$ is absent or selected from the group consisting of hydrogen, alkyl, and cyanoalkenyl; and each $R^{12}$ is selected from the group consisting of hydrogen, alkenyl, alkyl, alkynyl, amino, aryl, cyano, halo, heteroaryl, heterocycle, and nitro.

In another embodiment, the present invention provides a compound of formula (I) wherein X is selected from the group consisting of $C(R^8)$ and N, wherein $R^8$ is hydrogen; X' is C; Y is C; Y' is $C(R^9)$, wherein $R^9$ is $-L^2-L^3(R^3)(R^6)$; Z is C; $L^1$ is a bond; $L^3$ is alkylidene, wherein the alkylidene is substituted with one substituent selected from the group consisting of alkoxy, amino, cyano, and hydroxy; $R^1$ is heteroaryl wherein the heteroaryl is isoquinolinyl; $R^4$ and $L^2$, together with the carbon atoms to which they are attached, form a heterocycle wherein the heterocycle is pyrrolidinyl substituted with oxo; $R^3$ is hydrogen; $R^6$ is heteroaryl, wherein the heteroaryl is indolyl; and $R^7$ is hydrogen.

In another embodiment, the present invention provides a compound of formula (I) wherein X is selected from the group consisting of $C(R^8)$ and N; wherein $R^8$ is selected from the group consisting of hydrogen, alkyl, amino, carboxy, cyano, halo, hydroxy, and amido; and X' is selected from the group consisting of C and N; Y is C; Y' is $C(R^9)$, wherein $R^9$ is $-L^2-L^3(R^3)(R^6)$; Z is C; $R^2$ and $L^1$, together with the carbon atoms to which they are attached, form a ring that is aryl wherein the aryl ring is phenyl; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^3$ is absent; $R^6$ is heteroaryl; and $R^7$ is absent or selected from the group consisting of hydrogen, alkyl, and cyanoalkenyl.

In another embodiment, the present invention provides a compound of formula (I) wherein X is N; X' is C; Y is C; Y' is $C(R^9)$, wherein $R^9$ is $-L^2-L^3(R^3)(R^6)$; Z is C; $R^2$ and $L^1$, together with the carbon atoms to which they are attached, form a ring that is aryl wherein the aryl ring is phenyl; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^3$ is absent; $R^6$ is heteroaryl; and $R^7$ is hydrogen.

In another embodiment, the present invention provides a compound of formula (I) wherein X is N; X' is C; Y is C; Y' is $C(R^9)$, wherein $R^9$ is $-L^2-L^3(R^3)(R^6)$; Z is C; $R^2$ and $L^1$, together with the carbon atoms to which they are attached, form a ring that is aryl wherein the aryl ring is phenyl; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^3$ is absent; $R^6$ is aryl; and $R^7$ is hydrogen.

In another embodiment, the present invention provides a compound of formula (I) wherein X is selected from the group consisting of $C(R^8)$ and N; wherein $R^8$ is selected from the group consisting of hydrogen, alkyl, amino, carboxy, cyano, halo, hydroxy, and amido; X' is selected from the group consisting of C and N; Y is C; Y' is $C(R^9)$, wherein $R^9$ is $-L^2-L^3(R^3)(R^6)$; Z is C; $R^2$ and $L^1$, together with the carbon atoms to which they are attached, form a ring that is heteroaryl wherein the heteroaryl is pyrazolyl; $L^2$ is a bond; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^3$ is hydrogen; $R^6$ is selected from the group consisting of aryl, heterocycle, and heteroaryl; and $R^7$ is absent or selected from the group consisting of hydrogen, alkyl, and cyanoalkenyl.

In another embodiment, the present invention provides a compound of formula (I) wherein X is $C(R^8)$, wherein $R^8$ is hydrogen; X' is N; Y is C; Y' is $C(R^9)$, wherein $R^9$ is $-L^2-L^3(R^3)(R^6)$; Z is C; $R^2$ and $L^1$, together with the carbon atoms to which they are attached, form a ring that is heteroaryl wherein the heteroaryl is pyrazolyl; $L^2$ is a bond; $L^3$ is alkylene, wherein the alkylene is optionally substituted with one substituent selected from the group consisting of alkoxy, amino, cyano, and hydroxy; $R^1$ is heteroaryl; $R^3$ is hydrogen; $R^6$ is aryl; and $R^7$ is absent.

In another embodiment, the present invention provides a compound of formula (I) wherein X is $C(R^8)$, wherein $R^8$ is hydrogen; X' is N; Y is C; Y' is $C(R^9)$, wherein $R^9$ is $-L^2-L^3(R^3)(R^6)$; Z is C; $R^2$ and $L^1$, together with the carbon atoms to which they are attached, form a ring that is heteroaryl wherein the heteroaryl is pyrazolyl; $L^2$ is a bond; $L^3$ is alkylene, wherein the alkylene is optionally substituted with one substituent selected from the group consisting of alkoxy, amino, cyano, and hydroxy; $R^1$ is aryl; $R^3$ is hydrogen; $R^6$ is aryl; and $R^7$ is absent.

In another embodiment, the present invention provides a compound of formula (I) wherein X is selected from the group consisting of C($R^8$) and N; wherein $R^8$ is selected from the group consisting of hydrogen, alkyl, amino, carboxy, cyano, halo, hydroxy, and amido; X is C; Y is C; Y' is C($R^9$), wherein $R^9$ is -$L^2$-$L^3$($R^3$)($R^6$); Z is C; $R^7$ and $L^1$, together with the carbon atoms to which they are attached, form a ring selected from the group consisting aryl, heteroaryl and heterocycle; $L^2$ is —O—; $L^3$ is alkylene, wherein the alkylene is optionally substituted with one substituent selected from the group consisting of alkoxy, amino, cyano, and hydroxy; $R^1$ is selected from the group consisting of aryl, heterocycle, and heteroaryl; $R^3$ is hydrogen; and $R^6$ is selected from the group consisting of aryl, heterocycle, and heteroaryl.

In another embodiment, the present invention provides a compound of formula (I) wherein X is N; and X' is C; Y is C; Y' is C($R^9$), wherein $R^9$ is -$L^2$-$L^3$($R^3$)($R^6$); Z is C; $R^7$ and $L^1$, together with the carbon atoms to which they are attached, form a ring that is a heteroaryl wherein the heteroaryl is pyridinyl; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^3$ is hydrogen; and $R^6$ is heteroaryl.

In another embodiment, the present invention provides a compound of formula (I) wherein X is N; and X' is C; Y is C; Y' is C($R^9$), wherein $R^9$ is -$L^2$-$L^3$($R^3$)($R^6$); Z is C; $R^7$ and $L^1$, together with the carbon atoms to which they are attached, form a ring that is a heteroaryl wherein the heteroaryl is pyridinyl; $L^2$ is —O—; $L^3$ is alkylene, wherein the alkylene is optionally substituted with one substituent selected from the group consisting of alkoxy, amino, cyano, and hydroxy; $R^1$ is heteroaryl; $R^3$ is hydrogen; and $R^6$ is aryl.

In another embodiment the invention provides a pharmaceutical composition comprising a compound of formula (I), or a therapeutically acceptable salt thereof, in combination with a pharmaceutically acceptable carrier.

In another embodiment the invention provides a method of inhibiting protein kinases in a patient in recognized need of such treatment comprising administering to the patient a therapeutically acceptable amount of a compound of formula (I), or a therapeutically acceptable salt thereof.

DETAILED DESCRIPTION OF THE INVENTION

As used in the present specification the following terms have the meanings indicated:

The term "alkenyl," as used herein, refers to a group derived from a straight or branched chain hydrocarbon of up to six atoms containing at least one double bond.

The term "alkoxy," as used herein, refers to an alkyl group attached to the parent molecular moiety through an oxygen atom.

The term "alkoxyalkyl," as used herein, refers to an alkoxy group attached to the parent molecular moiety through an alkyl group.

The term "alkoxycarbonyl," as used herein, refers to an alkoxy group attached to the parent molecular moiety through an alkyl group.

The term "alkyl," as used herein, refers to a group derived from a straight or branched chain saturated hydrocarbon of one to six atoms.

The term "alkylene," as used herein, refers to a divalent group derived from a straight or branched chain saturated hydrocarbon of one to six atoms.

The term "alkylcarbonyl," as used herein, refers to an alkyl group attached to the parent molecular moiety through a carbonyl group.

The term "alkylidene," as used herein, refers to an alkenyl group in which one carbon atom of the carbon-carbon double bond belongs to the moiety to which the alkenyl group is attached.

The term "alkylsulfonyl," as used herein, refers to an alkyl group attached to the parent molecular moiety through a sulfonyl group.

The term "alkynyl," as used herein, refers to a group derived from a straight or branched chain hydrocarbon of two to six atoms containing at least one triple bond.

The term "amido," as used herein, refers to an amino group attached to the parent molecular moiety through a carbonyl group.

The term "amino," as used herein, refers to —$NR^aR^b$, wherein $R^a$ and $R^b$ are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, (N$R^cR^d$)alkylcarbonyl, heteroaryl, heteroarylalkenyl, heteroarylalkyl, heterocycle, (heterocycle)alkenyl, and (heterocycle)alkyl, wherein the aryl, the aryl part of the arylalkenyl, the arylalkyl, the heteroaryl, the heteroaryl part of the heteroarylalkenyl and the heteroarylalkyl, the heterocycle, and the heterocycle part of the (heterocycle) alkenyl and the (heterocycle)alkyl can be optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxyalkyl, nitro, and oxo.

The term "aminoalkyl," as used herein, refers to an amino group attached to the parent molecular moiety through an alkyl group.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylthio, amino, aminoalkyl, a second aryl group, arylalkoxy, arylalkyl, arylcarbonyl, carboxy, cyano, cycloalkyl, halo, haloalkoxy, haloalkyl, heteroaryl, heteroarylalkoxy, heteroarylalkyl, heterocycle, (heterocycle) alkoxy, (heterocycle)alkyl, hydroxy, hydroxyalkyl, nitro, oxo, —C(=NOH)$NH_2$, —C(=NH)$NH_2$; wherein the second aryl group, the aryl part of the arylalkoxy, the arylalkyl, and the arylcarbonyl, the heteroaryl, the heteroaryl part of the heteroarylalkoxy and the heteroarylalkyl, the heterocycle, and the heterocycle part of the (heterocycle) alkoxy and the (heterocycle)alkyl can be further optionally substituted with one, two, three, four, or five substituents independently selected from the group consisting of alkenyl, alkoxy, alkyl, halo, haloalkoxy, haloalkyl, hydroxy, hydroxyalkyl, and nitro.

The term "arylalkenyl," as used herein, refers to an aryl group attached to the parent molecular moiety through an alkenyl group.

The term "arylalkoxy," as used herein, refers to an aryl group attached to the parent molecular moiety through an alkoxy group.

The term "arylalkyl," as used herein, refers to an aryl group attached to the parent molecular moiety through an alkyl group.

The term "arylalkylamino," as used herein, refers to an arylalkyl group attached to the parent molecular moiety through a nitrogen atom, wherein the nitrogen atom is substituted with hydrogen.

The term "arylalkylidene," as used herein, refers to an aryl group attached to the parent molecular moiety through an alkylidene group The term "arylalkylthio," as used herein, refers to an arylalkyl group attached to the parent molecular moiety through a sulfur atom.

The term "arylalkynyl," as used herein, refers to an aryl group attached to the parent molecular moiety through an alkynyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "arylsulfonyl," as used herein, refers to an aryl group attached to the parent molecular moiety through an sulfonyl group.

The term "arylthio," as used herein, refers to an aryl group attached to the parent molecular moiety through a sulfur atom.

The term "carbonyl," as used herein, refers to a —C(O)— group.

The term "carboxy," as used herein, refers to —C(O)OH.

The term "cyano," as used herein, refers to —CN.

The term "cyanoalkenyl," as used herein, refers to a cyano group attached to the parent molecular moiety through an alkenyl group The term "cycloalkyl," as used herein, refers to a saturated monocyclic, bicyclic, or tricyclic hydrocarbon ring system having three to twelve carbon atoms. Examples of cycloalkyl groups include cyclopropyl, cyclopentyl, bicyclo[3.1.1]heptyl, adamantyl, and the like.

The term "(cycloalkyl)alkylidene," as used herein, refers to a cycloalkyl group attached to the parent molecular moiety through an alkylidene group.

The term "halo," or "halogen," as used herein, refers to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "haloalkylcarbonyl," as used herein, refers to an haloalkyl group attached to the parent molecular moiety through a carbonyl group.

The term "heteroaryl," as used herein, refers to an aromatic five- or six-membered ring where at least one atom is selected from the group consisting of N, O, and S, and the remaining atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes systems where a heteroaryl ring is fused to an aryl group, as defined herein, a heterocycle group, as defined herein, or an additional heteroaryl group. Heteroaryls are exemplified by benzothienyl, benzoxadiazolyl, benzofuranyl, benzimidazolyl, benzotriazolyl, cinnolinyl, furyl, imidazolyl, indazolyl, indolyl, isoxazolyl, isoquinolinyl, isothiazolyl, naphthyridinyl, oxadiazolyl, oxadiazolyl, oxazolyl, purinyl, thiazolyl, thienopyridinyl, thienyl, triazolyl, thiadiazolyl, pyridinyl, pyridazinyl, pyrimidinyl, pyrazinyl, pyrazolyl, pyrrolyl, pyrido[2,3-d]pyrimidinyl, pyrrolo[2,3-b]pyridinyl, quinazolinyl, quinolinyl, thieno[2,3-c]pyridinyl, tetrazolyl, triazinyl, and the like. The heteroaryl groups of the present invention can be optionally substituted with one, two, three, four, or five substituents independently selected from the group consisting of alkenyl, alkoxy, alkoxyalkyl, alkoxycarbonyl, alkyl, alkynyl, alkylcarbonyl, amino, aminoalkyl, aryl, arylalkoxy, arylalkyl, arylalkylthio, arylalkynyl, aryloxy, carboxy, cyano, cycloalkyl, halo, haloalkoxy, haloalkyl, a second heteroaryl group, heteroarylalkoxy, heteroarylalkyl, heterocycle, (heterocycle)alkoxy, (heterocycle)alkyl, hydroxy, hydroxyalkyl, nitro, and oxo, wherein the aryl, the aryl part of the arylalkoxy, the arylalkyl, the arylalkylthio, the arylalkynyl, and the aryloxy, the second heteroaryl group, the heteroaryl part of the heteroarylalkoxy and the heteroarylalkyl, the heterocycle, and the heterocycle part of the (heterocycle)alkoxy and the (heterocycle)alkyl can be further optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxyalkyl, nitro, and oxo.

The term "heteroarylalkenyl," as used herein, refers to a heteroaryl group attached to the parent molecular moiety through an alkenyl group.

The term "heteroarylalkoxy," as used herein, refers to a heteroaryl group attached to the parent molecular moiety through an alkoxy group.

The term "heteroarylalkyl," as used herein, refers to a heteroaryl group attached to the parent molecular moiety through an alkyl group.

The term "heteroarylalkylidene," as used herein, refers to a heteroaryl group attached to the parent molecular moiety through an alkylidene group.

The term "heteroaryloxy," as used herein, refers to a heteroaryl group attached to the parent molecular moiety through an oxygen atom.

The term "heteroarylsulfonyl," as used herein, refers to a heteroaryl group attached to the parent molecular moiety through a sulfonyl group.

The term "heterocycle," as used herein, refers to cyclic, non-aromatic, three-, four-, five-, six-, or seven-membered rings containing at least one atom selected from the group consisting of oxygen, nitrogen, and sulfur. The five-membered rings have zero or one double bonds and the six- and seven-membered rings have zero, one, or two double bonds. The heterocycle groups of the invention are connected to the parent molecular group through a substitutable carbon or nitrogen atom in the ring. The term "heterocycle" also includes systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylidene, amino, aminoalkyl, aryl, arylalkoxy, arylalkyl, arylalkylidene, cyano, (cycloalkyl)alkylidene, halo, haloalkoxy, haloalkyl, heteroaryl, heteroarylalkoxy, heteroarylalkyl, heteroarylalkylidene, iminohydroxy, a second heterocycle, (heterocycle)alkoxy, (heterocycle)alkyl, (heterocycle)alkylidene, hydroxy, hydroxyalkyl, nitro, and oxo, wherein the aryl, the aryl part of the arylalkoxy and the arylalkyl, the heteroaryl, the heteroaryl part of the heteroarylalkoxy, the heteroarylalkyl, and the heteroarylalkylidene, the second heterocycle, and the heterocycle part of the (heterocycle)alkoxy, the (heterocycle) alkyl, and the (heterocycle)alkylidene can be further optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxyalkyl, nitro, and oxo.

The term "(heterocycle)alkenyl," as used herein, refers to a heterocycle group attached to the parent molecular moiety through an alkenyl group.

The term "(heterocycle)alkoxy," as used herein, refers to a heterocycle group attached to the parent molecular group through an oxygen atom.

The term "(heterocycle)alkyl," as used herein, refers to a heterocycle group attached to the parent molecular moiety through an alkyl group.

The term "(heterocycle)alkylidene," as used herein, refers to a heterocycle group attached to the parent molecular moiety through an alkylidene group.

The term "hydroxy," as used herein, refers to —OH.

The term "hydroxyalkyl," as used herein, refers to a hydroxy group attached to the parent molecular moiety through an alkyl group.

The term "iminohydroxy," as used herein, refers to =N(OH).

The term "—$NR^cR^d$," as used herein, refers to two groups, $R^c$ and $R^d$, which are attached to the parent molecular moiety through a nitrogen atom. $R^c$ and $R^d$ are each independently selected from hydrogen and alkyl.

The term "($NR^cR^d$)alkyl," as used herein, refers to a —$NR^cR^d$ group attached to the parent molecular moiety through an alkyl group.

The term "($NR^cR^d$)alkylcarbonyl," as used herein, refers to a ($NR^cR^d$)alkyl group attached to the parent molecular moiety through a carbonyl group.

The term "nitro," as used herein, refers to —$NO_2$.

The term "oxo," as used herein, refers to =O.

The term "sulfonyl," as used herein, refers to —$S(O)_2$—.

The compounds of the present invention can exist as therapeutically acceptable salts.

The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are transformed in vivo to parent compounds of formula (I) for example, by hydrolysis in blood.

When any variable, substituent, or term (e.g. aryl, heterocycle, $R^{12}$, etc.) occurs more than one time in a formula or generic structure, its definition at each occurrence is independent of the definition at every other occurrence. Also, combinations of substituents and/or variables are permissible only if such combinations result in stable combinations.

Because carbon-carbon double bonds exist in the present compounds, the invention contemplates various geometric isomers and mixtures thereof resulting from the arrangement of substituents around these carbon-carbon double bonds. It should be understood that the invention encompasses both isomeric forms, or mixtures thereof, which possess the ability to inhibit protein kinases. These substituents are designated as being in the E or Z configuration wherein the term "E" represents higher order substituents on opposite sides of the carbon-carbon double bond, and the term "Z"

represents higher order substituents on the same side of the carbon-carbon double bond.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to inhibit protein kinases. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

In accordance with methods of treatment and pharmaceutical compositions of the invention, the compounds can be administered alone or in combination with other anticancer agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally adminstered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The anticancer effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

Enzymatic Assays:

The Akt1 assay uses His-Akt1-S36, a truncated Akt1 containing a His tag at the N-terminus, amino acid 139–460 of Akt1 and the following point mutations: S378A, S381A, T450D and S473D. The His-Akt1-S36 assay is run in 96 well plates by incubating 1 nM His-Akt1-S36, 5 $\mu$M Biotin-BAD-peptide (Biotin) and 5 $\mu$M $^{33}$P-ATP in 50 $\mu$L of reaction buffer (20 mM HEPES, pH 7.5, 10 mM MgCl$_2$, 0.009% Triton X-100) for 30 minutes at room temperature. The reactions are stopped by adding 25 $\mu$L of stopping buffer (4M NaCl and 0.1M EDTA). The samples are transferred to a Flash plate coated with streptavidin. The phosphorylation of BAD-peptide in the reactions is measured by counting the plate with the TopCount. Other kinase assays (Akt2, Akt3, PKA, PKC, Erk2, Chk1, Cdc2, Src, CK2, MAPK AP kinase 2, and SGK) are carried out similarly using their specific biotinylated peptide substrates and buffer conditions. Compounds of the invention inhibited Akt by 0–100% at a concentration of 1 $\mu$M. Preferred compounds had percent inhibitions of between 77 and 100 at 1 $\mu$M and more preferred compounds had percent inhibitions of between 92 and 100 at 1 μM. Thus, the compounds of the invention are useful in treating disorders which are caused or exacerbated by increased protein kinase levels.

Synthetic Methods

Abbreviations which have been used in the descriptions of the scheme and the examples that follow are: DEAD for diethyl azodicarboxylate; THF for tetrahydrofuran; MTBE for methyl tert-butyl ether, PPh$_3$ for triphenylphosphine; OAc for acetate; P(o-tol)$_3$ for tri-o-tolylphoshphine; dba for dibenzylideneacetone; DME for 1,2-dimethoxyethane; BINAP for 2,2'-bis(diphenylphosphino)-1,1'-binaphthyl; DMAP for 4-dimethylaminopyridine; dppf for diphenylphosphinoferrocene; dppe for diphenylphosphinoethane; EDC for 1-ethyl-3-[3-(dimethylamino)propyl]carbodiimide hydrochloride; HOBt for 1-hydroxybenzotriazole; DCC for 1,3-dicyclohexylcarbodiimide; DMF for dimethylformamide; NMP for N-methylpyrrolidinone; DMSO for dimethylsulfoxide; Boc for tert-butoxycarbonyl; TFA for trifluoroacetic acid; DIBAL for diisobutylaluminum hydride; n-BuLi for n-butyllithium; 9-BBN for 9-borabicyclo[3.3.1]nonane; OiPr for isopropoxide; DMA for dimethylacetamide; AIBN for 2,2'-azobisisobutyronitrile; TEA for triethylamine; and NBS for N-bromosuccinimide.

The compounds and processes of the present invention will be better understood in connection with the following synthetic schemes which illustrate the methods by which the compounds of the invention may be prepared. The groups $L^1$, $L^2$, $L^3$, $R^1$, $R^2$, $R^3$, $R^4$, $R^6$, and $R^7$ are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

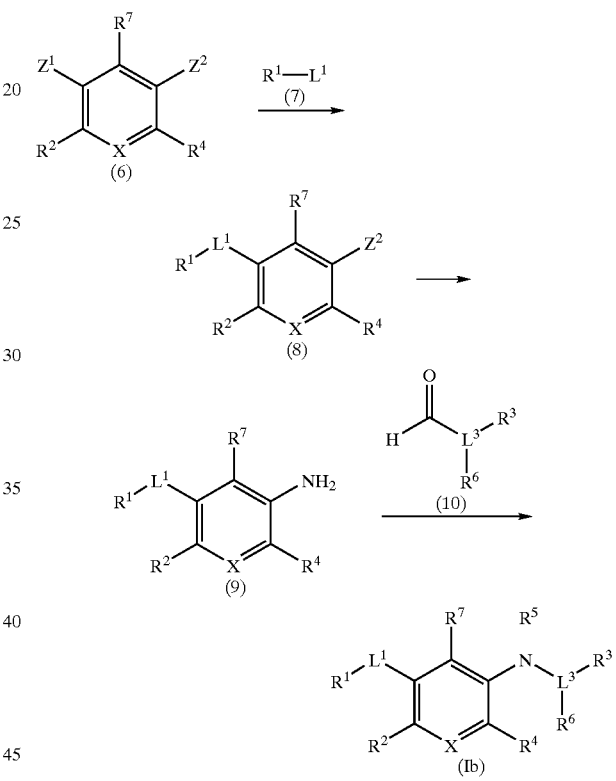

As shown in Scheme 1, compounds of formula (2) (Z is Cl, Br, I, or OTf) can be converted to compounds of formula (4) by treatment with compounds of formula (3) in the presence of triphenylphosphine and an activating agent such as DEAD. The reaction can be carried out neat or in the presence of a solvent such as THF, diethyl ether, and MTBE. The reaction temperature is typically about −10° C. to about 35° C. and reaction times are typically about 8 to about 24 hours.

Compounds of formula (4) can be converted to compounds of formula (Ia) by treatment with compounds of formula (5) (M is selected from B(OH)$_2$; Sn(R$^a$)$_3$, where R$^a$ is an alkyl or aryl group; and hydrogen) in the presence of a palladium catalyst and an optional additive such as triethylamine. Examples of palladium catalysts include Pd(PPh$_3$)$_4$, and Pd(OAc)$_2$ and P(o-tol)$_3$. Representative solvents include toluene, acetonitrile, and DME. The reaction is typically conducted at temperatures between about 60° C. and about 110° C. and reaction times are typically about 4 to about 12 hours.

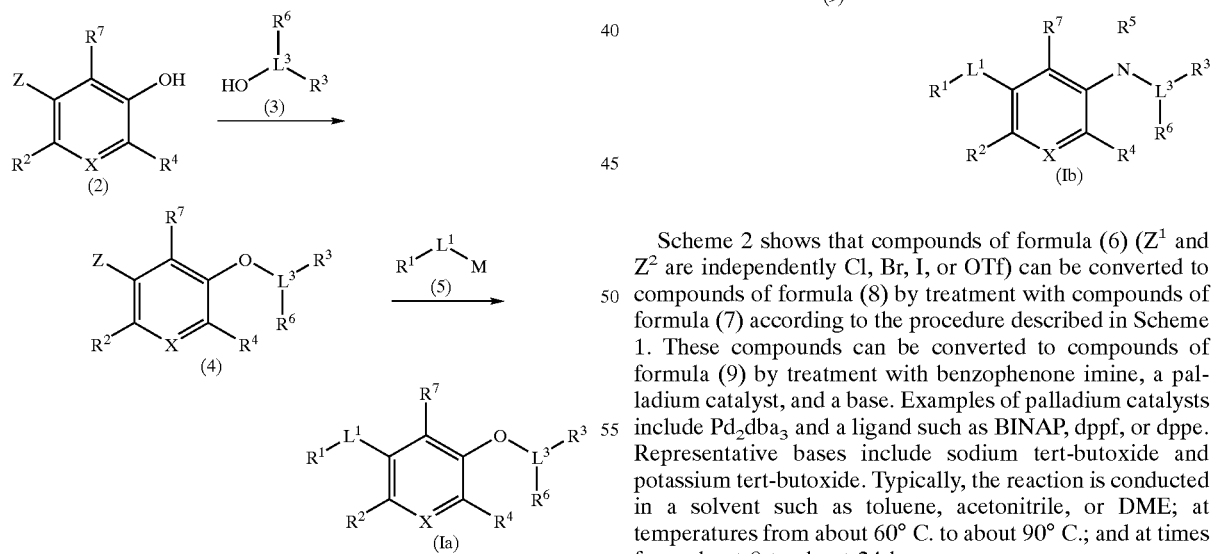

Scheme 2 shows that compounds of formula (6) (Z$^1$ and Z$^2$ are independently Cl, Br, I, or OTf) can be converted to compounds of formula (8) by treatment with compounds of formula (7) according to the procedure described in Scheme 1. These compounds can be converted to compounds of formula (9) by treatment with benzophenone imine, a palladium catalyst, and a base. Examples of palladium catalysts include Pd$_2$dba$_3$ and a ligand such as BINAP, dppf, or dppe. Representative bases include sodium tert-butoxide and potassium tert-butoxide. Typically, the reaction is conducted in a solvent such as toluene, acetonitrile, or DME; at temperatures from about 60° C. to about 90° C.; and at times from about 8 to about 24 hours.

Compounds of formula (9) can be treated with compounds of formula (10) in the presence of an acid such as acetic acid and then treated with sodium cyanoborohydride to provide compounds of formula (Ib). Representative solvents include methanol and ethanol. The reaction is typically conducted at about 20° C. to about 70° C. and reaction times are typically about 1 to about 4 hours.

Scheme 3

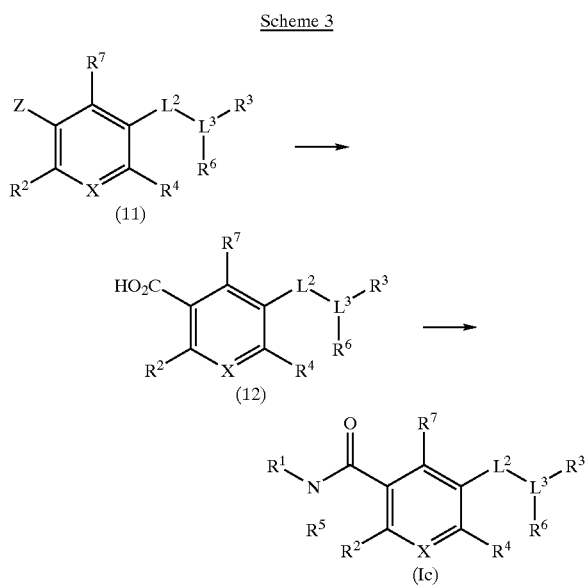

Scheme 3 shows the preparation of compounds of formula (Ic). Compounds of formula (11) (Z is Br) can be treated with a palladium catalyst under CO atmosphere to provide compounds of formula (12). Examples of palladium catalysts include $PdCl_2.dppf$, $PdCl_2$ and BINAP, and $PdCl_2.dppe$. Representative solvents include THF, water, DME, and mixtures thereof. The reaction is typically conducted at about 80° C. to about 100° C. and reaction times are typically between 12 and 24 hours.

Compounds of formula (12) can be converted to compounds of formula (Ic) by treatment with a substituted amine in the presence of a coupling agent. Representative coupling agents include EDC, HOBt, DCC, DMAP, and mixtures thereof. Examples of solvents used include dichloromethane, DMF, and DME. The reaction is typically conducted at about 0° C. to about 35° C. and reaction times are typically about 12 to about 24 hours.

Scheme 4

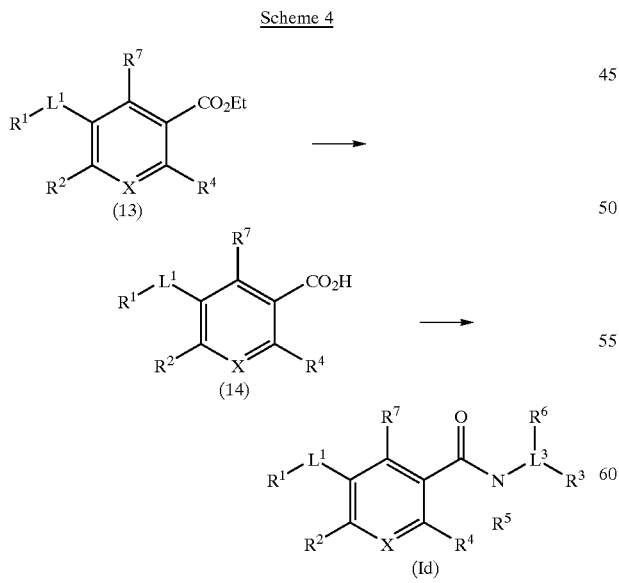

As shown in Scheme 4, compounds of formula (13) can be hydrolyzed to provide compounds of formula (14) using methods known to those of ordinary skill in the art. Compounds of formula (14) can be converted to compounds of formula (Id) using the conditions described in Scheme 3.

Scheme 5

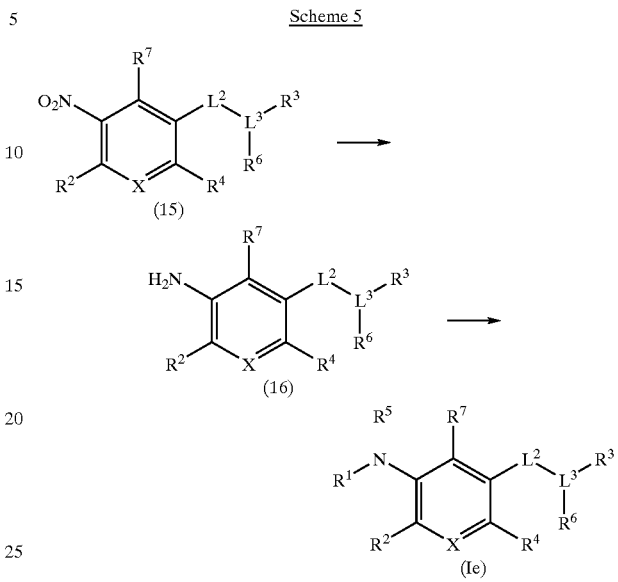

Scheme 5 shows the synthesis of compounds of formula (Ie). Compounds of formula (15) can be converted to compounds of formula (16) by treatment with a reducing agent. Examples of reducing agents include Pd/C and ammonium formate, Pd/C and hydrogen, and $PtO_2$ and hydrogen. Representative solvents include methanol and ethanol. The reaction is typically conducted at about 50° C. to about 70° C. for about 15 minutes to about 2 hours.

Compounds of formula (16) can be converted to compounds of formula (Ie) by treatment with an electrophile such as a halo-substituted heteroaryl group. Examples of solvents used in these reactions include ethanol and methanol. The reaction is typically conducted at about 50° C. to about 70° C. for about 6 to about 18 hours.

Scheme 6

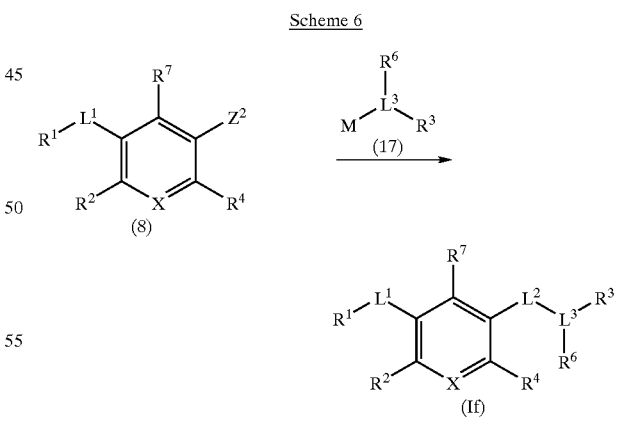

As shown in Scheme 6, compounds of formula (8) can be converted to compounds of formula (If) (where $L^2$ is a bond) by treatment with compounds of formula (17) (M is $B(OR^z)_2$, wherein $R^z$ is hydrogen or alkyl) in the presence of a palladium catalyst and a base such as cesium carbonate or sodium carbonate. Representative palladium catalysts include $PdCl_2.dppf$, $Pd(PPh_3)_4$, and $PdCl_2 (PPh_3)_2$. Examples of solvents used in these reactions include DMF, DME, and NMP. The reaction is typically conducted at about 30° C. to about 100° C. for about 4 to about 12 hours.

Scheme 7

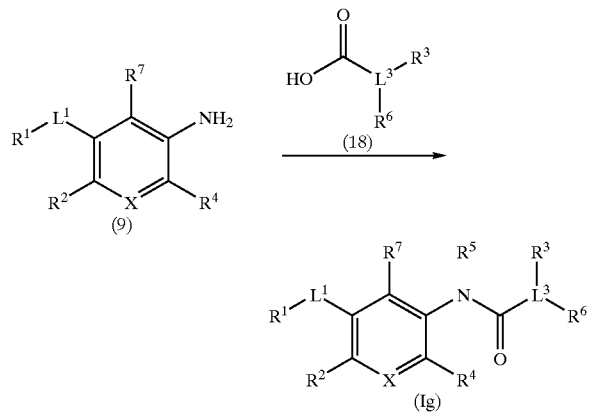

As shown in Scheme 7, compounds of formula (9) can be reacted with compounds of formula (18) using the conditions described in Scheme 3 to provide compounds of formula (Ig).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

EXAMPLE 1

N,N-dimethyl-N-[2-({5-[(E)-2-pyridin-4-ylvinyl]pyridin-3-yl}oxy)ethyl]amine

Example 1A

N-{2-[(5-bromopyridin-3-yl)oxy]ethyl}-N,N-dimethylamine

A solution of N,N-dimethylethanolamine(0.5 mL) in DMF (10 mL) at room temperature was treated with sodium hydride (0.2 g, 8.4 mmol), stirred for 30 minutes, and treated with 3,5-dibromopyridine (1.0 g, 4.2 mmol). The mixture was stirred at 90° C. for 8 hours, and partitioned between ethyl acetate and water. The organic layer was washed with brine, dried (Na$_2$SO$_4$), filtered, and concentrated under vacuum. Purification by flash column chromatography on silica gel with 50% ethyl acetate/hexane provided the desired product (0.8 g, 78%). MS (DCI/NH$_3$) m/e 246 (M+H)$^+$.

Example 1B

N,N-dimethyl-N-[2-({5-[(E)-2-pyridin-4-ylvinyl]pyridin-3-yl}oxy)ethyl]amine

A mixture of Example 1A (0.8 g, 3.27 mmol), 4-vinylpyridine (0.69 g, 5.53 mmol), tri-o-tolylphosphine (0.6 g, 1.96 mmol), palladium acetate (0.16 g, 0.65 mmol) and triethylamine (0.66 g, 6.53 mmol) in acetonitrile (15 mL) was stirred for 8 hours at 80° C. The reaction solution was partitioned between ethyl acetate and water. The organic layer was washed with brine, dried (Na$_2$SO$_4$), filtered, and concentrated under vacuum. Purification by flash column chromatography on silica gel with 10% methanol/dichloromethane provided the desired product (0.64 g, 73%). MS (DCI/NH$_3$) m/e 270 (M+H)$^+$; $^1$H NMR (DMSO-d$_6$) δ 8.58 (d, J=6.0 Hz, 2H), 8.39 (s, 1H), 8.24 (s, 1H), 7.73 (s, 1H), 7.56 (d, J=6.0 Hz, 1H), 7.56 (m, 2H), 7.45 (d, J=16.5 Hz, 2H), 4.19 (t, J=6.0 Hz, 2H), 2.67 (t, J=6.0 Hz, 2H), 2.23 (s, 6H).

EXAMPLE 2

(1S)-2-(1H-indol-3-yl)-1-[({5-[(E)-2-pyridin-4-ylvinyl]pyridin-3-yl}oxy)methyl]ethylamine

Example 2A tert-butyl (1S)-2-[(5-hydroxypyridin-3-yl)oxy]-1-(1H-indol-3-ylmethyl)ethylcarbamate A solution of 3-bromo-5-hydroxypyridine (2.0 g, 11.5 mmol), L-Boc-tryptophanol (3.67 g, 12.6 mmol), and triphenylphosphine (4.53 g, 17.3 mmol) at 0° C. was treated dropwise with DEAD (3.01 g, 17.3 mmol), warmed to room temperature, stirred overnight, and concentrated. The concentrate was purified by flash column chromatography on silica gel with hexane/ethyl acetate (4:1) to provide the desired product (4.55 g, 88.7%). MS (DCI/NH$_3$):m/e 446, 448 (M+H)$^+$.

Example 2B tert-butyl (1S)-2-(1H-indol-3-yl)-1-[({5-[(E)-2-pyridin-4-ylvinyl]pyridin-3-yl}oxy)methyl]ethylcarbamate The desired product was prepared by substituting Example 2A for Example 1A in Example 1B. MS (DCI/NH$_3$) m/e 471 (M+H)$^+$.

Example 2C (1S)-2-(1H-indol-3-yl)-1-[({5-[(E)-2-pyridin-4-ylvinyl]pyridin-3-yl}oxy)methyl]ethylamine A solution of Example 2B (603 mg, 1.28 mmol) in dichloromethane (20 mL) at room temperature was treated with 4N HCl in dioxane (5 mL), stirred for 2 hours, and concentrated. The residue was dissolved in water (1.5 mL) and freeze-dried to provide the desired product as the hydrochloride salt (610 mg, 99%). MS (DCI/NH$_3$) m/e 371 (M+H)$^+$, $^1$HNMR (CD$_3$OD) δ 8.76 (d, J=6.8 Hz, 2H), 8.52 (d, J=1.4 Hz, 1H), 8.38 (d, J=2.4 Hz, 1H), 8.16 (d, J=7.1 Hz, 2H), 7.86 (d, J=16.6 Hz, 1H), 7.77 (m, 1H), 7.60 (d, J=8.1 Hz, 1H), 7.52 (d, J=8.1 Hz, 1H), 7.50 (d, J=16.6 Hz, 1H), 7.39 (d, J=8.1 Hz, 1H), 7.28 (s, 1H), 7.13 (m, 1H), 7.03 (m, 1H), 4.39 (dd, J=3.4, 10.5 Hz, 1H), 4.25 (dd, J=5.4, 10.5 Hz, 1H), 4.00 (m, 1H), 3.30 (m, 2H).

Example 2D (1S)-2-(1H-indol-3-yl)-1-[({5-[(E)-2-pyridin-4-ylvinyl]pyridin-3-yl}oxy)methyl]ethylamine A solution of Example 2B (500 mg, 1.06 mmol) in dichloromethane (5 mL) at room temperature was treated with trifluoroacetic acid (5 mL), stirred for 2 hours, and concentrated. The residue was dissolved in water (1.5 mL) and freeze-dried to provide the desired product as the trifluoroacetate salt (643 mg, 85%). MS (DCI/NH$_3$) m/e 371 (M+H)$^+$; $^1$HNMR (CD$_3$OD) δ 8.83,(d, J=7 Hz, 2H), 8.77 (br s, 1H), 8.58 (br s, 1H), 8.39 (br s, 1H), 8.29 (d, J=7 Hz, 2H), 7.98 (d, J=17 Hz, 1H), 7.82 (d, J=17 Hz, 1H), 7.61 (d, J=7 Hz, 1H), 7.48 (d, J=7 Hz, 1H), 7.28 (s, 1H), 7.09–7.14 (m, 1H), 6.99–7.04 (m, 1H), 4.50–4.57 (m, 1H), 4.39–4.45 (m, 1H), 4.02–4.08 (m, 1H), 3.30–3.38 (m, 2H).

EXAMPLE 3

(1R)-2-(1H-indol-3-yl)-1-[({5-[(E)-2-pyridin-4-ylvinyl]pyridin-3-yl}oxy)methyl]ethylamine The desired product was prepared as the hydrochloride salt by substituting D-Boc-tryptophanol for L-Boc-tryptophanol in Example 2A then proceeding as described for Examples 2B and 2C. MS (DCI/NH$_3$) m/e 371 (M+H)$^+$; $^1$HNMR (CD$_3$OD) δ 8.76 (d, J=6.1 Hz, 2H), 8.52 (m,1H), 8.37 (m, 1H), 8.17 (d, J=6.1 Hz, 2H), 7.86 (d, J=16.6 Hz, 1H), 7.79 (m, 1H), 7.59 (d, J=7.8 Hz, 1H), 7.53 (d, J=16.6 Hz, 1H), 7.50 (d, J=16.6 Hz, 1H), 7.38 (d, J=8.1 Hz, 1H), 7.23 (s, 1H), 7.12 (m, 1H), 7.02 (m, 1H), 4.38 (dd, J=3.1, 10.5 Hz, 1H), 4.25 (dd, J=5.4, 10.5 Hz, 1H), 3.99, (m, 1H), 3.26 (m, 2H).

EXAMPLE 4

1-(1H-indol-3-yl)-3-({5-[(E)-2-pyridin-4-ylvinyl]pyridin-3-yl}oxy)propan-2-ol

A solution of Example 2C (150 mg, 0.400 mmol) in acetic acid (2.4 mL) at room temperature was treated portionwise with NaNO$_2$ (117 mg. 1.70 mmol), stirred for 18 hours, quenched with water (40 μL), stirred for an additional hour, poured into 2N NaOH, and extracted with isopropanol/dichloromethane. The combined extracts were concentrated. The residue was treated with LiOH.H$_2$O (25 mg) in THF/water (1 mL/0.5 mL), heated to 55° C. overnight, diluted with dichloromethane, washed with water, dried (MgSO$_4$), filtered, and concentrated. The residue was purified by HPLC on a C18 column with 0–100% CH$_3$CN/H$_2$O/0.1% TFA to provide the desired product as the trifluoroacetate salt (9.7 mg, 5%). MS (DCI/NH$_3$) m/e 372 (M+H)$^+$; $^1$H NMR (DMSO-d$_6$) δ 10.82 (s, 1H), 8.85 (d, J=6.6 Hz, 2H), 8.49 (s, 1H), 8.37 (s, 1H), 8.08 (d, J=6.6 Hz, 2H), 7.90 (d, J=16.5 Hz, 1H), 7.79 (m, 1H), 7.65 (d, J=16.6 Hz, 1H), 7.56 (d, J=7.8 Hz, 1H), 7.32 (d, J=8.1 Hz, 1H), 7.18 (d, J=2.2 Hz, 1H), 7.04 (m, 1H), 6.95 (m, 1H), 4.06 (m, 2H), 3.83 (m, 1H), 3.03 (dd, J=6.2, 14.5 Hz, 1H), 2.91 (dd, J=6.2, 14.5 Hz, 1H).

EXAMPLE 5

(1S)-2-(1-benzothien-3-yl)-1-[({5-[(E)-2-pyridin-4-ylvinyl]pyridin-3-yl}oxy)methyl]ethylamine The desired product was prepared as the trifluoroacetate salt by substituting 2-tert-butoxycarbonylamino-3-benzo[b]thiophen-3-yl-propan-1-ol for L-Boc-tryptophanol in Example 2A then proceeding as described for Examples 2B and 2D. MS (DCI/NH$_3$) m/e 388 (M+H)$^+$; $^1$H NMR (DMSO-d$_6$) δ 8.87 (d, J=6.3 Hz, 2H), 8.55 (s, 1H), 8.49 (br.s, 2H), 8.40 (d, J=7.2 Hz, 1H), 8.10 (d, J=6.3 Hz, 2H), 8.02 (d, J=7.2 Hz, 1H), 7.96 (d, J=7.2 Hz, 1H), 7.90 (d, J=16.2 Hz, 1H), 7.80 (m, 1H), 7.68 (s, 1H), 7.63 (d, J=16.2 Hz, 1H), 7.42 (m, 2H), 4.36 (dd, J=3.1, 10.6 Hz, 1H), 4.20 (dd, J=5.3, 10.6 Hz, 1H), 3.99 (m, 1H), 3.36 (m, 2H).

EXAMPLE 6

(1S)-2,2-diphenyl-1-[({5-[(E)-2-pyridin-4-ylvinyl]pyridin-3-yl}oxy)methyl]ethylamine The desired product was prepared as the hydrochloride salt by substituting L-Boc-diphenylalaminol for L-Boc-tryptophanol in Example 2A then proceeding as described for Examples 2B and 2C. MS (DCI/NH$_3$) m/e 408 (M+H)$^+$; $^1$H NMR (DMSO-d$_6$) δ 8.89 (d, J=6.8 Hz, 2H), 8.57 (s, 1H), 8.45 (br s, 2H), 8.42 (d, J=2.4 Hz, 1H), 8.16 (d, J=6.8 Hz, 2H), 7.99 (d, J=16.6 Hz, 1H), 7.84 (s, 1H), 7.73 (d, J=16.6 Hz, 1H), 7.62 (m, 2H), 7.49 (m, 2H), 7.39 (m, 2H), 7.28 (m, 3H), 7.18 (m, 1H), 4.77 (m, 1H), 4.46 (m, 2H), 4.03 (m, 1H).

EXAMPLE 7

(1S)-1-{4-[(2,6-dichlorobenzyl)oxy]benzyl}-2-({5-[(E)-2-pyridin-4-ylvinyl]pyridin-3-yl}oxy)ethylamine The desired product was prepared as the hydrochloride salt by substituitng L-Boc-(4-(2,6-dichlorobenzyloxy)phenyl)alaninol for L-Boc-tryptophanol in Example 2A then proceeding as described for Examples 2B and 2C. MS (DCI/NH$_3$) m/e 506, 508, 510 (M+H)$^+$; $^1$H NMR (CD$_3$OD) δ 8.81 (d, J=7.1 Hz, 2H), 8.71 (d, J=1.0 Hz, 1H), 8.55 (d, J=2.7 Hz, 1H), 8.28 (d, J=7.1 Hz, 2H), 8.25 (m, 1H), 7.99 (d, J=16.3 Hz, 1H), 7.79 (d, J=16.3 Hz, 1H), 7.46 (d, J=1.7 Hz, 1H), 7.43 (s, 1H), 7.36 (m, 1H), 7.30 (m, 2H), 7.05 (m, 2H), 5.28 (s, 2H), 4.45 (dd, J=3.1, 10.5 Hz, 1H), 4.31 (dd, J=5.8, 10.5 Hz, 1H), 3.95 (m, 1H), 3.21 (m, 2H).

EXAMPLE 8

(1S)-2-(benzyloxy)-1-[({5-[(E)-2-pyridin-4-ylvinyl]pyridin-3-yl}oxy)methyl]ethylamine The desired product was prepared as the hydrochloride salt by substituting L-Boc-3-benzyloxyalaminol for L-Boc-tryptophanol in Example 2A then proceeding as described for Examples 2B and 2C. MS (DCI/NH$_3$) m/e 362 (M+H)$^+$; $^1$H NMR (CD$_3$OD) δ 8.80–8.89 (m, 4H), 8.53–8.62 (m, 3H), 8.28–8.34 (m, 3H), 8.00–8.06 (m, 1H), 7.98 (d, J=16.3 Hz, 1H), 7.87 (d, J=16.3 Hz, 1H), 7.28–7.43 (m, 3H), 4.66 (s, 2H), 4.56–4.64 (m, 2H), 3.94–3.99 (m, 1H), 3.83–3.87 (m, 2H).

EXAMPLE 9

N,N-dimethyl-N-[(1S,2S)-1-methyl-2-phenyl-2-({5-[(E)-2-pyridin-4-ylvinyl]pyridin-3-yl}oxy)ethyl]amine

Example 9A 5-bromopyridin-3-yl acetate

A mixture of 3-bromo-5-hydroxypyridine (9.00 g, 51.7 mmol), acetic anhydride (6.0 mL) and triethylamine (12.0 mL) in THF (50 mL) was heated to reflux overnight, cooled to room temperature, diluted with diethyl ether, washed with water, 5% NaHCO$_3$, water, and brine, dried (MgSO$_4$), filtered, and concentrated to provide the desired product (9.37 g, 84%).

Example 9B

5-[(E)-2-pyridin-4-ylvinyl]pyridin-3-ol

A mixture of Example 9A (9.37 g, 43,3 mmol), 4-vinylpyridine (14.0 mL, 130 mmol), tri-o-tolylphosphine (13.5 g, 44.4 mmol), palladium acetate (2.65 g, 11.8 mmol) and triethylamine (120 mL, 0.861 mol) in acetonitrile (40 mL) was heated to reflux overnight and partitioned between ethyl acetate and water. The organic layer was washed with brine, dried (Na$_2$SO$_4$), filtered, and concentrated under vacuum. Purification by flash column chromatography on silica gel with 5% methanol/dichloromethane containing 0.5% ammonia provided the acetate (8.53 g). This was stirred with LiOH.H$_2$O (6.00 g, 143 mmol) in THF/water (40 mL/20 mL) at room temperature for 4 hours, concentrated, adjusted to pH 7 with 1N HCl (aq.), and filtered. The filter cake was washed with water and dried under vacuum at 60° C. to provide the desired product (7.23 g, 84%). MS (DCI/NH$_3$) m/e 199 (M+H)$^+$; $^1$H NMR (CD$_3$OD) δ 8.51 (m, 2H), 8.24 (d, J=1.4 Hz, 1H), 8.04 (d, J=2.4 Hz, 1H), 7.61 (m, 2H), 7.50 (m, 1H), 7.49 (d, J=16.6 Hz, 1H), 7.27 (d, J=16.6 Hz, 1H).

Example 9C

N,N-dimethyl-N-[(1S,2S)-1-methyl-2-phenyl-2-({5-[(E)-2-pyridin-4-ylvinyl]pyridin-3-yl}oxy)ethyl]amine The desired product was prepared as the trifluoracetate salt by substituting Example 9B and (1S,2S)-2-(dimethylamino)-1-phenylpropan-1-ol for 3-bromo-5-hydroxypyridine and L-Boc-tryptophanol, respectively, in Example 2A then proceeding as described for Examples 2B and 2D. MS (DCI/NH$_3$) m/e 360 (M+H)$^+$; $^1$H NMR (DMSO-d$_6$) δ 8.78 (d, 2H), 8.44 (s, 1H), 8.33 (d, 1H), 7.94 (d, 1H), 7.80 (s, 1H), 7.75 (d, 1H), 7.59 (d, 2H), 7.46–7.34 (m, 5H), 5.84 (d, 1H), 3.55–3.45 (m, 1H), 2.95 (s, 3H), 2.84 (s, 3H), 1.02 (d, 3H).

EXAMPLE 10

(1S)-2-(2-naphthyl)-1-[({5-[(E)-2-pyridin-4-ylvinyl]pyridin-3-yl}oxy)methyl]ethylamine The desired product was prepared as the trifluoracetate salt by substituting L-Boc-(2-naphthyl)alaninol for L-Boc-tryptophanol in Example 2A then proceeding as described for Examples 2B and 2D. MS (DCI/NH$_3$) m/e 382 (M+H)$^+$; $^1$HNMR (DMSO-d$_6$) δ 8.88 (d, J=6.8 Hz, 2H), 8.57 (d, J=1.0 Hz, 1H), 8.43 (d, J=2.4 Hz, 1H), 8.15 (d, J=6.8 Hz, 2H), 7.99 (d, J=16.6 Hz, 1H), 7.90 (m, 5H), 7.73 (d, J=16.6 Hz, 1H), 7.50 (m, 3H), 4.35 (dd, J=3.4, 10.5 Hz, 1H), 4.21 (dd, J=5.4, 10.5 Hz, 1H), 3.97 (m, 1H), 3.32 (dd, J=5.8, 13.6 Hz, 1H), 3.21 (dd, J=9.2, 13.6 Hz, 1H).

EXAMPLE 11

N-[(2S)-2-amino-3-(1H-indol-3-yl)propyl]-N-{5-[(E)-2-pyridin-4-ylvinyl]pyridin-3-yl}amine Example 11A 3-bromo-5-[(E)-2-pyridin-4-ylvinyl]pyridine A solution of 3,5-dibromopyridine (5.56 g, 23.4 mmol), 4-vinylpyridine (5.1 mL), palladium acetate (1.05 g), tri-o-tolylphosphine (5.00 g) and triethylamine (33 mL) in acetonitrile (100 mL) was heated overnight at 80° C. and concentrated. The residue was partitioned between 5% NaHCO$_3$ and dichloromethane and filtered. The filtrate was separated and the organic layer was washed with water, dried (MgSO$_4$), filtered, and concentrated. The concentrate was purified by flash column chromatography on silica gel with 4% methanol/dichloromethane to provide the desired product (2.18 g, 36%). (DCI/NH$_3$) m/e 261, 263 (M+H)$^+$.

Example 11B

5-[(E)-2-pyridin-4-ylvinyl]pyridin-3-amine

A mixture of Example 11A (1.88 g, 7.2 mmol), benzophenone imine (1.22 mL), Pd$_2$(dba)$_3$ (66 mg), BINAP (125 mg), sodium tert-butoxide (0.97 g), and toluene (19 mL) was heated to 80° C. overnight and concentrated. The residue was purified by flash column chromatography on silica gel with ethyl acetate to provide a solid (2.44 g). This was stirred with 2N HCl (aq.) (5.0 mL) in THF (50 mL) at room temperature for 2 hours and concentrated. The residue was dissolved in 0.5N HCl (aq.) (100 mL) and washed three times with ethyl acteate. The aqueous layer was adjusted to pH 11 with 1N NaOH and extracted with dichloromethane. The combined extracts were washed with water, dried (MgSO$_4$), filtered, and concentrated to provide the desired product (1.23 g, 87%). MS (DCI/NH$_3$) m/e 198 (M+H)$^+$; $^1$H NMR (DMSO-d$_6$) δ 8.55 (m; 2H), 8.00 (d, J=1.7 Hz, 1H), 7.89 (d, J=2.4 Hz, 1H), 7.56 (m, 2H), 7.42 (d, J=16.6 Hz, 1H), 7.17 (d, J=16.6 Hz, 1H), 7.15 (m, 1H).

Example 11C tert-butyl (1S)-2-(1H-indol-3-yl)-1-[({5-[(E)-2-pyridin-4-ylvinyl]pyridin-3-yl}amino)methyl]ethylcarbamate A mixture of Example 11B (52 mg, 0.264 mmol), L-Boc-tryptophanal (J. Med. Chem., 1985, 28 (12), 1874.) (80 mg, 0.277 mmol) and acetic acid (80 μL) in methanol (4 mL) was stirred at room temperature for 3 hours, refluxed for 2 hours, cooled to room temperature, treated with sodium cyanoborohydride (35 mg) stirred for 1 hour, and filtered. The filtrate was concentrated and the residue was purified by HPLC on a C18 column with 0–100% CH$_3$CN/H$_2$O/0.1% TFA to provide the designed product (43 mg, 35%). MS (DCI/NH$_3$) m/e 470 (M+H)$^+$.

Example 11D

N-[(2S)-2-amino-3-(1H-indol-3-yl)propyl]-N-{5-[(E)-2-pyridin-4-ylvinyl]pyridin-3-yl}amine A solution of Example 11C (40 mg, 0.085 mmol) in dichloromethane (3.0 mL) at room temperature was treated with 4N HCl in dioxane (0.5 mL), stirred for 1 hour, and concentrated to provide the desired product as the hydrochloride salt (30 mg, 74%). MS (DCI/NH$_3$) m/e 370 (M+H)$^+$; $^1$H NMR (DMSO-d$_6$) δ 11.09 (br s, 1H), 8.90 (d, J=5.8 Hz, 2H), 8.47 (br s, 2H), 8.33 (s, 1H), 8.22 (d, J=1.8 Hz, 1H), 8.14 (d, J=5.8 Hz, 2H), 7.98 (s, 1H), 7.94 (d, J=16.5 Hz, 1H), 7.86 (d, J=16.5 Hz, 1H), 7.62 (d, J=7.9 Hz, 1H), 7.37 (d, J=4.5 Hz, 1H), 7.36 (s, 1H), 7.08 (m, 1H), 6.98 (m, 1H), 3.71 (m, 1H), 3.67 (m, 1H), 3.54 (m, 1H), 3.15 (m, 2H).

EXAMPLE 12

(1S)-2-({2-chloro-5-[(E)-2-pyridin-4-ylvinyl]pyridin-3-yl}oxy)-1-(1H-indol-3-ylmethyl)ethylamine Example 12A 3-(benzyloxy)-5-bromo-2-chloropyridine A solution of 3-(benzyloxy)-5-bromopyridine N-oxide (2.0 g, 7.1 mmol) in POCl$_3$ (20 mL) was stirred at 100° C. for 7 hours, cooled to room temperature, concentrated, treated with ethyl acetate (50 mL), washed with brine, dried (MgSO$_4$), filtered, and concentrated. The concentrate was purified by flash column chromatography on silica gel with 10% ethyl acetate/hexane to provide the desired product (1.0 g, 40%). MS (DCI/NH$_3$) m/e 299 (M+H)$^+$.

Example 12B 5-bromo-2-chloro-3-hydroxypyridine

A mixture of Example 12A in HBr/HOAc (30%, 50 mL) was stirred at 100° C. for 8 hours, cooled to room temperature and concentrated. The concentrate was partitioned between ethyl acetate and saturated $Na_2CO_3$ (aq.). The organic layer was washed with brine, dried ($Na_2SO_4$), filtered, and concentrated under vacuum. Purification by flash column chromatography on silica gel with 30% ethyl acetate/hexane provided the desired product (0.51 g, 72%). MS ($DCI/NH_3$) m/e 209 (M+H)$^+$.

Example 12C tert-butyl (1S)-2-[(5-bromo-2-chloropyridin-3-yl)oxy]-1-(1H-indol-3-ylmethyl)ethylcarbamate The desired product was prepared by substituting Example 12B for 3-bromo-5-hydroxypyridine in Example 2A (0.78 g, 66%). MS ($DCI/NH_3$) m/e 481 (M+H)$^+$.

Example 12D (1S)-2-({2-chloro-5-[(E)-2-pyridin-4-ylvinyl]pyridin-3-yl}oxy)-1-(1H-indol-3-ylmethyl)ethylamine The desired product was prepared as the trifluoroacetate salt by substituting Example 12C for Example 2A in Examples 2B and 2D. MS ($DCI/NH_3$) m/e 405, 407 (M+H)$^+$; $^1$H NMR (DMSO-$d_6$) δ 11.04 (s, 1H), 8.72 (d, J=6.0 Hz, 2H), 8.30 (s, 1H), 8.23 (br s, 2H), 7.84 (s, 1H), 7.78 (d, J=6.0 Hz, 2H), 7.70 (d, J=16.8 Hz, 1H), 7.62 (d, J=8.1 Hz, 1H), 7.50 (d, J=16.8 Hz, 1H), 7.38 (d, J=8.1 Hz, 1H), 7.28 (s, 1H), 7.10 (t, J=7.2 Hz, 1H), 7.00 (t, J=7.2 Hz, 1H), 4.38 (m; 1H), 4.18 (m, 1H), 3.91 (m, 1H), 3.20 (m, 2H).

EXAMPLE 13

(1S)-2-({6-chloro-5-[(E)-2-pyridin-4-ylvinyl]pyridin-3-yl}oxy)-1-(1H-indol-3-ylmethyl)ethylamine Example 13A tert-butyl (1S)-2-[(5-bromo-6-chloropyridin-3-yl)oxy]-1-(1H-indol-3-ylmethyl)ethylcarbamate A solution of 5-bromo-6-chloro-3-hydroxypyridine (2.50 g, 12 mmol) N-α-(tert-butoxycarbonyl)-L-tryptophanol (3.77 g, 18 mmol) and triphenylphosphine (4.72 g, 18 mmol) in THF (100 mL) was stirred at 0° C. for 20 minutes, treated with DEAD (2.83 mL, 18 mmol), stirred for 1 hour, warmed to room temperature, stirred for 15 hours, treated with ethyl acetate (300 mL), washed with brine, dried ($MgSO_4$), filtered, and concentrated. The concentrate was purified by flash column chromatography on silica gel with 25% ethyl acetate/hexane to provide the desired product (4.58 g, 80%). MS (APCI) m/e 480, 482 (M+H)$^+$.

Example 13B tert-butyl (1S)-2-({6-chloro-5-[(E)-2-pyridin-4-ylvinyl]pyridin-3-yl}oxy)-1-(1H-indol-3-ylmethyl)ethylcarbamate A solution Example 13A (1.50 g, 3.125 mmol), $Pd_2(dba)_3$ (71 mg, 0.078 mmol) and tri-o-tolylphosphine (71 mg, 0.23 mmol) in DMF (30 mL) was treated with 4-vinylpyridine (492 mg, 4.68 mmol) and triethylamine (1.30 mL, 9.4 mmol), purged with nitrogen, and heated to 100° C. for 4 hours. The mixture was cooled to room temperature, treated with ethyl acetate (200 mL), washed with brine, dried ($MgSO_4$), filtered, and concentrated. The concentrate was purified by flash column chromatography on silica gel with 75% ethyl acetate/hexanes to provide the desired product (1.37 g, 87%). MS (APCI) m/e 505, 507 (M+H)$^+$.

Example 13C (1S)-2-({6-chloro-5-[(E)-2-pyridin-4-ylvinyl]pyridin-3-yl}oxy)-1-(1H-indol-3-ylmethyl)ethylamine The desired product was prepared as the trifluoroacetate salt by substituting Example 13B for Example 2B in Example 2D. MS (APCI) m/e 405, 407 (M+H)$^+$; $^1$H NMR (300 MHz, $CD_3OD$) δ 8.76 (d, J=6.7 Hz, 2H), 8.18 (d, J=2.7 Hz, 1H), 8.15 (d, J=6.5 Hz, 2H), 7.95 (d, J=16.2 Hz, 1H), 7.86 (d, J=3.0 Hz, 1H), 7.58 (d, J=7.8 Hz, 1H), 7.43 (d, J=16.3 Hz, 1H), 7.38 (d, J=8.1 Hz, 1H), 7.23 (s, 1H), 7.13 (t, J=7.1 Hz, 1H), 7.03 (t, J=7.8 Hz, 1H), 4.38 (dd, J=10.5, 3.0 Hz, 1H), 4.25 (dd, J=10.6, 5.8 Hz, 1H), 3.97 (m, 1H), 3.31 (m, 2H); Anal. Calcd for $C_{23}H_{21}ClN_4O.2.3TFA$: C, 49.69; H, 3.52; N, 8.40. Found: C, 49.82; H, 3.48; N, 8.32.

EXAMPLE 14

(1S)-2-(1H-indol-3-yl)-1-({[5-(pyridin-4-ylethynyl)pyridin-3-yl]oxy}methyl)ethylamine Example 14A tert-butyl (1S)-2-(1H-indol-3-yl)-1-[({5-[(trimethylsilyl)ethynyl]pyridin-3-yl}oxy)methyl]ethylcarbamate A mixture of Example 2A (500 mg, 1.12 mmol), $Pd_2Cl_2(PPh_3)_2$ (77 mg, 0.112 mmol), and CuI (52 mg, 0.27 mmol) was purged with nitrogen, treated with DMF (7 mL), trimethylsilylacetylene (475 μL, 3.36 mmol) and triethylamine (468 μL, 3.36 mmol) stirred at 50° C. for 15 hours, cooled to room temperature, treated with ethyl acetate (50 mL), washed with brine, dried ($MgSO_4$), filtered, and concentrated. The residual oil was purified by flash column chromatography on silica gel with 1:2 ethyl acetate/hexanes to provide the desired product (417 mg, 80%). MS (APCI) m/e 464 (M+H)$^+$.

Example 14B tert-butyl (1S)-2-[(5-ethynylpyridin-3-yl)oxy]-1-(1H-indol-3-ylmethyl)ethylcarbamate A solution of Example 14A (400 mg, 0.86 mmol) in THF (6 mL) at room temperature was treated with tetrabutylammonium fluoride (1.0 M solution in THF, 1.12 mL, 1.12 mmol), stirred for 1 hour, treated with ethyl acetate (50 mL), washed with brine, dried ($MgSO_4$), filtered, and concentrated. The residual oil was purified by flash column chromatography on silica gel with 40% ethyl acetate/hexanes to provide the desired product (290 mg, 86%). MS (APCI) m/e 392 (M+H)$^+$.

Example 14C tert-butyl (1S)-2-(1H-indol-3-yl)-1-({[5-(pyridin-4-ylethynyl)pyridin-3-yl}oxy]methyl)ethylcarbamate A mixture of Example 14B (150 mg, 0.384 mmol), 4-bromopyridine hydrochloride (75 mg, 0.34 mmol), $Pd_2Cl_2(PPh_3)_2$ (27 mg, 0.0384 mmol), and CuI (18 mg, 0.093 mmol), was purged with nitrogen, treated with DMF (4 mL) and triethylamine (214 μL, 1.54 mmol), stirred at 50° C. for 20 hours, cooled to room temperature, treated with ethyl acetate (50 mL), washed with brine, dried (MgSO$_4$), filtered, and concentrated. The residual oil was purified by flash column chromatography on silica gel with 2:1 ethyl acetate/hexanes to provide the desired product (122 mg, 68%). MS (APCI) m/e 469 (M+H)$^+$.

Example 14D (1S)-2-(1H-indol-3-yl)-1-({[5-(pyridin-4-ylethynyl)pyridin-3-yl}oxy]methyl)ethylamine The desired product was prepared as the trifluoroacetate salt by substituting Example 14C for Example 2B in Example 2D. MS (APCI) m/e 369 (M+H)$^+$; $^1$H NMR (300 MHz, CD$_3$OD) δ 8.76 (d, J=6.5 Hz, 2H), 8.47 (d, J=1.7 Hz, 1H), 8.42 (d, J=2.7 Hz, 1H), 7.92 (d, J=6.5 Hz, 2H), 7.66 (dd, J=2.7, 1.7 Hz, 1H), 7.58 (d, J=7.8 Hz, 1H), 7.38 (d, J=8.2 Hz, 1H), 7.23 (s, 1H), 7.13 (td, J=7.1, 1.0 Hz, 1H), 7.03 (td, J=7.8, 1.1 Hz, 1H), 4.34 (dd, J=10.1, 3.0 Hz, 1H), 4.19 (dd, J=10.5, 5.8 Hz, 1H), 3.98 (m, 1H), 3.28 (m, 2H); Anal. Calcd for C$_{23}$H$_{20}$N$_4$O.3.3 TFA: C, 47.74; H, 3.15; N, 7.52. Found: C, 47.53; H, 3.18; N, 7.48.

EXAMPLE 15

(1S)-2-(1H-indol-3-yl)-1-[({5-[(Z)-2-pyridin-4-ylvinyl]pyridin-3-yl}oxy)methyl]ethylamine A mixture of Example 14D (40 mg, 0.11 mmol), 5% Pd/BaSO$_4$ (8.1 mg) and quinoline (8.1 μL) in methanol (3 mL) was stirred under hydrogen (20 psi) at room temperature for 12 minutes and filtered. The filtrate was concentrated and the residual oil was purified by HPLC on a C18 column with 0–100% CH$_3$CN/H$_2$O/0.1% TFA to provide the desired product (30 mg, 75%). MS (APCI) m/e 369 (M–H)$^-$; $^1$H NMR (300 MHz, CD$_3$OD) δ 8.57 (d, J=6.8 Hz, 2H), 8.29 (d, J=2.4 Hz, 1H), 8.04 (s, 1H), 7.69 (d, J=6.4 Hz, 2H), 7.57 (d, J=7.8 Hz, 1H), 7.53 (d, J=7.8 Hz, 1H), 7.40 (d, J=8.1 Hz, 1H), 7.33 (t, J=1.7 Hz, 1H), 7.21 (s, 1H), 7.14 (m, 2H), 7.02 (td, J=8.1, 1.0 Hz, 1H), 6.95 (d, J=12.2 Hz, 1H), 4.24 (dd, J=10.5, 3.0 Hz, 1H), 4.08 (dd, J=10.5, 5.6 Hz, 1H), 3.92 (m, 1H), 3.26 (m, 2H); Anal. Calcd for C$_{23}$H$_{22}$N$_4$O. 3.6 TFA: C, 46.45; H, 3.30; N, 7.17. Found: C, 46.56; H, 3.35; N, 7.34.

EXAMPLE 16

(2S)-2-amino-4-phenyl-N-{5-[(E)-2-pyridin-4-ylvinyl]pyridin-3-yl}butanamide

Example 16A tert-butyl (1S)-3-phenyl-1-[({5-[(E)-2-pyridin-4-ylvinyl]pyridin-3-yl}amino)carbonyl]propylcarbamate A mixture of Example 11B (200 mg, 1.0 mmol), HOBt (210 mg), EDC (290 mg), DMAP (25 mg) and Boc-homophenylalanine was stirred at room temperature overnight and concentrated. The residue was dissolved in ethyl acetate, washed sequentially with water, 5% NaHCO$_3$, and water, dried (MgSO$_4$), filtered, and concentrated. The residue was purified by flash column chromatography on silica gel with 3% methanol/dichloromethane to provide the desired product (192 mg, 41%). MS (DCI/NH$_3$) m/e 459 (M+H)$^+$.

Example 16B (2S)-2-amino-4-phenyl-N-{5-[(E)-2-pyridin-4-ylvinyl]pyridin-3-yl}butanamide The desired product was prepared as the hydrochloride salt by substituting Example 16A for Example 2B in Example 2C (173 mg, 89%). MS (DCI/NH$_3$) m/e 359 (M+H)$^+$; $^1$H NMR (DMSO-d$_6$) δ 12.03 (s, 1H), 8.97 (s, 1H), 8.91 (d, J=6.6 Hz, 2H), 8.85 (s, 1H), 8.70 (d, J=4.1 Hz, 2H), 8.60 (s, 1H), 8.28 (d, J=6.6 Hz, 2H), 8.09 (d, J=16.5 Hz, 1H), 7.68 (d, J=16.5 Hz, 1H), 7.24 (m, 5H), 4.33 (m, 1H), 2.78 (m, 2H), 2.25 (m, 2H).

EXAMPLE 17

5-{[(2S)-2-amino-3-(1H-indol-3-yl)propyl]oxy}-N-pyridin-4-ylnicotinamide

Example 17A

5-{[(2S)-2-[(tert-butoxycarbonyl)amino]-3-(1H-indol-3-yl)propyl]oxy}nicotinic acid A solution of Example 2A (1.30 g, 3.02 mmol) and PdCl$_2$.dppf (123 mg) in THF/water (6.3 mL/6.3 mL) was heated to 100° C. under CO (800 psi) for 19 hours, cooled to room temperature, and diluted with water. The mixture was extracted with dichloromethane and the combined extracts were washed with water, dried (MgSO$_4$), filtered, and concentrated to provide the desired product (912 mg, 76%). MS (DCI/NH$_3$) m/e 396 (M+H)$^+$.

Example 17B tert-butyl (1S)-2-(1H-indol-3-yl)-1-[({5-[(pyridin-4-ylamino)carbonyl]pyridin-3-yl}oxy)methyl]ethylcarbamate A solution of Example 17A (410 mg, 1.0 mmol), 4-aminopyridine (100 mg, 1.0 mmol), EDC (960 mg), and HOBt (680 mg) in DMF (10 mL) was stirred at room temperature overnight, diluted with dichloromethane, washed with water, dried (MgSO$_4$), filtered, and concentrated. The residue was purified by flash column chromatography on silica gel with ethyl acetate/methanol (8:1) to provide the desired product (87 mg, 18%). MS (DCI/NH$_3$) m/e 488 (M+H)$^+$.

Example 17C

5-{[(2S)-2-amino-3-(1H-indol-3-yl)propyl]oxy}-N-pyridin-4-ylnicotinamide

The desired product was prepared as the hydrochloride salt by substituting Example 17B for Example 2B in Example 2C (27 mg, 31%). MS (DCI/NH$_3$) m/e 388 (M+H)$^+$; $^1$H NMR (DMSO-d$_6$) δ 11.32 (br s, 1H), 11.04 (br s, 1H), 8.83 (d, J=1.4 Hz, 1H), 8.69 (apparent d, J=6.8 Hz, 2H), 8.59 (d, J=2.7 Hz, 1H), 8.15 (br s, 2H), 8.08 (apparent d, J=6.8 Hz, 2H), 7.85 (dd, J=1.4, 2.7 Hz, 1H), 7.61 (d, J=7.8 Hz, 1H), 7.38 (d, J=8.12 Hz, 1H), 7.29 (d, J=2.7 Hz, 1H), 7.10 (m, 1H), 7.01 (m, 1H), 4.33 (m, 1H), 4.16 (m, 1H), 3.87 (m, 1H), 3.16 (m, 2H).

EXAMPLE 18

N-(aminoethyl)-5-[(E)-2-pyridin-4-ylvinyl]nicotinamide

Example 18A ethyl 5-[(E)-2-pyridin-4-ylvinyl]nicotinate

The desired product was prepared by substituting 3-bromo-5-ethoxycarbonylpyridine for Example 1A in Example 1B. MS (DCI/NH$_3$) m/e 355 (M+H)$^+$.

Example 18B

5-[(E)-2-pyridin-4-ylvinyl]nicotinic acid

A mixture of Example 18A (1.60 g, 6.3 mmol) and LiOH.H$_2$O (2.64 g) in THF/water (50 mL/50 mL) was stirred at room temperature for 2 hours. The THF was removed under vacuum and the aqueous layer was acidified with 1N HCl (aq.). The solid was collected by filtration and dried to provide the desired product. MS (DCI/NH$_3$) m/e 227 (M+H)$^+$.

Example 18C

N-(aminoethyl)-5-[(E)-2-pyridin-4-ylvinyl] nicotinamide

The desired product was prepared as the hydrochloride salt by substituting Example 18B and N-tert-butoxycarbonylaminoethylamine for Example 17A and 4-aminopyridine, respectively, in Examples 17B and 17C. MS (DCI/NH$_3$) m/e 384 (M+H)$^+$; $^1$HNMR (DMSO-d$_6$) δ 9.19 (t, J=5.4 Hz, 1H), 9.09 (d, J=1.7 Hz, 1H), 9.01 (d, J=2.0 Hz, 1H), 8.89 (d, J=6.5 Hz, 2H), 8.82 (dd, J=1.7, 2.0 Hz, 1H), 8.18 (d, J=6.5 Hz, 2H), 8.07 (d, J=16.6 Hz, 1H), 7.87 (d, J=16.6 Hz, 1H), 3.72 (br s, 2H), 3.59 (m, 2H), 3.05 (m, 2H).

EXAMPLE 19

N-[(2E)-3-(4-bromophenyl)prop-2-enyl]-N-[2-({5-[(E)-2-pyridin-4-ylvinyl]pyridin-3-yl}oxy)ethyl] amine

Example 19A (2E)-3-(4-bromophenyl)prop-2-en-1-ol

A solution of ethyl 4-bromocinnamide (5.430 g, 22.07 mmol) in toluene (20 mL) at −78° C. was treated over 10 minutes with DIBAL (1.5 M in toluene, 37.0 mL, 55.5 mmol), stirred for 30 minutes at −78° C., warmed to room temperature, stirred for 1 hour, quenched with 10% HCl (aq.), and extracted twice with diethyl ether. The combined extracts were washed with water and brine, dried (MgSO$_4$), filtered, and concentrated to provide the desired product (4.463 g, 95%). MS (DCI/NH$_3$) m/e 212, 214 (M+H)$^+$, 228, 230 (M+18)$^+$.

Example 19B 1-bromo-4-[(1E)-3-chloroprop-1-enyl]benzene

A mixture of Example 19A (2.0 g, 9.387 mmol) and SOCl$_2$ (3.5 mL, 47.9 mmol) in benzene (10 mL) was stirred at room temperature for 24 hours and concentrated to provide the desired product (2.167 g, 99%). (DCI/NH$_3$) m/e 231, 233, 235 (M+H)$^+$.

Example 19C 2-({5-[(E)-2-pyridin-4-ylvinyl]pyridin-3-yl}oxy) ethanamine

The desired product was prepared as the hydrochloride salt by substituting Example 9B and N-tert-butoxylcarbonylaminoethanol (200 mg, 1.00 mmol) for 3-bromo-5-hydroxypyridine and L-Boc-tryptophanol, respectively, in Examples 2A and 2C. MS (DCI/NH$_3$) m/e 242 (M+H)$^+$; $^1$H NMR (CD$_3$OD) δ 8.88 (d, J=6.1 Hz, 2H), 8.59 (s, 1H), 8.43 (s, 1H), 8.19 (d, J=6.1 Hz, 2H), 8.03 (d, J=16.3 Hz, 1H), 8.01 (s, 1H), 7.82 (d, J=16.3 Hz, 1H), 4.42 (t, J=4.9 Hz, 2H), 3.28 (m, 2H).

Example 19D

N-[(2E)-3-(4-bromophenyl)prop-2-enyl]-N-[2-({5-[(E)-2-pyridin-4-ylvinyl]pyridin-3-yl}oxy)ethyl] amine A solution of Example 19C (100 mg, 0.285 mmol), Example 19B (66.0 mg, 0.285 mmol), and triethylamine (250 µL, 1.79 mmol) in DMF (5 mL) at room temperature was stirred for 3 days, and poured into water. The aqueous layer was extracted three times with dichloromethane and the combined extracts were washed with water, dried (MgSO$_4$), filtered, and concentrated. The residue was chromatographed on silica gel with dichloromethane/methanol/NH$_4$OH (100:5:0.5) to provide the free base. The material was treated with 2M HCl/Et$_2$O to provide the hydrochloride salt (34.0 mg, 22%). MS (DCI/NH$_3$) m/e 436, 438 (M+H)$^+$; $^1$H NMR (CDCl$_3$) δ 8.61 (m, 2H), 8.37 (d, J=1.7 Hz, 1H), 8.27 (d, J=2.7 Hz, 1H), 7.37 (m, 4H), 7.26 (m, 5H), 7.25 (d, J=16.3 Hz, 1H), 7.05 (d, J=16.3 Hz, 1H), 6.53 (d, J=15.9 Hz, 1H), 6.31 (dt, J=6.1, 15.9 Hz, 1H), 4.23 (t, J=5.1 Hz, 2H), 3.53 (dd, J=1.1, 6.1 Hz, 1H), 3.13 (t, J=5.1 Hz, 1H).

EXAMPLE 20

N$^4$-(3-{[(2S)-2-amino-3-(1H-indol-3-yl)propyl] oxy}phenyl)pyrimidine-2,4-diamine

Example 20A tert-butyl (1S)-2-(1H-indol-3-yl)-1-[(3-nitrophenoxy)methyl]ethylcarbamate The desired product was prepared by substituting 3-nitrophenol for 3-bromo-5-hydroxypyridine in Example 2A (257 mg, 61%). MS (DCI/NH$_3$) m/e 412 (M+H)$^+$, 419 (M+18)$^+$.

Example 20B tert-butyl (1S)-2-(3-aminophenoxy)-1-(1H-indol-3-ylmethyl)ethylcarbamate A solution of Example 20A (247 mg, 0.600 mmol), ammonium formate (400 mg, 6.34 mmol) and 10% Pd/C (25 mg) in methanol (10 mL) was heated to reflux for 30 minutes, cooled to room temperature, filtered through diatomaceous earth (Celite®), and concentrated. The concentrate was purified by flash column chromatography on silica gel with ethyl acetate/hexanes (1:1) to provide the desired product (200 mg, 87%). MS (DCI/NH$_3$) m/e 382 (M+H)$^+$.

Example 20C tert-butyl (1S)-2-{3-[(2-aminopyrimidin-4-yl)amino] phenoxy}-1-(1H-indol-3-ylmethyl)ethylcarbamate A solution of Example 20B (41.2 mg, 0.108 mmol) and 2-amino-4-chloropyrimidine (14.0 mg, 0.108 mmol) in ethanol (0.5 mL) was heated to 80° C. for 13 hours and purified by flash column chromatography on silica gel with dichloromethane/methanol/NH$_4$OH (100:5:0.5) to provide the desired product (50 mg, 98%). MS (DCI/NH$_3$) m/e 475 (M+H)$^+$.

Example 20D

N$^4$-(3-{[(2S)-2-amino-3-(1H-indol-3-yl)propyl] oxy}phenyl)pyrimidine-2,4-diamine The desired product was prepared as the hydrochloride salt by substituting Example 20C for Example 2B in Example 2C (33 mg, 81%). MS (DCI/NH$_3$) m/e 375 (M+H)$^+$; $^1$H NMR (DMSO-d$_6$) δ 12.3 (br s, 1H), 10.8 (br s, 1H), 8.35 (br s, 4H), 7.85 (d, J=7.1 Hz, 1H), 7.61 (d, J=7.8 Hz, 1H), 7.45 (br s, 2H), 7.37 (d, J=7.8 Hz, 1H), 7.30 (m, 2H), 7.09 (m, 1H), 6.99 (m, 1H), 6.75 (m, 1H), 6.35 (m, 1H), 4.17 (dd, J=3.4, 10.5 Hz, 1H), 4.03 (dd, J=5.8, 10.5 Hz, 1H), 3.77 (m, 1H), 3.18 (d, J=7.5 Hz, 2H).

EXAMPLE 21

(1R)-3-{6-chloro-5-[(E)-2-pyridin-4-ylvinyl]pyridin-3-yl}-1-(1H-indol-3-ylmethyl)propylamine Example 21A 6-chloro-5-[(E)-2-pyridin-4-ylvinyl]pyridin-3-amine A solution of 3-amino-5-bromo-6-chloropyridine (2.0 g, 9.64 mmol), Pd$_2$(dba)$_3$ (440 mg, 0.48 mmol), tri-o-tolylphosphine (438 mg, 1.44 mmol), 4-vinylpyridine (2.08 mL, 19.28 mmol), and triethylamine (4.03 mL, 29 mmol) in DMF (30 mL) was stirred at 100° C. for 15 hours, cooled to room temperature, treated with ethyl acetate (200 mL), washed twice with brine, dried (MgSO$_4$), filtered and concentrated. The residual solid recrystallized from hexanes/dichloromethane to provide desired product (1.86 g, 84%). MS (APCI) m/e 232 (M+H)$^+$.

Example 21B 2-chloro-5-iodo-3-[(E)-2-pyridin-4-ylvinyl]pyridine

A solution of Example 21A (1.0 g, 4.3 mmol) in 30% H$_2$SO$_4$ (10 mL) at 0° C. was treated with NaNO$_2$ (386 mg, 5.6 mmol), stirred for 5 hours, treated with a solution of NaI (2.1 g, 14 mmol) in H$_2$O (2 mL), stirred for 2 hours, treated with additional NaI (2.1 g, 14 mmol), stirred for 2 hours, poured into 30% NaOH (aq.) (200 mL) at 0° C. and extracted three times with 10% methanol/ethyl acetate. The combined organic phases were dried (MgSO$_4$), filtered, and concentrated. The residual solid was purified by flash column chromatography on silica gel with 70% ethyl acetate/hexanes to provide the desired product (1.03 g, 70%). MS (DCI) m/e 343 (M+H)$^+$.

Example 21C tert-butyl (1S)-1-(1H-indol-3-ylmethyl)prop-2-enylcarbamate

A suspension of methyltriphenylphosphonium bromide (5.65 g, 15.81 mmol) in THF (50 mL) at 0° C. was treated with n-BuLi (2.5 M solution in hexane, 6.33 mL, 15.81 mmol), stirred for 10 minutes, warmed to room temperature, stirred for 30 minutes, cooled to 0° C., treated with a solution of L-Boc-tryptophanal (3.80 g, 13.2 mmol) in THF (10 mL), stirred for 2 hours, treated with diethyl ether (200 mL), washed with brine, dried (MgSO$_4$), filtered, and concentrated. The residual oil was purified by flash column chromatography on silica gel with 20% ethyl acetate/hexanes to provide the desired product (700 mg, 18%). MS (DCI) m/e 287 (M+H)$^+$.

Example 21D tert-butyl (1R)-3-{6-chloro-5-[(E)-2-pyridin-4-ylvinyl]pyridin-3-yl}-1-(1H-indol-3-ylmethyl)propylcarbamate A solution of Example 21C (100 mg, 0.35 mmol) in THF (3 mL) at 0° C. was treated with 9-BBN (0.5 M solution in THF, 0.70 mL, 0.35 mmol), stirred overnight while gradually warming to room temperature, cannulated into a mixture of Example 21B (108 mg, 0.32 mmol), PdCl$_2$ (dppf) (26 mg, 0.032 mmol) and Cs$_2$CO$_3$ (228 mg, 0.7 mmol) in DMF, purged with nitrogen, and stirred at 50° C. for 8 hours. The mixture was treated with ethyl acetate (50 mL), washed with brine, dried (MgSO$_4$), filtered, and concentrated. The residual oil was purified by flash column chromatography on silica gel with 80% ethyl acetate/hexanes to provide the desired product (69 mg, 40%).

Example 21E (1R)-3-{6-chloro-5-[(E)-2-pyridin-4-ylvinyl]pyridin-3-yl}-1-(1H-indol-3-ylmethyl)propylamine The desired product was prepared as the trifluoroacetate salt by substituting Example 21D for Example 2B in Example 2D. MS (APCI) m/e 403, 405 (M+H)$^+$; $^1$H NMR (300 MHz, CD$_3$OD) δ 8.78 (d, J=6.8 Hz, 2H), 8.19 (d, J=1.7 Hz, 1H), 8.18 (d, J=6.8 Hz, 2H), 7.97 (d, J=2.4 Hz, 1H), 7.93 (d, J=16.3 Hz, 1H), 7.48 (d, J=7.8 Hz, 1H), 7.34 (d, J=9.5 Hz, 1H), 7.33 (d, J=16.0 Hz, 1H), 7.20 (s, 1H), 7.11 (td, J=7.1, 1.0 Hz, 1H), 7.00 (td, J=6.8, 1.0 Hz, 1H), 3.55 (p, J=6.4 Hz, 1H), 3.16 (m, 2H), 2.82 (m, 2H), 2.06 (m, 2H); Anal. Calcd for C$_{24}$H$_{23}$ClN$_4$.2.8 TFA: C, 49.23; H, 3.60; N, 7.76. Found: C, 49.11; H, 3.64; N, 7.66.

EXAMPLE 22

4-(5-{[(2S)-2-amino-3-(1H-indol-3-yl)propyl]oxy}pyridin-3-yl)benzonitrile

Example 22A tert-butyl (1S)-2-{[5-(4-cyanophenyl)pyridin-3-yl]oxy}-1-(1H-indol-3-ylmethyl)ethylcarbamate A solution of Example 2A (250 mg, 0.56 mmol) in ethylene glycol dimethyl ether (20.0 mL) at room temperature was treated with tetrakis(triphenylphosphine)palladium (0) (32 mg, 0.03 mmol), stirred for 10 minutes, treated with a solution of (4-cyanophenyl)boronic acid (123 mg, 0.84 mmol) in ethanol (5.0 mL), stirred for 15 minutes, treated with 2M Na$_2$CO$_3$ (aq.) (1.4 mL), heated to reflux for 4 hours, cooled to room temperature, and concentrated. The concentrate was purified by flash column chromatography on silica gel with hexanes/ethyl acetate (1:1) to provide the desired product (230 mg, 88%). MS (DCI/NH$_3$) m/e 469 (M+H)$^+$.

Example 22B 4-(5-{[(2S)-2-amino-3-(1H-indol-3-yl)propyl]oxy}pyridin-3-yl)benzonitrile A solution of Example 22A (20 mg, 0.043 mmol) in dichloromethane (2.0 mL) at 0° C. was treated dropwise with trifluoroacetic acid (0.5 mL) and stirred for 2 hours while warming to room temperature. The reaction mixture was concentrated to provide the desired product as the trifluoroacetate salt (27 mg, 88%). MS (DCI/NH$_3$) m/e 369 (M+H)$^+$; $^1$H NMR (DMSO-d$_6$) δ 11.02 (s, 1H), 8.63 (d, J=1.9 Hz, 1H), 8.42 (d, J=2.8 Hz, 1H), 8.21 (br s, 2H), 7.99–7.92 (m, 4H), 7.73 (t, J=1.9 Hz, 1H), 7.61 (d, J=8.1 Hz, 1H), 7.38 (d, J=8.1 Hz, 1H), 7.29 (d, J=2.5 Hz, 1H), 7.10 (m, 1H), 7.01 (m, 1H), 4.36 (dd, J=10.6, 3.1 Hz, 1H), 4.19 (dd, J=10.9, 5.9 Hz, 1H), 3.89–3.82 (m, 1H), 3.16 (d, J=7.2 Hz, 2H).

EXAMPLE 23

N-[(2S)-2-amino-3-(1H-indol-3-yl)propyl]-N'-isoquinolin-5-ylpyridine-3,5-diamine Example 23A isoquinolin-5-yl trifluoromethanesulfonate A mixture of 5-hydroxyisoquinoline (1.6 g; 11.0 mmol) and triethylamine (1.38 g; 13.6 mmol) in dichloromethane (25 mL) at 0° C. was treated slowly with triflic anhydride (3.35 g; 12.1 mmol), stirred overnight while warming to room temperature, diluted with dichloromethane, washed twice with water and saturated NH$_4$Cl (aq.), once with water and brine, dried (Na$_2$SO$_4$), filtered, and concentrated. The concentrate was purified by flash column chromatography on silica gel with 7% ethyl acetate/dichloromethane to provide the desired product (1.54 g; 50%).

Example 23B 3-amino-5-bromopyridine

A solution of 3M NaOH (250 mL) at room temperature was treated with bromine (25.9 g, 162 mmol), stirred for 15 minutes, treated with 5-bromonicotinamide (25 g, 124 mmol), stirred for 45 minutes, heated to 85–100° C. for 3 hours, cooled to room temperature, adjusted to pH 1 with 10% HCl (aq.) washed twice with diethyl ether. The aqueous layer was adjusted to pH~10–11 with solid NaOH, and extracted four times with diethyl ether and twice with dichloromethane. The combined extracts were dried (MgSO$_4$), filtered, and concentrated to provide the desired product (13.3 g, 62%).

Example 23C

N-(5-bromopyridin-3-yl)isoquinolin-5-amine

A mixture Example 23A (500 mg, 1.8 mmol), Example 23B (600 mg, 3.5 mmol), Pd$_2$(dba)$_3$ (42 mg; 0.045 mmol), BINAP (56 mg; 0.09 mmol), and sodium tert-butoxide (350 mg; 3.6 mmol) in 10 mL toluene was heated to reflux for 2 hours, diluted with water, and extracted three times with ethyl acetate. The combined extracts were washed successively with saturated NaHCO$_3$, water, and brine, dried (Na$_2$SO$_4$), and concentrated. The concentrate was purified by flash column chromatography on silica gel with 3% methanol/dichloromethane to provide the desired product (97 mg, 18%).

Example 23D

N-(diphenylmethylene)-N'-isoquinolin-5-ylpyridine-3,5-diamine

A mixture of Example 23C (175 mg, 0.58 mmol), benzophenone imine (150 mg, 0.83 mmol), Pd$_2$(dba)$_3$ (54 mg, 0.06 mmol), BINAP (55 mg, 0.09 mmol), and sodium tert-butoxide (80 mg, 0.82 mmol) in 3 mL toluene was heated to 75–80° C. for 4 hours and concentrated. The concentrate was purified by flash column chromatography on silica gel with 3% methanol/dichloromethane to provide the desired product (150 mg, 64%).

Example 23E

N-isoquinolin-5-ylpyridine-3,5-diamine

A mixture of Example 23D (145 mg; 0.36 mmol) in 3 mL THF at room temperature was treated with 10 drops of water and 3 drops of conc. HCl, stirred for 2 hours, and concentrated. The residue was partitioned between ethyl acetate and concentrated NaHCO$_3$ (aq). The aqueous layer was extracted three times with ethyl acetate. The combined extracts were washed with brine, dried (MgSO$_4$), filtered, and concentrated. The concentrate was purified by flash column chromatography on silica gel with 10% methanol/dichloromethane to provide the desired product (59 mg, 68%).

Example 23F tert-butyl (1S)-2-(1H-indol-3-yl)-1-({[5-(isoquinolin-5-ylamino)pyridin-3-yl]amino}methyl) ethylcarbamate A mixture of Example 23E (55 mg, 0.23 mmol) and L-Boc-tryptophanal (84 mg, 0.29 mmol) in 2 mL dichloromethane at room temperature was treated with Ti(iPrO)$_4$ (1 mL), stirred for 2 hours, and concentrated. The residue was dissolved in 2 mL ethanol, treated with NaBH$_3$CN (30 mg; 0.46 mmol), stirred for 2 hours, diluted with water, and filtered. The filter cake was washed with methanol and the filtrate was concentrated. The residue was suspended in methanol/dichloromethane and filtered. The filtrate was concentrated and the concentrate was purified by flash column chromatography on silica gel with 5% methanol/dichloromethane to provide the desired product (28 mg, 24%).

Example 23G

N-[(2S)-2-amino-3-(1H-indol-3-yl)propyl]-N'-isoquinolin-5-ylpyridine-3,5-diamine A solution of Example 23F (26 mg, 0.05 mmol) in 2 mL dichloromethane at room temperature was treated with 0.5 mL TFA, stirred for 3 hours, and concentrated. The concentrate was purifed by reverse phase HPLC on a C18 column with 0–100% CH$_3$CN/H$_2$O/0.1% TFA and the residue was dissolved in water and lyophilized to provide the desired product as the trifluoroacetate salt (27 mg, 70%). MS (ESI(+)) m/e 409 (M+H)$^+$; $^1$H NMR (DMSO-d$_6$, 500 MHz) δ 11.02 (s, 1H), 9.44 (s, 1H), 9.07 (s, 1H), 8.57 (d, J=9 Hz, 1H), 7.95–8.01 (m, 2H), 7.88–7.93 (m, 2H), 7.68–7.73 (m, 3H), 7.57–7.59 (m, 1H), 7.53 (d, J=8 Hz, 1H), 7.38 (d, J=8 Hz, 1H), 7.24–7.27 (m, 1H),7.09 (t, J=9 Hz, 1H), 6.89 (t, J=9 Hz, 1H), 6.92 (s, 1H), 6.83 (br s, 1H), 3.33–3.40 (m, 1H), 3.00–3.14 (m, 4H); Anal. Calcd for C$_{25}$H$_{24}$N$_6$.3TFA.3H$_2$O: C, 46.28; H, 4.13; N, 10.44; F, 21.25. Found: C, 46.32; H, 3.54; N, 10.02; F, 21.58.

EXAMPLE 24

N-[(2S)-2-amino-3-(1H-indol-3-yl)propyl]-N-[5-(isoquinolin-5-yloxy)pyridin-3-yl]amine

Example 24A

5-[(5-bromopyridin-3-yl)oxy]isoquinoline

A sealed tube was charged with 5-hydroxyisoquinoline (0.15 g, 1.03 mmol), 3,5-dibromopyridine (0.24 g, 1.03 mmol), potassium carbonate (0.27 g, 2.0 mmol) and DMF (4 mL). The reaction was heated to 240° C. for 10 minutes in a personal chemistry microwave. The reaction was partitioned between water and ethyl acetate. The aqueous layer was extracted twice with ethyl acetate. The combined extracts were concentrated and the residue was purified by flash column chromatography on silica gel with 2:1 ethyl acetate/hexanes to provide the desired product (0.071 g, 23%).

Example 24B

N-[(2S)-2-amino-3-(1H-indol-3-yl)propyl]-N-[5-(isoquinolin-5-yloxy)pyridin-3-yl]amine The desired product was prepared by substituting Example 24A for Example 23C in Examples 23D then proceeding as described for Examples 23E, 23F, and 23G. MS (ESI) m/e 410 (M+H)+; $^1$H NMR (DMSO-$d_6$, 300 MHz) δ 11.00 (br s, 1H),9.47 (br s, 1H), 8.58 (d, J=8 Hz, 1H), 7.97–8.03 (m, 1H), 7.92–7.94 (m, 1H), 7.85–7.87 (m, 1H), 7.79–7.82 (m, 2H), 7.66–7.72 (m, 2H), 7.51–7.54 (m, 1H), 7.26–7.36 (m, 3H), 7.02–7.08 (m, 1H), 6.94–6.98 (m, 1H), 6.68–6.71 (m, 1H), 6.39 (br s, 1H), 3.73–3.80 (m, 1H), 3.43–3.52 (m, 2H), 3.16–3.19 (m, 2H); Anal. Calcd for $C_{25}H_{23}N_5O.3TFA$: C, 49.53; H, 3.46; N, 9.30; F, 22.76. Found: C, 49.44; H, 3.58; N, 9.14; F, 22.30.

EXAMPLE 25

(2S)-2-amino-3-(1H-indol-3-yl)-N-[5-(1,6-naphthyridin-2-yl)pyridin-3-yl]propanamide

Example 25A 2,2-dimethyl-N-pyridin-4-ylpropanamide

A mixture of 4-aminopyridine (10 g, 106 mmol) and pivaloyl chloride (12.9 g, 107 mmol) in 200 mL dichloromethane was cooled to 0° C. and treated slowly with triethylamine (10.9 g, 108 mmol), warmed to room temperature, stirred overnight, and diluted with water. The aqueous layer was extracted three times with dichloromethane and the combined extracts were washed with brine, dried ($Na_2SO_4$), filtered, and concentrated. The product was recrystallized from toluene to provide the desired product (14 g, 74%).

Example 25B

N-(3-formylpyridin-4-yl)-2,2-dimethylpropanamide

A mixture of Example 25A (11.4 g, 64 mmol) in 200 mL THF was cooled to −78° C., treated with 1.6 M nBuLi in hexanes (100 mL, 160 mmol), warmed to 0° C., stirred for 1 hour, treated with a solution of DMF (22 g, 215 mmol) in 100 mL THF, warmed to room temperature, stirred for 1 hour, diluted with brine, and extracted three times with ethyl acetate. The combined extracts were washed with water, washed twice with brine, dried ($MgSO_4$), filtered, and concentrated. The concentrate was purified by flash column chromatography on silica gel with 3% methanol/dichloromethane to provide the desired product (9.1 g, 69%).

Example 25C 4-aminonicotinaldehyde

A solution of Example 25B (870 mg, 4.2 mmol) in 3N HCl (aq.) (10 mL) was heated to reflux overnight, and extracted three times with diethyl ether. The aqueous layer was adjusted to pH >7 with solid $K_2CO_3$ and extracted six times with 20% isopropanol/chloroform. The combined extracts were dried ($Na_2SO_4$), filtered, and concentrated to provide the desired product (450 mg; 87%).

Example 25D 5-acetylnicotinamide

A mixture of 5-bromonicotinamide (2.5 g, 12.4 mmol), tributyl(1-ethoxyvinyl)tin (5.0 g, 13.8 mmol) and dichlorobis(triphenylphosphine)palladium(II) (800 mg, 1.1 mmol) in 25 mL toluene was heated to reflux for 3 hours. The mixture was cooled to room temperature, treated with 25 mL 2N HCl (aq.), and stirred for 1 hour. The aqueous layer was washed with ethyl acetate, adjusted to pH >7 with solid $K_2CO_3$, and extracted six times into 20% isopropanol/chloroform. The combined extracts were dried ($Na_2SO_4$), filtered, and concentrated to provide the desired product (1.6 g, 78%).

Example 25E 5-(1,6-naphthyridin-2-yl)nicotinamide

A mixture of Example 25C (450 mg, 3.68 mmol) and Example 25D (605 mg, 3.68 mmol) in 20 mL ethanol and 1.2 mL of 10% NaOH (aq) was heated to reflux for 3 hours and concentrated. The solid was collected and rinsed with ethyl acetate to provide the desired product (740 mg, 80%).

Example 25F 5-(1,6-naphthyridin-2-yl)pyridin-3-amine

The desired product was prepared by substituting Example 25E for 5-bromonicotinamide in Example 23B.

Example 25G tert-butyl (1S)-1-(1H-indol-3-ylmethyl)-2-{[5-(1,6-naphthyridin-2-yl)pyridin-3-yl]amino}-2-oxoethylcarbamate The desired product was prepared by substituting Example 25F (100 mg, 0.45 mmol) and L-Boc-tryptophan (150 mg, 0.49 mmol) for Example 11B and Boc-homophenylalanine, respectively, in Example 16A.

Example 25H (2S)-2-amino-3-(1H-indol-3-yl)-N-[5-(1,6-naphthyridin-2-yl)pyridin-3-yl]propanamide The desired product was prepared as the trifluoroacetate salt by substituting Example 25G for Example 2B in Example 2D. MS (ESI) m/e 409 (M+H)+; $^1$H NMR (DMSO-$d_6$, 500 MHz) δ 11.04 (br s, 1H), 10.91 (s, 1H), 9.50 (s, 1H), 9.23 (d, J=3 Hz, 1H), 8.95 (d, J=3 Hz, 1H), 8.77–8.83 (m, 3H), 8.42 (d, J=8 Hz, 1H), 8.28–8.32 (m, 2H), 7.97–8.00 (m, 1H), 7.65–7.69 (m, 1H), 7.37 (d, J=8 Hz, 1H), 7.26–7.28 (m, 1H), 7.06–7.11 (m, 1H), 6.96–7.01 (m, 1H), 4.18–4.25 (m, 1H), 3.25–3.45 (m, 2H); Anal. Calcd for $C_{24}H_{20}N_6O.3TFA.1H_2O$: C, 46.88; H, 3.28; N, 10.93; F, 22.25. Found: C, 47.19; H, 3.39; N, 11.14; F, 21.81.

EXAMPLE 26

N-[(2S)-2-amino-3-(1H-indol-3-yl)propyl]-N-[5-(1,6-naphthyridin-2-yl)pyridin-3-yl]amine The desired product was prepared as the trifluoroacetate salt by substituting Example 25F for Example 23E in Examples 23F and 23G. MS (ESI) m/e 395 (M+H)+; $^1$H NMR (DMSO-$d_6$, 500 MHz) δ 11.07 (br s, 1H), 9.51 (s, 1H), 8.74–8.83 (m, 3H), 8.27 (d, J=9 Hz, 1H), 8.18 (d, J=4 Hz, 1H), 7.93–7.97 (m, 4H), 7.60–7.64 (m, 1H), 7.39 (d, J=9 Hz, 1H), 7.34 (d, J=4 Hz, 1H), 7.06–7.12 (m, 1H), 6.96–7.02 (m, 1H), 6.78 (br s, 1H), 3.40–3.67 (m, 3H), 3.11–3.16 (m, 2H); Anal. Calcd for $C_{24}H_{22}N_6.3.25TFA$: C, 47.88; H, 3.33; N, 10.98; F, 24.21. Found: C, 47.51; H, 3.29; N, 10.94; F, 24.16.

EXAMPLE 27

(1S)-2-(1H-indol-3-yl)-1-{[(5-isoquinolin-6-ylpyridin-3-yl)oxy]methyl}ethylamine

Example 27A 6-(trimethylstannyl)isoquinoline

A solution of 6-bromoisoquinoline (0.35 g, 1.7 mmol) in DMA (6 mL) was treated with hexamethylditin (0.55 mL,

Example 27B tert-butyl (1S)-2-(1H-indol-3-yl)-1-{[(5-isoquinolin-6-ylpyridin-3-yl)oxy]methyl}ethylcarbamate A solution of Example 27A (0.25 g, 0.86 mmol) and Example 2A (0.444 g, 1.00 mmol) in 6 mL of DMF was treated with $Pd_2(dba)_3$ (0.08 g, 0.086 mmol), tri-o-tolylphosphine (0.02 g, 0.04 mmol), and triethylamine (0.15 mL, 1.0 mmol), heated to 75° C. in a sealed tube for 8 hours, and concentrated. The residue was purified by flash column chromatography on silica gel with 2.5% methanol/dichloromethane to provide the desired product (0.125 g, 30%).

Example 27C (1S)-2-(1H-indol-3-yl)-1-{[(5-isoquinolin-6-ylpyridin-3-yl)oxy]methyl}ethylamine A solution of Example 27B (0.125 g, 0.25 mmol) in dichloromethane (3 mL) at room temperature was treated with TFA (400 µL), stirred for 1 hour, and concentrated. The concentrate was azeotropically distilled with diethyl ether two times and the residue was purified by reverse phase HPLC on a C18 column with 0–100% $CH_3CN/H_2O/0.1\%$ TFA to provide the desired product as the di-trifluoroacetate salt (0.110 g, 70%). MS (ESI) m/e 395 (M+H)$^+$; $^1$H NMR (DMSO-$d_6$, 300 MHz) δ 11.02 (br s, 1H), 9.52 (s, 1H), 8.76 (d, J=3 Hz, 1H), 8.62 (d, J=8 Hz, 1H), 8.44–8.46 (m, 2H), 8.38 (d, J=9 Hz, 1H), 8.11–8.20 (m, 3H), 8.04–8.08 (m, 1H), 7.83–7.86 (m, 1H), 7.62 (d, J=9 Hz, 1H), 7.37–7.40 (m, 1H), 7.31 (d, J=3 Hz, 1H), 7.08–7.12 (m, 1H), 6.99–7.03 (m, 1H), 4.37–4.41 (m, 1H), 4.18–4.23 (m, 1H), 3.86–3.91 (m, 1H), 3.16–3.20 (m, 2H); Anal. Calcd for $C_{25}H_{22}N_4O.2TFA.H_2O$: C, 49.35; H, 3.61; N, 7.43; F, 22.67. Found: C, 49.04; H, 3.55; N, 7.42; F, 22.28.

EXAMPLE 28

(1R)-2-(1H-indol-3-yl)-1-{[(5-quinolin-6-ylpyridin-3-yl)oxy]methyl}ethylamine

Example 28A tert-butyl (1R)-2-[(5-hydroxypyridin-3-yl)oxy]-1-(1H-indol-3-ylmethyl)ethylcarbamate The desired product was prepared by substituting D-Boc-tryptophanol for L-Boc tryptophanol in Example 2A.

Example 28B (1R)-2-(1H-indol-3-yl)-1-{[(5-quinolin-6-ylpyridin-3-yl)oxy]methyl}ethylamine The desired product was prepared as the trifluoroacetate salt by substituting 28A for 2A in Example 27B then removing the Boc group as in Example 27C. MS (ESI) m/e 395 (M+H)$^+$; $^1$H NMR (DMSO-$d_6$, 500 MHz) δ 11.02 (s, 1H), 8.97–9.00 (m, 1H), 8.74 (d, J=3 Hz, 1H), 8.50–8.54 (m, 1H), 8.39–8.42 (m, 2H), 8.18–8.23 (m, 3H), 8.13–8.17 (m, 1H), 7.81–7.83 (m, 1H), 7.61–7.66 (m, 2H), 7.39 (d, J=8 Hz, 1H), 7.31 (d, J=3 Hz, 1H), 7.07–7.10 (m, 1H), 6.99–7.02 (m, 1H), 4.38–4.41 (m, 1H), 4.21–4.24 (m, 1H), 3.79–3.83 (m, 1H), 3.16–3.19 (m, 2H).

EXAMPLE 29

(1S)-2-[(6-chloro-5-isoquinolin-6-ylpyridin-3-yl)oxy]-1-(1H-indol-3-ylmethyl)ethylamine The desired product was prepared as the trifluoroacetate salt by substituting Example 13A for Example 2A in Example 27. MS (APCI) m/e 429, 431 (M+H)$^+$; $^1$H NMR (300 MHz, $CD_3OD$) δ 9.77 (s, 1H), 8.63 (d, J=6.4 Hz, 1H), 8.54 (d, J=8.8 Hz, 1H), 8.43 (d, J=6.4 Hz, 1H), 8.30 (s, 1H), 8.27 (d, J=3.1 Hz, 1H), 8.06 (dd, J=8.4, 1.7 Hz, 1H), 7.58 (s, 1H), 7.56 (d, J=5.4 Hz, 1H), 7.35 (d, J=8.1 Hz, 1H), 7.22 (s, 1H), 7.10 (td, J=7.1, 1.4 Hz, 1H), 7.00 (td, J=7.8, 1.0 Hz, 1H), 4.37 (dd, J=10.5, 3.4 Hz, 1H), 4.24 (dd, J=10.5, 5.8 Hz, 1H), 3.98 (m, 1H), 3.27 (m, 2H); Anal. Calcd for $C_{25}H_{21}ClN_4O.2.25TFA$: C, 51.69; H, 3.42; N, 8.17. Found: C, 51.75; H, 3.39; N, 8.13.

EXAMPLE 30

(1S)-2-[(2-chloro-5-isoquinolin-6-ylpyridin-3-yl)oxy]-1-(1H-indol-3-ylmethyl)ethylamine The desired product was prepared as the trifluoracetate salt by substituting Example 12C for Example 2A in Example 27 (0.02 g, 80%). MS (DCI/$NH_3$) m/e 429, 431 (M+H)$^+$; $^1$H NMR (DMSO-$d_6$) δ 11.04 (s, 1H), 9.50 (s, 1H), 8.62 (d, J=6.0 Hz, 1H), 8.57 (s, 1H), 8.44 (s, 1H), 8.35 (d, J=9.0 Hz, 1H), 8.22 (s, 2H), 8.13 (d, J=9.0 Hz, 1H), 8.00 (d, J=6.0 Hz, 1H), 7.98 (s, 1H), 7.64 (d, J=7.5 Hz, 1H), 7.38 (d, J=7.5 Hz, 1H), 7.30 (s, 1H), 7.10 (t, J=7.2 Hz, 1H), 7.00 (t, J=7.2 Hz, 1H), 4.46 (m, 1H), 4.30 (m, 1H), 3.92 (m, 1H), 3.21 (m, 2H).

EXAMPLE 31

(1R)-1-(1H-indol-3-ylmethyl)-3-(5-isoquinolin-6-ylpyridin-3-yl)propylamine

Example 31A 6-(5-bromopyridin-3-yl)isoquinoline

A solution of 3,5-dibromopyridine (284 mg, 1.2 mmol), $Pd_2(dba)_3$ (110 mg, 0.12 mmol) and tri-o-tolylphosphine (110 mg, 0.36 mmol) in DMF (15 mL) was treated with Example 27A (500 mg, 1.2 mmol) and triethylamine (500 µL, 3.6 mmol), purged with nitrogen, heated to 70° C. for 6 hours, cooled to room temperature, treated with ethyl acetate (100 mL), washed with brine, dried ($MgSO_4$), filtered, and concentrated. The residual oil was purified by flash column chromatography on silica gel with ethyl acetate to provide the desired product (110 mg, 32%). MS (APCI) m/e 285, 287 (M+H)$^+$.

Example 31B (1R)-1-(1H-indol-3-ylmethyl)-3-(5-isoquinolin-6-ylpyridin-3-yl)propylamine The desired product was prepared as the trifluoroacetate salt by substituting Example 31A for Example 21B in Example 21D then removing the Boc protecting group as described for Example 21E. MS (DCI/$NH_3$) m/e 458 (M+H)$^+$; $^1$H NMR ($CD_3OD$) δ 9.78 (s, 1H), 8.97 (d, J=1.1 Hz, 1H), 8.64 (d, J=6.4 Hz, 1H), 8.61 (d, J=8.9 Hz, 1H), 8.55

(s, 1H), 8.53 (s, 1H), 8.47 (d, J=6.5 Hz, 1H), 8.25 (dd, J-8.4, 1.7 Hz, 1H), 8.23 (s, 1H), 7.49 (d, J=7.9 Hz, 1H), 7.30 (d, J=8.2 Hz, 1H), 7.22 (s, 1H), 7.06 (td, J=7.1, 1.0 Hz, 1H), 6.97 (td, J=7.1, 1.0 Hz, 1H), 3.59 (p, J=6.5 Hz, 1H), 3.18 (dd, J=7.1, 3.4 Hz, 2H), 2.99 (m, 2H), 2.15 (m, 2H).

EXAMPLE 32

5-(5-{[(2S)-2-amino-3-(1H-indol-3-yl)propyl] oxy}pyridin-3-yl)-1H-isoindole-1,3(2H)-dione

Example 32A tert-butyl (1S)-2-(1H-indol-3-yl)-1-({[5-(trimethylstannyl)pyridin-3-yl]oxy}methyl) ethylcarbamate A solution of Example 2A (1 g, 2.23 mmol) in DMA (15 mL) was treated with hexamethylditin (1.8 mL, 5.6 mmol) and Pd(PPh$_3$)$_4$ (0.4 g, 0.2 mmol), heated to 75° C. for 1.5 days, added to water, and extracted three times with ethyl acetate. The combined extracts were concentrated and the residue was purified by flash column chromatography on silica gel with 1:1 hexanes/ethyl acetate to provide the desired product (0.4 g, 34%).

Example 32B tert-butyl (1S)-2-{[5-(1,3-dioxo-2,3-dihydro-1H-isoindol-5-yl)pyridin-3-yl]oxy}-1-(1H-indol-3-ylmethyl)ethylcarbamate A solution of Example 32A (0.2 g, 0.31 mmol) and 6-bromophthalimide (0.084 g, 0.4 mmol) in DMF (2 mL) was treated with Pd$_2$dba$_3$ (0.04 g, 0.02 mmol), tri-o-tolylphosphine (0.02 g, 0.01 mmol), and triethylamine (0.06 mL, 0.4 mmol). The reaction was heated to 75° C. for 6 hours in a sealed tube and concentrated. The residue was purified by flash column chromatography on silica gel with 1:1 hexanes/ethyl acetate to provide the desired product (0.116 g, 55%).

Example 32C 5-(5-{[(2S)-2-amino-3-(1H-indol-3-yl)propyl] oxy}pyridin-3-yl)-1H-isoindole-1,3(2H)-dione The desired product was prepared as the trifluoracetate salt by substituting Example 32B for Example 27B in Example 27C. MS (ESI) m/e 413 (M+H)$^+$; $^1$H NMR (DMSO-d$_6$, 300 MHz) δ 11.43 (s, 1H), 11.02 (br s, 1H), 8.67 (d, J=3 Hz, 1H), 8.42 (d, J=6 Hz, 1H), 8.14–8.18 (m, 4H), 7.92–7.96 (m, 1H), 7.79–7.81 (m, 1H), 7.61 (d, J=9 Hz, 1H), 7.38 (d, J=9 Hz, 1H), 7.30 (d, J=3 Hz, 1H), 7.08–7.12 (m, 1H), 6.98–7.03 (m, 1H), 4.35–4.40 (m, 1H), 4.17–4.22 (m, 1H), 3.83–3.88 (m, 1H), 3.13–3.17 (m, 2H). Anal. Calcd for C$_{24}$H$_{20}$N$_4$O$_3$.2.1TFA: C, 51.96; H, 3.42; N, 8.59; F, 18.30. Found: C, 51.45; H, 3.46; N, 8.56; F, 17.47.

EXAMPLE 33

5-(5-{[(2S)-2-amino-3-(1H-indol-3-yl)propyl] oxy}pyridin-3-yl)isoindolin-1-one

Example 33A methyl 4-bromo-2-methylbenzoate

A solution of 4-bromo-2-methyl benzoic acid (1.0 g, 4.7 mmol) in methanol (24 mL) was treated with 20 drops of HCl, heated at reflux for 6 hours, and concentrated to provide the desired product (1.07 g, 100%).

Example 33B methyl 4-bromo-2-(bromomethyl)benzoate

A solution of Example 33A (1.02 g, 4.47 mmol) in CCl$_4$ (22 mL) was treated with AIBN (0.065 g, 0.4 mmol) and NBS (0.955 g, 5.4 mmol), heated to reflux for 4 hours, washed with water, dried (Na$_2$SO$_4$), filtered, and concentrated to provide the desired product (1.1 g, 79%).

Example 33C 5-bromoisoindolin-1-one

A solution of Example 33B (1.1 g, 3.57 mmol) in THF (20 mL) at room temperature was treated with 1N NH$_3$ in methanol (7.14 mL, 7.14 mmol), stirred for 24 hours, and filtered. The filter cake was washed with diethyl ether (100 mL) to provide the desired product (0.4 g, 52%).

Example 33D 5-(5-{[(2S)-2-amino-3-(1H-indol-3-yl)propyl] oxy}pyridin-3-yl)isoindolin-1-one The desired product was prepared as the trifluoroacetate salt by substituitng Example 33C for 6-bromophthalimide in Example 32. MS (ESI) m/e 399 (M+H)$^+$; $^1$H NMR (DMSO-d$_6$, 300 MHz) δ 11.03 (br s, 1H), 8.63 (s, 1H), 8.57 (s, 1H), 8.35 (br s, 3H), 7.90 (s, 1H), 7.78 (s, 2H), 7.67 (s, 1H), 7.61 (d, J=8 Hz, 1H), 7.37 (d, J=8 Hz, 1H), 7.79 (d, J=2 Hz, 1H), 7.03–7.10 (m, 1H), 6.96–7.01 (m, 1H), 4.32–4.36 (m, 1H), 4.17–4.22 (m, 1H), 3.80–3.83 (m, 1H), 3.18 (d, J=8 Hz, 2H), 2.50 (s, 2H).

EXAMPLE 34

(1S)-2-[(5-cinnolin-6-ylpyridin-3-yl)oxy]-1-(1H-indol-3-ylmethyl)ethylamine

Example 34A

N-(2-acetylphenyl)acetamide

A solution of 2'-aminoacetophenone (5.0 g, 37 mmol) in dichloromethane (150 mL) at room temperature was treated with triethylamine (5.3 mL, 40 mmol) and acetyl chloride (3.2 mL, 45 mmol), stirred for 3 hours, then washed with water. The aqueous layer was extracted with ethyl acetate (2×20 mL) and the combined extracts were concentrated to provide the desired product (6.5 g, 100%).

Example 34B

N-(2-acetyl-4-bromophenyl)acetamide

A solution Example 34A (6.5 g, 37 mmol) in acetic acid (100 mL) at room temperature was treated with Br$_2$ (4 mL, 84 mmol), stirred for 1 hour and 15 minutes, poured into water (200 mL), and filtered. The solid was washed with water (2×100 mL), and hexanes (2×100 mL), dissolved in diethyl ether, washed with brine (50 mL), and concentrated to provide the desired product (8.5 g, 89%).

Example 34C 6-bromocinnolin-4(1H)-one

A solution of Example 34B (6.28 g, 24.4 mmol) in THF (75 mL) was treated with concentrated HCl (aq.) (15 mL)

and water (15 mL), heated to reflux for 1 hour, and concentrated to remove the THF. The aqueous solution was treated with additional water (5 mL) and concentrated HCl (5 mL), cooled to 0° C., treated with a solution of $NaNO_2$ (1.85 g, 26.84 mmol) in water (10 mL) in 5 portions, warmed to room temperature gradually over a 2-hour period, and stirred overnight at room temperature. The reaction was heated to reflux for 6 hours, and filtered. The solid was washed with water (50 mL) and diethyl ether (50 mL) and dried under vacuum to provide the desired product (3.0 g, 54%).

Example 34D 6-bromo-4-chlorocinnoline

A solution of Example 34C (0.4 g, 1.8 mmol) in $POCl_3$ (2.5 mL) was heated to 100° C. for 2 hours, and poured slowly onto ice. The aqueous layer was cooled to 0° C. and adjusted to pH 5–7 with 50% NaOH. The aqueous layer was extracted with ethyl acetate (2×50 mL), and the combined organic layers were concentrated. The residue was purified by flash column chromatography on silica gel with 4:1 hexanes/ethyl acetate to provide the desired product (0.190 g, 43%).

Example 34E 6-bromo-4-hydrazinocinnoline

A solution of Example 34D (2.6 g, 10.6 mmol) in ethanol (70 mL) was treated with hydrazine monohydrate (3 mL, 90% solution), stirred at room temperature for 3 days, and filtered. The solid washed with water (50 mL) and diethyl ether (50 mL) and dried under vacuum to provide the desired product (2.5 g, 100%).

Example 34F 6-bromocinnoline

A solution of Example 34E (3.5 g, 14 mmol) in water (50 mL) was heated to reflux, treated dropwise with a solution of $CuSO_4$ (2.8 g, 17.5 mmol) in water (20 mL), refluxed for 2 hours, cooled to room temperature, adjusted to pH 7 with saturated $NaHCO_3$ (aq), and extracted with ethyl acetate (2×25 mL). The combined extracts were concentrated and the residue was purified by flash column chromatography on silica gel with 1:1 hexanes/ethyl acetate to provide the desired product (0.7 g, 24%).

Example 34G (1S)-2-[(5-cinnolin-6-ylpyridin-3-yl)oxy]-1-(1H-indol-3-ylmethyl)ethylamine The desired product was prepared as the trifluoroacetate salt by substituting Example 34F for 6-bromophthalimide in Example 32. MS (ESI) m/e 396 (M+H)+; $^1$H NMR (DMSO-$d_6$, 300 MHz) δ 11.04 (s, 1H), 9.43 (d, J=6 Hz, 1H), 8.78 (d, J=2 Hz, 1H), 8.60 (d, J=8 Hz, 1H), 8.45–8.49 (m, 2H), 8.30–8.34 (m, 1H), 8.26 (d, J=6 Hz, 1H), 8.21–8.25 (m, 2H), 7.89 (t, J=2 Hz, 1H), 7.63 (d, J=8 Hz, 1H), 7.39 (d, J=8 Hz, 1H), 7.31 (d, J=2 Hz, 1H), 7.08–7.12 (m, 1H), 7.01–7.04 (m, 1H), 4.38–4.42 (m, 1H), 4.22–4.26 (m, 1H), 3.83–3.88 (m, 1H), 3.17–3.20 (m, 2H).

EXAMPLE 35

(1S)-2-{[5-(1H-indazol-5-yl)pyridin-3-yl]oxy}-1-(1H-indol-3-ylmethyl)ethylamine

Example 35A 5-bromo-1H-indazole

A mixture of 5-bromo-2-fluorobenzaldehyde (10 g, 49.2 mmol) and 98% hydrazine (20 mL) was heated to reflux for 5 hours, poured over ice, and filtered. The solid was recrystallized from $H_2O$/methanol to provide the desired product (3.7 g, 38%).

Example 35B (1S)-2-{[5-(1H-indazol-5-yl)pyridin-3-yl]oxy}-1-(1H-indol-3-ylmethyl)ethylamine The desired product was prepared as the trifluoroacetate salt by substituting Example 35A for 6-bromophthalimide in Example 32. MS (ESI) m/e 384 (M+H)+; $^1$H NMR (DMSO-$d_6$, 300 MHz) δ 13.22 (br s, 1H), 11.04 (br s, 1H), 8.62 (d, J=2 Hz, 1H), 8.33 (d, J=3 Hz, 1H), 8.13–8.21 (m, 3H), 8.12 (s, 1H), 7.67–7.72 (m, 3H), 7.64 (d, J=8 Hz, 1H), 7.39 (d, J=8 Hz, 1H), 7.30 (d, J=2 Hz, 1H), 7.06–7.13 (m, 1H), 6.98–7.04 (m, 1H), 4.14–4.39 (m, 2H), 3.33–3.38 (m, 1H), 3.13–3.16 (m, 2H); Anal. Calcd for $C_{23}H_{21}N_5O.2TFA.H_2O$: C, 51.52; H, 4.00; N, 11.13. Found: C, 51.80; H, 3.61; N, 11.03.

EXAMPLE 36

5-(5-{[(2S)-2-amino-3-(1H-indol-3-yl)propyl]oxy}pyridin-3-yl)-1,3-dihydro-2H-indol-2-one The desired product was prepared as the trifluoroacetate salt by substituting 5-bromooxindole for 6-bromophthalimide in Example 32. MS (APCI) m/e 399 (M+H)+; $^1$H NMR (300 MHz, $CD_3OD$) δ 8.59 (s, 1H), 8.35 (s, 1H), 7.92 (s, 1H), 7.60 (d, J=6.9 Hz, 1H), 7.58 (s, 1H), 7.55 (d, J=10.1 Hz, 1H), 7.38 (d, J=8.1 Hz, 1H), 7.24 (s, 1H), 7.13 (t, J=7.6 Hz, 1H), 7.03 (d, J=8.0 Hz, 1H), 7.03 (t, J=7.5 Hz, 1H), 4.45 (dd, J=10.5, 3.2 Hz, 1H), 4.31 (dd, J=10.5, 5.8 Hz, 1H), 4.01 (m, 1H), 3.62 (s, 2H), 3.32 (m, 1H), 3.29 (m, 1H); Anal. Calcd for $C_{24}H_{22}N_4O_2.2.5$ TFA: C, 50.96; H, 3.61; N, 8.20. Found: C, 50.96; H, 3.62; N, 8.12.

EXAMPLE 37

(1S)-2-{[5-(2,1,3-benzoxadiazol-5-yl)pyridin-3-yl]oxy}-1-(1H-indol-3-ylmethyl)ethylamine The desired product was prepared as the trifluoroacetate salt by substituting 5-chloro-2,1,3-benzoxadiazole for 6-bromophthalimide in Example 32. MS (APCI) m/e 386 (M+H)+; $^1$H NMR (300 MHz, $CD_3OD$) δ 8.64 (s, 1H), 8.44 (s, 1H), 8.18 (s, 1H), 8.05 (d, J=10.4 Hz, 1H), 7.81 (d, J=10.9 Hz, 1H), 7.78 (s, 1H), 7.59 (d, J=6.7 Hz, 1H), 7.37 (d, J=7.1 Hz, 1H), 7.24 (s, 1H), 7.12 (t, J=8.1 Hz, 1H), 7.03 (t, J=6.9 Hz, 1H), 4.44 (dd, J=10.5, 3.1 Hz, 1H), 4.29 (dd, J=10.6, 5.8 Hz, 1H), 3.99 (m, 1H), 3.32 (s, 1H), 3.30 (s, 1H); Anal. Calcd for $C_{22}H_{19}N_5O_2.2.45$ TFA: C, 48.60; H, 3.25; N, 10.53. Found: C, 48.68; H, 3.48; N, 10.58.

EXAMPLE 38

(1S)-2-(1H-indol-3-yl)-1-{[(5-thieno[2,3-c]pyridin-2-ylpyridin-3-yl)oxy]methyl}ethylamine Example 38A 2-(trimethylstannyl)thieno[2,3-c]pyridine A solution of thieno[2,3-c]pyridine (J. Wikel, et al., J. Heterocycl. Chem., 1993, 30, 289) (2.0 g, 14.8 mmol) in THF (50 mL) at −78° C. was treated with n-butyllithium (2.5 M solution in hexane, 7.1 mL, 17.8 mmol), warmed to 0° C., stirred for 15 minutes, cooled to −78° C., treated slowly with trimethyltin chloride (3.54 g, 17.8 mmol) in THF (10 mL), warmed to room temperature for 2 hours, and partitioned between ethyl acetate and brine. The ethyl acetate solution was washed with water, and concentrated. The residue was purified by flash chromatography (10–35% ethyl acetate in hexane) to provide the desired product (3.15 g, 71%). MS (APCI) m/e 298 (M+H)+.

Example 38B (1S)-2-(1H-indol-3-yl)-1-{[(5-thieno[2,3-c]pyridin-2-ylpyridin-3-yl)oxy]methyl}ethylamine The desired product was prepared as the trifluoroacetate by substituting Example 38A for Example 27A in Examples 27B and 27C. MS (APCI) m/e 402 (M+H)+; $^1$H NMR (300 MHz, CD$_3$OD) δ 9.58 (s, 1H), 8.78 (s, 1H), 8.63 (d, J=6.4 Hz, 1H), 8.49 (s, 1H), 8.36 (d, J=6.4 Hz, 1H), 8.20 (s, 1H), 7.86 (s, 1H), 7.60 (d, J=8.6 Hz, 1H), 7.38 (d, J=8.1 Hz, 1H), 7.25 (s, 1H), 7.12 (t, J=8.1 Hz, 1H), 7.03 (t, J=7.5 Hz, 1H), 4.45 (dd, J=10.6, 3.2 Hz, 1H), 4.30 (dd, J=10.5, 5.7 Hz, 1H), 4.02 (m, 1H), 3.32 (s, 1H), 3.30 (s, 1H); Anal. Calcd for C$_{23}$H$_{20}$N$_4$OS.3.6 TFA: C, 44.73; H, 2.93; N, 6.91. Found: C, 44.74; H, 2.91; N, 6.77.

EXAMPLE 39

(3Z)-5-(5-{[(2S)-2-amino-3-(1H-indol-3-yl)propyl]oxy}pyridin-3-yl)-3-(1H-pyrrol-2-ylmethylene)-1,3-dihydro-2H-indol-2-one The desired product was prepared by as the trifluoroacetate salt substituting 5-bromo-3-(1H-pyrrol-2-ylmethylene)-1,3-dihydro-indol-2-one for 6-bromophthalimide (L. Sun, et al., J. Med. Chem., 1998, 41, 2588.) in Example 32. MS (APCI) m/e 476 (M+H)+; $^1$H NMR (400 MHz, DMSO-d$_6$) δ 13.33 (br s, 1H), 11.05 (s, 1H), 11.04 (d, J=6.5 Hz, 1H), 8.64 (s, 1H), 8.34 (s, 1H), 8.22 (br s, 2H), 8.09.(s, 1H), 7.91 (s, 1H), 7.74 (br s, 1H), 7.62 (d, J=7.7 Hz, 1H), 7.51 (dd, J=8.3 Hz, 1H), 7.40 (s, 1H), 7.38 (d, J=8.3 Hz, 1H), 7.30 (d, J=2.2 Hz, 1H), 7.1 (dd, J=7.9 Hz, 1H), 7.01 (d, J=7.7 Hz, 1H), 7.00 (d, J=8.0 Hz, 1H), 6.85 (br s, 1H), 6.39 (s, 1H), 4.37 (dd, J=12.00, 3.1 Hz, 1H), 4.20 (dd, J=8.00, 6.0 Hz, 1H), 3.15–3.21 (m, 1H); Anal. Calcd for C$_{29}$H$_{25}$N$_5$O$_2$.2.6TFA: C, 53.21; H, 3.60; N, 9.07. Found: C, 53.36; H, 3.67; N, 8.92.

EXAMPLE 40

6-(5-{[(2R)-2-amino-3-(1H-indol-3-yl)propyl]oxy}pyridin-3-yl)-1,3-benzothiazol-2(3H)-one The desired product was prepared by substituting 6-bromo-2-benzothiazolinone for 6-bromophthalimide in Example 32. MS (APCI) m/e 417 (M+H)+; $^1$H NMR (300 MHz, CD$_3$OD) δ 8.52 (s, 1H), 8.31 (d, J=2.4 Hz, 1H), 7.77 (d, J=1.7 Hz, 1H), 7.71 (t, J=1.7 Hz, 1H), 7.59 (d, J=7.8 Hz, 1H), 7.56 (dd, J=6.0, 1.7 Hz, 1H), 7.39 (d, J=8.2 Hz, 1H), 7.25 (d, J=8.2 Hz, 1H), 7.23 (s, 1H), 7.14 (t, J=7.2 Hz, 1H), 7.03 (t, J=7.2 Hz, 1H), 4.41 (dd, J=12.0, 3.4 Hz, 1H), 4.26 (dd, J=9.0, 5.7 Hz, 1H), 3.97–4.02 (m, 1H); Anal. Calcd for C$_{23}$H$_{20}$N$_4$O$_2$.1.9 TFA: C, 50.84; H, 3.49; N, 8.85. Found: C, 51.22; H, 3.67; N, 8.49.

EXAMPLE 41

2-(1H-indol-3-yl)-2-(5-isoquinolin-6-ylpyridin-3-yl)ethanamine

Example 41A tert-butyl 3-(cyanomethyl)-1H-indole-1-carboxylate

A solution of 3-cyanomethylindole (7.50 g, 48 mmol), di-tert-butyl dicarbonate (11.5 g, 52.8 mmol), and DMAP (300 mg) in dichloromethane (200 mL) was stirred at room temperature overnight. The mixture was concentrated and the residue was purified by flash column chromatography on silica gel with dichloromethane to provide the desired product (11.44 g, 93%). MS (DCI/NH$_3$) m/e 257 (M+H)+.

Example 41B tert-butyl 3-[(5-bromopyridin-3-yl)(cyano)methyl]-1H-indole-1-carboxylate A solution of Example 41A (5.46 g, 21.3 mmol) and 3,5-dibromopyridine (5.03 g, 21.3 mmol) in DMF (25 mL) at room temperature was treated with NaH (60% in mineral oil, 1.08 g, 25.6 mmol) in several portions. The reaction was stirred at room temperature for 20 minutes, heated to 60° C. for 2 hours, and poured into water. The aqueous layer was extracted with diethyl ether and the combined extracts were washed with water, dried (MgSO$_4$), filtered, and concentrated. The residue was purified by flash column chromatography on silica gel with ethyl acetate/hexanes (1:7) to provide the desired product (336 mg, 4%). MS (DCI/NH$_3$) m/e 413 (M+H)+.

Example 41C tert-butyl 3-[cyano(5-isoquinolin-6-ylpyridin-3-yl)methyl]-1H-indole-1-carboxylate The desired product was prepared by substituting Example 41B for Example 2A in Example 27B. MS (DCI/NH$_3$) m/e 461 (M+H)+.

Example 41D 2-(1H-indol-3-yl)-2-(5-isoquinolin-6-ylpyridin-3-yl)ethanamine

A mixture of Example 41C (159 mg, 0.345 mmol), RaNi 2800 (525 mg), ammonia (2 mL), and triethylamine (2 mL) in methanol (20 mL) was stirred under hydrogen (60 psi) at room temperature for 73 hours and concentrated. The residue was triturated with ethyl acetate and methanol. The resulting solid was dissolved in trifluoroacetic acid (1 mL), stirred for 5 minutes at room temperature, and concentrated. The residue was purified by HPLC on a C18 column with 0–100% CH$_3$CN/H$_2$O/0.1% TFA to provide the desired product as the trifluoroacetate salt (64 mg, 26%). MS (DCI/NH$_3$) m/e 365 (M+H)+; $^1$H NMR (CD$_3$OD) δ 9.80 (s, 1H), 9.12 (br s, 1H), 8.87 (br s, 1H), 8.68 (s, 1H), 8.64 (m, 3H), 8.51 (d, J=6.6 Hz, 1H), 8.35 (dd, J=1.6, 8.4 Hz, 1H), 7.52 (d, J=8.1 Hz, 1H), 7.50 (s, 1H), 7.42 (d, J=8.4 Hz, 1H), 7.15 (m, 1H), 7.03 (m, 1H), 4.95 (t, J=7.8 Hz, 1H), 3.91 (m, 2H).

EXAMPLE 42

2-(1H-indol-3-yl)-3-(5-isoquinolin-6-ylpyridin-3-yl)propan-1-amine

Example 42A (2Z)-3-(5-bromopyridin-3-yl)-2-(1H-indol-3-yl)acrylonitrile

A solution of 3-cyanomethylindole (156 mg, 1.0 mmol) in anhydrous ethanol (1.5 mL) at room temperature was treated with 21% sodium ethoxide in ethanol (450 μL), stirred for 1 hour, treated with 3-bromopyridine-5-carboxaldehyde (J. Heterocycl. Chem., 1995, 32, 1801.) (187 mg, 1.0 mmol), stirred overnight, and concentrated. The residue was purified by flash column chromatography on silica gel with 2% methanol/dichloromethane to provide the desired product (52 mg, 16%). MS (DCI/NH$_3$) m/e 325 (M+H)$^+$.

Example 42B 2-(1H-indol-3-yl)-3-(5-isoquinolin-6-ylpyridin-3-yl) propan-1-amine

The desired product was prepared as the trifluoroacetate salt by substituting Example 42A for Example 41B in Examples 41C and 41D. MS (DCI/NH$_3$) m/e 379 (M+H)$^+$; $^1$H NMR (CD$_3$OD) δ 9.70 (s, 1H), 8.88 (s, 1H), 8.61 (d, J=6.6 Hz, 1H), 8.47 (m, 2H), 8.86 (d, J=6.6 Hz, 1H), 8.03 (s, 1H), 7.86 (s, 1H), 7.83 (dd, J=1.6, 8.4 Hz, 1H), 7.54 (d, J=7.8 Hz, 1H), 7.45 (d, J=8.1 Hz, 1H), 7.21 (s, 1H), 7.17 (m, 1H), 7.04 (m, 1H), 8.82 (m 1H), 3.61 (m, 2H), 3,36 (dd, J=4.1, 13.4 Hz, 1H), 3.30 (m, 1H).

EXAMPLE 43

(1S)-2-(1H-indol-3-yl)-1-{[(6-pyridin-4-ylquinolin-3-yl)oxy]methyl}ethylamine

Example 43A 6-bromo-3-hydroxyquinoline-4-carboxylic acid

A solution of 5-bromoisatin (2.26 g, 10 mmol) and potassium hydroxide (4.48 g, 80 mmol) in water (10 mL) was warmed until the materials were dissolved then cooled to room temperature, treated with bromopyruvic acid (2.3 g, 14 mmol), stirred for 6 days, adjusted to pH <7 with concentrated HCl, and filtered. The solid was washed with water and ethanol and dried to provide the desired product (1.5 g, 58%). MS (DCI/NH$_3$) m/e 269 (M+H)$^+$.

Example 43B 6-bromo3-hydroxyquinoline

A solution of Example 43A (1.5 g, 5.6 mmol) in nitrobenzene (10 mL) was refluxed for 5 minutes, filtered, cooled to room temperature and filtered again. The solid was washed with hexanes and dried to provide the desired product (0.68 g, 55%). MS (DCI/NH$_3$) m/e 225 (M+H)$^+$.

Example 43C tert-butyl (1S)-2-[(6-bromoquinolin-3-yl)oxy]-1-(1H-indol-3-ylmethyl)ethylcarbamate The desired product was prepared by substituting Example 43B for 3-bromo-5-hydroxypyridine in Example 2A. Purification by flash column chromatography on silica gel with 100% ethyl acetate provided the desired product (0.89 g, 72%). MS (DCI/NH$_3$) m/e 497 (M+H)$^+$.

Example 43D tert-butyl (1S)-2-(1H-indol-3-yl)-1-{[(6-pyridin-4-ylquinolin-3-yl)oxy]methyl}ethylcarbamate A mixture of Example 43C (0.33 g, 0.67 mmol), pyridine-4-boronic acid (0.13 g, 0.99 mmol), cesium floride (0.2 g, 1.34 mmol) and tetrakistriphenylphosphine palladium (0.038 g, 0.034 mmol) in DMF (10 mL) was stirred at 100° C. for 8 hours, treated with ethyl acetate (10 mL), washed with brine, dried (MgSO$_4$), filtered, and concentrated. The concentrate was purified by flash column chromatography on silica gel with 10% methanol/dichloromethane to provide the desired product (0.25 g, 76%). MS (DCI/NH$_3$) m/e 495 (M+H)$^+$.

Example 43E (1S)-2-(1H-indol-3-yl)-1-{[(6-pyridin-4-ylquinolin-3-yl)oxy]methyl}ethylamine The desired product was prepared as the trifluoroacetate salt by substituting Example 43D for Example 27B in Example 27C. MS (DCI/NH$_3$) m/e 395 (M+H)$^+$; $^1$H NMR (DMSO-d$_6$) δ 10.89 (s, 1H), 8.74 (d, J=3.0 Hz, 1H), 8.71 (d, J=5.0 Hz, 2H), 8.25 (s, 1H), 8.07 (d, J=9.0 Hz, 1H), 7.99 (d, J=9.0 Hz, 1H), 7.83 (d, J=5.0 Hz, 2H), 7.72 (d, J=3.0 Hz, 1H), 7.58 (d; J=7.5 Hz, 1H), 7.35 (d, J=8.4 Hz, 1H), 7.23 (s, 1H), 7.06 (t, J=7.5 Hz, 1H), 6.95 (t, J=8.4 Hz, 1H), 4.05 (m, 2H), 3.53 (m, 1H), 3.01 (dd, J=6.3, 14.9 Hz, 1H), 2.87 (dd, J=6.9, 14.9 Hz, 1H).

EXAMPLE 44

(3Z)-3-[(2S)-2-amino-3-(1H-indol-3-yl) propylidene]-5-isoquinolin-6-yl-1,3-dihydro-2H-pyrrolo[2,3-b]pyridin-2-one Example 44A tert-butyl (1S,2Z)-2-(5-bromo-2-oxo-1,2-dihydro-3H-pyrrolo[2,3-b]pyridin-3-ylidene)-1-(1H-indol-3-ylmethyl)ethylcarbamate A mixture of 5-bromo-7-aza-oxindole (D. Mazeas, et al., Heterocycles 1999, 50, 1065.) (213 mg, 1.0 mmol), L-BOC-tryptophanal (290 mg, 1.0 mmol) and piperidine (40 µL) in ethanol was refluxed for 2.5 hours and concentrated. The residue was triturated with dichloromethane (1 mL) and hexane (6 mL) and dried to provide the desired product (512 mg). MS (DCI/NH$_3$) m/e 483, 485 (M+H)$^+$.

Example 44B (3Z)-3-[(2S)-2-amino-3-(1H-indol-3-yl) propylidene]-5-isoquinolin-6-yl-1,3-dihydro-2H-pyrrolo[2,3-b]pyridin-2-one The desired product was prepared by substituting Example 44A (260 mg) for Example 2A in Example 27. MS (DCI/NH$_3$) m/e 432 (M+H)$^+$; $^1$H NMR (CD$_3$OD) δ 9.57 (s, 1H), 8.64 (d, J=2.5 Hz, 1H), 8.52 (d, J=7.6 Hz, 1H), 8.26 (s, 1H), 8.24 (s, 1H), 8.08 (d, J=6.4 Hz, 1H), 7.64 (s, 1H), 7.60 (dd, J=8.7, 1.7 Hz, 1H), 7.55 (d, J=6.6 Hz, 1H), 7.54 (d, J=7.1 Hz, 1H), 7.33 (dd, J=7.0, 1.1 Hz, 1H), 7.29 (dd, J=3.3, 1.3 Hz, 1H), 7.26 (dd, J=7.1, 1.0 Hz, 1H), 6.26 (d, J=2.2 Hz, 1H), 4.20 (s, 1H), 3.94 (d, J=6.8 Hz, 1H), 3.61 (s, 1H), 2.78 (d, J=14.7 Hz, 1H), 2.68 (dd, J=16.3, 6.9 Hz, 1H). New Examples Following the procedures described in Example 1, using the appropriate alcohols, the following compounds were made.

EXAMPLE 45

3-Butoxyl-5-[2-(4-pyridinyl)vinyl]pyridine

MS (DCI/NH$_3$) m/e 255 (M+1). $^1$H NMR (DMSO-d$_6$): δ 58.58 (d; J=6.0 Hz, 1H), 8.39 (s; 1H), 8.22 (s; 1H), 7.70 (s; 1H), 7.56 (d; J=6.0 Hz, 1H), 7.56 (d, J=16.5 Hz, 1H), 7.45 (d; J=16.5 Hz, 2H), 4.12 (t; J=8.6 Hz, 3H), 1.74 (m; 2H), 1.47 (m; 2H), 0.96 (t; J=8.6 Hz, 2H).

EXAMPLE 46

3-Methoxyl-5-[2-(4-pyridinyl)vinyl]pyridine

MS (DCI/NH$_3$) m/e 213 (M+1). $^1$H NMR (DMSO-d$_6$): δ ppm 8.58 (m, 2 H), 8.41 (d, J=1.7 Hz, 1 H), 8.24 (d, J=2.7 Hz, 1 H), 7.71 (m, 1 H) 7.57 (m, 3 H), 7.47 (d, J=16.5 Hz, 1H), 3.89 (s, 3 H).

EXAMPLE 47

S-3-[2-Amino-3-phenyl-propyloxyl]-5-[2-(4-pyridinyl)vinyl]pyridine Hydrochloride MS (DCI/NH$_3$) m/e 332 (M+1). $^1$H NMR (DMSO-d$_6$): δ 58.58 (d; J=6.0 Hz, 2H), 8.40 (s; 1H), 8.25 (s; 1H), 7.69 (s; 1H), 7.56 (d; J=6.0 Hz, 1H), 7.56 (d; J=16.5 Hz, 1H), 7.43 (d; J=16.5 Hz, 1H), 7.26 (m; 5H), 3.94 (m; 2H), 3.28 (m; 1H), 2.87 (dd; J=6.0 Hz and 13.5 Hz, 1H), 2.65 (dd; J=9 Hz, 13.5 Hz, 1H).

EXAMPLE 48

3-[2-(1H-3-Indolyl)-ethoxyl]-5-[2-(4-pyridinyl)vinyl]pyridine Hydrochloride

MS (DCI/NH$_3$): m/z 342 (M+1). 1H NMR (DMSO-d$_6$): δ 10.39 (br s, 1H), 8.60 (d, J=6.6 Hz, 2H), 8.38 (d, J=2.5 Hz, 1H), 8.25 (d, J=3.3 Hz, 1H), 7.72 (dd, J=2.5, 3.3 Hz, 1H), 7.62 (d, J=8.5 Hz, 1H), 7.55 (d, J=17.4 Hz, 1H), 7.36 (d, J=8.1 Hz, 1H), 7.54 (d, J=6.6 Hz, 2H), 7.28 (d, J=3.3 Hz, 1H), 4.36 (t, J=7.5 Hz, 2H), 3.11 (t, J=3.11 Hz, 2H).

EXAMPLE 49

3-[2-(1H-3-Indolyl)-propyloxyl]-5-[2-(4-pyridinyl)vinyl]pyridine

MS (DCI/NH$_3$): m/z 356 (M+1). 1H NMR (DMSO-d$_6$): δ 510.79 (br s, 1H), 8.57 (m, 2H), 8.39 (d, J=1.7 Hz, 1H), 8.25 (d, J=3.1 Hz, 1H), 7.69 (t, J=2.0 Hz, 1H), 7.56 (m, 2H), 7.55 (d, J=16.6 Hz, 1H), 7.52 (m, 1H), 7.43 (d, J=16.6 Hz, 1H), 7.33 (d, J=8.1 Hz, 1H), 7.15 (d, J=2.4 Hz, 1H), 7.06 (m, 1H), 6.96 (m, 1H), 4.16 (t, J=6.5 Hz, 2H), 2.89 (t, J=8.1 Hz, 2H), 2.14 (m, 2H).

EXAMPLE 50

S-3-[2-Amino-3-(4-benzyloxylphenyl)-propyloxyl]-5-[2-(4-pyridinyl)vinyl]pyridine hydrochloride MS (DCI/NH$_3$): m/z 438 (M+1). 1H NMR (DMSO-d$_6$): δ 110.04 (br s, 3H), 8.86 (d, J=7.5 Hz, 2H), 8.54 (s, 1H), 8.39 (d, J=3.3 Hz, 1H), 8.13 (d, J=7.5 Hz, 2H), 7.98 (d, J=17.4 Hz, 1H), 7.88 (m, 1H), 7.73 (d, J=17.4 Hz, 1H), 7.39 (m, 5H), 7.24 (d, J=9.0 Hz, 2H), 6.99 (d, J=9.0 Hz, 2H), 4.28 (dd, J=3.9, 11.5 Hz, 1H), 5.07 (s, 2H), 4.12 (dd, J=6.5, 11.5 Hz, 1H), 3.29 (m, 1H), 3.05 (m, 2H).

EXAMPLE 51

3-(Piperidin-4-yl)-5-[2-(4-pyridinyl)vinyl]pyridine

MS (DCI/NH$_3$): m/z 282 (M+1). $^1$H NMR (DMSO-d$_6$): δ 8.55 (m, 2H), 8.34 (d, J=1.7 Hz, 1H), 8.18 (d, J=2.7 Hz, 1H), 7.72 (m, 1H), 7.62 (m, 2H), 7.52 (d, J=16.3 Hz, 1H), 7.35 (d, J=16.3 Hz, 1H), 4.66 (m, 1H), 3.10 (m, 2H), 2.78 (m, 2H), 2.06 (m, 2H), 1.70 (m, 2H).

EXAMPLE 52

R-3-{2-Amino-3-benzyloxypropyloxyl}-5-[2-(4-pyridinyl)vinyl]pyridine hydrochloride MS (DCI/NH$_3$): m/z 362 (M+1). $^1$H NMR (CD$_3$CD): δ 8.84 (m, 2H), 8.81 (m, 1H), 8.58 (m, 1H), 8.53 (m, 1H), 8.32 (m, 2H), 7.98 (d, J=16.3 Hz, 1H), 7.87 (d, J=16.3 Hz, 1H), 7.35 (m, 5H), 4.66 (s, 2H), 3.95 (m, 2H), 3.85 (m, 1H).

EXAMPLE 53

3-(1-Methyl-imidazole-4-methoxyl)-5-[2-(4-pyridinyl)vinyl]pyridine

MS (DCI/NH$_3$): m/z 393 (M+1). $^1$H NMR (CD$_3$OD): δ 8.52 (m, 2H), 8.39 (d, J=1.6 Hz, 1H), 8.27 (d, J=2.5 Hz, 1H), 7.84 (m, 1H), 7.69 (s, 1H), 7.62 (m, 2H), 7.53 (d, J=16.5 Hz, 1H), 7.88 (d, J=16.5 Hz, 1H), 7.15 (s, 1H), 5.29 (s, 2H), 3.78 (s, 3H).

EXAMPLE 54

S-3-{2-Amino-3-[3-hydroxylphenyl]-propyloxyl}-5-[2-(4-pyridinyl)vinyl]pyridine trifluoroacetic acid salt MS (DCI/NH$_3$): m/z 348 (M+1). $^1$H NMR (DMSO-d$_6$): δ 8.84 (d, j=6.8 Hz, 2H), 8.54 (m, 1H), 8.37 (d, J=2.7 Hz, 1H), 8.06 (d, J=6.8 Hz, 2H), 7.91 (m, J=16.6 Hz, 1H), 7.62 (d, J=16.6 Hz, 1H), 7.09 (d, J=8.5 Hz, 2H), 6.73 (d, J=8.5 Hz, 2H), 4.22 (dd, J=3.1, 10.5 Hz, 1H), 4.06 (dd, J=5.4, 10.5 Hz, 1H), 3.77 (m, 1H), 2.93 (m, 2H).

EXAMPLE 55

S-3-{2-Amino-3-[3-cyanophenyl]-propyloxyl}-5-[2-(4-pyridinyl)vinyl]pyridine hydrochloride salt MS (DCI/NH$_3$): m/z 357 (M+1). $^1$H NMR (DMSO-d$_6$): δ 8.92 (d, j=6.4 Hz, 2H), 8.66 (s, 1H), 8.49 (d, J=1.8 Hz, 1H), 8.21 (d, J=6.4 Hz, 2H), 8.13 (s, 1H), 8.06 (d, J=16.5 Hz, 1H), 7.90 (d, J=16.5 Hz, 1H), 7.83 (d, J=8.2 Hz, 1H), 7.59 (d, J=8.2 Hz, 2H), 4.40 (dd, J=3.4, 10.7 Hz, 1H), 4.24 (dd, J=5.8, 10.7 Hz, 1H), 3.91 (m, 1H), 3.29 (dd, J=6.1, 13.7 Hz, 1H), 3.16 (dd, J=8.5, 13.7 Hz, 1H).

EXAMPLE 56

3-[1-(4-Cyanobenzyl)-imidazole-4-methoxyl]-5-[2-(4-pyridinyl)vinyl]pyridine

MS (DCI/NH$_3$): m/z 394 (M+1). $^1$HNMR (CD$_3$OD) δ 8.51 (d; J=6.1 Hz, 2H), 8.33 (d, J=1.5 Hz, 1H), 7.94 (d, J=2.5 Hz, 1H), 7.93 (s, 1H), 7.67 (d, J=8.2 Hz, 2H), 7.62 (d, J=6.1 Hz, 2H), 7.48 (m, 1H), 7.47 (d, J=16.5 Hz, 1H), 7.30 (d, J=16.5 Hz, 1H), 7.27 (s, 1H), 7.25 (d, J=8.2 Hz, 2H), 5.47 (s, 2H), 5.26 (s, 2H).

EXAMPLE 57

S-3-[2-Amino-3-(1-methyl-1H-3-indolyl)-propyloxyl]-5-[2-(4-pyridinyl)vinyl]pyridine hydrochloride salt MS (DCI/NH$_3$): m/z 385 (M+1). $^1$HNMR (CD$_3$OD) δ 8.87 (d; J=6.8 Hz, 2H), 8.55 (s, 1H), 8.41 (d, J=2.7 Hz, 1H), 8.13 (d, J=6.8 Hz, 2H), 7.96 (d, J=6.8 Hz, 2H), 7.96 (d, J=16.6 Hz, 1H), 7.86 (m, 1H), 7.71 (d, J=16.6 Hz, 1H), 7.65 (d, J=8.1 Hz, 1H), 7.42 (d, J=8.1 Hz, 1H), 7.29 (s, 1H), 7.17 (m, 1H), 7.04 (m, 1H), 4.84 (dd, J=3.4, 10.5 Hz, 1H), 4.21 (dd, J=5.8, 10.5 Hz, 1H), 3.90 (m, 1H), 3.19 (m, 2H), 3.17 (s, 3H).

EXAMPLE 58

S-3-[2-Dimethylamino-3-(1H-3-indolyl)-propyloxyl]-5-[2-(4-pyridinyl)vinyl]pyridine hydrochloride salt MS (DCI/NH$_3$): m/z 399 (M+1). $^1$HNMR (DMSO-d$_6$) δ 8.88 (d; J=6.6 Hz, 2H), 8.58 (s, 1H), 8.45 (s, 1H), 8.16 (d, J=6.6 Hz, 2H), 7.96 (d, J=16.5 Hz, 1H), 7.95 (s, 1H), 7.76 (d, J=16.5 Hz, 1H), 7.74 (d, J=7.8 Hz, 1H), 7.35 (d, J=8.1 Hz, 1H), 7.29 (d, J=2.2 Hz, 1H), 7.07 (m, 1H), 6.97 (m, 1H), 4.54 (dd, J=1.6, 11.9 HZ), 4.35 (dd, J=5.0, 11.9 Hz, 1H), 3.95 (m, 1H), 3.51 (dd, J=3.1, 13.7 Hz, 1H), 3.29 (dd, J=11.5, 13.7 Hz, 1H), 2.96 (s, 6H).

EXAMPLE 59

S-3-[2-Amino-3-(1-naphthyl)-propyloxyl]-5-[2-(4-pyridinyl)vinyl]pyridine hydrochloride salt MS (DCI/NH$_3$): m/z 382 (M+1). $^1$HNMR (DMSO-d$_6$) δ 8.66 (d; J=6.1 Hz, 2H), 8.48 (d, J=1.4 Hz, 1H), 8.32 (d, J=2.7 Hz, 1H), 8.20 (m, 1H), 7.98 (m, 1H), 7.90 (m, 1H), 7.69 (m, 3H), 7.60 (m, 3H), 7.46 m, 3H), 4.25 (dd, J=2.7, 10.5 Hz, 1H), 4.09 (dd, J=5.1, 10.5 Hz, 1H), 3.92 (m, 1H), 3.53 (m, 2H).

EXAMPLE 60

3-(2-Aminoethoxyl)-5-[2-(4-pyridinyl)vinyl]pyridine hydrochcloride salt

MS (DCI/NH$_3$) m/e 242 (M+1). $^1$H NMR (CD$_3$OD): δ 8.88 (d, J=6.1 Hz, 2H), 8.59 (s, 1H), 8.43 (s, 1H), 8.19 (d, J=6.1 Hz, 2H), 8.03 (d, J=16.3 Hz, 1H), 8.01 (s, 1H), 7.82 (d, J=16.3 Hz, 1H), 4.42 (t, J=4.9 Hz, 2H), 3.28 (m, 2H).

EXAMPLE 61

3-(3-Aminopropyloxyl)-5-[2-(4-pyridinyl)vinyl] pyridine hydrochloride salt

MS (DCI/NH$_3$) m/e 256 (M+1). $^1$H NMR (DMSO-d$_6$): δ 8.88 (d; J=6.4 Hz, 2H), 8.53 (d; J=1.4 Hz, 1H), 8.40 (d, J=2.7 Hz, 1H), 8.15 (d, J=6.4 Hz, 2H), 8.00 (d, J=16.6 Hz, 1H), 7.93 (m, 1H), 7.78 (d, J=16.6 Hz, 1H), 4.27 (t, J=6.1 Hz, 2H), 2.99 (m, 2H), 2.10 m(m, 2H).

EXAMPLE 62

S-3-(2-Amino3-methylbutyloxyl)-5-[2-(4-pyridinyl)vinyl]pyridine hydrochloride salt MS (DCI/NH$_3$) m/e 284 (M+1). $^1$H NMR (DMSO-d$_6$): δ 8.85 (d; J=6.5 Hz, 2H), 8.54 (d; J=1.4 Hz, 1H), 8.40 (d, J=3.1 Hz, 1H), 8.09 (d, J=6.5 Hz, 2H), 7.95 (d, J=16.3 Hz, 1H), 7.90 (m, 1H), 7.71 (d, J=16.3 Hz, 1H), 4.39 (m, 1H), 4.24 (m, 1H), 3.08 (m, 1H), 2.10 (m, 1H), 1.06 (d, J=8.1 Hz, 3H), 1.03 (d, J=7.8 Hz, 3H).

EXAMPLE 63

3-(1-Methyl-3-piperidinyloxyl)-5-[2-(4-pyridinyl)vinyl]pyridine trifluoroacetic acid salt MS (DCI/NH$_3$) m/z 296 (M+H). $^1$H NMR (DMSO-d$_6$): δ 8.82 (d, 2H), 8.53 (s, 1H), 8.41 (d, 1H), 8.00 (t, 2H), 7.88 (dd, 2H), 7.59 (dd, 2H), 4.53 (dd, 1H), 4.37 (dd, 1H), 3.89 (bs, 1H), 3.64 (bs, 1H), 3.24–3.13 (m, 1H), 3.01 (s, 3H), 2.35–2.28 (m, 1H), 2.13–2.07 (m, 1H), 2.02–1.93 (m, 1H), 1.90–1.83 (m, 1H).

EXAMPLE 64

3-(2-Chlorobenzyl)-5-[2-(4-pyridinyl)vinyl]pyridine trifluoroacetic acid salt

MS (DCI/NH$_3$) m/z 323 (M+H). $^1$H NMR (DMSO-d$_6$): δ 8.84 (d, 2H), 8.53 (s, 1H), 8.44 (d, 1H), 8.07 (d, 2H), 7.96–7.92 (m, 2H), 7.70–7.67 (m, 2H), 7.57–7.55 (m, 1H), 7.46–7.43 (m, 2H), 5.33 (s, 2H).

EXAMPLE 65

3-(N-Benzyl-N-methylaminoethoxyl)-5-[2-(4-pyridinyl)vinyl]pyridine trifluoroacetic acid salt MS (DCI/NH$_3$) m/z 346 (M+H). $^1$H NMR (DMSO-d$_6$): δ 8.80 (d, 2H), 8.53 (s, 1H), 8.37 (d, 1H), 7.98 (d, 2H), 7.87 (d, 1H), 7.81 (s, 1H), 7.60 (d, 1H), 7.58–7.47 (m, 5H), 4.58–4.50 (m, 2H), 3.59–3.56 (m, 2H), 2.85 (s, 3H), 2.79 (t, 2H).

EXAMPLE 66

3-(6-(N,N-Dimathylamino)hexyloxyl)-5-[2-(4-pyridinyl)vinyl]pyridine trifluoroacetic acid salt MS (DCI/NH$_3$) m/z 326 (M+H). $^1$H NMR (DMSO-d$_6$): δ 8.82 (d, 2H), 8.49 (d, 1H), 8.33 (d, 1H), 8.04 (d, 2H), 7.89 (d, 1H), 7.80 (t, 1H), 7.66 (d, 1H), 4.14 (t, 2H), 3.06–3.02 (m, 2H), 2.78 (s, 3H), 2.77 (s, 3H), 1.82–1.76 (m, 2H), 1.68–1.62 (m, 2H), 1.51–1.45 (m, 2H), 1.40–1.34 (m, 2H).

EXAMPLE 67

3-(2-Thiophenoxyl-ethoxyl)-5-[2-(4-pyridinyl)vinyl] pyridine trifluoroacetic acid salt MS (DCI/NH$_3$) m/z 335 (M+H). $^1$H NMR (DMSO-d$_6$): δ 8.76 (d, 2H), 8.46 (s, 1H), 8.27 (d, 1H), 7.93 (d, 1H), 7.80 (d, 1H), 7.77–7.74 (m, 2H), 7.59 (d, 1H), 7.43–742 (m, 1H), 7.36–7.31 (m, 3H), 7.24–7.16 (m, 1H), 4.33 (t, 2H), 3.43 (t, 2H).

EXAMPLE 68

3-(1-Methyl-3-pyrrolidinyloxyl)-5-[2-(4-pyridinyl) vinyl]pyridine trifluoroacetic acid salt MS (DCI/NH$_3$) m/z 282 (M+H). $^1$H NMR (DMSO-d$_6$): δ 8.75 (d, 2H), 8.52 (s, 1H), 8.31 (d, 1H), 7.88 (d, 2H), 7.80–7.77 (m, 2H), 7.57 (d, 1H), 5.36–5.30 (m, 1H), 3.46–3.39 (m, 1H), 3.23–3.15 (m, 1H), 2.97–2.95 (m, 1H), 2.91 (s, 3H), 2.73–2.63 (m, 1H), 2.36–2.25 (m, 1H), 2.17–2.09 (m, 1H).

EXAMPLE 69

3-[(1-Methyl-2-piperidinyl)methoxyl]-5-[2-(4-pyridinyl)vinyl]pyridine trifluoroacetic acid salt MS (DCI/NH$_3$) m/z 310 (M+H). $^1$H NMR (DMSO-d$_6$): δ 8.81 (d, 2H), 8.54–8.53 (m, 1H), 8.40–8.38 (m, 1H), 8.01–7.99 (m, 2H), 7.91–7.85 (m, 2H), 7.64–7.59 (m, 1H), 4.55–4.52 (m, 1H), 4.38–4.31 (m, 1H), 3.71–3.62 (m, 1H), 3.55–3.45 (m, 1H), 3.35–3.23 (m, 1H), 2.91 (s, 3H), 2.88 (dt, 1H), 2.10–1.52 (m, 5H).

EXAMPLE 70

3-(1-Pyridinyl-ethoxyl)-5-[2-(4-pyridinyl)vinyl] pyridine trifluoroacetic acid salt MS (DCI/NH$_3$) m/z 304 (M+H). $^1$H NMR (DMSO-d$_6$) δ 8.81 (d, 2H), 8.73 (d, 2H), 8.48 (s, 1H), 8.34 (d, 1H), 8.01 (d, 1H), 7.85–7.81 (m, 2H), 7.74 (d, 2H), 7.57 (d, 1H), 5.89 (q, 1H), 1.65 (d, 3H).

EXAMPLE 71

4-{5-[(2S)-2-Amino-3-(1H-indol-3-yl)-propoxy]-pyridin-3-yl}-N-hydroxyl-benzamidine trifluoroacetic acid salt Example 71A 4-{5-[(2S)-2-BOCamino-3-(1H-indol-3-yl)-propoxy]-pyridin-3-yl}-N-hydroxyl-benzamidine To a solution of Example 22 (200 mg, 0.43 mmol) in toluene (7.0 ml) and methanol (0.5 ml) were added hydroxylamine hydrochloride (33 mg, 0.48 mmol) and potassium tert-butoxide (54 mg, 0.48 mmol) and the mixture was stirred for 8 h at room temperature under a nitrogen atmosphere. Another portion of hydroxylamine hydrochloride (33 mg, 0.48 mmol) and potassium tert-butoxide (54 mg, 0.48 mmol) was added and the mixture was heated to 80° C. for 16 h. The mixture was concentrated and purified by column chromatography on silica gel using dichloromethane/methanol (15:1) as solvent system. Obtained were 130 mg (61%) of the product as a white powder.

MS (DCI/NH$_3$) m/z 487 (M–OH+2H).

Example 71B

4-{5-[(2S)-2-Amino-3-(1H-indol-3-yl)-propoxy]-pyridin-3-yl}-N-hydroxyl-benzamidine trifluoroacetic acid salt The desired product was prepared by substituting Example 71A for Example 22A in example 22B. MS (DCI/NH$_3$) m/z 369 (M–NHOH). $^1$H NMR (DMSO-d$_6$) δ 11.02 (s, 1H), 8.63 (d, 1H), 8.40 (d, 1H), 8.23 (bs, 2H), 8.01–7.91 (m, 2H), 7.85–7.79 (m, 2H), 7.71 (t, 1H), 7.62 (d, 1H), 7.38 (d, 1H), 7.29 (d, 1H), 7.10 (t, 1H), 7.01 (q, 1H), 4.35 (dd, 1H), 4.19 (dd, 1H), 3.85–3.82 (m, 1H), 3.16 (m, 2H).

EXAMPLE 72

4-{5-[(2S)-2-Amino-3-(1H-indol-3-yl)-propoxy]-pyridin-3-yl}-benzamidine trifluoroacetic acid salt

Example 72A

4-{5-[(2S)-2-BOC-amino-3-(1H-indol-3-yl)-propoxy]-pyridin-3-yl}-benzamidine

To a solution of the product of Example 71 (110 mg, 0.22 mmol) in glacial acetic acid (5.0 ml) was added acetic anhydride (0.15 ml, 1.6 mmol) and the mixture was stirred for 2 h at ambient temperature. The acetic anhydride was hydrolyzed by addition of water (0.1 ml), 10% palladium on charcoal (25 mg) was added and the mixture was stirred vigorously under a hydrogen atmosphere (1 atm.) for 4 h. The mixture was filtered through a pad of diatomaceous earth (Celite®) and the filtercake was washed with acetic acid. The combined filtrates were evaporated in high vacuum and the residue was triturated with ethyl acetate to give 80 mg (39%) of the product as a beige powder.

MS (DCI/NH$_3$) m/z 486 (M+H). $^1$H NMR (DMSO-d$_6$): δ 10.93 (s, 1H), 8.56 (s, 1H), 8.32 (d, 1H), 7.93–7.88 (m, 4H), 7.66 (s, 1H), 7.57 (d, 1H), 7.34 (d, 1H), 7.17 (s, 1H), 7.07–7.05 (m, 2H), 6.96 (t, 1H), 4.17–4.11 (m, 2H), 4.09–4.05 (m, 1H), 3.00 (dd, 1H), 2.92 (dd, 1H), 1.36 (s, 9H).

Example 72B

4-{5-[(2S)-2-Amino-3-(1H-indol-3-yl)-propoxy]-pyridin-3-yl}-benzamidine trifluoroacetic acid salt The desired product was prepared by substituting Example 72A for Example 22A in Example 22B. MS (DCI/NH$_3$) m/z 386 (M+H). $^1$H NMR (DMSO-d$_6$): δ 11.03 (s, 1H), 9.38 (s, 2H), 9.24 (s, 2H), 8.65 (d, 1H), 8.42 (d, 1H), 8.25 (bs, 2H), 8.00–7.94 (m, 4H), 7.74 (t, 1H), 7.62 (d, 1H), 7.38 (d, 1H), 7.29 (d, 1H), 7.10 (t, 1H), 7.01 (t, 1H), 4.36 (dd, 1H), 4.20 (dd, 1H), 3.90–3.82 (m, 1H), 3.17 (m, 2H).

EXAMPLE 73

3-[(2S)-2-Amino-3-(1H-3-indolyl)-propyloxyl]-6-(3-pyridinyl)-quinoline

The desired product was prepared by substituting pyridine-3-boronic acid for pyridine-4-boronic acid in Example 43. MS (DCI/NH$_3$) m/e 395 (M+1). $^1$H NMR (DMSO-d6): δ 10.89 (s; 1H), 9.02 (s; 1H), 8.72 (d; J=3.0 Hz, 1H), 8.62 (d; J=5.0 Hz, 1H), 8.20 (d; J=7.5 Hz, 1H), 8.15 (s; 1H), 8.06 (d; J=9.0 Hz, 1H), 7.95 (d; J=9.0 Hz, 1H), 7.70 (S; 1H), 7.59 (d; J=6.0 Hz, 1H), 7.57 (m; 1H), 7.35 (d; J=8.4 Hz, 1H), 7.22 (s; 1H), 7.06 (t; J=7.5 Hz, 1H), 6.95 (t; J=7.5 Hz, 1H), 4.05 (m; 2H), 3.53 (m; 1H), 3.01 (dd; J=6.3, 14.9 Hz, 1H), 2.87 (dd; J=6.9, 14.9 Hz, 1H)

EXAMPLE 74

3-[(2S)-2-Amino-3-(1H-3-indolyl)-propyloxyl]-6-(3-quinolinyl)-quinoline

The desired product was prepared by substituting quinoline-3-boronic acid for pyridine-4-boronic acid in Example 43. MS (DCI/NH$_3$) m/e 445 (M+1). $^1$H NMR (DMSO-d6): δ 0.89 (s; 1H), 9.49 (s; 1H), 8.80 (s; 1H), 8.74 (s; 1H), 8.31 (s; 1H), 8.10 (m; 4H), 7.82 (t; J=6.6 Hz, 1H), 7.73 (s; 1H), 7.69 (t; J=6.6 Hz, 1H), 7.49 (d; J=8.4 Hz, 1H), 7.35 (d; J=8.4 Hz, 1H), 7.23 (s; 1H), 7.06 (t; J=7.5 Hz, 1H), 6.95 (t; J=7.5 Hz, 1H), 4.05 (m; 2H), 3.52 (m; 1H), 3.01 (dd; J=6.3, 14.9 Hz, 1H), 2.87 (dd; J=6.9, 14.9 Hz, 1H).

EXAMPLE 75

3-[(2S)-2-Amino-3-(1H-3-indolyl)-propyloxyl]-5-[2-(2-amino-4-pyridinyl)vinyl]pyridine trifluoroacetic acid salt

Example 75A

2-Amino-4-iodopyridine

A mixture of 2-floro-4-iodopyridine (3.0 g, 13.5 mmol), acetylamide (15.8 g, 269 mmol) and potassium carbonate (9.2 g, 67 mmol) was stirred at 180° C. for 7 hours, poured into ice (100 g), extracted with ethyl acetate, washed with brine, dried (MgSO$_4$), filtered, and concentrated. The concentrate was purified by flash column chromatography on silica gel with 50% ethyl acetate/hexane to provide the title compound (1.1 g, 37%). MS (DCI/NH$_3$) m/e 221 (M+H).

Example 75B

N,N-Bis(tert-butyloxylcarbonyl)amino-4-iodopyridine

A solution of the product from Example 75A above (1.0 g, 4.5 mmol) in THF (25 mL) was treated dropwise with 1.0M LiHMDS (9.0 mL, 9.0 mmol), stirred for 30 minutes, treated with di-t-butyl dicarbonate(1.96 g, 9.0 mmol) and stirred for 1 hour. The mixture was quenched with water (10 mL), warmed to room temperature and extracted with ethyl acetate. The combined extracts were washed with brine, dried (MgSO$_4$), filtered, and concentrated. The concentrate was triturated with 1:1 hexanes/ethyl acetate to provide the desired product (1.0 g, 53%). MS (DCI/NH$_3$) m/z 421 (M+H).

Example 75C

N,N-Bis(tert-butyloxylcarbonyl)amino-4-vinylyridine

A mixture of the product from Example 75B above (0.7 g, 1.67 mmol), vinyltributyltin (0.83 g, 2.6 mmol) and tetrakis-(triphenylphosphine)-palladium(0) (0.12 g, 0.11 mmol) was heated at 100° C. for 6 hours, cooled to room temperature, treated with ethyl acetate (10 mL), washed with brine, dried (MgSO$_4$), filtered, and concentrated. The concentrate was purified by flash column chromatography on silica gel with 20% ethyl acetate/hexane to provide the title compound (0.4 g, 75%). MS (DCI/NH$_3$) m/e 321 (M+H).

Example 75D

3-[(2S)-2-(N-tert-Butoxylcarbonyl)amino-3-(1H-3-indolyl)-propyloxyl]-5-{2-[2-(N,N-bis(tert-butoxylcarbonyl)amino]-4-pyridinyl)vinyl}pyridine The desired product was prepared by substituting Example 75C for 4-vinylpyridine in Example 2B. Purification on silica gel eluting with 100% ethyl acetate provided the title compound (0.15 g, 49%). MS (DCI/NH$_3$) m/e 685 (M+H).

Example 75E 4-(2-{5-[(2S)-2-Amino-3-(1H-indol-3-yl)-propoxy]-pyridin-3-yl}-vinyl)-pyridin-2-ylamine The desired product was prepared by substituting Example 75D for Example 2B in Example 2C. Purification on HPLC provided the title compound (0.06 g, 70%). MS (DCI/NH$_3$) m/e 386 (M+1). $^1$H NMR (DMSO-d6): δ 11.05 (s; 1H), 8.50 (s; 1H), 8.35 (s; 1H), 8.23 (bs; 2H), 8.13 (bs; 2H), 7.95 (d; J=6.3 Hz, 1H), 7.72 (s; 1H), 7.65 (d; J=15.9 Hz, 1H), 7.61 (d; J=6.3 Hz), 7.42 (d; J=15.9 Hz, 1H), 7.38 (d; J=6.9 Hz, 1H), 7.28 (s; 1H), 7.18 (d; J=6.9 Hz, 1H), 7.10 (t; J=6.9 Hz, 1H), 7.00 (t; J=6.9 Hz, 1H), 6.93 (s; 1H), 4.29 (m; 1H), 4.14 (m; 1H), 3.87 (m; 1H), 3.17 (m; 2H).

EXAMPLE 76

5-[(2S)-2-(Amino-3-(1H-3-indolyl)-propyloxyl]-3-[2-(2-amino-4-pyridinyl)vinyl]-2-chloro-pyridine trifluoroacetic acid salt The desired product was prepared by substituting 3-bromo-2-chloro-5-hydroxylpyridine for 3-bromo-5-hydroxylpyridine in Example 75. MS (DCI/NH$_3$) m/e 420 (M+1). $^1$H NMR (DMSO-d6): δ 11.05 (s; 1H), 8.21 (s; 1H), 8.21 (bs; 2H), 8.04 (bs; 2H), 7.95 (d; J=6.3 Hz, 1H), 7.93 (s; 1H), 7.61 (d; J=6.3 Hz, 1H), 7.58 (d; J=15.9 Hz, 1H), 7.39 (d; J=15.9 Hz, 1H), 7.39 (d; J=6.9 Hz, 1H), 7.28 (s; 1H), 7.18 (d; J=6.9 Hz, 1H), 7.10 (t; J=6.9 Hz, 1H), 7.00 (t; J=6.9 Hz, 1H), 6.99 (s; 1H), 4.32 (m; 1H), 4.16 (m; 1H), 3.87 (m; 1H), 3.17 (m; 2H).

EXAMPLE 77

(1S)-1-(1H-Indol-3-ylmethyl)-2-(5-naphthalen-2-yl-pyridin-3-yloxy)-ethylamine

The desired product was prepared by substituting 2-bromonaphthalene for 6-bromoisoquinoline in Example 27. $^1$H NMR (d$_6$-DMSO, 500 MHz) δ : 11.02 (s, 1H), 8.74 (s, 1H), 8.38 (s, 1H), 8.30 (s, 1H), 8.18–8.21 (m, 2H), 8.04 (d, J=8 Hz, 1H), 7.97–8.01 (m, 2H), 8.85 (d, J=8 Hz, 1H), 7.81 (s, 1H), 7.62 (d, J=8 Hz, 1H), 7.50–7.58 (m, 1H), 7.35–7.39 (m, 1H), 7.23–7.31 (m, 1H), 7.08–7.12 (m, 1H), 6.96–7.03 (m, 2H), 4.18–4.41 (m, 2H), 3.82–3.87 (m, 1H), 3.17–3.21 (m, 2H).
MS: (ESI) (M+H)$^+$ m/z=394

EXAMPLE 78

(1S)-1-(1H-Indol-3-ylmethyl)-2-(5-isoquinolin-5-yl-pyridin-3-yloxy)-ethylamine

Example 78A

5-Bromoisoquinoline

To a solution of 5-aminoisoquinoline (2.0 g, 13.8 mmol) and 48% HBr (6 mL) in 20 mL water cooled to 0° C. was added a solution of sodium nitrite (0.95 g, 13.8 mmol) in 6 mL water. The solution was stirred at 0° C. for 20 minutes. The solution, while kept at 0° C., was added to a solution of CuBr (2.11 g, 15.9 mmol) in 48% HBr (4.77 mL) and water (10 mL). The reaction was stirred at room temperature for an additional 1 hr. The reaction was neutralized with NaOH (50%) and extracted with ethyl acetate (3×). The combined organic layer was concentrated in vacuo and chromatographed using 1:1 hexanes/ethyl acetate to yield 1.4 g product (50%).

Example 78B (1S)-1-(1H-Indol-3-ylmethyl)-2-(5-isoquinolin-5-yl-pyridin-3-yloxy)-ethylamine The desired product was prepared by substituting Example 78A for 6-bromoisoquinoline in Example 27. MS (ESI) m/z 395 (M+H)$^+$; $^1$H NMR (d$_6$-DMSO, 300 MHz) δ 11.02 (bs, 1H), 9.53 (s, 1H), 8.52 (d, J=8 Hz, 1H), 8.49 (d, J=4 Hz, 1H), 8.37 (d, J=3 Hz, 1H), 8.30–8.34 (m, 1H), 8.15–8.19 (m, 2H), 7.84–7.88 (m, 2H), 7.68 (d, J=8 Hz, 1H), 7.56–7.60 (m, 2H), 7.47 (d, J=8 Hz, 1H), 7.28 (d, J=4 Hz, 1H), 7.60–7.12 (m, 1H), 6.94–6.99 (m, 1H), 4.12–4.32 (m, 2H), 3.82–3.87 (m, 1H), 3.13–3.17 (m, 2H).

EXAMPLE 79

6-{5-[(2S)-2-Amino-3-(1H-indol-3-yl)-propoxy]-pyridin-3-yl}-2H-isoquinolin-1-one The desired product was prepared by substituting 2-hydroxylisoquinoline for 6-bromoisoquinoline in Example 27. MS (ESI) m/z 411 (M+H)$^+$; $^1$H NMR (DMSO-d$_6$, 300 MHz) δ 11.30 (bs, 1H), 11.04 (bs, 1H), 8.66–8.68 (m, 1H), 8.41 (d, J=3 Hz, 1H), 8.27 (d, J=8 Hz, 1H), 8.17–8.20 (m, 2H), 8.02–8.03 (m, 1H), 7.76–7.81 (m, 2H), 7.62 (d, J=8 Hz, 1H), 7.38 (d, J=8 Hz, 1H), 7.29–7.31 (m, 1H), 7.20–7.26 (m, 1H), 7.07–7.12 (m, 1H), 6.98–7.04 (m, 1H), 6.60 (d, J=8 Hz, 1H), 4.14–4.39 (m, 2H), 3.33–3.38 (m, 1H), 3.13–3.16 (m, 2H). Anal. Calcd for C$_{25}$H$_{22}$N$_4$O.2TFA: C, 54.54; H, 3.78; N, 8.78; F, 17.86. Found: C, 54.54; H, 4.00; N, 8.56; F, 17.10.

EXAMPLE 80

(1S)-2-[5-(3-Chloro-isoquinolin-6-yl)-pyridin-3-yloxy]-1-(1H-indol-3-ylmethyl)-ethylamine Example 80A 6-Bromo-indan-1,2-dione 1-oxime A solution of 5-bromo-1-indanone (1.8 g, 8.5 mmol) in ethanol (150 ml) was cooled to 0° C., treated with t-butylnitrite (2.1 ml), stirred at room temperature for 2 hours, filtrated and washed the desired product with ether. The yield is 76%. MS (DCI/NH$_3$) m/e 242 (M+1)$^+$.

Example 80B

6-Bromo-1,3-dichloro-isoquinoline

A suspension solution of Example 80A (1.5 g, 6.2 mmol) in POCl$_3$ (40 ml) was treated with PCl$_5$ (1.55 g, 7.4 mmol) and introduced HCl gas until solution was saturated. The reaction was stirred at 60° C. for 6 hours and concentrated under vacumm.

The residue was slowly hydrolysed by adding water, treated with ethyl acetate (200 mL), washed with brine, dried (MgSO₄), filtered, and concentrated. The concentrate was purified by flash column chromatography on silica gel with 10% ethyl acetate/hexane to provide the title compound (1.7 g, 100%). MS (DCI/NH$_3$) m/e 278 (M+H)$^+$.

Example 80C

6-Bromo-3-chloro-isoquinoline

A mixture of Example 80B (1.8 g, 6.5 mmol), P (0.48 g, 15.5 mmol) and HI (3 ml, 48%) in acetic acid (20 ml) was refluxed for 8 hours, filtrated under hot condition and concentrated under vacumm. The residue was basified by adding sodium hydroxide solution, treated with ethyl acetate (200 mL), washed with brine, dried (MgSO$_4$), filtered, and concentrated. The concentrate was purified by flash column chromatography on silica gel with 30% ethyl acetate/hexane to provide the title compound (0.81 g, 50%). MS (DCI/NH$_3$) m/e 244 (M+H)$^+$.

Example 80D

3-Chloro-6-trimethylstannanyl-isoquinoline

The desired product was prepared by substituting Example 80C for 6-bromoisoquinoline in Example 27A. MS (DCI/NH$_3$) m/e 327 (M+H)$^+$.

Example 80E (1S)-[2-[5-(3-Chloro-isoquinolin-6-yl)-pyridin-3-yloxy]-1-(1H-indol-3-ylmethyl)-ethyl]-carbamic acid tert-butyl ester The desired product was prepared by substituting Example 80D for Example 27A in Example 27B. MS (DCI/NH$_3$) m/e 530 (M+H)$^+$.

Example 80F (1S)-2-[5-(3-Chloro-isoquinolin-6-yl)-pyridin-3-yloxy]-1-(1H-indol-3-ylmethyl)-ethylamine The desired product was prepared by substituting Example 80E for Example 27B in Example 27C. MS (DCI/NH$_3$) m/e 429 (M+1)$^+$; $^1$H NMR (DMSO-d$_6$, 300 MHz) δ 11.04 (s; 1H), 9.28 (s; 1H), 8.72 (s; 1H), 8.44 (s; 1H), 8.33 (s; 1H), 8.32 (d; 1H; J=8.4 Hz), 8.17 (s; 2H), 8.07 (s; 1H), 8.05 (d; 1H; J=8.4 Hz), 7.80 (s; 1H), 7.63 (d; 1H; J=7.5. Hz), 7.48 (d; 1H; J=7.5 Hz), 7.30 (s; 1H), 7.10 (t; 1H; J=7.2 Hz), 7.00 (t; 1H; J=7.2 Hz), 4.38 (m; 1H), 4.20 (m; 1H), 3.88 (m; 1H), 3.18 (m; 2H).

EXAMPLE 81

(1S)-2-([3,4']Bipyridinyl-5-yloxy)-1-(1H-indol-3-ylmethyl)-ethylamine trifluoroacetic acid The desired product was prepared by substituting 4-tributylstannylpyridine for Example 27A in Example 27. MS (APCI) m/z 345 (M+1)$^+$; $^1$H NMR (CD$_3$OD, 300 MHz) δ 8.85 (d, J=6.8 Hz, 2H), 8.73 (d, J=1.7 Hz, 1H), 8.53 (d, J=2.7 Hz, 1H), 8.20 (d, J=6.8 Hz, 2H), 7.84 (t, J=1.7 Hz, 1H), 7.59 (d, J=7.8 Hz, 1H), 7.38 (d, J=8.2 Hz, 1H), 7.24 (s, 1H), 7.12 (t, J=6.8 Hz, 1H), 7.01 (t, J=8.1 Hz, 1H), 4.44 (dd, J=10.8, 3.4 Hz, 1H), 4.30 (dd, J=10.5, 5.8 Hz, 1H), 4.01 (m, 1H), 3.33 (m, 2H); Anal. Calcd for C$_{21}$H$_{20}$N$_4$O.2.7 TFA: C, 48.61; H, 3.51; N, 8.59. Found: C, 48.69; H, 3.50; N, 8.46.

EXAMPLE 82

(1S)-1-(1H-Indol-3-ylmethyl)-2-[5-(2-pyridin-2-yl-vinyl)-pyridin-3-yloxy]-ethylamine The desired product was prepared by substituting 2-vinylpyridine for 4-vinylpyridine in Example 2. MS (APCI) m/z 371 (M+1)$^+$; $^1$H NMR (CD$_3$OD, 300 MHz) δ 8.72 (d, J=5.5 Hz, 1H), 8.55 (s, 1H), 8.39 (d, J=2.4 Hz, 1H), 8.34 (td, J=7.8, 1.7 Hz, 1H), 8.12 (d, J=8.2 Hz, 1H), 7.88 (t, J=1.7 Hz, 1H), 7.82 (d, J=16.3 Hz, 1H), 7.74 (t, J=6.7 Hz, 1H), 7.59 (d, J=7.8 Hz, 1H), 7.53 (d, J=16.3 Hz, 1H), 7.38 (d, J=8.1 Hz, 1H), 7.24 (s, 1H), 7.12 (td, J=7.1, 1.0 Hz, 1H), 7.03 (td, J=7.1, 1.0 Hz, 1H), 4.41 (tt, J=10.5, 3.4 Hz, 1H), 4.27 (dd, J=10.5, 5.5 Hz, 1H), 4.00 (m, 1H), 3.33 (m, 2H); Anal. Calcd for C$_{23}$H$_{22}$N$_4$O.3.8 TFA: C, 45.73; H, 3.24; N, 6.97. Found: C, 45.60; H, 3.34; N, 6.86.

EXAMPLE 83

(1S)-1-(1H-Indol-3-ylmethyl)-2-(5-pyridin-3-ylethynyl-pyridin-3-yloxy)-ethylamine trifluoroacetic acid salt The desired product was prepared by substituting 3-bromopyridine for 4-bromopyridine in Example 14. MS (APCI) m/z 367 (M−1)$^-$; $^1$H NMR (CD$_3$OD, 300 MHz) δ 8.80 (s, 1H), 8.62 (br d, J=4.7 Hz, 1H), 8.42 (s, 1H), 8.36 (d, J=2.7 Hz, 1H), 8.12 (dt, J=8.2, 1.7 Hz, 1H), 7.60 (m, 3H), 7.39 (d, J=8.1 Hz, 1H), 7.22 (s, 1H), 7.14 (td, J=7.1, 1.4 Hz, 1H), 7.04 (td, J=8.2, 1.1 Hz, 1H), 4.33 (dd, J=10.5, 3.0 Hz, 1H), 4.19 (dd, J=10.5, 5.4 Hz, 1H), 3.97 (m, 1H), 3.29 (m, 2H); Anal. Calcd for C$_{23}$H$_{20}$N$_4$O.3.0 TFA: C, 49.02; H, 3.26; N, 7.89. Found: C, 48.86; H, 3.14; N, 8.01.

EXAMPLE 84

(1S)-2-[5-(2-Fluoro-pyridin-4-ylethynyl)-pyridin-3-yloxy]-1-(1H-indol-3-ylmethyl)-ethylamine trifluoroacetic acid salt The desired product was prepared by substituting 4-iodo-2-fluoropyridine for 4-bromopyridine in Example 14. MS (APCI) m/z 385 (M−1)$^-$; $^1$H NMR (CD$_3$OD, 300 MHz) δ 8.42 (d, J=1.4 Hz, 1H), 8.38 (d, J=2.7 Hz, 1H), 8.26 (d, J=5.1 Hz, 1H), 7.61 (dd, J=2.7, 1.7 Hz, 1H), 7.58 (d, J=7.8 Hz, 1H), 7.43 (dt, J=5.1, 1.7 Hz, 1H), 7.38 (d, J=8.1 Hz, 1H), 7.23 (m, 2H), 7.13 (td, J=7.1, 1.3 Hz, 1H), 7.04 (td, J=7.8, 1.3 Hz, 1H), 4.33 (dd, J=10.5, 3.4 Hz, 1H), 4.18 (dd, J=10.5, 5.8 Hz, 1H), 3.97 (m, 1H), 3.30 (m, 2H); Anal. Calcd for C$_{23}$H$_{19}$FN$_4$O.2.3 TFA: C, 51.10; H, 3.31; N, 8.64. Found: C, 51.06; H, 3.32; N, 8.69.

EXAMPLE 85

(1S)-4-{5-[2-Amino-3-(1H-indol-3-yl)-propoxy]-pyridin-3-ylethynyl}-pyridin-2-ol trifluoroacetic acid salt A solution of N-BOC protected Example 84 (45 mg, 0.093 mmol)) in acetic acid (5 mL) was heated at 80° C. for 15 h and at 100° C. for 5 h. The solution was concentrated and the residual oil was dissolved in CH$_2$Cl$_2$ (5 mL). Trifluoroacetic acid (1.25 mL) was added at 0° C. The solution was stirred at 0° C. for 10 min and at rt for 30 min, and was concentrated. The residual material was purified on HPLC (Zorbax, C-18) to provide the title compound (15 mg, 33%). MS (APCI) m/z 383 (M−1)$^-$; $^1$H NMR (CD$_3$OD, 300 MHz) δ 8.40 (s, 1H), 8.36 (d, J=2.3 Hz, 1H), 7.58 (m, 2H), 7.46 (d, J=6.8 Hz, 1H), 7.39 (d, J=8.2 Hz, 1H), 7.22 (s, 1H), 7.14 (td, J=7.1, 1.0 Hz, 1H), 7.03 (td, J=8.2, 1.1 Hz, 1H), 6.69 (brs, 1H), 6.46 (dd, J=6.8, 1.7 Hz, 1H), 4.32 (dd, J=10.5, 3.4 Hz, 1H), 4.18 (dd, J=10.5, 5.8 Hz, 1H), 3.98 (m, 1H), 3.34 (m, 2H).

EXAMPLE 86

(1S)-2-[6-Chloro-5-(1-chloro-isoquinolin-6-yl)-pyridin-3-yloxy]-1-(1H-indol-3-ylmethyl)-ethylamine trifluoroacetic acid salt The title compound was prepared by substituting Example 13A for Example 2A and Example 80D for Example 27A in Example 27. MS (APCI) m/z 464 (M+1)+; $^1$H NMR (CD$_3$OD, 300 MHz) δ 8.44 (d, J=8.8 Hz, 1H), 8.31 (d, J=5.8 Hz, 1H), 8.22 (d, J=3.1 Hz, 1H), 8.03 (d, J=1.7 Hz, 1H), 7.84 (m, 2H), 7.57 (dt, J=7.8, 1.0 Hz, 1H), 7.53 (d, J=3.0 Hz, 1H), 7.34 (d, J=7.2 Hz, 1H), 7.22 (s, 1H), 7.10 (td, J=7.2, 1.4 Hz, 1H), 7.01 (td, J=7.7, 1.0 Hz, 1H), 4.36 (dd, J=10.5, 3.0 Hz, 1H), 4.22 (dd, J=10.5, 5.7 Hz, 1H), 3.97 (m, 1H), 3.27 (m, 2H); Anal. Calcd for C$_{25}$H$_{20}$Cl$_2$N$_4$O.2.05 TFA: C, 50.14; H, 3.19; N, 8.04. Found: C, 50.16; H, 3.03; N, 7.88.

EXAMPLE 87

Bis-[3-(4-Bromo-phenyl)-allyl]-{2-[5-(2-pyridin-4-yl-vinyl)-pyridin-3-yloxy]-ethyl}-amine hydrochloride The title compound was obtained from the less polar product in Example 19D (5.3 mg, 3%). MS (DCI/NH$_3$) m/z 630, 632, 634 (M+H)+; $^1$H NMR (CDCl$_3$, 300 MHz) δ 8.62 (m, 2H), 8.36 (s, 1H), 8.26 (d, J=2.7 Hz, 1H0, 7.0–7.5 (m, 13H0, 6.52 (m, 2H), 6.35 (m, 2H), 4.25 (m, 2H), 3.49 (m, 4H), 3.08 (m, 2H).

EXAMPLE 88

N$^4$-[3-(2-Amino-ethoxy)-phenyl]-pyrimidine-2,4-diamine Hydrochloride

The title compound was prepared by substituting N-Boc-aminoethanol for BOC-tryptophanol in Example 20. MS (DCI/NH$_3$) m/z 246 (M+1)+; $^1$H NMR (DMSO-d6, 300 mHz) δ 12.4 (br s, 1H), 11.0 (br s, 1H), 8.26 (br, 5H), 7.86 (d, J=7.1 Hz, 1H), 7.55 (m, 1H), 7.44 (m, 1H), 7.31 9t, J=8.1 Hz, 1h0, 6.79 (d, J=8.1 Hz, 1H), 6.46 (d, J=7.1 Ha, 1H), 4.22 (t, J=5.1 Hz, 2H), 3.22 (m, 2H).

EXAMPLE 89 trans-[4-(2-{5-[(2S)-2-Amino-3-(1H-indol-3-yl)-propylamino]-pyridin-3-yl}-vinyl)-pyrimidin-2-yl]-carbamic acid ethyl ester trifluoroacetic acid salt

Example 89A trans-4-[(5-Bromo-pyridin-3-yl)-vinyl]-2-amino-pyrimidine

A solution of 5-bromo-pyridine-3-carbaldehyde (436 mg, 2.34 mmol) and 2-amino-4-methylpyrimidine (246 mg, 2.35 mmol) in formic acid (96%, 3 mL) was heated for 18 h. After cooling to rt, it was then diluted with water and basified to pH ~13 with 1 N NaOH. The mixture was then extracted with methylene chloride. The combined extracts was washed with water (1×), dried over MgSO$_4$ and concentrated. The residue was chromatographed on silica gel eluting with CH$_2$Cl$_2$:MeOH:NH$_4$OH (100:5:0.5) to give the title compound (463 mg, 71%). MS (DCI/NH$_3$) m/z 277, 279 (M+1)+.

Example 89B trans-4-[(5-Bromo-pyridin-3-yl)-vinyl]-2-[bis(tert-butoxycarbonyl)amino]-pyrimidine A suspension of Example 89A (439 mg, 1.58 mmol), (BOC)$_2$O (1.040 g, 4.77 mmol), DMAP (50 mg, 0.41 mmol), and triethylamine (670 mL, 4.81 mmol) in THF (10 mL) was stirred at rt overnight. Reaction was concentrated and chromatographed on silica gel eluting with AcOEt:hexane (1:1) to give the title compound (511 mg, 68%). MS (DCI/NH$_3$) m/z 477, 479 (M+1).

Example 89C trans-4-[(5-amino-pyridin-3-yl)-vinyl]-2-(tert-butoxycarbonyl)amino-pyrimidine Example 89B was converted to the title compound according to the procedures described for Example 51, Steps 4 and 5. MS (DCI/NH$_3$) m/z 314 (M+1)+.

Example 89D trans-[4-(2-{5-[(2S)-2-Amino-3-(1H-indol-3-yl)-propylamino]-pyridin-3-yl}-vinyl)-pyrimidin-2-yl]-carbamic acid ethyl ester trifluoroacetic acid salt The title compound was prepared by substituting Example 89C for Example 11B in Example 11. (DCI/NH$_3$) m/z 458 (M+1)+; NMR (DMSO-d6): δ 8.58 (d, J=5.3 Hz, 1H), 8.17 (s, 1H), 7.91 (d, J=2.2 Hz, 1H), 7.75 (d, J=15.9 Hz, 1H), 7.58 (m, 1H), 7.35 (m, 2H), 7.32 (s, 1H), 7.22 (d, J=5.3 Hz, 1H), 7.15 (d, J=15.9 Hz, 1H), 7.11 (m, 1H), 7.04 (m, 1H), 4.28 (q, J=7.2 Hz, 2H), 3.80 (m, 1H), 3.62 (dd, J=4.4, 14.7 Hz, 1H), 3.50 (dd, J=8.1, 14.7 Hz, 1H), 3.20 (m, 2H), 1.35 (t, J=7.2 Hz, 3H).

EXAMPLE 90

1-Amino-6-{5-[(2S)-2-amino-3-(1H-indol-3-yl)-propoxy]-pyridin-3-yl}-isoquinoline trifluoroacetic acid salt

Example 90A

6-Bromo-1-chloroisoquinoline

A solution of 6-bromo-1-hydroxylisoquinoline (9.205 g, 41.0 mmol) in POCl$_3$ (100 mL) was heated to 100° C. for 4 h. The reaction was concentrated to dryness. The residue was dissolved in ethyl acetate and the organic layer was washed with 5% NaHCO$_3$, water, brine, dried over MgSO$_4$ and concentrated. The residue was was chromatographed on silica gel eluting with CH$_2$Cl$_2$:hexane (3:7) to give the title compound (6.176 g, 62%). MS (DCI/NH$_3$) m/z 241, 243 (M+1)+.

Example 90B

1-Amino-6-bromoisoquinoline

A mixture of the chloride from Example 90A (264 mg, 1.09 mmol), acetamide (1.3 g) and K$_2$CO$_3$ (0.45 g) was heated to 180° C. for 5 h. After cooling to rt, the mixture was dissolved in ethyl acetate, which was washed with water, brine, dried over MgSO$_4$, and concentrated. The residue was chromatographed on silica gel eluting with CH$_2$Cl$_2$:MeOH:NH$_4$OH (100:5:0.5) to give the title compound (159 mg, 65%). MS (DCI/NH$_3$) m/z 223, 225 (M+1)+.

Example 90C

1-[(Bis(tert-butoxycarbonyl)]amino-6-bromoisoquinoline

A solution of Example 90B (616 mg, 2.76 mmol), BOC$_2$O (1.81 g), DMAP (67 mg), and triethylamine (1.15 mL) in acetonitrile (15 mL) was stirred at rt for 2 h. The reaction was concentrated and the residue was chromatographed on silica gel eluting with AcOEt: hexane (3:7) to give the title compound (1.18 g, 71%). MS (DCI/NH$_3$) m/z 423 (M+1)+.

Example 90D

1-Amino-6-{5-[(2S)-2-amino-3-(1H-indol-3-yl)-propoxy]-pyridin-3-yl}-isoquinoline trifluoroacetic acid salt The title compound was prepared by substituting Example 90C for 6-bromophthalimide in Example 32. MS (DCI/NH$_3$)

m/z 410 (M+1)⁺; ¹H NMR (DMSO-d6, 300 MHz) δ 8.77 (s, 1H), 8.55 (d, J=8.6 Hz, 1H), 8.45 (d, J=2.5 Hz, 1H), 8.20 (d, J=1.5 Hz, 1H), 8.05 (dd, J=1.8. 8.6 Hz, 1H), 7.83 (dd, J=1.8, 2.5 Hz, 1H), 7.61 (m, 2H), 7.38 (d, J=7.1 Hz, 1H), 7.24 (s, 1H), 7.12 (m, 1H), 7.02 (m, 1H), 4.44 (dd, J=3.1, 10.4 Hz, 1H), 4.30 (dd, J=5.8, 10.4 Hz, 1 H), 4.01 (m, 1H), 3.32 (m, 2 H).

EXAMPLE 91

6-{5-[(2S)-2-amino-3-(1H-indol-3-yl)-propoxy]-pyridin-3-yl}-1-chloro-isoquinoline trifluoroacetic acid salt The title compound was prepared by substituting Example 90A for 6-bromophthalimide in Example 32. MS (ESI) m/z 429, 431 (M+1)⁺; ¹H NMR (DMSO-d6, 300 MHz) 11.03 (br s, 1H), 8.75 (d, J=1.6 Hz, 1H), 8.47 (d, J=1.6 Hz, 1H), 8.45 (d, J=5.6 Hz, 1H), 7.84 (m, 1H), 7.62 (d, J=8.1 Hz, 1H), 7.39 (d, J=8.1 Hz, 1H), 7.31 (d, J=2.2 Hz, 1H), 7.10 (m, 1H), 7.01 (m, 1H), 4.38 (dd, J=3.1, 10.6 Hz, 1H), 4.22 (dd, J=6.2, 10.4 Hz, 1H), 3.88 (m, 1H), 3.18 (m, 2H).

EXAMPLE 92

(2S)-2-Amino-3-(1H-indol-3-yl)-N-[5-(2-pyridin-4-yl-vinyl)-pyridin-3-yl]-propionamide The title compound was prepared by substituting Boc-tryptophane for Boc-homnophenyalanine in Example 16. MS (DCI/NH₃) m/z 384 (M+1)⁺; ¹H NMR (DMSO-d6, 300 MHz) δ 11.37 (s, 1 H), 11.05 (s, 1 H), 8.88 (d, J=6.44 Hz, 2 H), 8.74 (m, 2H), 8.42 (m, 1H), 8.35 (s, 1 H), 8.22 (d, J=6.10 Hz, 2 H), 8.02 (d, J=16.61 Hz, 1 H), 7.71 (d, J=7.80 Hz, 1 H), 7.56 (d, J=16.27 Hz, 1 H), 7.36 (d, J=7.80 Hz, 1 H), 7.30 (m, 1 H), 7.07 (m, 1 H), 6.95 (m, 1 H), 4.31 (m, 1 H), 3.36 (m, 2H).

EXAMPLE 93

(2S)-2-Amino-3-(naphtha-1-yl)-N-[5-(2-pyridin-4-yl-vinyl)-pyridin-3-yl]-propionamide hydrochloride The title compound was prepared by substituting Boc-3-(1-naphthyl)alanine for Boc-homnophenyalanine in Example 16. MS (DCI/NH₃) m/z 395 (M+1)⁺. ¹H NMR (DMSO-d6, 500 MHz,) δ 11.86 (s, 1 H), 8.90 (d, J=6.86 Hz, 2 H), 8.78 (m, 1 H), 8.85 (m, 1 H), 8.58 (m, 1 H), 8.45 (m, 1H), 8.26 (d, J=6.86 Hz, 2 H), 8.04 (d, J=16.53 Hz, 1 H), 7.89 (m, 2 H) 7.84 (m, 1 H), 7.60 (d, J=16.53 Hz, 1 H), 7.58 (m, 1H), 7.49 (m, 2 H), 4.53 (m, 1H), 3.49 (m, 1H), 3.36 (m, 1H).

EXAMPLE 94

(2S)-2-Amino-3-phenyl-N-[5-(2-pyridin-4-yl-vinyl)-pyridin-3-yl]-propionamide hydrochloride The title compound was prepared by substituting Boc-phenylalanine for Boc-homnophenyalanine in Example 16. MS (DCI/NH₃) m/z 345 (M+1)⁺; ¹H NMR (,DMSO-d6, 500 MHz) δ ) 11.85 (s, 1 H), 8.93 (m, 2 H) 8.53 (m, 2 H), 8.49 (m, 1H), 8.29 (m, 2 H), 8.07 (d, J=16.22 Hz, 1 H), 7.63 (d, J=16.53 Hz, 1 H,) 7.32 (m, 5 H), 4.44 (m, 1H), 3.24 (m, 2 H)

EXAMPLE 95

S-2-Amino-3-(imidazol-4-yl)-N-[5-(2-pyridin-4-yl-vinyl)-pyridin-3-yl]-propionamide hydrochloride The title compound was prepared by substituting bis (Boc)-histidine for Boc-homnophenyalanine in Example 16. MS (DCI/NH₃) m/z 335 (M+1)⁺, ¹H NMR (DMSO-d₆, 300 MHz) δ 10.95 (s, 1 H), 9.04 (s, 1 H), 8.74 (m, 1 H), 8.70 (m, 1 H), 8.52 (m, 2 H) 8.32 (m, 1 H) 8.08 (m, 2 H), 7.93 (d, J=16.61 Hz, 1 H), 7.50 (m, 2 H), 4.50 (m, 1H), 3.33 (m, 2H).

EXAMPLE 96

(1R)-2-(1H-indol-3-yl)-1-{[(5-isoquinolin-6-ylpyridin-3-yl)oxy]methyl}ethylamine The title compound was prepared as the trifluoroacetate salt by substituting R-Boc-tryptophanol for L-Boc-tryptophanol in Example 27. MS (ESI) m/e 395 (M+H)⁺; ¹H NMR (DMSO-d₆, 300 MHz) δ 11.02 (br s, 1H), 9.52 (s, 1H), 8.76 (d, J=3 Hz, 1H), 8.62 (d, J=8 Hz, 1H), 8.44–8.46 (m, 2H), 8.38 (d, J=9 Hz, 1H), 8.11–8.20 (m, 3H), 8.04–8.08 (m, 1H), 7.83–7.86 (m, 1H), 7.62 (d, J=9 Hz, 1H), 7.37–7.40 (m, 1H), 7.31 (d, J=3 Hz, 1H), 7.08–7.12 (m, 1H), 6.99–7.03 (m, 1H), 4.37–4.41 (m, 1H), 4.18–4.23 (m, 1H), 3.86–3.91 (m, 1H), 3.16–3.20 (m, 2H); Anal. Calcd for C₂₅H₂₂N₄O.2.65 TFA: C, 52.24; H, 3.57; N, 8.04;. Found: C, 52.26; H, 3.70; N, 7.42.

EXAMPLE 97

(1S)-5-{5-[2-Amino-3-(1H-indol-3-yl)-propoxy]-pyridin-3-yl}-1H-indazol-3-ylamine

Example 97A

2-Fluoro-5-(trimethylstannyl)benzonitrile

The desired product was prepared by substituting 5-bromo-2-fluorobenzonitrile for 6-bromoisoquinoline in Example 27A.

Example 97B (1S)-[2-[5-(3-Cyano-4-fluoro-phenyl)-pyridin-3-yloxy]-1-(1H-indol-3-ylmethyl)-ethyl]-carbamic acid tert-butyl ester The desired product was prepared by substituting Example 97A for in Example 27A in Example 27B.

Example 97C (1S)-[2-[5-(3-Amino-1H-indazol-5-yl)-pyridin-3-yloxy]-1-(1H-indol-3-ylmethyl)-ethyl]-carbamic acid tert-butyl ester A mixture of Example 97B (120 mg, 0.25 mmol) and 98% hydrazine (5 mL) was heated to reflux for 5 hours, poured over ice, diluted with brine, extracted with ethyl acetate, dried over MgSO₄, and concentrated. Purification by flash chromatography (7% MeOH/CH₂Cl₂) provided the desired product (103 mg, 84%).

Example 97D (1S)-5-{5-[2-Amino-3-(1H-indol-3-yl)-propoxy]-pyridin-3-yl}-1H-indazol-3-ylamine The desired product was prepared as the trifluoroacetate salt by substituting Example 97C for Example 27B in Example 27C. MS (ESI) m/e 399 (M+H)⁺; ¹H NMR (DMSO-d₆, 300 MHz) δ 3.17 (d, J=7.12 Hz, 2 H) 3.84 (m, 1 H) 4.18 (dd, J=10.51, 5.76 Hz, 1 H) 4.36 (m, 1 H) 7.12 (m, 4 H) 7.30 (d, J=2.37 Hz, 1 H) 7.38 (m, 1 H) 7.42 (s, 1 H) 7.63 (d, J=7.46 Hz, 1 H) 7.66 (s, 1 H) 8.18 (m, 4 H) 8.32 (d, J=2.71 Hz, 1 H) 8.57 (d, J=1.70 Hz, 1H) 11.04 (s, 1H) 11.92

(bs, 1H); Anal. Calcd for $C_{23}H_{22}N_6O$ 2.9 TFA: C, 47.44; H, 3.44; N, 11.53;. Found: C, 47.87; H, 3.49; N, 11.19.

EXAMPLE 98

(1S)-6-{5-[2-Amino-3-(1H-indol-3-yl)-propoxy]-pyridin-3-yl}-1H-indazol-3-ylamine The desired product was prepared as the trifluoroacetate salt by substituting 4-bromo-2-fluorobenzonitrile for 5-bromo-2-fluorobenzonitrile in Example 97. MS (ESI) m/e 399 (M+H)$^+$; $^1$H NMR (DMSO-d$_6$, 300 MHz) δ 3.16 (d, J=5.42 Hz, 2 H) 3.91 (d, J=30.85 Hz, 1H) 4.19 (s, 1 H) 4.35 (m, 1 H) 7.07 (m, 2 H) 7.34 (m, 3 H) 7.63 (m, 2 H) 7.71 (s, 1 H) 7.88 (d, J=8.14 Hz, 1 H) 8.17 (s, 4 H) 8.37 (d, J=2.37 Hz, 1 H) 8.60 (d, J=1.36 Hz, 1 H) 11.03 (s, 1 H) 11.93 (bs, 1 H); Anal. Calcd for $C_{23}H_{22}N_6O$.3.5 TFA: C, 45.18; H, 3.22; N, 10.54, F, 25.01; Found: C, 44.83; H, 3.19; N, 10.40, F, 25.01.

EXAMPLE 99

2-Amino-N-[(1S)-1-(1H-indol-3-ylmethyl)-2-(5-isoquinolin-6-yl-pyridin-3-yloxy)-ethyl]-acetamide

Example 99A

{[(1S)-1-(1H-Indol-3-ylmethyl)-2-(5-isoquinolin-6-yl-pyridin-3-yloxy)-ethylcarbamoyl]-methyl}-carbamic acid tert-butyl ester A solution of Example 27C (175 mg, 0.35 mmol), N-Boc-glycine (91 mg, 0.52 mmol), EDC (100 mg), iPr$_2$EtN (0.30 mL) and DMAP (10 mg) in CH$_2$Cl$_2$ (7 mL) was stirred at room temperature overnight, diluted with EtOAc, washed with water and brine, dried (MgSO$_4$), filtered, and concentrated. The residue was purified by flash column chromatography on silica gel with 3% methanol/CH$_2$Cl$_2$ to provide the desired product (112 mg, 58%).

Example 99B

2-Amino-N-[(1S)-1-(1H-indol-3-ylmethyl)-2-(5-isoquinolin-6-yl-pyridin-3-yloxy)-ethyl]-acetamide The desired product was prepared as the trifluoroacetate salt by substituting Example 99A for Example 27B in Example 27C. MS (ESI) m/e 452 (M+H)$^+$; $^1$H NMR (DMSO-d$_6$, 300 MHz) δ ppm 3.07 (m, 2 H) 3.58 (m, 2 H) 4.22 (m, 2 H) 4.48 (m, 1 H) 6.97 (t, J=6.95 Hz, 1 H) 7.06 (t, J=6.95 Hz, 1 H) 7.21 (d, J=2.37 Hz, 1 H) 7.34 (d, J=8.14 Hz, 1 H) 7.64 (d, J=7.46 Hz, 1 H) 7.86 (m, 1 H) 7.99 (bs, 2 H) 8.13 (d, J=6.10 Hz, 1 H) 8.19 (dd, J=8.82, 1.70 Hz, 1 H) 8.42 (m, 2 H) 8.51 (s, 1 H) 8.64 (d, J=6.10 Hz, 1 H) 8.67 (d, J=7.80 Hz, 1 H) 8.74 (d, J=1.70 Hz, 1 H) 9.60 (s, 1 H) 10.88 (s, 1 H); Anal. Calcd for $C_{27}H_{25}N_5O_2$.2.9 TFA: C, 50.37; H, 3.60; N, 8.95;. Found: C, 50.59; H, 3.43; N, 8.83.

EXAMPLE 100

(2S)-2-Amino-N-[(1S)-1-(1H-indol-3-ylmethyl)-2-(5-isoquinolin-6-yl-pyridin-3-yloxy)-ethyl]-propionamide The desired product was prepared by substituting L-Boc-alanine for N-Boc-glycine in Example 99. MS (ESI) m/e 466 (M+H)$^+$; $^1$H NMR (DMSO-d$_6$, 500 MHz) δ 1.36 (d, J=6.86 Hz, 3 H) 3.09 (m, 2 H) 3.88 (m, 1 H) 4.35 (m, 2 H) 4.46 (m, 1 H) 6.97 (t, J=7.33 Hz, 1 H) 7.05 (t, J=7.33 Hz, 1 H) 7.29 (d, J=1.87 Hz, 1 H) 7.35 (d, J=8.11 Hz, 1 H) 7.66 (d, J=7.80 Hz, 1 H) 8.30 (s, 1 H) 8.34 (bs, 2 H) 8.47 (dd, J=8.74, 1.56 Hz, 1 H) 8.53 (d, J=6.55 Hz, 1 H) 8.62 (d, J=1.87 Hz, 1 H) 8.70 (d, J=6.74, 1 H) 8.75 (d, J=6.24, 1 H) 8.89 (s, 1 H) 8.93 (s, 1 H) 9.01 (d, J=8.11 Hz, 1 H) 9.99 (s, 1 H) 10.98 (s, 1 H)

EXAMPLE 101

2-Dimethylamino-N-[(1S)-1-(1H-indol-3-ylmethyl)-2-(5-isoquinolin-6-yl-pyridin-3-yloxy)-ethyl]-acetamide The desired product was prepared by substituting N,N-dimethylglycine for N-Boc-glycine in Example 99A. MS (ESI) m/e 480 (M+H)$^+$; $^1$H NMR (DMSO-d$_6$, 500 MHz) δ 2.71 (s, 3 H) 2.77 (s, 3 H) 3.10 (m, 2 H) 3.95 (m, 2 H) 4.40 (m, 2 H) 4.52 (m, 1 H) 6.97 (t, J=7.33 Hz, 1 H) 7.05 (t, J=7.49 Hz, 1 H) 7.28 (s, 1 H) 7.34 (d, J=8.11 Hz, 1 H) 7.67 (d, J=7.80 Hz, 1 H) 8.38 (s, 1 H) 8.50 (d, J=8.73 Hz, 1 H) 8.55 (d, J=6.24 Hz, 1 H) 8.67 (d, J=1.87 Hz, 1 H) 8.71 (d, J=8.73 Hz, 1 H) 8.75 (d, J=6.55 Hz, 1 H) 8.92 (s, 1 H) 8.98 (s, 1 H) 9.34 (d, J=8.42 Hz, 1 H) 10.00 (s, 1 H) 11.02 (s, 1 H).

EXAMPLE 102

(1S)-1-(1H-Indol-3-ylmethyl)-2-[5-(3-methyl-1H-indazol-5-yl)-pyridin-3-yloxy]-ethylamine

Example 102A

A solution of 5-bromo-2-fluorobenzaldehyde (24.75 g; 122 mmol) in Et$_2$O (125 mL) at 0° C. was treated with 3.0 M MeMgBr in Et$_2$O (43 mL, 129 mmol), stirred for 30 min., carefully diluted with water then acidified with 10% HCl (aq). The aqueous was extracted with Et$_2$O, rinsed successively with 10% HCl (aq), water, and brine, dried (MgSO$_4$), and evaporated to give the desired product (26.6 g; 99%) of sufficient purity to carry on to the next step.

Example 102B 1-(5-Bromo-2-fluoro-phenyl)-ethanone

A solution of Example 102A (26.6 g; 121 mmol) and manganese(IV) oxide (53 g; 610 mmol) in p-dioxane (500 mL) was heated at reflux for 4 hrs., cooled, filtered through Celite®, evaporated, and purified by flash chromatography (5–10% Et$_2$O/hexane) to yield the desired product as a nearly colorless oil that solidified upon standing (20.5 g; 78%).

Example 102C

5-Bromo-3-methyl-1H-indazole

A mixture of 102B (10 g, 46 mmol) and 98% hydrazine (25 mL) was heated to reflux for 9 hours, and poured over ice. The precipitate was collected and purified by flash chromatography (1:1 Et$_2$O:hexane) to give the desired product as a white solid (5.8 g, 60%).

Example 102D

3-Methyl-5-trimethylstannanyl-1H-indazole

A mixture of Example 102C (10.08 g, 47.8 mmol), hexamethyl-di-tin 2 (18 g, 55 mmol) and tetrakis(triphenylphosphine)palladium (5.5 g, 4.8 mmol) in toluene (100 ml) was stirred at 95° C. for 6 h. The mixture was then evaporated and the residue was taken into ethyl acetate (300 ml), washed with saturated sodium bicarbonate (100 ml), water (100 ml) and brine (100 ml). The ethyl acetate was evaporated off and the residue was purified by flash column chromatography on silica gel, eluting with 1:4 ethyl acetate/hexanes to give 11.2 g desired product (80%). MS: (ESI) m/z 409 (M+H)$^+$.

Example 102E (1S)-{1-(1H-Indol-3-ylmethyl)-2-[5-(3-methyl-1H-indazol-5-yl)-pyridin-3-yloxy]-ethyl}-carbamic acid tert-butyl ester The desired product was prepared by substituting Example Example 102D for Example 27A in Example 27B.

Example 102F (1S)-1-(1H-Indol-3-ylmethyl)-2-[5-(3-methyl-1H-indazol-5-yl)-pyridin-3-yloxy]-ethylamine The desired product was prepared as the trifluoroacetate salt by substituting Example 102E for Example 27B in Example 27C. MS (ESI) m/e 398 (M+H)$^+$; $^1$H NMR (DMSO-d$_6$, 300 MHz) δ 2.55 (s, 3 H) 2.79 (dd, J=14.07, 7.29 Hz, 1 H) 2.99 (dd, J=14.07, 7.29 1 H) 3.32 (s, 2H) 3.40 (m, 1 H) 4.03 (m, 2 H) 6.95 (t, J=7.46 Hz, 1 H) 7.05 (t, J=6.95 Hz, 1 H) 7.21 (d, J=2.37 Hz, 1 H) 7.34 (d, J=7.80 Hz, 1 H) 7.56 (m, 2 H) 7.67 (m, 2 H) 8.08 (s, 1 H) 8.26 (d, J=2.37 Hz, 1 H) 8.54 (d, J=2.03 Hz, 1 H) 10.85 (s, 1 H) 12.73 (s, 1 H); Anal. Calcd for C$_{24}$H$_{23}$N$_5$O.2.25 HCl: C, 59.62; H, 5.31; N, 14.60;. Found: C, 59.62; H, 5.31; N, 14.28.

EXAMPLE 103

(1S)-1-(1H-Indol-3-ylmethyl)-2-{5-[3-(1H-pyrrol-2-yl)-1H-indazol-5-yl]-pyridin-3-yloxy}-ethylamine

Example 103A

5-Bromo-2-fluoro-benzoic acid

A mixture of 5-bromo-2-fluorobenzaldehyde (810 mg; 4.0 mmol), 15% NaOH (aq.) (3 mL), MeOH (5 mL), and 30% H$_2$O$_2$ (5 mL) was stirred at r.t. for 2 hrs., then acidified with 10% HCl (aq.). The resulting white solid was collected, rinsed with water, and dried to give the desired product (670 mg; 77%).

Example 103B

5-Bromo-2-fluoro-benzoyl Chloride

Example 103A (665 mg; 3.0 mmol) in thionyl chloride (7 mL) was heated at reflux for 2 hrs., concentrated, and azeotroped with toluene to give a colorless oil that was carried on with no further purification.

Example 103C (5-Bromo-2-fluoro-phenyl)-(1H-pyrrol-2-yl)-methanone

A solution of 103B (720 mg; 3.0 mmol), and pyrrole (203 mg; 3.0 mmol) in 1,2-dichloroethane (10 mL) at 0° C. was treated portionwise with AlCl$_3$, stirred overnight while gradually warming to r.t., treated with ice and 1 N HCl, stirred for 1.5 hrs., and extracted with CH$_2$Cl$_2$. The extracts were rinsed with water and saturated NaHCO$_3$ (aq.), dried over Na$_2$SO$_4$, concentrated, and isolated by flash chromatography (10% EtOAc/hexane) to give the desired product as a purple solid (252 mg; 31%).

Example 103D

5-Bromo-3-(1H-pyrrol-2-yl)-1H-indazole

The desired product was prepared by substituting Example 103C for Example 102B in Example 102C.

Example 103E (1S)-1-(1H-Indol-3-ylmethyl)-2-{5-[3-(1H-pyrrol-2-yl)-1H-indazol-5-yl]-pyridin-3-yloxy}-ethylamine The desired product was prepared as the trifluoroacetate salt by substituting Example 103D for 6-bromoisoquinoline in Example 27. MS (ESI) m/e 449 (M+H)$^+$; $^1$H NMR (DMSO-d$_6$, 300 MHz) δ 3.18 (m, 2 H) 3.87 (m, 1 H) 4.20 (dd, J=10.51, 5.76 Hz, 1 H) 4.38 (m, 1 H) 6.21 (m, 1 H) 6.86 (m, 2 H) 7.01 (t, J=7.46 Hz, 1 H) 7.10 (t, J=7.46 Hz, 1 H) 7.30 (d, J=2.03 Hz, 1 H) 7.38 (d, J=8.14 Hz, 1 H) 7.67 (m, 4 H) 8.15 (bs, 2 H) 8.26 (s, 1 H) 8.35 (d, J=2.37 Hz, 1 H) 8.68 (s, 1 H) 11.03 (s, 1 H) 11.38 (s, 1 H) 13.10 (bs, 1 H); Anal. Calcd for C$_{27}$H$_{24}$N$_6$O.2.5 TFA: C, 52.39; H, 3.64; N, 11.46;. Found: C, 52.26; H, 3.67; N, 11.39.

EXAMPLE 104

(1S)-1-(1H-Indol-3-ylmethyl)-2-[5-(3-phenyl-1H-indazol-5-yl)-pyridin-3-yloxy]-ethylamine The desired product was prepared as the trifluoroacetate salt by substituting phenyl magnesium bromide for methyl magnesium bromide in Example 102. MS (ESI) m/e 460 (M+H)$^+$; $^1$H NMR (300 MHz, DMSO-D6) δ ppm 3.17 (m, 2 H) 3.87 (m, 1 H) 4.19 (dd, J=10.51, 5.76 Hz, 1 H) 4.38 (m, 1 H) 7.00 (t, J=7.46 Hz, 1 H) 7.09 (t, J=7.46 Hz, 1 H) 7.30 (d, J=2.37 Hz, 1 H) 7.39 (m, 1 H) 7.44 (d, J=7.12 Hz, 1 H) 7.54 (m, J=7.46, 7.46 Hz, 2 H) 7.62 (d, J=7.46 Hz, 1 H) 7.72 (s, 2 H) 7.76 (m, 1 H) 8.05 (s, 1 H) 8.08 (s, 1 H) 8.16 (m, 2 H) 8.30 (s, 1 H) 8.36 (d, J=2.71 Hz, 1 H) 8.68 (d, J=1.70 Hz, 1 H) 11.03 (s, 1 H) 13.45 (bs, 1 H); Anal. Calcd for C$_{27}$H$_{24}$N$_6$O.3 TFA.2H$_2$O: C, 53.24; H, 4.08; N, 8.87;. Found: C, 52.91; H, 3.68; N, 8.80.

EXAMPLE 105

(1S)-2-[5-(3-Cyclopropyl-1H-indazol-5-yl)-pyridin-3-yloxy]-1-(1H-indol-3-ylmethyl)-ethylamine The desired product was prepared as the trifluoroacetate salt by substituting cyclopropyl magnesium bromide for methyl magnesium bromide in Example 102. MS (ESI) m/e 424 (M+H)$^+$; $^1$H NMR (300 MHz, DMSO-D6) δ ppm 1.02 (m, 4 H) 2.36 (m, 1 H) 3.15 (m, 2 H) 3.86 (m, 1 H) 4.19 (dd, J=10.68, 5.93 Hz, 1 H) 4.37 (dd, J=10.68, 3.22 Hz, 1 H) 7.01 (t, J=7.46 Hz, 1 H) 7.10 (t, J=6.95 Hz, 1 H) 7.30 (d, J=2.37 Hz, 1 H) 7.38 (d, J=8.14 Hz, 1 H) 7.56 (d, J=8.48 Hz, 1 H) 7.65 (m, 2 H) 7.73 (m, 1 H) 8.12 (s, 1 H) 8.19 (m, 2 H) 8.33 (d, J=2.37 Hz, 1 H) 8.63 (d, J=1.36 Hz, 1 H) 11.03 (d, J=2.03 Hz, 1 H) 12.73 (m, 1 H); Anal. Calcd for C$_{26}$H$_{25}$N$_5$O.2.6 TFA: C, 52.05; H, 3.86; N, 9.73;. Found: C, 52.03; H, 3.89; N, 9.69.

EXAMPLE 106

(1S)-2-[5-(3-Ethyl-1H-indazol-5-yl)-pyridin-3-yloxy]-1-(1H-indol-3-ylmethyl)-ethylamine The desired product was prepared as the trifluoroacetate salt by substituting ethyl magnesium bromide for methyl magnesium bromide in Example 102. MS (ESI) m/e 412

(M+H)⁺; ¹H NMR (300 MHz, DMSO-D6) δ ppm 1.35 (t, J=7.63 Hz, 3 H) 2.99 (q, J=7.57 Hz, 2 H) 3.17 (m, 2 H) 3.86 (m, 1 H) 4.19 (dd, J=10.85, 6.10 Hz, 1 H) 4.37 (m, 1 H) 7.01 (t, J=7.46 Hz, 1 H) 7.11 (t, J=7.46 Hz, 1 H) 7.30 (d, J=2.37 Hz, 1 H) 7.38 (d, J=7.80 Hz, 1 H) 7.63 (m, 3 H) 7.72 (m, 1 H) 8.08 (s, 1 H) 8.16 (m, 2 H) 8.33 (d, J=2.71 Hz, 1 H) 8.63 (d, J=1.70 Hz, 1 H) 11.04 (d, J=2.03 Hz, 1 H) 12.80 (m, 1 H); Anal. Calcd for $C_{25}H_{25}N_5O$.2.7 TFA: C, 50.76; H, 3.88; N, 9.74;. Found: C, 51.09; H, 3.88; N, 9.66.

EXAMPLE 107

(1S)-1-(1H-Indol-3-ylmethyl)-2-{5-[3-(1-methyl-1H-imidazol-2-yl)-1H-indazol-5-yl]-pyridin-3-yloxy}-ethylamine The desired product was prepared as the trifluoroacetate salt by substituting N-methyl-2-imidazolyl lithium chloride for methyl magnesium bromide in Example 102. MS (ESI) m/e 464 (M+H)⁺; ¹H NMR (400 MHz, DMSO-D6) δ ppm 3.18 (m, 2 H) 3.84 (s, 1 H) 4.07 (s, 3 H) 4.20 (dd, J=10.59, 5.98 Hz, 1 H) 4.36 (m, 1 H) 7.00 (t, J=7.36 Hz, 1 H) 7.09 (t, J=7.36 Hz, 1 H) 7.18 (s, 1 H) 7.31 (d, J=2.15 Hz, 1 H) 7.37 (m, 2 H) 7.64 (m, 2 H) 7.72 (s, 2 H) 8.33 (m, 3 H) 8.56 (d, J=1.53 Hz, 1 H) 8.63 (s, 1 H) 11.06 (s, 1 H) 13.56 (s, 1 H).

EXAMPLE 108

(1S)-1-(1H-Indol-3-ylmethyl)-2-[5-(3-thiazol-2-yl-1H-indazol-5-yl)-pyridin-3-yloxy]-ethylamine The desired product was prepared as the trifluoroacetate salt by substituting 2-thiozolyl lithium chloride for methyl magnesium bromide in Example 102. MS (ESI) m/e 467 (M+H)⁺; ¹H NMR (500 MHz, DMSO-D6) δ ppm 3.19 (d, J=7.18 Hz, 2 H) 3.86 (m, 1 H) 4.22 (dd, J=10.29, 5.93 Hz, 1 H) 4.38 (dd, J=10.45, 2.65 Hz, 1 H) 7.01 (t, J=7.49 Hz, 1 H) 7.09 (t, J=7.49 Hz, 1 H) 7.31 (d, J=1.56 Hz, 1 H) 7.38 (d, J=8.11 Hz, 1 H) 7.64 (d, J=7.80 Hz, 1 H) 7.73 (s, 1 H) 7.78 (s, 2 H) 7.79 (d, J=3.12 Hz, 1 H) 8.04 (d, J=3.43 Hz, 1 H) 8.28 (s, 2 H) 8.38 (d, J=2.18 Hz, 1 H) 8.60 (s, 2 H) 11.04 (s, 1 H) 13.74 (s, 1 H)

EXAMPLE 109

(1S)-2-{5-[3-(1H-Imidazol-2-yl)-1H-indazol-5-yl]-pyridin-3-yloxy}-1-(1H-indol-3-ylmethyl)-ethylamine

Example 109A (1S)-[1-(1H-Indol-3-ylmethyl)-2-(5-{3-[1-(2-trimethylsilanyl-ethoxymethyl)-1H-imidazol-2-yl]-1H-indazol-5-yl}-pyridin-3-yloxy)-ethyl]-carbamic acid tert-butyl ester The desired product was prepared as the trifluoroacetate salt by substituting N-[2-trimethylsilanyl)ethoxy]methyl)-2-imidazolyl lithium chloride for methyl magnesium bromide in Example 102 without doing the last step.

Example 109B (1S)-2-{5-[3-(1H-Imidazol-2-yl)-1H-indazol-5-yl]-pyridin-3-yloxy}-1-(1H-indol-3-ylmethyl)-ethylamine A solution of Example 109A (40 mg; 0.06 mmol) in MeOH (4 mL) was treated with conc. HCl (1 mL) and heated at reflux for 6 hrs., concentrated and purified by reverse phase HPLC on a C18 column with 0–100% $CH_3CN/H_2O$/0.1% TFA to provide the desired product as the trifluoroacetate salt. MS (ESI) m/e 450 (M+H)⁺; ¹H NMR (500 MHz, DMSO-D6) δ ppm 3.19 (d, J=7.17 Hz, 2 H) 3.86 (s, 1 H) 4.22 (dd, J=10.45, 5.77 Hz, 1 H) 4.37 (dd, J=10.45, 2.96 Hz, 1 H) 7.00 (t, J=7.49 Hz, 1 H) 7.09 (t, J=7.49 Hz, 1 H) 7.30 (d, J=2.18 Hz, 1 H) 7.38 (d, J=8.11 Hz, 1 H) 7.63 (d, J=8.11 Hz, 1 H) 7.76 (s, 1 H) 7.83 (s, 1 H) 7.86 (s, 2 H) 8.26 (bs, 3 H) 8.39 (d, J=2.50 Hz, 1 H) 8.61 (s, 1 H) 8.72 (s, 1 H) 11.04 (s, 1 H) 14.36 (s, 1 H)

EXAMPLE 110

(1S)-1-(1H-Indol-3-ylmethyl)-2-[5-(3-thiophen-2-yl-1H-indazol-5-yl)-pyridin-3-yloxy]-ethylamine The desired product was prepared by substituting 2-thiophenyl lithium chloride for methylmagnesium bromide in Example 102. MS (ESI) m/e 466 (M+H)⁺; ¹H NMR (400 MHz, DMSO-D6) δ ppm 3.21 (d, J=7.06 Hz, 2 H) 3.86 (bs, 1 H) 4.23 (dd, J=10.43, 5.83 Hz, 1 H) 4.38 (m, 1 H) 7.00 (t, J=7.52 Hz, 1 H) 7.10 (t, J=7.06 Hz, 1 H) 7.23 (dd, J=5.22, 3.68 Hz, 1 H) 7.31 (d, J=2.15 Hz, 1 H) 7.39 (d, J=7.98 Hz, 1 H) 7.59 (d, J=6.14 Hz, 1 H) 7.64 (d, J=7.98 Hz, 1 H) 7.73 (m, 3 H) 7.91 (d, J=2.76 Hz, 1 H) 8.34 (m, 4 H) 8.67 (s, 1 H) 11.06 (s, 1 H) 13.39 (s, 1 H)

EXAMPLE 111

(1S)-1-(1H-Indol-3-ylmethyl)-2-[5-(3-morpholin-4-yl-1H-indazol-5-yl)-pyridin-3-yloxy]-ethylamine

Example 111A

5-Bromo-3-morpholin-4-yl-1H-indazole

The reaction between Example 35A and morpholine was carried out according to the procedure described by U. Wrzeciono, K. Majewska, J. Dudzinska-Usarewicz, M. Bernas, *Pharmzie*, 1986, 41, 472–474.

Example 111B (1S)-1-(1H-Indol-3-ylmethyl)-2-[5-(3-morpholin-4-yl-1H-indazol-5-yl)-pyridin-3-yloxy]-ethylamine The desired product was prepared by substituting Example 111A for 6-bromoisoquinoline in Example 27. MS (ESI) m/e 469 (M+H)⁺; ¹H NMR (300 MHz, DMSO-D6) δ ppm 3.16 (d, J=7.12 Hz, 2 H) 3.35 (m, 4 H) 3.81 (m, 4 H) 3.88 (m, 1 H) 4.19 (dd, J=10.68, 5.93 Hz, 1 H) 4.35 (m, 1 H) 7.01 (t, J=7.46 Hz, 1 H) 7.10 (t, J=7.46 Hz, 1 H) 7.30 (d, J=2.37 Hz, 1 H) 7.38 (d, J=7.80 Hz, 1 H) 7.48 (d, J=8.82 Hz, 1 H) 7.62 (m, 2 H) 7.72 (m, 1 H) 8.09 (s, 1 H) 8.17 (m, 2 H) 8.33 (d, J=2.71 Hz, 1 H) 8.65 (d, J=1.70 Hz, 1 H) 11.03 (s, 1 H) 12.21 (s, 1 H); Anal. Calcd for $C_{27}H_{28}N_6O_2$.3.4 TFA: C, 47.41; H, 3.70; N, 9.82;. Found: C, 47.10; H, 3.86; N, 9.95.

EXAMPLE 112

(1S)-2-[5-(1,3-Dimethyl-1H-indazol-5-yl)-pyridin-3-yloxy]-1-(1H-indol-3-ylmethyl)-ethylamine

Example 112A

5-Bromo-1,3-dimethyl-1H-indazole

Example 102C (500 mg; 2.37 mmol) was added to a mixture of 60% NaH (115 mg; 2.84 mmol) in DMF (10 mL).

After 15 min. at r.t. iodomethane (456 mg; 3.21 mmol) was added, the reaction was stirred for 2 hrs then diluted with water and extracted with EtOAc. The extracts were rinsed with water and brine, dried (MgSO$_4$), evaporated, and isolated by flash chromatography (1:1 Et$_2$O:hexane) to give the desired product (360 mg; 67%).

Example 112B

The desired product was prepared as the trifluoroacetate salt by substituting Example 112A for Example 6-bromoisoquinoline in Example 27. MS (ESI) m/e 412 (M+H)$^+$; $^1$H NMR (300 MHz, DMSO-D6) δ ppm 2.54 (s, 3 H) 3.18 (m, 2 H) 3.86 (s, 1 H) 4.00 (s, 3 H) 4.20 (dd, J=10.51, 6.10 Hz, 1 H) 4.37 (m, 1 H) 7.01 (t, J=7.46 Hz, 1 H) 7.10 (t, J=7.12 Hz, 1 H) 7.30 (d, J=2.37 Hz, 1 H) 7.39 (d, J=7.80 Hz, 1 H) 7.63 (d, J=7.80 Hz, 1 H) 7.73 (m, 2 H) 8.08 (s, 1 H) 8.18 (m, 3 H) 8.34 (d, J=2.71 Hz, 1 H) 8.66 (d, J=1.70 Hz, 1 H) 11.04 (s, 1 H); Anal. Calcd for C$_{25}$H$_{25}$N$_5$O.2.8 TFA: C, 50.29; H, 3.83; N, 9.58;. Found: C, 50.36; H, 3.84, N, 9.60.

EXAMPLE 113

(1S)-1-(1H-Indol-3-ylmethyl)-2-[3-(3-methyl-1H-indazol-5-yl)-phenoxy]-ethylamine The desired product was prepared as the trifluoroacetate salt by substituting 3-bromophenol for 3-bromo-5-hydroxypyridine in Example 102. MS (ESI) m/e 397 (M+H)$^+$; $^1$H NMR (300 MHz, DMSO-D6) δ ppm 2.54 (s, 3 H) 3.17 (m, 2 H) 3.81 (m, 1 H) 4.09 (dd, J=10.51, 5.76 Hz, 1 H) 4.25 (dd, J=10.51, 3.05 Hz, 1 H) 6.93 (m, 1 H) 7.01 (t, J=7.46 Hz, 1 H) 7.10 (t, J=7.46 Hz, 1 H) 7.28 (m, 2 H) 7.37 (m, 3 H) 7.52 (d, J=8.48 Hz, 1 H) 7.61 (m, 2 H) 7.93 (s, 1 H) 8.15 (bs, 2 H) 11.03 (s, 1 H) 12.62 (bs, 1 H)

EXAMPLE 114

(1S)-1-(1H-Indol-3-ylmethyl)-2-{5-[3-(4-methyl-piperazin-1-yl)-1H-indazol-5-yl]-pyridin-3-yloxy}-ethylamine

Example 114A

5-Bromo-3-(4-methyl-piperazin-1-yl)-1H-indazole

The reaction between Example 35A and N-methyl piperazine was carried out according to the procedure described by U. Wrzeciono, K. Majewska, J. Dudzinska-Usarewicz, M. Bernas, *Pharmzie,* 1986, 41, 472–474.

Example 114B (1S)-1-(1H-Indol-3-ylmethyl)-2-{5-[3-(4-methyl-piperazin-1-yl)-1H-indazol-5-yl]-pyridin-3-yloxy}-ethylamine The desired product was prepared by substituting Example 114A for 6-bromoisoquinoline in Example 27. MS (ESI) m/e 482 (M+H)$^+$; $^1$H NMR (300 MHz, DMSO-D6) δ ppm 2.54 (s, 3 H) 2.90 (m, 2 H) 3.21 (m, 4 H) 3.54 (m, 2 H) 3.83 (m, 1 H) 4.06 (m, 2 H) 4.19 (dd, J=10.68, 5.93 Hz, 1 H) 4.35 (dd, J=10.51, 2.71 Hz, 1 H) 7.01 (t, J=6.95 Hz, 1 H) 7.10 (t, J=7.12 Hz, 1 H) 7.30 (d, J=2.03 Hz, 1 H) 7.38 (d, J=8.14 Hz, 1 H) 7.51 (d, J=8.82 Hz, 1 H) 7.65 (m, 3 H) 8.15 (s, 1 H) 8.21 (m, 2 H) 8.33 (d, J=2.71 Hz, 1 H) 8.66 (d, J=1.70 Hz, 1 H) 11.04 (s, 1 H) 12.36 (s, 1 H); Anal. Calcd for C$_{28}$H$_{31}$N$_7$O.4.45 TFA: C, 44.81; H, 3.61; N, 9.91;. Found: C, 44.83; H, 3.53, N, 9.97.

EXAMPLE 115

(1S)-(5-{5-[2-Amino-3-(1H-indol-3-yl)-propoxy]-pyridin-3-yl}-1H-indazol-3-yl)-dimethyl-amine

Example 115A (5-Bromo-1H-indazol-3-yl)-dimethyl-amine

The reaction between Example 35A and dimethylamine was carried out according to the procedure described by U. Wrzeciono, K. Majewska, J. Dudzinska-Usarewicz, M. Bernas, *Pharmzie,* 1986, 41, 472–474.

Example 115B (1S)-(5-{5-[2-Amino-3-(1H-indol-3-yl)-propoxy]-pyridin-3-yl}-1H-indazol-3-yl)-dimethyl-amine The desired product was prepared by substituting Example 115A for 6-bromoisoquinoline in Example 27. MS (ESI) m/e 427 (M+H)$^+$; $^1$H NMR (300 MHz, DMSO-D6) δ ppm 3.04 (s, 6 H) 3.16 (m, 2 H) 3.86 (s, 1 H) 4.19 (m, 1 H) 4.36 (m, 1 H) 7.01 (t, J=6.95 Hz, 1 H) 7.10 (t, J=7.12 Hz, 1 H) 7.30 (d, J=2.37 Hz, 1 H) 7.38 (d, J=8.14 Hz, 1 H) 7.45 (d, J=8.82 Hz, 1 H) 7.61 (m, 2 H) 7.73 (s, 1 H) 8.07 (s, 1 H) 8.17 (m, 2 H) 8.33 (d, J=2.37 Hz, 1 H) 8.62 (d, J=1.36 Hz, 1 H) 11.03 (s, 1 H) 12.04 (s, 1 H); Anal. Calcd for C$_{25}$H$_{26}$N$_6$O.3.5 TFA: C, 46.55; H, 3.60; N, 10.18;. Found: C, 46.71; H, 3.65, N, 10.02.

EXAMPLE 116

(1S)-(4-(5-(2-Amino-3-(1H-indol-3-yl)-propoxy)-pyridin-3-yl)-benzyl)-phenyl-amine

Example 116A (1S)-[2-[5-(4-Formyl-phenyl)-pyridin-3-yloxy]-1-(1H-indol-3-ylmethyl)-ethyl]-carbamic acid tert-butyl ester The desired product was prepared by substituting 4-formylphenylboronic acid for 4-cyanophenylboronice acid in Example 22. MS: (ESI) m/z 472 (M+H)$^+$.

Example 116B (1S)-{1-(1H-Indol-3-ylmethyl)-2-[5-(4-phenylaminomethyl-phenyl)-pyridin-3-yloxy]-ethyl}-carbamic acid tert-butyl ester A solution of Example 116A (0.03 g, 0.06 mmol) in 2 mL of MeOH was cooled to 0° C. then treated with aniline (0.018 g 0.2 mmol), NaBH$_3$CN (0.004 g, 0.06 mmol) and AcOH (1 ml). The mixture was allowed to warm to room temperature overnight. The mixture was diluted with ethyl acetate (20 ml), washed with water (10 ml) and brine (10 ml). The ethyl acetate was evaporated off and the residue was used without further purification.

Example 116C (1S)-(4-(5-(2-Amino-3-(1H-indol-3-yl)-propoxy)-pyridin-3-yl)-benzyl)-phenyl-amine The desired product was prepared by substituting Example 116B for Example 27B in Example 27C. MS: (ESI) (M+H)$^+$ m/z=449. 1H NMR (500 MHz, DMSO-D6) δ ppm 3.82 (m, 7 H) 4.18 (m, 1 H) 4.32 (d, J=4.06 Hz, 2 H) 6.55 (d, J=32.76 Hz, 1 H) 6.59 (d, J=7.49 Hz, 1 H) 6.89 (d, J=7.49 Hz, 1 H) 7.04 (m, 3 H) 7.18 (m, 1H) 7.29 (d, J=2.50 Hz, 1H) 7.37 (d, J=7.80 Hz, 1 H) 7.48 (d, J=8.11 Hz, 1 H) 7.62 (m, 3 H) 8.31 (bs, 3 H) 8.52 (d, J=1.56 Hz, 1 H) 11.04 (d, J=1.87 Hz, 1 H)

EXAMPLE 117

(1S)-(4-(5-(2-Amino-3-(1H-indol-3-yl)-propoxy)-pyridin-3-yl)-phenyl)-methanol

Example 117A (1S)-{2-[5-(4-Hydroxymethyl-phenyl)-pyridin-3-yloxy]-1-phenyl-ethyl}-carbamic acid tert-butyl ester Example 116A (0.03 g, 0.06 mmol) was dissolved in 2 mL of MeOH and cooled to 0° C., then treated with NaBH$_4$ (0.003 g, 0.08 mmol). The mixture was allowed to warm to room temperature over 2 h. The mixture was diluted with ethyl acetate (20 ml), washed with water (10 ml) and brine (10 ml). The ethyl acetate was evaporated off and the residue was used without further purification.

Example 117B (1S)-(4-(5-(2-Amino-3-(1H-indol-3-yl)-propoxy)-pyridin-3-yl)-phenyl)-methanol The desired product was prepared by substituting Example 117A for Example 27B in Example 27C. MS: (ESI) m/z 374 (M+H)$^+$; 1H NMR (500 MHz, DMSO-D6) δ ppm 3.15 (m, 4 H) 3.72 (m, 1 H) 4.16 (dd, J=10.29, 5.93 Hz, 1 H) 4.29 (m, 1 H) 4.55 (s, 2 H) 5.29 (s, 1 H) 6.99 (t, J=7.02 Hz, 1 H) 7.09 (t, J=7.02 Hz, 1 H) 7.28 (d, J=2.18 Hz, 1 H) 7.37 (d, J=8.11 Hz, 1 H) 7.43 (d, J=8.42 Hz, 2 H) 7.59 (m, 1 H) 7.64 (dd, J=10.61, 8.42 Hz, 3 H) 8.30 (d, J=2.81 Hz, 1 H) 8.51 (d, J=1.56 Hz, 1 H) 11.03 (s, 1 H)

EXAMPLE 118

(1S)-2-(5-(4-Fluoro-phenyl)-pyridin-3-yloxy)-1-(1H-indol-3-ylmethyl)-ethylamine

The desired product was prepared by substituting 4-fluorophenylboronic acid for 4-cyanophenylboronice acid in Example 22. MS: (ESI) m/z 362 (M+H)$^+$; 1H NMR (500 MHz, DMSO-D6) δ ppm 3.09 (m, 2 H) 3.17 (d, J=4.68 Hz, 1 H) 3.71 (s, 1 H) 4.12 (dd, J=10.29, 6.24 Hz, 1 H) 4.26 (dd, J=10.29, 3.43 Hz, 1 H) 6.99 (t, J=7.49 Hz, 1 H) 7.09 (m, 1 H) 7.26 (d, J=2.18 Hz, 1 H) 7.34 (m, 3 H) 7.59 (m, 2 H) 7.74 (m, 2 H) 8.32 (d, J=2.50 Hz, 1 H) 8.50 (d, J=1.87 Hz, 1 H) 10.97 (s, 1 H).

EXAMPLE 119

(1S)-4-(5-(2-Amino-3-(1H-indol-3-yl)-propoxy)-pyridin-3-yl)-benzoic acid

The desired product was prepared by substituting 4-hydroxycarbonylphenylboronic acid for 4-cyanophenylboronice acid in Example 22. MS (ESI) m/z 388 (M+H)$^+$; 1H NMR (500 MHz, DMSO-D6) δ ppm 3.17 (m, 1 H) 3.84 (m, 1 H) 4.20 (m, 1 H) 4.35 (m, 1 H) 7.00 (t, J=6.86 Hz, 1 H) 7.10 (t, J=7.02 Hz, 1 H) 7.30 (d, J=2.18 Hz, 1 H) 7.38 (d, J=8.11 Hz, 1 H) 7.63 (d, J=7.49 Hz, 1 H) 7.68 (m, 1 H) 7.83 (d, J=8.42 Hz, 1 H) 8.04 (m, 2 H) 8.26 (s, 3 H) 8.38 (d, J=2.50 Hz, 1 H) 8.59 (d, J=1.87 Hz, 1 H) 11.02 (d, J=1.87 Hz, 1 H)

EXAMPLE 120

(1S)-2-(3-Bromo-5-isoquinolin-6-yl-phenoxyoxy)-1-(1H-indol-3-ylmethyl)-ethylamine Step 1.

Example 120A (2S)-[1-(3,5-Dibromo-phenoxymethyl)-2-(1H-indol-3-yl)-ethyl]-carbamic acid tert-butyl ester A solution of 3,5-dibromo-phenol (1 g, 4.1 mmol), (2-hydroxy-1-phenyl-ethyl)-carbamic acid tert-butyl ester (1.2 g, 4.1 mmol), and triphenylphosphine (1.6 g, 2 mmol) in THF (30 mL) was stirred at 0° C. for 30 min. To the mixture was added a solution of di-t-butyl azidodicarboxylate (1.45 g, 9.2 mmol) in 5 ml of THF. The mixture was allowed to warm to room temperature then stirred at room temperature for 20 h. The THF was evaporated off and the residue was taken into ethyl acetate (75 ml), washed with saturated sodium bicarbonate (50 ml) water (50 ml) and brine (50 ml). The ethyl acetate was evaporated of and the residue was purified by flash column chromatography on silica gel, eluting with a solvent gradient of 1:4 to 1:1 ethyl acetate/hexane. Recovered 1.33 g of product (64%).

Example 120B (2S)-[1-(3-Bromo-5-isoquinolin-6-yl-phenoxymethyl)-2-(1H-indol-3-yl)-ethyl]-carbamic acid tert-butyl ester A solution of Example 120A above (0.6 g, 01.1 mmol) and 6-trimethylstannanyl-isoquinoline (0.26 g, 1 mmol) in 5 mL of DMF was treated with Pd$_2$(dba)$_3$ (0.1 g, 0.1 mmol), P(o-tol)$_3$ (0.07 g, 0.2 mmol), and TEA (0.3 mL, 2.3 mmol). The reaction was heated to 95° C. for 6.5 h, then cooled and diluted with ethyl acetate (75 ml), washed with saturated sodium bicarbonate (50 ml) water (50 ml) and brine (50 ml). The ethyl acetate was evaporated off and the residue was purified by flash column chromatography on silica gel, eluting with a solvent gradient of 1:4 to 1:1 ethyl acetate/hexane.

0.2 g of product (30%). MS (ESI) m/z 572 (M+H)$^+$.

Example 120C (1S)-2-(3-Bromo-5-isoquinolin-6-yl-phenoxyoxy)-1-(1H-indol-3-ylmethyl)-ethylamine The desired product was prepared by substituting Example 120B for Example 27B in Example 27C. MS (ESI) m/z 472 (M+H)$^+$; $^1$H NMR (500 MHz, DMSO-D6) δ ppm 2.87 (d, J=6.55 Hz, 1 H) 3.00 (d, J=6.55 Hz, 1 H) 3.47 (m, 2 H) 3.99 (dd, J=9.67, 6.24 Hz, 1 H) 4.07 (d, J=4.37 Hz, 1 H) 6.96 (t, J=7.02 Hz, 1 H) 7.06 (t, J=7.02 Hz, 1 H) 7.22 (d, J=2.18 Hz, 1 H) 7.24 (m, 1 H) 7.35 (d, J=8.11 Hz, 1 H) 7.41 (m, 1 H) 7.58 (d, J=7.80 Hz, 1 H) 7.62 (s, 1 H) 7.89 (d, J=5.93 Hz, 1 H) 8.00 (dd, J=8.42, 1.87 Hz, 1 H) 8.21 (d, J=8.73 Hz, 1 H) 8.32 (s, 1 H) 8.54 (d, J=5.62 Hz, 1 H) 9.35 (s, 1 H) 10.87 (s, 1 H)

EXAMPLE 121

N4-(3-(5-(2-Amino-3-(1H-indol-3-yl)-propoxy)-pyridin-3-yl)-phenyl)-pyrimidine-2,4-diamine

Example 121A (1S)-[2-[5-(3-Amino-phenyl)-pyridin-3-yloxy]-1-(1H-indol-3-ylmethyl)-ethyl]-carbamic acid tert-butyl ester The desired product was prepared by substituting 3-aminophenylboronic acid for 4-cyanophenylboronice acid in Example 22.

Example 121B (1S)-[2-{5-[3-(2-Amino-pyrimidin-4-ylamino)-phenyl]-pyridin-3-yloxy}-1-(1H-indol-3-ylmethyl)-ethyl]-carbamic acid tert-butyl ester A mixture of Example 121A (0.07 g, 0.153 mmol) and 4-chloro-2-pyrimidinylamine (0.021 g, 0.163 mmol) was dissolved in EtOH (1 mL). The mixture was heated to 80° C. overnight then cooled and evaporated. The product was used without further purification.

Example 121C (1S)-[2-[5-(3-Amino-phenyl)-pyridin-3-yloxy]-1-(1H-indol-3-ylmethyl)-ethyl]-carbamic acid tert-butyl ester The desired product was prepared by substituting Example 121B for Example 27B in Example 27C. MS (ESI) m/z 452 (M+H)+. $^1$H NMR (500 MHz, DMSO-D6) δ ppm 3.17 (m, 2 H) 3.85 (m, 1 H) 3.97 (s, 1 H) 4.19 (m, 1 H) 4.35 (m, 1 H) 6.35 (d, J=6.86 Hz, 1 H) 7.00 (t, J=7.49 Hz, 1 H) 7.10 (m, 1 H) 7.29 (d, J=2.18 Hz, 1 H) 7.38 (d, J=8.11 Hz, 1 H) 7.52 (m, J=7.80 Hz, 2 H) 7.62 (d, J=7.80 Hz, 1 H) 7.66 (m, 1 H) 7.88 (d, J=7.18 Hz, 1 H) 8.25 (d, J=4.37 Hz, 2 H) 8.38 (d, J=2.50 Hz, 1 H) 8.58 (d, J=1.56 Hz, 1 H) 10.73 (s, 1 H) 11.02 (d, J=1.87 Hz, 1 H).

EXAMPLE 122

(1S)-3-(2-Amino-3-(1H-indol-3-yl)-propoxy)-5-isoquinolin-6-yl-phenylamine

Example 122A (1S)-[2-[3-(Benzhydrylidene-amino)-5-isoquinolin-6-yl-phenoxy]-1-(1H-indol-3-ylmethyl)-ethyl]-carbamic acid tert-butyl ester A solution of Example 120B (0.165 g, 0.29 mmol) and benzophenone imine (0.1 mL, 0.6 mmol) in 5 mL of toluene was treated with Pd$_2$dba$_3$ (0.026 g, 0.028 mmol), BINAP (0.036 g, 0.058 mmol) and sodium tbutoxide (0.042 g, 0.44 mmol). The reaction was heated to 80° C. overnight then to 95° C. for 24 h. The mixture was cooled and filtered through celite. The residue was purified by flash column chromatography on silica gel, eluting with 1:1 ethyl acetate/hexane. Recovered 0.175 g of product (90%). MS (ESI) m/z 673 (M+H)+.

Example 122B (1S)-3-(2-Amino-3-(1H-indol-3-yl)-propoxy)-5-isoquinolin-6-yl-phenylamine A solution of Example 122A (0.175 g, 0.26 mmol) in 2 mL of THF was cooled to 0° C. then treated with 1 mL of 3N HCl. The mixture was stirred at 0° C. for 15 minutes then at room temperature for 4 h. The mixture was evaporated and the residue was purified by flash column chromatography on silica gel, eluting with 10% methanol in methylene chloride. Recovered 0.029 g of product (23%). MS (ESI) m/z 408 (M+H)+; $^1$H NMR (500 MHz, DMSO-D6) δ ppm 3.20 (m, 2 H) 3.77 (m, 1 H) 4.12 (d, J=5.62 Hz, 1 H) 4.21 (d, J=3.43 Hz, 1 H) 6.58 (s, 1 H) 6.86 (m, 1 H) 6.95 (s, 1 H) 7.01 (m, 1 H) 7.08 (d, J=7.18 Hz, 1 H) 7.29 (d, J=2.18 Hz, 1 H) 7.37 (d, J=8.11 Hz, 1 H) 7.66 (d, J=7.80 Hz, 1 H) 8.13 (d, J=8.73 Hz, 1 H) 8.38 (d, J=6.24 Hz, 1 H) 8.43 (s, 1 H) 8.52 (m, 3 H) 8.65 (d, J=6.24 Hz, 1 H) 9.78 (s, 1 H) 11.06 (d, J=1.87 Hz, 1 H)

EXAMPLE 123

4-(5-Isoquinolin-6-yl-pyridin-3-yl)-piperazine-1-carboxylic acid tert-butyl ester

Example 123A 4-(5-Bromo-pyridin-3-yl)-piperazine-1-carboxylic acid tert-butyl ester A solution of the 3,5-dibromo-pyridine (12.8 g, 68.8 mmol) and piperazine-1-carboxylic acid tert butyl ester (10 g, 42.4 mmol) in 200 mL of dioxane was treated with Pd$_2$(dba)$_3$ (5 g, 5.5 mmol), 2-(di-tbutyl-phosphino)biphenyl (4 g, 13.4 mmol), and sodium t-butoxide (7.2 g, 75 mmol). The reaction was heated to 95° C. for 8 h then cooled and filtered through celite. The mixture was evaporated and the residue was purified by flash column chromatography on silica gel, eluting with a solvent gradient of 1:4 ethyl acetate/hexane to 100% ethyl acetate. Recovered 2.9 g of product (20%). MS (ESI) m/z 344 (M+H)+.

Example 123B 4-(5-Isoquinolin-6-yl-pyridin-3-yl)-piperazine-1-carboxylic acid tert-butyl ester The desired product was prepared by substituting Example 123A for Example 27A in Example 123B. MS (ESI) m/z 408 (M+H)+; $^1$H NMR (500 MHz, CHLOROFORM-D) δ ppm 1.50 (m, 9 H) 3.29 (m, 4 H) 3.65 (m, 4 H) 7.46 (m, 1 H) 7.72 (d, J=5.62 Hz, 1 H) 7.83 (d, J=1.87 Hz, 1 H) 7.99 (s, 1 H) 8.09 (d, J=8.74 Hz, 1 H) 8.37 (d, J=2.81 Hz, 1 H) 8.46 (d, J=1.87 Hz, 1 H) 8.59 (d, J=5.93 Hz, 1 H) 9.31 (s, 1 H).

EXAMPLE 124

6-(5-Piperazin-1-yl-pyridin-3-yl)-isoquinoline

The desired product was prepared by substituting Example 123 for Example 27B in Example 27C. MS (ESI) m/z 291 (M+H)+; $^1$H NMR (500 MHz, Solvent) δ ppm 3.47 (m, 4 H) 3.79 (m, 4 H) 8.30 (m, 1 H) 8.39 (dd, J=8.58, 1.72 Hz, 1 H) 8.49 (d, J=6.55 Hz, 1 H) 8.57 (d, J=2.50 Hz, 1 H) 8.63 (m, 2 H) 8.70 (m, 2 H) 9.78 (s, 1 H).

EXAMPLE 125

((2S)-2-Amino-5-(5-(2-amino-3-(1H-indol-3-yl)-propoxy)-pyridin-3-yl)-phenyl-(3-chloro-phenyl-methanone The title compound was prepared by substituting 2-amino-5-iodo-3'-chloro benzophenone for Example 32A in Example 32. MS (ESI) m/z 291 (M+H)+; $^1$H NMR (500 MHz, DMSO-D6) δ ppm 3.15 (m, 2 H) 3.81 (m, 1 H) 4.11 (m, 1 H) 4.26 (m, 1 H) 7.00 (m, 2 H) 7.09 (m, 1 H) 7.27 (m, 1 H) 7.39 (m, 2 H) 7.60 (m, 4 H) 8.21 (m, 1 H) 8.32 (m, 3 H) 11.07 (m, 1 H).

EXAMPLE 126

(1S)-N-6-(3-(5-(2-Amino-3-(1H-indol-3-yl)-propoxy)-pyridin-3-yl)-phenyl)-9H-purine-2,6-diamine The title compound was prepared by substituting 6-Chloro-9H-purin-2-ylamine for 4-chloro-2-pyrimidinylamine in Example 121. MS (ESI) m/z 492 (M+H)+; $^1$H NMR (400 MHz, DMSO-D6) δ ppm 3.18 (d, J=8.29 Hz, 2 H) 3.83 (m, 1 H) 4.01 (m, 1 H) 4.19 (m, 1 H) 4.36 (m, 1 H) 7.01 (m, 2 H) 7.09 (t, J=7.06 Hz, 1 H) 7.16 (s, 1 H) 7.30 (m, 2 H) 7.38 (d, J=8.29 Hz, 1 H) 7.63 (m, 2 H) 8.18 (s, 2 H) 8.30 (m, 2 H) 8.35 (d, J=2.45 Hz, 1 H) 8.56 (d, J=1.84 Hz, 1 H) 11.02 (s, 1 H).

EXAMPLE 127

(3-(5-((2S)-2-Amino-3-(1H-indol-3-yl)-propoxy)-pyridin-3-yl)-phenyl)-pyrimidin-2yl-amine The title compound was prepared by substituting 2-chloropyrimidine for 4-chloro-2-pyrimidinylamine in Example 121. MS (ESI) m/z 437 (M+H)+; 1H NMR (500 MHz, DMSO-D6) δ ppm 3.17 (d, J=5.30 Hz, 1 H) 4.06 (q, J=5.30 Hz, 5 H) 6.86 (t, J=4.84 Hz, 2 H) 6.96 (d, J=7.18 Hz, 1 H) 7.05 (s, 1 H) 7.26 (m, 1 H) 7.34 (d, J=8.11 Hz, 1 H) 7.40 (t, J=7.96 Hz, 1 H) 7.54 (m, 1 H) 7.55 (s, 1 H) 7.85 (m, 2 H) 8.07 (t, J=1.72 Hz, 1 H) 8.30 (d, J=2.50 Hz, 1 H) 8.44 (d, J=1.87 Hz, 1 H) 8.50 (d, J=4.68 Hz, 2 H) 9.68 (s, 1 H) 10.85 (s, 1 H).

EXAMPLE 128

(3-(5-((2S)-2-Amino-3-(1H-indol-3-yl)-propoxy)-pyridin-3-yl)-phenyl)-thiazol-2yl-amine The title compound was prepared by substituting 2-chlorothiazole for 4-chloro-2-pyrimidinylamine in Example 121. MS (ESI) m/z 442 (M+H)+; 1H NMR (500 MHz, DMSO-D6) δ ppm 3.16 (m, 3 H) 4.16 (m, 1 H) 4.34 (m, 1 H) 6.94 (d, J=3.74 Hz, 1 H) 7.01 (m, 1 H) 7.10 (m, 1 H) 7.22 (m, 1 H) 7.28 (dd, J=7.96, 2.96 Hz, 2 H) 7.38 (d, J=8.42 Hz, 1 H) 7.42 (d, J=7.80 Hz, 1 H) 7.57 (m, 1 H) 7.62 (d, J=8.11 Hz, 1 H) 8.02 (s, 1 H) 8.14 (s, 2 H) 8.35 (d, J=2.50 Hz, 1 H) 8.48 (d, J=1.87 Hz, 1 H) 10.31 (s, 1 H) 11.01 (s, 1 H).

EXAMPLE 129

N-(3-(5-((2S)-2-Amino-3-(1H-indol-3-yl)-propoxy)-pyridin-3-yl)-phenyl)-acetamide

Example 129A (1S)-[2-[5-(3-Acetylamino-phenyl)-pyridin-3-yloxy]-1-(1H-indol-3-ylmethyl)-ethyl]-carbamic acid tert-butyl ester Example 121A (0.05 g, 0.11 mmol) was taken in methylene chloride (1.5 mL) and treated with acetic anhydride (0.2 mL, 2.1 mmol) and triethylamine (0.1 mL, 0.77 mmol). The mixture was stirred overnight at room temperature then diluted with methylene chloride (25 mL) and washed with water (15 mL) and brine (15 mL). The mixture was evaporated and used without further purification.

Example 129B

N-(3-(5-((2S)-2-Amino-3-(1H-indol-3-yl)-propoxy)-pyridin-3-yl)-phenyl)-acetamide The desired product was prepared by substituting Example 129A for Example 27B in Example 27C. MS (ESI) m/z 401 (M+H)+; 1H NMR (400 MHz, DMSO-D6) δ ppm 2.07 (m, 3 H) 3.16 (m, 3 H) 4.16 (m, 1 H) 4.33 (m, 1 H) 7.01 (m, 1 H) 7.10 (m, 1 H) 7.29 (m, 1 H) 7.38 (m, 3 H) 7.55 (m, 2 H) 7.62 (m, 1 H) 7.99 (m, 1 H) 8.14 (m, 2 H) 8.35 (m, 1 H) 8.48 (m, 1 H) 10.06 (m, 1 H) 1.01 (m, 1 H).

EXAMPLE 130

6-(5-(4-(1H-Indol-3-ylmethyl)-piperazin-1-yl)-pyridin-3-yl)-isoquinoline

The title compound was prepared by substituting Example 124 for aniline, and 3-formylindole for Example 116A in example 116B. MS (ESI) (m/z 420M+H)+; 1H NMR (400 MHz, DMSO-D6) δ ppm 1.89 (s, 2 H) 2.50 (m, 4 H) 2.60 (m, 4 H) 7.02 (m, 2 H) 7.27 (d, J=2.46 Hz, 1 H) 7.36 (d, J=7.98 Hz, 1 H) 7.68 (m, 2 H) 7.87 (d, J=5.83 Hz, 1 H) 8.05 (dd, J=8.59, 1.53 Hz, 1 H) 8.22 (d, J=8.90 Hz, 1 H) 8.34 (m, 2 H) 8.44 (d, J=1.84 Hz, 1 H) 8.54 (d, J=5.83 Hz, 1 H) 9.35 (s, 1 H) 10.93 (s, 1 H).

EXAMPLE 131

3-((2S)-2-Amino-3-(1H-indol-3-yl)-propoxy)-5-isoquinolin-6-yl-benzoic acid

Example 131A

3-[(2S)-2-tert-Butoxycarbonylamino-3-(1H-indol-3-yl)-propoxy]-5-isoquinolin-6-yl-benzoic acid A solution of Example 120 (0.2 g, 0.3 mmol) 6 mL of DMF was treated with Pd(dppf)2Cl2 (0.039 g, 0.07 mmol), Pd(OAc)2 (0.016 g, 0.07 mmol), ammonium hydroxide (0.15 mL), and triethylamine (0.5 mL, 3.9 mmol). The reaction was heated to 80° C. after which CO was bubbled through for 30 minutes. The mixture was heated to 80° C. overnight then cooled, neutralized with HCl and washed with ethyl acetate. The water was evaporated off to yield the product. MS (ESI) m/z 538 (M+H)+.

Example 131B 3-((2S)-2-Amino-3-(1H-indol-3-yl)-propoxy)-5-isoquinolin-6-yl-benzoic acid The desired product was prepared by substituting Example 131A for Example 27B in Example 27C. MS (ESI) m/z 438 (M+H)+; 1H NMR (500 MHz, DMSO-D6) δ ppm 3.14 (m, 3 H) 4.20 (m, 1 H) 4.35 (d, J=2.81 Hz, 1 H) 7.02 (m, 1 H) 7.09 (d, J=8.11 Hz, 1 H) 7.30 (d, J=2.50 Hz, 1 H) 7.38 (d, J=8.11 Hz, 1 H) 7.63 (m, 2 H) 7.68 (s, 1 H) 8.04 (s, 1 H) 8.11 (m, 2 H) 8.18 (s, 3 H) 8.36 (d, J=8.73 Hz, 1 H) 8.42 (s, 1 H) 8.61 (d, J=5.93 Hz, 1 H) 9.53 (s, 1 H) 11.02 (d, J=1.56 Hz, 1 H).

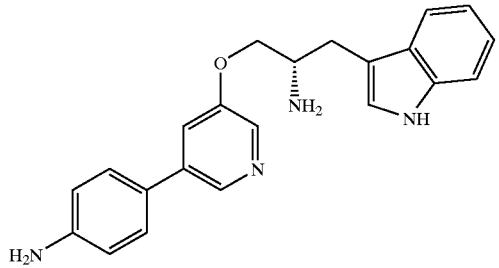

EXAMPLE 132

4-(5-((2S)-2-Amino-3-(1H-indol-3-yl)-propoxy)-pyridin-3-yl)-phenylamine

The desired product was prepared by substituting 4-aminophenylboronic acid for 4-cyanophenylboronice acid in Example 22. MS (ESI) m/z 359 (M+H)+; 1H NMR (500 MHz, DMSO-D6) δ ppm 3.16 (m, 2 H) 3.90 (d, J=63.33 Hz, 3 H) 4.16 (dd, J=10.61, 6.24 Hz, 1 H) 4.33 (m, 1 H) 6.77 (d, J=8.42 Hz, 1 H) 7.01 (m, 1 H) 7.11 (s, 1 H) 7.29 (d, J=2.18 Hz, 1 H) 7.38 (d, J=8.11 Hz, 1 H) 7.47 (d, J=8.42 Hz, 1 H) 7.61 (m, 2 H) 8.17 (s, 2 H) 8.24 (d, J=2.50 Hz, 1 H) 8.50 (d, J=1.56 Hz, 1 H) 11.02 (s, 1 H).

EXAMPLE 133

N-(4-(5-((2S)-2-Amino-3-(1H-indol-3-yl)-propoxy)-pyridin-3-yl)-phenyl)-acetamide The desired product was prepared by substituting Example 132 for Example 121A in Example 129. MS (ESI)

m/z 401 (M+H)+; 1H NMR (500 MHz, DMSO-D6) δ ppm 3.17 (d, J=6.86 Hz, 5 H) 4.18 (d, J=5.93 Hz, 1 H) 4.32 (d, J=3.12 Hz, 1 H) 7.01 (m, 1 H) 7.09 (d, J=7.18 Hz, 1 H) 7.29 (d, J=2.18 Hz, 1 H) 7.38 (d, J=8.11 Hz, 1 H) 7.58 (d, J=2.18 Hz, 1 H) 7.65 (m, 4H) 8.28 (m, 4 H) 8.51 (d, J=1.25 Hz, 1 H) 10.10 (s, 1 H) 11.03 (d, J=1.25 Hz, 1 H).

EXAMPLE 134

N6-(4-(5-((2S)-2-Amino-3-(1H-indol-3-yl)-propoxy)-pyridin-3-yl)-phenyl)-9H-purine-2,6-diamine The title compound was prepared by substituting Example 132 for Example 121A in Example 126. MS (ESI) m/z 492 (M+H)+; 1H NMR (500 MHz, DMSO-D6) δ ppm 2.51 (m, 3 H) 3.16 (t, J=7.49 Hz, 1 H) 3.91 (d, J=53.97 Hz, 2 H) 4.19 (dd, J=10.76, 6.08 Hz, 1 H) 4.35 (dd, J=10.76, 2.96 Hz, 1 H) 7.01 (t, J=7.18 Hz, 1 H) 7.11 (t, J=7.02 Hz, 1 H) 7.30 (d, J=2.18 Hz, 1 H) 7.39 (d, J=8.11 Hz, 1 H) 7.64 (m, 2 H) 7.74 (d, J=8.73 Hz, 1 H) 8.02 (d, J=8.42 Hz, 1 H) 8.20 (d, J=3.74 Hz, 2 H) 8.26 (s, 1 H) 8.34 (d, J=2.50 Hz, 1 H) 8.58 (d, J=1.56 Hz, 1 H) 10.52 (s, 1 H) 11.03 (d, J=1.87 Hz, 1 H).

EXAMPLE 135

N4-(4-(5-((2S)-2-Amino-3-(1H-indol-3-yl)-propoxy)-pyridin-3-yl)-phenyl)-pyrimidine-2,4-diamine The title compound was prepared by substituting Example 132 for Example 121A in Example 121. MS (ESI) m/z 452 (M+H)+; 1H NMR (500 MHz, DMSO-D6) δ ppm 3.16 (d, J=7.18 Hz, 2 H) 3.86 (m, 2 H) 4.18 (m, 1 H) 4.33 (d, J=3.12 Hz, 1 H) 6.35 (d, J=7.18 Hz, 1 H) 7.01 (t, J=7.33 Hz, 1 H) 7.10 (t, J=7.02 Hz, 1 H) 7.29 (d, J=2.18 Hz, 1 H) 7.39 (d, J=8.11 Hz, 1 H) 7.62 (dd, J=4.52, 2.03 Hz, 2 H) 7.73 (d, J=8.73 Hz, 2 H) 7.88 (d, J=7.49 Hz, 2 H) 8.20 (s, 3 H) 8.34 (d, J=2.81 Hz, 1 H) 8.56 (d, J=1.87 Hz, 1 H) 10.69 (s, 1 H) 11.02 (d, J=1.87 Hz, 1 H).

EXAMPLE 136

(4-(5-((2S)-2-Amino-3-(1H-indol-3-yl)-propoxy)-pyridin-3-yl)-phenyl)-pyrimidin-2-yl-amine The title compound was prepared by substituting Example 132 for Example 121A in Example 127. MS (ESI) m/z 437 (M+H)+; 1H NMR (500 MHz, DMSO-D6) δ ppm 2.94 (d, J=6.55 Hz, 1 H) 3.04 (m, 1 H) 3.17 (d, J=3.74 Hz, 1 H) 3.55 (m, 1 H) 4.04 (dd, J=9.83, 6.40 Hz, 1 H) 4.16 (dd, J=9.98, 4.06 Hz, 1 H) 6.88 (t, J=4.84 Hz, 1 H) 6.98 (t, J=7.49 Hz, 1 H) 7.08 (t, J=7.64 Hz, 1 H) 7.24 (d, J=2.18 Hz, 1 H) 7.36 (d, J=8.11 Hz, 1 H) 7.55 (m, 1 H) 7.59 (d, J=7.80 Hz, 1 H) 7.64 (d, J=8.73 Hz, 2 H) 7.90 (d, J=9.05 Hz, 2 H) 8.25 (d, J=2.81 Hz, 1 H) 8.49 (d, J=1.56 Hz, 1 H) 8.52 (d, J=4.99 Hz, 2 H) 9.78 (s, 1 H).

EXAMPLE 137

3-((2S)-2-Amino-3-(1H-indol-3-yl)-propoxy)-5-isoquinolin-6-yl-benzonitrile

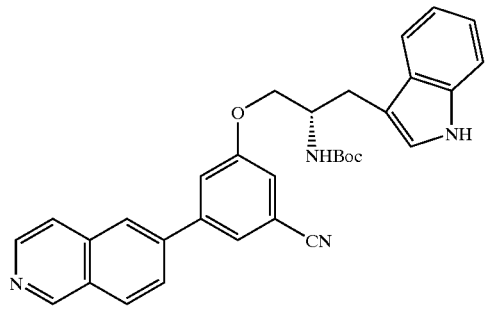

Example 137A (1S)-[2-(3-Cyano-5-isoquinolin-6-yl-phenoxy)-1-(1H-indol-3-ylmethyl)-ethyl]-carbamic acid tert-butyl ester A solution of Example 120 (0.15 g, 0.3 mmol) 3 mL of dioxane and 1 mL of DMF was treated with Pd(PPh3)4 (0.030 g, 0.026 mmol), and zinc cyanide (0.037 g, 0.3 mmol). The reaction was heated to 95° C. for 3 days. The mixture was diluted with ethyl acetate (25 mL) and washed with water (15 mL) and brine (15 mL). The mixture was evaporated and the residue was purified by flash column chromatography on silica gel, eluting 1:1 ethyl acetate/hexane. Recovered 0.108 g of product (79%). MS (ESI) m/z 519 (M+H)+.

Example 137B 3-((2S)-2-Amino-3-(1H-indol-3-yl)-propoxy)-5-isoquinolin-6-yl-benzonitrile The desired product was prepared by substituting Example 137A for Example 27B in Example 27C. MS (ESI) m/z 419 (M+H)+; 1H NMR (500 MHz, DMSO-D6) δ ppm 2.95 (d, J=6.55 Hz, 1 H) 3.05 (dd, J=14.35, 7.18 Hz, 1 H) 3.57 (m, 1 H) 4.07 (m, 1 H) 4.16 (d, J=4.06 Hz, 1 H) 6.96 (t, J=7.18 Hz, 1 H) 7.06 (t, J=7.18 Hz, 1 H) 7.23 (d, J=2.18 Hz, 1 H) 7.34 (d, J=8.11 Hz, 1 H) 7.50 (s, 1 H) 7.58 (d, J=7.80 Hz, 1 H) 7.73 (s, 1 H) 7.87 (d, J=5.93 Hz, 1 H) 7.93 (s, 1 H) 8.04 (dd, J=8.58, 1.72 Hz, 1 H) 8.23 (d, J=8.42 Hz, 1 H) 8.36 (s, 1 H) 8.55 (d, J=5.62 Hz, 1 H) 9.36 (s, 1 H) 10.91 (s, 1 H).

EXAMPLE 138

5'-Benzyloxy-5-isoquinolin-6-yl-(3,3 ')bipyridinyl

Example 138A 6-(5-Bromo-pyridin-3-yl)-isoquinoline

The title compound was prepared by substituting 3,5-dibromopyridine for Example 2A in Example 27B.

Example 138B

3-Benzyloxy-5-trimethylstannanyl-pyridine

The title compound was prepared by substituting 3-benzyloxy-5-bromopyridine for 6-bromoisoquinoline in Example 27A.

Example 138C

5'-Benzyloxy-5-isoquinolin-6-yl-(3,3')bipyridinyl

The title compound was prepared by substituting Example 138A for Example 2A, Example 138B for Example 27A in Example 27B. MS (ESI) m/z 390 (M+H)+; 1H NMR (400 MHz, DMSO-D6) δ ppm 5.35 (s, 2 H) 7.38 (d, J=7.36 Hz, 1 H) 7.44 (t, J=7.21 Hz, 2 H) 7.53 (d, J=6.75 Hz, 2 H) 8.11 (m, 1 H) 8.32 (d, J=6.14 Hz, 1 H) 8.50 (m, 2 H) 8.57 (m, 1 H) 8.70 (d, J=6.14 Hz, 1 H) 8.74 (t, J=2.15 Hz, 1 H) 8.79 (m, 2 H) 9.14 (d, J=2.15 Hz, 1 H) 9.22 (d, J=1.84 Hz, 1 H) 9.76 (s, 1 H).

EXAMPLE 140

(7-(5-((2S)-2-Amino-3-(1H-indol-3-yl)-propoxy)-pyridin-3-yl)-pyrido(2,3-d)pyrimidin-4-yl)-phenyl-amine

Example 140A

2-Amino-6-chloro-nicotinic acid

A mixture of 2,6-dichloro-nicotonic acid (17.77 g, 92.6 mmol) in concenterated aqueous ammonia (173 mL) at 200 psi, was heated to 130° C. for 24 h. The mixture evaporated and the residue was taken into water (200 mL) and neuteralized with conc HCl then extracted into ether (200 ml). The ether was evaporated off to yield 12 g of product (75%). MS (DCI/NH3) m/z 173 (M+1)+.

Example 140B

2-Amino-6-chloro-nicotinamide

To a mixture of Example 140A (11.9 g, 69.2 mmol) in 1,2-dichloroethane (100 mL) was added thionyl chloride (30 mL, 411 mmol) and DMF (catalytic). The mixture was refluxed for 4 h then evaporated. The residue was taken in ether (200 mL) and ammonia was bubbled through for 15 min. The mixture was stirred overnight at rt then washed with water (100 mL) and brine (100 ml). The ether was evaporated off to yield 9.2 g of product (78%). MS (DCI/NH3) m/z 172 (M+1)+.

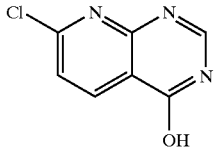

Example 140C

7-Chloro-pyrido[2,3-d]pyrimidin-4-ol

A mixture of Example 140B (1 g, 5.8 mmol) in triethylorthoformate (30 mL) was refluxed for 6 h then cooled. Hexane (150 mL) was added and the solid formed was filtered and washed with water and hexane to yield 0.27 g of product (26%). MS: (DCI/NH3) m/z=182 (M+1)

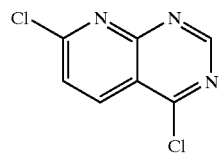

Example 140D 4,7-Dichloro-pyrido[2,3-d]pyrimidine

A mixture of Example 140C (1 g, 5.5 mmol) in phosphorus oxychloride (40 mL) was refluxed for 2 h then cooled and evaporated. The residue was taken into ethyl acetate (75 ml), washed with saturated sodium bicarbonate (50 ml) water (50 ml) and brine (50 ml). The ethyl acetate was evaporated to yield 0.8 g of product (73%).

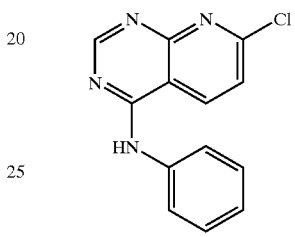

Example 140E (7-Chloro-pyrido[2,3-d]pyrimidin-4-yl)-phenyl-amine

A solution of Example 140D (0.5 g, 2.5 mmol), and aniline (0.23 mL, 2.5 mmol) in THF (25 mL) and 2-propanol (2.5 mL) was stirred at 0° C. for 1 h then at room temperature for 2 days. The THF was evaporated off and the residue was taken into ethyl acetate (75 ml), washed with water (50 ml) and brine (50 ml). The ethyl acetate was evaporated off and the residue was purified by flash column chromatography on silica gel, eluting with 1:1 ethyl acetate/hexane. Recovered 0.15 g of product (23%). MS (ESI) m/z 390 (M+H)+.

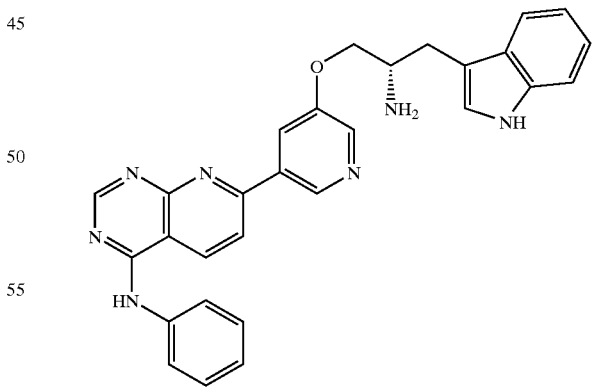

Example 140F (7-(5-((2S)-2-Amino-3-(1H-indol-3-yl)-propoxy)-pyridin-3-yl)-pyrido(2,3-d)pyrimidin-4-yl)-phenyl-amine The title compound was prepared by substituting Example 140E for 6-bromoisoquinoline in Example 27. MS (ESI) m/z 257 (M+H)+; ¹H NMR (500 MHz, DMSO-D6) δ ppm 3.15 (m, 3 H) 3.38 (s, 4 H) 4.06 (dd, J=10.29, 5.93 Hz, 4 H) 4.21 (dd, J=110.45, 2.96 Hz, 1 H) 6.99 (t, J=7.18 Hz, 1 H) 7.09 (t, J=7.18 Hz, 1 H) 7.26 (d, J=2.18 Hz, 1 H) 7.35 (m, 4 H) 8.21 (d, J=4.37 Hz, 3 H) 11.02 (s, 1 H)

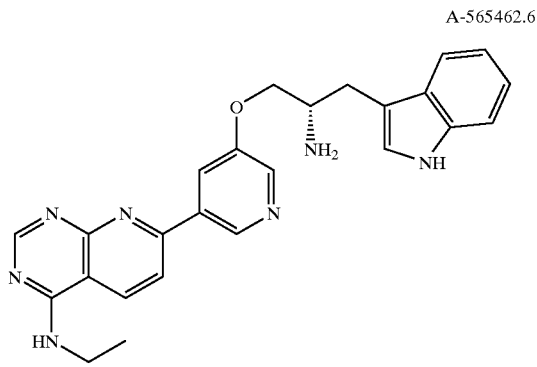

A-565462.6

EXAMPLE 141

(7-(5-((2S)-2-Amino-3-(1H-indol-3-yl)-propoxy)-pyridin-3-yl)-pyrido(2,3-d)pyrimidin-4-yl)-ethyl-amine The title compound was prepared by substituting ethylamine for aniline in Example 140. MS (ESI) m/z 440 (M+H)+; ¹H NMR (500 MHz, DMSO-D6) δ ppm 1.30 (m, 3 H) 3.19 (m, 2 H) 3.78 (m, 2 H) 4.05 (s, 2 H) 4.21 (dd, J=10.45, 5.77 Hz, 1 H) 4.38 (dd, J=10.45, 2.96 Hz, 1 H) 7.00 (t, J=7.49 Hz, 1 H) 7.09 (t, J=7.49 Hz, 1 H) 7.30 (d, J=2.18 Hz, 1 H) 7.38 (d, J=7.80 Hz, 1 H) 7.61 (d, J=7.80 Hz, 1 H) 8.15 (s, 1 H) 8.24 (d, J=4.06 Hz, 2 H) 8.51 (d, J=8.42 Hz, 1 H) 8.56 (d, J=1.56 Hz, 1 H) 8.96 (s, 1 H) 9.01 (d, J=8.74 Hz, 1 H) 9.12 (s, 1 H) 11.03 (d, J=1.56 Hz, 1 H).

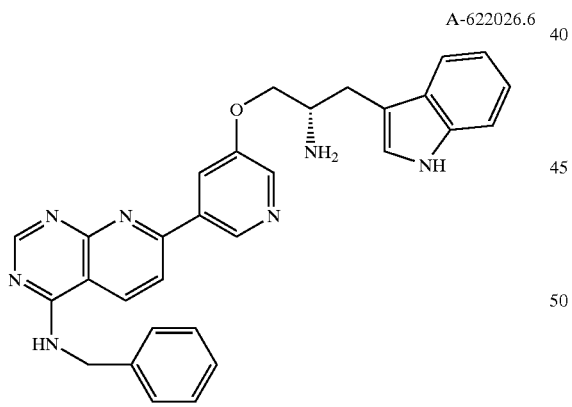

A-622026.6

EXAMPLE 142

(7-(5-((2S)-2-Amino-3-(1H-indol-3-yl)-propoxy)-pyridin-3-yl)-pyrido(2,3-d)pyrimidin-4-yl)-benzyl-amine The title compound was prepared by substituting benzylamine for aniline in Example 140. MS (ESI) m/z 502 (M+H)+; ¹H NMR (400 MHz, DMSO-D6) δ ppm 3.19 (m, J=6.60, 6.60 Hz, 2 H) 3.89 (m, 1 H) 4.22 (dd, J=110.43, 5.52 Hz, 1 H) 4.38 (m, 1 H) 5.00 (d, J=5.52 Hz, 2 H) 7.00 (m, 1 H) 7.09 (m, 1 H) 7.34 (m, 5 H) 7.45 (m, 1 H) 7.62 (d, J=7.98 Hz, 1 H) 8.17 (m, 1 H) 8.31 (d, J=3.68 Hz, 2 H) 8.54 (m, 2 H) 8.97 (s, 1 H) 9.07 (d, J=8.90 Hz, 1 H) 9.12 (d, J=1.84 Hz, 1 H) 10.81 (s, 1 H) 11.05 (d, J=2.15 Hz, 1 H).

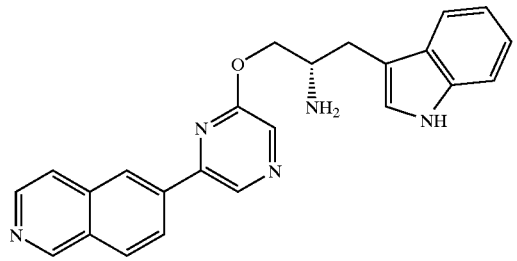

A-640684.7

EXAMPLE 143

(1S)-1-(1H-Indol-3-ylmethyl)-2-(6-isoquinolin-6-yl-pyrazin-2-yloxy)-ethylamine

The title compound was prepared by substituting 6-chloro-pyrazin-2-ol for 3-bromo-5-hydroxypyridine in Example 27. MS (ESI) m/z 396 (M+H)+; ¹H NMR (400 MHz, DMSO-D6) δ ppm 3.20 (m, 1 H) 3.95 (m, 1 H) 4.52 (m, J=7.36 Hz, 1 H) 4.76 (m, 1 H) 7.02 (m, J=7.06 Hz, 1 H) 7.11 (m, J=7.98 Hz, 1 H) 7.34 (d, J=2.15 Hz, 1 H) 7.41 (d, J=8.29 Hz, 1 H) 7.65 (d, J=7.98 Hz, 1 H) 7.99 (d, J=5.83 Hz, 1 H) 8.17 (s, 3 H) 8.28 (m, 2 H) 8.41 (s, 1 H) 8.62 (m, 1 H) 8.72 (s, 1 H) 9.10 (s, 1 H) 11.05 (s, 1 H).

A-646435.2

EXAMPLE 144

(1S)-2-(5-isoquinolin-6-yl-pyridin-3-yloxy)-1-phenyl-ethylamine

Example 144A (1S)-[2-(5-Bromo-pyridin-3-yloxy)-1-phenyl-ethyl]-carbamic acid tert-butyl ester A solution of 5-bromo-pyridin-3-ol (0.3 g, 1.7 mmol), (2-hydroxy-1-phenyl-ethyl)-carbamic acid tert-butyl ester (0.41 g 1.7 mmol), and triphenylphosphine (0.52 g, 2 mmol) in THF (15 mL) was stirred at 0° C. for 30 min. To the mixture was added a solution of di-t-butyl azidodicarboxylate (0.46 g, 2 mmol) in 5 ml of THF. The mixture was allowed to warm to room temperature then stirred at room temperature for 20 h. The THF was evaporated off and the residue was taken into ethyl acetate (75 ml), washed with saturated sodium bicarbonate (50 ml) water (50 ml) and brine (50 ml). The ethyl acetate was evaporated off and the residue was purified by flash column chromatography on silica gel, eluting with a solvent gradient of 1:4 to 1:2 ethyl acetate/hexane. Recovered 0.82 g of a mixture of product and di-tert-butyl azidodicarboxylate. MS (ESI) m/z 395 (M+H)+.

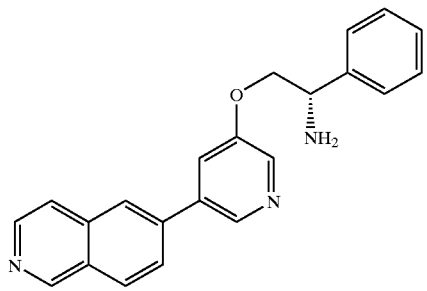

Example 144B (1S)-2-(5-isoquinolin-6-yl-pyridin-3-yloxy)-1-phenyl-ethylamine The title compound was prepared by substituting Example 144A for Example 2A in Example 27. MS (ESI) m/z 342 (M+H)+; 1H NMR (500 MHz, DMSO-D6) δ ppm 4.51 (m, J=8.74 Hz, 1 H) 4.57 (m, 1 H) 4.87 (m, 1 H) 7.49 (m, 3 H) 7.63 (d, J=7.18 Hz, 2 H) 7.90 (d, J=5.62 Hz, 1 H) 7.93 (m, 1 H) 8.10 (dd, J=8.73, 1.56 Hz, 1 H) 8.26 (d, J=8.73 Hz, 1 H) 8.39 (s, 1 H) 8.45 (d, J=2.50 Hz, 1 H) 8.56 (d, J=5.62 Hz, 1 H) 8.69 (m, 2 H) 8.74 (d, J=1.56 Hz, 1 H) 9.39 (s, 1 H).

A-656339.6

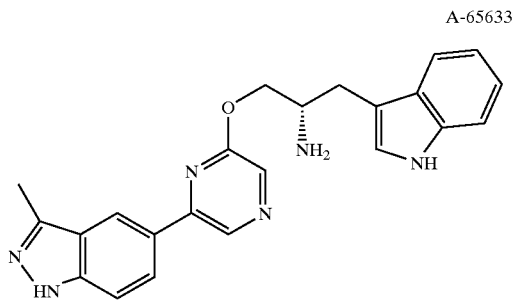

EXAMPLE 145

(1S)-1-(1H-Indol-3-ylmethyl)-2-(6-(3-methyl-1H-indazol-5-yl)-pyrazin-2-yloxy)-ethylamine The title compound was prepared by substituting 102C for 6-bromoisoquinoline in Example 143. MS (ESI) m/z 399 (M+H)+; 1H NMR (400 MHz, DMSO-D6) δ ppm 2.54 (s, 3 H) 3.18 (m, 2 H) 3.92 (m, 1 H) 4.47 (d, J=7.06 Hz, 1 H) 4.70 (m, 1 H) 7.02 (d, J=7.06 Hz, 1 H) 7.10 (m, 1 H) 7.32 (d, J=2.15 Hz, 1 H) 7.39 (d, J=8.29 Hz, 1 H) 7.49 (d, J=8.59 Hz, 1 H) 7.64 (d, J=8.29 Hz, 1 H) 7.92 (dd, J=8.75, 1.69 Hz, 1 H) 8.15 (m, 2 H) 8.24 (s, 1 H) 8.46 (s, 1 H) 8.95 (s, 1 H) 11.04 (d, J=1.53 Hz, 1 H).

The following compounds were made according the procedures used in Example 27 or 102, using the appropriate Boc protected N-Boc-aminoethanols.

A-659228.2

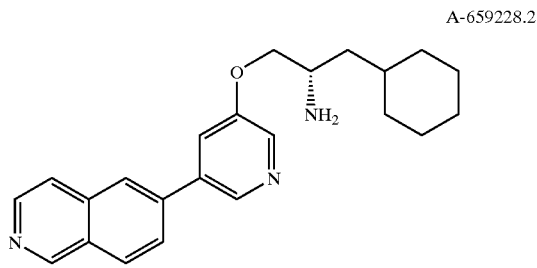

EXAMPLE 146

(1S)-1-Cyclohexylmethyl-2-(5-isoquinolin-6-yl-pyridin-3-yloxy)-ethylamine

MS (ESI) m/z 362 (M+H)+; 1H NMR (500 MHz, DMSO-D6) δ ppm 0.92 (s, 2 H) 1.24 (m, 3 H) 1.64 (m, 6 H) 3.52 (s, 2 H) 4.23 (dd, J=10.61, 6.55 Hz, 1 H) 4.40 (dd, J=10.61, 3.12 Hz, 1 H) 7.91 (m, 1 H) 7.96 (d, J=5.93 Hz, 1 H) 8.13 (dd, J=8.58, 1.72 Hz, 4 H) 8.32 (d, J=8.73 Hz, 1 H) 8.43 (m, 2 H) 8.59 (m, J=5.62 Hz, 1 H) 8.74 (d, J=1.56 Hz, 1 H) 9.44 (s, 1 H).

A-674563.7

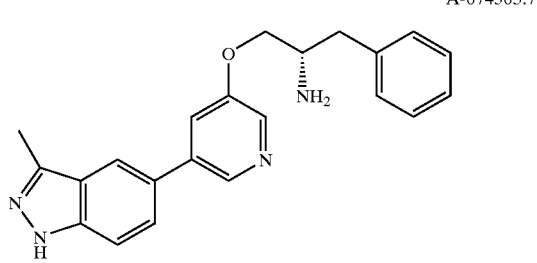

EXAMPLE 147

(1S)-1-Benzyl-2-(5-(3-methyl-1H-indazol-5-yl)-pyridin-3-yloxy)-ethylamine

MS (ESI) m/z 359 (M+H)+; 1H NMR (500 MHz, DMSO-D6) δ ppm 2.55 (m, 3 H) 3.05 (m, 1 H) 3.38 (m, 1 H) 3.87 (m, 1 H) 4.12 (dd, J=10.76, 5.77 Hz, 1 H) 4.28 (dd, J=10.76, 2.96 Hz, 1 H) 7.33 (m, 4 H) 7.57 (d, J=8.73 Hz, 1 H) 7.67 (m, 2 H) 8.06 (s, 1 H) 8.21 (s, 2 H) 8.31 (d, J=1.56 Hz, 1 H) 8.61 (s, 1 H) 12.74 (s, 1 H).

A-679219.7

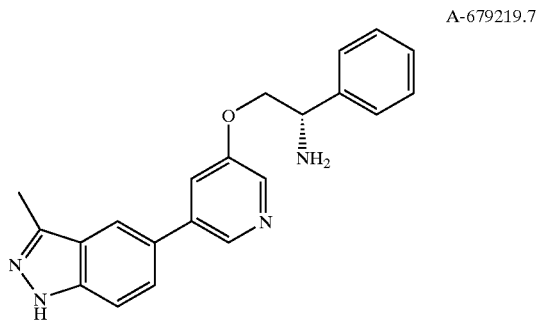

EXAMPLE 148

(1S)-2-(5-(3-Methyl-1H-indazol-5-yl)-pyridin-3-yloxy)-1-phenyl-ethylamine

MS (ESI) m/z 345 (M+H)+; 1H NMR (400 MHz, DMSO-D6) δ ppm 2.55 (m, 3 H) 4.01 (s, 1 H) 4.31 (m, 1 H) 4.39

(m, 1 H) 4.57 (m, 1 H) 7.36 (m, 1 H) 7.43 (t, J=7.36 Hz, 2 H) 7.55 (t, J=7.67 Hz, 4 H) 7.70 (m, 1 H) 8.08 (s, 1 H) 8.29 (d, J=2.76 Hz, 1 H) 8.57 (d, J=1.84 Hz, 1 H) 12.72 (s, 1 H).

H) 4.21 (dd, J=10.74, 5.52 Hz, 1 H) 4.37 (dd, J=10.74, 3.07 Hz, 1 H) 7.51 (m, 3 H) 7.56 (d, J=8.29 Hz, 1 H) 7.67 (dd, J=8.59, 1.84 Hz, 1 H) 7.78 (m, 1 H) 7.86 (m, 2 H) 7.91 (m, 2 H) 8.07 (s, 1 H) 8.26 (m, 2 H) 8.36 (d, J=2.76 Hz, 1 H) 8.65 (d, J=1.84 Hz, 1 H).

A-682487.7

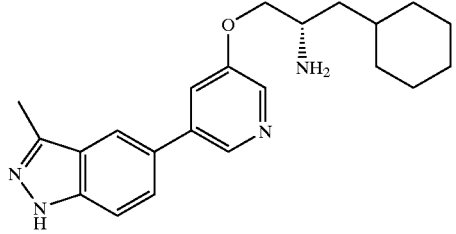

EXAMPLE 149

(1S)-2-(5-(3-Methyl-1H-indazol-5-yl)-pyridin-3-yloxy)-1-phenyl-ethylamine

MS (ESI) m/z 365 (M+H)+; 1H NMR (400 MHz, DMSO-D6) δ ppm 0.90 (d, J=14.12 Hz, 2 H) 1.16 (m, 3 H) 1.44 (m, 3 H) 1.69 (m, 3 H) 2.55 (d, J=5.22 Hz, 3 H) 3.37 (m, 3 H) 4.03 (m, 1 H) 4.17 (dd, J=9.97, 4.14 Hz, 1 H) 7.56 (d, J=8.59 Hz, 1 H) 7.71 (m, 2 H) 8.08 (s, 1 H) 8.28 (d, J=2.76 Hz, 1 H) 8.57 (d, J=1.53 Hz, 1 H) 12.73 (s, 1 H).

A-697738.2

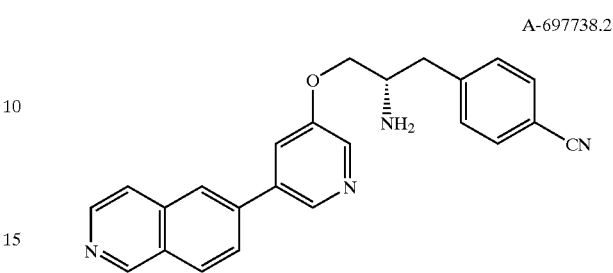

EXAMPLE 152

4-((2S)-2-Amino-3-(5-isoquinolin-6-yl-pyridin-3-yloxy-propyl)-benzonitrile

MS (ESI) m/z 381 (M+H)+; 1H NMR (400 MHz, DMSO-D6) δ ppm 3.16 (m, 2 H) 3.97 (s, 1 H) 4.26 (m, 2 H) 7.56 (d, J=8.29 Hz, 2 H) 7.84 (d, J=8.29 Hz, 2 H) 7.90 (m, 1 H) 8.24 (m, 2 H) 8.33 (m, 2 H) 8.48 (m, 2 H) 8.55 (s, 1 H) 8.67 (d, J=6.14 Hz, 1 H) 8.79 (d, J=1.84 Hz, 1 H) 9.67 (s, 1 H).

A-697376.7

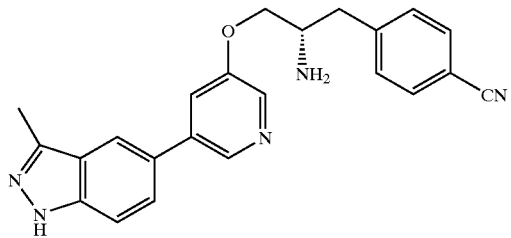

EXAMPLE 150

4-((2S)-2-Amino-3-(5-(3-methyl-1H-indazol-5-yl)-pyridin-3-yloxy)propyl)-benzonitrile MS (ESI) m/z 384 (M+H)+; 1H NMR (400 MHz, DMSO-D6) δ ppm 2.55 (s, 3 H) 3.14 (d, J=7.06 Hz, 2 H) 3.94 (m, 1 H) 4.15 (dd, J=10.74, 5.52 Hz, 1 H) 4.32 (dd, J=10.74, 3.07 Hz, 1 H) 7.57 (t, J=8.13 Hz, 2 H) 7.69 (m, 1 H) 7.73 (t, J=1.99 Hz, 1 H) 7.85 (d, J=7.98 Hz, 2 H) 8.07 (s, 1 H) 8.24 (m, 2 H) 8.32 (d, J=2.45 Hz, 1 H) 8.64 (d, J=1.53 Hz, 1 H).

A-697741.2

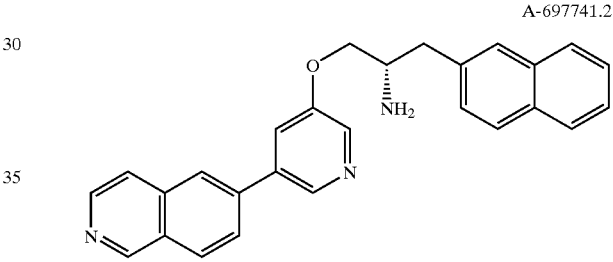

EXAMPLE 153

(1S)-2-(5-Isoquinolin-6-yl-pyridin-3-yloxy)-1-nanpthalen-2-ylmethyl)-ethylamine

MS: (ESI) m/z 406 (M+H)+; 1H NMR (400 MHz, DMSO-D6) δ ppm 3.24 (m, 2 H) 4.03 (s, 1 H) 4.31 (m, 2 H) 7.50 (m, 3 H) 7.89 (m, 5 H) 8.22 (m, 2 H) 8.33 (s, 3 H) 8.48 (m, 2 H) 8.54 (s, 1 H) 8.66 (m, J=6.14 Hz, 1 H) 8.78 (d, J=1.84 Hz, 1 H).

A-697379.7

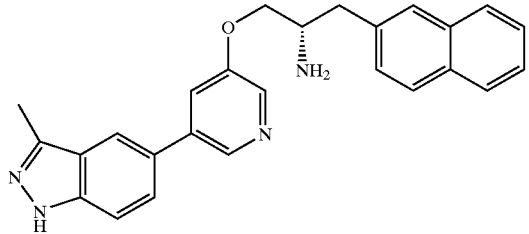

EXAMPLE 151

(1S)-2-(5-(3-Methyl-1H-indazol-5-yl)-pyridin-3-yloxy)-1-napthalen-2-ylmethyl-ethylamine MS: (ESI) m/z 409 (M+H)+; 1H NMR (400 MHz, DMSO-D6) δ ppm 2.54 (s, 3 H) 3.23 (d, J=7.06 Hz, 2 H) 4.00 (s, 1

A-703291.2

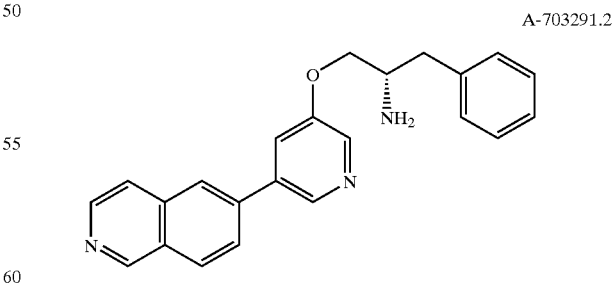

EXAMPLE 154

(1S)-1-Benzyl-2-(5-isoquinolin-6-yl-pyridin-3-yloxy)-ethylamine

MS (ESI) m/z 356 (M+H)+; 1H NMR (500 MHz, DMSO-D6) δ ppm 3.05 (m, 2 H) 3.88 (s, 1 H) 4.16 (dd, J=10.61, 5.62 Hz, 1 H) 4.32 (dd, J=10.76, 2.96 Hz, 1 H) 7.29 (m, 1 H) 7.35 (m, 3 H) 7.85 (m, 1 H) 7.99 (d, J=5.62 Hz, 1 H) 8.12 (dd, J=8.58, 1.72 Hz, 1 H) 8.27 (m, 3 H) 8.33 (d, J=8.74 Hz, 1 H) 8.43 (m, 2 H) 8.60 (d, J=5.93 Hz, 1 H) 8.75 (d, J=1.87 Hz, 1 H) 9.47 (s, 1 H).

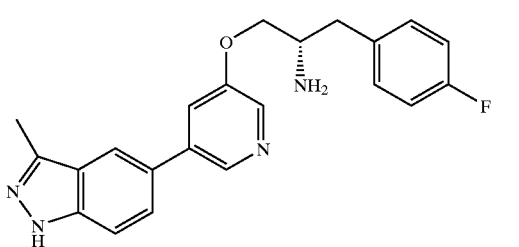

A-726437.7

EXAMPLE 155

(1S)-1-(4-Fluoro-benzyl)-2-(5-(3-methyl-1H-indazol-5-yl)-pyridin-3-yloxy)-ethylamine MS (ESI) m/z 377 (M+H)$^+$; $^1$H NMR (500 MHz, DMSO-D6) δ ppm 2.55 (s, 3 H) 3.04 (d, J=7.18 Hz, 2 H) 3.85 (m, 1 H) 4.14 (dd, J=10.76, 5.77 Hz, 1 H) 4.30 (m, 1 H) 7.19 (m, J=8.89, 8.89 Hz, 2 H) 7.37 (dd, J=8.58, 5.46 Hz, 2 H) 7.58 (d, J=8.73 Hz, 1 H) 7.69 (dd, J=8.74, 1.56 Hz, 1 H) 7.75 (s, 1 H) 8.08 (s, 1 H) 8.23 (s, 3 H) 8.34 (s, 1 H) 8.65 (s, 1 H)

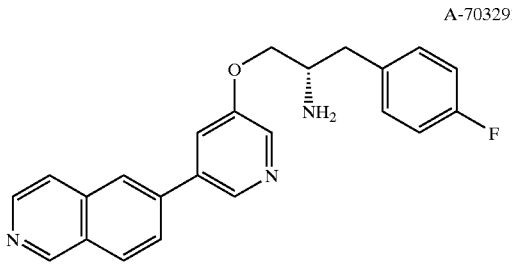

A-703291.2

EXAMPLE 156

(1S)-1-(4-Fluoro-benzyl)-2-(5-isoquinolin-6-yl-pyridin-3-yloxy)-ethylamine

MS (ESI) m/z 374 (M+H)$^+$; $^1$H NMR (500 MHz, DMSO-D6) δ ppm 3.05 (m, 2 H) 3.88 (s, 1 H) 4.17 (dd, J=10.92, 5.62 Hz, 1 H) 4.34 (dd, J=10.76, 2.96 Hz, 1 H) 7.18 (m, 2 H) 7.38 (dd, J=8.58, 5.46 Hz, 2 H) 7.90 (m, 1 H) 8.24 (m, 5 H) 8.47 (d, J=8.73 Hz, 1 H) 8.53 (d, J=9.98 Hz, 1 H) 8.79 (s, 1 H) 9.67 (s, 1 H).

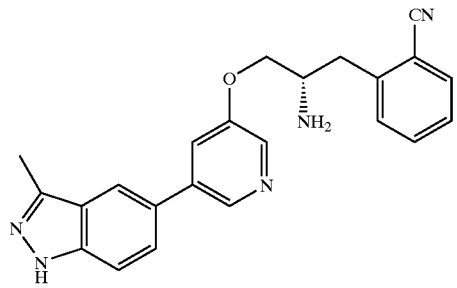

A-733910.7

EXAMPLE 157

2-((2S)-2-Amino-3-(5-(3-methyl-1H-indazol-5-yl)-pyridin-3-yloxy)-propyl)-benzonitrile MS (ESI) m/z 384 (M+H)$^+$; $^1$H NMR (500 MHz, DMSO-D6) δ ppm 2.54 (d, J=4.06 Hz, 3 H) 3.34 (m, 2 H) 4.03 (m, 1 H) 4.11 (dd, J=10.61, 4.99 Hz, 1 H) 4.33 (dd, J=10.92, 3.12 Hz, 1 H) 7.50 (t, J=7.64 Hz, 1 H) 7.65 (m, 7 H) 7.85 (d, J=7.80 Hz, 1 H) 8.06 (s, 1 H) 8.37 (s, 2 H) 8.65 (s, 1 H).

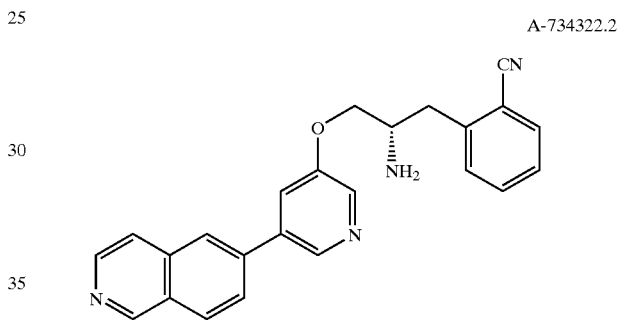

A-734322.2

EXAMPLE 158

2-((2S)-2-Amino-3-(5-isoquinolin-6-yl)-pyridin-3-yloxy)-propyl)-benzonitrile

MS (ESI) m/z 381 (M+H)$^+$; $^1$H NMR (500 MHz, DMSO-D6) δ ppm 3.32 (m, 2 H) 4.04 (m, 1 H) 4.16 (m, 1 H) 4.37 (dd, J=10.76, 3.28 Hz, 1 H) 7.50 (t, J=7.64 Hz, 1 H) 7.64 (d, J=7.49 Hz, 1 H) 7.71 (d, J=7.49 Hz, 1 H) 7.84 (m, 2 H) 8.00 (d, J=5.62 Hz, 1 H) 8.12 (dd, J=8.73, 1.87 Hz, 1 H) 8.34 (d, J=8.73 Hz, 1 H) 8.40 (m, 2 H) 8.54 (s, 2 H) 8.60 (d, J=5.61 Hz, 1 H) 8.74 (d, J=1.56 Hz, 1 H) 9.48 (s, 1 H).

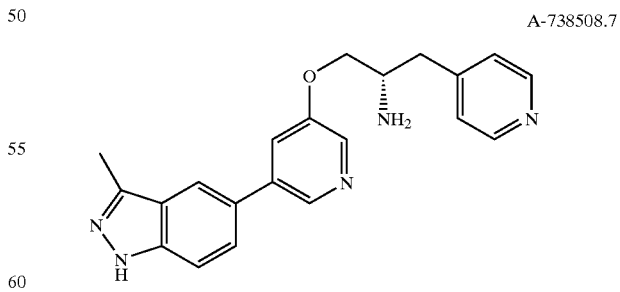

A-738508.7

EXAMPLE 159

(1S)-2-5-(3-methyl-1H-indazol-5-yl)-pyridin-3-yloxy)-1-pyridin-4-ylmethyl-ethylamine MS (ESI) m/z 360 (M+H)$^+$; $^1$H NMR (500 MH1H N z, DMSO-D6) δ ppm 2.50 (s, 3 H) 3.24 (d, J=6.86 Hz, 2 H)

4.05 (m, 1 H) 4.12 (m, 1 H) 4.25 (m, J=3.43 Hz, 1 H) 7.49 (m, J=4.68 Hz, 2 H) 7.53 (d, J=1.87 Hz, 1 H) 7.59 (m, 1 H) 7.71 (m, 1 H) 7.80 (m, 3 H) 8.09 (s, 1 H) 8.30 (d, J=4.06 Hz, 1 H) 8.40 (s, 2 H) 8.78 (m, J=4.99 Hz, 1 H).

(dd, J=10.76, 5.77 Hz, 1 H) 4.30 (m, 1 H) 7.18 (m, 6 H) 7.84 (m, 1 H) 7.97 (d, J=5.93 Hz, 1 H) 8.10 (dd, J=8.58, 1.72 Hz, 1 H) 8.24 (m, 2 H) 8.31 (d, J=8.74 Hz, 1 H) 8.59 (d, J=5.93 Hz, 1 H) 8.74 (d, J=1.87 Hz, 1 H) 9.45 (s, 1 H)

A-738511.2

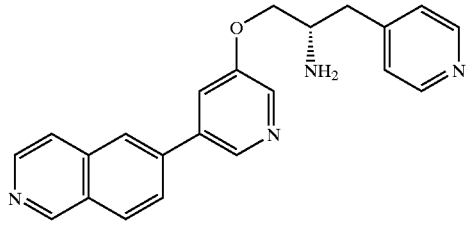

EXAMPLE 160

(1S)-2-(5-Isoquinolin-6-yl-pyridin-3-yloxy)-1-pyridin-4-ylmethyl-ethylamine

MS (ESI) m/z 357 (M+H)+; 1H NMR (500 MHz, DMSO-D6) δ ppm 3.24 (d, J=7.17 Hz, 1 H) 3.28 (d, J=7.18 Hz, 1 H) 4.04 (m, 1 H) 4.26 (m, 1 H) 4.40 (d, J=3.43 Hz, 1 H) 7.83 (dd, J=14.66, 6.24 Hz, 3 H) 7.93 (m, 1 H) 8.26 (m, 2 H) 8.38 (m, 1 H) 8.47 (d, J=2.81 Hz, 2 H) 8.51 (d, J=8.42 Hz, 1 H) 8.58 (s, 1 H) 8.68 (d, J=6.24 Hz, 1 H) 8.80 (m, 2 H) 9.71 (s, 1 H).

A-741302.7

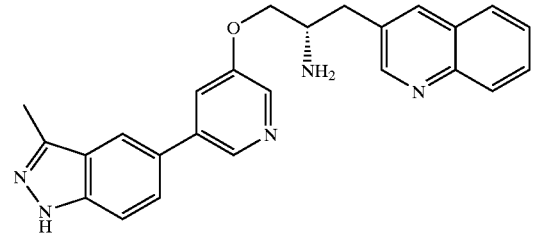

EXAMPLE 163

(1S)-2-(5-(3-methyl-1H-indazol-5-yl)-pyridin-3-yloxy)-1-quinolin-3-ylmethyl-ethylamine MS (ESI) m/z 410 (M+H)+; 1H NMR (500 MHz, DMSO-D6) δ ppm 2.56 (m, 3 H) 3.29 (m, 2 H) 4.12 (m, 1 H) 4.29 (m, 1 H) 4.42 (dd, J=10.76, 3.28 Hz, 1 H) 7.56 (d, J=8.73 Hz, 1 H) 7.66 (m, 2 H) 7.78 (m, 2 H) 7.97 (t, J=7.18 Hz, 2 H) 8.05 (m, 2 H) 8.36 (m, 4 H) 8.91 (m, 2 H)

A-740051.7

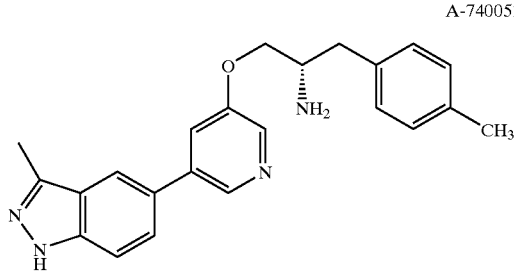

EXAMPLE 161

(1S)-1-(4-Methyl-benzyl)-2-(5-(3-methyl-1H-indazol-5-yl)-pyridin-3-yloxy)-ethylamine MS (ESI) m/z 373 (M+H)+; 1H NMR (500 MHz, DMSO-D6) δ ppm 2.28 (m, 3 H) 2.55 (s, 3 H) 2.98 (m, 2 H) 3.81 (s, 1 H) 4.11 (dd, J=10.45, 6.08 Hz, 1 H) 4.27 (dd, J=10.76, 2.96 Hz, 1 H) 7.16 (m, 3 H) 7.21 (m, 1 H) 7.57 (d, J=8.73 Hz, 1 H) 7.69 (m, 2 H) 8.07 (s, 1 H) 8.21 (m, 3 H) 8.31 (d, J=2.18 Hz, 1 H) 8.62 (s, 1 H).

A-741305.2

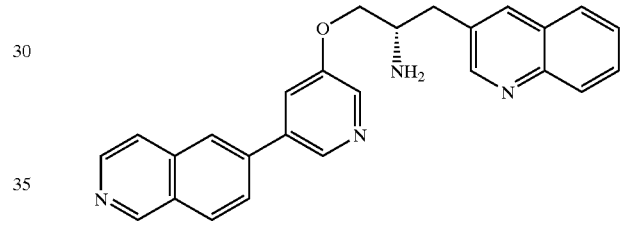

EXAMPLE 164

(1S)-2-(5-Isoquinolin-6-yl-pyridin-3-yloxy)-1-quinolin-3-ylmethyl-ethylamine

MS (ESI) m/z 407 (M+H)+; 1H NMR (500 MHz, DMSO-D6) δ ppm 3.27 (m, 2 H) 4.09 (d, J=5.62 Hz, 1 H) 4.27 (dd, J=10.92, 5.62 Hz, 1 H) 4.43 (dd, J=10.61, 3.43 Hz, 1 H) 5.75 (s, 1 H) 7.62 (m, 1 H) 7.76 (m, 1 H) 7.86 (m, 1 H) 7.94 (m, 2 H) 8.06 (m, 1 H) 8.30 (m, 5 H) 8.46 (d, J=2.81 Hz, 1 H) 8.59 (d, J=5.93 Hz, 1 H) 8.74 (m, J=1.87 Hz, 1 H) 8.89 (dd, J=20.28, 2.18 Hz, 1 H) 9.43 (s, 1 H).

A-741300.2

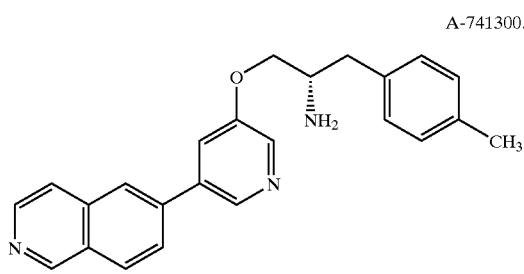

EXAMPLE 162

(1S)-2-(5-Isoquinolin-6-yl-pyridin-3-yloxy)-1-(4-methyl-benzyl)-ethylamine

MS (ESI) m/z 370 (M+H)+; 1H NMR (500 MHz, DMSO-D6) δ ppm 2.28 (m, 3 H) 3.01 (m, 2 H) 3.83 (s, 1 H) 4.14

A-742710.7

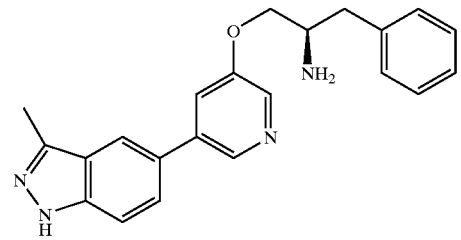

EXAMPLE 165

(1R)-1-Benzyl-2-(5-(3-methyl-1H-indazol-5-yl)-pyridin-3-yloxy)-ethylamine

MS (ESI) m/z 358 (M+H)+; 1H NMR (500 MHz, DMSO-D6) δ ppm 2.49 (s, 3 H) 2.99 (m, 2 H) 3.79 (s, 1 H) 4.07 (dd, J=10.61, 5.93 Hz, 1 H) 4.23 (dd, J=10.76, 2.96 Hz, 1 H) 7.22 (m, 2 H) 7.29 (m, 3 H) 7.51 (d, J=8.73 Hz, 1 H) 7.62 (dd, J=8.73, 1.56 Hz, 1 H) 7.64 (m, 1 H) 8.00 (s, 1 H) 8.19 (s, 3 H) 8.26 (m, 1 H) 8.56 (s, 1 H).

(m, 1 H) 4.28 (m, 1 H) 5.07 (s, 2 H) 6.99 (d, J=8.59 Hz, 3 H) 7.24 (d, J=8.59 Hz, 2 H) 7.32 (m, J=7.06 Hz, 1 H) 7.40 (m, 4 H) 7.69 (dd, J=8.75, 1.69 Hz, 1 H) 7.73 (m, 1 H) 8.08 (s, 1 H) 8.19 (m, 3 H) 8.33 (m, J=2.46 Hz, 1 H) 8.64 (d, J=1.53 Hz, 1 H).

A-746444.2

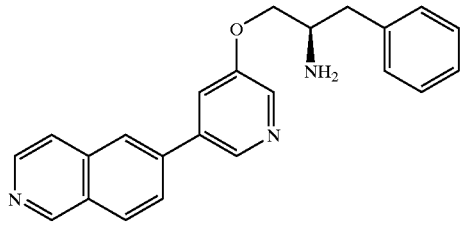

EXAMPLE 166

(1R)-1-Benzyl-2-(5-isoquinolin-6-yl-pyridin-3-yloxy)-ethylamine

MS (ESI m/z 356) (M+H)$^+$; $^1$H NMR (500 MHz, DMSO-D6) δ ppm 2.86 (m, 1 H) 2.95 (m, 1 H) 3.58 (m, 1 H) 4.08 (m, 1 H) 4.18 (m, 1 H) 7.28 (m, 5 H) 7.81 (m, 1 H) 7.88 (m, 1 H) 8.06 (m, 1 H) 8.25 (m, 1 H) 8.36 (m, 1 H) 8.39 (m, 1 H) 8.55 (m, 1 H) 8.69 (m, 1 H) 9.37 (m, 1 H)

A-751256.7

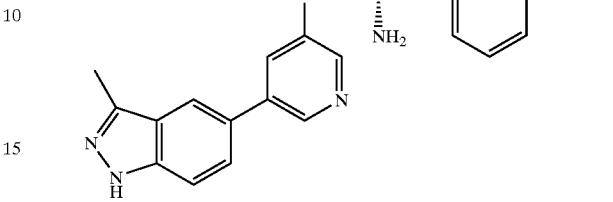

EXAMPLE 169

(1S)-1-(3-Methyl-benzyl)-2-(5-(3-methyl-1H-indazol-5-yl)-pyridin-3-yloxy)-ethylamine MS (ESI) m/z 373 (M+H)$^+$; $^1$H NMR (500 MHz, DMSO-D6) δ ppm 2.28 (s, 3 H) 2.56 (s, 3 H) 3.01 (m, 2 H) 4.15 (dd, J=10.92, 5.62 Hz, 1 H) 4.30 (m, J=2.81 Hz, 1 H) 7.11 (m, J=17.00, 7.64 Hz, 3 H) 7.23 (m, J=7.49 Hz, 1 H) 7.58 (d, J=8.73 Hz, 1 H) 7.70 (dd, J=8.73, 1.56 Hz, 1 H) 7.80 (m, 1 H) 8.10 (s, 1 H) 8.26 (s, 3 H) 8.35 (d, J=2.81 Hz, 1 H) 8.67 (d, J=1.56 Hz, 1 H).

A-748632.7

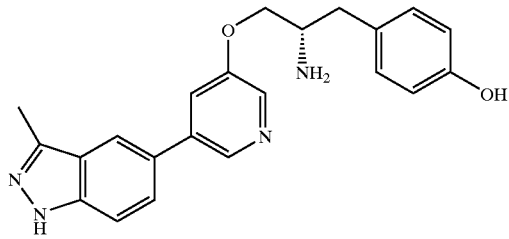

EXAMPLE 167

4-((2S)-2-Amino-3-(5-(3-methyl-1H-indazol-5-yl)-pyridin-3-yloxy)-propyl)-phenol

MS (ESI) m/z 374 (M+H)$^+$; $^1$H NMR (400 MHz, DMSO-D6) δ ppm 2.55 (s, 3 H) 3.50 (m, 8 H) 6.73 (dd, J=8.44, 2.92 Hz, 1 H) 7.09 (m, 1 H) 7.59 (m, 2 H) 7.69 (m, 2 H) 7.87 (s, 1 H) 8.14 (m, 2 H) 8.23 (d, J=1.84 Hz, 1 H) 8.62 (s, 1 H).

A-751278.7

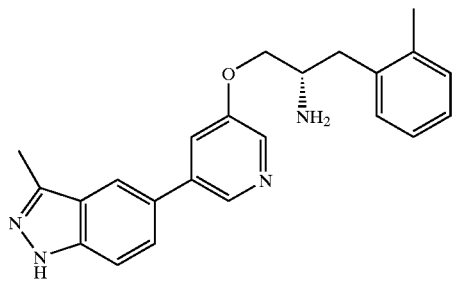

EXAMPLE 170

(1S)-1-(2-Methyl-benzyl)-2-(5-(3-methyl-1H-indazol-5-yl)-pyridin-3-yloxy)-ethylamine

A-748633.7

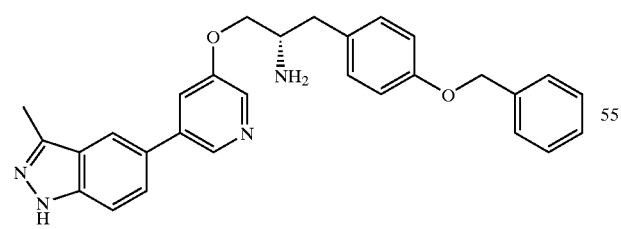

EXAMPLE 168

(1S)-1-(4-Benzyloxy-benzyl)-2-(5-(3-methyl-1H-indazol-5-yl)-pyridin-3-yloxy)-ethylamine MS m/z 465 (ESI) (M+H)$^+$; $^1$H NMR (400 MHz, DMSO-D6) δ ppm 2.55 (s, 3 H) 2.97 (m, 2 H) 3.82 (m, 1 H) 4.13

MS (ESI) m/z 373 (M+H)$^+$; $^1$H NMR (500 MHz, DMSO-D6) δ ppm 2.30 (d, J=7.80 Hz, 1 H) 2.33 (s, 3 H) 2.56 (m, 3 H) 3.07 (d, J=7.80 Hz, 1 H) 3.80 (s, 1 H) 4.12 (dd, J=10.76, 4.84 Hz, 1 H) 4.26 (dd, J=10.61, 2.81 Hz, 1 H) 7.19 (m, 4 H) 7.57 (d, J=8.73 Hz, 1 H) 7.68 (dd, J=11.07, 2.03 Hz, 2 H) 8.06 (s, 1 H) 8.31 (s, 3 H) 8.62 (s, 1 H).

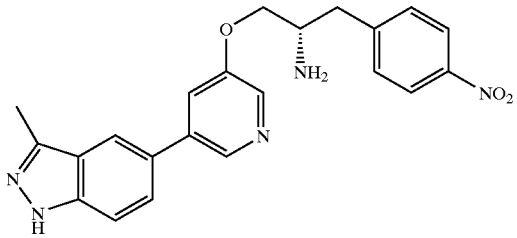

A-751282.7

EXAMPLE 171

(1S)-2-(5-(3-methyl-1H-indazol-5-yl)-pyridin-3-yloxy)-1-(4-nitro-benzyl)-ethylamine MS (ESI) m/z 404 (M+H)$^+$; $^1$H NMR (500 MHz, DMSO-D6) δ ppm 2.55 (s, 3 H) 3.19 (m, 2 H) 3.97 (s, 1 H) 4.18 (dd, J=10.92, 5.62 Hz, 1 H) 4.34 (dd, J=10.76, 3.28 Hz, 1 H) 7.57 (d, J=8.74 Hz, 1 H) 7.64 (m, J=8.73 Hz, 2 H) 7.69 (dd, J=8.58, 1.72 Hz, 1 H) 7.77 (m, 1 H) 8.08 (s, 1 H) 8.23 (d, J=8.73 Hz, 2 H) 8.29 (m, 2 H) 8.34 (d, J=2.50 Hz, 1 H) 8.66 (d, J=1.25 Hz, 1 H).

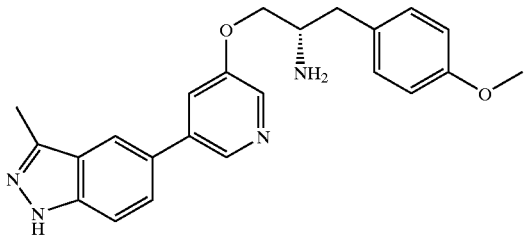

A-755097.7

EXAMPLE 172

(1S)-1-(4-Methoxy-benzyl)-2-(5-(3-methyl-1H-indazol-5-yl)-pyridin-3-yloxy)-ethylamine MS (ESI) m/z 389 (M+H)$^+$; $^1$H NMR (500 MHz, DMSO-D6) δ ppm 2.56 (s, 3 H) 2.98 (dd, J=15.13, 6.08 Hz, 2 H) 3.73 (m, 3 H) 3.80 (m, 1 H) 4.16 (dd, J=10.76, 5.77 Hz, 1 H) 4.32 (dd, J=10.61, 3.12 Hz, 1 H) 6.91 (m, 2 H) 7.21 (dd, J=8.58, 2.65 Hz, 1 H) 7.25 (d, J=8.73 Hz, 2 H) 7.59 (d, J=8.73 Hz, 1 H) 7.71 (dd, J=8.73, 1.87 Hz, 1 H) 7.84 (m, 1 H) 8.11 (s, 1 H) 8.28 (m, 2 H) 8.37 (d, J=2.81 Hz, 1 H) 8.69 (d, J=1.56 Hz, 1 H).

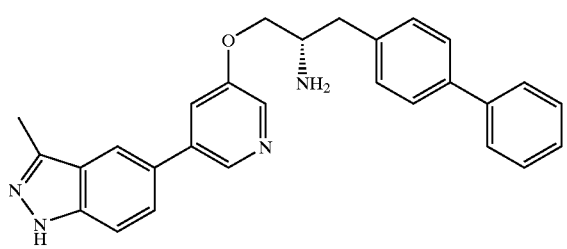

A-757584.7

EXAMPLE 173

(1S)-1-Biphenyl-4-ylmethyl-2-(5-(3-methyl-1H-indazol-5-yl)-pyridin-3-yloxy)-ethylamine MS (ESI) m/z 435 (M+H)$^+$; $^1$H NMR (500 MHz, DMSO-D6) δ ppm 2.55 (s, 3 H) 3.10 (m, 2 H) 3.92 (s, 1 H) 4.21 (dd, J=110.92, 5.62 Hz, 1 H) 4.36 (dd, J=10.76, 2.96 Hz, 1 H) 7.36 (t, J=7.49 Hz, 1 H) 7.44 (m, 4 H) 7.57 (d, J=8.73 Hz, 1 H) 7.65 (dd, J=10.29, 7.80 Hz, 4 H) 7.70 (dd, J=8.73, 1.56 Hz, 1 H) 7.82 (s, 1 H) 8.10 (s, 1 H) 8.30 (d, J=2.81 Hz, 3 H) 8.37 (d, J=2.50 Hz, 1 H) 8.67 (d, J=1.25 Hz, 1 H).

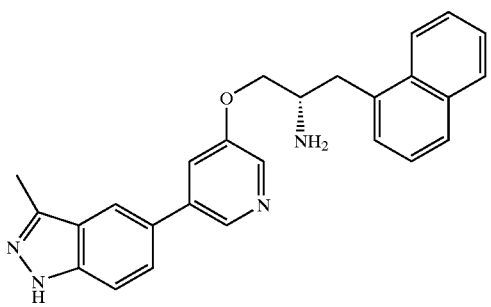

A-757602.7

EXAMPLE 174

(1S)-2-(5-(3-Methyl-1H-indazol-5-yl)-pyridin-3-yloxy)-1-napthalen-1-ylmethyl-ethylamine MS (ESI) m/z 409 (M+H)$^+$; $^1$H NMR (500 MHz, DMSO-D6) δ ppm 2.55 (s, 3 H) 3.44 (dd, J=14.04, 6.86 Hz, 2 H) 3.93 (s, 1 H) 4.17 (dd, J=10.61, 4.99 Hz, 1 H) 4.32 (m, 1 H) 7.48 (m, 2 H) 7.59 (m, 3 H) 7.66 (dd, J=8.58, 1.72 Hz, 1 H) 7.69 (m, 1 H) 7.89 (dd, J=6.24, 3.12 Hz, 1 H) 7.98 (d, J=8.11 Hz, 1 H) 8.05 (s, 1 H) 8.21 (d, J=8.42 Hz, 1 H) 8.29 (m, 2 H) 8.32 (d, J=2.81 Hz, 1 H) 8.63 (d, J=1.56 Hz, 1 H).

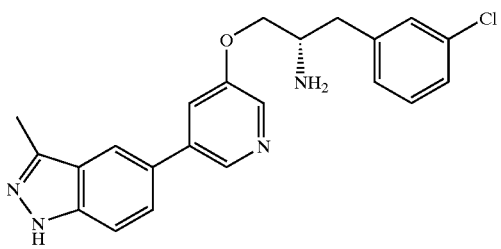

A-763516.7

EXAMPLE 175

(1S)-1-(3-Chloro-benzyl)-2-(5-(3-methyl-1H-indazol-5-yl)-pyridin-3-yloxy)-ethylamine MS (ESI) m/z 393 (M+H)$^+$; $^1$H NMR (500 MHz, DMSO-D6) δ ppm 2.55 (s, 3 H) 3.06 (d, J=7.49 Hz, 2 H) 3.92 (m, 1 H) 4.16 (m, 1 H) 4.33 (dd, J=10.92, 3.12 Hz, 1 H) 7.31 (d, J=7.49 Hz, 1 H) 7.37 (m, J=14.51, 7.02 Hz, 2 H) 7.45 (s, 1 H) 7.58 (d, J=8.73 Hz, 1 H) 7.70 (dd, J=8.73, 1.56 Hz, 1 H) 7.77 (s, 1 H) 8.08 (s, 1 H) 8.23 (s, 3 H) 8.34 (d, J=2.50 Hz, 1 H) 8.65 (s, 1 H).

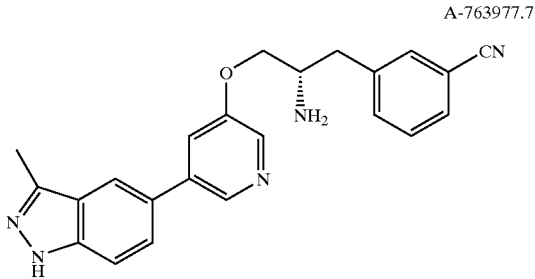

A-763977.7

EXAMPLE 176

3-((2S)-2-Amino-3-(5-(3-methyl-1H-indazol-5-yl)-pyridin-3-yloxy)-propyl)-benzonitrile MS (ESI) m/z 384 (M+H)$^+$; $^1$H NMR (500 MHz, DMSO-D6) δ ppm 2.55 (s, 3 H) 3.12 (d, J=7.49 Hz, 2 H) 3.96 (s, 1 H) 4.17 (dd, J=10.76, 5.77 Hz, 1 H) 4.33 (m, 1 H) 7.57 (dd, J=8.11, 6.55 Hz, 2 H) 7.69 (dd, J=8.42, 1.56 Hz, 2 H) 7.76 (m, 2 H) 7.84 (s, 1 H) 8.08 (s, 1 H) 8.23 (s, 3 H) 8.33 (d, J=2.81 Hz, 1 H) 8.64 (d, J=1.56 Hz, 1 H).

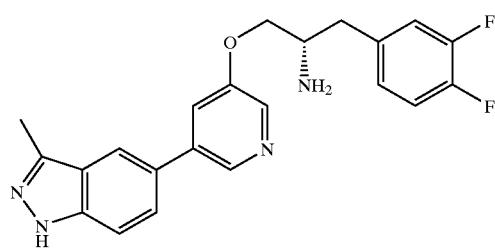

A-764024.7

EXAMPLE 177

(1S)-1-(3,4-Difluoro-benzyl)-2-(5-(3-methyl-1H-indazol-5-yl)-pyridin-3-yloxy)-ethylamine MS (ESI) m/z 395 (M+H)$^+$; $^1$H NMR (500 MHz, DMSO-D6) δ ppm 2.56 (s, 3 H) 3.05 (d, J=7.18 Hz, 2 H) 3.90 (m, 1 H) 4.17 (dd, J=10.92, 5.93 Hz, 1 H) 4.34 (dd, J=10.61, 3.12 Hz, 1 H) 7.19 (m, J=2.18 Hz, 1 H) 7.44 (m, 2 H) 7.58 (d, J=8.73 Hz, 1 H) 7.70 (dd, J=8.73, 1.56 Hz, 1 H) 7.77 (d, J=2.50 Hz, 1 H) 8.08 (s, 1 H) 8.23 (s, 3 H) 8.34 (d, J=2.50 Hz, 1 H) 8.65 (d, J=1.56 Hz, 1 H).

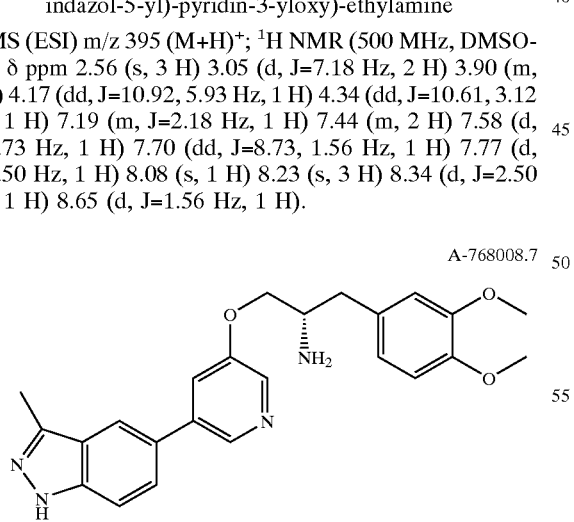

A-768008.7

EXAMPLE 178

(1S)-1-(3,4-Dimethoxy-benzyl)-2-(5-(3-methyl-1H-indazol-5-yl)-pyridin-3-yloxy)-ethylamine MS (ESI) m/z 419 (M+H)$^+$; $^1$H NMR (500 MHz, DMSO-D6) δ ppm 2.55 (s, 3 H) 2.98 (m, 2 H) 3.70 (s, 3 H) 3.71 (s, 3 H) 3.82 (s, 1 H) 4.14 (dd, J=10.61, 5.62 Hz, 1 H) 4.31 (dd, J=10.76, 2.96 Hz, 1 H) 6.82 (d, J=8.11 Hz, 1 H) 6.91 (m, 2 H) 7.57 (d, J=8.42 Hz, 1 H) 7.68 (m, 1 H) 7.71 (s, 1 H) 8.07 (s, 1 H) 8.28 (s, 3 H) 8.32 (s, 1 H) 8.62 (s, 1 H).

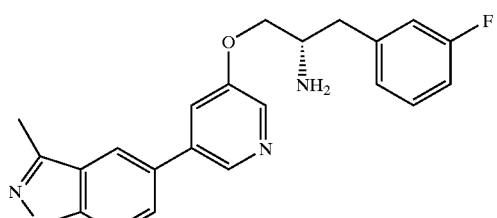

A-768009.7

EXAMPLE 179

(1S)-1-(3-Fluoro-benzyl)-2-(5-(3-methyl-1H-indazol-5-yl)-pyridin-3-yloxy)-ethylamine MS (ESI) m/z 377 (M+H)$^+$; $^1$H NMR (500 MHz, DMSO-D6) δ ppm 2.55 (s, 3 H) 3.08 (m, 2 H) 3.91 (s, 1 H) 4.15 (dd, J=10.61, 5.93 Hz, 1 H) 4.32 (dd, J=10.61, 3.12 Hz, 1 H) 7.12 (m, 1 H) 7.20 (m, 2 H) 7.40 (m, 1 H) 7.57 (d, J=8.73 Hz, 1 H) 7.69 (dd, J=8.42, 1.56 Hz, 1 H) 7.71 (d, J=1.87 Hz, 1 H) 8.07 (s, 1 H) 8.29 (s, 3 H) 8.31 (d, J=2.81 Hz, 1 H) 8.62 (s, 1 H).

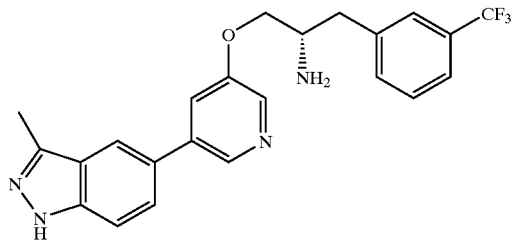

A-770247.7

EXAMPLE 180

(1S)-2-(5-(3-methyl-1H-indazol-5-yl)-pyridin-3-yloxy)-1-(3-trifluoromethy 1-benzyl)-ethylamine MS (ESI) m/z 427. (M+H)$^+$; $^1$H NMR (500 MHz, DMSO-D6) δ ppm 2.55 (s, 3 H) 3.16 (dd, J=7.33, 2.34 Hz, 2 H) 3.97 (s, 1 H) 4.16 (dd, J=10.61, 5.62 Hz, 1 H) 4.34 (dd, J=10.76, 3.28 Hz, 1 H) 7.58 (d, J=8.42 Hz, 1 H) 7.61 (d, J=7.49 Hz, 1 H) 7.65 (s, 1 H) 7.66 (s, 1 H) 7.69 (dd, J=8.74, 1.56 Hz, 1 H) 7.73 (s, 1 H) 7.75 (m, 1 H) 8.07 (s, 1 H) 8.22 (s, 3 H) 8.33 (d, J=2.50 Hz, 1 H) 8.64 (d, J=1.56 Hz, 1 H).

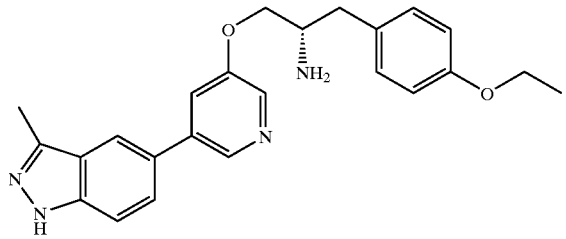

A-770248.7

EXAMPLE 181

(1S)-1-(4-Ethoxy-benzyl)-2-[5-(3-methyl-1H-indazol-5-yl)-pyridin-3-yloxy]-ethylamine MS (ESI) m/z 403 (M+H)$^+$; $^1$H NMR (500 MHz, DMSO-D6) δ ppm 1.30 (t, J=7.02 Hz, 3 H) 2.55 (s, 3 H) 2.97 (m, 2 H) 3.79 (s, 1 H) 3.98 (q, J=6.86 Hz, 2 H) 4.13 (dd, J=10.76, 5.77 Hz, 1 H) 4.29 (dd, J=10.76, 2.96 Hz, 1 H) 6.89 (d, J=8.42 Hz, 1 H) 7.22 (d, J=8.42 Hz, 1 H) 7.57 (d, J=8.42 Hz, 2 H) 7.61 (m, J=11.85 Hz, 1 H) 7.69 (dd, J=8.73, 1.56 Hz, 1 H) 7.75 (s, 1 H) 8.08 (s, 1 H) 8.18 (s, 3 H) 8.33 (d, J=2.50 Hz, 1 H) 8.65 (d, J=1.56 Hz, 1 H).

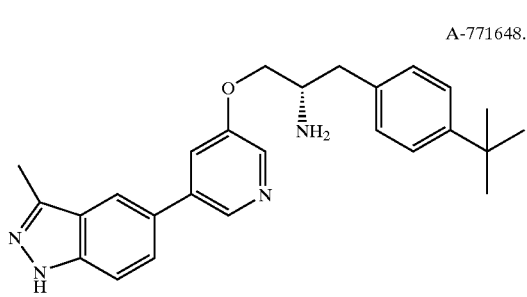

A-771648.7

EXAMPLE 182

(1S)-1-(4-tert-Butyl-benzyl)-2-(5-(3-methyl-1H-indazol-5-yl)-pyridin-3-yloxy)-ethylamine MS (ESI) m/z 415 (M+H)$^+$; $^1$H NMR (500 MHz, DMSO-D6) δ ppm 1.26 (m, 9 H) 2.55 (s, 3 H) 2.80 (dd, J=13.73, 6.86 Hz, 1 H) 2.92 (m, 1 H) 3.55 (m, 1 H) 4.06 (dd, J=9.98, 5.93 Hz, 1 H) 4.15 (m, 1 H) 7.21 (d, J=8.11 Hz, 2 H) 7.34 (d, J=8.42 Hz, 2 H) 7.56 (d, J=8.42 Hz, 1 H) 7.69 (m, 2 H) 8.08 (s, 1 H) 8.28 (d, J=2.50 Hz, 1 H) 8.57 (d, J=1.56 Hz, 1 H) 12.73 (s, 1 H).

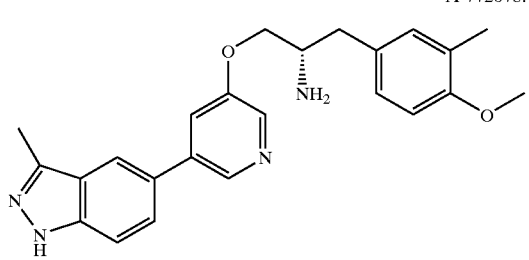

A-772078.7

EXAMPLE 183

(1S)-1-(4-Methoxy-3-methyl-benzyl)-2-(5-(3-methyl-1H-indazol-5-yl)-pyridin-3-yloxy)-ethylamine MS (ESI) m/z 403 (M+H)$^+$; $^1$H NMR (500 MHz, DMSO-D6) δ ppm 2.11 (s, 3 H) 2.55 (s, 3 H) 2.71 (m, 1 H) 2.83 (dd, J=13.73, 6.86 Hz, 1 H) 3.17 (d, J=3.74 Hz, 2 H) 3.47 (m, 1 H) 3.74 (m, 3 H) 4.07 (m, 2 H) 6.86 (d, J=8.11 Hz, 1 H) 7.05 (m, 2 H) 7.56 (m, J=8.73 Hz, 1 H) 7.67 (m, 2 H) 8.07 (s, 1 H) 8.27 (d, J=2.81 Hz, 1 H) 8.57 (d, J=1.56 Hz, 1 H) 12.72 (s, 1 H).

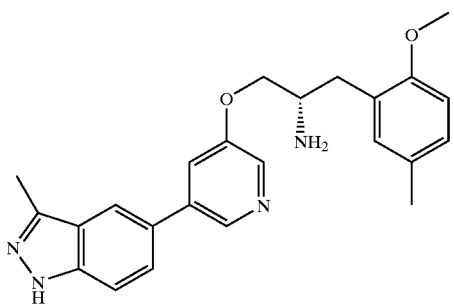

A-772635.7

EXAMPLE 184

2-((2S)-2-Amino-3-(5-(3-methyl-1H-indazol-5-yl)-pyridin-3-yloxy)-propyl)-4-methyl-phenol MS (ESI) m/z 403 (M+H)$^+$; $^1$H NMR (500 MHz, DMSO-D6) δ ppm 2.18 (s, 3 H) 2.55 (s, 3 H) 2.98 (d, J=7.49 Hz, 2 H) 3.73 (d, J=3.74 Hz, 3 H) 3.79 (m, 1 H) 4.12 (dd, J=10.61, 5.62 Hz, 1 H) 4.27 (dd, J=10.61, 3.12 Hz, 1 H) 6.90 (d, J=8.11 Hz, 1 H) 7.02 (s, 1 H) 7.07 (d, J=8.42 Hz, 1 H) 7.57 (d, J=8.73 Hz, 1 H) 7.68 (dd, J=8.73, 1.56 Hz, 1 H) 7.71 (s, 1 H) 8.07 (s, 1 H) 8.17 (s, 3 H) 8.31 (d, J=2.50 Hz, 1 H) 8.64 (d, J=1.56 Hz, 1 H).

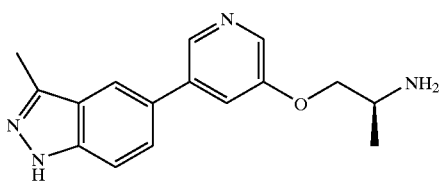

(A-755387)

EXAMPLE 185

(1S)-1-Methyl-2-[5-(3-methyl-1H-indazol-5-yl)-pyridin-3-yloxy]-ethylamine

MS (ESI) m/e 283 (M+H)$^+$; $^1$H NMR (300 MHz, DMSO-D6) δ ppm 1.32 (d, J=6.78 Hz 3 H) 2.56 (s, 3 H) 3.66 (m, 1 H) 4.16 (dd, J=10.51, 7.12 Hz, 1 H) 4.35 (dd, J=10.51, 3.73 Hz, 1 H) 7.57 (d, J=8.81 Hz, 1 H) 7.72 (m, 1 H) 7.78 (m, 1 H) 8.01 (m, 2 H) 8.10 (m, 1 H) 8.33 (d, J=2.71 Hz, 1 H) 8.63 (d, J=1.70 Hz, 1 H) 12.70 (bs, 1 H); Anal. Calcd for $C_{16}H_{18}N_4O$.2.2 TFA: C, 45.95; H, 3.82; N, 10.51. Found: C, 46.11; H, 3.76; N, 10.55.

(A-444277)

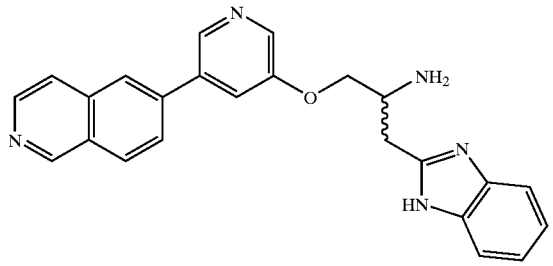

EXAMPLE 186

(±)-1-(1H-Benzoimidazol-2-ylmethyl)-2-(5-isoquinolin-6-yl-pyridin-3-yloxy)-ethylamine MS (ESI) m/e 396 (M+H)+; $^1$H NMR (500 MHz, DMSO-D6) δ ppm 3.51 (m, 2 H) 4.32 (m, 1 H) 4.44 (m, 1 H) 4.55 (m, 1 H) 7.36 (dd, J=6.24, 3.12 Hz, 2 H) 7.68 (dd, J=5.93, 3.12 Hz, 2 H) 7.88 (d, J=2.18 Hz, 1 H) 8.12 (d, J=6.24 Hz, 1 H) 8.19 (dd, J=8.58, 1.40 Hz, 1 H) 8.42 (m, 2 H) 8.49 (s, 1 H) 8.64 (d, J=5.93 Hz, 1 H) 8.77 (d, J=1.56 Hz, 1 H) 9.60 (s, 1 H).

(A-475104)

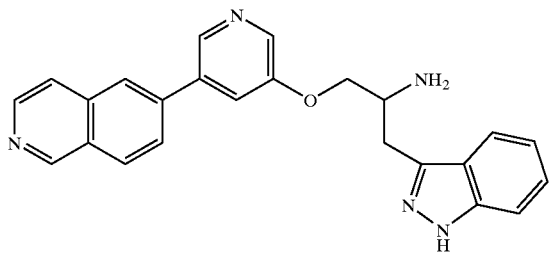

EXAMPLE 187

(±)-1-(1H-Indazol-3-ylmethyl)-2-(5-isoquinolin-6-yl-pyridin-3-yloxy)-ethylamine

MS (ESI) m/e 396 (M+H)+; $^1$H NMR (400 MHz, DMSO-D6) δ ppm 3.21 (m, 2 H) 3.84 (m, 1 H) 4.21 (dd, J=9.97, 5.98 Hz, 1 H) 4.31 (dd, J=9.97, 5.98 Hz, 1 H) 7.08 (t, J=7.21 Hz, 1 H) 7.33 (t, J=7.21 Hz, 1 H) 7.49 (d, J=8.59 Hz, 1 H) 7.80 (m, 2 H) 7.89 (d, J=5.83 Hz, 1 H) 8.06 (dd, J=8.59, 1.84 Hz, 1 H) 8.25 (d, J=8.59 Hz, 1 H) 8.36 (s, 1 H) 8.39 (d, J=2.76 Hz, 1 H) 8.56 (d, J=5.83 Hz, 1 H) 8.69 (d, J=1.84 Hz, 1 H) 9.37 (s, 1 H) 12.87 (s, 1 H).

(A-757590)

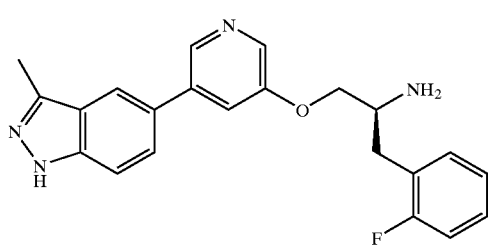

EXAMPLE 188

(1S)-1-(2-Fluoro-benzyl)-2-[5-(3-methyl-1H-indazol-5-yl)-pyridin-3-yloxy]-ethylamine MS (ESI) m/e 377 (M+H)+; $^1$H NMR (300 MHz, DMSO-D6) δ ppm 2.55 (s, 3 H) 3.11 (d, J=7.12 Hz, 2 H) 3.86 (m, 1 H) 4.15 (m, 1 H) 4.31 (dd, J=10.85, 3.39 Hz, 1 H) 7.20 (m, 2 H) 7.37 (m, 2 H) 7.57 (d, J=9.49 Hz, 1 H) 7.71 (m, 2 H) 8.08 (s, 1 H) 8.29 (s, 2 H) 8.31 (d, J=2.71 Hz, 1 H) 8.64 (d, J=1.69 Hz, 1 H) 12.74 (bs, 1 H).

(A-760116)

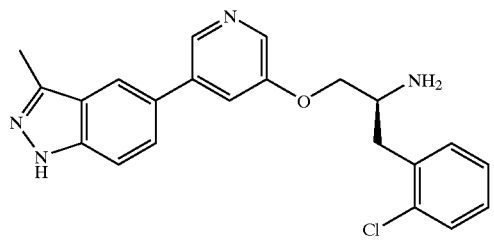

EXAMPLE 189

(1S)-1-(2-Chloro-benzyl)-2-[5-(3-methyl-1H-indazol-5-yl)-pyridin-3-yloxy]-ethylamine MS (ESI) m/e 393 (M+H)+; $^1$H NMR (300 MHz, DMSO-D6) δ ppm 2.55 (s, 3 H) 3.22 (m, 2 H) 3.89 (m, 1 H) 4.15 (m, 1 H) 4.31 (m, 1 H) 7.35 (m, 2 H) 7.48 (m, 3 H) 7.58 (d, J=8.82 Hz, 1 H) 7.70 (m, 2 H) 8.08 (s, 1 H) 8.31 (d, J=2.71 Hz, 2 H) 8.64 (d, J=1.70 Hz, 1 H) 12.84 (bs, 1 H).

(A-760117)

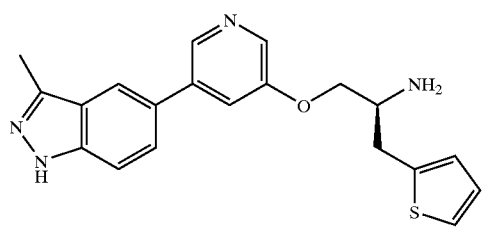

EXAMPLE 190

(1S)-2-[5-(3-Methyl-1H-indazol-5-yl)-pyridin-3-yloxy]-1-thiophen-2-ylmethyl-ethylamine MS (ESI) m/e 365 (M+H)+; $^1$H NMR (300 MHz, DMSO-D6) δ ppm 2.55 (s, 3 H) 3.28 (m, 2 H) 3.90 (m, 1 H) 4.20 (m, 1 H) 4.35 (m, 1 H) 7.03 (m, 2 H) 7.46 (m, 1 H) 7.58 (d, J=8.82 Hz, 1 H) 7.70 (m, 1 H) 7.75 (m, 1 H), 8.09 (s, 1 H) 8.26 (m, 2 H) 8.33 (d, J=2.71 Hz, 1 H) 8.64 (d, J=1.70 Hz, 1 H) 12.53 (bs, 1 H).

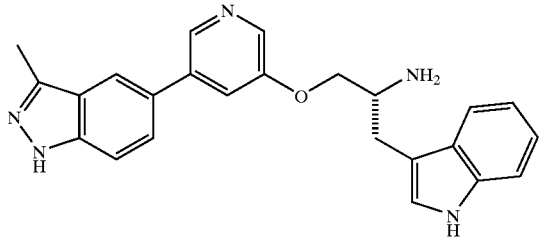

(A-751365)

EXAMPLE 191

(1R)-1-(1H-Indol-3-ylmethyl)-2-[5-(3-methyl-1H-indazol-5-yl)-pyridin-3-yloxy]-ethylamine MS (ESI) m/e 398 (M+H)$^+$; $^1$H NMR (300 MHz, DMSO-D6) δ ppm 2.55 (s, 3 H) 3.16 (m, 2 H) 3.86 (d, J=1.70 Hz, 1 H) 4.19 (dd, J=10.51, 6.10 Hz, 1 H) 4.36 (dd, J=10.85, 3.39 Hz, 1 H) 7.01 (t, J=7.46 Hz, 1 H) 7.10 (t, J=6.95 Hz, 1 H) 7.30 (d, J=2.37 Hz, 1 H) 7.38 (d, J=8.14 Hz, 1 H) 7.65 (m, 5 H) 8.07 (s, 1 H) 8.16 (s, 2 H) 8.33 (d, J=2.71 Hz, 1 H) 8.63 (d, J=1.70 Hz, 1 H) 11.04 (bs, 1 H); Anal. Calcd for C$_{24}$H$_{23}$N$_5$O.2.9 TFA: C, 49.16; H, 3.59; N, 9.62. Found: C, 49.36; H, 3.66; N, 9.78.

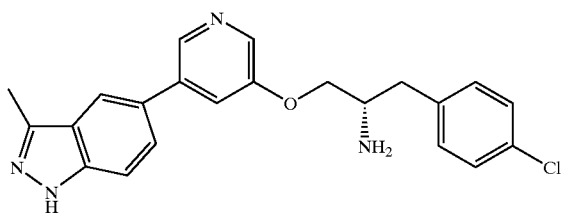

A-752674.7

EXAMPLE 192

1-(4-Chloro-benzyl)-2-[5-(3-methyl-1H-indazol-5-yl)-pyridin-3-yloxy]-ethylamine

MS (ESI) m/e 393 (M+1)$^+$; $^1$H NMR (300 MHz, Solvent) δ ppm 2.63 (s, 3 H) 3.16 (m, 2 H) 3.98 (m, 1 H) 4.29 (m, 1 H) 4.44 (m, 1 H) 7.34 (m, 2 H) 7.39 (m, 2 H) 7.63 (d, J=8.82 Hz, 1 H) 7.74 (dd, J=8.82, 1.70 Hz, 1 H) 8.09 (m, 1 H) 8.11 (m, 1 H) 8.42 (br. s., 1 H) 8.73 (br. s., 1 H).

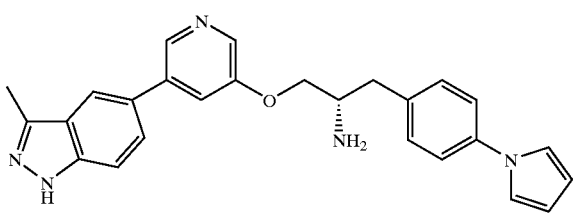

A-768094.0

EXAMPLE 193

(1S)-2-[5-(3-Methyl-1H-indazol-5-yl)-pyridin-3-yloxy]-1-(4-pyrrol-1-yl-benzyl)-ethylamine MS (ESI) m/e 424 (M+1)$^+$; $^1$H NMR (300 MHz, Solvent) δ ppm 2.61 (m, 3 H) 3.19 (m, 2 H) 4.10 (m, 1 H) 4.30 (m, 1 H) 4.44 (m, 1 H) 6.27 (t, J=2.03 Hz, 2 H) 7.16 (t, J=2.03 Hz, 2 H) 7.41 (d, J=8.48 Hz, 1 H) 7.49 (d, J=8.48 Hz, 2 H) 7.59 (d, J=8.48 Hz, 1 H) 7.70 (m, 1 H) 7.94 (m, 1 H) 8.07 (m, 1 H) 8.38 (br. s., 1 H) 8.66 (br. s., 1 H).

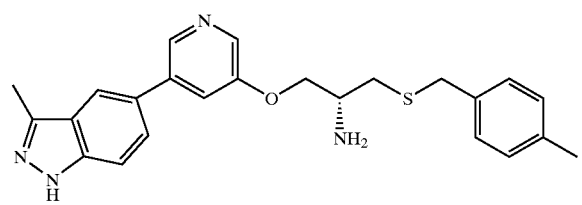

A-770737.7

EXAMPLE 194

(1S)-1-(4-Methyl-benzylsulfanylmethyl)-2-[5-(3-methyl-1H-indazol-5-yl)-pyridin-3-yloxy]-ethylamine MS (ESI) m/e 419 (M+1)$^+$; $^1$H NMR (300 MHz, MeOH) δ ppm 2.26 (s, 3 H) 2.62 (s, 3 H) 2.88 (m, 2 H) 3.67 (m, 1 H) 3.82 (s, 2 H) 4.38 (m, 2 H) 7.18 (m, 6 H) 7.62 (d, J=8.81 Hz, 1 H) 7.72 (dd, J=8.81, 1.70 Hz, 1 H) 7.85 (dd, J=2.71, 1.70 Hz, 1 H) 8.06 (m, 1 H) 8.30 (d, J=2.71 Hz, 1 H) 8.62 (d, J=1.70 Hz, 1 H).

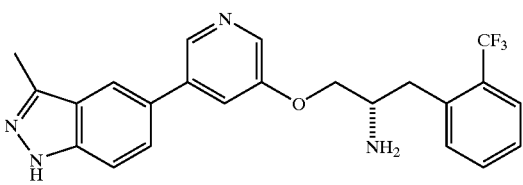

A-750982.3

EXAMPLE 195

(1S)-2-[5-(3-Methyl-1H-indazol-5-yl)-pyridin-3-yloxy]-1-(2-trifluoromethyl-benzyl)-ethylamine MS m/z 427 (M+H)$^+$; $^1$H NMR (300 MHz, DMSO-D6) δ ppm 2.57 (s, 3 H) 3.30 (m, 2 H) 3.93 (s, 1 H) 4.32 (dd, J=10.85, 5.42 Hz, 1 H) 4.45 (m, 1 H) 7.53 (td, J=8.22, 3.90 Hz, 1 H) 7.61 (dd, J=8.82, 0.68 Hz, 1 H) 7.68 (m, 2 H) 7.77 (m, 2 H) 8.14 (s, 1 H) 8.23 (d, J=0.68 Hz, 1 H) 8.46 (d, J=2.03 Hz, 1 H) 8.65 (s, 3 H) 8.83 (s, 1 H).

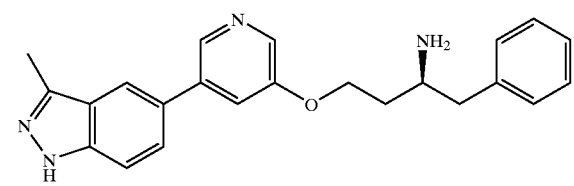

A-754683.3

EXAMPLE 196

(1R)-1-Benzyl-3-[5-(3-methyl-1H-indazol-5-yl)-pyridin-3-yloxy]-propylamine

MS m/z 373 (M+H)$^+$; $^1$H NMR (300 MHz, DMSO-D6) δ ppm 2.05 (m, 2 H) 2.57 (s, 3 H) 2.91 (dd, J=13.73, 8.65 Hz, 1 H) 3.11 (m, 1 H) 3.63 (m, 1 H) 4.41 (m, 2 H) 7.25 (m, 1 H) 7.33 (m, 4 H) 7.61 (dd, J=8.81, 0.68 Hz, 1 H) 7.81 (dd, J=8.81, 1.70 Hz, 1 H) 8.21 (s, 1 H) 8.28 (s, 2 H) 8.47 (d, J=2.37 Hz, 1 H) 8.82 (s, 1 H).

(m, 1 H) 4.33 (dd, J=10.61, 5.93 Hz, 1 H) 4.46 (dd, J=10.61, 3.12 Hz, 1 H) 7.04 (m, 1 H) 7.17 (m, 1 H) 7.17 (s, 1 H) 7.36 (d, J=8.42 Hz, 1 H) 7.59 (d, J=7.80 Hz, 1 H) 7.93 (m, 1 H) 8.28 (dd, J=8.73, 1.87 Hz, 1 H) 8.49 (m, 2 H) 8.59 (m, 3 H) 8.76 (s, 1 H) 9.77 (s, 1 H).

A-761612.3

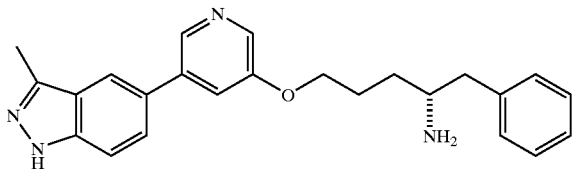

EXAMPLE 197

(1R)-1-Benzyl-4-[5-(3-methyl-1H-indazol-5-yl)-pyridin-3-yloxy]-butylamine

MS m/z 387 (M+H)$^+$; $^1$H NMR (300 MHz, DMSO-D6) δ ppm 1.70 (q, J=7.23 Hz, 2 H) 1.91 (m, 2 H) 2.57 (s, 3 H) 2.82 (dd, J=13.56, 8.48 Hz, 1 H) 3.06 (dd, J=13.73, 5.26 Hz, 1 H) 3.47 (s, 1 H) 4.27 (m, 2 H) 7.27 (m, 5 H) 7.61 (d, J=8.48 Hz, 1 H) 7.84 (dd, J=8.81, 1.70 Hz, 1 H) 8.29 (s, 2 H) 8.33 (s, 1 H) 8.49 (d, J=2.37 Hz, 1 H) 8.87 (s, 1 H).

A-437689.6

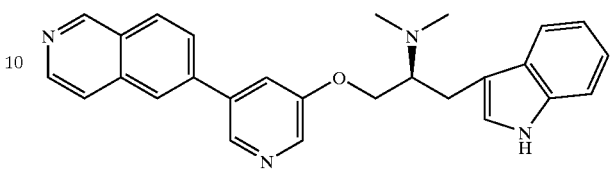

EXAMPLE 199

(1S)-[1-(1H-Indol-3-ylmethyl)-2-(5-isoquinolin-6-yl-pyridin-3-yloxy)-ethyl]-dimethyl-amine $^1$HNMR (400 MHz, MeOD) δ ppm 3.16 (s, 6 H) 3.44 (m, 2 H) 4.11 (m, 1 H) 4.46 (m, 1 H) 4.55 (m, 1 H) 7.00 (m, 1 H) 7.09 (m, 1 H) 7.26 (m, 1 H) 7.35 (d, J=8.29 Hz, 1 H) 7.60 (d, J=7.98 Hz, 1 H) 7.81 (m, 1 H) 8.22 (dd, J=8.59, 1.53 Hz, 1 H) 8.42 (m, 2 H) 8.50 (m, 1 H) 8.55 (d, J=8.90 Hz, 1 H) 8.61 (m, 1 H) 8.72 (m, 1 H) 9.73 (s, 1 H)

A-761613.3

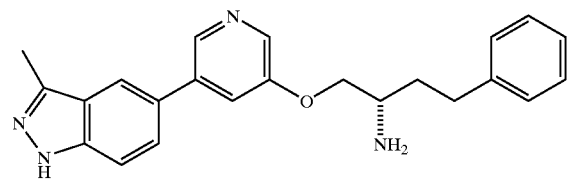

EXAMPLE 198

(1S)-1-[5-(3-Methyl-1H-indazol-5-yl)-pyridin-3-yloxymethyl]-3-phenyl-propylamine MS m/z 373 (M+H)$^+$; $^1$H NMR (300 MHz, DMSO-D6) δ ppm 2.04 (m, 2 H) 2.57 (s, 3 H) 2.80 (m, 2 H) 3.57 (m, 1 H) 4.44 (dd, J=10.68, 6.61 Hz, 1 H) 4.59 (m, 1 H) 7.24 (m, 5 H) 7.62 (d, J=8.82 Hz, 1 H) 7.82 (dd, J=8.65, 1.53 Hz, 1 H) 8.27 (s, 2 H) 8.50 (s, 2 H) 8.54 (d, J=2.71 Hz, 1 H) 8.86 (s, 1 H).

A-431070.6

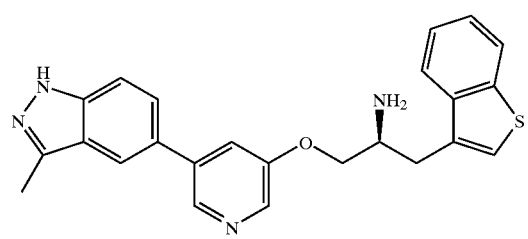

EXAMPLE 199

(1S)-2-(5-Isoquinolin-6-yl-pyridin-3-yloxy)-1-(1-methyl-1H-indol-3-ylmethyl)-ethylamine trifloroacetic acid Salt MS (DCI/NH$_3$) m/z 409 (M+1)$^+$; $^1$HNMR (500 MHz, MeOD) δ ppm 3.28 (m, 1 H) 3.33 (m, 1 H) 3.77 (s, 3 H) 4.00

A-750069.7

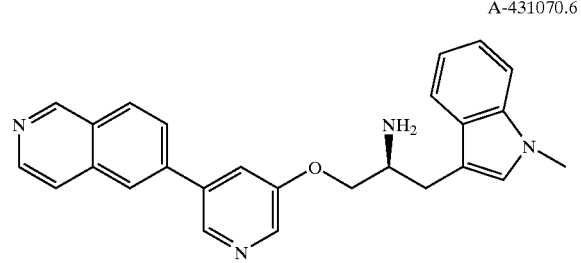

EXAMPLE 200

(1S)-1-Benzo[b]thiophen-3-ylmethyl-2-[5-(3-methyl-1H-indazol-5-yl)-pyridin-3-yloxy]-ethylamine MS (DCI/NH$_3$) m/z 415 (M+1); $^1$HNMR (400 MHz, MeOD) δ ppm 2.62 (s, 3 H) 3.41 (dd, J=14.73, 6.75 Hz, 1 H) 3.50 (dd, J=14.42, 8.59 Hz, 1 H) 4.12 (m, 1 H) 4.32 (dd, J=10.43, 5.22 Hz, 1 H) 4.45 (dd, J=10.74, 3.07 Hz, 1 H) 7.40 (m, 2 H) 7.55 (m, 1 H) 7.61 (d, J=8.90 Hz, 1 H) 7.68 (dd, J=8.59, 1.53 Hz, 1 H) 7.91 (m, 3 H) 8.03 (s, 1H) 8.35 (s, 1H) 8.64 (s, 1 H).

A-759277.2

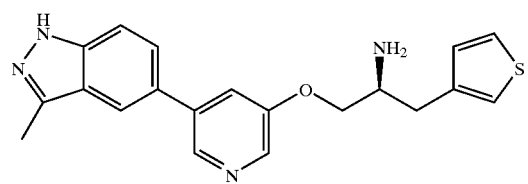

EXAMPLE 201

(1S)-2-[5-(3-Methyl-1H-indazol-5-yl)-pyridin-3-yloxy]-1-thiophen-3-ylmethyl-ethylamine MS (DCI/NH$_3$) m/z 365 (M+1)$^+$; $^1$HNMR (500 MHz, MeOD) δ ppm 2.63 (s, 3 H) 3.43 (m, 2 H) 3.98 (m, 1 H) 4.40

(dd, J=10.61, 5.62 Hz, 3 H) 4.52 (dd, J=10.61, 3.12 Hz, 1 H) 7.03 (dd, J=8.42, 3.43 Hz, 1 H) 7.06 (m, 1 H) 7.36 (dd, J=4.99, 1.25 Hz, 1 H) 7.64 (d, J=8.73 Hz, 1 H) 7.75 (dd, J=8.73, 1.87 Hz, 1 H) 8.14 (s, 1 H) 8.21 (m, 1 H) 8.47 (brs, 1 H) 8.77 (s, 1 H).

A-713679.21

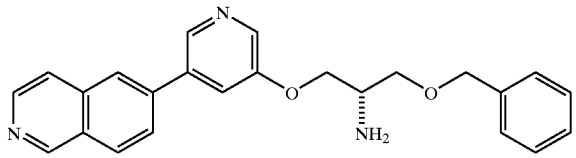

EXAMPLE 202

(1S)-1-Benzyloxymethyl-2-(5-isoquinolin-6-yl-pyridin-3-yloxy)-ethylamine

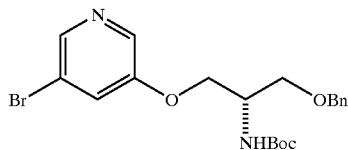

Example 202A (1S)-[1-Benzyloxymethyl-2-(5-bromo-pyridin-3-yloxy)-ethyl]-carbamic acid tert-butyl ester The product was prepared by substituting Boc-serinol (Bn) for Boc-tryptophanol in Example 2A. MS m/z 437, 439 (M+H)+; $^1$H NMR (300 MHz, DMSO-D6) δ ppm 1.37 (s, 9 H) 3.50 (d, J=6.10 Hz, 2 H) 3.97 (m, 1 H) 4.11 (m, 2 H) 4.50 (s, 2 H) 6.99 (d, J=7.80 Hz, 1 H) 7.29 (m, 5 H) 7.70 (m, 1 H) 8.28 (dd, J=4.75, 2.37 Hz, 2 H).

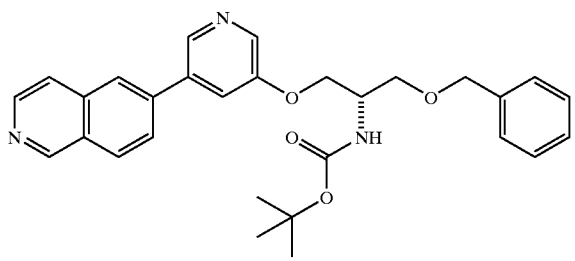

Example 202B (1S)-[1-Benzyloxymethyl-2-(5-isoquinolin-6-yl-pyridin-3-yloxy)-ethyl]-carbamic acid tert-butyl ester The desired product was prepared by substituting 202A for Example 2A in Example 27B. $^1$H NMR (300 MHz, DMSO-D6) δ ppm 1.38 (s, 9 H) 3.56 (d, J=6.10 Hz, 2 H) 4.04 (m, 1 H) 4.22 (d, J=5.43 Hz, 2 H) 4.52 (s, 2 H) 7.05 (d, J=8.14 Hz, 1 H) 7.28 (m, 5 H) 7.87 (m, 2 H) 8.10 (dd, J=8.65, 1.53 Hz, 1 H) 8.25 (d, J=8.82 Hz, 1 H) 8.35 (d, J=2.71 Hz, 1 H) 8.40 (s, 1 H) 8.56 (d, J=5.76 Hz, 1 H) 8.68 (d, J=1.70 Hz, 1 H) 9.37 (s, 1 H).

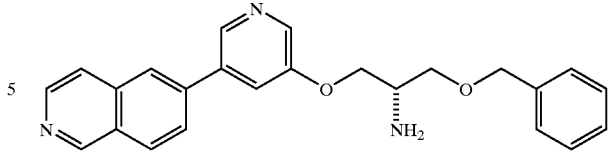

Example 202C (1S)-1-Benzyloxymethyl-2-(5-isoquinolin-6-yl-pyridin-3-yloxy)-ethylamine The desired product was prepared by substituting Example 202B for Example 27A in Example 202. in Example 27C. MS m/z 386 (M+1)+; $^1$H NMR (300 MHz, DMSO-D6) δ ppm 3.76 (m, 3 H) 3.97 (s, 2 H) 4.44 (m, 2 H) 4.60 (s, 2 H) 7.35 (m, 5H) 8.00 (m, 1 H) 8.33 (m, 2 H) 8.48 (d, J=2.71 Hz, 1 H) 8.54 (d, J=8.81 Hz, 1 H) 8.66 (s, 1 H) 8.68 (d, J=6.10 Hz, 1 H) 8.81 (d, J=1.70 Hz, 1 H) 9.75 (s, 1 H).

A-750983.3

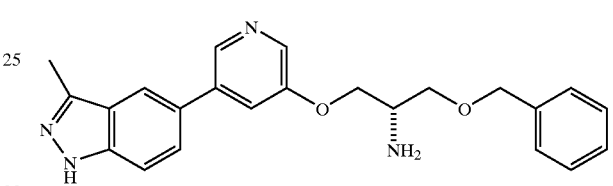

EXAMPLE 203

(1S)-1-Benzyloxymethyl-2-[5-(3-methyl-1H-indazol-5-yl)-pyridin-3-yloxy]-ethylamine

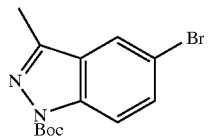

Example 203A

5-Bromo-3-methyl-indazole-1-carboxylic acid tert-butyl ester

A solution of Example 102C (1.0 g; 4.7 mmol), TEA (526 mg; 5.2 mmol), DMAP (200 mg; 1.6 mmol) and di-tert-butyldicarbonate (1.1 g; 5.0 mmol) in $CH_3CN$ (15 mL) was stirred at r.t. for 3 hrs, evaporated, and isolated by flash chromatography (30% $Et_2O$/hexane) to give the desired product as a white solid (1.4 g; 95%).

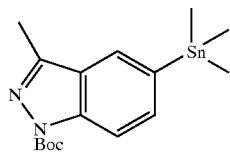

Example 203B

3-Methyl-5-trimethylstannanyl-indazole-1-carboxylic acid tert-butyl ester

A solution of Example 203A (1.35 g; 4.3 mmol), hexamethylditin (1.56 g; 4.8 mmol), and Pd(PPh$_3$)$_4$ (250 mg, 0.22 mmol) in toluene (15 mL) was stirred overnight at 85° C., evaporated and purified by flash chromatography (20% Et₂O/hexane) to provide the desired product (1.32 g; 77%).

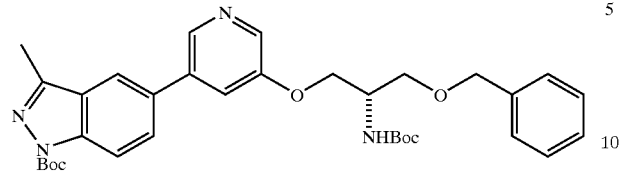

Example 203C (2S)-5-[5-(3-Benzyloxy-2-tert-butoxycarbonylamino-propoxy)-pyridin-3-yl]-3-methyl-indazole-1-carboxylic acid tert-butyl ester The desired product was prepared by substituting 203B for Example 27A in Example 202B. MS m/z 589 (M+H)⁺; ¹H NMR (300 MHz, DMSO-D6) δ ppm 1.38 (s, 9 H) 1.66 (s, 9 H) 2.59 (s, 3 H) 3.32 (m, 1 H) 3.56 (d, J=6.10 Hz, 2 H) 4.20 (d, J=5.76 Hz, 2 H) 4.52 (s, 2 H) 7.03 (d, J=8.14 Hz, 1 H) 7.27 (m, 1 H) 7.32 (m, 4 H) 7.78 (s, 1 H) 8.00 (dd, J=8.82, 1.70 Hz, 1 H) 8.12 (m, 1 H) 8.26 (d, J=1.02 Hz, 1 H) 8.29 (d, J=2.71 Hz, 1 H) 8.61 (d, J=1.70 Hz, 1 H).

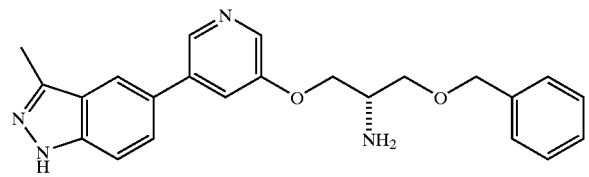

Example 203D (1S)-1-Benzyloxymethyl-2-[5-(3-methyl-1H-indazol-5-yl)-pyridin-3-yloxy]-ethylamine The desired product was prepared by substituting 203C for Example 27B in Example 27C. MS m/z 389 (M+H)⁺; ¹H NMR (300 MHz, DMSO-D6) δ ppm 2.57 (s, 3 H) 3.79 (m, 3 H) 4.51 (m, 2 H) 4.60 (s, 2 H) 4.90 (br s, 2 H) 7.34 (m, 5 H) 7.61 (d, J=8.81 Hz, 1 H) 7.80 (dd, J=8.81, 1.70 Hz, 1 H) 8.23 (s, 1 H) 8.27 (s, 1 H) 8.52 (m, 2 H) 8.85 (d, J=1.70 Hz, 1 H).

A-682707.0

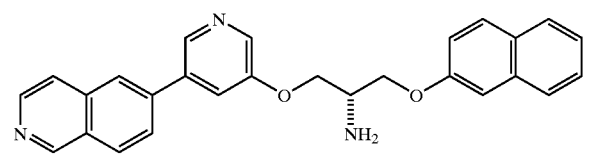

EXAMPLE 204

(1S)-2-(5-Isoquinolin-6-yl-pyridin-3-yloxy)-1-(naphthalen-2-yloxymethyl)-ethylamine

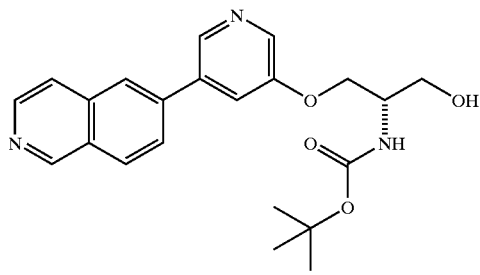

Example 204A (1S)-[1-Hydroxymethyl-2-(5-isoquinolin-6-yl-pyridin-3-yloxy)-ethyl]-carbamic acid tert-butyl ester To Example 202B (290 mg, 0.60 mmol) was added sequentially: ammonium formate (377 mg, 5.97 mmol), MeOH (wet) (15 mL), and 10% Pd/C (320 mg). The resulting black reaction mixture was warmed to 70° C. for 6 d and then cooled to room temperature and filtered through Celite. K₂CO₃ (50 mg) and silica gel were added and the volatiles removed on a rotary evaporator. Flash chromatography (2–3–5–7% MeOH/CH₂Cl₂) gave 40 mg (14%) recovered starting material and 89 mg (38%) of as a colorless waxy solid. R$_f$=0.32 (10% MeOH/CH₂Cl₂); ¹H NMR (300 MHz, DMSO-D6) δ ppm 1.38 (s, 9 H) 3.51 (td, J=5.76, 2.71 Hz, 2 H) 3.84 (m, 1 H) 4.19 (m, 2 H) 4.84 (t, J=5.76 Hz, 1 H) 6.82 (d, J=8.14 Hz, 1 H) 7.89 (m, 2 H) 8.11 (dd, J=8.65, 1.53 Hz, 1 H) 8.25 (d, J=8.82 Hz, 1 H) 8.36 (d, J=2.71 Hz, 1 H) 8.41 (s, 1 H) 8.56 (d, J=5.76 Hz, 1 H) 8.68 (d, J=1.70 Hz, 1 H) 9.37 (s, 1H).

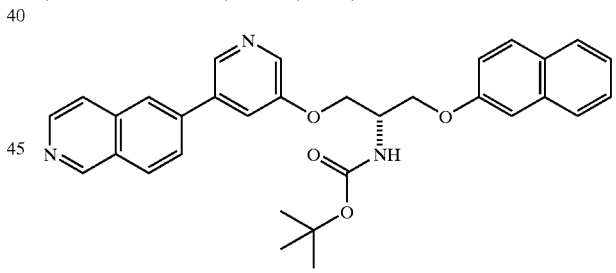

Example 204B (1S)-[2-(5-Isoquinolin-6-yl-pyridin-3-yloxy)-1-(naphthalen-2-yloxymethyl)-ethyl]-carbamic acid tert-butyl ester 2-Napthol (15 mg, 101 μmol), Example 204A (20 mg, 51 μmol), DBAD (17 mg, 76 μmol), and PPh₃-polymer (3 mmol/g) (34 mg, 101 μmol) were combined in a 10 mL round bottom flask. THF (2 mL) was added and the reaction mixture stirred 2 d at 23° C. and then rotavapped with silica gel. Flash chromatography (2–3–5–10% MeOH/CH₂Cl₂) gave 19 mg (73%) of as a colorless waxy solid. R$_f$=0.47 (10% MeOH/CH₂Cl₂); ¹H NMR (300 MHz, DMSO-D6) δ ppm 1.41 (s, 9 H) 4.24 (m, 3 H) 4.37 (m, 2 H) 7.19 (dd, J=8.82, 2.71 Hz, 1 H) 7.34 (m, 3 H) 7.45 (td, J=7.54, 1.19

Hz, 1 H) 7.78 (s, 1 H) 7.81 (s, 1 H) 7.84 (s, 1 H) 7.88 (d, J=5.76 Hz, 1 H) 7.92 (s, 1 H) 8.10 (dd, J=8.48, 1.70 Hz, 1 H) 8.24 (d, J=8.48 Hz, 1 H) 8.40 (m, 2 H) 8.56 (d, J=5.76 Hz, 1 H) 8.69 (d, J=1.70 Hz, 1 H) 9.37 (s, 1 H).

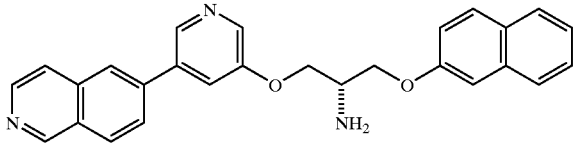

Example 204C (1S)-2-(5-Isoquinolin-6-yl-pyridin-3-yloxy)-1-(naphthalen-2-yloxymethyl)-ethylamine The desired product was prepared by substituting Example 204B for Example 27B in Example 27C. LCMS m/z 422 (M+1)$^+$; $^1$H NMR (300 MHz, DMSO-D6) δ ppm 3.54 (dt, J=11.44, 5.64 Hz, 1 H) 4.23 (m, 4 H) 7.20 (dd, J=8.98, 2.54 Hz, 1 H) 7.34 (m, 2 H) 7.45 (ddd, J=8.05, 6.87, 1.36 Hz, 1 H) 7.81 (m, 3 H) 7.88 (m, 2 H) 8.09 (m, 1 H) 8.24 (d, J=8.48 Hz, 1 H) 8.38 (s, 1 H) 8.42 (d, J=2.71 Hz, 1 H) 8.55 (d, J=5.76 Hz, 1 H) 8.67 (d, J=1.70 Hz, 1 H) 9.37 (s, 1 H).

EXAMPLE 205

(1S)-2-(5-Isoquinolin-6-yl-pyridin-3-yloxy)-1-(pyridin-3-yloxymethyl)-ethylamine The desired product was prepared as tri-TFA salt by substituting 3-hydroxypyridine for 2-naphthol in Example 204. MS m/z 373 (M+1)$^+$; $^1$H NMR (300 MHz, DMSO-D6) δ ppm 4.10 (m, 1 H) 4.48 (m, 4 H) 7.44 (dd, J=8.65, 4.92 Hz, 1 H) 7.54 (m, 1 H) 7.96 (t, J=2.03 Hz, 1 H) 8.09 (d, J=6.78 Hz, 1 H) 8.21 (dd, J=8.65, 1.53 Hz, 1 H) 8.27 (d, J=4.75 Hz, 1 H) 8.41 (m, 2 H) 8.49 (m, 4 H) 8.63 (d, J=5.76 Hz, 1 H) 8.79 (d, J=1.70 Hz, 1 H) 9.56 (s, 1 H).

EXAMPLE 206

(1S)-2-(5-Isoquinolin-6-yl-pyridin-3-yloxy)-1-(quinolin-7-yloxymethyl)-ethylamine The desired product was prepared as trifluoroacedic acid salt by substituting 7-hydroxyquinoline for 2-naphthol in Example 204. $^1$H NMR (300 MHz, DMSO-D6) δ ppm 4.24 (m, 4 H) 7.45 (m, 3 H) 7.90 (m, 3 H) 8.09 (dd, J=8.48, 1.70 Hz, 1 H) 8.23 (s, 1 H) 8.25 (s, 1 H) 8.39 (s, 1 H) 8.42 (d, J=2.71 Hz, 1 H) 8.56 (d, J=5.43 Hz, 1 H) 8.67 (d, J=1.70 Hz, 1 H) 8.73 (dd, J=4.41, 1.70 Hz, 1 H) 9.37 (s, 1 H).

EXAMPLE 207

(2S)-4-[2-Amino-3-(5-isoquinolin-6-yl-pyridin-3-yloxy)-propoxy]-benzonitrile

The desired product was prepared as trifluoroacedic acid salt by substituting 4-cyanophenol for 2-naphthol in Example 204. $^1$H NMR (300 MHz, DMSO-D6) δ ppm 2.27 (br s, 2 H) 3.49 (m, 1 H) 4.18 (m, 4 H) 7.16 (m, 2 H) 7.76 (m, 2H) 7.86 (dd, J=2.71, 2.03 Hz, 1H) 7.89 (d, J=5.76 Hz, 1 H) 8.09 (dd, J=8.65, 1.86 Hz, 1 H) 8.25 (d, J=8.82 Hz, 1 H) 8.39 (m, 2 H) 8.56 (d, J=5.76 Hz, 1 H) 8.68 (d, J=1.69 Hz, 1 H) 9.37 (s, 1 H).

EXAMPLE 208

(2S)-N'-(5-(3-methyl-1H-indazol-5-yl)-pyridin-3-yl)-3-phenyl-propane-1,2-diamine

Example 208A (2S)-{1-[(5-Bromo-pyridin-3-ylamino)-methyl]-2-phenyl-ethyl}-carbamic acid tert-butyl ester A solution of Example 23B (0.4 g, 2.3 mmol), (1-formyl-2-phenyl-ethyl)-carbamic acid tert-butyl ester (0.7 g, 2.8 mmol), and Ti(iPrO)$_4$ (10 ml) in CH$_2$Cl$_2$ (15 mL) was stirred at room temperature for 2 h. The solvent was evaporated off and the residue was dissolved in 15 ml of EtOH. The solution was treated with NaBH$_3$CN (0.5 g, 4.9 mmol) then stirred overnight at room temperature. The mixture was diluted with ethyl acetate (50 ml), washed with water (25 ml) and brine (25 ml). The ethyl acetate was evaporated off and the residue was purified by flash column chromatography on silica gel, eluting with a solvent gradient of 1:4 to 1:1 ethyl acetate/hexane to give 0.28 g of product (30%). MS: (ESI) m/z 408 (M+H)$^+$.

Example 208B (2S)-5-[5-(2-tert-Butoxycarbonylamino-3-phenyl-propylamino)-pyridin-3-yl]-3-methyl-indazole-1-carboxylic acid tert-butyl ester The desired product was prepared by substituting Example 208A for Example 202A in Example 203C.

Example 208C (2S)-N'-(5-(3-methyl-1H-indazol-5-yl)-pyridin-3-yl)-3-phenyl-propane-1,2-diamine The desired product was prepared by substituting Example 208B for Example 27B in Example 27C. MS: (ESI) m/z 358 (M+H)$^+$; $^1$H NMR (500 MHz, DMSO-D6) δ ppm 2.56 (d, J=3.74 Hz, 3 H) 3.00 (m, 2 H) 3.42 (d, J=5.30 Hz, 3 H) 6.89 (m, 1 H) 7.27 (m, 2 H) 7.35 (m, 3 H) 7.57 (s, 1 H) 7.62 (d, J=4.06 Hz, 2 H) 8.01 (s, 1 H) 8.07 (m, 1 H) 8.13 (s, 2 H) 8.38 (s, 1 H).

EXAMPLE 209

(2S)-N-(2-Amino-3-phenyl-propyl)-N-[5-(3-methyl-1H-indazol-5-yl)-pyridin-3-yl]-methanesulfonamide Example 208B (500 mg, 0.90 mmol) in pyridine (8 ml) was added dropwise with methyl sulfonyl chloride (308 mg, 2.7 mmol) in an ice-bath. The reaction mixture was allowed to warm up to rt and stirred for 12 hrs. The solvent was removed by bubbling nitrogen to the reaction flask. The residue was chromatographed on silica gel eluting with EtOAc to give the Boc protected product, which was deprotected according to the procedure described in Example 27C to give the title compound as trifluoroacetic acid salt (21.2 mg, 4%). MS (DCI/NH$_3$) m/z 436 (M+1)$^+$; $^1$HNMR (500 MHz, MeOD) δ ppm 2.62 (s, 3 H) 2.89 (dd, J=14.35, 9.36 Hz, 1 H) 3.03 (s, 3 H) 3.05 (dd, J=14.35, 5.62 Hz, 1 H) 3.59 (m, 1 H) 4.06 (d, J=5.93 Hz, 2 H) 7.07 (s, 1 H) 7.09 (s, 1 H) 7.18 (d, J=7.18 Hz, 1 H) 7.24 (m, 2 H) 7.60 (s, 1 H) 7.60 (s, 1 H) 7.95 (s, 1 H) 8.10 (t, J=1.87 Hz, 1 H) 8.59 (s, 1 H) 8.87 (s, 1 H).

EXAMPLE 210

(2S)-N-(2-Amino-3-phenyl-propyl)-N-[5-(3-methyl-1H-indazol-5-yl)-pyridin-3-yl]-benzenesulfonamide The desired product was prepared as trifluoroacetic acid salt by substituting benzenesulfonyl chloride for methanesulfonyl chloride in Example 209. MS (DCI/NH$_3$) m/z 498 (M+1)$^+$; $^1$H NMR (500 MHz, DMSO-D6) δ ppm 2.55 (s, 3 H) 2.84 (dd, J=114.04, 8.42 Hz, 1 H) 2.97 (dd, J=14.04, 5.62 Hz, 1 H) 3.45 (m, 1 H) 3.78 (m, 2 H) 7.17 (s, 1 H) 7.19 (s, 1 H) 7.24 (d, J=7.18 Hz, 1 H) 7.30 (m, 2 H) 7.43 (s, 1 H) 7.44 (d, J=0.62 Hz, 1 H) 7.50 (dd, J=8.73, 1.56 Hz, 1 H) 7.57 (d, J=8.42 Hz, 1 H) 7.62 (m, 3 H) 7.78 (t, J=7.49 Hz, 1 H) 7.82 (s, 1 H) 8.11 (s, 3 H) 8.25 (d, J=2.18 Hz, 1 H) 8.92 (d, J=1.87 Hz, 1 H).

EXAMPLE 211

(2S)-N-(2-Amino-3-phenyl-propyl)-N-[5-(3-methyl-1H-indazol-5-yl)-pyridin-3-yl]-benzamide The desired product was prepared as trifluoroacetic acid salt by substituting benzoyl chloride for methanesulfonyl chloride in Example 209. MS (DCI/NH$_3$) m/z 462 (M+1)$^+$; $^1$H NMR (500 MHz, DMSO-D6) δ ppm 2.54 (s, 3 H) 2.90 (dd, J=14.04, 9.05 Hz, 1 H) 3.03 (dd, J=14.04, 5.30 Hz, 1 H) 3.65 (m, 1 H) 4.09 (dd, J=14.97, 4.06 Hz, 1 H) 4.28 (dd, J=14.97, 8.42 Hz, 1 H) 7.19 (m, 3 H) 7.27 (m, 4 H) 7.33 (m, 2 H) 7.44 (dd, J=8.73, 1.56 Hz, 1 H) 7.54 (d, J=8.73 Hz, 1 H) 7.75 (s, 1 H) 7.86 (m, 1 H) 8.09 (s, 3 H) 8.22 (d, J=2.18 Hz, 1 H) 8.69 (d, J=1.87 Hz, 1 H).

EXAMPLE 212

(2S)-N-(2-Amino-3-phenyl-propyl)-N-[5-(3-methyl-1H-indazol-5-yl)-pyridin-3-yl]-acetamide The desired product was prepared as trifluoroacetic acid salt by substituting acetyl chloride for methanesulfonyl chloride in Example 209. MS (DCI/NH$_3$) m/z 400 (M+1)$^+$; $^1$H NMR (400 MHz, MeOD) δ ppm 1.98 (s, 3 H) 2.63 (s, 3 H) 2.90 (dd, J=14.12, 8.90 Hz, 1 H) 3.02 (dd, J=13.81, 5.83 Hz, 1 H) 3.68 (m, 1 H) 3.76 (dd, J=15.04, 2.46 Hz, 1 H) 4.31 (dd, J=15.04, 7.98 Hz, 1 H) 7.25–7.11 (m, 6 H) 7.64 (m, 2 H) 8.00 (s, 1 H) 8.03 (s, 1 H) 8.46 (s, 1 H) 8.93 s, 1 H)

EXAMPLE 213

(2S)-3-[2-Amino-3-(1H-indol-3-yl)-propylidene]-5-isoquinolin-6-yl-1,3-dihydro-indol-2-one The desired product was prepared as trifluoroacetic acid salt by substituting 5-bromooxindole for 5-bromo-7 aza-oxindole in Example 44. MS (DCI/NH$_3$) m/z 431 (M+1)$^+$; $^1$HNMR (500 MHz, MeOD) δ ppm 3.26 (dd, J=14.35, 9.67 Hz, 1 H) 3.57 (dd, J=14.66, 4.06 Hz, 1 H) 5.05 (dt, J=19.34, 4.06 Hz, 1 H) 6.71 (m, 1 H) 6.83 (d, J=9.98 Hz, 1 H) 6.85 (m, 1 H) 6.98 (d, J=8.42 Hz, 1 H) 7.03 (m, 1 H) 7.06 (d, J=8.11 Hz, 1 H) 7.14 (d, J=1.56 Hz, 1 H) 7.55 (dd, J=8.73, 1.87 Hz, 1 H) 7.64 (dd, J=8.11, 1.56 Hz, 1 H) 7.69 (d, J=8.11 Hz, 1 H) 7.94 (s, 1 H) 8.18 (d, J=6.24 Hz, 1 H) 8.31 (d, J=8.73 Hz, 1 H) 8.52 (s, 1 H) 9.55 (s, 1 H).

EXAMPLE 214

(1S)-2-(5-Isoquinolin-6-yl-pyridin-3-yloxy)-1-(1-methyl-1H-indol-3-ylmethyl)-ethylamine The title compound was prepared as trifluoroacetic acid salt by substituting 5-bromo-7-azaindole (D. Mazeas, et al., *Heterocycles* 1990, 50, 1065) for 6-bromophthalimide in Example 32. MS (DCI/NH$_3$) m/z 384 (M+1)$^+$; $^1$HNMR (500 MHz, MeOD) δ ppm 3.29 (m, 1 H) 3.33 (dd, J=8.11, 2.81 Hz, 1 H) 4.03 (m, 1 H) 4.36 (dd, J=10.61, 5.62 Hz, 1 H) 4.49 (dd, J=10.61, 3.12 Hz, 1 H) 6.69 (d, J=3.12 Hz, 1 H) 7.02 (m, 1 H) 7.10 (t, J=7.49 Hz, 1 H) 7.25 (s, 1 H) 7.36 (d, J=8.11 Hz, 1 H) 7.57 (m, 2 H) 8.08 (s, 1 H) 8.45 (s, 2 H) 8.58 (s, 1 H) 8.80 (s, 1 H).

EXAMPLE 215

(1S)-1-(1H-Indol-3-ylmethyl)-2-[5-(1H-pyrrolo[2,3-b]pyridin-5-yl)-pyridin-3-yloxy]-ethylamine

Example 215A (S)-N-[1-(1H-Indol-3-ylmethyl)-2-(5-isoquinolin-6-yl-pyridin-3-yloxy)-ethyl]-2-nitro-benzenesulfonamide To a solution of Example 27 (400 mg, 1.01 mmol) and DIEA (1.06 mL, 6.06 mmol) in THF (30 mL) in ice-bath cooling was added 2-nitrobenzylsulfonyl chloride (896 mg, 4.04 mmol). The reaction was allowed to warm up to rt for 12 hrs. The reaction mixture was concentrated and the resulting crude oil was purified by flash column chromatography eluting with EtOAc/Hex (1:1), EtOAc, and EtOAc/MeOH (20:1) to give the title compound (267 mg, 46%). MS (DCI/NH$_3$) m/z 580 (M+1)$^+$.

Example 215B (1S)-N-[1-(1H-Indol-3-ylmethyl)-2-(5-isoquinolin-6-yl-pyridin-3-yloxy)-ethyl]-N-methyl-2-nitro-benzenesulfonamide To a solution of Example 215A (260 mg, 0.45 mmol), MeOH (16 uL, 4.5 mmol), and Ph$_3$P (591 mg, 2.25 mmol) in THF (10 mL) in an ice-bath was added dropwise DEAD (392 mg, 2.25 mmol). The reaction was allowed to ward up to rt for 12 hrs. The reaction mixture was concentrated and the resulting crude oil was purified by flash column chromatography eluting with EtOAc, and EtOAc/MeOH (40:3) to give the title compound (47 mg, 18%). MS (DCI/NH$_3$) m/z 594 (M+1)$^+$.

Example 215C (1S)-1-(1H-Indol-3-ylmethyl)-2-[5-(1H-pyrrolo[2,3-b]pyridin-5-yl)-pyridin-3-yloxy]-ethylamine A mixture of Example 215B (47 mg, 0.08 mmol), PhSH (9.7 uL, 0.095 mmol), and K$_2$CO$_3$ (33 mg, 0.237 mmol) in DMF (5 mL) was stirred at rt for 2 hrs. The reaction was Concentrated to dryness. The resulting residue was purified on C18 HPLC to afford the title compound (34.2 mg, 58%). MS (DCI/NH$_3$) m/z 409 (M+1)$^+$; $^1$H NMR (500 MHz, MeOD) δ ppm 2.91 (s, 3 H) 2.99 (brs, 1H) 3.37 (dd, J=14.66, 9.36 Hz, 1H) 3.43 (dd, J=14.66, 5.93 Hz, 1H) 3.96 (m, 1 H) 4.38 (dd, J=10.92, 4.37 Hz, 1 H) 4.52 (dd, J=10.92, 2.81 Hz, 1 H) 6.99 (dt, J=8.11, 0.94 Hz, 1 H) 7.10 (dt, J=8.11, 0.94 Hz, 1 H) 7.25 (s, 1 H) 7.36 (d, J=8.11 Hz, 1 H) 7.58 (d, J=8.11 Hz, 1 H) 7.92 (m, 1 H) 8.29 (dd, J=8.73, 1.87 Hz, 1 H) 8.49 (d, J=6.55 Hz, 1 H) 8.50 (s, 1 H) 8.56 (s, 1 H) 8.60 (d, J=8.73 Hz, 1 H) 8.63 (d, J=6.55 Hz, 1 H) 8.77 (s, 1 H) 9.78 (s, 1 H).

EXAMPLE 216

(1S)-2-{5-[2-(2-Fluoro-pyridin-4-yl)-vinyl]-pyridin-3-yloxy}-1-(1H-indol-3-ylmethyl)-ethylamine

Example 216A

2-Fluoro-4-vinylpyridine

A mixture of 2-fluoro-4-iodopyridine (2.23 g, 10.0 mmol), tributyl vinyl tin (3.8 g, 12 mmol), and Pd$_2$Cl$_2$(PPh$_3$)$_2$ (703 mg, 1.0 mmol) in dioxane (20 mL) was heated under nitrogen at 80° C. overnight. After cooled, ethyl acetate (40 ml) and saturated KF aqueous solution were added to the reaction mixture. The mixture was stirred for 30 min. The organic layer was separated and washed with water, dried (MgSO$_4$), and concentrated. The resulting residue was purified by flash column chromatography eluting with hexane/ethyl acetate (20:1) to provide the title compound (463 mg, 38%). $^1$HNMR (500 MHz, CDCl$_3$) δ ppm 5.55 (d, J=10.92 Hz, 1 H) 5.99 (d, J=17.47 Hz, 1 H) 6.67 (dd, J=17.47, 10.61 Hz, 1 H) 6.88 (m, 1 H) 7.17 (dt, J=5.30, 1.56 Hz, 1 H) 8.16 (d, J=5.30 Hz, 1 H).

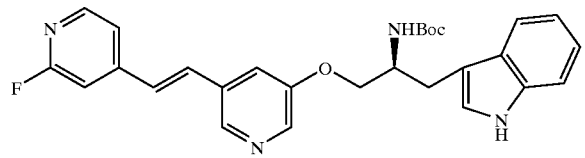

Example 216B (1S)-[2-{5-[2-(2-Fluoro-pyridin-4-yl)-vinyl]-pyridin-3-yloxy}-1-(1H-indol-3-ylmethyl)-ethyl]-carbamic acid tert-butyl ester The desired product was prepared as a trifluoroacetic acid salt by substituting Example 216A for 4-vinylpyridine in Example 2 (1.067 g, 84%). MS (DCI/NH$_3$) m/z 489 (M+1)$^+$; $^1$HNMR (400 MHz, MeOD) d ppm 1.42 (m, 9 H) 2.98 (m, 1 H) 3.04 (m, 1 H) 3.14 (m, 1 H) 4.09 (m, 2 H) 4.25 (m, 1 H) 6.96 (t, J=7.36 Hz, 1H) 7.07 (t, J=7.07 Hz, 1H) 7.09 (m, 1H) 7.20 (m, 1 H) 7.29 (m, 2 H) 7.45 (m, 2 H) 7.59 (m, 2 H) 8.16 (d, J=5.52 Hz, 1 H) 8.19 (s, 1 H) 8.32 (s, 1 H).

EXAMPLE 217

(1S)-1-(1H-Indol-3-ylmethyl)-2-{5-[2-(2-methoxy-pyridin-4-yl)-vinyl]-pyridin-3-yloxy}-ethylamine

Example 217A (1S)-(1-(1H-Indol-3-ylmethyl)-2-{5-[2-(2-methoxy-pyridin-4-yl)-vinyl]-pyridin-3-yloxy}-ethyl)-carbamic acid tert-butyl ester A mixture of Example 216B (100 mg, 0.2 mmol), NaOMe (25% in MeOH) (1 mL) in MeOH (10 mL) was refluxed for 8 hrs. The mixture was concentrated to give the crude product.

Example 217B (1S)-1-(1H-Indol-3-ylmethyl)-2-{5-[2-(2-methoxy-pyridin-4-yl)-vinyl]-pyridin-3-yloxy}-ethylamine Example 217A was treated with TFA (1 mL) at rt for 10 min. Upon Removal of the TFA, the crude product was purified on C18 HPLC to give the title compound (101.8 mg, 69%). MS (DCI/NH$_3$) m/z 401 (M+1)$^+$; $^1$HNMR (400 MHz, MeOD) δ ppm 3.31 (m, 2 H) 3.99 (s, 3 H) 4.00 (m, 1 H) 4.29 (dd, J=10.43, 5.52 Hz, 1 H) 4.41 (dd, J=10.43, 3.07 Hz, 1 H) 7.03 (m, 1 H) 7.06 (s, 1 H) 7.13 (m, 1 H) 7.24 (s, 1 H) 7.27 (dd, J=5.52, 1.23 Hz, 1 H) 7.34 (d, J=16.26 Hz, 1 H) 7.39 (d, J=8.29 Hz, 1 H) 7.48 (d, J=16.57 Hz, 1 H) 7.59 (d, J=7.98 Hz, 1 H) 7.87 (s, 1 H) 8.16 (d, J=5.22 Hz, 1 H) 8.40 (brs, 1 H) 8.57 (brs, 1 H).

EXAMPLE 218

(1S)-1-(1H-Indol-3-ylmethyl)-2-{5-[2-(2-phenoxy-pyridin-4-yl)-vinyl]-pyridin-3-yloxy}-ethylamine A mixture of Example 216B (50 mg, 0.1 mmol), phenol (94 mg, 1.0 mmol) and KOH (11.2 mg, 0.2 mmol) was heated at 140 C in a sealed bottle for 2 hrs. The mixture was concentrated to dryness. The residue was then treated with TFA (1 mL) at rt for 10 min. Upon Removal of TFA, the crude product was purified on C18 HPLC to give rhe title compound (4.3 mg, 5.3%). MS (DCI/NH$_3$) m/z 463 (M+1)$^+$; $^1$HNMR (400 MHz, MeOD) δ ppm 3.30 (m, 1 H) 3.48 (dd, J=13.81, 7.06 Hz, 1 H) 4.00 (m, 1 H) 4.27 (dd, J=10.43, 5.83 Hz, 1 H) 4.40 (dd, J=10.43, 3.07 Hz, 1 H) 7.15–7.01 (m, 5H) 7.26–7.23 (m, 2H) 7.48–7.32 (m, 6H) 7.59 (d, J=7.98 Hz, 1 H) 7.87 (m, 1 H) 8.16 (d, J=5.52 Hz, 1 H) 8.35 (s, 1 H) 8.53 (s, 1 H).

EXAMPLE 219

(1S)-2-{5-[2-(2-Benzylsulfanyl-pyridin-4-yl)-vinyl]-pyridin-3-yloxy}-1-(1H-indol-3-ylmethyl)-ethylamine The title compound was prepared as trifloroacetic acid salt by substituting benzylthiol for phenol in Example 218. MS (DCI/NH$_3$) m/z 493 (M+1)$^+$; $^1$HNMR (500 MHz, MeOD) δ ppm 3.31 (m, 1 H) 3.35 (m, 1 H) 4.00 (m, 1 H) 4.26 (dd, J=10.61, 5.62 Hz, 1 H) 4.39 (dd, J=10.61, 3.43 Hz, 1 H) 4.48 (m, 2 H) 7.03 (m, 1 H) 7.13 (m, 1 H) 7.27 (m, 6 H) 7.40 (m, 4 H) 7.47 (d, J=16.53 Hz, 1 H) 7.52 (m, 1 H) 7.59 (d, J=7.80 Hz, 1 H) 7.78 (s, 1H) 8.43 (d, J=5.30 Hz, 1 H) 8.56 (s, 1H).

EXAMPLE 220

[4-(2-{5-[(2S)-2-Amino-3-(1H-indol-3-yl)-propoxy]-pyridin-3-yl}-vinyl)-pyridin-2-yl]-cyclopropyl-amine A mixture of Example 216 (100 mg, 0.2 mmol) and cyclopropyl amine (1.5 mL) was heated at 125° C. for 36 hrs. The mixture was concentrated to dryness. The residue was then treated with TFA (1 mL) at rt for 10 min. Upon removal of TFA, the crude product was purified on C18 HPLC to give the title compound (4.1 mg, 3%). MS (DCI/NH$_3$) m/z 426 (M+1)$^+$; $^1$HNMR (500 MHz, MeOD) δ ppm 0.74 (m, 2 H) 1.03 (m, 2 H) 2.71 (m, 1 H) 3.29 (m, 1 H) 3.34 (m, 1 H) 4.00 (m, 1 H) 4.27 (dd, J=10.61, 5.62 Hz, 1 H) 4.39 (dd, J=10.61, 3.43 Hz, 1 H) 7.03 (m, J=15.91 Hz, 1 H) 7.10 (s, 1 H) 7.13 (m, 1 H) 7.23 (s, 1 H) 7.26 (dd, J=6.86, 1.56 Hz, 1 H) 7.39–7.34 (m, 2 H) 7.58 (d, J=5.30 Hz, 1 H) 7.60 (d, J=3.12 Hz, 1 H) 7.83 (m, 1 H) 7.87 (d, J=6.86 Hz, 1 H) 8.37 (s, 1 H) 8.52 (s, 1 H).

EXAMPLE 221

[4-(2-{5-[(2S)-2-Amino-3-(1H-indol-3-yl)-propoxy]-pyridin-3-yl}-vinyl)-pyridin-2-yl]-benzyl-amine The title compound was prepared as trifloroacetic acid salt by substituting benzylamine for cyclopropylamine in Example 220 (38.2 mg, 23%). MS (DCI/NH$_3$) m/z 476 (M+1)$^+$; $^1$HNMR $^1$H NMR (500 MHz, MeOD) δ ppm 3.30 (m, 1 H) 3.34 (m, 1 H) 3.99 (m, 1 H) 4.24 (dd, J=10.61, 5.62 Hz, 1 H) 4.37 (dd, J=10.61, 3.12 Hz, 1 H) 4.63 (s, 2 H) 7.02 (m, 1 H) 7.10 (m, 1 H) 7.12 (m, 1 H) 7.22 (m, 2 H) 7.41 (m, 3 H) 7.39–7.29 (m, 4 H) 7.57 (d, J=9.05 Hz, 1 H) 7.59 (m, 1 H) 7.73 (s, 1 H) 7.82 (d, J=6.86 Hz, 1 H) 8.37 (s, 1 H) 8.52 (s, 1 H).

EXAMPLE 222

[4-(2-{5-[(2S)-2-Amino-3-(1H-indol-3-yl)-propoxy]-pyridin-3-yl}-vinyl)-pyridin-2-yl]-ethyl-amine The title compound was prepared as trifloroacetic acid salt by substituting ethylamine for cyclopropylamine in Example 220 (16 mg, 15%). MS (DCI/NH$_3$) m/z 414 (M+1)$^+$; $^1$HNMR (400 MHz, MeOD) δ ppm 1.36 (t, J=7.06 Hz, 3 H) 3.98 (m, 4 H) 4.24 (dd, J=10.43, 5.52 Hz, 1 H) 4.37

(dd, J=10.74, 3.38 Hz, 1 H) 7.02 (m, 2 H) 7.12 (d, J=8.29 Hz, 1 H) 7.18 (d, J=8.29 Hz, 1 H) 7.23 (s, 1 H) 7.30 (d, J=16.26 Hz, 1 H) 7.38 (d, J=8.90 Hz, 1 H) 7.56 (d, J=11.97 Hz, 1 H) 7.59 (d, J=3.68 Hz, 1 H) 7.72 (s, 1 H) 7.77 (d, J=7.06 Hz, 1 H) 7.87 (m, 2 H) 8.33 (s, 1 H) 8.48 (s, 1 H).

EXAMPLE 223

[4-(2-{5-[(2S)-2-Amino-3-(1H-indol-3-yl)-propoxy]-pyridin-3-yl}-vinyl)-pyridin-2-yl]-methyl-amine The title compound was prepared as trifloroacetic acid salt by substituting methylamine for cyclopropylamine in Example 220 (11.9 mg, 8%). MS (DCI/NH$_3$): m/z 400 (M+1)$^+$; $^1$HNMR (400 MHz, MeOD) δ ppm ppm 3.05 (s, 3 H) 3.32 (m, 2 H) 3.99 (m, 1 H) 4.24 (dd, J=10.43, 5.52 Hz, 1 H) 4.37 (dd, J=10.74, 3.38 Hz, 1 H) 7.03 (m, 1 H) 7.05 (m, 1 H) 7.13 (m, 1 H) 7.19 (d, J=7.06 Hz, 1 H) 7.23 (m, 1 H) 7.31 (d, J=16.57 Hz, 1 H) 7.39 (d, J=7.36 Hz, 1 H) 7.57 (d, J=7.06 Hz, 1 H) 7.60 (m, 1 H) 7.74 (s, 1 H) 7.80 (d, J=7.06 Hz, 1 H) 8.41 (brs, 1 H) 8.57 (brs, 1 H).

EXAMPLE 224

(1S)-1-(1H-Indol-3-ylmethyl)-2-{5-[2-(2-indol-1-yl-pyridin-4-yl)-vinyl]-pyridin-3-yloxy}-ethylamine A mixture of Example 216 (100 mg, 0.2 mmol), indole (48 mg, 0.4 mmol), and NaH (60%) (29 mg, 0.72 mmol) in DMF (5 mL) was heated at 125° C. for 1.5 hrs. The mixture was concentrated to dryness. The residue was then treated with TFA (1 mL) at rt for 10 min. Upon removal of TFA, the crude product was purified on C18 HPLC to give the title compound (8.1 mg, 5%). MS (DCI/NH$_3$) m/z 486 (M+1)$^+$; $^1$HNMR (500 MHz, MeOD) δ ppm 3.29 (m, 1H) 3.35 (m, 1H) 4.00 (m, 1H) 4.26 (dd, J=10.61, 5.93 Hz, 1H) 4.39 (dd, J=10.29, 3.12 Hz, 1 H) 6.73 (d, J=3.43 Hz, 1 H) 7.05 (m, 1 H) 7.11–7.18 (m, 2 H) 7.24 (s, 1H) 7.26 (m, 1 H) 7.63–7.38 (m, 6 H) 7.75 (m, 1 H) 7.80 (m, 1 H) 7.84 (d, J=3.43 Hz, 1 H) 8.22 (dd, J=8.42, 0.62 Hz, 1 H) 8.32 (s, 1 H) 8.52 (s, 1 H) 8.53 (s, 1 H).

EXAMPLE 225

(±)-2-[5-(3-Methyl-1H-indazol-5-yl)-pyridin-3-yloxy]-1-(2-methyl-1H-indol-3-ylmethyl)-ethylamine Example 225A 3-Bromo-2-hydroxyimino-propionic acid ethyl ester Ethyl bromopyruvate (5.0 mL, 39.8 mmol) was added to hydroxylamine hydrochloride (2.52 g, 36.2 mmol) in H$_2$O (10 mL) and CHCl$_3$ (10 mL). The reaction mixture was capped and stirred overnight at 23° C. at which time CH$_2$Cl$_2$ and H$_2$O were added, the layers separated, the organics dried over Na$_2$SO$_4$, and the volatiles removed on a rotary evaporator to yield 7.58 g (100%) of as a white solid. $^1$H NMR (300 MHz, DMSO-D6) δ ppm 1.26 (t, J=7.12 Hz, 3 H) 4.20 (s, 2 H) 4.24 (m, 2 H) 13.19 (s, 1 H).

Example 225B

2-Hydroxyimino-3-(2-methyl-1H-indol-3-yl)-propionic acid ethyl ester

The desired compound was prepared by a reference method (*J. Chem. Soc. Chem. Comm.* 1979, 1089). To 2-methylindole (1.28 g, 9.76 mmol) and Na$_2$CO$_3$ (1.24 g, 11.7 mmol) in CH$_2$Cl$_2$ was added Example 225A (2.05 g, 9.76 mmol). The resulting reaction mixture was stirred overnight at 23° C. at which time H$_2$O was added, the layers separated, and the organics dried over Na$_2$SO$_4$. Flash chromatography (20–30–50–70% EtOAc/hexanes) gave 1.41 g (56%) of as a green solid. R$_f$=0.30 (50% EtOAc/hexanes); MS m/z 261 (M+H)$^+$; $^1$H NMR (300 MHz, DMSO-D6) δ ppm 1.13 (t, J=7.12 Hz, 3 H) 2.35 (s, 3 H) 3.84 (s, 2 H) 4.08 (q, J=7.12 Hz, 2 H) 6.92 (m, 2 H) 7.19 (d, J=7.80 Hz, 1 H) 7.44 (d, J=7.46 Hz, 1 H) 10.74 (s, 1 H) 12.34 (s, 1 H).

Example 225C (±)-2-tert-Butoxycarbonylamino-3-(2-methyl-1H-indol-3-yl)-propionic acid ethyl ester The desired compound was prepared by a reference method (*Angew. Chem. Int. Ed. Engl.* 1979, 78, and *Tet. Lett.* 1988, p447). Aluminum foil (1.18 g, 43.8 mmol) was cut into long thin (1 cm) strips then dipped into a 2% aqueous HgCl$_2$ solution (30 sec each strip). Each strip was immediately washed successively with H$_2$O, MeOH, then Et$_2$O. Each strip was then immediately cut into small pieces (~1×0.5 cm) into a solution of Example 225B (1.14 g, 4.38 mmol) in THF (60 mL) and H$_2$O (6 mL) which was kept at room temperature with a water bath. The mixture was stirred vigorously at 23° C. After a short time fine black solids began to form and much bubbling was observed. The reaction mixture was stirred 3 h then filtered through Celite, and the filter cake washed with Et$_2$O. All volatiles were removed on a rotary evaporator. MeOH (50 mL) was added followed by Na$_2$CO$_3$ (0.51 g, 4.82 mmol) and Boc$_2$O (1.00 g, 4.60 mmol). The resulting reaction mixture was stirred 30 min at 23° C. and then silica gel was added and the volatiles removed on a rotary evaporator. Flash chromatography (10–30–40–50% EtOAc/hexanes) gave 1.33 g (88%) of as an off-white solid. R$_f$=0.68 (70% EtOAc/hexanes); MS m/z 345 (M–H)$^+$; $^1$H NMR (300 MHz, DMSO-D6) δ ppm 1.02 (t, J=7.12 Hz, 3 H) 1.33 (s, 9 H) 2.28 (s, 3 H) 3.00 (m, 2 H) 3.97 (q, J=7.12 Hz, 2 H) 4.10 (m, 1 H) 6.94 (m, 2 H) 7.14 (d, J=8.14 Hz, 1 H) 7.21 (d, J=7.12 Hz, 1 H) 7.38 (d, J=7.12 Hz, 1 H) 10.73 (s, 1 H).

Example 225D (±)-[2-Hydroxy-1-(2-methyl-1H-indol-3-ylmethyl)-ethyl]-carbamic acid tert-butyl ester To Example 225C (1.30 g, 3.75 mmol) and CaCl$_2$ (anhydrous) (0.83 g, 7.51 mmol) in a 500 mL round bottom flask equipped with a stirbar was added sequentially: EtOH (wet) (30 mL), THF (20 mL) and NaBH$_4$ (0.57 g, 15.0 mmol). The resulting cloudy reaction mixture was stirred 1 h at 23° C. and then poured onto 1 M citric acid and extracted with EtOAc. The organic extracts were washed with brine and dried over MgSO$_4$. Silica gel and NaHCO$_3$ (100 mg) were added and the volatiles removed on a rotary evaporator. Flash chromatography (35–50–60% EtOAc/hexanes) gave 1.08 g (95%) of as a white solid. R$_f$=0.51 (70% EtOAc/hexanes); MS m/z 303 (M–H)$^+$; $^1$H NMR (300 MHz, DMSO-D6) δ ppm 1.35 (s, 9 H) 2.31 (s, 3 H) 2.71 (m, 2 H) 3.29 (t, J=5.42 Hz, 2 H) 3.57 (m, 1 H) 4.54 (t, J=5.42 Hz, 1 H) 6.45 (d, J=8.48 Hz, 1 H) 6.92 (m, 2 H) 7.19 (dd, J=6.78, 1.02 Hz, 1 H) 7.48 (d, J=7.12 Hz, 1 H) 10.64 (s, 1 H).

Example 225E (±)-[2-(5-Bromo-pyridin-3-yloxy)-1-(2-methyl-1H-indol-3-ylmethyl)-ethyl]-carbamic acid tert-butyl ester The desried product was prepared by substituting Example 225D for Boc-tryptophanol in Example 2A.

R$_f$=0.41 (50% EtOAc/hexanes); MS m/z 460, 462 (M+H)$^+$; $^1$H NMR (300 MHz, DMSO-D6) δ ppm 1.35 (s, 9 H) 2.30 (s, 3 H) 2.86 (m, 2 H) 3.97 (s, 2 H) 6.93 (m, 3 H) 7.21 (d, J=7.80 Hz, 1 H) 7.46 (d, J=7.46 Hz, 1 H) 7.59 (s, 1 H) 8.13 (dd, J=3.56, 2.20 Hz, 1 H) 8.25 (dd, J=5.09, 2.03 Hz, 2 H) 10.72 (s, 1 H).

Example 225F (±)-[1-(2-Methyl-1H-indol-3-ylmethyl)-2-(5-trimethylstannanyl-pyridin-3-yloxy)-ethyl]-carbamic acid tert-butyl ester Example 225D (350 mg, 0.76 mmol), Pd(PPh$_3$)$_4$ (88 mg, 0.08 mmol) and hexamethylditin (300 mg, 0.92 mmol) were combined in a 25 mL round bottom flask with a stirbar. The atmosphere of the flask was evacuated and replaced with argon. Toluene (4 mL) was added and the resulting reaction mixture warmed to 100° C. for 2 h and then cooled to room temperature. EtOAc and silica gel were added and the volatiles removed on a rotary evaporator. Flash chromatography (30–40–50–60% EtOAc/hexanes gave 294 mg (71%) of as a yellow solid. R$_f$=0.43 (70% EtOAc/hexanes); MS m/z 546 (M+H)$^+$; $^1$H NMR (300 MHz, DMSO-D6) δ ppm 0.28 (s, 9 H) 1.36 (s, 9 H) 2.30 (s, 3 H) 2.86 (m, 2 H) 3.95 (s, 3 H) 6.93 (m, 3 H) 7.21 (d, J=7.80 Hz, 1 H) 7.33 (d, J=2.03 Hz, 1 H) 7.44 (d, J=7.46 Hz, 1 H) 8.14 (s, 2 H) 10.72 (s, 1 H).

Example 225G (±)-[2-[5-(3-Methyl-1H-indazol-5-yl)-pyridin-3-yloxy]-1-(2-methyl-1H-indol-3-ylmethyl)-ethyl]-carbamic acid tert-butyl ester Bromo-methylindazole (71 mg, 0.33 mmol), Example 225F (200 mg, 367 mmol), Pd$_2$dba$_3$ (61 mg, 0.7 mmol), and P(o-tol)$_3$ (41 mg, 0.14 mmol) were combined in a 10 mL round bottom flask with a stirbar. DMF (2 mL) was added and the atmosphere of the flask evacuated and replaced with argon twice. Et$_3$N (0.09 mL, 0.67 mmol) was added and the reaction mixture warmed to 80° C. for 5 h and then cooled to room temperature. EtOAc was added and the resulting mixture filtered through Celite. The filtrate was washed twice with H$_2$O and once with brine. Silica gel was added and the volatiles removed on a rotary evaporator. Flash chromatography (70–85–100% EtOAc/hexanes) gave 48 mg (28%) of as a yellow solid. R$_f$=0.30 (EtOAc); MS m/z 512 (M+H)$^+$; $^1$H NMR (300 MHz, DMSO-D6) δ ppm 1.36 (s, 9 H) 2.31 (s, 3 H) 2.54 (s, 3 H) 2.90 (m, 2 H) 4.05 (m, 3H) 6.93 (m, 3 H) 7.20 (m, 2 H) 7.58 (m, 3 H) 8.06 (s, 1 H) 8.20 (d, J=2.71 Hz, 1 H) 8.53 (d, J=1.70 Hz, 1 H) 10.72 (s, 1 H) 12.72 (s, 1 H).

Example 225H (±)-2-[5-(3-Methyl-1H-indazol-5-yl)-pyridin-3-yloxy]-1-(2-methyl-1H-indol-3-ylmethyl)-ethylamine The title compound was prepared as trifluoroacetic acid salt by substituting Example 225G for Example 27B in Example 27C (31.9 mg, 84%). MS m/z 412 (M+H)$^+$; $^1$H NMR (300 MHz, DMSO-D6) δ ppm 2.33 (s, 3 H) 2.55 (s, 3 H) 2.75 (dd, J=14.41, 6.61 Hz, 1 H) 2.92 (m, 1 H) 3.18 (s, 2 H) 3.99 (m, 2 H) 4.09 (q, J=5.43 Hz, 1H) 6.89 (m, 1H) 6.96 (td, J=7.46, 1.02 Hz, 1 H) 7.22 (d, J=7.80 Hz, 1 H) 7.46 (d, J=7.46 Hz, 1 H) 7.54 (d, J=8.82 Hz, 1 H) 7.63 (m, 1 H) 7.67 (m, 1 H) 8.08 (s, 1 H) 8.25 (d, J=2.37 Hz, 1 H) 8.54 (d, J=1.70 Hz, 1 H) 10.75 (s, 1 H) 12.73 (s, 1 H).

EXAMPLE 226

7-{5-[(2S)-2-Amino-3-(1H-indol-3-yl)-propoxy]-pyridin-3-yl}-quinazolin-2-ylamine Example 226A 7-Bromo-quinazolin-2-ylamine The 4-Bromo-2-fluoro-benzaldehyde (0.61 g, 3 mmol), guanidine (1.05 g, 5.83 mmol) and DMF were heated at 140° C. for 2.5 hours. 50 ml water was added to the mixture. The orange precipitate was filtered and washed with water. The solid was dissolved in 2N HCl. and filtered. The HCl solution was neutralized by ammonia hydroxyl. The off white solid was filtered and dried under vacuum to afforded the desired product (91 mg, 14%). MS (ESI) m/e 224 (M+1)$^+$; $^1$H NMR (300 MHz, DMSO-D6) δ ppm 7.00 (br. s., 2 H) 7.36 (d, J=8.82 Hz, 1 H) 7.77 (dd, J=9.16, 2.37 Hz, 1 H) 8.05 (d, J=2.37 Hz, 1 H) 9.09 (br. s., 1 H).

Example 226B

7-{5-[(2S)-2-Amino-3-(1H-indol-3-yl)-propoxy]-pyridin-3-yl}-quinazolin-2-ylamine The desired product was prepared by substituting Example 226A for 6-bromophthalimide in Example 32 as the tri-TFA salt. MS m/z 11 (M+H)$^+$, (M–H)$^+$; $^1$H NMR (300 MHz, DMSO-D6) δ ppm 2.85 (m, 1 H) 3.01 (m, 1 H) 3.32 (m, 1 H) 4.06 (m, 2 H) 6.96 (m, 3 H) 7.05 (m, 1 H) 7.22 (d, J=2.03 Hz, 1 H) 7.34 (d, J=8.14 Hz, 1 H) 7.54 (m, 1 H) 7.68 (m, 1 H) 8.05 (dd, J=8.99, 2.20 Hz, 1 H) 8.19 (d, J=2.03 Hz, 1 H) 8.30 (d, J=2.71 Hz, 1 H) 8.57 (d, J=2.03 Hz, 1 H) 9.16 (s, 1 H) 10.88 (s, 1 H).

EXAMPLE 227

2-Phenyl-2-(3-pyridin-4-yl-1H-pyrazolo[3,4-b]pyridin-6-yl)-ethylamine

Example 227A (2,6-Difluoro-pyridin-3-yl)-pyridin-4-yl-methanol

To diisopropylamine (9.3 mL, 66.1 mmol) in THF (100 mL) at −78° C. was added n-BuLi (23.1 mL of a 2.5 M solution in hexanes, 57.8 mmol) dropwise via syringe. 2,6-difluoropyridine (5.0 mL, 55.1 mmol) in THF (100 mL) at −78° C. was added to the above prepared LDA solution dropwise via canula to give a clear yellow-green solution. isonicotinaldehyde (6.3 mL, 66.1 mmol) was added causing a white precipitate to form. The reaction mixture was warmed to room temperature and then glacial acetic acid (3.3 mL, 57.8 mmol) was added. Silica gel was added and the volatiles removed on a rotary evaporator. Flash chromatography (80–100% EtOAc/hexanes-3–5–7% MeOH/EtOAc) gave 8.48 g (69%) of as an off white solid. R$_f$=0.38 (5% MeOH/EtOAc); MS m/z 223 (M+H)$^+$; $^1$H NMR (300 MHz, DMSO-D6) δ ppm 5.91 (d, J=4.41 Hz, 1 H) 6.49 (d, J=4.41 Hz, 1 H) 7.20 (dd, J=8.31, 2.54 Hz, 1 H) 7.36 (m, 2 H) 8.19 (m, 1 H) 8.53 (m, 2 H); Found: 223, 221; Anal calcd for C$_{11}$H$_8$F$_2$N$_2$O: C, 59.46; H, 3.63; N, 12.61. Found: C, 59.45; H, 3.66; N, 12.62.

Example 227B (2,6-Difluoro-pyridin-3-yl)-pyridin-4-yl-methanone

Example 227A (7.36 g, 33.1 mmol) and MnO$_2$ (8.64 g, 99.4 mmol) were combined in a 500 mL round bottom flask with a stirbar. 1,4-dioxane (120 mL) was added and the resulting black mixture warmed to 110° C. $MnO_2$ (~22 g) was added in 2 g amounts every couple of hours over the next 2 days. The reaction mixture was cooled to room temperature and filtered through Celite. The filter cake was washed with EtOAc and then all volatiles were removed on a rotary evaporator. Flash chromatography (50–70–80% EtOAc/hexanes) gave 4.61 g (63%) of as a green solid. $R_f$=0.58 (5% MeOH/EtOAc); MS m/z 221. $(M+H)^+$; $^1H$ NMR (300 MHz, DMSO-D6) δ ppm 7.41 (ddd, J=8.14, 2.37, 0.68 Hz, 1 H) 7.72 (m, 2 H) 8.47 (dt, J=9.41, 8.01 Hz, 1 H) 8.85 (m, 2 H); Anal calcd for $C_{11}H_6F_2N_2O$: C, 60.01; H, 2.75; N, 12.72. Found: C, 60.05; H, 2.87; N, 12.97.

Example 227C

6-Fluoro-3-pyridin-4-yl-1H-pyrazolo[3,4-b]pyridine

To Example 227B (4.20 g, 19.1 mmol) in 1,4-dioxane (100 mL) was added hydrazine hydrate (0.93 mL, 19.1 mmol). The resulting yellow reaction mixture was stirred 20 min at 23° C. and then silica gel was added and the volatiles removed on a rotary evaporator. Flash chromatography (60–80–100% EtOAc/hexanes-1–5% MeOH/EtOAc) gave 2.49 g (61%) of as a white solid. $R_f$=0.40 (5% MeOH/EtOAc); MS m/z 215 $(M+H)^+$; $^1H$ NMR (300 MHz, DMSO-D6) δ ppm 7.14 (dd, J=8.65, 0.85 Hz, 1 H) 8.02 (m, 2 H) 8.71 (m, 2 H) 8.87 (dd, J=8.48, 7.80 Hz, 1 H) 14.25 (s, 1 H); Anal calcd for C, $H_7FN_4$: C, 61.68; H, 3.29; N, 26.16. Found: C, 61.35; H, 3.35; N, 25.81.

Example 227D

Phenyl-(3-pyridin-4-yl-1H-pyrazolo[3,4-b]pyridin-6-yl)-acetonitrile

To a stirred mixture of Example 227C (0.96 g, 4.48 mmol) in DMF (20 mL) at −35° C. was added benzyl cyanide (1.55 mL, 13.4 mmol) and then NaH (0.57 g of 95% NaH, 22.4 mmol). The resulting dark red mixture was stirred 15 min while being slowly warmed to ~−20° C. At this time most of the bubbling had stopped and the reaction mixture was then quickly warmed to room temperature and then to 100° C. overnight. The reaction mixture was cooled to room temperature and saturated aqueous $NH_4Cl$ was added. The mixture was extracted with EtOAc and the organic extracts washed twice with $H_2O$ and once with brine. Silica gel was added and the volatiles removed on a rotary evaporator. Flash chromatography (60–80–100% EtOAc-3% MeOH/EtOAc) gave 1.14 g (82%) of as an orange solid. $R_f$=0.40 (5% MeOH/EtOAc); MS m/z 312 $(M+H)^+$; $^1H$ NMR (300 MHz, DMSO-D6) δ ppm 6.17 (s, 1 H) 7.40 (m, 4 H) 7.52 (m, 2 H) 8.00 (m, 2 H) 8.70 (m, 2 H) 8.74 (d, J=8.48 Hz, 1 H) 14.36 (s, 1 H); Anal Calcd for $C_{19}H_{13}N_5$: C, 73.30; H, 4.21; N, 22.49. Found: C, 73.09; H, 4.10; N, 22.58.

Example 227E

2-Phenyl-2-(3-pyridin-4-yl-1H-pyrazolo[3,4-b]pyridin-6-yl)-ethylamine

The desire product was prepared by substituting Example 227D for Example 41C in Example 41D (84 mg, 27%). $R_f$=0.33 (20% MeOH/$CH_2Cl_2$); MS m/z 316 $(M+H)^+$; $^1H$ NMR (300 MHz, DMSO-D6) δ ppm 3.23 (m, 1 H) 3.34 (br s, 3 H) 3.52 (m, 1 H) 4.34 (m, 1 H) 7.27 (m, 6 H) 7.99 (d, J=6.10 Hz, 2 H) 8.57 (d, J=8.48 Hz, 1 H) 8.68 (d, J=6.10 Hz, 2 H).

EXAMPLE 228

Naphthalen-2-yl-(3-pyridin-4-yl-1H-pyrazolo[3,4-b]pyridin-6-yl)-acetonitrile

The desired product was obtained by substituting 2-napthyl acetonitrile for benzyl nitrile in Example 227D (244 mg, 42%). $R_f$=0.46 (EtOAc); MS m/z 362 $(M+H)^+$; $^1H$ NMR (300 MHz, DMSO-D6) δ ppm 6.36 (s, 1 H) 7.44 (d, J=8.48 Hz, 1 H) 7.57 (m, 3 H) 7.98 (m, 6 H) 8.09 (d, J=1.36 Hz, 1 H) 8.69 (m, 2 H) 8.75 (d, J=8.48 Hz, 1 H).

EXAMPLE 229

2-Naphthalen-2-yl-2-(3-pyridin-4-yl-1H-pyrazolo[3,4-b]pyridin-6-yl)-ethylamine

The desire product was prepared by substituting Example 228 for Example 41C in Example 41D. MS m/z 366 $(M+H)^+$; $^1H$ NMR (300 MHz, DMSO-D6) δ ppm 3.96 (m, 2 H) 4.82 (t, J=7.46 Hz, 1 H) 7.39 (d, J=8.48 Hz, 1 H) 7.52 (m, 3 H) 7.89 (m, 4 H) 8.20 (d, J=6.10 Hz, 2 H) 8.68 (d, J=8.48 Hz, 1 H) 8.80 (m, 3 H).

EXAMPLE 230

(3-Isoquinolin-6-yl-1H-pyrazolo[3,4-b]pyridin-6-yl)-phenyl-acetonitrile

Example 230A

Isoquinoline-6-carbaldehyde

A solution of 6-bromoisoquinoline (19.9 g, 95.6 mmol), $PdCl_2$ (dppf).$CH_2Cl_2$ (1.8 g), and triethylamine (30 mL) in toluene (50 mL) was heated to 130° C. under 850 psi of $H_2/CO$ (1:1) for 4 h. After cooling to rt, the reaction mixture was filtered. The filtrate was concentrated and the residue was purified by flash chromatography eluting with 70–80–90–100% EtOAc/hexanes to give 6.11 g (41%) of the aldehyde as a yellow solid. $R_f$=0.55 (EtOAc); $^1H$ NMR (300 MHz, DMSO-D6) δ ppm 8.07 (m, 2 H) 8.30 (dd, J=8.48, 0.68 Hz, 1 H) 8.64 (s, 1 H) 8.67 (d, J=5.76 Hz, 1 H) 9.47 (s, 1 H) 10.23 (s, 1 H).

Example 230B (3-Isoquinolin-6-yl-1H-pyrazolo[3,4-b]pyridin-6-yl)-phenyl-acetonitrile The desired product (244 mg, 42%) was obtained by substituting Example 230A for isonicotinaldehyde in Example 227. $R_f$=0.46 (EtOAc); MS m/z 362 $(M+H)^+$; $^1H$ NMR (300 MHz, DMSO-D6) δ ppm 6.18 (s, 1 H) 7.40 (m, 4 H) 7.54 (m, 2 H) 7.99 (d, J=5.76 Hz, 1 H) 8.25 (d, J=8.48 Hz, 1 H) 8.36 (m, 1 H) 8.56 (d, J=5.42 Hz, 1 H) 8.63 (s, 1 H) 8.87 (d, J=8.48 Hz, 1 H) 9.35 (s, 1 H) 14.27 (s, 1 H).

EXAMPLE 231

2-(3-Isoquinolin-6-yl-1H-pyrazolo[3,4-b]pyridin-6-yl)-2-phenyl-ethylamine

The desire product was prepared by substituting Example 230 for Example 41C in Example 41D. MS m/z 366 $(M+H)^+$; $^1H$ NMR (300 MHz, DMSO-D6) δ ppm 3.11 (m, 1 H) 3.90 (m, 1 H) 4.66 (dd, J=9.16, 6.10 Hz, 1 H) 7.31 (m, 8 H) 8.28 (d, J=6.10 Hz, 1 H) 8.42 (d, J=8.82 Hz, 1 H) 8.54 (d, J=8.48 Hz, 1 H) 8.63 (d, J=6.44 Hz, 1 H) 8.78 (s, 1 H) 8.82 (d, J=8.48 Hz, 1 H) 9.59 (s, 1 H) 14.26 (s, 1 H).

EXAMPLE 232

(1S)-1-Benzyl-2-(3-pyridin-4-yl-1H-pyrazolo[3,4-b]pyridin-5-yloxy)-ethylamine

Example 232B 5-(tert-Butyl-dimethyl-silanyloxy)-2-fluoro-pyridine

A mixture of 2-fluoro-5-hydroxypyridine (1.00 g, 8.84 mmol) and BDCS reagent (0.5 TBSCl, 1.0 imidazole in DMF) (35.4 mL, 17.7 mmol) was stirred at rt for 1 h. The reaction was poured into satd. aqueous NaHCO$_3$ solution. The aqueous layer was extracted with ether. The combined extracts were washed with water, brine, dried over MgSO$_4$, and concentrated. The residue was purified by flash column chromatography on silica gel eluting with 10% ethyl acetate/hexanes to give the title compound (1.96 g, 98%).

Example 232B 5-(tert-Butyl-dimethyl-silanyloxy)-3-pyridin-4-yl-1H-pyrazolo[3,4-b]pyridine The desired product was prepared according to the procedures used for Example 227C by substituting Example 232A for 2,6-difluoropyridine in Example 227A.

Example 232C 5-(tert-Butyl-dimethyl-silanyloxy)-3-pyridin-4-yl-pyrazolo[3,4-b]pyridine-1-carboxylic acid tert-butyl ester The desired product was prepared by substituting Example 232B for Example 102C in Example 203A (75%).

Example 232D

5-Hydroxy-3-pyridin-4-yl-pyrazolo[3,4-b]pyridine-1-carboxylic acid tert-butyl ester A mixture of Example 232C (91 mg, 0.213 mmol) and TBAF (1 in THF, 213 µL, 0.213 mmol) in THF (10 mL) was stirred at rt for 5 min. Reaction was concentrated. Flash column chromatography eluting with 5% methanol/CH$_2$Cl$_2$ to give the dedired product purified the residue (75%).

Example 232E 5-((2S)-2-tert-Butoxycarbonylamino-3-phenyl-propoxy)-3-pyridin-4-yl-pyrazolo[3,4-b]pyridine-1-carboxylic acid tert-butyl ester The title compound was prepared by substituting Example 232D for Example 238A and Boc-phenylalaminol for Boc-4'-bromophenylalaminol in Example 238B.

Example 232F (1S)-1-Benzyl-2-(3-pyridin-4-yl-1H-pyrazolo[3,4-b]pyridin-5-yloxy)-ethylamine To Example 232E (39 mg, 71 µmol) in CH$_2$Cl$_2$ (4 mL) was added 4-methoxybenzyl mercaptan (30 µL, 214 µmol) and then TFA (1 mL). The resulting yellow reaction mixture was stirred 50 min at 23° C. at which time all volatiles were removed on a rotary evaporator. K$_2$CO$_3$ (excess) and MeOH (5 mL) were added and the resulting mixture stirred 1 h at 23° C. at which time silica gel was added and the volatiles removed on a rotary evaporator. Flash chromatography (EtOAc-5–10–12% MeOH/CH$_2$Cl$_2$) gave a light yellow waxy product which was dissolved in 20% MeOH/CH$_2$Cl$_2$ and stirred for 1 h with 1 N HCl (1 mL of a 1 N solution in Et$_2$O, 1 mmol). The volatiles were removed to give 11 mg (17%, two steps) of a yellow solid which was the bis-HCl salt. MS m/z 346 (M+H)$^+$; $^1$H NMR (300 MHz, DMSO-D6) δ ppm 2.92 (dd, J=13.73, 8.98 Hz, 1 H) 3.12 (dd, J=14.24, 5.09 Hz, 1 H) 4.14 (dd, J=5.59, 1.86 Hz, 1 H) 4.74 (t, J=5.93 Hz, 2 H) 7.20 (m, 5 H) 7.97 (d, J=2.37 Hz, 1 H) 8.38 (m, 5 H) 8.90 (d, J=6.78 Hz, 2 H) 10.31 (s, 1 H).

EXAMPLE 233

2-Benzyl-3-[5-(3-methyl-1H-indazol-5-yl)-pyridin-3-yloxy]-propylamine

The desired product was prepared as trifluoroacetic acid by substituting (2-Benzyl-3-hydroxy-propyl)-carbamic acid tert-butyl ester (Khumtaveeporn, K.; Ullmann, A.; Matsumoto, K.; Davis, B. G.; Jones, J. B. Tetrahedron: Asymmetry 2001, 12, 249) for Example Boc-tryptophanol in Example 102. MS m/z 373 (M+H)$^+$, (M–H)$^+$; $^1$H NMR (300 MHz, DMSO-D6) δ ppm 2.55 (s, 3 H) 2.81 (dd, J=7.29, 3.56 Hz, 2 H) 2.92 (m, 1 H) 3.05 (m, 1 H) 4.09 (dd, J=10.17, 5.76 Hz, 2 H) 4.16 (m, 2 H) 7.28 (m, 5 H) 7.57 (dd, J=8.48, 0.68 Hz, 1 H) 7.69 (m, 1 H) 7.74 (m, 1 H) 7.82 (s, 2 H) 8.09 (m, 1 H) 8.30 (d, J=2.71 Hz, 1 H) 8.62 (d, J=1.70 Hz, 1 H).

EXAMPLE 234

(1S)-1-(1H-Indol-3-ylmethyl)-2-(2-pyridin-4-yl-[1,7]naphthyridin-5-yloxy)-ethylamine Example 234A 3-Bromo-5-(4-methoxy-benzyloxy)-pyridine 3-Bromo-5-hydroxypyridine (14.7 g, 84.3 mmol), tetrabutylammonium iodide (0.3 g, 0.8 mmol), and K$_2$CO$_3$ (14.0 g, 101 mmol) were combined in a dry 500 mL round bottom flask with a stirbar. DMF (170 mL) was added followed by PMBCl (12.0 mL, 88.5 mmol). The resulting brown colored mixture was stirred 3.5 days at 23° C. and then silica gel was added and the volatiles removed on a rotary evaporator. Flash chromatography (10–20–40% EtOAc/hexanes) gave 14.1 g (57%) of as an orange solid. R$_f$=0.52 (50% EtOAc/hexanes) $^1$H NMR (300 MHz, DMSO-D6) δ ppm 3.32 (s, 3 H) 5.12 (s, 2 H) 6.96 (m, 2 H) 7.39 (m, 2 H) 7.79 (m, 1 H) 8.28 (d, J=2.03 Hz, 1 H) 8.34 (d, J=2.71 Hz, 1 H). $^{13}$C NMR (100 MHz, DMSO-D6) δ ppm 55.0, 69.8, 113.8, 119.9, 124.0, 127.8, 129.8, 137.1, 142.1, 155.1, 159.2; Anal Calcd for C$_{12}$H$_{10}$BrNO: C, 53.08; H, 4.11; N, 4.76. Found: C, 53.00; H, 3.98; N, 4.66.

Example 234B

3-Amino-5-(4-methoxy-benzyloxy)-pyridine

Example 234A (16.15 g, 54.9 mmol), Pd$_2$dba$_3$ (0.50 g, 0.55 mmol), rac-BINAP (1.03 g, 1.65 mmol), and sodium tert-butoxide (7.39 g, 76.9 mmol) were combined in a 500 mL round bottom flask with a stirbar. Benzophenone imine (11.1 mL, 65.9 mmol) was added followed by toluene (180 mL). The resulting reaction mixture was warmed to 80° C. for 3 h and then allowed to cool to room temperature, diluted with Et$_2$O, and filtered through Celite. The volatiles were removed on a rotary evaporator. Flash chromatography (30–40–50% EtOAc/hexanes) yielded an impure orange oil which was dissolved in THF (180 mL) and 1 N HCl (60 mL). The resulting orange mixture was stirred 15 min and then partitioned between 30% EtOAc/hexanes and 0.5 M HCl. The layers were separated and the organic layer washed once with 0.5 M HCl. The combined HCl layers were washed once with 30% EtOAc/hexanes and then cooled to 0° C. 50% aqueous NaOH was added until the mixture was basic on litmus paper and then the mixture was extracted twice with CH$_2$Cl$_2$. The combined organic extracts were dried over Na$_2$SO$_4$ and the volatiles removed on a rotary evaporator to yield 8.92 g (71%, two steps) of as a yellow solid. $^1$H NMR (300 MHz, DMSO-D6) δ ppm 3.75 (s, 3 H)

4.97 (s, 2 H) 4.97 (s, 2 H) 5.29 (s, 2 H) 6.54 (t, J=2.37 Hz, 1 H) 7.35 (m, 2 H) 7.50 (d, J=2.37 Hz, 1 H) 7.54 (d, J=2.37 Hz, 1 H), $^{13}$C NMR (100 MHz, DMSO-D6) δ ppm 55.0, 68.9, 105.6, 113.8, 125.3, 128.7, 129.3, 129.4, 145.7, 155.1, 159.0.

Example 234C

[5-(4-Methoxy-benzyloxy)-pyridin-3-yl]-carbamic acid tert-butyl ester

To a stirred solution of Example 234B (8.92 g, 38.7 mmol) in THF (240 mL) at 23° C. was added NaHMDS (129 mL of a 0.6 M solution in toluene, 77.5 mmol) dropwise via syringe. The resulting cloudy yellow-brown mixture was stirred 5 min and then Boc$_2$O (8.45 g, 38.7 mmol) was added all at once. The cloudiness of the mixture disappeared leaving a clear yellow-brown solution. 0.1 M HCl was added and the resulting aqueous and organic layers separated. The pH of the aqueous layer was ~8. The organic layer was washed with brine and then combined with silica gel before the volatiles were removed on a rotary evaporator. Flash chromatography (30–40–50–70% EtOAc/hexanes-5–10% MeOH/CH$_2$Cl$_2$) gave 1.69 (10%) of bis-Boc protected as an orange solid, 7.04 g (55%) of the desired mono-Boc protected as a yellow solid, and 1.51 g (17%) of starting amine as an orange solid. Data for bis-Boc: R$_f$=0.38 (50% EtOAc/hexanes) $^1$H NMR (300 MHz, DMSO-D6) δ ppm 1.35 (s, 18 H) 3.75 (s, 3 H) 5.11 (s, 2 H) 6.94 (m, 2 H) 7.39 (m, 2 H) 7.43 (dd, J=2.71, 2.03 Hz, 1 H) 8.02 (d, J=2.03 Hz, 1 H) 8.28 (d, J=2.37 Hz, 1 H). Data for mono-Boc: R$_f$=0.30 (50% EtOAc/hexanes) $^1$H NMR (300 MHz, DMSO-D6) δ ppm 1.48 (s, 9 H) 3.76 (s, 3 H) 5.04 (s, 2 H) 6.95 (m, 2 H) 7.39 (m, 2 H) 7.60 (t, J=2.20 Hz, 1 H) 7.96 (d, J=2.71 Hz, 1 H) 8.22 (d, J=2.03 Hz, 1 H) 9.57 (s, 1 H). $^{13}$C NMR (100 MHz, DMSO-D6) δ ppm 28.0, 55.0, 69.3, 79.6, 110.8, 113.8, 128.3, 129.6, 131.1, 132.3, 136.9, 152.7, 154.4, 159.1, Anal Calcd for C$_{18}$H$_{22}$N$_2$O$_4$: C, 65.44; H, 6.71; N, 8.48. Found: C, 65.40; H, 6.66; N, 8.40.

Example 234D

[4-Formyl-5-(4-methoxy-benzyloxy)-pyridin-3-yl]-carbamic acid tert-butyl ester

To Example 234C (2.50 g, 7.54 mmol) in THF (125 mL) at −78° C. was added dropwise via syringe n-BuLi (6.64 mL of a 2.5 M solution in hexanes, 16.6 mmol). The resulting dark orange reaction mixture was slowly warmed to −10° C. over 45 min and then recooled to −78° C. Methyl formate (1.40 mL, 22.6 mmol) was added dropwise via syringe and the reaction was stirred an additional 10 min at −78° C. Saturated aqueous NH$_4$Cl was added and the quenched reaction mixture warmed to room temperature. H$_2$O and Et$_2$O were added and the layers separated. The organics were washed with brine and dried over MgSO$_4$. Flash chromatography (20–40–60–80% EtOAc/hexanes gave 0.3 g (12%) of recovered starting material, and 1.7 g (63%) of as a yellow solid. ($^1$H NMR (400 MHz, DMSO-D6) δ ppm 1.47 (s, 9 H) 3.75 (s, 3 H) 5.28 (s, 2 H) 6.95 (d, J=8.59 Hz, 2 H) 7.43 (d, J=8.59 Hz, 2 H) 8.38 (s, 1 H) 9.07 (s, 1 H) 10.17 (s, 1 H) 10.35 (s, 1 H), $^{13}$C NMR (100 MHz, DMSO-D6) δ ppm 27.7, 55.0, 70.8, 81.1, 113.9, 114.6, 127.7, 129.6, 130.0, 133.3, 134.6, 151.7, 154.7, 159.2, 192.8, Anal Calcd for C$_{19}$H$_{22}$N$_2$O$_5$: C, 63.67; H, 6.19; N, 7.82. Found: C, 63.59; H, 6.21; N, 7.64.

Example 234E 5-(4-Methoxy-benzyloxy)-[1,7]naphthyridin-2-ol

To Bis(2,2,2-trifluoroethyl) (methoxycarbonylmethyl) phosphonate (1.27 mL, 5.99 mmol) in THF (45 mL) at −78° C. was added KHMDS (11.1 mL of a 0.5 M solution in toluene, 5.53 mmol) dropwise via syringe. The resulting clear, light yellow solution was added dropwise via canula to Example 234D (1.65 g, 4.60 mmol) in THF (60 mL) at −78° C. The resulting cloudy yellow reaction mixture was stirred 20 min at −78° C. at which time saturated aqueous NH$_4$Cl was added and the quenched reaction mixture warmed to room temperature. H$_2$O and Et$_2$O were added and the layers separated. The organics were washed with brine and dried over MgSO$_4$. Flash chromatography (40–50–60–70% EtOAc/hexanes) gave 1.98 g of impure product which was a 5:1 mixture of Z:E olefin isomers. To the crude product in THF (150 mL) was added NaHMDS (11.6 mL of a 0.6 M solution in toluene, 6.95 mmol). The resulting reaction mixture was stirred 30 min at 23° C. at which time silica gel was added and the volatiles removed on a rotary evaporator. Flash chromatography (60–100% EtOAc/hexanes-5–10% MeOH/CH$_2$Cl$_2$) gave 0.23 g (12%) of E-olefin as a yellow solid and the desired product 0.98 g (75%, two steps) of as a white solid. R$_f$=0.32 (10% MeOH/CH$_2$Cl$_2$), $^1$H NMR (400 MHz, DMSO-D6) δ ppm 3.77 (s, 3 H) 5.27 (s, 2 H) 6.68 (d, J=9.51 Hz, 1 H) 6.98 (m, 2 H) 7.46 (m, 2 H) 8.00 (d, J=9.82 Hz, 1 H) 8.18 (s, 1 H) 8.31 (s, 1 H) 11.98 (s, 1 H), $^{13}$C NMR (100 MHz, DMSO-D6) δ ppm 55.0, 70.2, 113.7, 113.9, 125.7, 125.8, 128.1, 129.5, 131.0, 132.7, 134.9, 149.3, 159.2, 161.2, Anal Calcd for C$_{16}$H$_{14}$N$_2$O$_3$: C, 68.07; H, 5.00; N, 9.92. Found: C, 67.75; H, 4.89; N, 9.88.

Example 234F

2-Chloro-5-(4-methoxy-benzyloxy)-[1,7]naphthyridine

To a suspension of Example 234D (2.21 g, 7.83 mmol) in DMF (50 mL) at 23° C. was added POCl$_3$ (2.2 mL, 23.5 mmol). All the solid starting material dissolved and the resulting yellow reaction mixture was warmed to 45° C. for 6 h. The color of the reaction changed from yellow to dark red-brown. The reaction was poured onto NaHCO$_3$ (13.2 g 157 mmol) in ice water (250 mL) in a 1 L Ehrlenmeyer flask with vigorous stirring. The product was extracted with EtOAc and Et$_2$O and the organic extracts washed twice with H$_2$O and once with brine. Silica gel was added and the volatiles removed on a rotary evaporator. Flash chromatography (20–30–45–50% EtOAc/hexanes) gave 1.86 g (79%) of as an off-white solid. R$_f$=0.65 (10% MeOH/CH$_2$Cl$_2$), $^1$H NMR (400 MHz, DMSO-D6) δ ppm 3.79 (s, 3 H) 5.35 (s, 2 H) 6.99 (d, J=8.59 Hz, 2 H) 7.51 (d, J=8.90 Hz, 2 H) 7.77 (d, J=8.90 Hz, 1 H) 8.47 (s, 1 H) 8.52 (dd, J=8.90, 0.61 Hz, 1 H) 8.96 (s, 1 H), $^{13}$C NMR (100 Hz, DMSO-D6) δ ppm 55.0, 70.4, 113.9, 121.8, 125.9, 126.5, 127.9, 129.6, 133.7, 142.4, 144.0, 148.5, 151.7, 159.2; Anal Calcd for C$_{16}$H$_{13}$ClN$_2$O$_2$: C, 63.90; H, 4.36; N, 9.31. Found: C, 63.54; H, 4.17; N, 9.14.

Example 234G 5-(4-Methoxy-benzyloxy)-2-pyridin-4-yl-[1,7]naphthyridine

Example 234F (164 mg, 0.55 mmol), 4-tributylstannylpyridine (401 mg, 1.09 mmol), Pd$_2$dba$_3$ (50 mg, 0.06 mmol), and 2-dicyclohexylphosphino-2'-(N,N-dimethylamino)biphenyl (43 mg, 0.11 mmol) were combined in a 10 mL round bottom flask with a stirbar. The atmosphere of the flask was evacuated and replaced with argon twice. DMF (2 mL) and Et$_3$N (0.5 mL, 3.27 mmol) were added and the reaction mixture warmed to 100° C. for 5 h. The reaction mixture was cooled to room temperature, diluted with EtOAc and Et$_2$O, and filtered through Celite. The filtrate was washed twice with H$_2$O and once with brine. Silica gel was added and the volatiles removed by rotary evaporation. Flash chromatography (70–100% EtOAc/hexanes-2–5% MeOH/CH$_2$Cl$_2$ gave 92 mg (49%) of as a yellow solid. R$_f$=0.39 (10% MeOH/CH$_2$Cl$_2$), $^1$H NMR (400 Hz, DMSO-D6) δ ppm 3.79 (s, 3 H) 5.37 (s, 2 H) 7.01 (m, 2 H) 7.53 (m, 2 H) 8.21 (d, J=5.83 Hz, 2 H) 8.43 (m, 2 H) 8.64 (d, J=8.59 Hz, 1 H) 8.80 (d, J=4.30 Hz, 2 H) 9.13 (s, 1 H), $^{13}$C NMR (100 Hz, DMSO-D6) δ ppm 55.1, 70.3, 113.9, 121.3, 122.1, 122.6, 126.0, 128.1, 129.6, 131.3, 142.7, 144.6, 145.8, 148.4, 150.5, 155.5, 159.2; Anal Calcd for C$_{21}$H$_{17}$N$_3$O$_2$: C, 73.45; H, 4.99; N, 12.24. Found: C, 73.32; H, 5.10; N, 12.17.

Example 234I

2-Pyridin-4-yl-[1,7]naphthyridin-5-ol

To Example 234H (108 mg, 0.32 mmol) in a 50 mL round bottom flask with a stirbar was added a mixture of 1 N HCl (1.6 mL, 1.57 mmol) in EtOH (8 mL). The resulting reaction mixture was warmed to 90° C. for 2 h, cooled to room temperature, and then poured onto K$_2$CO$_3$ (120 mg, 0.87 mmol) in a 100 mL round bottom flask. MeOH (10 mL) was added and the mixture was stirred vigorously for 1 h at which time silica gel was added and the volatiles removed on a rotary evaporator. Flash chromatography (3–5–7–12% MeOH/CH$_2$Cl$_2$) gave 52 mg (74%) of as an off-white solid. R$_f$=0.24 (10% MeOH/CH$_2$Cl$_2$); MS m/z 224 (M+H)$^+$; $^1$H NMR (300 Hz, DMSO-D6) δ ppm 8.20 (s, 1 H) 8.24 (m, 2 H) 8.44 (d, J=8.82 Hz, 1 H) 8.69 (d, J=8.82 Hz, 1 H) 8.80 (m, 2 H) 9.01 (s, 1 H) 10.91 (Br S, 1 H).

Example 234J (1S)-[1-(1H-Indol-3-ylmethyl)-2-(2-pyridin-4-yl-[1,7]naphthyridin-5-yloxy)-ethyl]-carbamic acid tert-butyl ester The desired product was prepared by substituting Example 232I for 3-bromo-5-hydroxypyridine in Example 27A. R$_f$=0.41 (10% MeOH/CH$_2$Cl$_2$); $^1$H NMR (300 Hz, DMSO-D6) δ ppm 1.37 (s, 9 H) 3.07 (m, 1 H) 3.38 (m, 1 H) 4.25 (m, 3 H) 6.93 (m, 1 H) 7.05 (td, J=7.54, 1.19 Hz, 1 H) 7.15 (d, J=2.03 Hz, 1 H) 7.21 (d, J=7.80 Hz, 1 H) 7.33 (d, J=7.80 Hz, 1 H) 7.56 (d, J=7.80 Hz, 1 H) 8.27 (m, 3 H) 8.51 (d, J=8.82 Hz, 1 H) 8.82 (m, 3 H) 9.13 (s, 1 H) 10.82 (s, 1 H).

Example 234K (1S)-1-(1H-Indol-3-ylmethyl)-2-(2-pyridin-4-yl-[1,7]naphthyridin-5-yloxy)-ethylamine The desire product was prepared as trifluoroacetic acid salt by substituting Example 234K for Example 232D in Example 232E. MS m/z 396 (M+H)$^+$; $^1$H NMR (300 Hz, DMSO-D6) (of the free base) δ ppm 2.96 (m, 1 H) 3.11 (m, 1 H) 3.24 (m, 1 H) 3.61 (s, 1 H) 4.09 (q, J=5.09 Hz, 1 H) 4.16 (dd, J=9.49, 6.10 Hz, 1 H) 4.26 (m, 1 H) 6.93 (m, 1 H) 7.06 (td, J=7.46, 1.02 Hz, 1 H) 7.22 (d, J=2.37 Hz, 1 H) 7.34 (d, J=8.14 Hz, 1 H) 7.58 (d, J=8.14 Hz, 1 H) 8.27 (m, 3 H) 8.51 (d, J=8.82 Hz, 1 H) 8.82 (m, 2 H) 8.89 (d, J=8.82 Hz, 1 H) 9.14 (s, 1 H) 10.88 (s, 1 H).

EXAMPLE 235

(1R)-1-(1H-Indol-3-ylmethyl)-2-(2-pyridin-4-yl-[1,7]naphthyridin-5-yloxy)-ethylamine The desired product was prepared by substituting Boc-R-Tryptophanol for Boc-L-tryptophanol in Example 234.

MS m/z 396 (M+H)$^+$; $^1$H NMR (300 Hz, DMSO-D6) δ ppm 3.31 (m, 2 H) 4.34 (dd, J=10.51, 5.42 Hz, 1 H) 4.50 (dd, J=10.68, 2.54 Hz, 1 H) 6.95 (m, 1 H) 7.08 (m, 1 H) 7.29 (d, J=2.03 Hz, 1 H) 7.37 (d, J=8.14 Hz, 1 H) 7.63 (d, J=7.80 Hz, 1 H) 8.30 (s, 1 H) 8.65 (m, 6 H) 8.99 (d, J=5.76 Hz, 2 H) 9.23 (s, 1 H) 9.29 (m, 1 H) 11.04 (d, J=1.70 Hz, 1 H).

EXAMPLE 236

(1S)-1-(1H-Indol-3-ylmethyl)-2-(5-isoquinolin-6-yl-pyridin-3-ylsulfanyl)-ethylamine Example 236A 3-Bromo-5-(4-methoxy-benzylsulfanyl)-pyridine To a suspension of sodium hydride (370 mg, 60% in mineral oil, 9.25 mmol) in DMF (30 ml) (4-Methoxy-phenyl)-methanethiol (1.25 ml, 9 mmol) was added. The resulting solution was stirred at room temperature for 1 hour and added to 3.5-dibromopyridine (2.13 g, 8.99 mmol) in DMF (30 ml). The mixture was stirred at room temperature for 48 hours. The reaction solution was partitioned between ether and water. The organic layer was washed (brine), dried (Na$_2$SO$_4$), filtered and concentrated under vacuum. Purification on silica gel eluting with 5% ethyl acetate/hexane provides the title compound (1.75 g, 63%). MS (DCI/NH$_3$) m/e 310 (M+1)$^+$; $^1$H NMR (300 Hz, DMSO-D6) δ ppm 3.72 (s, 3 H) 4.30 (s, 2 H) 6.85 (d, J=2.03 Hz, 1 H) 6.89 (d, J=2.37 Hz, 1 H) 7.26 (d, J=2.37 Hz, 1 H) 7.29 (d, J=2.03 Hz, 1 H) 8.04 (dd, J=2.03 Hz, 1 H) 8.45 (d, J=2.03 Hz, 1 H) 8.48 (d, J=2.03 Hz, 1 H).

Example 236B

5-Bromo-pyridine-3-thiol

A mixture of Example 236A (1.43 g, 4.6 mmol), m-cresol (4.9 ml, 47 mmol) and TFA (4 ml) was refluxed for 24 hours. After cooled to room temperature, the solution was dried by vacuum. Purification on silica gel eluted with 5% ethyl acetate in hexanes to provide the crude title compound (contaminated with disulfide).

Example 236C (1S)-[2-(5-Bromo-pyridin-3-ylsulfanyl)-1-(1H-indol-3-ylmethyl)-ethyl]-carbamic acid tert-butyl ester A 100 ml RBF was charged with Example 236B (0.620 mg, 3.26 mmol), 2-Hydroxy-1-(1H-indol-3-ylmethyl)-ethyl]-carbamic acid tert-butyl ester (1.077 g, 3.71 mmol), Ph$_3$P (1.23 g, 4.69 mmol) and DBAD (1.0968 g, 4.763 mmol). THF (10 ml) was added at 0° C. The reaction mixture was stirred at 0° C. for 1 h and at room temperature for 22 hours. The reaction mixture was concentrated and the residue was separated by flash chromatography (30% EtOAc in hexane) to provide 0.614 g product with DBAD.

Example 236D (1S)-1-(1H-Indol-3-ylmethyl)-2-(5-isoquinolin-6-yl-pyridin-3-ylsulfanyl)-ethylamine The desired compound was prepared by substituting Example 236C for Example 2A in Example 27. MS (ESI) m/e 411 (M+1)$^+$; $^1$H NMR (300 Hz, DMSO-D6) δ ppm 3.13 (m, 2 H) 3.37 (m, 2 H) 3.57 (m, 1 H) 6.90 (t, J=8.14 Hz, 1 H) 7.02 (t, J=8.14 Hz, 1 H) 7.25 (d, J=2.37 Hz, 1 H) 7.31 (d, J=8.14 Hz, 1 H) 7.47 (m, 1 H) 8.06 (br. s., 2 H) 8.18 (m, 2

H) 8.28 (t, J=2.03 Hz, 1 H) 8.46 (m, 1 H) 8.52 (br. s., 1 H) 8.67 (d, J=6.10 Hz, 1 H) 8.69 (d, J=2.03 Hz, 1 H) 8.97 (d, J=2.03 Hz, 1 H) 9.66 (br. s., 1 H) 11.03 (br. s., 1 H).

EXAMPLE 237

(1S)-1-(1H-Indol-3-ylmethyl)-2-[5-(3-methyl-1H-indazol-5-yl)-pyridin-3-ylsulfanyl]-ethylamine The title compound was prepared by substituting Example 102C for 6-bromoisoquinoline in Example 236. MS (ESI) m/e 414 (M+1)+; $^1$H NMR (300 Hz, MeOH) δ ppm 3.20 (d, J=6.78 Hz, 2 H) 3.25 (m, 1 H) 3.50 (m, 1 H) 3.69 (m, 1 H) 6.91 (td, J=8.14, 6.10, 1.02 Hz, 1 H) 7.02 (td, J=8.14, 6.10, 1.02 Hz, 1 H) 7.15 (br. s., 1 H) 7.26 (d, J=8.14 Hz, 1 H) 7.40 (d, J=8.14 Hz, 1 H) 7.53 (t, J=8.82 Hz, 1 H) 7.60 (d, J=8.82 Hz, 1 H) 7.93 (m, 1 H) 8.12 (t, J=2.03 Hz, 1 H) 8.51 (br. s., 1 H) 8.74 (br. s., 1 H).

EXAMPLE 238

(1S)-1-(4-Bromo-benzyl)-2-[5-(3-methyl-1H-indazol-5-yl)-pyridin-3-yloxy]-ethylamine

Example 238A 5-(5-Hydroxy-pyridin-3-yl)-3-methyl-indazole-1-carboxylic acid tert-butyl ester The desired product was prepared by substituting 3-bromo-5-hydroxypyridine for Example 203B in Example 203C.

Example 238B (1S)-{1-(4-Bromo-benzyl)-2-[5-(3-methyl-1H-indazol-5-yl)-pyridin-3-yloxy]-ethyl}-carbamic acid tert-butyl ester The desired product was prepared according to the procedures described for Example 2A, substituting Example 238A for 3-bromo-5-hydroxypyridine, and 3'-bromo-Boc-phenylalaminol for Boc-tryptophanol in Example 2A.

Example 238C (1S)-1-(4-Bromo-benzyl)-2-[5-(3-methyl-1H-indazol-5-yl)-pyridin-3-yloxy]-ethylamine The desired product was prepared as trifluoroacetic acid salt by substituting Example 238B for Example 27B in Example 27. MS (ESI) m/e 437 (M+1); $^1$H NMR (300 Hz, TRIFLUOROACETIC ACID-D) δ ppm 3.16 (s, 3 H) 3.46 (m, 2 H) 4.48 (m, 1 H) 4.86 (m, 2 H) 7.34 (m, 2 H) 7.70 (m, 2 H) 8.24 (m, 2 H) 8.57 (m, 2 H) 8.86 (m, 1 H) 9.07 (m, 1 H).

EXAMPLE 239

(1S)-1-(1H-Indol-3-ylmethyl)-2-[5-(2-methyl-quinazolin-7-yl)-pyridin-3-yloxy]-ethylamine

Example 239A

7-Bromo-2-methyl-quinazoline

The 4-Bromo-2-fluoro-benzaldehyde (1 g, 4.9 mmol), acetamidine and DMA were mixed and heated to 140° C. for 5 hours. The mixture was cooled to room temperature and dried under vacuum. The mixture was purified by flash column afforded 47 mg product in 4% yield. MS (ESI) m/e 223 (M+1)+.

Example 239B (1S)-1-(1H-Indol-3-ylmethyl)-2-[5-(2-methyl-quinazolin-7-yl)-pyridin-3-yloxy]-ethylamine The desired product was prepared by substituting Example 239A for 6-bromophthalimide in Example 32. MS (ESI) m/e 410 (M+1)+; $^1$H NMR (300 Hz, DMSO-D6) δ ppm 2.57 (s, 3 H) 3.10 (m, 2 H) 3.85 (m, 1 H) 4.29 (m, 1 H) 4.46 (m, 1 H) 7.39 (m, 5 H) 7.62 (dd, J=8.81, 0.68 Hz, 1 H) 7.80 (dd, J=8.81, 1.70 Hz, 1 H) 8.28 (d, J=0.68 Hz, 2 H) 8.56 (m, 5 H) 8.89 (d, J=1.70 Hz, 1 H).

EXAMPLE 240

(1S)-1-(1H-Indol-3-ylmethyl)-2-[5-(1H-indol-5-yl)-pyridin-3-yloxy]-ethylamine

The desired product was prepared by substituting 5-bromoindole for 6-bromophthalimide in Example 32. MS (ESI) m/e 383 (M+1)+; $^1$H NMR (300 Hz, DMSO-D6) δ ppm 3.58 (m, 1 H) 4.09 (m, 3 H) 4.18 (m, 1 H) 6.67 (br. s., 2 H) 6.98 (m, 1 H) 7.08 (m, 1 H) 7.27 (m, 3 H) 7.38 (m, 4 H) 7.50 (m, 1 H) 7.60 (m, 2 H) 7.88 (br. s., 1 H) 8.23 (br. s., 1 H) 8.51 (br. s., 1 H).

EXAMPLE 241

(1S)-1-(1H-Indol-3-ylmethyl)-2-{5-[4-(1H-tetrazol-5-yl)-phenyl]-pyridin-3-yloxy}-ethylamine The desired product was prepared by substituting 5-(4-bromo-phenyl)-1H-tetrazole for 6-bromophthalimide in Example 32. MS (ESI) m/e 412 (M+1)+; $^1$H NMR (300 Hz, Solvent) δ ppm 3.24 (m, 2 H) 3.99 (m, 1 H) 4.29 (m, 1 H) 4.44 (m, 1 H) 7.04 (m, 1 H) 7.14 (m, 1 H) 7.24 (m, 1 H) 7.39 (m, 1 H) 7.61 (m, 1 H) 7.79 (m, 1 H) 7.86 (m, 2 H) 8.17 (br. s., 1 H) 8.20 (br. s., 1 H) 8.39 (br. s., 1 H) 8.61 (br. s., 1 H).

EXAMPLE 242

(1S)-1-(1H-Indol-3-ylmethyl)-2-(5-isoquinolin-6-yl-pyrimidin-4-yloxy)ethylamine

Example 242A

5-Bromo-pyrimidin-4-ol

The Pyrimidin-4-ol (366 mg, 3.8 mmol) and AcOH were cooled to 0° C. $Br_2$ (0.27 ml) was added slowly via syringe. The mixture was stirred at room temperature for 3 hours. The AcOH was removed under pressure. The residue was dissolved in $CH_2Cl_2$, washed with saturated $NaHCO_3$, brine, and dried over $MgSO_4$. The solvent was removed and the product was purified by flash column chromatography to afforded the desired product (605 mg, 91%). MS (ESI) m/e 175 (M+1)+; $^1$H NMR (300 Hz, DMSO-D6) δ ppm 8.23 (br. s., 1 H) 8.33 (br. s., 1 H) 13.08 (br. s., 1 H).

Example 242B (1S)-1-(1H-Indol-3-ylmethyl)-2-(5-isoquinolin-6-yl-pyrimidin-4-yloxy)-ethylamine The title compound was prepared by substituting Example 242A for 3-bromo-5-hydroxypyridine in Example 27. MS (ESI) m/e 396 (M+1)+; $^1$H NMR (300 Hz, DMSO-D6) δ ppm 3.10 (m, 2 H) 4.35 (m, 1 H) 4.48 (m, 1 H) 4.72 (m, 1 H) 6.96 (m, 2 H) 7.31 (m, 3 H) 8.26 (m, 3 H) 8.50 (m, 3 H) 8.68 (m, 1 H) 8.88 (s, 2 H) 9.74 (br. s., 1 H) 10.99 (br. s., 1 H)

EXAMPLE 243

(1S)-1-Benzyl-2-[3-(3-methyl-1H-indazol-5-yl)-phenoxy]-ethylamine

Example 243A

[1-Benzyl-2-(3-bromo-phenoxy)-ethyl]-carbamic acid tert-butyl ester

The desired product was prepared by substituting 3-bromophenol for 3-bromo-5-hydroxypyridine and L-Boc-phenylalaminol for L-Boc-tryptophanol in Example 2A.

Example 243B

5-[3-((2S)-2-tert-Butoxycarbonylamino-3-phenyl-propoxy)-phenyl]-3-methyl-indazole-1-carboxylic acid tert-butyl ester The desired product was prepared by substituting Example 243A for Example 2A in Example 102E.

Example 243C (1S)-1-Benzyl-2-[3-(3-methyl-1H-indazol-5-yl)-phenoxy]-ethylamine The desired product was prepared as the trifluoroacetate salt by substituting Example 243B for Example 27B in Example 27C. MS (ESI) m/e 358 (M+H)+; $^1$H NMR (500 Hz, DMSO-D6) δ ppm 2.54 (s, 3 H) 3.06 (m, 2 H) 3.82 (m, 1 H) 4.02 (dd, J=10.61, 5.62 Hz, 1 H) 4.18 (dd, J=10.61, 3.12 Hz, 1 H) 6.93 (dd, J=7.80, 1.56 Hz, 1 H) 7.28 (d, J=2.18 Hz, 1 H) 7.36 (m, 7 H) 7.53 (d, J=8.42 Hz, 1 H) 7.62 (m, 1 H) 7.94 (s, 1 H) 8.27 (s, 2 H) 12.68 (bs, 1 H); Anal. Calcd for $C_{23}H_{23}N_3O.1.45$ TFA: C, 59.50; H, 4.71; N, 8.04. Found: C, 59.46; H, 4.69; N, 8.25.

EXAMPLE 244

(1S)-1-Benzyl-2-[6-(3-methyl-1H-indazol-5-yl)-pyridin-2-yloxy]-ethylamine

The desired product was prepared as the trifluoroacetate salt by substituting Example 3-bromo-6-hydroypyridine for 3-bromophenol in Example 243. MS (ESI) m/e 359 (M+H)+; $^1$H NMR (300 Hz, DMSO-D6) δ ppm 2.54 (s, 3 H) 3.05 (m, 2 H) 3.90 (m, 1 H) 4.33 (dd, J=11.70, 6.27 Hz, 1 H) 4.60 (dd, J=11.87, 3.39 Hz, 1 H) 6.80 (d, J=8.14 Hz, 1 H) 7.33 (m, 5 H) 7.49 (d, J=7.80 Hz, 1 H) 7.68 (d, J=7.12 Hz, 1 H) 7.83 (m, 1 H) 7.96 (dd, J=8.81, 1.70 Hz, 1 H) 8.20 (s, 2 H) 8.35 (s, 1 H) 12.69 (bs, 1 H); Anal. Calcd for $C_{22}H_{22}N_4O.1.4$ TFA.1H$_2$O: C, 55.56; H, 4.78; N, 10.45;. Found: C, 55.45; H, 4.51; N, 10.50.

EXAMPLE 245

(1S)-2-[5-(3-Methyl-1H-indazol-5-yl)-pyridin-3-yloxy]-1-(4-thiophen-3-yl-benzyl)-ethylamine

Example 245A (1S)-[2-Hydroxy-1-(4-iodo-benzyl)-ethyl]-carbamic acid tert-butyl ester The material was prepared from L-Boc-(4-iodophenyl) alanine according to the procedure described by M. Rodriguez, M. Llinares, S. Doulut, A. Heitz, J. Martinez *Tetrahedron Letters* 1991, 32 (7), 923–926.

Example 245B (1S)-[2-(5-Bromo-pyridin-3-yloxy)-1-(4-iodo-benzyl)-ethyl]-carbamic acid tert-butyl ester The desired product was prepared by substituting Example 245A for L-Boc-tryptophanol in Example 2A.

Example 245C (1S)-[2-(5-Bromo-pyridin-3-yloxy)-1-(4-thiophen-3-yl-benzyl)-ethyl]-carbamic acid tert-butyl ester A solution of Example 245B (200 mg; 0.37 mmol), 3-thiopheneboronic acid (50 mg; 0.39 mmol), Pd(PPh$_3$)$_4$ (25 mg; 0.02 mmol) and CsF (115 mg; 0.76 mmol) in 1:2 eOH:DME (5 mL) was heated at reflux for 4 hrs, cooled, diluted with water, and extracted with EtOAc. The extracts were rinsed with brine, dried (MgSO$_4$), evaporated, and purified by flash chromatography (30% Et$_2$O/hexane) to provide the desired product (145 mg, 79%).

Example 245D (1S)-[2-[5-(3-Methyl-1H-indazol-5-yl)-pyridin-3-yloxy]-1-(4-thiophen-3-yl-benzyl)-ethyl]-carbamic acid tert-butyl ester The desired product was prepared by substituting Example 245C for Example 2A in Example 102E.

Example 245E (1S)-2-[5-(3-Methyl-1H-indazol-5-yl)-pyridin-3-yloxy]-1-(4-thiophen-3-yl-benzyl)-ethylamine The desired product was prepared as the trifluoroacetate salt by substituting Example 245D for Example 27B in Example 27C. MS (ESI) m/e 441 (M+H)+; $^1$H NMR (300 Hz, DMSO-D6) δ ppm 2.54 (s, 3 H) 3.06 (d, J=7.12 Hz, 2 H) 3.89 (m, 1 H) 4.16 (dd, J=10.68, 5.59 Hz, 1 H) 4.33 (dd, J=10.68, 2.88 Hz, 1 H) 7.37 (d, J=8.48 Hz, 2 H) 7.55 (m, 2 H) 7.63 (m, 1 H) 7.70 (m, 3 H) 7.76 (m, 1 H) 7.85 (dd, J=3.05, 1.36 Hz, 1 H) 8.08 (s, 1 H) 8.22 (m, 2 H) 8.35 (d, J=2.71 Hz, 1 H) 8.64 (d, J=1.70 Hz, 1 H) 12.47 (bs, 1 H).

EXAMPLE 246

(1S)-1-(4-Iodo-benzyl)-2-[5-(3-methyl-1H-indazol-5-yl)-pyridin-3-yloxy]-ethylamine The desired product was prepared as the trifluoroacetate salt by substituting Boc-3'-bromophenylalaminol for Example 245A in Example 238. MS (ESI) m/e 485 (M+H)+; $^1$H NMR (300 Hz, DMSO-D6) δ ppm 2.55 (s, 3 H) 3.00 (d, J=7.12 Hz, 2 H) 3.85 (m, 1 H) 4.13 (m, 1 H) 4.30 (m, 1 H) 7.16 (d, J=8.14 Hz, 2 H) 7.58 (d, J=8.82 Hz, 1 H) 7.70 (m, 3 H) 8.08 (s, 1 H) 8.19 (d, J=3.05 Hz, 2 H) 8.32 (d, J=2.71 Hz, 1 H) 8.63 (d, J=1.70 Hz, 1 H) 8.97 (s, 1 H) 12.72 (bs, 1 H).

EXAMPLE 247

[4-((2S)-2-Amino-3-phenyl-propoxy)-2-(3-methyl-1H-indazol-5-yl)-phenyl]-methanol

Example 247A (1S)-[1-Benzyl-2-(3-chloro-4-formyl-phenoxy)-ethyl]-carbamic acid tert-butyl ester The desired product was prepared by substituting 2-chloro-4-hydroxybenzaldehyde for 3-bromo-5-hydroxypyridine and L-Boc-phenylalaminol for L-Boc-tryptophanol in Example 2A.

Example 247B (1S)-{1-Benzyl-2-[4-formyl-3-(3-methyl-1H-indazol-5-yl)-phenoxy]-ethyl}-carbamic acid tert-butyl ester A solution of Example 102D (230 mg; 0.78 mmol) and Example 247A (300 mg; 0.77 mmol) in DMF (4 mL) was treated with Pd2 (dba)3 (73 mg; 0.0.08 mmol),2-dicyclohexylphosphino-2'-(N,N-dimethylamino)biphenyl (61 mg; 0.15 mmol), and triethylamine (97 mg; 0.96 mmol), heated at 110° C. for 4 hrs., partitioned between brine and EtOAc, filtered through Celite®, and extracted with EtOAc. The extracts were rinsed with brine, dried (MgSO4), concentrated, and purified by flash chromatography (40% EtOAc/hexane) to provide the desired product (235 mg; 63%).

Example 247C (1S)-{1-Benzyl-2-[4-hydroxymethyl-3-(3-methyl-1H-indazol-5-yl)-phenoxy]-ethyl}-carbamic acid tert-butyl ester A solution of Example 247B (225 mg; 0.46 mmol) in EtOH (4 mL) was treated portionwise with $NaBH_4$ (26 mg; 0.70 mmol) and stirred for 30 min., diluted with water, and extracted into EtOAc. The extracts were rinsed with brine, dried ($MgSO_4$), concentrated, and purified by flash chromatography (60% EtOAc/hexane) to provide the desired product (150 mg; 66%).

Example 247D

[4-((2S)-2-Amino-3-phenyl-propoxy)-2-(3-methyl-1H-indazol-5-yl)-phenyl]-methanol Example 247C (115 mg; 0.23 mmol) was heated neat at 190° C. for 45 min. then purified by flash chromatography on silica gel eluting with 10% $MeOH/CH_2Cl_2$ to provide the desired product (17 mg; 19%). MS (ESI) m/e 388 $(M+H)^+$; $^1H$ NMR (300 Hz, DMSO-D6) δ ppm 2.50 (s, 3 H) 2.60 (dd, J=13.22, 7.80 Hz, 1 H) 2.83 (dd, J=13.22, 5.76 Hz, 1 H) 3.25 (m, 1 H) 3.82 (t, J=5.59 Hz, 2 H) 4.33 (d, J=5.09 Hz, 2 H) 4.99 (t, J=5.26 Hz, 1 H) 6.81 (d, J=2.37 Hz, 1 H) 6.93 (dd, J=8.48, 2.37 Hz, 1 H) 7.23 (m, 5 H) 7.36 (d, J=8.48 Hz, 1 H) 7.46 (m, 3 H) 7.69 (s, 2 H) 12.66 (s, 1 H).

EXAMPLE 248

(1S)-2-[5-(1H-Benzotriazol-5-yl)-pyridin-3-yloxy]-1-(1H-indol-3-ylmethyl)-ethylamine Example 248A 4-Bromo-benzene-1,2-diamine A mixture of 4-bromo-2-nitroaniline (1 g; 4.6 mmol) and $SnCl_2.2H_2O$ (6.2 g; 27.6 mmol) in MeOH (30 mL) with 5–6 drops of conc. HCl was heated at reflux for 5 hrs., concentrated, suspended in sat'd $NaHCO_3$ (aq.) and extracted with EtOAc. The extracts were rinsed with brine, dried ($MgSO_4$), and concentrated to provide the product of sufficient purity to carry on.

Example 248B

5-Bromo-1H-benzotriazole

A mixture of Example 248A (262 mg; 1.4 mmol) in 10% $H_2SO_4$ (4 mL) was treated with $NaNO_2$ (120 mg; 1.7 mmol) in water (1 mL), stirred for 30 min., diluted with water, and extracted with EtOAc. The extracts were rinsed with brine, dried ($Na_2SO_4$), concentrated and purified by flash chromatography (5% $MeOH/CH_2Cl_2$) to provide the desired product.

Example 248C

5-Bromo-benzotriazole-1-carboxylic acid tert-butyl ester

A solution of Example 248B (770 mg; 5 mmol) in THF (5 mL) was added to a solution of 20% phosgene in toluene (10 mL) at −20° C., stirred for 1 hr. at −20° C. then 2 hrs. at r.t., evaporated and dissolved in THF (4 mL). This solution was added to a solution of tBuOH (1 mL), and pyridine (426 mg; 5.4 mmol) in THF (3 mL) at −20° C. then stirred overnight at r.t. The solids were removed by filtration and rinsed with EtOAc. The filtrate was rinsed with water and brine, dried ($MgSO_4$), concentrated, and isolated by flash chromatography (1:1 $Et_2O$:hexane) to provide the desired product (970 mg; 76%).

Example 248D (1S)-2-[5-(1H-Benzotriazol-5-yl)-pyridin-3-yloxy]-1-(1H-indol-3-ylmethyl)-ethylamine The desired product was prepared as the trifluoroacetate salt by substituting Example 248C for 6-bromophthalimide in Example 32. MS (ESI) m/e 385 $(M+H)^+$; $^1H$ NMR (300 Hz, DMSO-D6) δ ppm 3.17 (d, J=7.12 Hz, 2 H) 3.86 (m, 1 H) 4.21 (dd, J=10.68, 6.27 Hz, 1 H) 4.38 (dd, J=10.68, 2.88 Hz, 1 H) 7.01 (t, J=6.95 Hz, 1 H) 7.10 (t, J=7.12 Hz, 1 H) 7.30 (d, J=2.37 Hz, 1 H) 7.38 (d, J=8.14 Hz, 1 H) 7.63 (d, J=7.80 Hz, 1 H) 7.78 (m, 1 H) 8.01 (m, 1 H) 8.18 (m, 3 H) 8.27 (m, 1 H) 8.38 (d, J=2.71 Hz, 1 H) 8.66 (d, J=1.36 Hz, 1 H) 11.03 (s, 1 H).

EXAMPLE 249

(1S)-2-[5-(1H-Benzotriazol-5-yl)-pyridin-3-yloxy]-1-benzyl-ethylamine

Example 249A (1S)-[1-Benzyl-2-(5-bromo-pyridin-3-yloxy)-ethyl]-carbamic acid tert-butyl ester The desired product was prepared by substituting L-Boc-phenylalaminol for L-Boc-tryptophanol in Example 2A.

Example 249B (1S)-[1-Benzyl-2-(5-trimethylstannanyl-pyridin-3-yloxy)-ethyl]-carbamic acid tert-butyl ester The desired product was prepared by substituting Example 249A for Example 2A in Example 32A.

Example 249C

5-[5-((2S)-2-tert-Butoxycarbonylamino-3-phenyl-propoxy)-pyridin-3-yl]-benzotriazole-1-carboxylic acid tert-butyl ester A solution of Example 249B (400 mg; 0.81 mmol) and Example 73C (255 mg; 0.85 mmol) in DMF (6 mL) was treated with $Pd_2(dba)_3$ (111 mg; 0.12 mmol),tri-o-tolylphosphine (74 mg; 0.24 mmol), and triethylamine (102 mg; 1.0 mmol), heated at 110° C. for 4 hrs., partitioned between brine and EtOAc, filtered through Celite®, and extracted with EtOAc. The extracts were rinsed with brine, dried (MgSO4), concentrated, and purified by flash chromatography (80% $EtOAc/CH_2Cl_2$) to provide the desired product (110 mg; 25%).

Example 249D (1S)-2-[5-(1H-Benzotriazol-5-yl)-pyridin-3-yloxy]-1-benzyl-ethylamine The desired product was prepared as the trifluoroacetate salt by substituting Example 249C for Example 27B in Example 27C. MS (ESI) m/e 346 (M+H)$^+$; $^1$H NMR (300 Hz, DMSO-D6) δ ppm 3.04 (m, 2 H) 3.86 (m, 1 H) 4.14 (m, 1 H) 4.30 (m, 1 H) 7.32 (m, 5 H) 7.78 (m, 2 H) 8.02 (m, 1 H) 8.22 (m, 3 H) 8.38 (d, J=2.37 Hz, 1 H) 8.66 (d, J=2.03 Hz, 1 H); Anal. Calcd for $C_{20}H_{19}N_5O.2.6$ TFA: C, 47.16; H, 3.39; N, 10.91. Found: C, 46.90; H, 3.26; N, 11.01.

EXAMPLE 250

(1S)-1-Benzyl-2-[5-(3-morpholin-4-yl-1H-indazol-5-yl)-pyridin-3-yloxy]-ethylamine The desired product was prepared as the trifluoroacetate salt by substituting Example 111A for Example 249A in Example 249. MS (ESI) m/e 430 (M+H)$^+$; $^1$H NMR (400 Hz, DMSO-D6) δ ppm 3.04 (m, 2 H) 3.36 (m, 4 H) 3.81 (m, 4 H) 3.87 (m, 1 H) 4.13 (dd, J=10.74, 5.83 Hz, 1 H) 4.29 (dd, J=10.74, 2.76 Hz, 1 H) 7.30 (m, 5 H) 7.49 (d, J=8.90 Hz, 1 H) 7.64 (d, J=8.59 Hz, 1 H) 7.71 (s, 1 H) 8.09 (s, 1 H) 8.26 (bs, 2 H) 8.32 (d, J=2.15 Hz, 1 H) 8.64 (s, 1 H) 12.20 (bs, 1 H).

EXAMPLE 251

(1S)-1-Benzyl-2-{5-[3-(4-methyl-piperazin-1-yl)-1H-indazol-5-yl]-pyridin-3-yloxy}-ethylamine The desired product was prepared as the trifluoroacetate salt by substituting Example 114A for Example 249A in Example 249. MS (ESI) m/e 443 (M+H)$^+$; $^1$H NMR (300 Hz, DMSO-D6) δ ppm 2.53 (s, 3 H) 2.90 (m, 4 H) 3.04 (m, 2 H) 3.17 (m, 2 H) 3.53 (m, 2 H) 3.84 (m, 1 H) 4.10 (m, 1 H) 4.27 (dd, J=11.02, 3.22 Hz, 1 H) 7.32 (m, 5 H) 7.52 (d, J=8.82 Hz, 1 H) 7.66 (m, 2 H) 8.15 (s, 1 H) 8.24 (m, 2 H) 8.32 (d, J=2.71 Hz, 1 H) 8.66 (d, J=1.70 Hz, 1 H) 12.36 (s, 1 H); Anal. Calcd for $C_{26}H_{30}N_6O.3$ TFA: C, 48.98; H, 4.21; N, 10.71. Found: C, 48.60; H, 4.39; N, 11.05.

EXAMPLE 252

(1S)-{5-[5-(2-Amino-3-phenyl-propoxy)-pyridin-3-yl]-1H-indazol-3-yl}-dimethyl-amine The desired product was prepared as the trifluoroacetate salt by substituting Example 115A for Example 249A in Example 249. MS (ESI) m/e 388 (M+H)$^+$; $^1$H NMR (300 Hz, DMSO-D6) δ ppm 3.03 (m, 8 H) 3.83 (m, 1 H) 4.13 (m, 1 H) 4.29 (m, 1 H) 7.34 (m, 5 H) 7.46 (d, J=8.81 Hz, 1 H) 7.63 (dd, J=8.65, 1.53 Hz, 1 H) 7.75 (m, 1 H) 8.08 (s, 1 H) 8.21 (m, 2 H) 8.33 (d, J=2.71 Hz, 1 H) 8.64 (d, J=1.70 Hz, 1 H) 12.01 (bs, 1 H); Anal. Calcd for $C_{23}H_{25}N_5O.3$ TFA: C, 47.74; H, 3.87; N, 9.60;. Found: C, 47.76; H, 3.76; N, 9.52.

EXAMPLE 253

(1S)-{5-[5-(2-Amino-3-phenyl-propoxy)-pyridin-3-yl]-1H-indazol-3-yl}-(2-methoxy-ethyl)-amine Example 253A (5-Bromo-1H-indazol-3-yl)-(2-methoxy-ethyl)-amine The reaction between Example 35A and O-methyl ethanolamine was carried out according to the procedure described by U. Wrzeciono, K. Majewska, J. Dudzinska-Usarewicz, M. Bernas, *Pharmzie,* 1986, 41, 472–474.

Example 253A (1S)-{5-[5-(2-Amino-3-phenyl-propoxy)-pyridin-3-yl]-1H-indazol-3-yl}-(2-methoxy-ethyl)-amine The desired product was prepared as the trifluoroacetate salt by substituting Example 253A for Example 249A in Example 249. MS (ESI) m/e 418 (M+H)$^+$; $^1$H NMR (300 Hz, DMSO-D6) δ ppm 3.04 (m, 2 H) 3.30 (s, 3 H) 3.46 (m, 2 H) 3.57 (m, 2 H) 3.83 (m, 1 H) 4.11 (dd, J=10.68, 5.60 Hz, 1 H) 4.28 (m, 1 H) 7.34 (m, 5 H) 7.64 (dd, J=10.68, 1.87 Hz, 3 H) 8.21 (s, 3 H) 8.30 (d, J=2.37 Hz, 1 H) 8.58 (d, J=1.70 Hz, 1 H) 11.67 bs, 1 H); Anal. Calcd for $C_{24}H_{27}N_5O_2.3$ TFA: C, 46.34; H, 4.15; N, 9.01. Found: C, 46.54; H, 4.34; N, 8.79.

EXAMPLE 254

{5-[5-((2S)-2-Amino-3-phenyl-propoxy)-pyridin-3-yl]-1H-indazol-3-yl}-(2-morpholin-4-yl-ethyl)-amine Example 254A (5-Bromo-1H-indazol-3-yl)-(2-morpholin-4-yl-ethyl)-amine The reaction between Example 35A and 4-(2-aminoethyl)morpholine was carried out according to the procedure described by U. Wrzeciono, K. Majewska, J. Dudzinska-Usarewicz, M. Bernas, *Pharmzie,* 1986, 41, 472–474.

Example 254B

{5-[5-((2S)-2-Amino-3-phenyl-propoxy)-pyridin-3-yl]-1H-indazol-3-yl}-(2-morpholin-4-yl-ethyl)-amine The desired product was prepared as the trifluoroacetate salt by substituting Example 254A for Example 249A in Example 249. MS (ESI) m/e 473 (M+H)$^+$; $^1$H NMR (300 Hz, DMSO-D6) δ ppm 2.50 (m, 8 H) 3.04 (m, 2 H) 3.43 (m, 2 H) 3.68 (m, 2 H) 3.87 (m, 1 H) 4.10 (m, 1 H) 4.28 (m, 1 H) 7.36 (m, 7 H) 7.65 (m, 2 H) 8.07 (s, 1 H) 8.21 (m, 2 H) 8.31 (d, J=2.71 Hz, 1 H) 8.55 (d, J=1.70 Hz, 1 H) 11.83 (bs, 1 H)

EXAMPLE 255

5-[5-((2S)-2-Amino-3-phenyl-propoxy)-pyridin-3-yl]-1H-indazol-3-ylamine

The desired product was prepared as the trifluoroacetate salt by substituting Example 249A for Example 2A in Example 97. MS (ESI) m/e 360 (M+H)$^+$; $^1$H NMR (300 Hz, DMSO-D6) δ ppm 3.04 (m, 2 H) 3.85 (m, 1 H) 4.11 (dd, J=10.68, 5.59 Hz, 1 H) 4.28 (dd, J=10.68, 2.88 Hz, 1 H) 7.35 (m, 6 H) 7.65 (m, 2 H) 8.14 (s, 1 H) 8.21 (m, 4 H) 8.31 (d, J=2.71 Hz, 1 H) 8.56 (d, J=2.03 Hz, 1 H) 11.87 (bs, 1 H); Anal. Calcd for $C_{21}H_{21}N_5O.3.1$ TFA: C, 45.83; H, 3.41; N, 9.82. Found: C, 45.58; H, 3.34; N, 9.57.

EXAMPLE 256

N-{5-[5-((2S)-2-Amino-3-phenyl-propoxy)-pyridin-3-yl]-1H-indazol-3-yl}-2,2,2-trifluoro-acetamide Example 256A 5-Bromo-1H-indazol-3-ylamine The desired product was prepared by substituting 5-bromo-2-fluorobenzonitrile for 5-bromo-2-fluorobenzaldehyde in Example 35A.

Example 256B

N-(5-Bromo-1H-indazol-3-yl)-2,2,2-trifluoro-acetamide

A solution of 256A (2.5 g; 12 mmol) and trifluoroacetic anhydride (3.4 mL; 24 mmol) in pyridine (50 mL) was stirred at r.t. for 2 days, acidified with 10% HCl (aq), and extracted with EtOAc. The extracts were rinsed with water and brine, dried (MgSO$_4$), concentrated and purified by flash chromatography (1:1 EtOAc:hexane) to provide the desired product (3.0 g; 84%).

Example 256C

N-{5-[5-((2S)-2-Amino-3-phenyl-propoxy)-pyridin-3-yl]-1H-indazol-3-yl}-2,2,2-trifluoro-acetamide The desired product was prepared as the trifluoroacetate salt by substituting Example 256B for Example 249A in Example 249. MS (ESI) m/e 454 (M−H)$^+$; $^1$H NMR (300 Hz, DMSO-D6) δ ppm 3.04 (m, 2 H) 3.84 (m, 1 H) 4.11 (dd, J=10.85, 5.76 Hz, 1 H) 4.28 (dd, J=10.68, 2.88 Hz, 1 H) 7.35 (m, 6 H) 7.68 (m, 2 H) 8.16 (s, 1 H) 8.22 (m, 3 H) 8.32 (d, J=2.71 Hz, 1 H) 8.57 (d, J=1.70 Hz, 1 H) 11.87 (bs, 1 H).

EXAMPLE 257

(2S)-2-Amino-N-[5-(3-methyl-1H-indazol-5-yl)-pyridin-3-yl]-3-phenyl-propionamide Example 257A 5-(5-Amino-pyridin-3-yl)-3-methyl-indazole-1-carboxylic acid tert-butyl ester The desired product was prepared by substituting Example 203B for Example 27A and Example 23B for Example 2A in Example 27B.

Example 257B

5-[5-((2S)-2-tert-Butoxycarbonylamino-3-phenyl-propionylamino)-pyridin-3-yl]-3-methyl-indazole-1-carboxylic acid tert-butyl ester The desired product was prepared by substituting Example 257A for Example 25E and L-Boc-phenylalanine for Boc-tryptophane in Example 25G.

Example 257C (2S)-2-Amino-N-[5-(3-methyl-1H-indazol-5-yl)-pyridin-3-yl]-3-phenyl-propionamide The desired product was prepared as the trifluoroacetate salt by substituting Example 257B for Example 27B in Example 27C. MS (ESI) m/e 372 (M+H)$^+$; $^1$H NMR (300 Hz, DMSO-D6) δ ppm 2.55 (s, 3 H) 3.19 (m, 2 H) 4.23 (m, 1 H) 7.32 (m, 6 H) 7.62 (s, 1 H) 8.01 (s, 1 H) 8.19 m, 1 H) 8.36 (s, 2 H) 8.68 (d, J=2.03 Hz, 1 H) 8.74 (d, J=2.03 Hz, 1 H) 10.70 (s, 1 H) 12.85 (bs, 1 H); Anal. Calcd for C$_{22}$H$_{21}$N$_5$O.2.6 TFA: C, 48.91; H, 3.56; N, 10.49;. Found: C, 48.96; H, 3.71; N, 10.64.

EXAMPLE 258

(1S)-2-[5-(3-Benzyl-1H-indazol-5-yl)-pyridin-3-yloxy]-1-(1H-indol-3-ylmethyl)-ethylamine The desired product was prepared as the trifluoroacetate salt by substituting benzyl magnesium chloride for methyl magnesium bromide in Example 102. MS (ESI) m/e 474 (M+H)$^+$; $^1$H NMR (300 Hz, DMSO-D6) δ ppm 3.17 (m, 2 H) 3.86 (m, 1 H) 4.17 (dd, J=10.68, 5.93 Hz, 1 H) 4.35 (s, 2 H) 4.42 (dd, J=10.68, 5.93 Hz, 1 H) 7.02 (t, J=7.12 Hz, 1 H) 7.08 (m, 1 H) 7.29 (m, 7 H) 7.61 (m, 4 H) 7.98 (s, 1 H) 8.15 (m, 3 H) 8.32 (d, J=2.71 Hz, 1 H) 8.55 (d, J=1.70 Hz, 1 H) 11.03 (s, 1 H); Anal. Calcd for C$_{30}$H$_{27}$N$_5$O.3.9 TFA: C, 49.44; H, 3.39; N, 7.63. Found: C, 49.07; H, 3.75; N, 7.42.

EXAMPLE 259

(1S)-1-Benzyl-2-[5-(3-benzyl-1H-indazol-5-yl)-pyridin-3-yloxy]-ethylamine

The desired product was prepared as the trifluoroacetate salt by substituting 249B for Example 2A in Example 258. MS (ESI) m/e 435 (M+H)$^+$; $^1$H NMR (300 Hz, DMSO-D6) δ ppm 3.03 (m, 2 H) 3.86 (m, 1 H) 4.11 (dd, J=10.85, 5.76 Hz, 1 H) 4.28 (dd, J=10.68, 2.88 Hz, 1 H) 5.72 (s, 2 H) 7.30 (m, 8 H) 7.72 (m, 3 H) 7.84 (m, 1 H) 8.13 (s, 1 H) 8.21 (m, 3 H) 8.33 (d, J=2.71 Hz, 1 H) 8.60 (d, J=1.70 Hz, 1 H)

EXAMPLE 260

(1S)-2-[5-(3-Benzyl-1H-indazol-5-yl)-pyridin-3-yloxy]-1-methyl-ethylamine

Example 260A (1S)-[2-(5-Bromo-pyridin-3-yloxy)-1-methyl-ethyl]-carbamic acid tert-butyl ester The desired product was prepared by substituting Boc-alaminol for Boc-tryprophanol in Example 2A.

Example 260B (1S)-[1-Methyl-2-(5-trimethylstannanyl-pyridin-3-yloxy)-ethyl]-carbamic acid tert-butyl ester The desire product was prepared by substituting Example 260A for Example 249A in Example 249B.

Example 260C (1S)-2-[5-(3-Benzyl-1H-indazol-5-yl)-pyridin-3-yloxy]-1-methyl-ethylamine The desired product was prepared as the trifluoroacetate salt by substituting 260B for Example 32A in Example 258. MS (ESI) m/e 359 (M+H)$^+$; $^1$H NMR (300 Hz, DMSO-D6) δ ppm 1.31 (m, 3 H) 4.10 (m, 1 H) 4.30 (m, 1 H) 4.35 (s, 2 H) 4.41 (m, 1 H) 7.17 (m, 1 H) 7.29 (m, 2 H) 7.36 (m, 2 H) 7.61 (s, 2 H) 7.69 (s, 2 H) 8.02 (bs, 2 H) 8.33 (d, J=2.37 Hz, 1 H) 8.56 (s, 1 H) 12.71 (bs, 1 H); Anal. Calcd for C$_{22}$H$_{22}$N$_4$O.3.2 TFA: C, 47.16; H, 3.51; N, 7.75;. Found: C, 47.27; H, 3.60; N, 7.60.

EXAMPLE 261

(6-{5-[(2S)-2-Amino-3-(1H-indol-3-yl)-propoxy]-pyridin-3-yl}-cinnolin-4-yl)-phenyl-amine Example 261A (6-Bromo-cinnolin-4-yl)-phenyl-amine A solution of Example 34D (500 mg; 2.5 mmol) and aniline (1.5 mL) in MeOH (11 mL) was stirred at r.t. for 2.5 hrs, the resulting precipitate was collected, rinsed with water and dried under vacuum to provide the desired product (400 mg; 62%).

Example 261B (6-{5-[(2S)-2-Amino-3-(1H-indol-3-yl)-propoxy]-pyridin-3-yl}-cinnolin-4-yl)-phenyl-amine The desired product was prepared as the trifluoroacetate salt by substituting Example 261A for Example 27A in Example 27. MS (ESI) m/e 487 (M+H)+; 1H NMR (500 Hz, DMSO-D6) δ ppm 3.18 (m, 2 H) 3.86 (m, 1 H) 4.25 (dd, J=10.61, 5.93 Hz, 1 H) 4.39 (m, 1 H) 6.99 (t, J=7.49 Hz, 1 H) 7.09 (t, J=7.02 Hz, 1 H) 7.31 (d, J=2.50 Hz, 1 H) 7.38 (d, J=8.11 Hz, 1 H) 7.45 (t, J=7.33 Hz, 1 H) 7.60 (m, 6 H) 7.90 (m, 1 H) 8.19 (d, J=9.05 Hz, 1 H) 8.35 (bs, 2 H) 8.44 (m, 2 H) 8.64 (s, 1 H) 8.81 (d, J=1.56 Hz, 1 H) 9.08 (s, 1 H) 11.04 (d, J=1.87 Hz, 1 H).

EXAMPLE 262

(1S)-2-[5-(1H-Indazol-6-yl)-pyridin-3-yloxy]-1-(H-indol-3-ylmethyl)-ethylamine

The desired product was prepared as the trifluoroacetate salt by substituting 4-bromo-2-fluorobenzaldehyde for 5-bromo-2-fluorobenzaldehyde in Example 35. MS (ESI) m/e 384 (M+H)+; 1H NMR (500 Hz, DMSO-D6) δ ppm 2.97 (m, 2 H) 3.60 (m, 1 H) 4.13 (m, 2 H) 6.99 (m, 2 H) 7.24 (m, 1 H) 7.38 (m, 2 H) 7.61 (m, 3 H) 7.84 (m, 3 H) 8.11 (m, 1 H) 8.31 (m, 1 H) 8.55 (m, 1 H) 11.03 (m, 1 H) 12.98 (m, 1 H)

EXAMPLE 263

5-{5-[(2S)-2-Amino-3-(1H-indol-3-yl)-propoxy]-pyridin-3-yl}-2,3-dihydro-isoindol-1-one

Example 263A

4-Bromo-2-methyl-benzoic acid methyl ester

A solution of 4-bromo-2-methyl benzoic acid (1.0 g; 4.7 mmol) in MeOH (24 mL) with 20 drops conc. HCl was heated at reflux for 6 hrs. the concentrated to provide the desired product (1.1 g; 100%).

Example 263B

4-Bromo-2-bromomethyl-benzoic acid methyl ester

A solution of Example 263A (1.02 g; 4.5 mmol) in CCl4 (22 mL) was treated with AIBN (65 mg; 0.4 mmol), heated at reflux for 4 hrs., washed with water, dried (Na2SO4) and concentrated to provide the desired product (1.1 g; 79%).

Example 263C

5-Bromo-2,3-dihydro-isoindol-1-one

Example 263D

5-{5-[(2S)-2-Amino-3-(1H-indol-3-yl)-propoxy]-pyridin-3-yl}-2,3-dihydro-isoindol-1-one The desired product was prepared as the trifluoroacetate salt by substituting Example 263C for 5-bromooxindole in Example 36. MS (ESI) m/e 399 (M+H)+; 1H NMR (d6-DMSO, 300 MHz) δ: 11.03 (bs, 1H), 8.63 (s, 1H), 8.57 (s, 1H), 8.35 (bs, 3H), 7.90 (s, 1H), 7.78 (s, 2H), 7.67 (s, 1H), 7.61 (d, J=8 Hz, 1H), 7.37 (d, J=8 Hz, 1H), 7.79 (d, J=2 Hz, 1H), 7.03–7.10 (m, 1H), 6.96–7.01 (m, 1H), 4.32–4.36 (m, 1H), 4.17–4.22 (m, 1H), 3.80–3.83 (m, 1H), 3.18 (d, J=8 Hz, 2H), 2.50 (s, 2H).

EXAMPLE 264

6-{5-[(2S)-2-Amino-3-(1H-indol-3-yl)-propoxy]-pyridin-3-yl}-1H-cinnolin-4-one

The desired product was prepared as the trifluoroacetate salt by substituting Example 34A for 6-bromophthalimide in Example 32. MS (ESI) m/e 412 (M+H)+; 1H NMR (500 Hz, DMSO-D6) δ ppm 3.19 (d, J=7.18 Hz, 2 H) 3.84 (m, 1 H) 4.24 (dd, J=10.61, 5.93 Hz, 1 H) 4.39 (dd, J=10.61, 3.12 Hz, 1 H) 7.01 (t, J=7.02 Hz, 1 H) 7.10 (t, J=7.18 Hz, 1 H) 7.31 (d, J=2.50 Hz, 1 H) 7.38 (d, J=8.11 Hz, 1 H) 7.64 (d, J=7.80 Hz, 1 H) 7.76 (d, J=8.73 Hz, 1 H) 7.80 (m, 2 H) 7.96 (s, 1 H) 8.17 (dd, J=8.73, 2.18 Hz, 1 H) 8.32 (d, J=2.18 Hz, 2 H) 8.40 (d, J=2.81 Hz, 1 H) 8.65 (d, J=1.87 Hz, 1 H) 11.05 (d, J=1.56 Hz, 1 H) 13.72 (bs, 1 H); Anal. Calcd for C24H21N5O2.3 TFA: C, 47.82; H, 3.21; N, 9.29;. Found: C, 47.88; H, 3.41; N, 9.35.

EXAMPLE 265

(1S)-1-(1H-Indol-3-ylmethyl)-2-[5-(4-phenyl-cinnolin-6-yl)-pyridin-3-yloxy]-ethylamine

Example 265A 1-(1H-Indol-3-ylmethyl)-2-[5-(4-phenyl-cinnolin-6-yl)-pyridin-3-yloxy]-ethylamine A solution of Example 34C (200 mg; 0.8 mmol) in THF (10 mL) was treated with 3.0 phenylmagnesium bromide in Et2O (1.6 mL; 4.8 mmol), stirred at r.t. for 4 hrs., sat;d NH4Cl (aq) was added, and extracted with EtOAc. The extracts were rinsed with brine, dried (MgSO4), concentrated and purified by flash chromatography (30% EtOAc/hexane) to provide the desired product (67 mg; 29%).

Example 265B (1S)-1-(1H-Indol-3-ylmethyl)-2-[5-(4-phenyl-cinnolin-6-yl)-pyridin-3-yloxy]-ethylamine The desired product was prepared as the trifluoroacetate salt by substituting Example 265A for 6-bromophthalimide in Example 32. MS (ESI) m/e 472 (M+H)+; 1H NMR (500 Hz, DMSO-D6) δ ppm 3.15 (d, J=7.18 Hz, 2 H) 3.84 (m, 1 H) 4.17 (dd, J=10.61, 5.93 Hz, 1 H) 4.33 (dd, J=10.61, 3.12 Hz, 1 H) 6.98 (t, J=7.49 Hz, 1 H) 7.08 (t, J=7.49 Hz, 1 H) 7.28 (d, J=2.18 Hz, 1 H) 7.37 (d, J=8.11 Hz, 1 H) 7.64 (m, 5 H) 7.70 (d, J=1.87 Hz, 1 H) 7.78 (d, J=6.55 Hz, 2 H) 8.16 (bs, 2 H) 8.30 (dd, J=8.89, 1.72 Hz, 1 H) 8.42 (d, J=2.50 Hz, 1 H) 8.61 (d, J=1.56 Hz, 1 H) 8.69 (d, J=9.05 Hz, 1 H) 9.41 (s, 1 H) 11.01 (s, 1 H); Anal. Calcd for C30H25N5O.1.9 TFA: C, 58.99; H, 3.94; N, 10.18; Found: C, 58.87; H, 3.85; N, 10.08.

EXAMPLE 266

(6-{5-[(2S)-2-Amino-3-(1H-indol-3-yl)-propoxy]-pyridin-3-yl}-cinnolin-4-yl)-benzyl-amine

Example 266A

Benzyl-(6-bromo-cinnolin-4-yl)-amine

A solution of 34D (100 mg; 0.41 mmol) and benzylamine (0.5 mL) in MeOH (3 mL) was stirred at r.t. for 24 hrs., concentrated, suspended in Et2O, and the precipitate was collected to provide the desired product (100 mg; 78%).

Example 266B (6-{5-[(2S)-2-Amino-3-(1H-indol-3-yl)-propoxy]-pyridin-3-yl}-cinnolin-4-yl)-benzyl-amine The desired product was prepared as the trifluoroacetate salt by substituting Example 266A for 6-bromophthalimide in Example 32. MS (ESI) m/e 501 (M+H)+; ¹H NMR (500 Hz, DMSO-D6) δ ppm 3.18 (d, J=7.18 Hz, 2 H) 3.87 (m, 1 H) 4.23 (dd, J=10.61, 5.62 Hz, 1 H) 4.38 (dd, J=10.45, 2.96 Hz, 1 H) 5.00 (d, J=5.62 Hz, 2 H) 7.00 (t, J=7.49 Hz, 1 H) 7.09 (t, J=7.18 Hz, 1 H) 7.30 (d, J=2.50 Hz, 1 H) 7.37 (m, 4 H) 7.50 (d, J=7.49 Hz, 2 H) 7.62 (d, J=8.11 Hz, 1 H) 7.83 (d, J=2.18 Hz, 1 H) 8.10 (d, J=9.05 Hz, 1 H) 8.29 (bs, 2 H) 8.40 (dd, J=8.89, 1.40 Hz, 1 H) 8.45 (d, J=2.50 Hz, 1 H) 8.78 (d, J=1.56 Hz, 1 H) 8.80 (s, 1 H) 8.98 (s, 1 H) 10.35 (bs, 1 H) 11.03 (s, 1 H); Anal. Calcd for $C_{31}H_{28}N_6O.3.1$ TFA: C, 52.31; H, 3.67; N, 9.84;. Found: C, 52.36; H, 3.47; N, 9.67.

EXAMPLE 267

(6-{5-[(2S)-2-Amino-3-(1H-indol-3-yl)-propoxy]-pyridin-3-yl}-cinnolin-4-yl)-methyl-amine The desired product was prepared as the trifluoroacetate salt by substituting methylamine for benzylamine in Example 266. MS (ESI) m/e 425 (M+H)+; ¹H NMR (500 Hz, DMSO-D6) δ ppm 2.50 (d, J=1.87 Hz, 3 H) 3.19 (m, 2 H) 3.85 (m, 1 H) 4.26 (dd, J=10.92, 5.93 Hz, 1 H) 4.40 (dd, J=10.61, 3.12 Hz, 1 H) 6.99 (t, J=7.49 Hz, 1 H) 7.09 (t, J=7.33 Hz, 1 H) 7.32 (d, J=1.87 Hz, 1 H) 7.37 (d, J=8.11 Hz, 1 H) 7.63 (d, J=8.11 Hz, 1 H) 7.87 (s, 1 H) 8.10 (d, J=9.05 Hz, 1 H) 8.37 (m, 3 H) 8.43 (d, J=2.81 Hz, 1 H) 8.72 (s, 1 H) 8.76 (d, J=1.56 Hz, 1 H) 8.93 (s, 1 H) 10.00 (bs, 1 H) 11.04 (d, J=1.25 Hz, 1 H)

EXAMPLE 268

6-{5-[(2S)-2-Amino-3-(1H-indol-3-yl)-propoxy]-pyridin-3-yl}-cinnolin-4-ylamine

The desired product was prepared as the trifluoroacetate salt by substituting ammonia for benzylamine in Example 266. MS (ESI) m/e 411 (M+H)+; ¹H NMR (500 Hz, DMSO-D6) δ ppm 3.18 m, 2 H) 3.86 (m, 1 H) 4.27 (m, 1 H) 4.41 (m, 1 H) 6.99 (m, 1 H) 7.08 (m, 1 H) 7.36 (m, 2 H) 7.64 (d, J=6.55 Hz, 1 H) 7.89 (s, 1 H) 8.10 (d, J=8.42 Hz, 1 H) 8.46 (m, 4 H) 8.59 (s, 1 H) 8.76 (s, 1 H) 9.00 (s, 1 H) 10.06 (s, 2 H) 11.08 (s, 1 H)

EXAMPLE 269

[(3S)-3-(5-Isoquinolin-6-yl-pyridin-3-yloxymethyl)-1,2,3,4-tetrahydro-b-carbolin-9-yl]-methanol A solution of Example 27 (100 mg; 0.19 mmol) and 37% formaldehyde (aq) (18 μL) in water (1 mL) with 2 drops conc. $H_2SO_4$ was heated at reflux for 3 hrs., evaporated and purified by reverse phase HPLC on a C18 column with 0–100% $CH_3CN/H_2O/0.1\%$ TFA to provide the desired product as the trifluoroacetate salt. MS (ESI) m/e 412 (M+H)+; ¹H NMR (400 Hz, DMSO-D6) δ ppm 3.04 (m, 1 H) 3.20 (m, 3 H) 4.19 (bs, 1 H) 4.53 (m, 6.75 Hz, 1 H) 4.64 (m, 1 H) 4.70 (m, 1 H) 5.52 (m, 2 H) 7.12 ((t, J=7.67 Hz, 1 H) 7.22 (t, J=7.67 Hz, 1 H) 7.52 (d, J=7.98 Hz, 1 H) 7.58 (d, J=8.29 Hz, 1 H) 8.05 (s, 1 H) 8.26 (d, J=6.44 Hz, 1 H) 8.33 (d, J=8.59 Hz, 1 H) 8.53 (m, 2 H) 8.63 (s, 1 H) 8.68 (d, J=5.83 Hz, 1 H) 8.83 (s, 1 H) 9.71 (s, 1 H) 9.94 (bs, 1 H)

EXAMPLE 270

3-(5-Isoquinolin-6-yl-pyridin-3-yloxymethyl)-2,3,4,9-tetrahydro-1H-β-carboline

A solution of Example 27 (100 mg; 0.19 mmol) and 37% formaldehyde (aq) (17 μL) in water (1 mL) with conc. $H_2SO_4$ (6 μL) was stirred overnight at r.t., neutralized with $NH_3$/MeOH, concentrated and purified by flash chromatography (10% MeOH/$CH_2Cl_2$) to provide the desired product. MS (ESI) m/e 407 (M+H)+; ¹H NMR (500 Hz, DMSO-D6) δ ppm 2.58 (dd, J=14.66, 9.98 Hz, 1 H) 2.85 (dd, J=14.97, 3.74 Hz, 1 H) 3.38 (m, 2 H) 4.02 (d, J=4.99 Hz, 1 H) 4.33 (m, 2 H) 6.95 (t, J=7.02 Hz, 1 H) 7.02 (t, J=7.49 Hz, 1 H) 7.29 (d, J=8.11 Hz, 1 H) 7.39 (d, J=8.11 Hz, 1 H) 7.91 (m, 2 H) 8.12 (dd, J=8.42, 1.56 Hz, 1 H) 8.25 (d, J=8.42 Hz, 1 H) 8.41 (s, 1 H) 8.45 (t, J=2.65 Hz, 1 H) 8.56 (d, J=5.62 Hz, 1 H) 8.69 (d, J=11.56 Hz, 1 H) 9.37 (s, 1 H) 10.72 (s, 1 H).

EXAMPLE 271

5-{5-[(2S)-2-Amino-3-(1H-indol-3-yl)-propoxy]-pyridin-3-yl}-1H-indazole-3-carboxylic acid

Example 271A

1H-Indazole-3-carboxylic acid methyl ester

A solution of 3-carboxyindazole (2.0 g; 12.3 mmol) and conc.HCl (2 mL) in MeOH (50 mL) was heated at reflux overnight, concentrated, diluted with 2N NaOH (aq), and extracted with EtOAc. The extracts were rinsed with brine, dried ($MgSO_4$), and concentrated to provide the desired product.

Example 271B

5-Iodo-1H-indazole-3-carboxylic acid methyl ester

A solution of Example 271A (300 mg; 1.7 mmol), bis(trifluoroacetoxy)iodobenzene (800 mg; 1.9 mmol), and iodine (253 mg; 1.0 mmol) in $CH_2Cl_2$ (10 mL) was stirred overnight at r.t., and treated with sodium bisulfite (aq). The precipitate was collected, rinsed with water and hexane, and dried under vacuum to provide the desired product (180 mg; 36%).

Example 271C

5-{5-[(2S)-2-tert-Butoxycarbonylamino-3-(1H-indol-3-yl)-propoxy]-pyridin-3-yl}-1H-indazole-3-carboxylic acid methyl ester The desired product was prepared by substituting Example 271B for 6-bromophthalimide in Example 32B.

Example 271D

5-{5-[(2S)-2-Amino-3-(1H-indol-3-yl)-propoxy]-pyridin-3-yl}-1H-indazole-3-carboxylic acid methyl ester The desired product was prepared by substituting Example 271C for Example 27B in Example 27C.

Example 271E

5-{5-[(2S)-2-Amino-3-(1H-indol-3-yl)-propoxy]-pyridin-3-yl}-1H-indazole-3-carboxylic acid A solution of Example 271D (150 mg; 0.34 mmol) and 1N NaOH (5 mL) in MeOH (1 mL) was heated at reflux for 6 hrs., concentrated, and purified by reverse phase HPLC on a C18 column with 0–100% $CH_3CN/H_2O/0.1\%$ TFA to provide the desired product as the trifluoroacetate salt. MS (ESI) m/e 428 (M+H)+; ¹H NMR (500 Hz, DMSO-D6) δ ppm 3.18 (d, J=7.49 Hz, 2 H) 3.86 (m, 1 H) 4.21 (dd, J=10.29, 5.93 Hz, 1 H) 4.37 (dd, J=10.29, 2.50 Hz, 1 H) 7.01 (t, J=7.33 Hz, 1 H) 7.10 (t, J=7.33 Hz, 1 H) 7.30 (d, J=1.87

Hz, 1 H) 7.38 (d, J=8.11 Hz, 1 H) 7.63 (d, J=7.80 Hz, 1 H) 7.71 (s, 1 H) 7.77 (m, 2 H) 8.26 (s, 3 H) 8.32 (s, 1 H) 8.37 (s, 1 H) 8.59 (s, 1 H) 11.03 (s, 1 H) 13.64 (m, 1 H).

EXAMPLE 272

5-[5-((2S)-2-tert-Butoxycarbonylamino-3-hydroxy-propoxy)-pyridin-3-yl]-3-methyl-indazole-1-carboxylic acid tert-butyl ester Example 203 (719 mg, 1.22 mmol) was dissolved in 30 mL EtOAc in a 100 mL round bottom flask with a stirbar. A combination vacuum/Ar/$H_2$ manifold was attached and the flask evacuated and filled with Ar twice. Pd/C (800 mg, 10 wt. % (dry basis)) was added and the flask evacuated and filled with $H_2$ twice. The resultant black mixture was stirred vigorously and warmed to 50° C. for 20 h at which time TLC indicated ~70% consumption of starting material. Another 480 mg of the Pd/C was added and a fresh $H_2$ balloon attached. The reaction was stirred another 26 h at 50° C. at which time it was cooled to room temperature and the flask evacuated and filled with Ar. The cooled reaction mixture was filtered through Celite and the filter cake washed with EtOAc. The filtrate was subjected to rotary evaporation and then dried with house vacuum to yield the desired product (540 mg, 89%) as a colorless foam/solid. $R_f$=0.26 (EtOAc); MS m/z 499 (M+H)$^+$; $^1$H NMR (300 MHz, DMSO-D6) δ ppm 1.39 (s, 9 H) 1.66 (s, 9 H) 2.60 (s, 3 H) 3.50 (m, 2 H) 3.82 (m, 1 H) 4.17 (m, 2 H) 4.83 (t, J=5.59 Hz, 1 H) 6.82 (d, J=8.14 Hz, 1 H) 7.79 (s, 1 H) 8.02 (dd, J=8.65, 1.53 Hz, 1 H) 8.12 (m, 1 H) 8.27 (d, J=1.02 Hz, 1 H) 8.29 (d, J=2.71 Hz, 1 H) 8.61 (d, J=2.03 Hz, 1 H).

EXAMPLE 273

5-[5-((2S)-Aziridin-2-ylmethoxy)-pyridin-3-yl]-3-methyl-1H-indazole

Example 273A (1R)-[2-(5-Bromo-pyridin-3-yloxy)-1-(tert-butyl-dimethyl-silanyloxymethyl)-ethyl]-carbamic acid tert-butyl ester A 100 mL RBF was charged with 3-bromo-5-hydroxypyridine (1.20 g, 6.87 mmol), (R)-[1-(tert-butyl-dimethyl-silanyloxymethyl)-2-hydroxy-ethyl]-carbamic acid tert-butyl ester (2.1 g, 6.87 mmol) and $Ph_3P$ (2.34 g, 8.93 mmol), and was purged with nitrogen. THF (30 mL) was added at 0° C. After stirring at 0° C. for 10 min, DEAD (1.41 mL, 8.93 mmol) was added via syringe. The reaction mixture was stirred at 0° C. for 0.5 h and at rt for 2 h. The reaction mixture was concentrated and the residue was separated by flash chromatography (5–25% EtOAc in hexane) to provide the desired product (3.14 g, 99%). MS (DCI) m/z 461, 463 (M+1)$^+$.

Example 273B (1S)-[2-(5-Bromo-pyridin-3-yloxy)-1-hydroxymethyl-ethyl]-carbamic acid tert-butyl ester To a solution of Example 273A (3.14 g, 6.8 mmol) in THF (40 mL) was added TBAF (7.14 mL, 7.14 mmol) at rt. The solution was stirred at rt for 1 h and was concentrated. The residual oil was purified by flash chromatography (40–80% EtOAc in hexane) to give the desired product (2.19 g, 93%). MS (DCI) m/z 347, 349 (M+1)$^+$.

Example 273C (2S)-2-(5-Bromo-pyridin-3-yloxymethyl)-aziridine-1-carboxylic acid tert-butyl ester $Ph_3P$ (1.13 g, 4.32 mmol) was dissolved in 9:1 THF/$CH_3CN$ (30 mL) and cooled to 4° C. with an ice/water bath. DIAD (850 μL, 4.32 mmol) was added slowly. After stirring 15 min, a solution of Example 273B (1.0 g, 2.88 mmol) in THF (4 mL) was added slowly. The solution was allowed to warm to rt and stirred for over night. The solution was concentrated and the residual oil was purified by flash chromatography (20–40% EtOAc in hexane) to give the desired product (1.0 g, 75%). MS (DCI) m/z 329, 331 (M+1)$^+$.

Example 273D

5-[5-((2S)-1-tert-Butoxycarbonyl-aziridin-2-ylmethoxy)-pyridin-3-yl]-3-methyl-indazole-1-carboxylic acid tert-butyl ester Method 1. A 100 mL RBF was charged with Example 273C (950 mg, 2.88 mmol), Example 203B (1.14 g, 2.88 mmol), $Pd_2(dba)_3$ (263 mg, 0.288 mmol), and tri-o-tolylphosphine (263 mg), and was purged with $N_2$. Anhydrous DMF (35 mL) and $Et_3N$ (1.2 mL) were added via syringe. The solution was purged with $N_2$ again and was heated at 72° C. for 4 h. After cooled, ethyl acetate (150 mL) was added. The mixture was washed with brine (200 mL) and water (200 mL). The ethyl acetate solution was concentrated and the residual oil was separated by flash chromatography (50–80% EtOAc in hexane) to give the desired product (634 mg, 65%). MS (APCI) m/z 481 (M+1)$^+$.

Method 2. To a stirred solution of $PPh_3$ (2.16 g, 8.24 mmol) in THF (130 mL) and $CH_3CN$ (20 mL) at 0° C. was added DIAD (1.62 mL, 8.24 mmol) slowly via syringe. After 20 min the resulting light yellow solution was canulated onto Example 272 (2.74 g, 5.50 mmol) in THF (150 mL). The reaction mixture was stirred 6 h at 23° C. and then silica gel was added and the volatiles removed on a rotary evaporator. Flash chromatography (50–60–70–80% EtOAc/hexanes) gave 3.72 g of a white solid which was a 1.33:1 mixture of triphenylphosphine oxide: aziridine. $R_f$=0.50 (EtOAc). This was used without further purification.

Example 273E

5-[5-((2S)-Aziridin-2-ylmethoxy)-pyridin-3-yl]-3-methyl-1H-indazole

The desired product was prepared as the trifluoroacetate by substituting Example 273D for Example 27B in Examples 27C. MS (APCI) m/z 281 (M+1)$^+$; $^1$H NMR (300 Hz, $CD_3OD$) δ 2.63 (s, 3 H), 3.31 (dd, J=3.30, 1.83 Hz, 2 H), 3.62 (dd, J=6.23, 1.83 Hz, 2 H), 3.89 (m, 1 H), 4.60 (m, 2 H), 7.64 (d, J=8.79 Hz, 1 H), 7.77 (d, J=8.79 Hz, 1 H), 8.15 (s, 1 H), 8.22 (s, 1 H).

EXAMPLE 274

(1S)-2-[5-(3-Methyl-1H-indazol-5-yl)-pyridin-3-yloxy]-1-(3-trifluoromethoxy-benzyl)-ethylamine

Example 274A

5-{5-[(2S)-2-tert-Butoxycarbonylamino-3-(3-trifluoromethoxy-phenyl)-propoxy]-pyridin-3-yl}-3-methyl-indazole-1-carboxylic acid tert-butyl ester To a suspension of CuBr—$SMe_2$ (25 mg, 0.12 mmol) and Example 273D (100 mg, 0.21 mmol) in THF (6 mL) was added 3-trifluoromethoxyphenylmagnesium bromide (0.5 solution in THF, 1.6 mL, 0.8 mmol) at approximately −35° C. The formed clear solution was allowed to warm up to −20° C. within 40 min and was partitioned between ether and water. The organic layer was concentrated and the residue was separated by flash chromatography (40–65% EtOAc in hexane) to give the desired product (88 mg, 66%). MS (APCI) m/z 643 (M+1)+.

Example 274B (1S)-2-[5-(3-Methyl-1H-indazol-5-yl)-pyridin-3-yloxy]-1-(3-trifluoromethoxy-benzyl)-ethylamine The desired product was prepared as the trifluoroacetate by substituting Example 274A for Example 27B in Examples 27C. MS (APCI) m/z 444 (M+1)+; $^1$H NMR (300 Hz, CD$_3$OD) δ 2.62 (s, 3 H), 3.22 (dd, J=7.29, 5.26 Hz, 2 H), 4.00 (m, 1 H), 4.26 (dd, J=10.51, 5.09 Hz, 1H), 4.43 (dd, J=10.85, 3.05 Hz, 1 H), 7.25 (d, J=8.48 Hz, 1 H), 7.30 (s, 1 H), 7.36 (d, J=7.46 Hz, 1 H), 7.49 (t, J=7.97 Hz, 1 H), 7.62 (d, J=8.48 Hz, 1 H), 7.72 (dd, J=8.82, 1.70 Hz, 1 H), 8.00 (s, 1 H), 8.08 (s, 1 H), 8.40 (d, J=2.03 Hz, 1 H), 8.68 (s, 1 H). Anal. Calcd for C$_{23}$H$_{21}$F$_3$N$_4$O$_2$.2.6 TFA: C, 45.84; H, 3.22; N, 7.58. Found: C, 45.87; H, 3.17; N, 7.28.

The following compounds were prepared by substituting the appropriate Grignard reagents for 3-trifluoromethoxyphenylmagnesium bromide in Example 274.

EXAMPLE 275

(1S)-1-(3,5-Dichloro-benzyl)-2-[5-(3-methyl-1H-indazol-5-yl)-pyridin-3-yloxy]-ethylamine MS (APCI) m/z 427 (M+1)+; $^1$H NMR (300 Hz, CD$_3$OD) δ 2.63 (s, 3 H), 3.18 (dd, J=7.32, 3.30 Hz, 2 H), 4.02 (m, 1 H), 4.32 (dd, J=10.44, 5.31 Hz, 1 H), 4.47 (dd, J=10.62, 2.93 Hz, 1 H), 7.37 (s, 1 H), 7.39 (d, J=8.06 Hz, 1 H), 7.63 (d, J=8.79 Hz, 1 H), 7.74 (d, J=8.06 Hz, 1H), 8.10 (s, 3 H), 8.44 (s, 1 H), 8.73 (s, 1 H); Anal. Calcd for C$_{22}$H$_{20}$Cl$_2$N$_4$O.3.2 TFA: C, 43.38; H, 2.98; N, 7.18. Found: C, 43.49; H, 3.18; N, 6.92.

EXAMPLE 276

(1S)-1-(2,3-Dichloro-benzyl)-2-[5-(3-methyl-1H-indazol-5-yl)-pyridin-3-yloxy]-ethylamine MS (APCI) m/z 427 (M+1)+; $^1$H NMR (300 Hz, CD$_3$OD) δ 2.63 (s, 3 H), 3.40 (dd, J=7.32, 5.13 Hz, 2 H), 4.10 (m, 1 H), 4.33 (dd, J=10.62, 4.76 Hz, 1 H), 4.47 (dd, J=10.99, 2.93 Hz, 1H), 7.30 (t, J=7.69 Hz, 1 H), 7.39 (d, J=7.32 Hz, 1 H), 7.52 (d, J=7.69 Hz, 1 H), 7.63 (d, J=8.79 Hz, 1 H), 7.74 (d, J=8.79 Hz, 1 H), 8.11 (s, 2 H), 8.45 (s, 1 H), 8.75 (s, 1 H); Anal. Calcd for C$_{22}$H$_{20}$Cl$_2$N$_4$O.3.5TFA: C, 42.15; H, 2.87; N, 6.78. Found: C, 41.86; H, 3.05; N, 6.60.

EXAMPLE 277

(1S)-1-Biphenyl-3-ylmethyl-2-[5-(3-methyl-1H-indazol-5-yl)-pyridin-3-yloxy]-ethylamine MS (APCI) m/z 435 (M+1)+; $^1$H NMR (300 Hz, CD$_3$OD) δ 2.61 (s, 3 H), 3.25 (d, J=7.69 Hz, 2 H), 4.05 (m, 1 H), 4.33 (dd, J=10.62, 5.13 Hz, 1 H), 4.46 (d, J=10.25 Hz, 1 H), 7.36 (m, 4 H), 7.46 (t, J=7.14 Hz, 1 H), 7.57 (m, 6 H), 8.06 (s, 2 H), 8.42 (s, 1 H), 8.69 (s, 1 H); Anal. Calcd for C$_{28}$H$_{26}$N$_4$O.3.2 TFA: C, 51.68; H, 3.68; N, 7.01. Found: C, 51.94; H, 3.66; N, 6.85.

EXAMPLE 278

(1S)-1-(3-Chloro-4-fluoro-benzyl)-2-[5-(3-methyl-1H-indazol-5-yl)-pyridin-3-yloxy]-ethylamine MS (APCI) m/z 411 (M+1)+; $^1$H NMR (300 Hz, CD$_3$OD) δ 2.62 (s, 3 H) 3.15 (t, J=7.12 Hz, 2 H) 3.98 (m, 1 H) 4.28 (dd, J=10.51, 5.42 Hz, 1 H) 4.44 (dd, J=10.51, 3.05 Hz, 1 H) 7.23 (d, J=8.48 Hz, 1 H) 7.30 (m, 1 H) 7.51 (dd, J=7.12, 2.03 Hz, 1 H) 7.62 (d, J=8.81 Hz, 1 H) 7.72 (dd, J=8.48, 1.36 Hz, 1 H) 7.99 (s, 1 H) 8.08 (s, 1 H) 8.39 (s, 1 H) 8.68 (s, 1 H); Anal. Calcd for C$_{22}$H$_{20}$ClFN$_4$O.2.7 TFA: C, 45.79; H, 3.18; N, 7.80. Found: C, 45.86; H, 3.44; N, 7.66.

EXAMPLE 279

(1S)-1-(4-Chloro-3-fluoro-benzyl)-2-[5-(3-methyl-1H-indazol-5-yl)-pyridin-3-yloxy]-ethylamine MS (APCI) m/z 411 (M+1)+; $^1$H NMR (300 Hz, CD$_3$OD) δ 2.63 (s, 3 H), 3.17 (t, J=6.95 Hz, 2 H), 4.00 (m, 1 H), 4.28 (dd, J=10.51, 5.43 Hz, 1 H), 4.44 (dd, J=10.51, 3.05 Hz, 1 H), 7.17 (dd, J=8.14, 1.70 Hz, 1 H), 7.29 (dd, J=10.00, 1.87 Hz, 1 H), 7.49 (t, J=7.97 Hz, 1 H), 7.62 (d, J=8.82 Hz, 1 H), 7.73 (d, J=7.12 Hz, 1 H), 8.01 (m, 1 H), 8.09 (s, 1 H), 8.40 (d, J=2.37 Hz, 1 H), 8.68 (d, J=1.70 Hz, 1 H); Anal. Calcd for C$_{22}$H$_{20}$ClFN$_4$O.2.7 TFA: C, 45.79; H, 3.18; N, 7.80. Found: C, 45.86; H, 3.44; N, 7.66.

EXAMPLE 280

(1S)-2-[$_5$-(3-Methyl-1H-indazol-5-yl)-pyridin-3-yloxy]-1-(4-trifluoromethoxy-benzyl)-ethylamine MS (APCI) m/z 443 (M+1)+; $^1$H NMR (300 Hz, CD$_3$OD) δ 2.62 (s, 3 H) 3.20 (t, J=6.95 Hz, 2 H) 3.98 (m, 1 H) 4.28 (dd, J=10.51, 5.42 Hz, 1 H) 4.43 (dd, J=10.51, 2.71 Hz, 1 H) 7.30 (d, J=7.80 Hz, 2 H) 7.45 (d, J=8.48 Hz, 2 H) 7.62 (d, J=8.48 Hz, 1 H) 7.73 (d, J=8.81 Hz, 1 H) 8.00 (s, 1 H) 8.08 (s, 1 H) 8.40 (s, 1 H) 8.68 (s, 1 H). Anal. Calcd for C$_{23}$H$_{21}$F$_3$N$_4$O$_2$.2.4 TFA: C, 46.63; H, 3.29; N, 7.82. Found: C, 46.57; H, 3.30; N, 7.80.

EXAMPLE 281

(1S)-1-(2-Fluoro-4-trifluoromethyl-benzyl)-2-[5-(3-methyl-1H-indazol-5-yl)-pyridin-3-yloxy]-ethylamine MS (APCI) m/z 445 (M+1)+; $^1$H NMR (300 Hz, CD$_3$OD) δ 2.62 (s, 3 H), 3.31 (m, 2 H), 4.04 (m, 1 H), 4.29 (dd, J=10.85, 5.09 Hz, 1 H), 4.45 (dd, J=10.85, 3.39 Hz, 1 H), 7.54 (d, J=8.81 Hz, 1 H), 7.55 (s, 1 H), 7.60 (dd, J=4.07, 3.39 Hz, 1 H), 7.63 (s, 1 H), 7.72 (dd, J=8.81, 1.70 Hz, 1 H), 7.96 (s, 1 H), 8.07 (s, 1 H), 8.39 (s, 1 H), 8.67 (s, 1 H).

EXAMPLE 282

(1S)-1-(3-Fluoro-5-trifluoromethyl-benzyl)-2-[5-(3-methyl-1H-indazol-5-yl)-pyridin-3-yloxy]-ethylamine MS (APCI) m/z 445 (M+1)+; $^1$H NMR (300 Hz, CD$_3$OD) δ 2.62 (s, 3 H), 3.30 (m, 2 H), 4.06 (m, 1 H), 4.29 (dd, J=10.51, 5.09 Hz, 1 H), 4.45 (dd, J=10.85, 3.05 Hz, 1 H), 7.45 (dd, J=7.80, 5.76 Hz, 2 H), 7.55 (s, 1 H), 7.62 (d, J=8.81 Hz, 1 H), 7.73 (d, J=8.48 Hz, 1 H), 7.98 (s, 1 H), 8.07 (s, 1 H), 8.42 (br s, 1 H), 8.73 (br s, 1 H).

EXAMPLE 283

(1S)-1-(2-Methoxy-benzyl)-2-[5-(3-methyl-1H-indazol-5-yl)-pyridin-3-yloxy]-ethylamine MS (APCI) m/z 389 (M+1)+; $^1$H NMR (300 Hz, CD$_3$OD) δ 2.62 (s, 3 H), 3.16 (d, J=7.46 Hz, 2 H), 3.85 (s, 3 H), 3.99 (m, 1 H), 4.23 (dd, J=10.51, 5.76 Hz, 1 H), 4.39 (dd, J=10.85, 3.39 Hz, 1 H), 6.94 (t, J=7.46 Hz, 1 H), 7.03 (d, J=8.14 Hz, 1 H), 7.23 (d, J=7.46 Hz, 1 H), 7.32 (dd, J=8.14, 7.46 Hz, 1 H), 7.62 (d, J=8.48 Hz, 1 H), 7.71 (d, J=8.82 Hz, 1 H), 7.91 (d, J=2.03 Hz, 1 H), 8.06 (s, 1 H), 8.34 (d, J=2.71 Hz, 1 H), 8.65 (s, 1 H).

EXAMPLE 284

(3-{(2S)-2-Amino-3-[5-(3-methyl-1H-indazol-5-yl)-pyridin-3-yloxy]-propyl}-phenyl)-dimethyl-amine MS (DCI/NH$_3$) m/e 402 (M+1)$^+$; $^1$H NMR (300 Hz, CD$_3$OD) δ=8.73 (s; 1H), 8.43 (s; 1H), 8.10 (m; 2H), 7.74 (d; 1H; J=7.5 Hz), 7.63 (d; 1H; J=7.5 Hz), 7.38 (t; 1H; J=7.5 Hz), 7.09 (s; 1H), 7.08 (d; 1H; J=7.5 Hz), 7.04 (d; 1H; J=7.5 Hz), 4.45 (dd; 1H; J=10.8 Hz; J=3.0 Hz), 4.31 (dd; 1H; J=10.8 Hz; J=6.0 Hz), 4.00 (m; 1H), 3.17 (m; 2H), 3.05 (s; 6H), 2.64 (s; 3H).

EXAMPLE 285

(1S)-1-(4-Chloro-2-methyl-benzyl)-2-[5-(3-methyl-1H-indazol-5-yl)-pyridin-3-yloxy]-ethylamine MS (DCI/NH$_3$) m/e 407 (M+1)$^+$; $^1$H NMR (300 Hz, CD$_3$OD) δ=8.71 (s; 1H), 8.41 (s; 1H), 8.10 (s; 1H), 8.04 (s; 1H), 7.73 (d; 1H; J=8.1 Hz), 7.62 (d; 1H; J=8.1 Hz), 7.28 (s; 1H), 7.22 (m; 2H), 4.40 (dd; 1H; J=10.8 Hz; J=3.0 Hz), 4.26 (dd; 1H; J=10.8 Hz; J=4.5 Hz), 3.94 (m; 1H), 3.17 (m; 2H), 2.62 (s; 3H), 2.39 (s; 3H).

EXAMPLE 286

(1S)-1-(3-Iodo-benzyl)-2-[5-(3-methyl-1H-indazol-5-yl)-pyridin-3-yloxy]-ethylamine MS (DCI/NH$_3$) m/e 485 (M+1)$^+$; $^1$H NMR (300 Hz, CD$_3$OD) δ=8.65 (s; 1H), 8.36 (s; 1H), 8.07 (s; 1H), 7.92 (s; 1H), 7.75 (s; 1H), 7.72 (d; 1H; J=8.1 Hz), 7.68 (d; 1H; J=7.8 Hz), 7.62 (d; 1H; J=8.1 Hz), 7.35 (d; 1H; J=7.8 Hz), 7.16 (d; 1H; J=7.8 Hz), 4.40 (dd; 1H; J=10.8 Hz; J=3.0 Hz), 4.24 (dd; 1H; J=10.8 Hz; J=4.5 Hz), 3.96 (m; 1H), 3.12 (m; 2H), 2.62 (s; 3H).

EXAMPLE 287

(1S)-(1S)-1-(3-Fluoro-4-methyl-benzyl)-2-[5-(3-methyl-1H-indazol-5-yl)-pyridin-3-yloxy]-ethylamine MS (DCI/NH$_3$) m/e 391 (M+1)$^+$; $^1$H NMR (300 Hz, CD$_3$OD) δ=8.73 (s; 1H), 8.42 (s; 1H), 8.12 (s; 1H), 8.10 (s; 1H), 7.74 (d; 1H; J=8.1 Hz), 7.63 (d; 1H; J=8.1 Hz), 7.24 (t; 1H; J=8.4 Hz), 7.05 (m; 2H), 4.44 (dd; 1H; J=10.8 Hz; J=3.0 Hz), 4.28 (dd; 1H; J=10.8 Hz; J=4.5 Hz), 3.97 (m; 1H), 3.13 (m; 2H), 2.62 (s; 3H), 2.23 (s; 3H).

EXAMPLE 288

(1S)-1-(3-Fluoro-4-methoxy-benzyl)-2-[5-(3-methyl-1H-indazol-5-yl)-pyridin-3-yloxy]-ethylamine MS (DCI/NH$_3$) m/e 407 (M+1)$^+$; $^1$H NMR (300 Hz, CD$_3$OD) δ=8.73 (s; 1H), 8.42 (s; 1H), 8.12 (s; 1H), 8.10 (s; 1H), 7.74 (d; 1H; J=8.1 Hz), 7.63 (d; 1H; J=8.1 Hz), 7.24 (t; 1H; J=8.4 Hz), 7.05 (m; 2H), 4.44 (dd; 1H; J=10.8 Hz; J=3.0 Hz), 4.28 (dd; 1H; J=10.8 Hz; J=4.5 Hz), 3.97 (m; 1H), 3.13 (m; 2H), 2.62 (s; 3H), 2.23 (s; 3H).

EXAMPLE 289

(1S)-2-[6-Chloro-5-(3-methyl-1H-indazol-5-yl)-pyridin-3-yloxy]-1-(3,4-dichloro-benzyl)-ethylamine MS (DCI/NH$_3$) m/e 462 (M+1)$^+$; $^1$H NMR (300 Hz, CD$_3$OD) δ=8.16 (s; 1H), 7.78 (s; 1H), 7.54 (m; 4H), 7.48 (d; 1H; J=8.1 Hz), 7.25 (d; 1H; J=8.1 Hz), 4.32 (dd; 1H; J=10.8 Hz; J=3.0 Hz), 4.15 (dd; 1H; J=10.8 Hz; J=4.5 Hz), 3.93 (m; 1H), 3.12 (m; 2H), 2.58 (s; 3H).

EXAMPLE 290

(1S)-1-(2-Fluoro-6-trifluoromethyl-benzyl)-2-[5-(3-methyl-1H-indazol-5-yl)-pyridin-3-yloxy]-ethylamine MS (DCI/NH$_3$) m/e 445 (M+1)$^+$; $^1$H NMR (300 Hz, CD$_3$OD) δ=8.69 (s; 1H), 8.36 (s; 1H), 8.08 (s; 1H), 7.96 (s; 1H), 7.73 (d; 1H; J=8.1 Hz), 7.63 (m; 3H), 7.50 (t; 1H; J=9.0 Hz), 4.44 (dd; 1H; J=10.8 Hz; J=3.0 Hz), 4.32 (dd; 1H; J=10.8 Hz; J=4.5 Hz), 4.08 (m; 1H), 3.48 (m; 1H), 3.35 (m; 1H), 2.62 (s; 3H).

EXAMPLE 291

(1S)-1-(4-Fluoro-3-trifluoromethyl-benzyl)-2-[5-(3-methyl-1H-indazol-5-yl)-pyridin-3-yloxy]-ethylamine MS (DCI/NH$_3$) m/e 445 (M+1)$^+$; $^1$H NMR (300 Hz, CD$_3$OD) δ=8.70 (s; 1H), 8.41 (s; 1H), 8.09 (s; 1H), 8.04 (s; 1H), 7.74 (d; 1H; J=8.1 Hz), 7.68 (m; 1H), 7.62 (d; 1H; J=8.1 Hz), 7.36 (t; 1H; J=9.0 Hz), 4.44 (dd; 1H; J=10.8 Hz; J=3.0 Hz), 4.28 (dd; 1H; J=10.8 Hz; J=4.5 Hz), 4.02 (m; 1H), 3.23 (m; 2H), 2.62 (s; 3H).

EXAMPLE 292

(1S)-1-Furan-2-ylmethyl-2-[5-(3-methyl-1H-indazol-5-yl)-pyridin-3-yloxy]-ethylamine MS (DCI/NH$_3$) m/e 349 (M+1)$^+$; $^1$H NMR (300 Hz, CD$_3$OD) δ=8.68 (s; 1H), 8.39 (s; 1H), 8.09 (m; 1H), 8.00 (s; 1H), 7.73 (d; 1H; J=9.0 Hz), 7.62 (d; 1H; J=9.0 Hz), 7.50 (s; 1H), 6.42 (m; 1H), 6.33 (m; 1H), 4.49 (dd; 1H; J=10.8 Hz; J=3.0 Hz), 4.31 (dd; 1H; J=10.8 Hz; J=4.5 Hz), 4.02 (m; 1H), 3.24 (m; 2H), 2.62 (s; 3H).

EXAMPLE 293

(1S)-1-Benzofuran-2-ylmethyl-2-[5-(3-methyl-1H-indazol-5-yl)-pyridin-3-yloxy]-ethylamine MS (DCI/NH$_3$) m/e 398 (M+1)$^+$; $^1$H NMR (300 Hz, CD$_3$OD) δ=8.72 (s; 1H), 8.42 (s; 1H), 8.09 (m; 2H), 7.72 (d; 1H; J=9.0 Hz), 7.62 (d; 1H; J=9.0 Hz), 7.55 (d; 1H; J=8.4 Hz), 7.45 (d; 1H; J=8.4 Hz), 7.44 (m; 2H), 6.78 (s; 1H), 4.58 (dd; 1H; J=10.8 Hz; J=3.0 Hz), 4.44 (dd; 1H; J=10.8 Hz; J=4.5 Hz), 4.18 (m; 1H), 3.41 (m; 2H), 2.62 (s; 3H).

EXAMPLE 294

(1S)-1-(3-Fluoro-4-trifluoromethyl-benzyl)-2-[5-(3-methyl-1H-indazol-5-yl)-pyridin-3-yloxy]-ethylamine MS (DCI/NH$_3$) m/e 445 (M+1)$^+$; $^1$H NMR (300 Hz, CD$_3$OD) δ=8.74 (s; 1H), 8.44 (s; 1H), 8.13 (m; 2H), 7.75 (d; 1H; J=8.1 Hz), 7.70 (t; 1H; J=8.4 Hz), 7.43 (d; 1H; J=8.4 Hz), 7.40 (d; 1H; J=12.0 Hz), 7.38 (d; 1H; J=8.1 Hz), 4.48 (dd; 1H; J=10.8 Hz; J=3.0 Hz), 4.32 (dd; 1H; J=10.8 Hz; J=4.5 Hz), 4.08 (m; 1H), 3.28 (m; 2H), 2.62 (s; 3H).

EXAMPLE 295

(1S)-1-(4-Chloro-3-methyl-benzyl)-2-[5-(3-methyl-1H-indazol-5-yl)-pyridin-3-yloxy]-ethylamine MS (DCI/NH$_3$) m/e 407 (M+1)$^+$; $^1$H NMR (300 Hz, CD$_3$OD) δ=8.71 (s; 1H), 8.41 (s; 1H), 8.10 (s; 1H), 8.05 (s;

1H), 7.73 (d; 1H; J=8.4 Hz), 7.63 (d; 1H; J=8.4 Hz), 7.36 (d; 1H; J=8.4 Hz), 7.27 (s; 1H), 7.15 (d; 1H; J=8.4 Hz), 4.44 (dd; 1H; J=10.8 Hz; J=3.0 Hz), 4.28 (dd; 1H; J=10.8 Hz; J=4.5 Hz), 3.96 (m; 1H), 3.11 (m; 2H), 2.62 (s; 3H), 2.34 (s; 3H).

EXAMPLE 296

(1S)-1-Furan-3-ylmethyl-2-[5-(3-methyl-1H-indazol-5-yl)-pyridin-3-yloxy]-ethylamine MS (DCI/NH$_3$) m/e 349 (M+1)$^+$; $^1$H NMR (300 Hz, CD$_3$OD) δ=8.73 (s; 1H), 8.43 (s; 1H), 8.12 (m; 2H), 7.74 (d; 1H; J=8.4 Hz), 7.63 (d; 1H; J=8.4 Hz), 7.53 (m; 2H), 6.47 (m; 1H), 4.49 (dd; 1H; J=10.8 Hz; J=3.0 Hz), 4.33 (dd; 1H; J=10.8 Hz; J=4.5 Hz), 3.91 (m; 1H), 3.00 (m; 2H), 2.62 (s; 3H).

EXAMPLE 297

(1S)-1-(2-Fluoro-5-methyl-benzyl)-2-[5-(3-methyl-1H-indazol-5-yl)-pyridin-3-yloxy]-ethylamine MS (DCI/NH$_3$) m/e 391 (M+1)$^+$; $^1$H NMR (300 Hz, CD$_3$OD) δ=8.65 (s; 1H), 8.36 (s; 1H), 8.05 (s; 1H), 7.90 (s; 1H), 7.70 (d; 1H; J=8.4 Hz), 7.62 (d; 1H; J=8.4 Hz), 7.09 (s; 1H), 7.27 (d; 1H; J=8.1 Hz) 7.18 (t; 1H; J=8.1 Hz), 4.39 (dd; 1H; J=10.8 Hz; J=3.0 Hz), 4.25 (dd; 1H; J=10.8 Hz; J=4.5 Hz), 4.04 (m; 1H), 3.28 (m; 2H), 2.62 (s; 3H), 2.30 (s; 3H).

EXAMPLE 298

(1S)-1-(3-Chloro-5-fluoro-benzyl)-2-[5-(3-methyl-1H-indazol-5-yl)-pyridin-3-yloxy]-ethylamine MS (DCI/NH$_3$) m/e 411 (M+1)$^+$; $^1$H NMR (300 Hz, CD$_3$OD) δ=8.71 (s; 1H), 8.41 (s; 1H), 8.10 (s; 1H), 8.06 (s; 1H), 7.73 (d; 1H; J=8.4 Hz), 7.63 (d; 1H; J=8.4 Hz), 7.26 (s; 1H), 7.18 (d; 1H; J=8.4 Hz), 7.12 (d; 1H; J=8.4 Hz), 4.46 (dd; 1H; J=10.8 Hz; J=3.0 Hz), 4.30 (dd; 1H; J=10.8 Hz; J=4.5 Hz), 4.02 (m; 1H), 3.18 (m; 2H), 2.62 (s; 3H).

EXAMPLE 299

(1S)-2-[5-(3-Methyl-1H-indazol-5-yl)-pyridin-3-yloxy]-1-(3,4,5-trifluoro-benzyl)-ethylamine MS (DCI/NH$_3$) m/e 413 (M+1)$^+$; $^1$H NMR (300 Hz, CD$_3$OD) δ=8.73 (s; 1H), 8.44 (s; 1H), 8.10 (m; 2H), 7.74 (d; 1H; J=8.4 Hz), 7.63 (d; 1H; J=8.4 Hz), 7.17 (t; 2H; J=9.0 Hz), 4.47 (dd; 1H; J=10.8 Hz; J=3.0 Hz), 4.32 (dd; 1H; J=10.8 Hz; J=4.5 Hz), 4.00 (m; 1H), 3.15 (m; 2H), 2.62 (s; 3H).

EXAMPLE 300

(1S)-1-(4-Fluoro-3-methyl-benzyl)-2-[5-(3-methyl-1H-indazol-5-yl)-pyridin-3-yloxy]-ethylamine MS (DCI/NH$_3$) m/e 391 (M+1)$^+$; $^1$H NMR (300 Hz, CD$_3$OD) δ=8.73 (s; 1H), 8.42 (s; 1H), 8.12 (s; 1H), 8.08 (s; 1H), 7.73 (d; 1H; J=8.4 Hz), 7.62 (d; 1H; J=8.4 Hz), 7.18 (m; 2H), 7.03 (t; 1H; J=9.0 Hz), 4.44 (dd; 1H; J=10.8 Hz; J=3.0 Hz), 4.28 (dd; 1H; J=10.8 Hz; J=4.5 Hz), 3.94 (m; 1H), 3.10 (m; 2H), 2.62 (s; 3H), 2.24 (s; 3H).

EXAMPLE 301

(1S)-1-(2,4-Dichloro-benzyl)-2-[5-(3-methyl-1H-indazol-5-yl)-pyridin-3-yloxy]-ethylamine MS (DCI/NH$_3$) m/e 428 (M+1)$^+$; $^1$H NMR (300 Hz, CD$_3$OD) δ=8.69 (s; 1H), 8.40 (s; 1H), 8.10 (s; 1H), 8.00 (s; 1H), 7.73 (d; 1H; J=8.4 Hz), 7.62 (d; 1H; J=8.4 Hz), 7.56 (s; 1H), 7.41 (d; 1H; J=8.1 Hz), 7.36 (d; 1H; J=8.1), 4.43 (dd; 1H; J=10.8 Hz; J=3.0 Hz), 4.28 (dd; 1H; J=10.8 Hz; J=4.5 Hz), 4.05 (m; 1H), 3.31 (m; 2H), 2.62 (s; 3H).

EXAMPLE 302

(1S)-1-(4-Chloro-3-trifluoromethyl-benzyl)-2-[5-(3-methyl-1H-indazol-5-yl)-pyridin-3-yloxy]-ethylamine MS (DCI/NH$_3$) m/e 461 (M+1)$^+$; $^1$H NMR (300 Hz, CD$_3$OD) δ=8.69 (s; 1H), 8.39 (s; 1H), 8.08 (s; 1H), 8.00 (s; 1H), 7.79 (s; 1H), 7.72 (d; 1H; J=8.4 Hz), 7.62 (m; 3H), 4.44 (dd; 1H; J=10.8 Hz; J=3.0 Hz), 4.28 (dd; 1H; J=10.8 Hz; J=4.5 Hz), 4.02 (m; 1H), 3.26 (m; 2H), 2.62 (s; 3H).

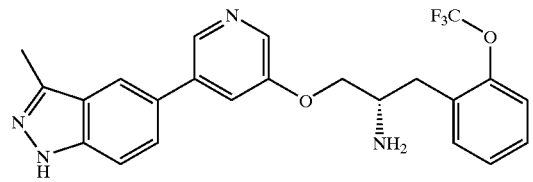

EXAMPLE 303

(1S)-2-[5-(3-Methyl-1H-indazol-5-yl)-pyridin-3-yloxy]-1-(2-trifluoromethoxy-benzyl)-ethylamine MS (DCI/NH$_3$) m/e 443 (M+1)$^+$; $^1$H NMR (300 Hz, CD$_3$OD) δ=8.70 (s; 1H), 8.39 (s; 1H), 8.09 (s; 1H), 8.01 (s; 1H), 7.73 (d; 1H; J=8.4 Hz), 7.63 (d; 1H; J=8.4 Hz), 7.42 (m; 4H), 4.40 (dd; 1H; J=10.8 Hz; J=3.0 Hz), 4.24 (dd; 1H; J=10.8 Hz; J=4.5 Hz), 4.00 (m; 1H), 3.28 (m; 2H), 2.62 (s; 3H).

EXAMPLE 304

(1S)-1-(2,5-Dimethoxy-benzyl)-2-[5-(3-methyl-1H-indazol-5-yl)-pyridin-3-yloxy]-ethylamine MS (DCI/NH$_3$) m/e 419 (M+1)$^+$; $^1$H NMR (300 Hz, CD$_3$OD) δ 8.71 (s; 1H), 8.40 (s; 1H), 8.10 (s; 1H), 8.04 (s; 1H), 7.73 (d; 1H; J=8.4 Hz), 7.63 (d; 1H; J=8.4 Hz), 6.95 (d; 1H; J=9.0 Hz), 6.85 (m; 2H), 4.43 (dd; 1H; J=10.8 Hz; J=3.0 Hz), 4.27 (dd; 1H; J=10.8 Hz; J=4.5 Hz), 4.00 (m; 1H), 3.80 (s; 3H), 3.69 (s; 3H), 3.13 (m; 2H), 2.62 (s; 3H).

EXAMPLE 305

(1S)-2-[5-(3-Methyl-1H-indazol-5-yl)-pyridin-3-yloxy]-1-(4-methylsulfanyl-benzyl)-ethylamine MS (DCI/NH$_3$) m/e 405 (M+1)$^+$; $^1$H NMR (300 Hz, CD$_3$OD) δ=8.73 (s; 1H), 8.62 (s; 1H), 8.12 (s; 1H), 8.08 (s; 1H), 7.73 (d; 1H; J=8.4 Hz), 7.63 (d; 1H; J=8.4 Hz), 7.28 (s; 4H), 4.44 (dd; 1H; J=10.8 Hz; J=3.0 Hz), 4.29 (dd; 1H; J=10.8 Hz; J=4.5 Hz), 3.95 (m; 1H), 3.12 (m; 2H), 2.62 (s; 3H), 2.44 (s; 3H).

EXAMPLE 306

(1S)-1-(2-Cyclohexyl-benzyl)-2-[5-(3-methyl-1H-indazol-5-yl)-pyridin-3-yloxy]-ethylamine MS (DCI/NH$_3$) m/e 441 (M+1)$^+$; $^1$H NMR (300 Hz, CD$_3$OD) δ=8.70 (s; 1H), 8.40 (s; 1H), 8.07 (s; 1H), 8.01 (s;

1H), 7.71 (d; 1H; J=8.4 Hz), 7.62 (d; 1H; J=8.4 Hz), 7.34 (d; 1H; J=7.8 Hz), 7.25 (m; 2H), 7.16 (t; 1H; J=7.8 Hz), 4.37 (dd; 1H; J=10.8 Hz; J=3.0 Hz), 4.23 (dd; 1H; J=10.8 Hz; J=4.5 Hz), 3.38 (m; 1H), 3.27 (m; 2H), 2.77 (m; 1H), 2.62 (s; 3H), 1.85 (m; 1H), 1.74 (m; 4H), 1.48 (m; 3H), 1.29 (m, 2H).

EXAMPLE 307

(1S)-1-(2,5-Dichloro-benzyl)-2-[5-(3-methyl-1H-indazol-5-yl)-pyridin-3-yloxy]-ethylamine MS (DCI/NH$_3$) m/e 428 (M+1)$^+$; $^1$H NMR (300 Hz, CD$_3$OD) δ=8.71 (s; 1H), 8.41 (s; 1H), 8.10 (s; 1H), 8.04 (s; 1H), 7.73 (d; 1H; J=8.4 Hz), 7.63 (d; 1H; J=8.4 Hz), 7.48 (m; 2H), 7.36 (d; 1H; J=8.4 Hz), 4.44 (dd; 1H; J=10.8 Hz; J=3.0 Hz), 4.28 (dd; 1H; J=10.8 Hz; J=4.5 Hz), 4.07 (m; 1H), 3.36 (m; 2H), 2.62 (s; 3H).

EXAMPLE 308

(1S)-1-(2,5-Dimethyl-benzyl)-2-[5-(3-methyl-1H-indazol-5-yl)-pyridin-3-yloxy]-ethylamine MS (DCI/NH$_3$) m/e 387 (M+1)$^+$; $^1$H NMR (300 Hz, CD$_3$OD) δ=8.74 (s; 1H), 8.2 (s; 1H), 8.11 (s; 1H), 8.08 (s; 1H), 7.73 (d; 1H; J=8.4 Hz), 7.63 (d; 1H; J=8.4 Hz), 7.11 (d; 1H; J=8.1 Hz), 7.03 (m; 2H), 4.41 (dd; 1H; J=10.8 Hz; J=3.0 Hz), 4.28 (dd; 1H; J=10.8 Hz; J=4.5 Hz), 3.94 (m; 1H), 3.14 (m; 2H), 2.62 (s; 3H), 2.34 (s; 3H), 2.23 (s; 3H).

EXAMPLE 309

(1S)-1-(2,3-Dimethyl-benzyl)-2-[5-(3-methyl-1H-indazol-5-yl)-pyridin-3-yloxy]-ethylamine MS (DCI/NH$_3$) m/e 387 (M+1)$^+$; $^1$H NMR (300 Hz, CD$_3$OD) δ=8.65 (s; 1H), 8.35 (s; 1H), 8.05 (s; 1H), 7.90 (s; 1H), 7.70 (d; 1H; J=8.4 Hz), 7.60 (d; 1H; J=8.4 Hz), 7.07 (m; 3H), 4.35 (dd; 1H; J=10.8 Hz; J=3.0 Hz), 4.22 (dd; 1H; J=10.8 Hz; J=4.5 Hz), 3.88 (m; 1H), 3.21 (m; 2H), 2.62 (s; 3H), 2.31 (s; 3H), 2.28 (s; 3H).

EXAMPLE 310

(1S)-1-(3,4-Dichloro-benzyl)-2-[5-(3-methyl-1H-indazol-5-yl)-pyridin-3-yloxy]-ethylamine MS (DCI/NH$_3$) m/e 428 (M+1)$^+$; $^1$H NMR (300 Hz, CD$_3$OD) δ 8.68 (s; 1H), 8.39 (s; 1H), 8.08 (s; 1H), 7.98 (s; 1H), 7.72 (d; 1H; J=8.4 Hz), 7.62 (d; 1H; J=8.4 Hz), 7.56 (s; 1H), 7.54 (d; 1H; J=8.4 Hz), 7.28 (d; 1H; J=8.4 Hz), 4.43 (dd; 1H; J=10.8 Hz; J=3.0 Hz), 4.27 (dd; 1H; J=10.8 Hz; J=4.5 Hz), 3.99 (m; 1H), 3.16 (m; 2H), 2.62 (s; 3H).

EXAMPLE 311

(1S)-1-(2,4-Dimethyl-benzyl)-2-[5-(3-methyl-1H-indazol-5-yl)-pyridin-3-yloxy]-ethylamine MS (DCI/NH$_3$) m/e 387 (M+1)$^+$; $^1$H NMR (300 Hz, CD$_3$OD) δ=8.68 (s; 1H), 8.37 (s; 1H), 8.08 (s; 1H), 7.96 (s; 1H), 7.71 (d; 1H; J=8.4 Hz), 7.61 (d; 1H; J=8.4 Hz), 7.10 (d; 1H; J=7.5 Hz), 7.06 (s; 1H), 6.98 (d; 1H; J=7.5 Hz), 4.37 (dd; 1H; J=10.8 Hz; J=3.0 Hz), 4.24 (dd; 1H; J=10.8 Hz; J=4.5 Hz), 3.90 (m; 1H), 3.14 (m; 2H), 2.62 (s; 3H), 2.35 (s; 3H), 2.26 (s; 3H).

EXAMPLE 312

(1S)-1-(3-Fluoro-4-trifluoromethyl-benzyl)-2-[5-(3-methyl-1H-indazol-5-yl)-pyridin-3-yloxy]-ethyl amine MS (DCI/NH$_3$) m/e 445 (M+1)$^+$; $^1$H NMR (300 Hz, CD$_3$OD) δ=8.68 (s; 1H), 8.39 (s; 1H), 8.08 (s; 1H), 7.98 (s; 1H), 7.72 (d; 1H; J=8.4 Hz), 7.70 (d; 1H; J=8.4 Hz), 7.62 (d; 1H; J=8.4 Hz), 7.39 (d; 1H; J=12.0 Hz), 7.35 (d; 1H; J=8.4 Hz), 4.44 (dd; 1H; J=10.8 Hz; J=3.0 Hz), 4.28 (dd; 1H; J=10.8 Hz; J=4.5 Hz), 4.05 (m; 1H), 3.28 (m; 2H), 2.62 (s; 3H).

EXAMPLE 313

(1S)-1-(3,5-Dimethyl-benzyl)-2-[5-(3-methyl-1H-indazol-5-yl)-pyridin-3-yloxy]-ethylamine MS (DCI/NH$_3$) m/e 387 (M+1)$^+$; $^1$H NMR (300 Hz, CD$_3$OD) δ=8.68 (s; 1H), 8.38 (s; 1H), 8.08 (s; 1H), 7.97 (s; 1H), 7.71 (d; 1H; J=8.4 Hz), 6.94 (m; 3H), 4.41 (dd; 1H; J=10.8 Hz; J=3.0 Hz), 4.25 (dd; 1H; J=10.8 Hz; J=4.5 Hz), 3.92 (m; 1H), 3.07 (m; 2H), 2.62 (s; 3H), 2.26 (s; 6H).

EXAMPLE 314

(1S)-1-Biphenyl-2-ylmethyl-2-[5-(3-methyl-1H-indazol-5-yl)-pyridin-3-yloxy]-ethylamine MS (DCI/NH$_3$) m/e 435 (M+1)$^+$; $^1$H NMR (300 Hz, CD$_3$OD) δ=8.64 (s; 1H), 8.11 (s; 1H), 8.05 (s; 1H), 7.70 (d; 1H; J=8.4 Hz), 7.68 (s; 1H), 7.63 (d; 1H; J=8.4 Hz), 7.34 (m; 9H), 4.12 (dd; 1H; J=10.8 Hz; J=3.0 Hz), 3.89 (dd; 1H; J=10.8 Hz; J=4.5 Hz), 3.64 (m; 1H), 3.39 (dd; 1H; J=14.4 Hz; J=9.3 Hz), 3.16 (dd; 1H; J=14.4 Hz, J=4.5 Hz), 2.62 (s; 3H).

EXAMPLE 315

(1S)-1-(3,4-Dimethyl-benzyl)-2-[5-(3-methyl-1H-indazol-5-yl)-pyridin-3-yloxy]-ethylamine MS (DCI/NH$_3$) m/e 387 (M+1)$^+$; $^1$H NMR (300 Hz, CD$_3$OD) δ=8.69 (s; 1H), 8.38 (s; 1H), 8.08 (s; 1H), 7.99 (s; 1H), 7.72 (d; 1H; J=8.4 Hz), 7.62 (d; 1H; J=8.4 Hz), 7.08 (m; 3H), 4.41 (dd; 1H; J=10.8 Hz; J=3.0 Hz), 4.26 (dd; 1H; J=10.8 Hz; J=4.5 Hz), 3.91 (m; 1H), 3.08 (m; 2H), 2.62 (s; 3H), 2.29 (s; 3H), 2.23 (s; 3H).

EXAMPLE 316

(1S)-1-(2,3-Difluoro-benzyl)-2-[5-(3-methyl-1H-indazol-5-yl)-pyridin-3-yloxy]-ethylamine MS (DCI/NH$_3$) m/e 395 (M+1)$^+$; $^1$H NMR (300 Hz, CD$_3$OD) δ=8.74 (s; 1H), 8.44 (s; 1H), 8.12 (s; 2H), 7.74 (d; 1H; J=8.4 Hz), 7.62 (d; 1H; J=8.4 Hz), 7.19 (m; 3H), 4.48 (dd; 1H; J=10.8 Hz; J=3.0 Hz), 4.32 (dd; 1H; J=10.8 Hz; J=4.5 Hz), 4.03 (m; 1H), 3.30 (m; 2H), 2.62 (s; 3H).

EXAMPLE 317

(1S)-1-(2,5-Difluoro-benzyl)-2-[5-(3-methyl-1H-indazol-5-yl)-pyridin-3-yloxy]-ethylamine MS (DCI/NH$_3$) m/e 395 (M+1)$^+$; $^1$H NMR (300 Hz, CD$_3$OD) δ=8.77 (s; 1H), 8.46 (s; 1H), 8.18 (s; 1H), 8.13 (s; 1H), 7.75 (d; 1H; J=8.4 Hz), 7.63 (d; 1H; J=8.4 Hz), 7.17 (m; 3H), 4.49 (dd; 1H; J=10.8 Hz; J=3.0 Hz), 4.33 (dd; 1H; J=10.8 Hz; J=4.5 Hz), 4.02 (m; 1H), 3.12 (m; 2H), 2.62 (s; 3H).

EXAMPLE 318

(1S)-1-(2,6-Dichloro-benzyl)-2-[5-(3-methyl-1H-indazol-5-yl)-pyridin-3-yloxy]-ethylamine MS (DCI/NH$_3$) m/e 428 (M+1)$^+$; $^1$H NMR (300 Hz, CD$_3$OD) δ=8.64 (s; 1H), 8.33 (s; 1H), 8.05 (s; 1H), 7.88 (s;

1H), 7.70 (d; 1H; J=8.4 Hz), 7.61 (d; 1H; J=8.4 Hz), 7.48 (d; 2H; J=7.2 Hz), 7.33 (t; 1H; J=7.2 Hz), 4.40 (dd; 1H; J=10.8 Hz; J=3.0 Hz), 4.29 (dd; 1H; J=10.8 Hz; J=4.5 Hz), 4.10 (m; 1H), 3.67 (dd; 1H; J=15.0 Hz; J=9.6 Hz), 3.43 (dd; 1H; J=15.0 Hz; J=5.4 Hz), 2.62 (s; 3H).

EXAMPLE 319

(1S)-1-(2,4-Difluoro-benzyl)-2-[5-(3-methyl-1H-indazol-5-yl)-pyridin-3-yloxy]-ethylamine MS (DCI/NH$_3$) m/e 395 (M+1)$^+$; $^1$H NMR (300 Hz, CD$_3$OD) δ=8.67 (s; 1H), 8.37 (s; 1H), 8.08 (s; 1H), 7.94 (s; 1H), 7.71 (d; 1H; J=8.4 Hz), 7.61 (d; 1H; J=8.4 Hz), 7.40 (m; 1H), 7.01 (m; 2H), 4.43 (dd; 1H; J=10.8 Hz; J=3.0 Hz), 4.27 (dd; 1H; J=10.8 Hz; J=4.5 Hz), 3.96 (m; 1H), 3.10 (m; 2H), 2.62 (s; 3H).

EXAMPLE 320

(1S)-1-(2,6-Dimethyl-benzyl)-2-[5-(3-methyl-1H-indazol-5-yl)-pyridin-3-yloxy]-ethylamine MS (DCI/NH$_3$) m/e 387 (M+1)$^+$; $^1$H NMR (300 Hz, CD$_3$OD) δ=8.62 (s; 1H), 8.32 (s; 1H), 8.03 (s; 1H), 7.83 (s; 1H), 7.69 (d; 1H; J=8.4 Hz), 7.60 (d; 1H; J=8.4 Hz), 7.70 (m; 3H), 4.29 (dd; 1H; J=10.8 Hz; J=3.0 Hz), 4.16 (dd; 1H; J=10.8 Hz; J=4.5 Hz), 3.92 (m; 1H), 3.37 (dd; 1H; J=15.0 Hz; J=10.5 Hz), 3.15 (dd; 1H; J=15.0 Hz; J=5.4 Hz), 2.62 (s; 3H), 2.38 (s; 6H).

EXAMPLE 321

(1S)-1-(2,3-Dihydro-benzo[1,4]dioxin-6-ylmethyl)-2-[5-(3-methyl-1H-indazol-5-yl)-pyridin-3-yloxy]-ethylamine MS (DCI/NH$_3$) m/e 417 (M+1)$^+$; $^1$H NMR (300 Hz, CD$_3$OD) δ=8.64 (s; 1H), 8.36 (s; 1H), 8.07 (s; 1H), 7.91 (s; 1H), 7.71 (d; 1H; J=8.4 Hz), 7.61 (d; 1H; J=8.4 Hz), 6.80 (m; 3H), 4.40 (dd; 1H; J=10.8 Hz; J=3.0 Hz), 4.23 (dd; 1H; J=10.8 Hz; J=4.5 Hz), 4.20 (s; 4H), 3.88 (m; 1H), 3.03 (m; 2H), 2.62 (s; 3H).

EXAMPLE 322

(1S)-1-(3,5-Difluoro-benzyl)-2-[5-(3-methyl-1H-indazol-5-yl)-pyridin-3-yloxy]-ethylamine MS (DCI/NH$_3$) m/e 395 (M+1)$^+$; $^1$H NMR (300 Hz, CD$_3$OD) δ=8.67 (s; 1H), 8.39 (s; 1H), 8.08 (s; 1H), 7.98 (s; 1H), 7.73 (d; 1H; J=8.4 Hz), 7.61 (d; 1H; J=8.4 Hz), 6.97 (m; 3H), 4.44 (dd; 1H; J=10.8 Hz; J=3.0 Hz), 4.29 (dd; 1H; J=10.8 Hz; J=4.5 Hz), 4.01 (m; 1H), 3.19 (m; 2H), 2.62 (s; 3H).

EXAMPLE 323

(1S)-1-(2,6-Difluoro-benzyl)-2-[5-(3-methyl-1H-indazol-5-yl)-pyridin-3-yloxy]-ethylamine MS (DCI/NH$_3$) m/e 395 (M+1)$^+$; $^1$H NMR (300 Hz, CD$_3$OD) δ=8.41 (s; 1H), 8.31 (s; 1H), 8.04 (s; 1H), 7.84 (s; 1H), 7.70 (d; 1H; J=8.4 Hz), 7.60 (d; 1H; J=8.4 Hz), 7.40 (m; 1H), 7.06 (m; 2H), 4.42 (dd; 1H; J=10.8 Hz; J=3.0 Hz), 4.24 (dd; 1H; J=10.8 Hz; J=4.5 Hz), 3.97 (m; 1H), 3.31 (m; 2H), 2.62 (s; 3H).

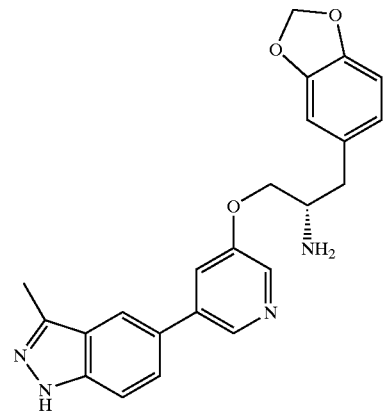

EXAMPLE 324

(1S)-1-Benzo[1,3]dioxol-5-ylmethyl-2-[5-(3-methyl-1H-indazol-5-yl)-pyridin-3-yloxy]-ethylamine MS (APCI) m/z 404 (M+1)$^+$; $^1$H NMR (500 Hz, CD$_3$OD) δ ppm 2.63 (s, 3H), 3.08 (dd, J=7.64, 2.65 Hz, 2H), 3.92 (m, 1H), 4.32 (dd, J=10.45, 5.77 Hz, 1H), 4.46 (dd, J=10.61, 2.81 Hz, 1H), 5.92 (d, J=1.87 Hz, 2H), 6.80 (d, J=1.87 Hz, 2H), 6.85 (s, 1H), 7.64 (d, J=8.73 Hz, 1H), 7.74 (dd, J=8.73, 1.56 Hz, 1H), 8.12 (s, 1H), 8.14 (d, J=1.87 Hz, 1H), 8.45 (d, J=1.87 Hz, 1H), 8.74 (s, 1H); Anal. Calcd for C$_{23}$H$_{22}$N$_4$O$_3$: C, 48.46; H, 3.55; N, 8.02. Found: C, 48.59; H, 3.65; N, 8.13.

EXAMPLE 325

(1S)-1-(4-Fluoro-3-methyl-benzyl)-2-[5-(3-methyl-1H-indazol-5-yl)-pyridin-3-yloxy]-ethylamine MS (APCI) m/z 392 (M+1)$^+$; $^1$H NMR (500 Hz, CD$_3$OD) δ ppm 2.24 (s, 3H), 2.63 (s, 3H), 3.11 (dd, J=7.64, 3.90 Hz, 2H), 3.94 (m, 1H), 4.29 (dd, J=10.61, 5.62 Hz, 1H), 4.44 (dd, J=10.61, 2.81 Hz, 1H), 7.03 (m, 1H), 7.16 (m, 1H), 7.21 (d, J=7.18 Hz, 1H), 7.63 (d, J=8.73 Hz, 1H), 7.74 (d, J=1.87 Hz, 1H), 8.06 (s, 1H), 8.10 (s, 1H), 8.42 (s, 1H), 8.71 (s, 1H); Anal. Calcd for C$_{23}$H$_{23}$FN$_4$O: C, 50.79; H, 3.91; N, 8.58. Found: C, 51.10; H, 4.02; N, 8.43.

EXAMPLE 326

(1S)-2-[5-(3-Methyl-1H-indazol-5-yl)-pyridin-3-yloxy]-1-(2,4,6-trimethyl-benzyl)-ethylamine MS (APCI) m/z 402 (M+1)$^+$; $^1$H NMR (500 Hz, CD$_3$OD) δ ppm 2.21 (s, 3H), 2.34 (s, 6H), 2.62 (s, 3H), 3.14 (dd, J=14.19, 5.46 Hz, 2H), 3.92 (m, J=8.73, 4.99 Hz, 1H), 4.26 (dd, J=10.45, 4.84 Hz, 1H), 4.36 (m, 1H), 6.89 (s, 2H), 7.63 (d, J=8.74 Hz, 1H), 7.72 (dd, J=8.73, 1.56 Hz, 1H), 8.11 (s, 2H), 8.42 (s, 1H), 8.75 (s, 1H); Anal. Calcd for C$_{25}$H$_{28}$N$_4$O: C, 52.56; H, 4.48; N, 8.17. Found: C, 52.49; H, 4.41; N, 8.06.

EXAMPLE 327

(1S)-1-(2,4-Dimethoxy-benzyl)-2-[5-(3-methyl-1H-indazol-5-yl)-pyridin-3-yloxy]-ethylamine MS (APCI) m/z 419 (M+1)$^+$; $^1$H NMR (500 Hz, CD$_3$OD) δ ppm 2.63 (s, 3H), 3.08 (dd, J=7.33, 2.96 Hz, 2H), 3.77 (s, 3H), 3.83 (s, 3H), 3.94 (m, 1H), 4.26 (dd, J=10.45, 5.77 Hz, 1H), 4.41 (dd, J=10.61, 3.12 Hz, 1H), 6.50 (dd, J=8.27, 2.34 Hz, 1H), 6.59 (d, J=2.50 Hz, 1H), 7.12 (d, J=8.42 Hz, 1H), 7.63 (d, J=8.73 Hz, 1H), 7.72 (m, 1H), 8.00 (s, 1H), 8.09 (s, 1H), 8.40 (s, 1H), 8.71 (s, 1H).

EXAMPLE 328

(1S)-2-[5-(3-Methyl-1H-indazol-5-yl)-pyridin-3-yloxy]-1-(4-trifluoromethyl-benzyl)-ethylamine MS (APCI) m/z 428 (M+1)$^+$; $^1$H NMR (500 Hz, CD$_3$OD) δ ppm 2.63 (s, 3H), 3.28 (m, 2H), 4.05 (m, 1H), 4.32 (dd, J=10.61, 5.30 Hz, 1H), 4.47 (dd, J=10.61, 2.81 Hz, 1H), 7.56 (d, J=7.80 Hz, 2H), 7.63 (d, J=8.74 Hz, 1H), 7.69 (d, J=8.11 Hz, 2H), 7.74 (dd, J=8.74, 1.56 Hz, 1H), 8.12 (d, J=6.55 Hz, 2H), 8.45 (br s, 1H), 8.74 (br s, 1H); Anal. Calcd for C$_{23}$H$_{21}$F$_3$N$_4$O: C, 46.45; H, 3.25; N, 7.63. Found: C, 46.55; H, 3.30; N, 7.64.

EXAMPLE 329

(1S)-1-(5-Fluoro-2-methyl-benzyl)-2-[5-(3-methyl-1H-indazol-5-yl)-pyridin-3-yloxy]-ethylamine MS (APCI) m/z 391 (M+1)$^+$; $^1$H NMR (500 Hz, CD$_3$OD) δ ppm 2.36 (s, 3H), 2.62 (s, 3H), 3.16 (dd, J=14.19, 6.71 Hz, 1H), 3.23 (m, 1H), 3.97 (m, 1H), 4.29 (dd, J=10.45, 4.84 Hz, 1H), 4.42 (dd, J=10.61, 3.12 Hz, 1H), 6.95 (td, J=8.42, 2.81 Hz, 1H), 7.04 (dd, J=9.67, 2.81 Hz, 1H), 7.25 (dd, J=8.42, 5.93 Hz, 1H), 7.63 (d, J=8.74 Hz, 1H), 7.73 (dd, J=8.73, 1.56 Hz, 1H), 8.05 (s, 1H), 8.09 (s, 1H), 8.42 (s, 1H), 8.71 (s, 11H); Anal. Calcd for C$_{23}$H$_{23}$FN$_4$O: C, 49.31; H, 3.76; N, 8.16. Found: C, 49.28; H, 3.61; N, 8.10.

EXAMPLE 330

(1S)-1-(3,5-Bis-trifluoromethyl-benzyl)-2-[5-(3-methyl-1H-indazol-5-yl)-pyridin-3-yloxy]-ethylamine MS (APCI) m/z 495 (M+1)$^+$; $^1$H NMR (500 Hz, CD$_3$OD) δ ppm 2.62 (s, 3H), 3.35 (m, 1H), 3.42 (m, 1H), 4.12 (m, 1H), 4.31 (dd, J=10.61, 5.30 Hz, 1H), 4.49 (dd, J=10.61, 3.12 Hz, 11H), 7.63 (d, J=8.73 Hz, 1H), 7.73 (dd, J=8.74, 1.87 Hz, 11H), 7.94 (s, 1H), 8.01 (s, 2H), 8.05 (s, 1H), 8.08 (s, 1H), 8.43 (s, 1H), 8.72 (s, 1H); Anal. Calcd for C$_{24}$H$_2$OF$_6$N$_4$O: C, 43.69; H, 2.82; N, 6.89. Found: C, 43.70; H, 2.65; N, 6.82.

EXAMPLE 331

(1S)-1-(4-Fluoro-2-methyl-benzyl)-2-[5-(3-methyl-1H-indazol-5-yl)-pyridin-3-yloxy]-ethylamine MS (APCI) m/z 392 (M+1)$^+$; $^1$H NMR (500 Hz, CD$_3$OD) δ ppm 2.40 (s, 3H), 2.62 (s, 3H), 3.15 (dd, J=14.19, 6.40 Hz, 1H), 3.22 (m, 1H), 3.94 (m, 1H), 4.29 (dd, J=10.61, 4.99 Hz, 1H), 4.42 (dd, J=10.61, 2.81 Hz, 1H), 6.91 (td, J=8.42, 2.50 Hz, 1H), 7.00 (dd, J=9.83, 2.34 Hz, 1H), 7.26 (dd, J=8.42, 5.93 Hz, 11H), 7.63 (d, J=8.74 Hz, 1H), 7.73 (dd, J=8.74, 1.25 Hz, 1H), 8.08 (s, 11H), 8.10 (s, 11H), 8.43 (s, 1H), 8.72 (s, 11H); Anal. Calcd for C$_{23}$H$_{23}$FN$_4$O: C, 48.40; H, 3.66; N, 7.89. Found: C, 48.59; H, 3.85; N, 7.90.

EXAMPLE 332

(1S)-1-(5-Fluoro-2-methoxy-benzyl)-2-[5-(3-methyl-1H-indazol-5-yl)-pyridin-3-yloxy]-ethylamine MS (APCI) m/z 408 (M+1)$^+$; $^1$H NMR (500 Hz, CD$_3$OD) δ ppm 2.63 (s, 3H), 3.16 (d, J=7.18 Hz, 2H), 3.84 (s, 3H), 4.02 (m, 1H), 4.30 (dd, J=10.61, 5.93 Hz, 1H), 4.45 (dd, J=10.45, 2.96 Hz, 1H), 7.04 (m, 3H), 7.64 (d, J=8.73 Hz, 1H), 7.74 (d, J=8.74 Hz, 1H), 8.12 (s, 2H), 8.43 (s, 1H), 8.74 (s, 1H); Anal. Calcd for C$_{23}$H$_{23}$FN$_4$O$_2$: C, 44.73; H, 3.32; N, 6.96. Found: C, 44.77; H, 3.46; N, 6.83.

EXAMPLE 333

(1S)-2-[5-(3-Methyl-1H-indazol-5-yl)-pyridin-3-yloxy]-1-(2-methyl-naphthalen-1-ylmethyl)-ethylamine MS (APCI) m/z 424 (M+1)$^+$; $^1$H NMR (500 Hz, CD$_3$OD) δ ppm 2.58 (s, 3H), 2.61 (s, 3H), 3.61 (dd, J=14.19, 4.84 Hz, 1H), 3.84 (dd, J=14.19, 10.76 Hz, 1H), 4.06 (m, J=9.20, 4.21 Hz, 1H), 4.14 (dd, J=10.29, 3.74 Hz, 1H), 4.28 (dd, J=10.45, 2.65 Hz, 1H), 7.41 (m, 3H), 7.60 (d, J=8.42 Hz, 1H), 7.65 (m, 1H), 7.75 (d, J=8.42 Hz, 1H), 7.84 (m, 2H), 8.01 (s, 1H), 8.12 (d, J=8.11 Hz, 1H), 8.33 (s, 1H), 8.66 (s, 1H); Anal. Calcd for C$_{27}$H$_{26}$N$_4$O: C, 52.30; H, 3.87; N, 7.44. Found: C, 52.56; H, 4.00; N, 7.38.

EXAMPLE 334

(1S)-1-(2,2-Difluoro-benzo[1,3]dioxol-4-ylmethyl)-2-[5-(3-methyl-1H-indazol-5-yl)-pyridin-3-yloxy]-ethylamine MS (APCI) m/z 437 (M−1)$^+$; $^1$H NMR (500 Hz, CD$_3$OD) δ ppm 2.63 (s, 3H), 3.28 (m, 2H), 4.07 (m, 1H), 4.34 (dd, J=10.61, 4.99 Hz, 1H), 4.51 (dd, J=10.61, 2.81 Hz, 1H), 7.17 (m, 3H), 7.64 (d, J=8.73 Hz, 1H), 7.75 (d, J=8.73 Hz, 1H), 8.12 (s, 1H), 8.16 (s, 1H), 8.46 (s, 1H), 8.76 (s, 1H); Anal. Calcd for C$_{23}$H$_2$OF$_2$N$_4$O$_3$: C, 44.63; H, 2.97; N, 7.18. Found: C, 44.74; H, 3.08; N, 7.23.

EXAMPLE 335

(1S)-1-(4-Fluoro-naphthalen-1-ylmethyl)-2-[5-(3-methyl-1H-indazol-5-yl)-pyridin-3-yloxy]-ethylamine MS (APCI) m/z 428 (M+1)$^+$; $^1$H NMR (500 Hz, CD$_3$OD) δ ppm 2.62 (s, 3H), 3.60 (dd, J=14.04, 6.55 Hz, 1H), 3.66 (m, 1H), 4.09 (m, 1H), 4.29 (dd, J=10.61, 4.99 Hz, 1H), 4.42 (dd, J=10.61, 3.12 Hz, 1H), 7.19 (dd, J=10.29, 7.80 Hz, 1H), 7.47 (dd, J=7.80, 5.30 Hz, 1H), 7.61 (d, J=8.73 Hz, 2H), 7.64 (d, J=7.18 Hz, 1H), 7.68 (t, J=8.11 Hz, 1H), 7.96 (s, 1H), 8.05 (s, 1H), 8.15 (d, J=8.11 Hz, 1H), 8.18 (d, J=8.42 Hz, 1H), 8.38 (s, 1H), 8.68 (s, 1H).

EXAMPLE 336

(1S)-2-[5-(3-Methyl-1H-indazol-5-yl)-pyridin-3-yloxy]-1-(2,2,3,3-tetrafluoro-2,3-dihydro-benzo[1,4]dioxin-6-ylmethyl)-ethylamine MS (APCI) m/z 487 (M−1)$^+$; $^1$H NMR (500 Hz, CD$_3$OD) δ ppm 2.63 (s, 3H), 3.18 (dd, J=14.19, 7.02 Hz, 1H), 3.24 (m, 1H), 4.02 (m, J=5.15, 2.65 Hz, 1H), 4.33 (dd, J=10.45, 5.46 Hz, 1H), 4.47 (dd, J=10.61, 3.12 Hz, 1H), 7.29 (m, 2H), 7.34 (s, 1H), 7.63 (d, J=8.73 Hz, 1H), 7.74 (dd, J=8.74, 1.25 Hz, 1H), 8.11 (s, 2H), 8.44 (s, 1H), 8.72 (s, 1H); Anal. Calcd for C$_{23}$H$_2$OF$_2$N$_4$O$_3$: C, 43.08; H, 2.77; N, 6.65. Found: C, 42.94; H, 2.79; N, 6.64.

EXAMPLE 337

(1S)-2-[5-(3-Methyl-1H-indazol-5-yl)-pyridin-3-yloxy]-1-(4-methyl-naphthalen-1-ylmethyl)-ethylamine MS (APCI) m/z 421 (M−1)$^+$; $^1$H NMR (500 Hz, CD$_3$OD) δ ppm 2.61 (d, J=8.11 Hz, 3H), 2.67 (s, 3H), 3.62 (m, 2H), 4.09 (m, 1H), 4.28 (dd, J=10.61, 4.99 Hz, 1H), 4.40 (dd, J=10.61, 3.12 Hz, 1H), 7.32 (d, J=7.49 Hz, 1H), 7.38 (m, 1H), 7.58 (m, 2H), 7.62 (d, J=8.73 Hz, 1H), 7.68 (m, 1H), 7.97 (s, 1H), 8.06 (s, 1H), 8.10 (m, 1H), 8.15 (m, 1H), 8.37 (d, J=2.50 Hz, 1H), 8.68 (s, 1H); Anal. Calcd for $C_{27}H_{26}N_4O$: C, 52.79; H, 3.91; N, 7.55. Found: C, 52.64; H, 3.85; N, 7.53.

EXAMPLE 338

(1S)-2-[5-(3-Methyl-1H-indazol-5-yl)-pyridin-3-yloxy]-1-(2,4,6-trifluoro-benzyl)-ethylamine MS (APCI) m/z 411 (M−1)$^+$; $^1$H NMR (500 Hz, CD$_3$OD) δ ppm 2.63 (s, 3H), 3.19 (m, 2H), 3.97 (m, 1H), 4.32 (dd, J=10.61, 4.99 Hz, 1H), 4.49 (dd, J=10.61, 3.12 Hz, 1H), 6.95 (t, J=8.27 Hz, 2H), 7.63 (d, J=8.73 Hz, 1H), 7.74 (dd, J=8.74, 1.56 Hz, 1H), 8.08 (d, J=2.18 Hz, 1H), 8.10 (s, 1H), 8.41 (s, 1H), 8.72 (s, 1H);Anal. Calcd for $C_{22}H_{19}F_3N_4O$: C, 44.57; H, 2.94; N, 7.43. Found: C, 44.47; H, 2.78; N, 7.46.

EXAMPLE 339

(1S)-2-[5-(3-Methyl-1H-indazol-5-yl)-pyridin-3-yloxy]-1-(2,3,4-trifluoro-benzyl)-ethylamine $^1$H NMR (500 Hz, CD$_3$OD) δ ppm 2.62 (s, 3H), 3.23 (m, 2H), 4.00 (m, 1H), 4.31 (dd, J=10.61, 5.30 Hz, 1H), 4.46 (dd, J=10.61, 3.12 Hz, 1H), 7.17 (m, 2H), 7.62 (d, J=8.73 Hz, 1H), 7.73 (dd, J=8.74, 1.56 Hz, 1H), 8.02 (s, 1H), 8.08 (s, 1H), 8.40 (s, 1H), 8.69 (s, 1H); Anal. Calcd for $C_{22}H_{19}F_3N_4O$: C, 45.31; H, 3.00; N, 7.66. Found: C, 45.59; H, 2.73; N, 7.84.

EXAMPLE 340

(1S)-1-(4-Bromo-2-fluoro-benzyl)-2-[5-(3-methyl-1H-indazol-5-yl)-pyridin-3-yloxy]-ethylamine $^1$H NMR (500 Hz, CD$_3$OD) δ ppm 2.63 (s, 3H), 3.22 (m, 2H), 4.00 (m, 1H), 4.34 (dd, J=10.61, 5.30 Hz, 1H), 4.49 (dd, J=10.61, 3.12 Hz, 1H), 7.33 (t, J=8.11 Hz, 1H), 7.37 (d, J=1.56 Hz, 1H), 7.41 (m, 1H), 7.64 (d, J=8.73 Hz, 1H), 7.75 (dd, J=8.74, 1.56 Hz, 1H), 8.13 (s, 1H), 8.19 (s, 1H), 8.46 (s, 1H), 8.77 (s, 1H); Anal. Calcd for $C_{22}H_{20}BrFN_4O$: C, 42.80; H, 2.97; N, 7.23. Found: C, 42.73; H, 3.17; N, 7.02.

EXAMPLE 341

(1S)-1-(4-Bromo-3-fluoro-benzyl)-2-[5-(3-methyl-1H-indazol-5-yl)-pyridin-3-yloxy]-ethylamine MS (ESI) m/z 456 (M+1)$^+$; $^1$H NMR (500 Hz, CD$_3$OD) δ ppm 2.63 (s, 3H), 3.18 (m, 2H), 4.01 (m, 1H), 4.32 (dd, J=10.61, 5.62 Hz, 1H), 4.46 (dd, J=10.61, 2.81 Hz, 1H), 7.11 (dd, J=8.11, 1.56 Hz, 1H), 7.26 (dd, J=9.36, 1.87 Hz, 1H), 7.62 (d, J=7.18 Hz, 1H), 7.63 (d, J=8.42 Hz, 1H), 7.74 (dd, J=8.73, 1.56 Hz, 1H), 8.10 (d, J=4.06 Hz, 2H), 8.43 (s, 1H), 8.72 (s, 1H);Anal. Calcd for $C_{22}H_{20}BrFN_4O$: C, 43.46; H, 3.03; N, 7.45. Found: C, 43.52; H, 3.07; N, 7.43.

EXAMPLE 342

(1S)-1-(2-Bromo-4,6-difluoro-benzyl)-2-[5-(3-methyl-1H-indazol-5-yl)-pyridin-3-yloxy]-ethylamine $^1$H NMR (500 Hz, CD$_3$OD) δ ppm 2.63 (s, 3H), 3.32 (m, 1H), 3.48 (m, 1H), 4.03 (m, 1H), 4.34 (dd, J=10.45, 4.84 Hz, 1H), 4.48 (dd, J=10.61, 3.43 Hz, 1H), 7.13 (t, J=8.11 Hz, 1H), 7.40 (d, J=8.11 Hz, 1H), 7.63 (d, J=8.73 Hz, 1H), 7.74 (dd, J=8.73, 1.56 Hz, 1H), 8.09 (s, 1H), 8.11 (s, 1H), 8.42 (s, 1H), 8.73 (s, 1H); Anal. Calcd for $C_{22}H_{19}BrF_2N_4O$: C, 41.24; H, 2.72; N, 6.87. Found: C, 41.35; H, 2.68; N, 6.76.

EXAMPLE 343

(1S)-1-(4-Bromo-3-methyl-benzyl)-2-[5-(3-methyl-1H-indazol-5-yl)-pyridin-3-yloxy]-ethylamine MS (ESI) m/z 452 (M+1)$^+$; $^1$H NMR (500 Hz, CD$_3$OD) δ ppm 2.37 (s, 3H), 2.63 (s, 3H), 3.11 (m, 2H), 3.97 (m, 1H), 4.29 (dd, J=10.61, 5.62 Hz, 1H), 4.44 (dd, J=10.61, 3.12 Hz, 1H), 7.07 (dd, J=8.11, 1.87 Hz, 1H), 7.27 (s, 1H), 7.54 (d, J=8.11 Hz, 1H), 7.63 (d, J=8.73 Hz, 1H), 7.73 (d, J=8.73 Hz, 1H), 8.06 (s, 1H), 8.10 (s, 1H), 8.41 (s, 1H), 8.71 (s, 1H); Anal. Calcd for $C_{23}H_{23}BrN_4O$: C, 44.93; H, 3.41; N, 7.38. Found: C, 45.11; H, 3.36; N, 7.28.

EXAMPLE 344

(1S)-Bromo-benzyl)-2-[5-(3-methyl-1H-indazol-5-yl)-pyridin-3-yloxy]-ethylamine $^1$H NMR (500 Hz, CD$_3$OD) δ ppm 2.62 (s, 3H), 3.37 (m, 2H), 4.10 (m, 1H), 4.30 (dd, J=10.61, 4.99 Hz, 1H), 4.43 (dd, J=10.61, 3.12 Hz, 1H), 7.25 (t, J=6.71 Hz, 1H), 7.37 (t, J=6.86 Hz, 1H), 7.42 (m, 1H), 7.63 (d, J=8.74 Hz, 1H), 7.66 (d, J=8.11 Hz, 1H), 7.73 (dd, J=8.73, 1.56 Hz, 1H), 8.03 (d, J=1.87 Hz, 1H), 8.09 (s, 1H), 8.40 (s, 1H), 8.70 (s, 1H); Anal. Calcd for $C_{22}H_{21}BrN_4O$: C, 43.48; H, 3.14; N, 7.30. Found: C, 43.67; H, 3.06; N, 7.10.

EXAMPLE 345

(1S)-1-(3-Methoxy-benzyl)-2-[5-(3-methyl-1H-indazol-5-yl)-pyridin-3-yloxy]-ethylamine MS m/z 389 (M+H)$^+$; $^1$H NMR (300 Hz, DMSO-D6) δ ppm 2.57 (s, 3 H) 3.00 (dd, J=13.56, 9.16 Hz, 1 H) 3.12 (m, 1 H) 3.73 (s, 3 H) 4.28 (dd, J=10.85, 5.43 Hz, 1 H) 4.44 (m, 2 H) 6.85 (dd, J=8.48, 2.37 Hz, 1 H) 6.91 (m, 2 H) 7.27 (t, J=7.80 Hz, 1 H) 7.61 (d, J=8.82 Hz, 1 H) 7.79 (dd, J=8.82, 1.70 Hz, 1 H) 8.23 (s, 1 H) 8.26 (s, 1 H) 8.53 (d, J=2.37 Hz, 4 H) 8.86 (s, 1 H).

EXAMPLE 346

(1S)-1-(3-Bromo-benzyl)-2-[5-(3-methyl-1H-indazol-5-yl)-pyridin-3-yloxy]-ethylamine MS m/z 437, 439 (M+H)$^+$; $^1$H NMR (300 Hz, DMSO-D6) δ ppm 2.57 (s, 3 H) 3.08 (m, 2 H) 4.27 (dd, J=10.85, 5.43 Hz, 1 H) 4.43 (m, 1 H) 7.34 (m, 2 H) 7.49 (dt, J=7.54, 1.65 Hz, 1 H) 7.61 (m, 2 H) 7.77 (dd, J=8.65, 1.53 Hz, 1 H) 8.14 (s, 1 H) 8.22 (s, 1 H) 8.49 (s, 2 H) 8.82 (s, 1 H).

EXAMPLE 347

(1S)-1-(2-Methoxy-naphthalen-1-ylmethyl)-2-[5-(3-methyl-1H-indazol-5-yl)-pyridin-3-yloxy]-ethylamine MS (ESI) m/e 439 (M+1)$^+$; $^1$H NMR (300 Hz, Solvent) δ ppm 2.62 (s, 3 H) 3.55 (m, 1 H) 3.74 (m, 1 H) 3.97 (s, 3 H) 4.03 (m, 1 H) 4.23 (m, 1 H) 4.39 (m, 1 H) 7.33 (m, 1 H) 7.46 (m, 2 H) 7.64 (m, 2 H) 7.84 (m, 1 H) 7.92 (m, 2 H) 8.03 (m, 2 H) 8.34 (br. s., 1 H) 8.67 (br. s., 1

EXAMPLE 348

(1R)-1-(4-Chloro-benzyl)-2-[5-(3-methyl-1H-indazol-5-yl)-pyridin-3-yloxy]-ethylamine

Example 348A

5-[5-((2R)-1-tert-Butoxycarbonyl-aziridin-2-ylmethoxy)-pyridin-3-yl]-3-methyl-indazole-1-caboxylic acid tert-butyl ester The desired product was prepared by substituting (S)-[1-(tert-Butyl-dimethyl-silanyloxymethyl)-2-hydroxy-ethyl]- carbamic acid tert-butyl ester for (R)-[1-(tert-Butyl-dimethyl-silanyloxymethyl)-2-hydroxy-ethyl]-carbamic acid tert-butyl ester in Example 273D. MS (APCI) m/z 481 (M+1)$^+$.

Example 348B (1R)-1-(4-Chloro-benzyl)-2-[5-(3-methyl-1H-indazol-5-yl)-pyridin-3-yloxy]-ethylamine The desired product was prepared as the trifluoroacetate by substituting Example 348A for Example 273D and 4-chlorophenylmagnesium bromide for 3-trifluoromethoxyphenyl-mangnesium bromide in Example 274. MS (APCI) m/z 393 (M+1)$^+$; $^1$H NMR (300 Hz, CD$_3$OD) δ 2.63 (s, 3 H), 3.16 (dd, J=7.63, 2.54 Hz, 2 H), 3.98 (m, 1 H), 4.30 (dd, J=10.51, 5.42 Hz, 1 H), 4.45 (dd, J=10.51, 3.05 Hz, 1 H), 7.34 (d, J=8.81 Hz, 2 H), 7.39 (d, J=8.81 Hz, 2 H), 7.63 (d, J=8.81 Hz, 1 H), 7.74 (dd, J=8.81, 1.70 Hz, 1 H), 8.11 (m, 2 H), 8.43 (d, J=2.03 Hz, 1 H), 8.73 (s, 1 H); Anal. Calcd for C$_{22}$H$_{21}$ClN$_4$O.3 TFA: C, 45.76; H, 3.29; N, 7.62. Found: C, 45.86; H, 3.28; N, 7.72.

The following compounds were prepared by substituting appropriate Girgnard reagents for 3-trifluoromethoxy-phenyl-mangnesium bromide in Example 348.

EXAMPLE 349

(1R)-1-Benzo[1,3]dioxol-5-ylmethyl-2-[5-(3-methyl-1H-indazol-5-yl)-pyridin-3-yloxy]-ethylamine MS (APCI) m/z 403 (M+1)$^+$; $^1$H NMR (300 Hz, CD$_3$OD) δ 2.63 (s, 3 H), 3.08 (dd, J=8.14, 2.03 Hz, 2 H), 3.92 (m, 1 H), 4.31 (dd, J=10.51, 5.76 Hz, 1 H), 4.46 (dd, J=10.51, 3.05 Hz, 1 H), 5.92 (s, 2 H), 6.79 (d, J=8.14 Hz, 1 H), 6.81 (d, J=8.14 Hz, 1 H), 6.85 (s, 1 H), 7.64 (d, J=8.81 Hz, 1 H), 7.75 (d, J=8.81 Hz, 1 H), 8.14 (m, 2 H), 8.44 (d, J=2.37 Hz, 1 H), 8.75 (d, J=1.70 Hz, 1 H); Anal. Calcd for C$_{23}$H$_{22}$N$_4$O$_3$.3.3 TFA: C, 45.65; H, 3.27; N, 7.19. Found: C, 45.71; H, 3.15; N, 7.21.

EXAMPLE 350

(1R)-1-(3-Fluoro-4-methyl-benzyl)-2-[5-(3-methyl-1H-indazol-5-yl)-pyridin-3-yloxy]-ethylamine MS (APCI) m/z 391 (M+1)$^+$; $^1$H NMR (300 Hz, CD$_3$OD) δ 2.24 (d, J=1.70 Hz, 3 H), 2.63 (s, 3 H), 3.11 (d, J=8.14 Hz, 2 H), 3.96 (m, 1 H), 4.31 (dd, J=10.51, 5.76 Hz, 1 H), 4.46 (dd, J=10.85, 3.05 Hz, 1 H), 7.03 (t, J=8.48 Hz, 1 H), 7.15 (m, 1 H), 7.21 (d, J=7.46 Hz, 1 H), 7.64 (d, J=8.48 Hz, 1 H), 7.74 (dd, J=8.81, 1.70 Hz, 1 H), 8.14 (m, 2 H), 8.45 (d, J=2.37 Hz, 1 H), 8.75 (d, J=1.36 Hz, 1 H); Anal. Calcd for C$_{23}$H$_{23}$FN$_4$O.2.9 TFA: C, 47.97; H, 3.62; N, 7.77. Found: C, 48.09; H, 3.75; N, 7.87.

EXAMPLE 351

(1S)-1-Benzyl-2-[6-chloro-5-(3-methyl-1H-indazol-5-yl)-pyridin-3-yloxy]-ethylamine Example 351A 5-(2-Chloro-5-hydroxy-pyridin-3-yl)-3-methyl-indazole-1-carboxylic acid tert-butyl ester A 250 mL RBF was charged with Example 12B (1.58 g, 7.59 mmol), Example 203B (3.0 g, 7.59 mmol), Pd$_2$(dba)$_3$ (696 mg, 0.76 mmol), and tri-o-tolylphosphine (696 mg), and was purged with N$_2$. Anhydrous DMF (60 mL) and Et$_3$N (3.17 mL) were added via syringe. The solution was purged with N$_2$ again and was heated at 70° C. for 15 h. After cooled, ethyl acetate (300 mL) was added. The mixture was washed with brine (500 mL) and water (500 mL). The ethyl acetate solution was concentrated and the residual oil was separated by flash chromatography (40–65% EtOAc in hexane) to give the desired produc. (1.86 g, 68%). MS (APCI) m/z 360 (M+1)$^+$.

Example 351B

5-[5-((2S)-2-tert-Butoxycarbonylamino-3-phenyl-propoxy)-2-chloro-pyridin-3-yl]-3-methyl-indazole-1-carboxylic acid tert-butyl ester A 25 mL RBF was charged with Example 351A (150 mg, 0.417 mmol), Boc-phenylalaminol (157 mg, 0.625 mmol), DBAD (144 mg, 0.625 mmol) and Ph$_3$P (163 mg, 0.625 mmol), and was purged with nitrogen. THF (8 mL) was added at 0° C. After stirring at 0° C. for 30 min the ice-H$_2$O bath was removed and the reaction mixture was stirred at rt overnight. The reaction mixture was concentrated and the residue was separated by flash chromatography (20–40% EtOAc in hexane) to provide the desired product (215.0 mg, 87%). MS (APCI) m/z 593 (M+1)$^+$.

Example 351C (1S)-1-Benzyl-2-[6-chloro-5-(3-methyl-1H-indazol-5-yl)-pyridin-3-yloxy]-ethylamine The desired product was prepared as the trifluoroacetate by substituting Example 351B for Example 27B in Examples 27C. MS (APCI) m/z 393 (M+1)$^+$; $^1$H NMR (300 Hz, CD$_3$OD) δ 2.58 (s, 3 H), 3.12 (d, J=7.46 Hz, 2 H), 3.91 (m, 1 H), 4.14 (dd, J=10.51, 5.43 Hz, 1 H), 4.30 (dd, J=10.51, 3.05 Hz, 1 H), 7.34 (m, 5 H), 7.47 (dd, J=8.65, 1.53 Hz, 1 H), 7.52 (d, J=3.05 Hz, 1 H), 7.56 (d, J=8.82 Hz, 1 H), 7.78 (s, 1 H), 8.14 (d, J=2.71 Hz, 1 H); Anal. Calcd for C$_{22}$H$_{21}$ClN$_4$O.1.6 TFA: C, 52.61; H, 3.96; N, 9.74. Found: C, 52.87; H, 3.90; N, 9.81.

The following compounds were prepared by substituting the appropriate Boc-aminoalcohol for Boc-phenylalaminol in Example 351.

EXAMPLE 352

(1S)-1-(4-Bromo-benzyl)-2-[6-chloro-5-(3-methyl-1H-indazol-5-yl)-pyridin-3-yloxy]-ethylamine MS (APCI) m/z 471, 473 (M+1)$^+$; $^1$H NMR (300 Hz, CD$_3$OD) δ 2.59 (s, 3 H), 3.10 (dd, J=7.63, 2.88 Hz, 2 H), 3.90 (m, 1 H), 4.15 (dd, J=10.85, 5.43 Hz, 1 H), 4.30 (dd, J=10.51, 3.05 Hz, 1 H), 7.24 (d, J=8.48 Hz, 2 H), 7.47 (dd, J=8.65, 1.53 Hz, 1 H), 7.51 (s, 1 H), 7.54 (s, 1 H), 7.56 (d, J=8.48 Hz, 2 H), 7.79 (s, 1 H), 8.15 (d, J=3.05 Hz, 1 H); Anal. Calcd for C$_{22}$H$_{20}$BrClN$_4$O.1.5 TFA: C, 46.71; H, 3.37; N, 8.72. Found: C, 46.62; H, 3.29; N, 8.64.

EXAMPLE 353

(1S)-1-(4-Chloro-benzyl)-2-[6-chloro-5-(3-methyl-1H-indazol-5-yl)-pyridin-3-yloxy]-ethylamine MS (APCI) m/z 427 (M+1)$^+$; $^1$H NMR (300 Hz, CD$_3$OD) δ 2.59 (s, 3 H), 3.12 (dd, J=7.63, 2.54 Hz, 2 H), 3.91 (m, 1 H), 4.15 (dd, J=10.51, 5.43 Hz, 1 H), 4.30 (dd, J=10.51, 3.05 Hz, 1 H), 7.30 (d, J=8.48 Hz, 2 H), 7.37 (d, J=8.82 Hz, 2 H), 7.47 (dd, J=8.65, 1.53 Hz, 1 H), 7.53 (d, J=3.05 Hz, 1 H), 7.56 (d, J=8.48 Hz, 1 H), 7.79 (s, 1 H), 8.15 (d, J=3.05 Hz, 1 H); Anal. Calcd for $C_{22}H_{20}Cl_2N_4O$ 1.6 TFA: C, 49.64; H, 3.57; N, 9.19. Found: C, 49.99; H, 3.56; N, 9.22.

EXAMPLE 354

(1S)-2-[6-Chloro-5-(3-methyl-1H-indazol-5-yl)-pyridin-3-yloxy]-1-cyclohexylmethyl-ethylamine MS (APCI) m/z 399 (M+1)$^+$; $^1$H NMR (300 Hz, CD$_3$OD) δ 1.01 (m, 2 H), 1.31 (m, 4 H), 1.49 (m, 1 H), 1.65 (q, J=6.89 Hz, 2 H), 1.78 (m, 4 H), 2.59 (s, 3 H), 3.74 (m, 1 H), 4.18 (dd, J=10.51, 6.44 Hz, 1 H), 4.37 (dd, J=10.51, 3.39 Hz, 1 H), 7.49 (dd, J=8.82, 1.70 Hz, 1 H), 7.56 (dd, J=8.48, 0.68 Hz, 1 H), 7.59 (d, J=3.05 Hz, 1 H), 7.80 (s, 1 H), 8.17 (d, J=3.05 Hz, 1H); Anal. Calcd for $C_{22}H_{27}ClN_4O$.1.75 TFA: C, 51.18; H, 4.84; N, 9.36. Found: C, 51.13; H, 4.75; N, 9.20.

EXAMPLE 355

(1S)-2-[6-Chloro-5-(3-methyl-1H-indazol-5-yl)-pyridin-3-yloxy]-1-(2,6-dimethyl-benzyl)-ethylamine MS (DCI/NH$_3$) m/e 421 (M+1)$^+$; $^1$H NMR (300 Hz, CD$_3$OD) δ=8.10 (d; 1H; J=8.4 Hz), 7.75 (d; 1H; J=8.4 Hz), 7.55 (s; 1H), 7.53 (s; 1H), 7.44 (m; 3H), 7.04 (s; 1H), 4.30 (dd; 1H; J=10.8 Hz; J=3.0 Hz), 4.09 (dd; 1H; J=10.8 Hz; J=4.5 Hz), 4.87 (m; 1H), 3.30 (m; 2H), 2.62 (s; 3H), 2.36 (s; 6H).

EXAMPLE 356

(1S)-1-[6-Chloro-5-(3-methyl-1H-indazol-5-yl)-pyridin-3-yloxymethyl]-2-phenyl-propylamine The desired product was prepared by substituting Example 12B for 3-bromo-5-hydroxypyridine and Boc-3-methyl-phenylalaminol for Boc-tryptophanol in Example 102.

MS (DCI/NH$_3$) m/e 407 (M+1)$^+$; $^1$H NMR (300 Hz, CD$_3$OD) δ=8.20 (d; 1H; J=3.0 Hz), 7.81 (s; 1H), 7.61 (d; 1H; J=3.0 Hz), 7.57 (d; 1H; J=8.4 Hz), 7.40 (m; 6H), 4.44 (d; 2H; J=4.5 Hz), 3.88 (m; 1H), 3.28 (m; 1H), 2.59 (s; 3H), 1.42 (d; 3H; J=7.5 Hz).

EXAMPLE 357

(1S)-1-[6-Chloro-5-(3-methyl-1H-indazol-5-yl)-pyridin-3-yloxymethyl]-2,2-diphenyl-ethylamine The desired product was prepared by substituting Example 12B for 3-bromo-5-hydroxypyridine and Boc-3,3-diphenylalaminol for Boc-tryptophanol in Example 102. MS (DCI/NH$_3$) m/e 469 (M+1)$^+$; $^1$H NMR (300 Hz, CD$_3$OD) δ=8.08 (d; 1H; J=3.0 Hz), 7.74 (s; 1H), 7.55 (m; 3H), 7.43 (m; 5H), 7.31 (m; 3H), 7.21 (m; 2H), 4.65 (d; 1H; J=11.1 Hz), 4.44 (d; 1H; J=11.1 Hz), 4.31 (d; 1H; J=11.1 Hz), 4.09 (d; 1H; J=11.1 Hz), 2.59 (s; 3H).

EXAMPLE 358

(1S)-1-[5-(3-Methyl-1H-indazol-5-yl)-pyridin-3-yloxymethyl]-2-phenyl-propylamine The desired product was prepared by substituting Boc-3-methyl-phenylalaminol for Boc-tryptophanol in Example 102. MS (DCI/NH$_3$) m/e 373 (M+1)$^+$; $^1$H NMR (300 Hz, CD$_3$OD) δ–8.11 (s; 2H), 8.05 (s; 2H), 7.74 (d; 1H; J=8.4 Hz), 7.62 (d; 1H; J=8.4 Hz), 7.40 (m; 1H), 7.39 (m; 5H), 4.56 (m; 2H), 3.92 (m; 2H), 2.62 (s; 3H), 1.6 (d; 3H; J=7.5 Hz).

EXAMPLE 359

(1S)-1-[5-(3-Methyl-1H-indazol-5-yl)-pyridin-3-yloxymethyl]-2,2-diphenyl-ethylamine The desired product was prepared by substituting Boc-3,3-diphenylalaminol for Boc-tryptophanol in Example 102. MS (DCI/NH$_3$) m/e 435 (M+1)$^+$; $^1$H NMR (300 Hz, CD$_3$OD) δ=8.62 (s; 1H), 8.31 (s; 1H), 8.02 (s; 1H), 7.82 (s; 1H), 7.67 (d; 1H; J=8.4 Hz), 7.60 (d; 1H; J=8.4 Hz), 7.58 (d; 1H; J=6.9 Hz), 7.43 (m; 4H), 7.30 (m; 5H), 4.61 (d; 1H; J=12.0 Hz), 4.48 (d; 1H; J=12 Hz), 4.40 (dd; 1H; J=11.4 Hz; J=3.0 Hz), 4.00 (dd; 1H; J=11.4 Hz), 2.62 (s; 3H).

EXAMPLE 360

(1S)-3-Methyl-1-[5-(3-methyl-1H-indazol-5-yl)-pyridin-3-yloxymethyl]-butylamine

The desired product was prepared by substituting Example 12B for 3-bromo-5-hydroxypyridine and Boc-leucinol for Boc-tryptophanol in Example 102. MS (APCI) m/z 357 (M−1)$^+$; $^1$H NMR (500 Hz, CD$_3$OD) δ ppm 1.02 (m, J=6.40, 3.90 Hz, 6H), 1.67 (m, 2H), 1.80 (dd, J=13.57, 6.71 Hz, 1H), 2.59 (s, 3H), 3.71 (m, J=6.86, 3.12 Hz, 1H), 4.20 (dd, J=10.61, 6.55 Hz, 1H), 4.38 (dd, J=10.45, 3.28 Hz, 1H), 7.49 (dd, J=8.58, 1.72 Hz, 1H), 7.56 (d, J=8.11 Hz, 1H), 7.59 (d, J=3.12 Hz, 1H), 7.80 (s, 1H), 8.17 (d, J=3.12 Hz, 1H); Anal. Calcd for $C_{19}H_{23}ClN_4O$: C, 49.56; H, 5.21; N, 10.88. Found: C, 49.86; H, 4.83; N, 10.49.

EXAMPLE 361

(1S)-2-[6-Chloro-5-(3-methyl-1H-indazol-5-yl)-pyridin-3-yloxy]-1-(1H-indol-3-ylmethyl)-ethylamine The desired product was prepared by substituting Example 12B for 3-bromo-5-hydroxypyridine in Example 102. MS (APCI) m/z 533 (M+1)$^+$; $^1$H NMR (500 Hz, CD$_3$OD) δ ppm 2.58 (s, 3H), 3.28 (m, 2H), 3.96 (m, 1H), 4.20 (dd, J=10.45, 5.77 Hz, 1H), 4.34 (dd, J=10.61, 3.12 Hz, 1H), 7.02 (t, J=7.49 Hz, 1H), 7.12 (t, J=7.64 Hz, 1H), 7.22 (s, 1H), 7.37 (d, J=8.42 Hz, 1H), 7.44 (dd, J=8.42, 1.56 Hz, 1H), 7.47 (d, J=3.12 Hz, 1H), 7.54 (d, J=8.42 Hz, 1H), 7.57 (d, J=8.11 Hz, 1H), 7.74 (s, 1H), 8.12 (d, J=2.81 Hz, 1H); Anal. Calcd for $C_{24}H_{22}ClN_5O$: C, 52.08; H, 4.12; N, 11.61. Found: C, 52.45; H, 4.08; N, 11.24.

EXAMPLE 362

(1S)-2-(6-Chloro-5-thieno[2,3-c]pyridin-2-yl-pyridin-3-yloxy)-1-(1H-indol-3-ylmethyl)-ethylamine

Example 362A (1S)-[2-(6-Chloro-5-thieno[2,3-c]pyridin-2-yl-pyridin-3-yloxy)-1-(1H-indol-3-ylmethyl)-ethyl]-carbamic acid tert-butyl ester The title compound was prepared by substituting Example 13A for Example 2A and Example 38A for Example 27A in Example 27B.

Example 362B (1S)-2-(6-Chloro-5-thieno[2,3-c]pyridin-2-yl-pyridin-3-yloxy)-1-(1H-indol-3-ylmethyl)-ethylamine The title compound was prepared by substituting Example 362A for Example 27B in Example 27C. MS (APCI) m/z 436 (M+1)⁺; ¹H NMR (300 Hz, CD₃OD) δ 3.29 (m, 2 H), 4.00 (m, 1 H), 4.26 (dd, J=10.51, 5.76 Hz, 1 H), 4.40 (dd, J=10.51, 3.05 Hz, 1 H), 7.02 (t, J=7.63 Hz, 1 H), 7.10 (t, J=6.95 Hz, 1 H), 7.23 (s, 1 H), 7.36 (d, J=8.14 Hz, 1 H), 7.58 (d, J=7.80 Hz, 1 H), 7.74 (d, J=3.05 Hz, 1 H), 8.05 (s, 1 H), 8.29 (d, J=3.05 Hz, 1 H), 8.35 (d, J=6.10 Hz, 1 H), 8.64 (d, J=6.10 Hz, 1 H), 9.57 (s, 1 H); Anal. Calcd for $C_{23}H_{19}ClN_4OS \cdot 2.6$ TFA: C, 46.31; H, 2.98; N, 7.66. Found: C, 46.22; H, 2.94; N, 7.52.

EXAMPLE 363

5-[(2S)-2-Amino-3-(1H-indol-3-yl)-propoxy]-3-isoquinolin-6-yl-pyridine-2-carbonitrile

Example 363A (1S)-[2-(6-Chloro-5-isoquinolin-6-yl-pyridin-3-yloxy)-1-(1H-indol-3-ylmethyl)-ethyl]-carbamic acid tert-butyl ester The title compound was prepared by substituting Example 13A for Example 2A in Example 27B. MS (APCI) m/z 529 (M+1)⁺.

Example 363B (1S)-[2-(6-Cyano-5-isoquinolin-6-yl-pyridin-3-yloxy)-1-(1H-indol-3-ylmethyl)-ethyl]-carbamic acid tert-butyl ester A 10 mL RBF was charged with Example 363A (100 mg, 0.189 mmol), zinc cyanide (56 mg, 0.47 mmol) and Pd(PPh₃)₄ (44 mg, 0.0378 mmol), and was purged with nitrogen. Anhydrous DMF (3 mL) was added and the solution was purged with nitrogen again. The reaction mixture was stirred at 90° C. for 70 h. After cooled, the mixture was partitioned between ethyl acetate and brine, and the organic phase was washed with water. The Organic layer was concentrated and the residue was separated by flash chromatography (40–100% EtOAc in hexane) to give the desired product (87.4 mg, 89%). MS (APCI) m/z 520 (M+1)⁺.

Example 363C

5-[(2S)-2-Amino-3-(1H-indol-3-yl)-propoxy]-3-isoquinolin-6-yl-pyridine-2-carbonitrile The desired product was prepared as the trifluoroacetate by substituting Example 363B for Example 27B in Examples 27C. MS (APCI) m/z 421 (M+1)⁺; ¹H NMR (300 Hz, CD₃OD) δ 3.31 (m, 2 H), 4.03 (m, 1 H), 4.34 (dd, J=10.85, 5.76 Hz, 1 H), 4.48 (dd, J=10.85, 3.39 Hz, 1 H), 7.00 (t, J=7.46 Hz, 1 H), 7.10 (t, J=6.95 Hz, 1 H), 7.23 (s, 1 H), 7.35 (d, J=8.14 Hz, 1H), 7.57 (d, J=7.80 Hz, 1 H), 7.64 (d, J=2.71 Hz, 1 H), 8.08 (dd, J=8.48, 1.69 Hz, 1 H), 8.39 (d, J=7.46 Hz, 1 H), 8.37 (d, J=6.44 Hz, 1 H), 8.55 (d, J=7.12 Hz, 1 H), 8.56 (m, 1 H), 8.65 (d, J=6.10 Hz, 1 H), 9.72 (s, 1 H); Anal. Calcd for $C_{26}H_{21}N_5O \cdot 2.9$ TFA: C, 50.92; H, 3.21; N, 9.34. Found: C, 50.98; H, 3.23; N, 9.48.

EXAMPLE 364

(1S)-1-(1H-Indol-3-ylmethyl)-2-[5-(3-phenyl-isoquinolin-6-yl)-pyridin-3-yloxy]-ethylamine

Example 364A (1S)-{1-(1H-Indol-3-ylmethyl)-2-[5-(3-phenyl-isoquinolin-6-yl)-pyridin-3-yloxy]-ethyl}-carbamic acid tert-butyl ester To a solution of Example 80E (150 mg, 0.28 mmol), (1,1,1-tributylstannyl)benzene (137 mg, 0.57 mmol), tris (dibenzylideneacetone)-dipalladium (27 mg, 0.028 mmol) and 2-dicyclohexylphosphino-2'-dimethylamino-1,1'-biphenyl (22 mg, 0.057 mmol) in dry DMF (10 ml) triethyl amine was added under N₂. The resulting solution was stirred 3 hours at 100° C. The reaction solution was partitioned between ethylacetate and water. The organic layer was washed (brine), dried (Na₂SO₄), filtered and concentrated under vacumm. Purification on silica gel with 60% ethyl acetate/hexane to provide the title compound (70 mg, 47%). MS (DCI/NH₃) m/e 571 (M+1)⁺.

Example 364B (1S)-1-(1H-Indol-3-ylmethyl)-2-[5-(3-phenyl-isoquinolin-6-yl)-pyridin-3-yloxy]-ethylamine The title compound was prepared as trifluoroacetic acid salt by substituting Example 354A for Example 27B in Example 27C. MS (DCI/NH₃) m/e 471 (M+1)⁺;. ¹H NMR (300 Hz, D₆-DMSO) δ 11.04 (s; 1H), 9.49 (s; 1H), 8.74 (s; 1H), 8.45 (s; 1H), 8.44 (s; 1H), 8.39 (s; 1H), 8.28 (d; 1H; J=8.4 Hz), 8.23 (d; 1H; J=7.5 Hz), 8.08 (s; 2H), 8.02 (d; 1H; J=8.4 Hz), 7.83 (s; 1H), 7.63 (d; 1H; J=8.4 Hz), 7.55 (t; 3H; J=7.5 Hz), 7.47 (d; 1H; J=7.5 Hz), 7.37 (d; 1H; J=8.4 Hz), 7.31 (s; 1H), 7.10 (t; 1H; J=7.2 Hz), 7.00 (t; 1H; J=7.2 Hz), 4.40 (m; 1H), 4.23 (m; 1H), 3.88 (m; 1H), 3.18 (m; 2H)

The following compounds were prepared by substituting the appropriate tributylsannyl reagents for (1,1,1-tributylstannyl)benzene in Example 364.

EXAMPLE 365

(1S)-2-[5-(3-Ethyl-isoquinolin-6-yl)-pyridin-3-yloxy 1-(H-indol-3-ylmethyl)-ethylamine MS (DCI/NH₃) m/e 423 (M+1)⁺;. ¹H NMR (300 Hz, D6-DMSO) δ=11.04 (s; 1H), 9.61 (s; 1H), 8.77 (s; 1H), 8.47 (s; 1H), 8.45 (s; 1H), 8.42 (d; 1H; J=9.0 Hz), 8.20 (s; 2H), 8.14 (d; 2H; J=9.0 Hz), 8.03 (s; 2H), 7.85 (s; 1H), 7.63 (d; 1H; J=7.5 Hz), 7.38 (d; 1H; J=7.5 Hz), 7.30 (s; 1H), 7.10 (t; 1H; J=7.5 Hz), 7.00 (t; 1H; J=7.5 Hz), 4.40 (m; 1H), 4.22 (m; 1H), 3.88 (m; 1H), 3.18 (m; 2H), 3.04 (q; 2H; J=7.5 Hz), 1.37 (t; 3H; J=7.5 Hz).

EXAMPLE 366

(1S)-1-(1H-Indol-3-ylmethyl)-2-[5-(3-pyridin-4-yl-isoquinolin-6-yl)-pyridin-3-yloxy]-ethylamine MS (DCI/NH₃) m/e 472 (M+1)⁺;. ¹H NMR (300 Hz, D₆-DMSO) δ=11.04 (s; 1H), 9.54 (s; 1H), 8.93 (d; 2H; J=7.5 Hz), 8.87 (d; 2H; J=7.5 Hz), 8.83 (s; 1H), 8.70 (s; 1H), 8.43 (s; 2H), 8.35 (d; 1H; J=8.4 Hz), 8.09 (d; 2H; J=8.4 Hz), 7.84 (s; 1H), 7.61 (d; 1H; J=8.4 Hz), 7.38 (d; 1H; J=8.4 Hz), 7.25 (s; 1H), 7.12 (t; 1H; J=8.4 Hz), 7.03 (t; 1H; J=8.4 Hz), 4.45 (m; 1H), 4.30 (m; 1H), 4.00 (m; 1H), 3.30 (m; 2H)

EXAMPLE 367

(1S)-2-[5-(3-Furan-2-yl-isoquinolin-6-yl)-pyridin-3-yloxy]-1-(1H-indol-3-ylmethyl)-ethylamine MS (DCI/NH₃) m/e 461 (M+1)⁺; ¹H NMR (300 Hz, D₆-DMSO) δ=11.04 (s; 1H), 9.39 (s; 1H), 8.74 (s; 1H), 8.44 (s; 1H), 8.41 (s; 1H), 8.25 (d; 1H; J=8.4 Hz), 8.18 (m; 3H), 8.00 (d; 2H; J=8.4 Hz), 7.89 (s; 1H), 7.83 (s; 1H), 7.63 (d; 1H; J=8.4 Hz), 7.39 (d; 1H; J=8.4 Hz), 7.31 (s; 1H), 7.18 (s; 1H), 7.11 (t; 1H; J=8.4 Hz), 7.01 (t; 1H; J=8.4 Hz), 6.71 (s; 1H), 4.40 (m; 1H), 4.21 (m; 1H), 3.88 (m; 1H), 3.18 (m; 2H)

EXAMPLE 368

(1S)-1-(1H-Indol-3-ylmethyl)-2-[5-(3-phenylethynyl-isoquinolin-6-yl)-pyridin-3-yloxy]-ethylamine MS (DCI/NH₃) m/e 495 (M+1)⁺; ¹H NMR (300 Hz, D₆-DMSO) δ=11.04 (s; 1H), 9.41 (s; 1H), 8.73 (s; 1H), 8.45

(s; 1H), 8.35 (s; 1H), 8.31 (d; 1H; J=5.4 Hz), 8.24 (s; 2H), 8.21 (s; 1H), 8.07 (d; 1H; J=5.4 Hz), 7.82 (s; 1H), 7.65 m; 4H), 7.48 (m; 2H), 7.39 (d; 1H; J=5.4 Hz), 7.30 (s; 1H), 7.10 (t; 1H; J=5.4 Hz), 7.00 (t; 1H; J=5.4 Hz), 4.40 (m; 1H), 4.22 (m; 1H), 4.13 (m; 1H), 3.18 (m; 2H).

EXAMPLE 369

(1S)-1-(1H-Indol-3-ylmethyl)-2-[5-(3-prop-1-ynyl-isoquinolin-6-yl)-pyridin-3-yloxy]-ethylamine MS (DCI/NH$_3$) m/e 433 (M+1)$^+$; $^1$H NMR (300 Hz, D$_6$-DMSO) δ=11.04 (s; 1H), 9.32 (s; 1H), 8.71 (s; 1H), 8.43 (s; 1H), 8.28 (s; 1H), 8.25 (d; 1H; J=8.4 Hz), 8.18 (s; 2H), 8.02 (d; 1H; J=8.4 Hz), 7.99 (s; 1H), 7.80 (s; 1H), 7.62 (d; 1H; J=8.4 Hz), 7.38 (d; 1H; J=8.4 Hz), 7.30 (s; 1H), 7.10 (t; 1H; J=8.4 Hz), 7.00 (t; 1H; J=8.4 Hz), 4.40 (m; 1H), 4.21 (m; 1H), 3.88 (m; 1H), 3.18 (m; 2H), 2.13 (s; 3H).

EXAMPLE 370

(1S)-1-(1H-Indol-3-ylmethyl)-2-[5-(3-vinyl-isoquinolin-6-yl)-pyridin-3-yloxy]-ethylamine MS (DCI/NH$_3$) m/e 421 (M+1)$^+$; $^1$H NMR (300 Hz, D6-DMSO) δ=11.04 (s; 1H), 9.36 (s; 1H), 8.71 (s; 1H), 8.42 (s; 1H), 8.28 (s; 1H), 8.25 (d; 1H; J=9.0 Hz), 8.18 (s; 2H), 8.00 (d; 1H; J=9.0 Hz), 7.85 (s; 1H), 7.81 (s; 1H), 7.63 (d; 1H; J=8.4 Hz), 7.38 (d; 1H; J=8.4 Hz), 7.29 (s; 1H), 7.10 (t; 1H; J=8.4 Hz), 7.01 (t; 1H; J=8.4 Hz), 6.98 (dd; 1H; J=17.4 Hz; J=12.0 Hz), 6.40 (d; 1H; J=17.4 Hz), 5.50 (d; 1H; J=12.0 Hz), 4.40 (m; 1H), 4.21 (m; 1H), 3.88 (m; 1H), 3.18 (m; 2H).

EXAMPLE 371

(1S)-6-{5-[2-Amino-3-(1H-indol-3-yl)-propoxy]-pyridin-3-yl}-isoquinoline-3-carbonitrile

Example 371A (1S)-[2-[5-(3-Cyano-isoquinolin-6-yl)-pyridin-3-yloxy]-1-(1H-indol-3-ylmethyl)-ethyl]-carbamic acid tert-butyl ester The desired product was obtained by substituting Example 80E for example 363A in Example 363B.

Example 371B (1S)-6-{5-[2-Amino-3-(1H-indol-3-yl)-propoxy]-pyridin-3-yl}-isoquinoline-3-carbonitrile The desired product was obtained as trifluoroacetic acid salt by substituting Example 371A for Example 27B in Example 27C. MS (DCI/NH$_3$) m/e 420 (M+1)$^+$; $^1$H NMR (300 Hz, D$_6$-DMSO) δ=11.04 (s; 1H), 9.52 (s; 1H), 8.75 (s; 1H), 8.64 (s; 1H), 8.47 (s; 2H), 8.42 (d; 1H; J=6.0 Hz), 8.26 (m; 3H), 7.84 (s; 1H), 7.62 (d; 1H; J=6.0 Hz), 7.38 (d; 1H; J=6.0 Hz), 7.31 (s; 1H), 7.10 (t; 1H; J=6.0 Hz), 7.00 (t; 1H; J=6.0 Hz), 4.40 (m; 1H), 4.22 (m; 1H), 3.88 (m; 1H), 3.18 (m; 2H).

EXAMPLE 372

(1S)-1-(1H-Indol-3-ylmethyl)-2-(5-isoquinolin-6-yl-6-vinyl-pyridin-3-yloxy)-ethylamine The desired product was prepared as the trifluoroacetate by substituting tributylvinyltin for tributylphenyltin and Example 363A for Example 80E in Example 364. MS (APCI) m/z 420 (M+1)$^+$; $^1$H NMR (300 Hz, CD$_3$OD) δ 3.30 (m, 2 H), 3.98 (m, 1 H), 4.24 (dd, J=10.51, 5.76 Hz, 1 H), 4.38 (dd, J=10.51, 3.05 Hz, 1 H), 5.39 (dd, J=10.85, 1.70 Hz, 1 H), 6.24 (dd, J=16.95, 1.70 Hz, 1 H), 6.66 (dd, J=17.12, 10.68 Hz, 1 H), 7.00 (dd, J=6.78, 6.10 Hz, 1 H), 7.09 (t, J=7.63 Hz, 1 H), 7.22 (s, 1 H), 7.35 (d, J=8.14 Hz, 1 H), 7.40 (d, J=2.71 Hz, 1 H), 7.57 (d, J=7.80 Hz, 1 H), 7.95 (dd, J=8.48, 1.70 Hz, 1 H), 8.22 (s, 1 H), 8.45 (d, J=7.46 Hz, 1H), 8.45 (s, 1 H), 8.56 (d, J=8.81 Hz, 1 H), 8.64 (d, J=6.44 Hz, 1 H), 9.79 (s, 1 H); Anal. Calcd for C$_{27}$H$_{24}$N$_4$O.4 TFA: C, 47.96, 3.22; N, 6.39. Found: C, 48.02; H, 3.00; N, 6.07.

EXAMPLE 373

(1S)-2-(6-Ethynyl-5-isoquinolin-6-yl-pyridin-3-yloxy)-1-(1H-indol-3-ylmethyl)-ethylamine The desired product was prepared as the trifluoroacetate by substituting tributylethynyltin for tributylphenyltin and Example 363A for Example 80E in Example 364. MS (APCI) m/z 419 (M+1)$^+$; $^1$H NMR (300 Hz, CD$_3$OD) δ 3.31 (m, 2 H), 3.67 (s, 1 H), 3.99 (m, 1 H), 4.28 (dd, (J=10.74, 5.83 Hz, 1 H), 4.42 (dd, J=10.74, 3.07 Hz, 1 H), 7.00 (t, J=7.06 Hz, 1 H), 7.09 t, J=7.21 Hz, 1 H), 7.23 (s, 1 H), 7.35 (d, J=8.29 Hz, 1 H), 7.55 (m, 1 H), 7.56 (d, J=7.98 Hz, 1 H), 8.19 (dd, J=8.59, 1.53 Hz, 1 H), 8.42 (s, 2 H), 8.47 (d, J=6.44 Hz, 1 H), 8.56 (d, J=8.59 Hz, 1 H), 8.63 (d, J=6.44 Hz, 1 H), 9.79 (s, 1 H); Anal. Calcd for C$_{27}$H$_{22}$N$_4$O.2.9 TFA: C, 52.59; H, 3.35; N, 7.48. Found: C, 52.52; H, 3.44; N, 7.01.

EXAMPLE 374

(1S)-2-(6-Furan-2-yl-5-isoquinolin-6-yl-pyridin-3-yloxy)-1-(1H-indol-3-ylmethyl)-ethylamine The desired product was prepared as the trifluoroacetate by substituting tributylethynyltin for tributylstannylfuran and Example 363A for Example 80E in Example 364. MS (APCI) m/z 461 (M+1)$^+$; $^1$H NMR (300 Hz, CD$_3$OD) δ 3.30 (m, 2 H), 3.98 (m, 1 H), 4.25 (dd, J=10.51, 5.76 Hz, 1 H), 4.40 (dd, J=10.51, 3.05 Hz, 1 H), 6.39 (dd, J=3.39, 1.70 Hz, 1 H), 6.44 (d, J=4.41 Hz, 1 H), 7.00 (dd, J=7.80, 7.12 Hz, 1 H), 7.09 (t, J=6.78 Hz, 1 H), 7.21 (s, 1 H), 7.28 (d, J=1.70 Hz, 1 H), 7.37 (d, J=8.14 Hz, 1 H), 7.47 (d, J=2.71 Hz, 1 H), 7.57 (d, J=7.80 Hz, 1 H), 7.80 (dd, J=8.65, 1.53 Hz, 1 H), 8.21 (s, 1 H), 8.42 (d, J=6.78 Hz, 1 H), 8.46 (d, J=7.12 Hz, 1 H), 8.48 (s, 1 H), 8.62 (d, J=6.44 Hz, 1 H), 9.77 (s, 1 H); Anal. Calcd for C$_{29}$H$_{24}$N$_4$O$_2$.3.9 TFA: C, 48.83; H, 3.11; N, 6.19. Found: C, 48.86; H, 3.31; N, 6.18.

EXAMPLE 375

(1S)-1-(1H-Indol-3-ylmethyl)-2-(5-isoquinolin-6-yl-6-phenylethynyl-pyridin-3-yloxy)-ethylamine The desired product was prepared as the trifluoroacetate by substituting tributyl(phenylethynyl)tin tributylphenyltin and Example 363A for Example 80E in Example 364. MS (APCI) m/z 495 (M+1)$^+$; $^1$H NMR (300 Hz, CD$_3$OD) δ 3.30 (m, 2 H), 4.02 (m, 1H), 4.30 (dd, J=10.51, 5.76 Hz, 1 H), 4.44 (dd, J=10.51, 3.05 Hz, 1 H), 7.01 (t, J=7.46 Hz, 1H), 7.11 (t, J=7.46 Hz, 1 H), 7.24 (s, 1 H), 7.29 (m, 5 H), 7.36 (d, J=8.14 Hz, 1 H), 7.61 (d, J=2.71 Hz, 1 H), 7.59 (d, J=7.80 Hz, 1 H), 8.24 (dd, J=8.65, 1.53 Hz, 1 H), 8.38 (d, J=6.44 Hz, 1 H), 8.46 (d, J=2.71 Hz, 1 H), 8.46 (s, 1 H), 8.55 (d, J=8.81 Hz, 1 H), 8.62 (d, J=6.44 Hz, 1 H), 9.72 (s, 1 H); Anal. Calcd for C$_{33}$H$_{26}$N$_4$O.2.3 TFA: C, 59.67; H, 3.77; N, 7.40. Found: C, 59.61; H, 4.04; N, 7.36.

EXAMPLE 376

6-{5-[(2S)-2-Amino-3-(1H-indol-3-yl)-propoxy]-pyridin-3-yl}-isoquinolin-5-ylamine The desired product was prepared as the trifluoroacetate by substituting 5-amino-6-bromoisoquinoline for 6-bromophthalimide in Example 32. MS (APCI) m/z 410 (M+1)$^+$; $^1$H NMR (300 MHz, CD$_3$OD) δ 3.32 (m, 2 H), 4.00 (m, 1 H), 4.27 (dd, J=10.51, 5.76 Hz, 1 H), 4.44 (dd, J=10.51, 3.39 Hz, 1 H), 7.01 (t, J=7.46 Hz, 1 H), 7.10 (t, J=7.46 Hz, 1 H), 7.24 (s, 1H), 7.36 (d, J=7.80 Hz, 1 H), 7.59 (d, J=7.80 Hz, 1 H), 7.67 (d, J=8.14 Hz, 1 H), 7.73 (s, 1H), 7.80 (d, J=8.48 Hz, 1 H) 8.45 (s, 2 H), 8.50 (d, J=6.78 Hz, 1 H), 8.66 (d, J=6.78 Hz, 1 H), 9.60 (s, 1 H); Anal. Calcd for C$_{25}$H$_{23}$N$_5$O.3.3 TFA: C, 48.30; H, 3.37; N, 8.91. Found: C, 48.35; H, 3.44; N, 8.91.

EXAMPLE 377

(1S)-1-(1H-Indol-3-ylmethyl)-2-[5-(8-methyl-isoquinolin-6-yl)-pyridin-3-yloxy]-ethylamine The desired product was prepared as the trifluoroacetate by substituting 6-bromo-8-methyl-isoquinoline for 6-bromophthalimide in Example 32. MS (APCI) m/z 409 (M+1)$^+$; $^1$H NMR (300 MHz, CD$_3$OD) δ 2.91 (s, 3 H), 3.32 (m, 2 H), 4.02 (m, 1 H), 4.32 (dd, J=10.51, 5.76 Hz, 1 H), 4.47 (dd, J=10.51, 3.39 Hz, 1 H), 7.02 (t, J=7.46 Hz, 1 H), 7.11 (t, J=7.63 Hz, 1 H), 7.25 (s, 1 H), 7.37 (d, J=8.14 Hz, 1 H), 7.60 (d, J=8.14 Hz, 1 H), 7.91 (dd, J=8.31, 4.92 Hz, 1H), 7.96 (d, J=1.70 Hz, 1 H), 8.15 (s, 1 H), 8.31 (d, J=2.03 Hz, 1 H), 8.46 (s, 1 H), 8.74 (s, 1H), 8.87 (dd, J=8.48, 1.70 Hz, 1 H), 9.08 (dd, J=4.92, 1.53 Hz, 1 H); Anal. Calcd for C$_{26}$H$_{24}$N$_4$O.3.5 TFA: C, 49.08; H, 3.43; N, 6.94. Found: C, 49.23; H, 3.24; N, 6.87.

EXAMPLE 378

(1S)-2-[5-(4-Chloro-thieno[2,3-c]pyridin-2-yl)-pyridin-3-yloxy]-1-(1H-indol-3-ylmethyl)-ethylamine The title compound was prepared by substituting 4-chlorothieno[2,3-c]pyridine for thieno[2,3-c]pyridine in Example 38. MS (APCI) m/z 435 (M+1)$^+$; $^1$H NMR (300 MHz, CD$_3$OD) δ 3.31 (m, 2 H), 4.01 (m, 1 H), 4.29 (dd, J=10.51, 5.76 Hz, 1 H), 4.44 (dd, J=10.51, 3.05 Hz, 1 H), 7.04 (t, J=8.14 Hz, 1 H), 7.12 (t, J=6.95 Hz, 1 H), 7.25 (s, 1 H), 7.39 (d, J=8.14 Hz, 1 H), 7.61 (d, J=7.80 Hz, 1 H), 7.84 (t, J=2.71 Hz, 1 H), 8.04 (s, 1 H), 8.42 (d, J=2.03 Hz, 1 H), 8.51 (s, 1 H), 8.72 (s, 1 H), 9.13 (s, 1 H); Anal. Calcd for C$_{23}$H$_{19}$ClN$_4$OS.2.8 TFA: C, 45.55; H, 2.91; N, 7.43. Found: C, 45.42; H, 2.70; N, 7.28.

EXAMPLE 379

(1S)-1-(1H-Indol-3-ylmethyl)-2-[5-(4-phenyl-thieno[2,3-c]pyridin-2-yl)-pyridin-3-yloxy]-ethylamine The title compound was prepared by substituting 4-phenylthieno[2,3-c]pyridine for thieno[2,3-c]pyridine in Example 38. MS (APCI) m/z 477 (M+1)$^+$; $^1$H NMR (300 MHz, CD$_3$OD) δ 3.31 (m, 2 H), 4.00 (m, 1 H), 4.26 (dd, J=10.51, 5.76 Hz, 1 H), 4.41 (dd, J=10.51, 3.39 Hz, 1 H), 6.99 (t, J=6.95 Hz, 1 H), 7.10 (t, J=7.12 Hz, 1 H), 7.22 (s, 1 H), 7.36 (d, J=7.80 Hz, 1 H), 7.57 (d, J=7.80 Hz, 1 H), 7.65 (m, 3 H), 7.73 (t, J=2.03 Hz, 1 H), 7.76 (d, J=1.70 Hz, 1 H), 7.84 (m, 1 H), 8.11 (s, 1 H), 8.46 (s, 1 H), 8.62 (s, 1 H), 8.74 (s, 1 H), 9.52 (s, 1 H);. Anal. Calcd for C$_{29}$H$_{24}$N$_4$OS.2.8 TFA: C, 52.22; H, 3.39; N, 7.04. Found: C, 52.11; H, 3.13;N, 6.91.

EXAMPLE 380

(1S)-1-(1H-Indol-3-ylmethyl)-2-[5-(4-phenoxy-thieno[2,3-c]pyridin-2-yl)-pyridin-3-yloxy]-ethylamine The title compound was prepared by substituting 4-phenoxythieno[2,3-c]pyridine for thieno[2,3-c]pyridine in Example 38. MS (APCI) m/z 493 (M+1)$^+$; $^1$H NMR (300 MHz, CD$_3$OD) δ 3.30 (m, 2 H), 4.01 (m, 1 H), 4.27 (dd, J=10.51, 5.76 Hz, 1 H), 4.42 (dd, J=10.51, 3.05 Hz, 1 H), 7.03 (t, J=7.46 Hz, 1 H), 7.11 (t, J=7.46 Hz, 1 H), 7.24 (s, 1 H), 7.25 (d, J=8.82 Hz, 1 H), 7.33 (t, J=7.46 Hz, 2 H), 7.38 (d, J=7.80 Hz, 1 H), 7.52 (t, J=7.97 Hz, 2 H), 7.60 (d, J=7.80 Hz, 1 H), 7.85 (s, 1 H), 8.00 (s, 1 H), 8.16 (s, 1 H), 8.44 (d, J=2.03 Hz, 1 H), 8.72 (s, 1 H), 9.17 (s, 1 H).

EXAMPLE 381

(1S)-1-(1H-Indol-3-ylmethyl)-2-[5-(4-vinyl-thieno[2,3-c]pyridin-2-yl)-pyridin-3-yloxy]-ethylamine Example 381A (1S)-[2-[5-(4-Chloro-thieno[2,3-c]pyridin-2-yl)-pyridin-3-yloxy]-1-(1H-indol-3-ylmethyl)-carbamic acid tert-butyl ester The title compound was prepared by substituting 4-chlorothieno[2,3-c]pyridine for thieno[2,3-c]pyridine in Example 38. MS (APCI) m/z 535 (M+1)$^+$.

Example 381B (1S)-{1-(1H-Indol-3-ylmethyl)-2-[5-(4-vinyl-thieno[2,3-c]pyridin-2-yl)-pyridin-3-yloxy]-ethyl}-carbamic acid tert-butyl ester A 25 mL RBF was charged with Example 381A (102 mg, 0.19 mmol), Pd$_2$(dba)$_3$ (18 mg, 0.019 mmol), and 2-dicyclohexylphosphino-2'-(N,N-dimethylamino)biphenyl (15 mg, 0.038 mmol), and was purged with N$_2$. Anhydrous DMF (5 mL), tributylvinyltin (111 μL, 0.38 mmol) and Et$_3$N (80 μL) were added via syringe. The solution was purged with N$_2$ again and was heated at 70° C. for 20 h. After cooled, ethyl acetate (50 mL) was added. The mixture was washed with brine (50 mL) and water (50 mL). The ethyl acetate solution was concentrated, and the residual oil was separated by flash chromatography (A: 2:1 EtOAc/hexane, 0–15% CH$_3$OH in A) to give the desired product (72 mg, 72%). MS (APCI) m/z 527 (M+1)$^+$.

Example 381C (1S)-1-(1H-Indol-3-ylmethyl)-2-[5-(4-vinyl-thieno[2,3-c]pyridin-2-yl)-pyridin-3-yloxy]-ethylamine The desired product was prepared as the trifluoroacetate by substituting Example 381B for Example 27B in Examples 27C. MS (APCI) m/z 427 (M+1)$^+$; $^1$H NMR (300 MHz, CD$_3$OD) δ 3.32 (m, 2 H), 4.03 (m, 1 H), 4.30 (dd, J=10.51, 5.76 Hz, 1 H), 4.46 (dd, J=10.51, 3.39 Hz, 1 H), 5.84 (d, J=11.19 Hz, 1 H), 6.26 (d, J=17.29 Hz, 1 H), 7.03 (t, J=7.46 Hz, 1 H), 7.12 (t, J=7.63 Hz, 1 H), 7.25 (s, 1 H), 7.35 (d, J=10.85 Hz, 1 H), 7.41 (d, J=10.85 Hz, 1 H), 7.60 (d, J=7.80 Hz, 1 H), 7.90 (m, 1 H), 8.44 (s, 1 H), 8.49 (d, J=2.37 Hz, 1 H), 8.79 (s, 2 H), 9.42 (s, 1 H); Anal. Calcd for C$_{25}$H$_{22}$N$_4$OS.3.2 TFA: C, 47.65; H, 3.21; N, 7.08. Found: C, 47.74; H, 3.13; N, 6.96.

EXAMPLE 382

(1S)-2-[5-(4-Ethyl-thieno[2,3-c]pyridin-2-yl)-pyridin-3-yloxy]-1-(1H-indol-3-ylmethyl)-ethylamine To a solution of Example 381A (50 mg, 0.063 mmol) in methanol (4 mL) was added triethylamine (56 μL) and 10%

Pd/C (20 mg) under nitrogen. The suspension was purged with H$_2$ (balloon) and was stirred at rt for 6 h. The solid material was filtered off. The filtrate was concentrated and the residue was purified by HPLC (Zorbax, C-18, 250×2.54 column, Mobile phase A: 0.1% TFA in H$_2$O; B: 0.1% TFA in CH$_3$CN; 0–100% gradient) to provide the title compound (37.2 mg, 74%). MS (APCI) m/z 429 (M+1)$^+$; $^1$H NMR (300 MHz, CD$_3$OD) δ 1.46 (t, J=7.46 Hz, 3 H), 3.23 (q, J=7.46 Hz, 2 H), 3.36 (m, 2 H), 4.03 (m, 1H), 4.31 (dd, J=10.51, 5.76 Hz, 1 H), 4.47 (dd, J=10.51, 3.39 Hz, 1 H), 7.02 (t, J=7.46 Hz, 1H), 7.12 (t, J=7.46 Hz, 1 H), 7.25 (s, 1 H), 7.38 (d, J=8.14 Hz, 1 H), 7.60 (d, J=7.80 Hz, 1 H), 7.92 (t, J=2.03 Hz, 1 H), 8.39 (s, 1 H), 8.49 (s, 1 H), 8.49 (d, J=3.05 Hz, 1 H), 8.81 (d, J=1.70 Hz, 1 H), 9.45 (s, 1 H); Anal. Calcd for C$_{25}$H$_{24}$N$_4$OS.3.3 TFA: C, 47.16; H, 3.42; N, 6.96. Found: C, 47.03; H, 3.34; N, 6.96.

EXAMPLE 383

(1S)-(2-{5-[2-Amino-3-(1H-indol-3-yl)-propoxy]-pyridin-3-yl}-thieno[2,3-c]pyridin-4yl)-phenyl-amine

Example 383A

(1S)-{1-(1H-Indol-3-ylmethyl)-2-[5-(4-phenylamino-thieno[2,3-c]pyridin-2-yl)-pyridin-3-yloxy]-ethyl}-carbamic acid tert-butyl ester A 25 mL RBF was charged with Example 381A (100 mg, 0.186 mmol), Pd$_2$(dba)$_3$ (17 mg, 0.0186 mmol), and 1,3-bis(2,6-di-1-propylphenyl)imidazolium chloride (Nolan ligand) (16 mg, 0.0372 mmol), and was purged with N$_2$. Anhydrous dioxane (3 mL), aniline (21 mg, 0.224 mmol) and potassium tert-butoxide (1.0 M solution in THF, 0.279 mL) were added via syringe. The solution was purged with N$_2$ again, and was heated at 100° C. for 20 h. After cooled, ethyl acetate (50 mL) was added, and the mixture was washed with brine (50 mL) and water. The EtOAc solution was concentrated, and the residue was separated by flash chromatography (30–80% EtOAc in hexane) to provide the desire product (34 mg, 31%). MS (APCI) m/z 592 (M+1)$^+$.

Example 383B

(1S)-(2-{5-[2-Amino-3-(1H-indol-3-yl)-propoxy]-pyridin-3-yl}-thieno[2,3-c]pyridin-4-yl)-phenyl-amine The desired product was prepared as the trifluoroacetate by substituting Example 383A for Example 27B in Examples 27C. MS (APCI) m/z 492 (M+1)$^+$; $^1$H NMR (300 MHz, DMSO-d$_6$) δ 3.19 (d, J=7.12 Hz, 2 H), 3.88 (m, 1 H), 4.20 (dd, J=10.51, 5.42 Hz, 1 H), 4.38 (d, J=10.51 Hz, 1 H), 7.01 (t, J=7.46 Hz, 1 H), 7.11 (m, 3 H), 7.38 (m, 6 H), 7.62 (d, J=8.14 Hz, 1 H), 7.78 (s, 1 H), 8.22 (s, 2 H), 8.29 (s, 1 H), 8.47 (s, 1 H), 8.74 (s, 1 H), 8.98 (s, 1 H), 9.06 (s, 1 H), 11.04 (s, 1 H); Anal. Calcd for C$_{29}$H$_{25}$N$_5$OS.3 TFA: C, 50.42; H, 3.39; N, 8.40. Found: C, 50.40; H, 3.58; N, 8.23.

EXAMPLE 384

5-{5-[(2S)-2-Amino-3-(1H-indol-3-yl)-propoxy]-pyridin-3-yl}-3,3-difluoro-1,3-dihydro-indol-2-one The desired product was prepared as the trifluoroacetate by substituting 5-Bromo-3,3-difluoro-1,3-dihydro-indol-2-one for 6-bromophthalimide in Example 32. MS (APCI) m/z 435 (M+1)$^+$; $^1$H NMR (300 MHz, CD$_3$OD) δ 3.36 (m, 2 H), 4.01 (m, 1 H), 4.26 (dd, J=10.51, 5.76 Hz, 1 H), 4.43 (dd, J=110.51, 3.05 Hz, 1 H), 7.03 (t, J=7.46 Hz, 1 H), 7.13 (t, J=7.46 Hz, 2 H), 7.24 (s, 1 H), 7.39 (d, J=8.14 Hz, 1 H), 7.60 (d, J=8.14 Hz, 1 H), 7.79 (m, 2 H), 7.90 (d, J=1.70 Hz, 1 H), 8.36 (d, J=2.03 Hz, 1 H), 8.56 (s, 1 H); Anal. Calcd for C$_{24}$H$_{20}$OF$_2$N$_4$O$_2$.2.5 TFA: C, 48.41; H, 3.15; N, 7.79. Found: C, 48.66; H, 3.20; N, 7.82.

EXAMPLE 385

6-{5-[(2S)-2-Amino-3-(1H-indol-3-yl)-propoxy]-pyridin-3-yl}-3H-oxazolo[4,5-b]pyridin-2-one The desired product was prepared as the trifluoroacetate by substituting 6-Bromo-3H-oxazolo[4,5-b]pyridin-2-one for 6-bromophthalimide in Example 32. MS (APCI) m/z 402 (M+1)$^+$; $^1$H NMR (300 MHz, CD$_3$OD) δ 3.34 (m, 2 H), 4.00 (m, 1 H), 4.28 (dd, J=10.51, 5.76 Hz, 1 H), 4.42 (dd, J=10.51, 3.05 Hz, 1 H), 7.02 (t, J=7.46 Hz, 1 H), 7.12 (t, J=7.63 Hz, 1 H), 7.23 (s, 1 H), 7.38 (d, J=8.14 Hz, 1 H), 7.59 (d, J=7.80 Hz, 1 H), 7.74 (d, J=1.70 Hz, 1 H), 7.83 (d, J=1.70 Hz, 1 H), 8.33 (d, J=2.03 Hz, 1 H), 8.38 (d, J=2.37 Hz, 1 H), 8.55 (s, 1 H); Anal. Calcd for C$_{22}$H$_{19}$N$_5$O$_3$.2.6 TFA: C, 46.81; H, 3.12; N, 10.04. Found: C, 46.67; H, 2.98; N, 9.89.

EXAMPLE 386

N1-(5-Isoquinolin-6-yl-pyridin-3-yl)-ethane-1,2-diamine

Example 386A

[2-(5-Bromo-pyridin-3-ylamino)-ethyl]-carbamic acid tert-butyl ester

A 50 mL RBF was charged with 3,5-dibromopyridine (3.70 g, 15.6 mmol), t-butyl N-(2-aminoethyl)carbamate (2.50 g, 15.6 mmol), Pd$_2$(dba)$_3$ (714 mg, 0.78 mmol), (R)-BINAP (1.46 g, 2.34 mol) and Cs$_2$CO$_3$ (7.62 g, 23.4 mmol), and was purged with N$_2$. Anhydrous toluene (120 mL) was added via syringe. The solution was purged with N$_2$ again, and was heated at 100° C. overnight. After cooled, ethyl acetate (500 mL) was added and the mixture was washed with water. The EtOAc solution was concentrated and the residue was separated by flash chromatography (20–80% EtOAc in hexane) to provide the desried product (2.1 g, 43%). MS (DCI) m/z 316, 318 (M+1)$^+$.

Example 386B

[2-(5-Isoquinolin-6-yl-pyridin-3-ylamino)-ethyl]-carbamic acid tert-butyl ester The desired product was prepared by substituting Example 386A for Example 2A in Example 27B. MS (APCI) m/z 365 (M+1)$^+$.

Example 386C

N1-(5-Isoquinolin-6-yl-pyridin-3-yl)-ethane-1,2-diamine

The desired product was prepared as the trifluoroacetate by substituting Example 386B for Example 27B in Examples 27C. MS (APCI) m/z 265 (M+1)$^+$; $^1$H NMR (300 MHz, CD$_3$OD) δ 3.26 (t, J=5.76 Hz, 2 H), 3.70 (t, J=5.76 Hz, 2 H), 8.10 (s, 1 H), 8.25 (s, 1 H), 8.33 (d, J=8.82 Hz, 1 H), 8.45 (d, J=6.44 Hz, 1 H), 8.56 (s, 1 H), 8.63 (m, 3 H), 9.76 (s, 1 H).

EXAMPLE 387

Naphthalene-2-sulfonic acid (2-amino-ethyl)-(5-isoquinolin-6-yl-pyridin-3-yl)-amide

Example 387A

{2-[(5-Isoquinolin-6-yl-pyridin-3-yl)-(naphthalene-2-sulfonyl)-amino]-ethyl}-carbamic acid tert-butyl ester To a solution of Example 386B (70 mg, 0.192 mmol) in pyridine (3 mL) was added 2-naphthalenesulfonyl chloride (87 mg, 0.384 mmol) at rt. The formed yellow solution was stirred at rt for 15 h. Pyridine was removed under reduced pressure and the residual oil was purified by flash chromatography (0–15% CH$_3$OH in 2:1 EtOAc/hexane) to provide the desire product (69 mg, 65%). MS (APCI) m/z 555 (M+1)$^+$.

Example 387B

Naphthalene-2-sulfonic acid (2-amino-ethyl)-(5-isoquinolin-6-yl-pyridin-3-yl)-amide The desired product was prepared as the trifluoroacetate by substituting Example 387B for Example 27B in Examples 27C. MS (APCI) m/z 455 (M+1)$^+$; $^1$H NMR (300 MHz, CD$_3$OD) δ 3.17 (t, J=5.76 Hz, 2 H), 4.09 (t, J=5.43 Hz, 2 H), 7.66 (t, J=6.78 Hz, 1 H) 7.75 (t, J=7.46 Hz, 1 H), 7.99 (m, 2 H), 8.06 (m, 3 H), 8.13 (d, J=8.82 Hz, 1 H), 8.26 (m, 2 H), 8.31 (s, 1 H), 8.47 (d, J=8.48 Hz, 1 H), 8.59 (m, 2 H), 9.08 (d, J=2.03 Hz, 1 H), 9.69 (s, 1 H).

EXAMPLE 388

Naphthalene-1-sulfonic acid (2-amino-ethyl)-(5-isoquinolin-6-yl-pyridin-3-yl)-amide The desired product was prepared as the trifluoroacetate by substituting 1-naphthalenesulfonyl chloride for 2-naphthalenesulfonyl chloride in Examples 387. MS (APCI) m/z 455 (M+1)$^+$; $^1$H NMR (300 MHz, CD$_3$OD) δ 3.14 (t, J=5.76 Hz, 2 H), 4.04 (t, J=5.76 Hz, 2 H), 7.33 (t, J=7.46 Hz, 1 H), 7.51 (t, J=7.12 Hz, 1 H), 7.70 (t, J=8.14 Hz, 1 H), 7.85 (t, J=2.20 Hz, 1 H), 7.92 (dd, J=8.48, 1.70 Hz, 1 H), 8.04 (dd, J=8.31, 3.56 Hz, 2 H), 8.15 (s, 1 H), 8.29 (d, J=4.75 Hz, 1 H), 8.31 (d, J=5.42 Hz, 2 H), 8.47 (d, J=8.48 Hz, 1 H), 8.60 (d, J=6.44 Hz, 1 H), 8.63 (d, J=2.37 Hz, 1 H), 9.03 (d, J=2.03 Hz, 1 H), 9.67 (s, 1 H).

EXAMPLE 389

5-Dimethylamino-naphthalene-1-sulfonic acid (2-amino-ethyl)-(5-isoquinolin-6-yl-pyridin-3-yl)-amide The desired product was prepared as the trifluoroacetate by substituting dansyl chloride for 2-naphthalenesulfonyl chloride in Example 387. MS (APCI) m/z 498 (M+1)$^+$; $^1$H NMR (300 MHz, CD$_3$OD) δ 2.81 (s, 6 H), 3.16 (d, J=5.76 Hz, 2 H), 4.06 (d, J=5.76 Hz, 2 H), 7.16 (d, J=7.12 Hz, 1 H), 7.25 (t, J=7.80 Hz, 1 H), 7.67 (dd, J=8.48, 7.80 Hz, 1 H), 7.75 (d, J=8.48 Hz, 1 H), 7.85 (t, J=2.20 Hz, 1 H), 7.98 (dd, J=8.48, 1.70 Hz, 1 H), 8.29 (d, J=7.12 Hz, 1 H), 8.30 (s, 1 H), 8.43 (d, J=6.44 Hz, 1 H), 8.53 (d, J=8.82 Hz, 1 H), 8.64 (m, 3 H), 9.03 (d, J=2.03 Hz, 1 H), 9.76 (s, 1 H); Anal. Calcd for C$_{28}$H$_{27}$N$_5$O$_2$S.4 TFA: C, 45.34; H, 3.28; N, 7.34. Found: C, 45.28; H, 3.11; N, 7.23.

EXAMPLE 390

Quinoline-5-sulfonic acid (2-amino-ethyl)-(5-isoquinolin-6-yl-pyridin-3-yl)-amide The desired product was prepared as the trifluoroacetate by substituting 8-quinolinesulfonyl chloride for 2-naphthalenesulfonyl chloride in Example 387. MS (APCI) m/z 456 (M+1)$^+$; $^1$H NMR (300 MHz, CD$_3$OD) δ 3.29 (t, J=5.43 Hz, 2 H), 4.57 (t, J=5.43 Hz, 2 H), 7.65 (t, J=7.46 Hz, 1 H), 7.76 (dd, J=8.48, 4.41 Hz, 1 H), 8.12 (dd, J=8.48, 1.70 Hz, 1 H), 8.18 (t, J=2.03 Hz, 1 H), 8.29 (s, 1 H), 8.31 (d, J=7.12 Hz, 1 H), 8.33 (dd, J=7.46, 1.36 Hz 1 H), 8.41 (s, 1 H), 8.42 (d, J=7.80 Hz, 1 H), 8.55 (d, J=8.82 Hz, 1 H), 8.56 (dd, J=8.31, 1.87 Hz, 1H), 8.62 (d, J=6.44 Hz, 1 H), 8.95 (d, J=1.70 Hz, 1 H), 9.08 (dd, J=4.41, 1.70 Hz, 1 H), 9.74 (s, 1 H); Anal. Calcd for C$_{25}$H$_{21}$N$_5$O$_2$S.3.3 TFA: C, 45.63; H, 2.94; N, 8.42. Found: C, 45.70; H, 2.64; N, 8.18.

EXAMPLE 391

Biphenyl-4-sulfonic acid (2-amino-ethyl)-(5-isoquinolin-6-yl-pyridin-3-yl)-amide The desired product was prepared as the trifluoroacetate by substituting biphenyl-4-sulfonyl chloride for 2-naphthalenesulfonyl chloride in Example 387. MS (APCI) m/z 481 (M+1)$^+$; $^1$H NMR (300 MHz, CD$_3$OD) δ 3.16 (t, J=5.76 Hz, 2 H), 4.10 (t, J=5.76 Hz, 2 H), 7.49 (m, 3H), 7.68 (d, J=8.14 Hz, 2 H), 7.72 (d, J=8.82 Hz, 2 H), 7.89 (d, J=8.48 Hz, 2 H), 8.07 (t, J=2.03 Hz, 1 H), 8.22 (dd, J=8.48, 1.70 Hz, 1 H), 8.29 (d, J=6.44 Hz, 1 H), 8.45 (s, 1 H), 8.53 (d, J=8.82 Hz, 1 H), 8.57 (d, J=6.44 Hz, 1 H), 8.63 (d, J=2.03 Hz, 1 H), 9.10 (d, J=1.70 Hz, 1 H), 9.72 (s, 1 H); Anal. Calcd for C$_{28}$H$_{24}$N$_4$O$_2$S.3.1 TFA: C, 49.25; H, 3.27; N, 6.72. Found: C, 49.20; H, 3.24; N, 6.62.

EXAMPLE 392

1-Methyl-1H-imidazole-4-sulfonic acid (2-amino-ethyl)-(5-isoquinolin-6-yl-pyridin-3-yl)-amide The desired product was prepared as the trifluoroacetate by substituting 1-methylimidazole-4-sulfonyl chloride for 2-naphthalenesulfonyl chloride in Example 387. MS (APCI) m/z 409 (M+1)$^+$; $^1$H NMR (300 MHz, CD$_3$OD) δ 3.19 (t, J=5.59 Hz, 2 H), 3.77 (s, 3 H), 4.18 (t, J=5.59 Hz, 2 H), 7.71 (s, 1 H), 7.89 (s, 1 H), 8.31 (m, 2 H), 8.50 (d, J=6.44 Hz, 1 H), 8.57 (d, J=8.14 Hz, 1 H), 8.59 (s, 1 H), 8.62 (d, J=8.48 Hz, 1 H), 8.64 (d, J=6.44 Hz, 1 H), 9.07 (d, J=2.03 Hz, 1 H), 9.78 (s, 1 H); Anal. Calcd for C$_{20}$H$_{20}$N$_6$O$_2$S.3.8 TFA: C, 39.38; H, 2.85; N, 9.98. Found: C, 39.35; H, 2.73; N, 9.79.

EXAMPLE 393

3-Amino-2-[5-(3-methyl-1H-indazol-5-yl)-pyridin-3-yloxy]-propan-1-ol

Example 393A

[3-(tert-Butyl-dimethyl-silanyloxy)-2-hydroxy-propyl]-carbamic acid tert-butyl ester To a solution of t-butyl N-(2,3-dihydroxypropyl) carbamate (9.0 g, 47 mmol) in CH$_2$Cl$_2$ (75 mL) was added t-butyldimethylsilyl chloride (7.80 g, 51.7 mmol), triethylamine (7.86 mL, 56.4 mmol) and DMAP (230 mg). The solution was stirred at rt overnight. After diluting with CH$_2$Cl$_2$ (50 mL), the solution was washed with water (2×100 mL), dried over MgSO$_4$ and concentrated. The residual oil was distilled by Kugelrohr under vacuum to give the desired product (13.6 g, 95%). MS (DCI) m/z 306 (M+1)$^+$.

Example 393B 2-(5-Bromo-pyridin-3-yloxy)-3-(tert-butyl-dimethyl-silanyloxy)-propyl]-carbamic acid tert-Butyl Ester A 100 mL RBF was charged with 3-bromo-5-hydroxypyridine (949 mg, 5.45 mmol), Example 393A (2.0 g, 6.45 mmol) and Ph$_3$P (1.72 g, 6.54 mmol), and was purged with nitrogen. THF (22 mL) was added at 0° C. After stirring at 0° C. for 10 min, DEAD (1.03 mL, 6.54 mmol) was added via syringe. The reaction mixture was stirred at 0° C. for 1 h and at rt overnight. The reaction mixture was concentrated and the residue was separated by flash chromatography (5–30% EtOAc in hexane) to provide the desired product (1.76 g, 70%). MS (DCI) m/z 461, 463 (M+1)+.

Example 393C

5-{5-[2-tert-Butoxycarbonylamino-1-(tert-butyl-dimethyl-silanyloxymethyl)-ethoxy]-pyridin-3-yl}-3-methyl-indazole-1-carboxylic acid tert-butyl ester A 100 mL RBF was charged with Example 393B (1.60 g, 3.47 mmol), Example 203B (1.37 g, 3.47 mmol), Pd$_2$(dba)$_3$ (318 mg, 0.347 mmol), and tri-o-tolylphosphine (318 mg), and was purged with N$_2$. Anhydrous DMF (50 mL) and Et$_3$N (1.45 mL) were added via syringe. The solution was purged with N$_2$ again and was heated at 75° C. for 5 h. After cooled, ethyl acetate (200 mL) was added. The mixture was washed with brine (250 mL) and water (250 mL). The ethyl acetate solution was concentrated and the residual oil was separated by flash chromatography (20–60% EtOAc in hexane) to give the desired product (1.51 g, 71%). MS (DCI) m/z 613 (M+1)+.

Example 393D

5-[5-(2-tert-Butoxycarbonylamino-1-hydroxymethyl-ethoxy)-pyridin-3-yl]-3-methyl-indazole-1-carboxylic acid tert-butyl ester To a solution of Example 393C (1.122 g, 1.83 mmol) in THF (20 mL) was added TBAF (1.92 mL) at rt. The solution was stirred at rt for 1 h and was concentrated. The residual oil was separated by flash chromatography (0–15% CH$_3$OH in 2:1 EtOAc/hexane) to give the title compound (0.82 g, 90%). MS (DCI) m/z 499 (M+1)+.

Example 393E

3-Amino-2-[5-(3-methyl-1H-indazol-5-yl)-pyridin-3-yloxy]-propan-1-ol

The desired product was prepared as HCl salt by substituting Example 393D for Example 27B in Examples 27C. MS (APCI) m/z 299 (M+1)+; $^1$H NMR (300 MHz, DMSO-d$_6$) δ 2.58 (s, 3 H), 3.26 (m, 2 H), 3.68 (dd, J=12.21, 5.09 Hz, 1 H), 3.75 (dd, J=12.54, 4.75 Hz, 1 H), 5.05 (m, J=4.07 Hz, 1 H), 7.62 (d, J=8.81 Hz, 1 H), 7.85 (dd, J=8.81, 1.70 Hz, 1 H) 8.35 (s, 4 H), 8.52 (s, 1 H), 8.64 (d, J=2.37 Hz, 1 H), 8.90 (s, 1 H); Anal. Calcd for C$_{16}$H$_{18}$N$_4$O$_2$.3.2 HCl: C, 46.31; H, 5.15; N, 13.50. Found: C, 46.46; H, 5.12; N, 13.42.

EXAMPLE 394

2-[5-(3-Methyl-1H-indazol-5-yl)-pyridin-3-yloxy]-3-phenoxy-propylamine

Example 394A

5-[5-(2-tert-Butoxycarbonylamino-1-phenoxymethyl-ethoxy)-pyridin-3-yl]-3-methyl-indazole-1-carboxylic acid tert-butyl ester A 25 mL RBF was charged with phenol (42 mg, 0.45 mmol), Example 393D (150 mg, 0.3 mmol) and Ph$_3$P (142 mg, 0.54 mmol), and was purged with nitrogen. THF (4 mL) was added at 0° C. After stirring at 0° C. for 10 min, DEAD (85 µL, 0.54 mmol) was added via syringe. The reaction mixture was stirred at 0° C. for 1 h and at rt overnight. The reaction mixture was concentrated and the residue was separated by flash chromatography (20–60% EtOAc in hexane) to provide the desire product (163 mg, 95%). MS (DCI) m/z 575 (M+1)+.

Example 394B

2-[5-(3-Methyl-1H-indazol-5-yl)-pyridin-3-yloxy]-3-phenoxy-propylamine

The desired product was prepared as the trifluoroacetate by substituting Example 394A for Example 27B in Examples 27C. MS (APCI) m/z 375 (M+1)+; $^1$H NMR (300 MHz, CD$_3$OD) δ 2.62 (s, 3 H), 3.58 (d, J=5.76 Hz, 2 H), 4.34 (dd, J=11.19, 5.09 Hz, 1 H), 4.42 (dd, J=11.19, 3.73 Hz, 1 H), 5.33 (m, 1 H), 6.94 (m, 3 H), 7.26 (dd, J=8.81, 7.46 Hz, 2 H), 7.62 (d, J=7.80 Hz, 1 H), 7.72 (dd, J=8.81, 1.70 Hz, 1 H), 8.09 (s, 1 H), 8.27 (s, 1 H), 8.52 (d, J=2.37 Hz, 1H), 8.75 (d, J=1.36 Hz, 1 H); Anal. Calcd for C$_{22}$H$_{22}$N$_4$O$_2$.2 TFA: C, 51.83; H, 4.02; N, 9.30. Found: C, 51.97; H, 3.97; N, 9.41.

EXAMPLE 395

2-[5-(3-Methyl-1H-indazol-5-yl)-pyridin-3-yloxy]-3-(naphthalen-2-yloxy)-propylamine The desired product was prepared as the trifluoroacetate by substituting 2-naphthol for phenol in Examples 394. MS (APCI) m/z 425 (M+1)+; $^1$H NMR (300 MHz, CD$_3$OD) δ 2.56 (s, 3 H), 3.62 (d, J=5.76 Hz, 2 H), 4.47 (dd, J=11.19, 5.09 Hz, 1 H), 4.56 (dd, J=11.19, 3.73 Hz, 1 H), 5.36 (m, 1 H), 7.08 (dd, J=8.98, 2.54 Hz, 1 H), 7.28 (m, 1 H), 7.33 (d, J=8.14 Hz, 1H), 7.40 (t, J=8.14 Hz, 1 H), 7.54 (d, J=8.48 Hz, 1 H), 7.62 (dd, J=10.17, 1.70 Hz, 1 H), 7.71 (d, J=8.14 Hz, 1 H), 7.72 (d, J=2.03 Hz, 1 H), 7.74 (s, 1 H), 8.00 (s, 1 H), 8.11 (m, 1 H), 8.50 (d, J=2.37 Hz, 1 H), 8.68 (d, J=1.36 Hz, 1 H); Anal. Calcd for C$_{26}$H$_{24}$N$_4$O$_2$.2.8 TFA: C, 51.03; H, 3.63; N, 7.53. Found: C, 51.18; H, 3.47; N, 7.55.

EXAMPLE 396

3-(Biphenyl-4-yloxy)-2-[5-(3-methyl-1H-indazol-5-yl)-pyridin-3-yloxy]-propylamine The desired product was prepared as the trifluoroacetate by substituting 4-phenylphenol for phenol in Examples 394. MS (APCI) m/z 452 (M+1)+; $^1$H NMR (300 MHz, CD$_3$OD) δ 2.57 (s, 3 H), 3.58 (d, J=6.10 Hz, 2 H), 4.39 (dd, J=11.19, 5.09 Hz, 1 H), 4.47 (dd, J=1.53, 3.73 Hz, 1 H), 5.30 (m, 1 H), 6.99 (d, J=8.81 Hz, 2 H), 7.27 (d, J=7.12 Hz, 1 H), 7.36 (t, J=7.46 Hz, 2 H), 7.51 (m, 4 H), 7.57 (d, J=8.48 Hz, 1 H), 7.67 (dd, J=8.81, 1.70 Hz, 1 H), 8.03 (s, 1H), 8.09 (dd, J=4.41, 2.37 Hz, 1 H), 8.49 (d, J=2.37 Hz, 1 H), 8.69 (s, 1 H); Anal. Calcd for C$_{28}$H$_{26}$N$_4$O$_2$.3.2 TFA: C, 50.67; H, 3.61; N, 6.87. Found: C, 50.77; H, 3.51; N, 6.64.

EXAMPLE 397

2-[5-(3-Methyl-1H-indazol-5-yl)-pyridin-3-yloxy]-3-(quinolin-7-yloxy)-propylamine The desired product was prepared as the trifluoroacetate by substituting 7-hydroxyquinoline for phenol in Examples 394. MS (APCI) m/z 426 (M+1)+; $^1$H NMR (300 MHz, CD$_3$OD) δ 2.59 (s, 3 H), 3.64 (d, J=5.76 Hz, 2 H), 4.62 (dd, J=10.85, 5.09 Hz, 1 H), 4.70 (d, J=11.19 Hz, 1 H), 5.42 (m, 1 H), 7.50 (dd, J=9.32, 2.20 Hz, 1 H), 7.58 (dd, J=5.26, 3.22 Hz, 2 H), 7.69 (d, J=8.48 Hz, 1 H), 7.78 (dd, J=8.14, 5.43 Hz, 1 H), 8.03 (s, 1 H), 8.07 (s, 1 H), 8.16 (d, J=9.16 Hz, 1 H), 8.47 (s, 1 H), 8.67 (s, 1 H), 8.88 (d, J=8.14 Hz, 1 H), 8.98 (d, J=4.41 Hz, 1H); Anal. Calcd for $C_{25}H_{23}N_5O_2.3.9$ TFA: C, 45.27; H, 3.12; N, 8.05. Found: C, 45.26; H, 3.05; N, 7.92.

EXAMPLE 398

2-[5-(3-Methyl-1H-indazol-5-yl)-pyridin-3-yloxy]-3-(pyridin-4-yloxy)-propylamine The desired product was prepared as HCl salt by substituting 4-hydroxypyridine for phenol in Examples 394. MS (APCI) m/z 376 (M+1)$^+$; $^1$H NMR (300 MHz, DMSO-$d_6$) δ 2.58 (s, 3 H), 3.40 (br s, 2 H), 4.75 (d, J=11.87 Hz, 1 H), 4.85 (d, J=11.49 Hz, 1 H), 5.61 (m, 1 H), 7.59 (m, 2 H), 7.86 (d, J=8.82 Hz, 1 H), 8.37 (s, 1 H), 8.56 (s, 1 H), 8.66 (s, 1 H), 8.73 (s, 2 H), 8.79 (s, 1 H), 8.81 (s, 1 H), 8.92 (s, 1 H); Anal. Calcd for $C_{21}H_{21}N_5O_2.4.5$ HCl C, 46.75; H, 4.76; N, 12.98. Found: C, 46.77; H, 4.41; N, 12.83.

EXAMPLE 399

2-[5-(3-Methyl-1H-indazol-5-yl)-pyridin-3-yloxy]-3-(naphthalen-1-yloxy)-propylamine The desired product was prepared as the trifluoroacetate by substituting 1-naphthol for phenol in Examples 394. MS (APCI) m/z 426 (M+1)$^+$; $^1$H NMR (300 MHz, CD$_3$OD) δ 3.34 (s, 3 H), 3.65 (d, J=5.76 Hz, 2 H), 4.57 (m, 2 H), 5.49 (m, 1 H), 6.97 (d, J=7.46 Hz, 1 H), 7.23 (t, J=7.63 Hz, 1 H), 7.37 (d, J=7.46 Hz, 1 H), 7.41 (d, J=8.82 Hz, 1 H), 7.44 (d, J=8.48 Hz, 1 H), 7.56 (s, 2 H), 7.74 (d, J=8.48 Hz, 1 H), 7.84 (d, J=7.80 Hz, 1 H), 7.92 (s, 1 H), 8.15 (s, 1 H), 8.50 (d, J=2.03 Hz, 1 H), 8.65 (s, 1 H); Anal. Calcd for $C_{26}H_{24}N_4O_2.3.1$ TFA: C, 49.71; H, 3.51; N, 7.20. Found: C, 49.70; H, 3.47; N, 7.07.

EXAMPLE 400

3-{(2S)-2-Amino-3-[5-(3-methyl-1H-indazol-5-yl)-pyridin-3-yloxy]-propyl}-

Example 400A (2S)-2-tert-Butoxycarbonylamino-3-(5-hydroxy-1H-indol-3-yl)-propionic acid methyl ester To a solution of BOC-5-hydroxy-tryptophan (5.9 g, 18.4 mmol) and iodomethane (3.43 mL) in DMF (80 mL) was added powered KHCO$_3$ (3.68 g). The reaction mixture was stirred at rt for 4 hours. EtOAc (500 mL) was added and the mixture was washed with brine (500 mL) and water (500 mL). The organic phase was concentrated and the residual oil was triturated with CH$_2$Cl$_2$ (20 mL). The formed white solid was collected by filtration, washed with CH$_2$Cl$_2$ (20 mL) and dried to give the desired product (4.48 g, 73%). MS (DCI) m/z 335 (M+1)$^+$.

Example 400B (2S)-2-tert-Butoxycarbonylamino-3-[5-(tert-butyl-dimethyl-silanyloxy)-1H-indol-3-yl]-propionic acid methyl ester To a solution of Example 400A (1.20 g, 3.59 mmol) in DMF (20 mL) was added t-butyldimethylsilyl chloride (649 mg, 4.3 mmol), imidazole (293 mg, 4.3 mmol) and DMAP (50 mg) at rt. The reaction mixture was stirred at rt for 16 hours. EtOAc (100 mL) was added and the mixture was washed with brine (100 mL) and water (100 mL). The organic phase was concentrated and the residual oil was purified by flash chromatography (10–40% EtOAc in hexane) to give the desire product (1.6 g, 100%). MS (DCI) m/z 466 (M+18)$^+$.

Example 400C (1S)-{2-[5-(tert-Butyl-dimethyl-silanyloxy)-1H-indol-3-yl]-1-hydroxymethyl-ethyl}-carbamic acid tert-butyl ester To a solution of Example 400B (1.50 g, 3.3 mmol) in THF (15 mL) was slowly added LiAlH$_4$ powder (127 mg, 3.3 mmol) in several portion at rt. After the addition, the reaction mixture was becoming sticky and the stirring stopped. The temperature of the mixture arises to ~50° C. Ether (30 mL) was added and the mixture was stirred for 20 min. Methanol (2 mL) and diluted HCl was added slowly and the mixture was extracted with ether. The organic phase was washed with water and concentrated. The residue was separated by flash chromatography (20–60% EtOAc in hexane) to give the desired product (982 mg, 70%). MS (DCI) m/z 421 (M+1)$^+$.

Example 400D (1S)-{2-(5-Bromo-pyridin-3-yloxy)-1-[5-(tert-butyl-dimethyl-silanyloxy)-1H-indol-3-ylmethyl]-ethyl}-carbamic acid tert-butyl ester A 100 mL RBF was charged with 3-bromo-5-hydroxypyridine (432 mg, 2.48 mmol), Example 400C (950 mg, 2.26 mmol) and Ph$_3$P (711 mg, 2.71 mmol), and was purged with nitrogen. THF (15 mL) was added at 0° C. After stirring at 0° C. for 10 min, DEAD (427 μL, 2.71 mmol) was added via syringe. The reaction mixture was stirred at 0° C. for 1 h and at rt overnight. The reaction mixture was concentrated and the residue was separated by flash chromatography (10–50% EtOAc in hexane) to provide the desired product (1.05 g, 80%). MS (APCI) m/z 576, 578 (M+1)$^+$.

Example 400E 5-(5-{(2S)-2-tert-Butoxycarbonylamino-3-[5-(tert-butyl-dimethyl-silanyloxy)-1H-indol-3-yl]-propoxy}-pyridin-3-yl)-3-methyl-indazole-1-carboxylic acid tert-butyl ester The desire product was prepared by substituting Example 400D for Example 202A in Example 203C. MS (DCI) m/z 728 (M+1)$^+$.

Example 400F

5-{5-[(2S)-2-tert-Butoxycarbonylamino-3-(5-hydroxy-1H-indol-3-yl)-propoxy]-pyridin-3-yl}-3-methyl-indazole-1-carboxylic acid tert-butyl ester To a solution of Example 400E (850 mg, 1.17 mmol) in THF (10 mL) was added TBAF (1.28 mL, 1.28 mmol) at rt. The solution was stirred at rt for 2 h and was concentrated. The residual oil was purified by flash chromatography (0–15% CH$_3$OH in 2:1 EtOAc/hexane) to give the desired product (530 mg, 74%). MS (DCI) m/z 614 (M+1)$^+$.

Example 400G

3-{(2S)-2-Amino-3-[5-(3-methyl-1H-indazol-5-yl)-pyridin-3-yloxy]-propyl}-1H-indol-5-ol The desired product was prepared as the trifluoroacetate by substituting Example 400F for Example 27B in Examples 27C. MS (APCI) m/z 414 (M+1)⁺; ¹H NMR (300 MHz, CD₃OD) δ 2.63 (s, 3 H), 3.25 (dd, J=7.12, 2.37 Hz, 2 H), 3.98 (m, 1 H), 4.35 (dd, J=10.51, 5.76 Hz, 1H), 4.48 (dd, J=10.51, 3.39 Hz, 1 H), 6.70 (dd, J=8.48, 2.37 Hz, 1 H), 6.93 (d, J=2.03 Hz, 1H), 7.18 (s, 1 H), 7.20 (d, J=8.48 Hz, H), 7.63 (d, J=8.81 Hz, 1 H), 7.71 (dd, J=8.81, 2.03 Hz, 1 H), 8.11 (m, 2 H), 8.41 (d, J=2.37 Hz, 1 H), 8.74 (d, J=1.70 Hz, 1 H); Anal. Calcd fo C₂₄H₂₃N₅O₂.3.7 TFA: C, 45.15; H, 3.22; N, 8.38. Found: C, 45.15; H, 3.45; N, 8.43.

EXAMPLE 401

(1S)-1-(5-Methoxy-1H-indol-3-ylmethyl)-2-[5-(3-methyl-1H-indazol-5-yl)-pyridin-3-yloxy]-ethylamine Example 401A 5-{5-[(2S)-2-tert-Butoxycarbonylamino-3-(5-methoxy-1H-indol-3-yl)-propoxy]-pyridin-3-yl}-3-methyl-indazole-1-carboxylic acid tert-butyl ester A 25 mL RBF was charged with Example 400F (100 mg, 0.163 mmol) and Ph₃P (85 mg, 0.325 mmol), and was purged with nitrogen. THF (4 mL) and methanol (14 μL) were added at 0° C. After stirring at 0° C. for 10 min, DEAD (51 μL, 0.325 mmol) was added via syringe. The reaction mixture was stirred at 0° C. for 1 h and at rt over weekend. The reaction mixture was concentrated and the residue was separated by flash chromatography (50–80% EtOAc in hexane) to provide the desired product (33 mg, 32%). MS (APCI) m/z 628 (M+1)⁺.

Example 401B (1S)-1-(5-Methoxy-1H-indol-3-ylmethyl)-2-[5-(3-methyl-1H-indazol-5-yl)-pyridin-3-yloxy]-ethylamine The desired product was prepared as the trifluoroacetate by substituting Example 401 A for Example 27B in Examples 27C. MS (APCI) m/z 428 (M+1)⁺; ¹H NMR (300 MHz, CD₃OD) δ 2.62 (s, 3 H), 3.33 (m, 2 H), 3.70 (s, 3 H), 3.98 (m, 1 H), 4.32 (dd, J=10.51, 5.42 Hz, 1 H), 4.45 (dd, J=10.51, 3.05 Hz, 1 H), 6.78 (dd, J=8.81, 2.37 Hz, 1 H), 7.05 (d, J=2.03 Hz, 1 H), 7.21 (s, 1 H), 7.27 (d, J=8.81 Hz, 1 H), 7.60 (d, J=7.80 Hz, 1 H), 7.67 (dd, J=8.81, 1.70 Hz, 1H), 7.91 (m, 1 H), 8.03 (s, 1 H), 8.35 (d, J=2.03 Hz, 1 H), 8.65 (s, 1 H).

EXAMPLE 402

(1S)-1-(5-Ethoxy-1H-indol-3-ylmethyl)-2-[5-(3-methyl-1H-indazol-5-yl)-pyridin-3-yloxy]-ethylamine The desired product was prepared as the trifluoroacetate by substituting ethanol for methanol in Example 401. MS (APCI) m/z 442 (M+1)⁺; ¹H NMR (300 MHz, CD₃OD) δ 1.26 (t, J=6.95 Hz, 3 H), 2.62 (s, 3 H), 3.35 (m, 2 H), 3.86 (q, J=7.12 Hz, 2 H), 3.95 (m, 1 H), 4.32 (dd, J=10.51, 5.42 Hz, 1 H), 4.45 (dd, J=10.51, 3.39 Hz, 1 H), 6.78 (dd, J=8.82, 2.37 Hz, 1 H), 7.02 (d, J=2.37 Hz, 1 H), 7.21 (s, 1 H), 7.26 (d, J=8.81 Hz, 1 H), 7.61 (d, J=9.49 Hz, 1H), 7.68 (d, J=8.81 Hz, 1 H), 7.97 (s, 1 H), 8.05 (s, 1 H), 8.37 (d, J=2.37 Hz, 1 H), 8.68 (d, J=1.36 Hz, 1 H); Anal. Calcd for C₂₆H₂₇N₅O₂.3.2 TFA: C, 48.26; H, 3.77; N, 8.68. Found: C, 48.14; H, 3.60; N, 8.45.

EXAMPLE 403

(1S)-1-(5-Butoxy-1H-indol-3-ylmethyl)-2-[5-(3-methyl-1H-indazol-5-yl)-pyridin-3-yloxy]-ethylamine The desired product was prepared as the trifluoroacetate by substituting n-butanol for methanol in Example 401. MS (APCI) m/z 470 (M+1)⁺; ¹H NMR (300 MHz, CD₃OD) δ 0.87 (t, J=7.36 Hz, 3 H), 1.37 (m, 2 H), 1.59 (m, 2 H), 2.61 (s, 3 H), 3.29 (m, 2 H), 3.81 (m, 2 H), 3.97 (s, 1 H), 4.35 (dd, J=10.13, 4.91 Hz, 1 H), 4.46 (d, J=7.98 Hz, 1 H), 6.76 (d, J=8.59 Hz, 1 H), 7.01 (s, 1 H), 7.21 (s, 1 H), 7.25 (d, J=8.59 Hz, 1 H), 7.61 (d, J=8.59 Hz, 1 H), 7.68 (d, J=8.59 Hz, 1 H), 8.06 (s, 2 H), 8.38 (s, 1 H), 8.71 (s, 1 H); Anal. Calcd for C₂₈H₃₁N₅O₂.2.8 TFA: C, 51.16; H, 4.32; N, 8.88. Found: C, 51.36; H, 4.51; N, 8.99.

EXAMPLE 404

(1S)-1-(5-Isopropoxy-1H-indol-3-ylmethyl)-2-[5-(3-methyl-1H-indazol-5-yl)-pyridin-3-yloxy]-ethylamine The desired product was prepared as the trifluoroacetate by substituting isopropanol for methanol in Example 401. MS (APCI) m/z 456 (M+1)⁺; ¹H NMR (400 MHz, CD₃OD) δ 1.18 (m, 6 H), 2.61 (s, 3 H), 3.30 (m, 2 H), 3.97 (s, 1 H), 4.38 (m, 2 H), 4.48 (d, J=8.29 Hz, 1 H), 6.77 (d, J=7.98 Hz, 1 H), 7.07 (s, 1 H), 7.23 (s, 1 H), 7.26 (d, J=8.90 Hz, 1 H), 7.61 (d, J=8.90 Hz, 1 H), 7.69 (d, J=8.59 Hz, 1 H), 8.08 (s, 1 H), 8.12 (s, 1 H), 8.42 (s, 1 H), 8.74 (s, 1H); Anal. Calcd for C₂₇H₂₉N₅O₂.3.2 TFA: C, 48.90; H, 3.96; N, 8.54. Found: C, 48.93; H, 3.88; N, 8.55.

EXAMPLE 405

3-(1H-Indol-3-yl)-2-[5-(3-methyl-1H-indazol-5-yl)-pyridin-3-yloxy]-propan-1

Example 405A 2-(5-Bromo-pyridin-3-yloxy)-3-(1H-indol-3-yl)-propionic acid methyl ester A 100 mL RBF was charged with 3-bromo-5-hydroxypyridine (1.67 g, 9.58 mmol), 2-hydroxy-3-(1H-indol-3-yl)-propionic acid methyl ester (2.1 g, 9.58 mmol) which was synthesized according to literature method (M. E. Jung et al J. Org. Chem. 1999, 64, 2976) and Ph₃P (3.01 g, 11.5 mmol), and was purged with nitrogen. THF (40 mL) was added at 0° C. After stirring at 0° C. for 10 min, DEAD (1.81 mL, 11.5 mmol) was added via syringe. The reaction mixture was stirred at 0° C. for 1 h and at rt overnight. The reaction mixture was concentrated and the residue was separated by flash chromatography (20–60% EtOAc in hexane) to provide the desired product (3.4 g, 94%). MS (DCI) m/z 375, 377 (M+1)⁺.

Example 405B 2-(5-Bromo-pyridin-3-yloxy)-3-(1H-indol-3-yl)-propan-1-ol

To a solution of Example 405A (3.2 g, 8.5 mmol) in THF (20 mL) and ether (30 mL) was slowly added LiAlH₄ powder (323 mg, 8.5 mmol) in several portion at rt. While LAH was added a lot of solid material precipitated from the solution and the temperature arises to about 40° C. Water (2 mL) and diluted HCl was added slowly and the mixture was neutralized with NaHCO₃ and extracted with ethyl acetate. The organic phase was washed with water and concentrated. The residue was separated by flash chromatography (20–80% EtOAc in hexane) to give the desired product (1.24 g, 42%). MS (DCI) m/z 347, 349 (M+1)⁺.

Example 405C

5-{5-[1-Hydroxymethyl-2-(1H-indol-3-yl)-ethoxy]-pyridin-3-yl}-3-methyl-indazole-1-carboxylic acid tert-butyl ester A 50 mL RBF was charged with Example 405B (580 mg, 1.67 mmol), Example 203B (660 mg, 1.67 mmol), Pd₂(dba)₃

(153 mg, 0.167 mmol), and tri-o-tolylphosphine (153 mg), and was purged with $N_2$. Anhydrous DMF (22 mL) and $Et_3N$ (0.698 mL) were added via syringe. The solution was purged with $N_2$ again and was heated at 70° C. for 15 h. After cooled, ethyl acetate (100 mL) was added. The mixture was washed with brine (100 mL) and water (100 mL). The ethyl acetate solution was concentrated and the residual oil was separated by flash chromatography (0–15% $CH_3OH$ in 2:1 EtOAc/hexane) to give the desired product (656 mg, 79%). MS (APCI) m/z 499 (M+1)$^+$.

Example 405D 3-(1H-Indol-3-yl)-2-[5-(3-methyl-1H-indazol-5-yl)-pyridin-3-yloxy]-propan-1-ol The desired product was prepared as the trifluoroacetate by substituting Example 405C for Example 27B in Examples 27C. MS (APCI) m/z 399 (M+1)$^+$; $^1$H NMR (400 MHz, $CD_3OD$) δ 2.56 (s, 3 H), 3.09 (dd, J=14.73, 8.90 Hz, 1 H), 3.19 (dd, J=15.04, 3.99 Hz, 1 H), 3.85 (dd, J=12.12, 6.60 Hz, 1 H), 3.92 (m, 1 H), 4.99 (m, 1 H), 6.97 (dd, J=6.14, 3.07 Hz, 2 H), 7.07 (s, 1 H), 7.16 (m, 1 H), 7.25 (dd, J=8.75, 1.38 Hz, 1 H), 7.49 (d, J=8.90 Hz, 1 H), 7.57 (dd, J=6.14, 2.76 Hz, 1 H), 7.84 (d, J=10.43 Hz, 2 H), 8.14 (s, 1 H), 8.38 (s, 1 H); Anal. Calcd for $C_{24}H_{22}N_4O_2$·1.7 TFA: C, 55.56; H, 4.03; N, 9.46. Found: C, 55.69; H, 4.02; N, 9.58.

EXAMPLE 406

3-(1H-Indol-3-yl)-2-[5-(3-methyl-1H-indazol-5-yl)-pyridin-3-yloxy]-propylamine

Example 406A

5-{5-[1-Azidomethyl-2-(1H-indol-3-yl)-ethoxy]-pyridin-3-yl}-3-methyl-indazole-1-carboxylic acid tert-butyl ester A 50 mL RBF was charged with Example 405C (580 mg, 1.16 mmol) and $Ph_3P$ (456 mg, 1.74 mmol), and was purged with nitrogen. THF (14 mL) was added at 0° C., followed by addition of DPPA (375 μL, 1.74 mmol). After stirring at 0° C. for 1 min, DEAD (274 μL, 1.74 mmol) was added via syringe. The reaction mixture was stirred at 0° C. for 0.5 h and at rt overnight. The reaction mixture was concentrated and the residue was separated by flash chromatography (20–80% EtOAc in hexane) to provide the desired product (534 mg, 87%). MS (APCI) m/z 524 (M+1)$^+$.

Example 406B

5-{5-[1-Aminomethyl-2-(1H-indol-3-yl)-ethoxy]-pyridin-3-yl}-3-methyl-indazole-1-carboxylic acid tert-butyl ester To a solution of Example 406A (480 mg) in ethanol was added 10% Pd/C (160 mg) under nitrogen. This suspension was purged with hydrogen (3 circles) and was stirred under hydrogen (balloon) for 4 h. The solid material was filtered off and the filtrate was concentrated to give the desired product (443 mg, 97%). MS (APCI) m/z 498 (M+1)$^+$.

Example 406C 3-(1H-Indol-3-yl)-2-[5-(3-methyl-1H-indazol-5-yl)-pyridin-3-yloxy]-propylamine The desired product was prepared as the trifluoroacetate by substituting Example 406B for Example 27B in Examples 27C. MS (APCI) m/z 398 (M+1)$^+$; $^1$H NMR (300 MHz, $CD_3OD$) δ 2.62 (s, 3 H), 3.29 (m, 2 H), 3.40 (dd, J=13.56, 9.15 Hz, 1 H), 3.53 (dd, J=13.90, 2.71 Hz, 1H), 5.32 (m, 1 H), 7.03 (m, 2 H), 7.14 (s, 1 H), 7.20 (dd, J=6.27, 2.54 Hz, 1 H), 7.28 (dd, J=8.81, 1.70 Hz, 1 H), 7.55 (d, J=8.48 Hz, 1 H), 7.59 (dd, J=6.10, 2.37 Hz, 1 H), 7.80 (s, 1H), 7.85 (s, 1 H), 8.22 (d, J=2.37 Hz, 1 H), 8.47 (s, 1 H); Anal. Calcd for $C_{24}H_{23}N_5O$·3.3 TFA: C, 47.50; H, 3.43; N, 9.05. Found: C, 47.41; H, 3.71; N, 9.11.

EXAMPLE 407

Naphthalene-2-sulfonic acid (2-amino-ethyl)-[5-(3-methyl-1H-indazol-5-yl)-pyridin-3-yl]-amide Example 407A {2-[(5-Bromo-pyridin-3-yl)-(naphthalene-2-sulfonyl)-amino]-ethyl}-carbamic acid tert-Butyl ester To a solution of Example 386A (50 mg, 0.158 mmol) in pyridine (2 mL) was added 2-naphthalenesulfonyl chloride (72 mg, 0.316 mmol) at rt. The formed yellow solution was stirred at rt for 15 h. Pyridine was removed by blowing with nitrogen and the residual yellow solid was purified by flash chromatography (30–60% EtOAc in hexane) to the desired product (81 mg, 100%). MS (DCI) m/z 506, 508 (M+1)$^+$.

Example 407B

{2-[[5-(3-Methyl-1H-indazol-5-yl)-pyridin-3-yl]-(naphthalene-2-sulfonyl)-amino]-ethyl}-carbamic acid tert-butyl ester A 25 mL RBF was charged with Example 407A (78 mg, 0.154 mmol), Example 203B (45 mg, 0.154 mmol), $Pd_2(dba)_3$ (14 mg, 0.0154 mmol), and tri-o-tolylphosphine (14 mg), and was purged with $N_2$. Anhydrous DMF (4 mL) and $Et_3N$ (64 μL) were added via syringe. The solution was purged with $N_2$ again and was heated at 70° C. for 15 h. After cooled, ethyl acetate (50 mL) was added. The mixture was washed with brine (50 mL) and water (50 mL). The ethyl acetate solution was concentrated and the residual oil was separated by flash chromatography (A: 2:1 EtOAc/hexane, 0–15% $CH_3OH$/A) to give the desired product (54 mg, 63%). MS (APCI) m/z 558 (M+1)$^+$.

Example 407C

Naphthalene-2-sulfonic acid (2-amino-ethyl)-[5-(3-methyl-1H-indazol-5-yl)-pyridin-3-yl]-amide The desired product was prepared as the trifluoroacetate by substituting Example 407B for Example 27B in Examples 27C. MS (APCI) m/z 458 (M+1)$^+$; $^1$H NMR (300 MHz, $CD_3OD$) δ 2.50 (s, 3 H), 3.14 (t, J=5.59 Hz, 2 H), 4.06 (t, J=5.59 Hz, 2 H), 7.48 (m, 2 H), 7.66 (m, 2 H), 7.74 (d, J=8.14 Hz, 1 H), 7.77 (d, J=8.14 Hz, 1 H), 7.80 (t, J=2.03 Hz, 1 H), 8.02 (d, J=8.14 Hz, 1 H), 8.06 (d, J=8.48 Hz, 1 H), 8.14 (d, J=8.48 Hz, 1 H), 8.28 (s, 1 H), 8.47 (d, J=2.37 Hz, 1 H), 8.92 (d, J=1.70 Hz, 1 H); Anal. Calcd for $C_{25}H_{23}N_5O_2S$·3.3 TFA: C, 45.52; H, 3.18; N, 8.40. Found: C, 45.42; H, 3.13; N, 8.43.

EXAMPLE 408

Biphenyl-4-sulfonic acid (2-amino-ethyl)-[5-(3-methyl-1H-indazol-5-yl)-pyridin-3-yl]-amide The desired product was prepared as the trifluoroacetate by substituting 4-biphenylsulfonyl chloride for 2-naphthalenesulfonyl chloride in Examples 407. MS (APCI) m/z 484 (M+1)+; $^1$H NMR (300 MHz, DMSO-d$_6$) δ 2.42 (s, 3 H), 2.96 (m, 2 H), 3.95 (m, 2 H), 7.54 (m, 4 H), 7.69 (d, J=8.48 Hz, 2 H), 7.77 (d, J=7.12 Hz, 2 H), 7.95 (m, 5 H), 8.45 (s, 1 H), 8.98 (s, 1 H); Anal. Calcd for $C_{27}H_{25}N_5O_2S \cdot 1.3$ TFA: C, 56.27; H, 4.20; N, 11.08. Found: C, 56.00; H, 4.21; N, 10.87.

EXAMPLE 409

5-{5-[(2S)-2-Amino-3-(1H-indol-3-yl)-propoxy]-pyridin-3-yl}-3-isopropylidene-1,3-dihydro-indol-2-one The desired compound was prepared by as the trifluoroacetate salt substituting 5-Bromo-3-isopropylidene-1,3-dihydro-indol-2-one (L. Sun, et al.,*J. Med. Chem.*, 1998, 41, 2588.) for 6-bromophthalimide in Example 32. $^1$H NMR (400 MHz, CD$_3$OD) δ ppm 2.47 (s, 3H), 2.60 (s, 3H), 3.31 (m, 2H), 4.01 (m, 1H), 4.34 (dd, J=10.43, 5.83 Hz, 1H), 4.47 (dd, J=10.43, 3.38 Hz, 1H), 7.01 (t, J=7.06 Hz, 1H), 7.04 (d, J=7.98 Hz, 1H), 7.12 (t, J=7.06 Hz, 1H), 7.24 (s, 1H), 7.38 (d, J=8.29 Hz, 1H), 7.50 (dd, J=7.98, 1.84 Hz, 1H), 7.58 (d, J=7.98 Hz, 1H), 7.79 (d, J=1.53 Hz, 1H), 7.97 (d, J=1.84 Hz, 1H), 8.37 (s, 1H), 8.63 (s, 1H); Anal. Calcd for $C_{27}H_{26}N_4O_2$: C, 52.14; H, 3.88; N, 7.51. Found: C, 52.19; H, 3.67; N, 7.42.

EXAMPLE 410

5-{5-[(2S)-2-Amino-3-(1H-indol-3-yl)-propoxy]-pyridin-3-yl}-3-(1H-imidazol-2-ylmethylene)-1,3-dihydro-indol-2-one The desired compound was prepared by as the trifluoroacetate salt substituting 5-Bromo-3-(1H-imidazol-2-ylmethylene)-1,3-dihydro-indol-2-one (L. Sun, et al., *J. Med. Chem.*, 1998, 41, 2588.) for 6-bromophthalimide in Example 32. MS (DCI/NH$_3$) m/z 477 (M+1)+; $^1$H NMR (500 MHz, CD$_3$OD) δ ppm 3.31 (m, 2H), 4.04 (m, 1H), 4.37 (dd, J=10.45, 5.77 Hz, 1 H), 4.50 (dd, J=10.29, 3.12 Hz, 1 H), 7.02 (t, J=7.49 Hz, 1H), 7.11 (d, J=7.49 Hz, 1 H), 7.13 (m, 1H), 7.25 (s, 1H), 7.38 (d, J=8.11 Hz, 1H), 7.60 (d, J=7.80 Hz, 1H), 7.72 (d, J=8.11 Hz, 1H), 7.77 (s, 2H), 7.85 (s, 1H), 8.02 (s, 1H), 8.13 (s, 1H), 8.42 (s, 1H), 8.67 (s, 1H).

EXAMPLE 411

5-{5-[2-Amino-3-(1H-indol-3-yl)-propoxy]-pyridin-3-yl}-3-pyridin-2-ylmethylene-1,3-dihydro-indol-2-one The desired compound was prepared by as the trifluoroacetate salt substituting 5-Bromo-3-pyridin-2-ylmethylene-1,3-dihydro-indol-2-one (L. Sun, et al., *J. Med. Chem.*, 1998, 41, 2588.) for 6-bromophthalimide in Example 32. MS (DCI/NH$_3$) m/z 488 (M+1)+; $^1$H NMR (500 MHz, CD$_3$OD) δ ppm 3.32 (m, 2H), 4.02 (m, 1H), 4.34 (dd, J=10.61, 5.62 Hz, 1H), 4.47 (dd, J=10.45, 3.28 Hz, 1H), 7.03 (t, J=7.02 Hz, 1H), 7.13 (m, 1H), 7.19 (d, J=8.11 Hz, 1H), 7.25 (s, 1H), 7.38 (d, J=8.42 Hz, 1H), 7.60 (d, J=7.80 Hz, 1H), 7.76 (dd, J=8.11, 1.87 Hz, 1H), 7.94 (dd, J=2.50, 1.87 Hz, 1H), 8.14 (m, 1H), 8.17 (s, 1H), 8.26 (d, J=1.56 Hz, 1H), 8.38 (d, J=7.80 Hz, 1H), 8.41 (s, 1H), 8.66 (s, 1H), 8.72 (m, 1H), 9.08 (dd, J=5.62, 1.56 Hz, 1H); Anal. Calcd for $C_{30}H_{25}N_5O_2$: C, 47.41; H, 3.02; N, 7.16. Found: C, 47.40; H, 2.93; N, 6.98.

EXAMPLE 412

5-{5-[(2S)-2-Amino-3-(1H-indol-3-yl)-propoxy]-pyridin-3-yl}-3-furan-2-ylmethylene-1,3-dihydro-indol-2-one The desired compound was prepared by as the trifluoroacetate salt substituting 5-Bromo-3-furan-2-ylmethylene-1,3-dihydro-indol-2-one (L. Sun, et al., *J. Med. Chem.*, 1998, 41, 2588.) for 6-bromophthalimide in Example 32. MS (DCI/NH$_3$) m/z 477 (M+1)+; $^1$H NMR (500 MHz, CD$_3$OD) δ ppm 3.34 (m, 4H), 4.06 (m, 2H), 4.37 (dd, J=10.45, 5.77 Hz, 2H), 4.51 (dd, J=10.45, 3.28 Hz, 2H), 6.68 (dd, J=3.28, 1.40 Hz, 1H), 6.72 (dd, J=3.59, 1.72 Hz, 1H), 7.02 (t, J=7.64 Hz, 2H), 7.05 (d, J=8.11 Hz, 2H), 7.12 (m, 3H), 7.26 (s, 1H), 7.27 (s, 1H), 7.38 (d, J=8.11 Hz, 2H), 7.43 (s, 1H), 7.55 (d, J=1.87 Hz, 1H), 7.58 (dd, J=8.11, 1.87 Hz, 1H), 7.61 (d, J=7.80 Hz, 2H), 7.73 (s, 1H), 7.77 (d, J=1.56 Hz, 1H), 7.85 (d, J=1.87 Hz, 1H), 7.97 (d, J=1.56 Hz, 1H), 8.06 (d, J=4.37 Hz, 1H), 8.15 (d, J=1.87 Hz, 1H), 8.30 (d, J=3.43 Hz, 1H), 8.44 (m, 2H), 8.69 (s, 1H), 8.73 (d, J=1.87 Hz, 2H); Anal. Calcd for $C_{29}H_{24}N_4O_3$: C, 50.33; H, 3.24; N, 6.61. Found: C, 50.30; H, 3.12; N, 6.65.

EXAMPLE 413

5-{5-[(2S)-2-Amino-3-(1H-indol-3-yl)-propoxy]-pyridin-3-yl}-3-(5-methyl-furan-2-ylmethylene)-1,3-dihydro-indol-2-one The desired compound was prepared by as the trifluoroacetate salt substituting 5-Bromo-3-(5-methyl-furan-2-ylmethylene)-1,3-dihydro-indol-2-one (L. Sun, et al., *J. Med. Chem.*, 1998, 41, 2588.) 6-bromophthalimide in Example 32. MS (DCI/NH$_3$) m/z 477 (M+1)+; $^1$H NMR (500 MHz, CD$_3$OD) δ ppm 2.41 (s, 3H), 3.32 (m, 2H), (4.02 (m, 1H), 4.31 (dd, J=10.45, 5.77 Hz, 1H), 4.45 (dd, J=10.45, 3.28 Hz, 1H), 6.38 (dd, J=3.43, 0.94 Hz, 1H), 7.03 (m, 3H), 7.12 (t, J=7.18 Hz, 1H), 7.24 (s, 1H), 7.37 (s, 1H), 7.38 (d, J=8.11 Hz, 1H), 7.54 (dd, J=8.11, 1.87 Hz, 1H), 7.60 (d, J=8.11 Hz, 1H), 7.90 (dd, J=2.50, 1.87 Hz, 1H), 8.38 (s, 1H), 8.64 (s, 1H), 8.73 (s, 1H); Anal. Calcd for $C_{30}H_{26}N_4O_3$: C, 49.59; H, 3.31; N, 6.22. Found: C, 49.90; H, 3.18; N, 6.10.

EXAMPLE 414

5-{5-[(2S)-2-Amino-3-(1H-indol-3-yl)-propoxy]-pyridin-3-yl}-3-(4,5-dimethyl-furan-2-ylmethylene)-1,3-dihydro-indol-2-one The desired compound was prepared by as the trifluoroacetate salt substituting 5-Bromo-3-(4,5-dimethyl-furan-2-ylmethylene)-1,3-dihydro-indol-2-one (L. Sun, et al., *J. Med. Chem.*, 1998, 41, 2588.) for 6-bromophthalimide in Example 32. MS (DCI/NH$_3$) m/z 505 (M+1)+; $^1$H NMR (500 MHz, CD$_3$OD) δ ppm 1.99 (s, 3H), 2.27 (s, 3H), 3.34 (m, 2H), 4.06 (m, 1H), 4.37 (dd, J=10.45, 5.77 Hz, 1H), 4.51 (dd, J=10.45, 3.28 Hz, 1H), 6.82 (s, 1H), 6.99 (d, J=8.42 Hz, 1H), 7.03 (t, J=7.02 Hz, 1H), 7.13 (t, J=7.02 Hz, 1H), 7.21 (s, 1H), 7.27 (s, 1H), 7.39 (d, J=8.11 Hz, 1H), 7.52 (dd, J=8.11, 1.87 Hz, 1H), 7.61 (d, J=8.11 Hz, 1H), 8.05 (s, 1H), 8.45 (s, 1H), 8.62 (d, J=1.56 Hz, 1H), 8.66 (s, 1H); Anal. Calcd for $C_{31}H_{28}N_4O_3$: C, 52.92; H, 3.73; N, 6.71. Found: C, 52.90; H, 3.45; N, 6.97.

EXAMPLE 415

5-{5-[(2S)-2-Amino-3-(1H-indol-3-yl)-propoxy]-pyridin-3-yl}-3-thiophen-2-ylmethylene-1,3-dihydro-indol-2-one The desired compound was prepared by as the trifluoroacetate salt substituting 5-Bromo-3-thiophen-2-ylmethylene-1,3-dihydro-indol-2-one (L. Sun, et al., *J. Med. Chem.*, 1998, 41, 2588.) for 6-bromophthalimide in Example 32. MS (APCI) m/z 493 (M+1)+; $^1$H NMR (500 MHz, CD$_3$OD) δ ppm 3.32 (m, 4H), 4.03 (m, 2H), 4.30 (dd, J=10.45, 5.77 Hz, 1H), 4.35 (dd, J=10.61, 5.93 Hz, 1H), 4.44 (dd, J=10.29, 3.12 Hz, 1H), 4.48 (dd, J=10.61, 3.12 Hz, 1H), 7.02 (m, 2H), 7.04 (s, 1H), 7.06 (d, J=0.94 Hz, 1H), 7.08 (d, J=8.11 Hz, 1H), 7.14 (t, J=7.49 Hz, 2H), 7.20 (dd, J=4.99, 3.74 Hz, 1H), 7.23 (d, J=1.25 Hz, 1H), 7.24 (s, 1H), 7.26 (m, 1H), 7.37 (s, 1H), 7.39 (d, J=8.11 Hz, 1H), 7.53 (dd, J=8.11, 1.87 Hz, 1H), 7.56 (dd, J=8.11, 1.56 Hz, 1H), 7.59 (s, 1H), 7.61 (d, J=7.80 Hz, 1H), 7.71 (d, J=2.50 Hz, 1H), 7.74 (d, J=5.30 Hz, 1H), 7.79 (d, J=4.99 Hz, 1H), 7.92 (s, 1H), 7.93 (s, 1H), 7.96 (s, 1H), 7.98 (d, J=1.56 Hz, 1H), 8.09 (s, 1H), 8.37 (s, 2H), 8.48 (d, J=1.56 Hz, 1H), 8.56 (s, 1H), 8.65 (s, 1H); Anal. Calcd for $C_{29}H_{24}N_4O_2S$: C, 50.37; H, 3.26; N, 6.71. Found: C, 50.52; H, 3.45; N, 6.84.

(A-441246) EXAMPLE 416

5-{5-[(2S)-2-Amino-3-(1H-indol-3-yl)-propoxy]-pyridin-3-yl}-3-(1-methyl-1H-pyrrol-2-ylmethylene)-1,3-dihydro-indol-2-one The desired compound was prepared by as the trifluoroacetate salt substituting 5-Bromo-3-(1-methyl-1H-pyrrol-2-ylmethylene)-1,3-dihydro-indol-2-one (L. Sun, et al., *J. Med. Chem.*, 1998, 41, 2588.) for 6-bromophthalimide in Example 32. MS (APCI) m/z 490 (M+1)$^+$; $^1$H NMR (500 MHz, CD$_3$OD) δ ppm 3.32 (m, 4H), 3.81 (s, 3H), 3.89 (s, 3H), 4.03 (m, 2H), 4.30 (dd, J=10.61, 5.93 Hz, 1H), 4.37 (dd, J=10.61, 5.93 Hz, 1H), 4.44 (dd, J=10.45, 3.28 Hz, 1H), 4.50 (dd, J=10.29, 3.12 Hz, 1H), 6.28 (m, 2H), 7.02 (m, 3H), 7.07 (m, 3H), 7.12 (m, 2H), 7.19 (d, J=3.74 Hz, 1H), 7.24 (s, 1H), 7.26 (s, 1H), 7.38 (d, J=8.11 Hz, 1H), 7.39 (d, J=8.11 Hz, 1H), 7.46 (dd, J=8.11, 1.87 Hz, 1H), 7.50 (dd, J=8.27, 1.72 Hz, 1H), 7.59 (d, J=7.80 Hz, 1H), 7.61 (d, J=8.11 Hz, 1H), 7.70 (s, 1H), 7.74 (s, 1H), 7.86 (s, 1H), 7.98 (d, J=1.87 Hz, 1H), 8.08 (s, 1H), 8.30 (dd, J=4.37, 1.56 Hz, 1H), 8.34 (d, J=1.56 Hz, 1H), 8.38 (s, 2H), 8.57 (s, 1H), 8.73 (s, 1H); Anal. Calcd for $C_{30}H_{27}N_5O_2$: C, 55.28; H, 3.93; N, 9.32. Found: C, 55.32; H, 3.57; N, 9.08

EXAMPLE 417

5-{5-[(2S)-2-Amino-3-(1H-indol-3-yl)-propoxy]-pyridin-3-yl}-3-(1H-indol-3-ylmethylene)-1,3-dihydro-indol-2-one The desired compound was prepared by as the trifluoroacetate salt substituting 5-Bromo-3-(1H-indol-3-ylmethylene)-1,3-dihydro-indol-2-one (L. Sun, et al., *J. Med. Chem.*, 1998, 41, 2588.) 6-bromophthalimide in Example 32. MS (APCI) m/z 526 (M+1)$^+$; $^1$H NMR (500 MHz, CD$_3$OD) δ ppm 3.32 (m, 4H), 4.05 (m, 2H), 4.15 (m, 1H), 4.25 (m, 1H), 4.38 (d, J=5.93 Hz, 1H), 4.49 (dd, J=10.29, 3.12 Hz, 1H), 7.02 (m, 2H), 7.06 (m, 1H), 7.09 (m, 2H), 7.14 (t, J=7.64 Hz, 2H), 7.23 (m, 4H), 7.28 (s, 1H), 7.39 (m, 2H), 7.43 (d, J=4.99 Hz, 1H), 7.47 (m, 4H), 7.56 (d, J=8.11 Hz, 1H), 7.59 (s, 1H), 7.63 (d, J=8.11 Hz, 2H), 8.01 (m, 2H), 8.06 (d, J=1.56 Hz, 1H), 8.12 (s, 2H), 8.24 (s, 1H), 8.28 (s, 1H), 8.35 (s, 2H), 8.72 (s, 1H), 9.40 (s, 1H); Anal. Calcd for $C_{33}H_{27}N_5O_2$: C, 53.99; H, 3.48; N, 8.07. Found: C, 54.27; H, 3.64; N, 7.84

EXAMPLE 418

5-{5-[(2S)-2-Amino-3-(1H-indol-3-yl)-propoxy]-pyridin-3-yl}-3-(1-phenyl-1H-pyrrol-3-ylmethylene)-1,3-dihydro-indol-2-one The desired compound was prepared by as the trifluoroacetate salt substituting 5-Bromo-3-(2,5-dimethyl-1-phenyl-1H-pyrrol-3-ylmethylene)-1,3-dihydro-indol-2-one (L. Sun, et al., *J. Med. Chem.*, 1998, 41, 2588.) 6-bromophthalimide in Example 32. MS (APCI) m/z 580 (M+1)$^+$; $^1$H NMR (500 MHz, CD$_3$OD) δ ppm 1.98 (s, 3 H) 2.01 (s, 3 H) 2.18 (s, 3 H) 2.28 (s, 3 H) 3.32 (m, 4 H), 4.02 (m, 2 H) 4.32 (dd, J=10.45, 5.46 Hz, 1 H) 4.37 (dd, J=10.61, 5.93 Hz, 1 H) 4.49 (m, 2 H) 6.68 (m, 1 H) 7.01 (m, 3 H) 7.10 (m, 3 H) 7.25 (m, 6 H) 7.36 (t, J=8.73 Hz, 2 H) 7.47 (m, 3 H) 7.57 (m, 8H) 7.84 (d, J=2.18 Hz, 2 H) 7.93 (s, 2 H) 8.13 (s, 1H) 8.32 (s, 1 H) 8.38 (s, 2 H) 8.60 (s, 1 H) 8.73 (s, 1 H); Anal. Calcd for $C_{37}H_{33}N_5O_2$: C, 54.38; H, 3.79; N, 7.24. Found: C, 54.45; H, 3.92; N, 6.97.

EXAMPLE 419

5-{5-[(2S)-2-Amino-3-(1H-indol-3-yl)-propoxy]-pyridin-3-yl}-3-pyridin-3-ylmethylene-1,3-dihydro-indol-2-one The desired compound was prepared by as the trifluoroacetate salt substituting 5-Bromo-3-pyridin-3-ylmethylene-1,3-dihydro-indol-2-one (L. Sun, et al., *J. Med. Chem.*, 1998, 41, 2588.) 6-bromophthalimide in Example 32. MS (APCI) m/z 488 (M+1)$^+$; $^1$H NMR (500 MHz, CD$_3$OD) δ ppm 3.32 (m, 4H), 4.03 (m, 2H), 4.26 (dd, J=10.45, 5.46 Hz, 1H), 4.36 (dd, J=10.45, 5.77 Hz, 1H), 4.40 (dd, J=10.29, 3.12 Hz, 1H), 4.49 (dd, J=10.29, 3.12 Hz, 1H), 7.01 (m, 1H), 7.05 (m, 3H), 7.08 (d, J=8.11 Hz, 1H), 7.12 (t, J=7.64 Hz, 2H), 7.23 (s, 1H), 7.25 (s, 1H), 7.38 (d, J=8.11 Hz, 1H), 7.57 (m, 1H), 7.59 (m, 1H), 7.61 (s, 1H), 7.64 (dd, J=8.11, 1.87 Hz, 1H), 7.66 (m, 1H), 7.71 (m, 1H), 7.78 (s, 1H), 7.93 (s, 1H), 7.99 (n, J=8.27, 5.77 Hz, 3H), 8.09 (d, J=1.56 Hz, 1H), 8.34 (d, J=8.11 Hz, 2H), 8.41 (m, 2H), 8.56 (d, J=4.68 Hz, 1H), 8.67 (s, 1H), 8.77 (d, J=5.30 Hz, 1H), 9.01 (s, 1H), 9.11 (d, J=8.11 Hz, 1H), 9.69 (s, 1H); Anal. Calcd for $C_{30}H_{25}N_5O_2$: C, 49.22; H, 3.17; N, 7.65. Found: C, 49.23; H, 3.15; N, 7.38.

EXAMPLE 420

5-{5-[(2S)-2-Amino-3-(1H-indol-3-yl)-propoxy]-pyridin-3-yl}-3-(1H-pyrrol-3-ylmethylene)-1,3-dihydro-indol-2-one The desired compound was prepared by as the trifluoroacetate salt substituting 5-Bromo-3-(1H-pyrrol-3-ylmethylene)-1,3-dihydro-indol-2-one (L. Sun, et al., *J. Med. Chem.*, 1998, 41, 2588.) for 6-bromophthalimde in Example 32. MS (APCI) m/z 476 (M+1)$^+$; $^1$H NMR (500 MHz, CD$_3$OD) δ ppm 3.32 (m, 4H), 4.04 (m, 2H), 4.32 (dd, J=10.45, 5.77 Hz, 1H), 4.38 (dd, J=10.61, 5.93 Hz, 1H), 4.46 (dd, J=10.45, 3.28 Hz, 1H), 4.50 (dd, J=10.29, 3.12 Hz, 1H), 6.77 (dd, J=2.81, 1.56 Hz, 1H), 6.85 (dd, J=2.65, 2.03 Hz, 1H), 6.91 (m, 1H), 7.04 (m, 5H), 7.13 (m, 2H), 7.24 (s, 1H), 7.26 (s, 1H), 7.39 (t, J=7.49 Hz, 2H), 7.43 (s, 1H), 7.48 (m, 2H), 7.60 (m, J=8.73, 8.73 Hz, 2H), 7.80 (s, 1H), 7.84 (s, 1H), 7.90 (m, 2H), 8.09 (s, 1H), 8.16 (s, 1H), 8.28 (d, J=1.56 Hz, 1H), 8.39 (s, 2H), 8.59 (s, 1H), 8.70 (s, 1H); Anal. Calcd for $C_{29}H_{25}N_5O_2$: C, 51.42; H, 3.45; N, 8.57. Found: C, 51.73; H, 3.41; N, 8.58.

EXAMPLE 421

5-{5-[(2S)-2-Amino-3-(1H-indol-3-yl)-propoxy]-pyridin-3-yl}-3-(tetrahydro-pyran-4-ylidene)-1,3-dihydro-indol-2-one The desired compound was prepared by as the trifluoroacetate salt substituting 5-Bromo-3-(tetrahydro-pyran-4- ylidene)-1,3-dihydro-indol-2-one (L. Sun, et al., *J. Med. Chem.*, 1998, 41, 2588.) 6-bromophthalimide in Example 32. MS (APCI) m/z 481 (M+1)+; 1H NMR (400 MHz, DMSO-d6) δ ppm 3.02 (t, J=5.52 Hz, 2H), 3.19 (m, 2H) 3.44 (t, J=5.52 Hz, 2H), 3.80 (m, 5H), 4.18 (dd, J=10.74, 5.83 Hz, 1H), 4.34 (m, 1H), 7.00 (m, 1H), 7.10 (t, J=7.06 Hz, 1H), 7.29 (d, J=2.15 Hz, 1H), 7.38 (d, J=7.98 Hz, 1H), 7.49 (dd, J=8.13, 1.69 Hz, 1H), 7.62 (m, 2H), 7.85 (s, 1H), 8.23 (s, 2H), 8.24 (s, 1H), 8.32 (d, J=2.76 Hz, 1H), 8.55 (d, J=1.53 Hz, 1H), 10.67 (s, 1H), 11.03 (d, J=1.84 Hz, 1H); Anal. Calcd for $C_{29}H_{28}N_4O_3$: C, 55.38; H, 4.21; N, 7.78. Found: C, 55.29; H, 4.12; N, 7.70.

EXAMPLE 422

5-{5-[(2S)-2-Amino-3-(1H-indol-3-yl)-propoxy]-pyridin-3-yl}-3-(4-ethyl-3,5-dimethyl-1H-2-ylmethylene)-1,3-dihydro-indol-2-one The desired compound was prepared by as the trifluoroacetate salt substituting 5-Bromo-3-(4-ethyl-3,5-dimethyl-1H-pyrrol-2-ylmethylene)-1,3-dihydro-indol-2-one (L. Sun, et al., *J. Med. Chem.*, 1998, 41, 2588.) 6-bromophthalimide in Example 32. MS (APCI) m/z 530 (M−1)+; 1H NMR (500 MHz, CD3OD) δ ppm 1.10 (t, J=7.52 Hz, 3H), 2.31 (s, 3H), 2.34 (s, 3H), 2.49 (q, J=7.57 Hz, 2H), 3.32 (m, 2H), 4.03 (m, 1H), 4.36 (dd, J=10.59, 5.68 Hz, 1H), 4.49 (m, 1H), 7.05 (m, 2H), 7.13 (t, J=7.06 Hz, 1H), 7.25 (s, 1H), 7.41 (m, 2H), 7.61 (d, J=7.67 Hz, 1H), 7.66 (s, 1H), 7.93 (d, J=1.53 Hz, 1H), 8.07 (m, 1H), 8.37 (s, 1H), 8.72 (s, 1H); Anal. Calcd for $C_{33}H_{33}N_5O_2$: C, 54.94; H, 4.29; N, 8.34. Found: C, 55.03; H, 4.09; N, 8.20.

(A-485149)

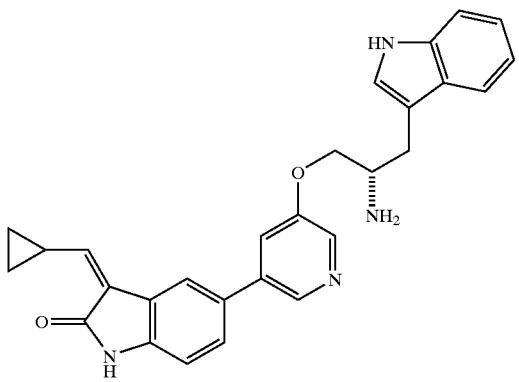

EXAMPLE 423

5-{5-[(2S)-2-Amino-3-(1H-indol-3-yl)-propoxy]-pyridin-3-yl}-3-cyclopropylmethylene-1,3-dihydro-indol-2-one The desired compound was prepared by as the trifluoroacetate salt substituting 5-Bromo-3-cyclopropylmethylene-1,3-dihydro-indol-2-one (L. Sun, et al., *J. Med. Chem.*, 1998, 41, 2588.) 6-bromophthalimide in Example 32. MS (APCI) m/z 451 (M+1)+; 1H NMR (400 MHz, DMSO-d6) δ ppm 0.79 (m, J=4.30, 2.45 Hz, 2H), 0.93 (m, 3H), 1.19 (m, 5H), 2.52 (m, 4H), 3.84 (s, 2H), 4.19 (m, 2H), 4.35 (m, 2H), 6.33 (d, J=11.66 Hz, 1H), 6.59 (d, J=11.05 Hz, 1H), 6.92 (d, J=7.98 Hz, 1H), 7.00 (m, 1H), 7.10 (t, J=7.06 Hz, 2H), 7.29 (d, J=2.15 Hz, 2H), 7.38 (d, J=8.29 Hz, 2H), 7.51 (m, 2H), 7.62 (d, J=7.67 Hz, 2H), 7.69 (m, J=5.06, 3.22 Hz, 2H), 7.86 (d, J=1.84 Hz, 1H), 8.03 (d, J=1.53 Hz, 1H), 8.23 (br s, 3H), 8.24 (br s, 3H), 8.32 (d, J=2.76 Hz, 1H), 8.33 (d, J=2.76 Hz, 1H), 8.57 (d, J=1.53 Hz, 1H), 8.60 (d, J=1.84 Hz, 1H), 10.54 (s, 1H), 10.58 (s, 1H), 11.03 (d, J=1.84 Hz, 2H); Anal. Calcd for $C_{28}H_{26}N_4O_2$: C, 55.48; H, 4.05; N, 7.99. Found: C, 55.63; H, 3.98; N, 7.90.

EXAMPLE 424

5-{5-[(2S)-2-Amino-3-(1H-indol-3-yl)-propoxy]-pyridin-3-yl}-3-pyrrolidin-2-ylmethylene-1,3-dihydro-indol-2-one The desired compound was prepared by as the trifluoroacetate salt substituting 5-Bromo-3-pyrrolidin-2-ylmethylene-1,3-dihydro-indol-2-one (L. Sun, et al., *J. Med. Chem.*, 1998, 41, 2588.) 6-bromophthalimide in Example 32. MS (APCI) m/z 480 (M+1)+; 1H NMR (400 MHz, CD3OD) δ ppm 1.53 (m, 1H), 1.60 (m, 1H), 1.70 (m, 1H), 2.01 (m, 1H), 2.20 (m, 2H), 2.49 (m, 1H), 3.44 (m, 2H), 4.01 (m, 1H), 4.32 (dd, J=10.43, 5.83 Hz, 1H), 4.46 (m, 1H), 7.05 (m, 3H), 7.13 (t, J=7.67 Hz, 1H), 7.24 (s, 1H), 7.38 (d, J=8.29 Hz, 1H), 7.61 (m, 2H), 7.92 (m, 2H), 8.36 (s, 1H), 8.59 (s, 1H); Anal. Calcd for $C_{29}H_{29}N_5O_2$: C, 52.24; H, 4.03; N, 8.83. Found: C, 52.32; H, 4.24; N, 8.63.

EXAMPLE 425

5-(5-{5-[(2S)-2-Amino-3-(1H-indol-3-yl)-propoxy]-pyridin-3-yl}-2-oxo-1,2-dihydro-indol-3-ylidenemethyl)-furan-2-carboxylic acid The desired compound was prepared by as the trifluoroacetate salt substituting 5-(5-Bromo-2-oxo-1,2-dihydro-indol-3-ylidenemethyl)-furan-2-carboxylic acid (L. Sun, et al., *J. Med. Chem.*, 1998, 41, 2588.) for 6-bromophthalimide in Example 32. MS (APCI) m/z 521 (M+1)+; 1H NMR (400 MHz, DMSO-d6) δ ppm 3.16 (d, J=6.75 Hz, 2H), 3.86 (m, 1H), 4.21 (dd, J=10.74, 6.44 Hz, 1H), 4.41 (m, 1H), 6.97 (t, J=6.90 Hz, 1H), 7.03 (d, J=7.98 Hz, 1H), 7.08 (t, J=7.06 Hz, 1H), 7.29 (d, J=2.46 Hz, 1H), 7.37 (d, J=8.29 Hz, 1H), 7.40 (d, J=3.99 Hz, 1H), 7.44 (m, 1H), 7.47 (s, 1H), 7.62 (m, 2H), 7.71 (m, 1H), 8.17 (br s, 2H), 8.33 (d, J=2.45 Hz, 1H), 8.71 (d, J=1.84 Hz, 1H), 8.98 (d, J=1.84 Hz, 1H), 10.84 (s, 1H), 11.01 (d, J=2.15 Hz, 1H); Anal. Calcd for $C_{30}H_{24}N_4O_5$: C, 51.75; H, 3.28; N, 6.86. Found: C, 51.69; H, 3.16; N, 6.71.

EXAMPLE 426

5-{5-[(2S)-2-Amino-3-(1H-indol-3-yl)-propoxy]-pyridin-3-yl}-3-benzylidene-1,3-dihydro-indol-2-one The desired compound was prepared by as the trifluoroacetate salt substituting 3-Benzylidene-5-bromo-1,3-dihydro-indol-2-one (L. Sun, et al., *J. Med. Chem.*, 1998, 41, 2588.) for 6-bromophthalimide in Example 32. MS (APCI) m/z 485 (M−1)+; 1H NMR (500 MHz, CD3OD) δ ppm 3.32 (m, 2H), 4.01 (m, 1H), 4.23 (dd, J=10.61, 5.62 Hz, 1H), 4.37 (m, 1H), 7.03 (m, 2H), 7.13 (t, J=7.64 Hz, 1H), 7.22 (s, 1H), 7.34 (t, J=7.49 Hz, 1H), 7.39 (d, J=8.42 Hz, 1H), 7.44 (m, 2H), 7.53 (dd, J=8.27, 1.72 Hz, 1H), 7.58 (d, J=8.11 Hz, 1H), 7.62 (s, 1H), 7.69 (d, J=7.80 Hz, 1H), 7.78 (d, J=1.87 Hz, 1H), 7.83 (s, 1H), 8.00 (d, J=1.56 Hz, 1H), 8.31 (m, J=6.40, 2.96 Hz, 1H), 8.37 (s, 1H); Anal. Calcd for $C_{31}H_{26}N_4O_2$: C, 55.53; H, 3.68; N, 7.16. Found: C, 55.74; H, 3.50; N, 7.05.

EXAMPLE 427

5-{5-[(2S)-2-Amino-3-(1H-indol-3-yl)-propoxy]-pyridin-3-yl}-1H-indole-2,3-dione 3-oxime The desired compound was prepared by as the trifluoroacetate salt substituting 5-Bromo-1H-indole-2,3-dione 3-oxime (L. Sun, et al., *J. Med. Chem.*, 1998, 41, 2588.) 6-bromophthalimide in Example 32. MS (ESI) m/z 428 (M+1)$^+$; $^1$H NMR (500 MHz, CD$_3$OD) δ ppm 3.32 (m, 2H), 4.00 (m, 1H), 4.29 (dd, J=10.45, 5.77 Hz, 1H), 4.44 (dd, J=10.61, 3.12 Hz, 1H), 7.05 (m, 2H), 7.13 (t, J=7.17 Hz, 1H), 7.24 (s, 1H), 7.38 (d, J=8.11 Hz, 1H), 7.60 (d, J=8.11 Hz, 1H), 7.65 (dd, J=8.27, 2.03 Hz, 1H), 7.78 (m, 1H), 8.32 (d, J=1.87 Hz, 1H), 8.34 (s, 1H), 8.52 (s, 1H); Anal. Calcd for C$_{24}$H$_{21}$N$_5$O$_3$: C, 51.30; H, 3.54; N, 10.68. Found: C, 50.99; H, 3.33; N, 10.47.

The following compounds were prepared by substituting the appropriate tributylsannyl reagents for (1,1,1-tributylstannyl)benzene and Example 362A for 80E in Example 364.

EXAMPLE 428

(1S)-2-(5-Benzo[b]thiophen-2-yl-6-furan-2-yl-pyridin-3-yloxy)-1-(1H-indol-3-ylmethyl)-ethylamine MS (APCI) m/z 465 (M−1)$^+$; $^1$H NMR (500 MHz, CD$_3$OD) δ ppm 3.32 (m, 2H), 3.99 (m, 1H), 4.27 (dd, J=10.61, 5.62 Hz, 1H), 4.41 (m, 1H), 6.47 (dd, J=3.43, 1.87 Hz, 1H), 6.66 (d, J=3.43 Hz, 1H), 7.01 (t, J=7.02 Hz, 1H), 7.10 (t, J=8.11 Hz, 1H), 7.23 (s, 1H), 7.35 (d, J=8.11 Hz, 1H), 7.39 (d, J=1.25 Hz, 1H), 7.56 (d, J=2.81 Hz, 1H), 7.58 (d, J=7.80 Hz, 1H), 7.72 (s, 1H), 8.31 (d, J=6.24 Hz, 1H), 8.50 (d, J=2.81 Hz, 1H), 8.61 (d, J=6.24 Hz, 1H), 9.51 (s, 1H); Anal. Calcd for C$_{27}$H$_{22}$N$_4$O$_2$S: C, 52.57; H, 3.40; N, 7.81. Found: C, 52.35; H, 3.20; N, 7.73.

EXAMPLE 429

(1S)-2-(5-Benzo[b]thiophen-2-yl-6-vinyl-pyridin-3-yloxy)-1-(1H-indol-3-ylmethyl)-ethylamine MS (APCI) m/z 427 (M+1)$^+$; $^1$H NMR (400 MHz, DMSO-d$_6$) δ ppm 3.15 (m, 2H), 3.85 (m, 1H), 4.17 (dd, J=10.76, 6.08 Hz, 1H), 4.33 (dd, J=10.76, 2.96 Hz, 1H), 5.44 (m, 1H), 6.30 (dd, J=16.85, 2.18 Hz, 1H), 6.93 (dd, J=16.69, 10.76 Hz, 1H), 7.00 (t, J=7.33 Hz, 1H), 7.08 (t, J=7.49 Hz, 1H), 7.29 (d, J=2.18 Hz, 1H), 7.36 (d, J=8.11 Hz, 1H), 7.51 (d, J=2.81 Hz, 1H), 7.60 (d, J=8.11 Hz, 1H), 7.77 (s, 1H), 8.18 (d, J=5.93 Hz, 1H), 8.25 (m, 2H), 8.51 (d, J=2.81 Hz, 1H), 8.67 (d, J=5.93 Hz, 1H), 9.56 (s, 1H), 11.02 (s, 1H); Anal. Calcd for C$_{25}$H$_{22}$N$_4$OS: C, 48.44; H, 3.28; N, 7.29. Found: C, 48.38; H, 3.32; N, 7.02.

EXAMPLE 430

(1S)-2-(5-Benzo[b]thiophen-2-yl-6-thiophen-2-yl-pyridin-3-yloxy)-1-(1H-indol-3-ylmethyl)-ethylamine MS (APCI) m/z 481 (M−1)$^+$; $^1$H NMR (500 MHz, DMSO-d$_6$) δ ppm 3.15 (m, 2H), 3.84 (m, 1H), 4.18 (dd, J=10.76, 6.08 Hz, 1H), 4.34 (dd, J=10.61, 3.12 Hz, 1H), 6.71 (dd, J=3.59, 1.09 Hz, 1H), 6.90 (dd, J=4.99, 3.74 Hz, 1H), 7.00 (t, J=7.02 Hz, 1H), 7.08 (t, J=7.18 Hz, 1H), 7.29 (d, J=2.18 Hz, 1H), 7.36 (d, J=7.80 Hz, 1H), 7.55 (dd, J=5.15, 1.09 Hz, 1H), 7.57 (d, J=2.81 Hz, 1H), 7.60 (d, J=7.80 Hz, 1H), 7.78 (s, 1H), 8.13 (d, J=5.93 Hz, 1H), 8.23 (br s, 2H), 8.50 (d, J=2.81 Hz, 1H), 8.64 (d, J=5.93 Hz, 1H), 9.50 (s, 1H), 11.02 (d, J=1.56 Hz, 1H); Anal. Calcd for C$_{27}$H$_{22}$N$_4$OS$_2$: C, 48.83; H, 3.12; N, 6.99. Found: C, 48.74; H, 3.07; N, 6.88.

EXAMPLE 431

(1S)-2-(5-Benzo[b]thiophen-2-yl-6-thiazol-2-yl-pyridin-3-yloxy)-1-(1H-indol-3-ylmethyl)-ethylamine MS (APCI) m/z 484 (M+1)$^+$; $^1$H NMR (500 MHz, DMSO-d$_6$) δ ppm 3.15 (m, 2H), 3.84 (m, J=14.12 Hz, 1H), 4.22 (dd, J=10.89, 5.98 Hz, 1H), 4.38 (dd, J=10.74, 3.07 Hz, 1H), 6.98 (t, J=7.06 Hz, 1H), 7.07 (t, J=7.52 Hz, 1H), 7.29 (d, J=2.15 Hz, 1H), 7.35 (d, J=7.98 Hz, 1H), 7.60 (d, J=7.98 Hz, 1H), 7.63 (d, J=2.76 Hz, 2H), 7.73 (s, 1H), 7.77 (d, J=3.38 Hz, 1H), 8.16 (d, J=5.83 Hz, 1H), 8.29 (br s, 2H), 8.56 (d, J=2.76 Hz, 1H), 8.63 (d, J=5.83 Hz, 1H), 9.52 (s, 1H), 11.02 (d, J=1.84 Hz, 1H); Anal. Calcd for C$_{26}$H$_{21}$N$_5$OS: C, 46.55; H, 2.93; N, 8.48. Found: C, 46.87; H, 2.97; N, 8.46.

EXAMPLE 432

(1S)-2-(5-Benzo[b]thiophen-2-yl-6-pyrazin-2-yl-pyridin-3-yloxy)-1-(1H-indol-3-ylmethyl)-ethylamine MS (APCI) m/z 479 (M−1)$^+$; $^1$H NMR (500 MHz, CD$_3$OD) δ ppm 3.32 (m, 2H), 4.02 (m, 1H), 4.33 (dd, J=10.61, 5.62 Hz, 1H), 4.47 (dd, J=10.61, 3.12 Hz, 1H), 7.02 (t, J=7.02 Hz, 1H), 7.10 (t, J=7.18 Hz, 1H), 7.25 (s, 1H), 7.36 (d, J=8.11 Hz, 1H), 7.60 (d, J=7.80 Hz, 1H), 7.63 (s, 1H), 7.67 (d, J=2.50 Hz, 1H), 8.25 (d, J=5.93 Hz, 1H), 8.32 (s, 1H) 8.52 (d, J=1.87 Hz, 1H), 8.58 (d, J=6.24 Hz, 1H), 8.63 (d, J=2.18 Hz, 1H), 9.09 (s, 1H), 9.46 (s, 1H).

EXAMPLE 433

{5-[(2S)-2-Amino-3-(1H-indol-3-yl)-propoxy]-3-benzo[b]thiophen-2-yl-pyridin-2-yl}-phenyl-amine The title compound was prepared by substituting Example 362A for Example 381A in Example 318. MS (APCI) m/z 492 (M+1)$^+$; $^1$H NMR (500 MHz, DMSO-d$_6$) δ ppm 3.16 (m, 2H), 3.83 (m, J=2.50 Hz, 1H), 4.13 (dd, J=10.61, 5.93 Hz, 1H), 4.29 (dd, J=10.45, 2.96 Hz, 1H), 6.86 (t, J=7.18 Hz, 1H), 7.01 (t, J=7.49 Hz, 1H), 7.09 (t, J=7.33 Hz, 1H), 7.20 (t, J=7.80 Hz, 2H), 7.25 (m, 2H), 7.30 (d, J=2.18 Hz, 1H), 7.38 (d, J=8.11 Hz, 1H), 7.62 (d, J=7.80 Hz, 1H), 7.72 (d, J=3.12 Hz, 1H), 8.11 (s, 1H), 8.16 (d, J=3.12 Hz, 1H), 8.20 (d, J=6.24 Hz, 1H), 8.25 (br s, 2H), 8.38 (s, 1H), 8.64 (d, J=6.24 Hz, 1H), 9.55 (s, 1H), 11.03 (d, J=1.56 Hz, 1H); Anal. Calcd for C$_{29}$H$_{25}$N5OS: C, 48.90; H, 3.26; N, 7.96. Found: C, 48.88; H, 3.13; N, 7.90

EXAMPLE 434

{5-[(2S)-2-Amino-3-(1H-indol-3-yl)-propoxy]-3-benzo[b]thiophen-2-yl-pyridin-2-yl}-pyridin-3-yl-amine The title compound was prepared by substituting 3-aminopyridine for aniline in Example 433. MS (APCI) m/z 491 (M−1)$^+$; $^1$H NMR (500 MHz, CD$_3$OD) δ ppm 3.32 (m, 2H), 3.97 (m, 1H), 4.24 (dd, J=10.29, 5.93 Hz, 1H), 4.37 (dd, J=10.45, 3.28 Hz, 1H), 7.03 (t, J=7.18 Hz, 1H), 7.11 (t, J=7.18 Hz, 1H), 7.24 (s, 1H), 7.37 (d, J=8.42 Hz, 1H), 7.59 (d, J=8.11 Hz, 1H), 7.68 (d, J=3.12 Hz, 1H), 7.87 (dd, J=8.74, 5.62 Hz, 1H), 8.05 (s, 1H), 8.24 (d, J=3.12 Hz, 1H), 8.30 (d, J=5.30 Hz, 1H), 8.32 (d, J=6.24 Hz, 1H), 8.42 (dd, J=8.73, 1.56 Hz, 1H), 8.63 (d, J=6.24 Hz, 1H), 9.15 (d, J=2.18 Hz, 1H), 9.53 (s, 1H); Anal. Calcd for C$_{28}$H$_{24}$N$_6$OS: C, 48.93; H, 3.26; N, 10.07. Found: C, 48.82; H, 3.35; N, 9.92.

EXAMPLE 435

6-{5-[(2S)-2-Amino-3-(1H-indol-3-yl)-propoxy]-pyridin-3-yl}-3H-benzooxazol-2-one The desired compound was prepared by substituting 6-Bromo-3H-benzooxazol-2-one (C. Flouzat, et al, *J. Med.*

*Chem.*, 1993, 36, 497) for 6-bromophthalimide in Example 32. MS (APCI) m/z 401 (M+1)+; $^1$H NMR (500 MHz, DMSO-d$_6$) δ ppm 3.16 (d, J=9.67 Hz, 2H), 3.85 (m, 1H), 4.18 (dd, J=10.61, 5.93 Hz, 1H), 4.34 (dd, J=10.76, 2.96 Hz, 1H), 7.01 (t, J=7.49 Hz, 1H), 7.10 (t, J=7.49 Hz, 1H), 7.20 (d, J=8.11 Hz, 1H), 7.29 (d, J=2.18 Hz, 1H), 7.38 (d, J=8.11 Hz, 1H), 7.50 (dd, J=8.11, 1.56 Hz, 1H), 7.62 (d, J=7.80 Hz, 1H), 7.65 (s, 1H), 7.70 (s, 1H), 8.18 (s, 2H), 8.33 (d, J=2.81 Hz, 1H), 8.55 (d, J=1.56 Hz, 1H), 11.02 (s, 1H), 11.81 (s, 1H); Anal. Calcd for $C_{23}H_{20}N_4O_3$: C, 50.53; H, 3.44; N, 8.60. Found: C, 50.71; H, 3.46; N, 8.42.

EXAMPLE 436

1-Benzoimidazol-1-ylmethyl-2-[5-(3-methyl-1H-indazol-5-yl)-pyridin-3-yloxy]-ethylamine

Example 436A

3-Bromo-5-oxiranylmethoxy-pyridine

To a solution of 5-Bromo-pyridin-3-ol (0.50 g, 2.87 mmol), oxiranyl-methanol (0.38 mL, 5.74 mmol) and triphenylphosphine (1.50 g, 5.74 mmol) in anhydrous THF (20 mL) was added di-tert-butyl azodicarboxylate (DBAD) (1.32 g, 5.74 mmol) and the reaction mixture stirred at room temperature for 18 hrs and concentrated. The residue was purified by flash column chromatography on silica gel eluting with 10%–35% ethyl acetate/hexanes to provide the desire product (0.48 g, 73%).

Example 436B

1-Benzoimidazol-1-yl-3-(5-bromo-pyridin-3-yloxy)-propan-2-ol

A solution of Example 436A (500 mg, 2.17 mmol) and 1H-Benzoimidazole (28 mg, 2.39 mmol) in 2-propanol (10 mL) was refluxed under N$_2$ for 2 hrs. The reaction mixture was cooled, diluted with ethyl acetate(50 mL) and washed with brine (2×25 mL). The residue was concentrated and purified by flash column chromatography on silica gel eluting with 100% ethyl acetate to 5% methanol/ethyl acetate to provide the desire product (1.08 mmol, 50%).

Example 436C

5-[5-(3-Benzoimidazol-1-yl-2-hydroxy-propoxy)-pyridin-3-yl]-3-methyl-indazole-1-carboxylic acid tert-butyl ester The product was prepared by substituting Example 436B for Example 202A in Example 203B.

Example 436D

1-Benzoimidazol-1-ylmethyl-2-[5-(3-methyl-1H-indazol-5-yl)-pyridin-3-yloxy]-ethylamine The desired compound was prepared by as trifluoroacetic acid salt by substituting Example 436C for Example 27B in Example 27C. MS (APCI) m/z 400 (M+1)+; $^1$H NMR (400 MHz, CD$_3$OD) δ ppm 2.53 (m, 3H), 4.31 (dd, J=13.81, 4.91 Hz, 2H), 4.42 (m, J=7.98, 3.38 Hz, 1H), 4.54 (m, 2H), 7.56 (m, 3H), 7.67 (dd, J=8.75, 1.07 Hz, 1H), 7.78 (dd, J=5.83, 3.38 Hz, 1H), 7.94 (dd, J=6.14, 3.07 Hz, 1H), 8.05 (s, 1H), 8.12 (s, 1H), 8.35 (s, 1H), 8.64 (s, 1H), 9.36 (s, 1H).

EXAMPLE 437

2-[5-(3-Methyl-1H-indazol-5-yl)-pyridin-3-yloxy]-1-morpholin-4-ylmethyl-ethylamine

Example 437A 1-(5-Bromo-pyridin-3-yloxy)-3-morpholin-4-yl-propan-2-ol

The desired compound was prepared by substituting morpholine for 1H-Benzoimidazole in Example 437B

Example 437B

[2-(5-Bromo-pyridin-3-yloxy)-1-morpholin-4-ylmethyl-ethyl]-carbamic acid tert-butyl ester To a solution of the Example 437A (250 mg, 0.79 mmol), isoindole-1,3-dione (121 mg, 0.82 mmol) and triphenylphosphine (240 mg, 0.92 mmol) in anhydrous THF (10 mL) was added DIAD (0.16 mL, 0.83 mmol) and stirred at room temperature for 45 mins. The concentrated residue was then purified by flash column chromatography eluting with 60% ethyl acetate/hexanes to give the desired intermediate which was dissolved in absolute ethanol (10 mL). Hydrazine monohydrate (40 μL) was added and the reaction mixture refluxed for 3 hrs. The cloudy solution was cooled, concentrated and dissolved in DMF (10 mL). Di-tert-butyl-dicarbonate (271 mg, 1.25 mmol) and triethyl amine (0.18 mL, 1.25 mmol) were added and the clear solution stirred at room temperature for 15 hrs. The clear solution was diluted with ethyl acetate (25 mL) and washed with brine (25 mL) and water (25 mL). The concentrated residue was further purified by flash column chromatography eluting with 15% ethyl acetate/hexanes to give the desired product.

Example 437C

5-[5-(2-tert-Butoxycarbonylamino-3-morpholin-4-yl-propoxy)-pyridin-3-yl]-3-methyl-indazole-1-carboxylic acid tert-butyl ester The product was prepared by substituting Example 437B for Example 202A in Example 203B.

Example 437D

2-[5-(3-Methyl-1H-indazol-5-yl)-pyridin-3-yloxy]-1-morpholin-4-ylmethyl-ethylamine The desired compound was prepared as trifluoroacetic acid salt by substituting Example 437C for Example 27B in Example 27C. MS (APCI) m/z 369 (M+1)+; $^1$H NMR (400 MHz, CD$_3$OD) δ ppm 2.62 (s, 3H), 2.73 (dd, J=11.51, 4.76 Hz, 2H), 2.86 (m, 2H), 2.98 (m, 2H), 3.79 (t, J=4.45 Hz, 4H), 4.04 (m, J=8.59, 3.38 Hz, 1H), 4.47 (dd, J=10.43, 5.52 Hz, 1H), 4.59 (m, 1H), 7.64 (d, J=8.59 Hz, 1H), 7.76 (dd, J=8.90, 1.23 Hz, 1H), 8.15 (s, 1H), 8.24 (s, 1H), 8.48 (s, 1H), 8.78 (s, 1H); Anal. Calcd for $C_{20}H_{25}N_5O_2$: C, 44.01; H, 3.98; N, 9.87. Found: C, 43.92; H, 3.92; N, 9.73.

EXAMPLE 438

5-[5-((2S)-2-Amino-3-phenyl-propoxy)-pyridin-3-yl]-1,3-dihydro-indol-2-one

The desired product was prepared by substituting Boc-phenylalaminol for Boc-tryptophanol in Example 36. MS (APCI) m/z 360 (M+1)+; $^1$H NMR (500 MHz, CD$_3$OD) δ ppm 3.15 (d, J=7.49 Hz, 2H), 3.61 (s, 2H), 3.95 (m, 1H), 4.26 (dd, J=10.61, 5.62 Hz, 1H), 4.40 (dd, J=10.61, 3.12 Hz, 1H), 7.04 (d, J=8.11 Hz, 1H), 7.33 (m, 5H), 7.58 (d, J=8.11 Hz, 1H), 7.62 (s, 1H), 7.96 (s, 1H), 8.38 (d, J=2.50 Hz, 1H), 8.60 (s, 1H); Anal. Calcd for $C_{22}H_{21}N_3O_2$: C, 51.39; H, 3.78; N, 6.76. Found: C, 51.48; H, 3.63; N, 6.75.

EXAMPLE 439

5-[5-((2S)-2-Amino-3-phenyl-propoxy)-pyridin-3-yl]-3-(1H-pyrrol-2-ylmethylene)-1,3-dihydro-indol-2-one The desired product was prepared by substituting Boc-phenylalaminol for Boc-tryptophanol in Example 39. MS (APCI) m/z 437 (M+1)+; 1H NMR (500 MHz, CD3OD) δ ppm 3.17 (d, J=7.80 Hz, 2H), 3.97 (m, 1H), 4.28 (dd, J=10.61, 5.62 Hz, 1H), 4.43 (dd, J=10.45, 2.96 Hz, 1H), 6.38 (m, 1H), 6.85 (d, J=3.74 Hz, 1H), 7.06 (d, J=8.11 Hz, 1H), 7.25 (s, 1H), 7.34 (m, 5H), 7.51 (dd, J=8.11, 1.87 Hz, 1H), 7.73 (s, 1H), 7.94 (s, 1H), 8.03 (s, 1H), 8.38 (d, J=1.87 Hz, 1H), 8.67 (s, 1H), 13.32 (s, 1H); Anal. Calcd for C27H24N4O2: C, 53.27; H, 3.70; N, 7.76. Found: C, 53.46; H, 3.69; N, 7.77.

EXAMPLE 440

5-[5-((2S)-2-Amino-3-phenyl-propoxy)-pyridin-3-yl]-3-furan-2-ylmethylene-1,3-dihydro-indol-2-one The desired product was prepared by substituting Boc-phenylalaminol for Boc-tryptophanol in Example 412. MS (APCI) m/z 438 (M+1)+; 1H NMR (500 MHz, CD3OD) δ ppm 3.85 (m, 4H), 4.75 (m, 2H), 4.93 (m, 2H), 5.10 (dd, J=10.61, 3.12 Hz, 2H), 7.64 (dd, J=3.43, 1.56 Hz, 1H), 7.77 (d, J=8.11 Hz, 1H), 7.82 (d, J=8.11 Hz, 1H), 8.08 (m, 2H), 8.14 (m, 8H), 8.22 (s, 1H), 8.39 (d, J=1.87 Hz, 1H), 8.42 (dd, J=8.11, 1.87 Hz, 1H), 8.45 (s, 1H), 8.53 (s, 1H), 8.68 (s, 1H), 8.80 (d, J=1.56 Hz, 1H), 8.90 (d, J=1.87 Hz, 1H), 9.00 (d, J=1.56 Hz, 1H), 9.07 (s, 2H), 9.11 (d, J=3.43 Hz, 1H), 9.16 (br s, 2H), 9.44 (d, J=1.56 Hz, 1H), 11.54 (s, 1H), 11.57 (s, 1H); Anal. Calcd for C27H23N3O3: C, 55.36; H, 3.74; N, 6.21. Found: C, 55.09; H, 3.74; N, 6.07.

EXAMPLE 441

(1S)-1-Benzoimidazol-1-ylmethyl-2-[5-(3-methyl-1H-indazol-5-yl)-pyridin-3-yloxy]-ethylamine

Example 441A

(2R)-1-Benzoimidazol-1-yl-3-benzyloxy-propan-2-ol

A solution of 2-(3-phenyl-propyl)-oxirane (3.0 g, 18.27 mmol) and benzimidazole (2.37 g, 20.1 mmol) in anhydrous 2-propanol (50 mL) was purged with nitrogen and refluxed for 2.5 hrs. The reaction mixture was cooled, concentrated and purified by flash column chromatography on silica gel [0 (1 min)-15% (16 min) methanol in 2:1 ethyl acetate/hexanes to provide the desired product (4.72 g, 91%).

Example 441B

(2S)-1-(2-Azido-3-benzyloxy-propyl)-1H-benzoimidazole

To a solution of Example 441A (1.0 g, 3.54 mmol) and triphenylphosphine (1.39 g, 5.31 mmol) in anhydrous THF (30 mL) was added diphenylphosphoryl azide (1.14 mL, 5,31 mmol) at 0° C. followed by the addition of DEAD (836 μL). The reaction mixture was stirred at 0° C. for 30 mins and at room temperature for 15 hrs. The concentrated residue was then purified by flash column chromatography on silica gel eluting with 60%–80% ethyl acetate/hexanes to provide the desired product.

Example 441C

(2-Benzoimidazol-1-yl-1-benzyloxymethyl-ethyl)-carbamic acid tert-butyl ester To a solution of the Example 441B (~1 g, ~3.54 mmol) in ethanol (25mL) was added 10% Pd/C (230 mg) under nitrogen. This suspension was purged with hydrogen and was stirred under hydrogen (balloon) for 1 h. The solid material was filtered off and the filtrate was concentrated. The residual foam was dissolved in anhydrous DMF (20 mL). Triethylamine (1.08 mL, 7.78 mmol) and di-tert-butyl dicarbonate (0.85 g, 3.89 mmol) were then added at room temperature and the solution stirred under nitrogen for 2 h. EtOAc (200 mL) was added and the mixture was washed with brine (200 mL), and water (100 mL). The organic phase was concentrated and the residue was purified by flash chromatography [60–80%(5 min) EtOAc in hexane] to give desired product.

Example 441D

(1S)-(2-Benzoimidazol-1-yl-1-hydroxymethyl-ethyl)-carbamic acid tert-butyl ester To a solution of the Example (0.78 g) in methanol (20 mL) was added 10% Pd—C (450 mg) under nitrogen. This reaction mixture was purged with hydrogen and was stirred under hydrogen at 86° C. for 3.5 days (balloon). The filtrate was concentrated and the residual oil was separated by flash chromatography (0–15% CH3OH in 2:1 EtOAc/hexane) to give the desired product (199.7 mg, 33%).

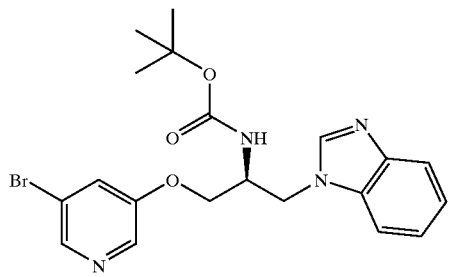

Example 441E

(1S)-[1-Benzoimidazol-1-ylmethyl-2-(5-bromo-pyridin-3-yloxy)-ethyl]-carbamic acid tert-Butyl Ester To a solution of 5-bromo-pyridin-3-ol (102 mg, 0.58 mmol), Example 441D (154 mg, 0.53 mmol) and triphenylphosphine (208 mg, 0.793 mmol) in anhydrous THF (20 mL) was added DEAD (125 μL, 0.79 mmol) and the reaction mixture stirred at room temperature for 2 hrs and concentrated. The residue was purified by flash column chromatography on silica gel (0–15% CH3OH in 2:1 EtOAc/hexane) to give the desired product (100 mg, 43%).

Example 441F

5-[5-(3-Benzoimidazol-1-yl-2-tert-butoxycarbonylamino-propoxy)-pyridin-3-yl]-3-methyl-indazole-1-carboxylic acid tert-butyl ester The product was prepared by substituting Example 447E for Example 202A in Example 203B.

Example 441G

(1S)-1-Benzoimidazol-1-ylmethyl-2-[5-(3-methyl-1H-indazol-5-yl)-pyridin-3-yloxy]-ethylamine The desired compound was prepared by as trifluoroacetic acid salt by substituting Example 441F for Example 27B in Example 27C. 1H NMR (300 MHz, CD3OD) δ ppm 2.63 (m, 3H), 4.53 (m, 2H), 4.65 (m, 1H), 5.09 (d, J=6.78 Hz, 2H), 7.66 (m, 2H), 7.74 (d, J=1.70 Hz, 1H), 7.77 (d, J=1.70 Hz, 1H), 7.90 (m, 1H), 8.02 (m, 1H), 8.12 (m, 1H), 8.15 (d, J=2.37 Hz, 1H), 8.46 (d, J=2.71 Hz, 1H), 8.77 (d, J=1.70 Hz, 1H), 9.40 (s, 1H); Anal. Calcd for $C_{23}H_{22}N_6O$: C, 42.16; H, 2.93; N, 9.22. Found: C, 42.08; H, 3.24; N, 9.13.

EXAMPLE 442

3-{3-[(2S)-2-Amino-3-(1H-indol-3-yl)-propoxy]-5-isoquinolin-6-yl-pyridin-4-yl}-acrylonitrile

Example 442A

3-Chloro-5-(4-methoxy-benzyloxy)-pyridine

To a solution of 3-chloro-5-hydroxypyridine (2.0 g, 17.0 mmol), 4-methoxybenzyl alcohol (2.85 g, 25.5 mmol) and triphenylphosphine (6.68 g, 25.5 mmol) in dry THF (100 ml) DEAD (4.44 g, 25.5 mmol) was added dropwise. The resulting solution was stirred 3 hours at room temperature. The reaction solution was partitioned between ethyl acetate and water. The organic layer was washed (brine), dried ($Na_2SO_4$), filtered and concentrated under vacumm. Purification on silica gel with 20% ethyl acetate/hexane to provide the title compound (1.9 g, 53%). MS (DCI/$NH_3$) m/e 250 (M+1)$^+$.

Example 442B

3-Chloro-5-(4-methoxy-benzyloxy)-pyridine-4-carbaldehyde

A solution of DIPA (1.73 g, 17.16 mmol) in THF (100 ml) was treated dropwise with n-BuLi (6.86 ml, 17.16 mmol) at 0° C., stirred for 30 min. at 0° C. To the reaction Example 442A (3.56 g, 14.3 mmol) in THF (10 ml) was added dropwise at −78° C. The resulting solution was stirred 1 hours at −78° C. The mixture was quenched with methyl formate (2.0 ml). The reaction solution was partitioned between ethylacetate and water. The organic layer was washed (brine), dried ($Na_2SO_4$), filtered and concentrated under vacumm. Purification on silica gel with 20% ethyl acetate/hexane to provide the title compound (2.2 g, 56%). MS (DCI/$NH_3$) m/e 278 (M+1)$^+$.

Example 442C

3-[3-Chloro-5-(4-methoxy-benzyloxy)-pyridin-4-yl]-acrylonitrile

A solution of diethylmethylcyanophosponate (212 mg, 1.2 mmol) in THF (4 ml) was treated dropwise with LiHMDS (1.2 ml, 1.2 mmol) at 0° C., stirred for 30 min. at 0° C. treated with Example 442B (277 mg, 1 mmol) in THF (1 ml). The resulting solution was stirred 1 hours. The mixture was quenched with water. The reaction solution was partitioned between ethylacetate and water. The organic layer was washed (brine), dried ($Na_2SO_4$), filtered and concentrated under vacumm. Purification on silica gel with 20% ethyl acetate/hexane to provide the title compound (210 mg, 70%). MS (DCI/$NH_3$) m/e 301 (M+1)$^+$.

Example 442D 3-(3-Chloro-5-hydroxy-pyridin-4-yl)-acrylonitrile

To a solution of Example 442C (1.02 g, 3.4 mmol) in dichloromethane (10 ml) THA (1 ml) was added. The resulting solution was stirred for two hours. The reaction solution was partitioned between ethylacetate and water. The organic layer was washed (brine), dried ($Na_2SO_4$), filtered and concentrated under vacumm. Purification on silica gel with 40% ethyl acetate/hexane to provide the title compound (600 mg, 98%). MS (DCI/$NH_3$) m/e 181 (M+1)$^+$.

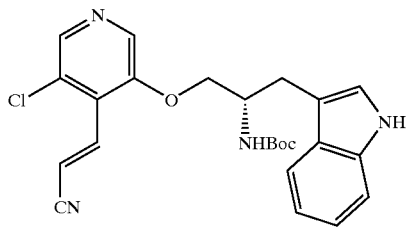

Example 442E (1S)-[2-[5-Chloro-4-(2-cyano-vinyl)-pyridin-3-yloxy]-1-(1H-indol-3-ylmethyl)-ethyl]-carbamic acid tert-butyl ester To a solution of Example 442D (430 mg, 2.39 mmol), N-alpha-(tert-butoxycarbonyl)-L-tryptophanol (762 mg, 2.6 mmol) and triphenylphosphine (1.38 g, 5.26 mmol) in dry THF (40 ml) DBAD (880 mg, 3.82 mmol) was added. The resulting solution was stirred 3 hours at room temperature. The reaction solution was partitioned between ethylacetate and water. The organic layer was washed (brine), dried ($Na_2SO_4$), filtered and concentrated under vacumm. Purification on silica gel with 20% ethyl acetate/hexane to provide the title compound (340 g, 32%). MS (DCI/$NH_3$) m/e 453 (M+1)$^+$.

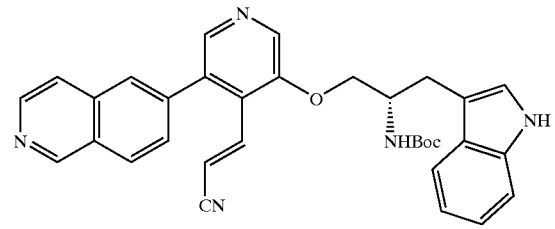

Example 442F (1S)-[2-[4-(2-Cyano-vinyl)-5-isoquinolin-6-yl-pyridin-3-yloxy]-1-(1H-indol-3-ylmethyl)-ethyl]-carbamic acid tert-butyl ester To a solution of Example 442E (330 mg, 0.73 mmol), 6-(1,1,1-trimethylstannyl)-isoquinoline(276 mg, 0.95 mmol), tris(dibenzylideneacetone)-dipalladium (66.8 mg, 0.073 mmol) and 2-dicyclohexylphosphino-2'-dimethylamino-1,1'-biphenyl (57.3 mg, 0.146 mmol) in dry DMF (10 ml) triethyl amine was added under $N_2$. The resulting solution was stirred 3 hours at 100° C. The reaction solution was partitioned between ethylacetate and water. The organic layer was washed (brine), dried ($Na_2SO_4$), filtered and concentrated under vacumm. Purification on silica gel with 60% ethyl acetate/hexane to provide the title compound (61 mg, 17%).MS (DCI/$NH_3$) m/e 546 (M+1)$^+$.

Example 442G

3-{3-[(2S)-2-Amino-3-(1H-indol-3-yl)-propoxy]-5-isoquinolin-6-yl-pyridin-4-yl}-acrylonitrile MS (DCI/$NH_3$) m/e 446 (M+1)$^-$; $^1$H NMR (300 MHz, $D_6$-DMSO) δ 11.06 (s; 1H), 1H), 8.68 (d; 1H; J=6.0 Hz), 8.58 (s; 1H), 8.44 (d; 1H; J=8.4 Hz), 8.40 (s; 1H), 8.23 (d; 1H; J=6.0 Hz), 8.20 (s; 3H), 7.80 (d; 1H; J=8.4 Hz), 7.60 (d; 1H; J=8.4 Hz), 7.44 (d; 1H; J=17.1 Hz), 7.40 (d; 1H; J=8.4 Hz), 7.30 (s; 1H), 7.11 (t; 1H; J=8.4 Hz), 7.01 (t; 1H; J=8.4 Hz), 6.24 (d; 1H; J=17.1 Hz), 4.48 (m; 1H), 4.31 (m; 1H), 3.97 (m; 1H), 3.17 (m; 2H)

EXAMPLE 443

(1S)-1-(1H-Indol-3-ylmethyl)-2-(5-isoquinolin-6-yl-4-methyl-pyridin-3-yloxy)-ethylamine The desire product was prepared by substituting methyl iodide for ethyl acetate in Example 442, omitting the step of Example 442C. MS (DCI/NH$_3$) m/e 409 (M+1)$^+$; $^1$H NMR (300 MHz, D$_6$-DMSO) δ 11.06 (s; 1H), 9.72 (s; 1H), 8.68 (d; 1H; J=6.0 Hz), 8.47 (d; 1H; J=8.4 Hz), 8.37 (s; 1H), 8.32 (s; 1H), 8.22 (m; 4H), 7.91 (d; 1H; J=8.4 Hz), 7.61 (d; 1H; J=8.4 Hz), 7.40 (d; 1H; J=8.4 Hz), 7.30 (s; 1H), 7.12 (t; 1H; J=8.4 Hz), 7.02 (t; 1H; J=8.4 Hz), 4.37 (m; 1H), 4.22 (m; 1H), 3.89 (m; 1H), 3.20 (m; 2H), 2.29 (s; 3H).

EXAMPLE 444

5-{5-[(2S)-2-Amino-3-(1H-indol-3-yl)-propoxy]-pyridin-3-yl}-3-methyl-1,3-dihydro-indol-2-one

Example 444A

3-Methyl-1,3-dihydro-indol-2-one

A solution of oxindole (665 mg, 5.0 mmol) in THF (10 ml) was treated dropwise with n-BuLi (4.4 ml, 11.0 mmol) at −78° C., stirred for 30 min. at −78° C. To the reaction methyliodine (2 ml) was added dropwise at −78° C. The resulting solution was warmed up to room temperature. The mixture was quenched with water. The reaction solution was partitioned between ethylacetate and water. The organic layer was washed (brine), dried (Na$_2$SO$_4$), filtered and concentrated under vacumm. Purification on silica gel with 30% ethyl acetate/hexane to provide the title compound (630 mg, 86%). MS (DCI/NH$_3$) m/e 148 (M+1)$^+$.

Example 444B

5-Bromo-3-methyl-1,3-dihydro-indol-2-one

To a solution of Example 444B (625 mg, 4.25 mmol) in acetonitrile (10 ml) NBS (757 mg, 4.25 mmol) was added at −10° C. The mixture was stirred at −10° C. for 1 hours and 0° C. for 2 hours. The reaction solution was partitioned between ethylacetate and water. The organic layer was washed (brine), dried (Na$_2$SO$_4$), filtered and concentrated under vacumm. Purification on silica gel with 30% ethyl acetate/hexane to provide the title compound (640 mg, 66%). MS (DCI/NH$_3$) m/e 227 (M+1)$^+$.

Example 444C

5-{5-[(2S)-2-Amino-3-(1H-indol-3-yl)-propoxy]-pyridin-3-yl}-3-methyl-1,3-dihydro-indol-2-one The desired product was prepared by substituting Example 44B for 6-bromophthalimide in Example 32. $^1$H NMR (300 MHz, D$_6$-DMSO) δ 11.04 (s; 1H), 10.49 (s; 1H), 8.53 (s; 1H), 8.30 (s; 1H), 8.16 (s; 2H), 7.64 (s; 1H), 7.62 (d; 1H; J=7.5 Hz), 7.53 (d; 1H; J=7.5 Hz), 7.38 (d; 1H; J=8.7 Hz), 7.30 (s; 1H), 7.10 (t; 1H; J=8.7 Hz), 7.01 (t; 1H; J=8.7 Hz), 6.93 (d; 1H; J=8.7 Hz), 4.33 (m; 1H), 4.14 (m; 1H), 3.84 (m; 1H), 3.49 (q; 1H; J=7.5), 3.14 (m; 2H), 1.39 (d; 3H; J=7.5 Hz); MS (DCI/NH$_3$) m/e 413 (M+1)$^+$.

EXAMPLE 445

5-{5-[(2S)-2-Amino-3-(1H-indol-3-yl)-propoxy]-pyridin-3-yl}-3,3-dimethyl-1,3-dihydro-indol-2-one

Example 445A 3,3-Dimethyl-1,3-dihydro-indol-2-one

A solution of Example 444A (500 mg, 3.4 mmol) in THF (10 ml) was treated dropwise with n-BuLi (2.7 ml, 6.8 mmol) at −78° C., stirred for 30 min. at −78° C. To the reaction methyliodine (2 ml) was added dropwise at −78° C. The resulting solution was warmed up to room temperature. The mixture was quenched with water. The reaction solution was partitioned between ethylacetate and water. The organic layer was washed (brine), dried (Na$_2$SO$_4$), filtered and concentrated under vacumm. Purification on silica gel with 30% ethyl acetate/hexane to provide the title compound (410 mg, 75%). MS (DCI/NH$_3$) m/e 162 (M+)$^+$.

Example 445B

5-{5-[(2S)-2-Amino-3-(1H-indol-3-yl)-propoxy]-pyridin-3-yl}-3,3-dimethyl-1,3-dihydro-indol-2-one The title compound was prepared by substituting Example 445A for Example 444A in Example 444. $^1$H NMR (300 MHz, D$_6$-DMSO) δ 11.03 (s; 1H), 10.49 (s; 1H), 8.56 (s; 1H), 8.31 (s; 1H), 8.18 (s; 2H), 7.70 (s; 1H), 7.64 (s; 1H), 7.61 (d; 1H; J=7.5 Hz), 7.57 (d; 1H; J=7.5 Hz), 7.38 (d; 1H; J=8.7 Hz), 7.27 (s; 1H), 7.10 (t; 1H; J=8.7 Hz), 7.01 (t; 1H; J=8.7 Hz), 6.96 (d; 1H; J=8.7 Hz), 4.33 (m; 1H), 4.17 (m; 1H), 3.84 (m; 1H), 3.17 (m; 2H), 1.31 (s; 6H); MS (DCI/NH$_3$) m/e 427 (M+1)$^+$.

EXAMPLE 446

5-{5-[(2S)-2-Amino-3-(1H-indol-3-yl)-propoxy]-pyridin-3-yl}-1,3,3-trimethyl-1,3-dihydro-indol-2-one

Example 446A 1,3,3-Trimethyl-1,3-dihydro-indol-2-one

The title compound was prepared by substituting Example 445A for Example 102A in Example 112. MS (DCI/NH$_3$) m/e 176 (M+1)$^+$.

Example 446B

5-{5-[(2S)-2-Amino-3-(1H-indol-3-yl)-propoxy]-pyridin-3-yl}-1,3,3-trimethyl-1,3-dihydro-indol-2-one The title compound was prepared by substituting Example 446A for Example 444A in Example 444. $^1$H NMR (300 MHz, D$_6$-DMSO) δ 11.03 (s; 1H), 8.60 (s; 1H), 8.32 (s; 1H), 8.20 (s; 2H), 7.78 (s; 1H), 7.67 (d; 1H; J=7.5 Hz), 7.62 (d; 1H; J=7.5 Hz), 7.39 (d; 1H; J=8.7 Hz), 7.29 (s; 1H), 7.14 (d; 1H; J=8.7 Hz), 7.10 (t; 1H; J=8.7 Hz), 7.01 (t; 1H; J=8.7 Hz), 4.35 (m; 1H), 4.28 (m; 1H), 3.83 (m; 1H), 3.19 (s; 3H), 3.17 (m; 2H), 1.33 (s; 6H); MS (DCI/NH$_3$) m/e 441 (M+1)$^+$.

EXAMPLE 447

5-{5-[(2S)-2-Amino-3-(1H-indol-3-yl)-propoxy]-pyridin-3-yl}-3-ethyl-1,3-dihydro-indol-2-one The title compound was prepared by substituting iodoethane for iodomethane in Example 444. $^1$H NMR (300 MHz, $D_6$-DMSO) δ 11.04 (s; 1H), 10.51 (s; 1H), 8.53 (s; 1H), 8.30 (s; 1H), 8.16 (s; 2H), 7.64 (s; 1H), 7.62 (d; 1H; J=7.5 Hz), 7.53 (d; 1H; J=7.5 Hz), 7.38 (d; 1H; J=8.7 Hz), 7.28 (s; 1H), 7.10 (t; 1H; J=8.7 Hz), 7.01 (t; 1H; J=8.7 Hz), 6.93 (d; 1H; J=8.7 Hz), 4.33 (m; 1H), 4.16 (m; 1H), 3.84 (m; 1H), 3.49 (t; 1H; J=7.5), 3.14 (m; 2H), 1.85 (m; 2H), 1.09 (d; 3H; J=7.5 Hz); MS (DCI/NH$_3$) m/e 427 (M+1)$^+$.

EXAMPLE 448

5-{5-[(2S)-2-Amino-3-(1H-indol-3-yl)-propoxy]-pyridin-3-yl}-3-benzyl-1,3-dihydro-indol-2-one The title compound was prepared by substituting benzyl chloride for iodomethane in Example 444. $^1$H NMR (300 MHz, D$_6$-DMSO) δ 11.04 (s; 1H), 10.48 (s; 1H), 8.38 (s; 1H), 8.27 (s; 1H), 8.15 (s; 2H), 7.62 (d; 1H; J=7.5 Hz), 7.44 (d; 1H; J=7.5 Hz), 7.40 (s; 1H), 7.39 (d; 1H; J=8.7 Hz), 7.29 (s; 1H), 7.17 (m; 5H), 7.10 (t; 1H; J=8.7 Hz), 7.01 (t; 1H; J=8.7 Hz), 6.82 (d; 1H; J=8.7 Hz), 4.30 (m; 1H), 4.12 (m; 1H), 3.86 (m; 1H), 3.40 (m; 1H), 3.17 (m; 2H), 3.01 (m; 1H); MS (DCI/NH$_3$) m/e 489 (M+1)$^+$.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

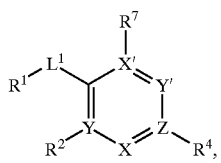

(I)

or a therapeutically acceptable salt thereof, wherein

X is selected from the group consisting of C(R$^8$) and N; wherein R$^8$ is selected from the group consisting of hydrogen, alkyl, amino, carboxy, cyano, halo, hydroxy, and amido;

X' is selected from the group consisting of C and N;

Y is C;

Y' is C(R$^9$); wherein R$^9$ is selected from the group consisting of hydrogen and -L$^2$-L$^3$(R$^3$)(R$^6$);

Z is C;

provided that X or X' is N, and provided that both X and X' are not N;

L$^1$ is selected from the group consisting of a bond, —O—, —NR$^5$—, alkenyl, alkynyl, —C(O)—, —S—, —S(O)—, —S(O)$_2$—, —S(O)$_2$N(R$^5$)—, —N(R$^5$)S(O)$_2$—, —C(R$^{12}$)$_2$—, —C(R$^{12}$)$_2$N(R$^5$)—, —N(R$^5$)C(O)—, and —C(O)N(R$^5$)—; wherein each group is drawn with its left end attached to R$^1$ and its right end attached to the aromatic ring;

L$^2$ is selected from the group consisting of a bond, —O—, —C(R$^{12}$)$_2$—, —S—, —N(R$^5$)—, —N(R$^5$)C(O)—, and —C(O)N(R$^5$)—;

L$^3$ is selected from the group consisting of a bond, alkylidene and alkylene, wherein the alkylidene and the alkylene are optionally substituted with one or two substituents independently selected from the group consisting of alkoxy, amino, cyano, and hydroxy, with the proviso that if L$^2$ is a bond, —O—, or —S— then L$^3$ is not a bond;

R$^1$ is selected from the group consisting of monocyclic or bicyclic aryl, heteroaryl, and heterocycle;

R$^2$ and R$^4$ are independently absent or selected from the group consisting of hydrogen, alkenyl, alkyl, alkynyl, amino, aryl, arylalkynyl, cyano, cyanoalkenyl, halo, heteroaryl, heterocycle, hydroxyalkyl, and nitro; or R$^2$ and L$^1$, together with the carbon atoms to which they are attached, form a ring selected from the group consisting of aryl, heteroaryl, and heterocycle; or R$^4$ and L$^2$, together with the carbon atoms to which they are attached, form a ring selected from the group consisting of aryl, heteroaryl, and heterocycle; provided that when L$^3$ is alkylidene, R$^4$ and L$^2$, together with the carbon atoms to which they are attached, form a ring selected from the group consisting of aryl, heteroaryl, and heterocycle;

R$^3$ is absent or selected from the group consisting of hydrogen, monocyclic or bicyclic aryl, arylalkoxy, arylalkylamino, arylalkylthio, aryloxy, arylthio, cycloalkyl, heteroaryl, heteroarylalkoxy, heteroaryloxy, and heterocycle;

R$^6$ is selected from the group consisting of hydrogen, monocyclic or bicyclic aryl, arylalkoxy, arylalkylamino, arylalkylthio, aryloxy, arylthio, cycloalkyl, heteroaryl, heteroarylalkoxy, heteroaryloxy, and heterocycle;

provided that when L$^1$ and L$^2$ are bonds, at least one of R$^3$ and R$^6$ other than hydrogen;

R$^5$ is selected from the group consisting of hydrogen, alkyl, alkylcarbonyl, alkylsulfonyl, arylcarbonyl, arylsulfonyl, and heteroarylsulfonyl;

R$^7$ is absent or selected from the group consisting of hydrogen, alkyl, cyanoalkenyl, and -L$^2$-L$^3$(R$^3$)(R$^6$); or R$^7$ and L$^1$, together with the carbon atoms to which they are attached, form a ring selected from the group consisting of aryl, heteroaryl, and heterocycle; and each R$^{12}$ is selected from the group consisting of hydrogen, alkenyl, alkyl, alkynyl, amino, aryl, cyano, halo, heteroaryl, heterocycle, and nitro.

2. A compound of formula (II)

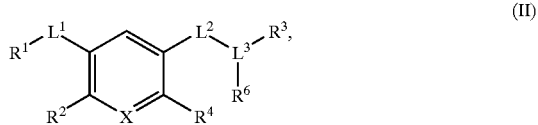

(II)

or a therapeutically acceptable salt thereof, wherein

L$^1$ is selected from the group consisting of a bond, —O—, —N(R$^5$)—, alkenyl, alkynyl, —N(R$^5$)C(O)—, and —C(O)N(R$^5$)—;

L$^2$ is selected from the group consisting of a bond, —O—, —N(R$^5$)—, —N(R$^5$)C(O)—, and —C(O)N(R$^5$)—;

L$^3$ is selected from the group consisting of a bond, alkylidene, and alkylene, wherein the alkylidene and the alkylene are optionally substituted with one or two substituents independently selected from the group consisting of amino, cyano, and hydroxy, with the proviso that if L$^2$ is a bond, —O—, or —S— then L$^3$ is not a bond;

R$^1$ is selected from the group consisting of monocyclic or bicyclic aryl, heteroaryl, and heterocycle;

R$^2$ and R$^4$ are independently selected from the group consisting of hydrogen, alkenyl, alkynyl, arylalkynyl, amino, cyano, cyanoalkenyl, halo, hydroxyalkyl, and heteroaryl; wherein the heteroaryl is selected from the group consisting of furyl, pyrazinyl, thiazolyl, and thienyl; or R$^2$ and L$^1$, together with the carbon atoms to which they are attached, form a ring selected from the group consisting of dihydropyrrolyl, pyrazolyl, and phenyl; or R$^4$ and L$^2$, together with the carbon atoms to which they are attached, form a ring selected from the group consisting of dihydropyrrolyl, phenyl, pyridinyl, and pyrrolyl; wherein the ring can be optionally substituted with oxo;

provided that when L$^3$ is alkylidene, R$^4$ and L$^2$, together with the carbon atoms to which they are attached, form a ring selected from the group consisting of dihydropyrrolyl, phenyl, pyridinyl, and pyrrolyl; wherein the ring can be optionally substituted with oxo;

R$^3$ is absent or selected from the group consisting of hydrogen, monocyclic or bicyclic aryl, arylalkoxy, arylalkylthio, aryloxy, arylthio, cycloalkyl, heteroaryl, heteroarylalkoxy, heteroaryloxy, and heterocycle;

R$^6$ are independently selected from the group consisting of hydrogen, monocyclic or bicyclic aryl, arylalkoxy, arylalkylthio, aryloxy, arylthio, cycloalkyl, heteroaryl, heteroarylalkoxy, heteroaryloxy, and heterocycle;

provided that when L$^1$ and L$^2$ are bonds, at least one of R$^3$ and R$^6$ is other than hydrogen;

R$^5$ is selected from the group consisting of hydrogen, alkyl, alkylcarbonyl, alkylsulfonyl, arylcarbonyl, arylsulfonyl, and heteroarylsulfonyl; and X is N.

3. A compound of formula (III)

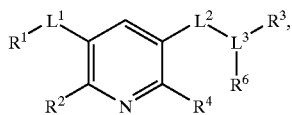

(III)

or a therapeutically acceptable salt thereof, wherein

L$^1$ is selected from the group consisting of a bond, —O—, —N(R$^5$)—, alkenyl, alkynyl, and —N(R$^5$)C(O)—;

L$^2$ is selected from the group consisting of a bond, —O—, —N(R$^5$)—, —N(R$^5$)C(O)—, and —C(O)N(R$^5$)—;

L$^3$ is alkylene, wherein the alkylene is substituted with one or two substituents independently selected from the group consisting of amino and hydroxy;

R$^1$ is selected from the group consisting of monocyclic or bicyclic aryl, heteroaryl, and heterocycle;

R$^2$ and R$^4$ are independently selected from the group consisting of hydrogen and halo;

R$^3$ and R$^6$ are independently selected from the group consisting of hydrogen, monocyclic or bicyclic aryl, arylalkoxy, and heteroaryl; provided that when L$^1$ and L$^2$ are bonds, at least one of R$^3$ and R$^6$ is other than hydrogen; and R$^5$ is selected from the group consisting of hydrogen and alkyl.

4. The compound according to claim 1 or claim 2 wherein L$^1$ is alkenyl.

5. The compound according to claim 4 wherein Y' is C(R$^9$) wherein R$^9$ is -L$^2$-L$^3$(R$^3$)(R$^6$) and wherein L$^2$ is —O—.

6. The compound according to claim 5 selected from the group consisting of N,N-dimethyl—N-[2-({5-[(E)-2-pyridin-4-ylvinyl]pyridin-3-yl}oxy)ethyl]amine;

(1S)-2-(1H-indol-3-yl)-1-[({5-[(E)-2-pyridin-4-ylvinyl]pyridin-3-yl}oxy)methyl]ethylamine;

(1R)-2-(1H-indol-3-yl)-1-[({5-[(E)-2-pyridin-4-ylvinyl]pyridin-3-yl}oxy)methyl]ethylamine;

1-(1H-indol-3-yl)-3-({5-[(E)-2-pyridin-4-ylvinyl]pyridin-3-yl}oxy)propan-2-ol;

(1S)-2-(1-benzothien-3-yl)-1-[({5-[(E)-2-pyridin-4-ylvinyl]pyridin-3-yl}oxy)methyl]ethylamine;

(1S)-2,2-diphenyl-1-[({5-[(E)-2-pyridin-4-ylvinyl]pyridin-3-yl}oxy)methyl]ethylamine;

(1S)-1-{4-[(2,6-dichlorobenzyl)oxy]benzyl}-2-({5-[(E)-2-pyridin-4-ylvinyl]pyridin-3-yl}oxy)ethylamine;

(1S)-2-(benzyloxy)-1-[({5-[(E)-2-pyridin-4-ylvinyl]pyridin-3-yl}oxy)methyl]ethylamine;

N,N-dimethyl-N-[(1S,2S)-1-methyl-2-phenyl-2-({5-[(E)-2-pyridin-4-ylvinyl]pyridin-3-yl}oxy)ethyl]amine;

(1S)-2-(2-naphthyl)-1-[({5-[(E)-2-pyridin-4-ylvinyl]pyridin-3-yl}oxy)methyl]ethylamine;

(1S)-2-({2-chloro-5-[(E)-2-pyridin-4-ylvinyl]pyridin-3-yl}oxy)-1-(1H-indol-3-ylmethyl)ethylamine;

(1S)-2-({6-chloro-5-[(E)-2-pyridin-4-ylvinyl]pyridin-3-yl}oxy)-1-(1H-indol-3-ylmethyl)ethylamine;

(1S)-2-(1H-indol-3-yl)-1-[({5-[(Z)-2-pyridin-4-ylvinyl]pyridin-3-yl}oxy)methyl]ethylamine; and N-[(2E)-3-(4-bromophenyl)prop-2-enyl]-N-[2-({5-[(E)-2-pyridin-4-ylvinyl]pyridin-3-yl}oxy)ethyl]amine.

7. The compound according to claim 4 wherein Y' is C(R$^9$) wherein R$^9$ is -L$^2$-L$^3$(R$^3$)(R$^6$) and wherein L$^2$ is selected from the group consisting of a bond, —N(R$^5$)—, —N(R$^5$)C(O)—, and —C(O)N(R$^5$)—.

8. The compound according to claim 7 selected from the group consisting of

N-[(2S)-2-amino-3-(1H-indol-3-yl)propyl]-N-{5-[(E)-2-pyridin-4-ylvinyl]pyridin-3-yl}amine;

(2S)-2-amino-4-phenyl-N-{5-[(E)-2-pyridin-4-ylvinyl]pyridin-3-yl}butanamide;

N-(aminomethyl)-5-[(E)-2-pyridin-4-ylvinyl]nicotinamide; and (1R)-3-{6-chloro-5-[(E)-2-pyridin-4-ylvinyl]pyridin-3-yl}-1-(1H-indol-3-ylmethyl)propylamine.

9. The compound according to claim 1 or claim 2 wherein L$^1$ is a bond.

10. The compound according to claim 9 wherein Y' is C(R$^9$) wherein R$^9$ is -L$^2$-L$^3$(R$^3$)(R$^6$) and wherein L$^2$ is —O—.

11. The compound according to claim 10 selected from the group consisting of 4-(5-{[(2S)-2-amino-3-(1H-indol-3-yl)propyl]oxy}pyridin-3-yl)benzonitrile;

(1S)-2-(1H-indol-3-yl)-1-{[(5-isoquinolin-6-ylpyridin-3-yl)oxy]methyl}ethylamine;

(1R)-2-(1H-indol-3-yl)-1-{[(5-quinolin-6-ylpyridin-3-yl)oxy]methyl}ethylamine;

(1S)-2-[(6-chloro-5-isoquinolin-6-ylpyridin-3-yl)oxy]-1-(1H-indol-3-ylmethyl)ethylamine;

(1S)-2-[(2-chloro-5-isoquinolin-6-ylpyridin-3-yl)oxy]-1-(1H-indol-3-ylmethyl)ethylamine;

5-(5-{[(2S)-2-amino-3-(1H-indol-3-yl)propyl]oxy}pyridin-3-yl)-1H-isoindole-1,3(2H)-dione;

5-(5-{[(2S)-2-amino-3-(1H-indol-3-yl)propyl]oxy}pyridin-3-yl)isoindolin-1-one;

(1S)-2-[(5-cinnolin-6-ylpyridin-3-yl)oxy]-1-(1H-indol-3-ylmethyl)ethylamine;

(1S)-2-{[5-(1H-indazol-5-yl)pyridin-3-yl]oxy}-1-(1H-indol-3-ylmethyl)ethylamine;

5-(5-{[(2S)-2-amino-3-(1H-indol-3-yl)propyl]oxy}pyridin-3-yl)-1,3-dihydro-2H-indol-2-one;

(1S)-2-{[5-(2,1,3-benzoxadiazol-5-yl)pyridin-3-yl]oxy}-1-(1H-indol-3-ylmethyl)ethylamine;

(1S)-2-(1H-indol-3-yl)-1-{[(5-thieno[2,3-c]pyridin-2-ylpyridin-3-yl)oxy]methyl}ethylamine;

(3Z)-5-(5-{[(2S)-2-amino-3-(1H-indol-3-yl)propyl]oxy}pyridin-3-yl)-3-(1H-pyrrol-2-ylmethylene)-1,3-dihydro-2H-indol-2-one; and 6-(5-{[(2R)-2-amino-3-(1H-indol-3-yl)propyl]oxy}pyridin-3-yl)-1,3-benzothiazol-2(3H)-one.

12. The compound according to claim 9 wherein Y' is C($R^9$) wherein $R^9$ is -$L^2$-$L^3$($R^3$)($R^6$) and wherein $L^2$ is selected from the group consisting of a bond, —N($R^5$)C(O)—, and —N($R^5$)—.

13. The compound according to claim 12 selected from the group consisting of (2S)-2-amino-3-(1H-indol-3-yl)-N-[5-(1,6-naphthyridin-2-yl)pyridin-3-yl]propanamide;

N-[(2S)-2-amino-3-(1H-indol-3-yl)propyl]-N-[5-(1,6-naphthyridin-2-yl)pyridin-3-yl]amine;

(1R)-1-(1H-indol-3-ylmethyl)-3-(5-isoquinolin-6-ylpyridin-3-yl)propylamine;

2-(1H-indol-3-yl)-2-(5-isoquinolin-6-ylpyridin-3-yl)ethanamine; and 2-(1H-indol-3-yl)-3-(5-isoquinolin-6-ylpyridin-3-yl)propan-1-amine.

14. The compound according to claim 9 wherein Y' is C($R^9$) wherein $R^9$ is -$L^2$-$L^3$($R^3$)($R^6$) and wherein $L^2$ and $R^4$, together with the atoms to which they are attached, form a heterocycle ring.

15. The compound according to claim 14 which is (3Z)-3-[(2S)-2-amino-3-(1H-indol-3-yl)propylidene]-5-isoquinolin-6-yl-1,3-dihydro-2H-pyrrolo[2,3-b]pyridin-2-one.

16. The compound according to claim 1 or claim 2 wherein $L^1$ is selected from the group consisting of alkynyl, —N($R^5$)C(O)—, —N($R^5$)—, and —O—.

17. The compound according to claim 16 selected from the group consisting of (1S)-2-(1H-indol-3-yl)-1-({[5-pyridin-4-ylethynyl)pyridin-3-yl]oxy}methyl)ethylamine;

5-{[(2S)-2-amino-3-(1H-indol-3-yl)propyl]oxy}-N-pyridin-4-ylnicotinamide;

$N^4$-(3-{[(2S)-2-amino-3-(1H-indol-3-yl)propyl]oxy}phenyl)pyrimidine-2,4-diamine;

N-[(2S)-2-amino-3-(1H-indol-3-yl)propyl]-N'-isoquinolin-5-ylpyridine-3,5-diamine; and N-[(2S)-2-amino-3-(1H-indol-3-yl)propyl]-N-[5-(isoquinolin-5-yloxy)pyridin-3-yl]amine.

18. The compound according to claim 1 or claim 2 wherein $L^1$ and $R^2$, together with the atoms to which they are attached, form an aryl ring.

19. The compound according to claim 18 which is (1S)-2-(1H-indol-3-yl)-1-{[(6-pyridin-4-ylquinolin-3-yl)oxy]methyl}ethylamine.

20. The compound according to claim 1 or claim 2 selected from the group consisting of 3-Butoxyl-5-[2-(4-pyridinyl)vinyl]pyridine;

3-Methoxyl-5-[2-(4-pyridinyl)vinyl]pyridine;

S-3-[2-Amino-3-phenyl-propyloxyl]-5-[2-(4-pyridinyl)vinyl]pyridine hydrochloride;

3-[2-(1H-3-Indolyl)-ethoxyl]-5-[2-(4-pyridinyl)vinyl]pyridine hydrochloride;

3-[2-(1H-3-Indolyl)-propyloxyl]-5-[2-(4-pyridinyl)vinyl]pyridine;

S-3-[2-Amino-3-(4-benzyloxylphenyl)-propyloxyl]-5-[2-(4-pyridinyl)vinyl]pyridine hydrochloride;

R-3-{2-Amino-3-benzyloxypropyloxyl}-5-[2-(4-pyridinyl)vinyl]pyridine hydrochloride;

3-(1-Methyl-imidazole-4-methoxyl)-5-[2-(4-pyridinyl)vinyl]pyridine;

S-3-{2-Amino-3-[3-hydroxylphenyl]-propyloxyl}-5-[2-(4-pyridinyl)vinyl]pyridine trifluoroacetic acid salt;

S-3-{2-Amino-3-[3-cyanophenyl]-propyloxyl}-5-[2-(4-pyridinyl)vinyl]pyridine hydrochloride salt;

3-[1-(4-Cyanobenzyl)-imidazole-4-methoxyl]-5-[2-(4-pyridinyl)vinyl]pyridine;

S-3-[2-Amino-3-(1-methyl-1H-3-indolyl)-propyloxyl]-5-[2-(4-pyridinyl)vinyl]pyridine hydrochloride salt;

S-3-[2-Dimethylamino-3-(1H-3-indolyl)-propyloxyl]-5-[2-(4-pyridinyl)vinyl]pyridine hydrochloride salt;

S-3-[2-Amino-3-(1-naphthyl)-propyloxyl]-5-[2-(4-pyridinyl)vinyl]pyridine hydrochloride salt;

3-(2-Aminoethoxyl)-5-[2-(4-pyridinyl)vinyl]pyridine hydrochloride salt;

3-(3-Aminopropyloxyl)-5-[2-(4-pyridinyl)vinyl]pyridine hydrochloride salt;

S-3-(2-Amino3-methylbutyloxyl)-5-[2-(4-pyridinyl)vinyl]pyridine hydrochloride salt;

3-(1-Methyl-3-piperidinyloxyl)-5-[2-(4-pyridinyl)vinyl]pyridine trifluoroacetic acid salt;

3-(2-Chlorobenzyl)-5-[2-(4-pyridinyl)vinyl]pyridine trifluoroacetic acid salt;

3-(N-Benzyl-N-methylaminoethoxyl)-5-[2-(4-pyridinyl)vinyl]pyridine trifluoroacetic acid salt;

3-(6-(N,N-Dimathylamino)hexyloxyl)-5-[2-(4-pyridinyl)vinyl]pyridine trifluoroacetic acid salt;

3-(2-Thiophenoxyl-ethoxyl)-5-[2-(4-pyridinyl)vinyl]pyridine trifluoroacetic acid salt;

3-(1-Methyl-3-pyrrolidinyloxyl)-5-[2-(4-pyridinyl)vinyl]pyridine trifluoroacetic acid salt;

3-[(1-Methyl-2-piperidinyl)methoxyl]-5-[2-(4-pyridinyl)vinyl]pyridine trifluoroacetic acid salt;

3-(1-Pyridinyl-ethoxyl)-5-[2-(4-pyridinyl)vinyl]pyridine trifluoroacetic acid salt;

4-{5-[(2S)-2-Amino-3-(1H-indol-3-yl)-propoxy]-pyridin-3-yl}-N-hydroxyl-benzamidine trifluoroacetic acid salt;

4-{5-[(2S)-2-Amino-3-(1H-indol-3-yl)-propoxy]-pyridin-3-yl}-benzamidine trifluoroacetic acid salt;

3-[(2S)-2-Amino-3-(1H-3-indolyl)-propyloxyl]-6-(3-pyridinyl)-quinoline;

3-[(2S)-2-Amino-3-(1H-3-indolyl)-propyloxyl]-6-(3-quinolinyl)-quinoline;

3-[(2S)-2-Amino-3-(1H-3-indolyl)-propyloxyl]-5-[2-(2-amino-4-pyridinyl)vinyl]pyridine trifluoroacetic acid salt;

5-[(2S)-2-(Amino-3-(1H-3-indolyl)-propyloxyl]-3-[2-(2-amino-4-pyridinyl)vinyl]-2-chloro-pyridine trifluoroacetic acid salt;

(1S)-1-(1H-Indol-3-ylmethyl)-2-(5-naphthalen-2-yl-pyridin-3-yloxy)-ethylamine;

(1S)-1-(1H-Indol-3-ylmethyl)-2-(5-isoquinolin-5-yl-pyridin-3-yloxy)-ethylamine;

6-{5-[(2S)-2-Amino-3-(1H-indol-3-yl)-propoxy]-pyridin-3-yl}-2H-isoquinolin-1-one;

(1S)-2-[5-(3-Chloro-isoquinolin-6-yl)-pyridin-3-yloxyl]-1-(1H-indol-3-ylmethyl)-ethylamine;

(1S)-2-([3,4']Bipyridinyl-5-yloxy)-1-(1H-indol-3-ylmethyl)-ethylamine trifluoroacetic acid;

(1S)-1-(1H-Indol-3-ylmethyl)-2-[5-(2-pyridin-2-yl-vinyl)-pyridin-3-yloxy]-ethylamine;

(1S)-1-(1H-Indol-3-ylmethyl)-2-(5-pyridin-3-ylethynyl-pyridin-3-yloxy)-ethylamine trifluoroacetic acid salt;

(1S)-2-[5-(2-Fluoro-pyridin-4-ylethynyl)-pyridin-3-yloxy]-1-(1H-indol-3-ylmethyl)-ethylamine trifluoroacetic acid salt;

(1S)-4-{5-[2-Amino-3-(1H-indol-3-yl)-propoxy]-pyridin-3-ylethynyl}-pyridin-2-ol trifluoroacetic acid salt;

(1S)-2-[6-Chloro-5-(1-chloro-isoquinolin-6-yl)-pyridin-3-yloxy]-1-(1H-indol-3-ylmethyl)-ethylamine trifluoroacetic acid salt;

Bis-[3-(4-Bromo-phenyl)-allyl]-{2-[5-(2-pyridin-4-yl-vinyl)-pyridin-3-yloxy]-ethyl}-amine hydrochloride;

trans-[4-(2-{5-[(2S)-2-Amino-3-(1H-indol-3-yl)-propylamino]-pyridin-3-yl}-vinyl)-pyrimidin-2-yl]-carbamic acid ethyl ester trifluoroacetic acid salt;

1-Amino-6-{5-[(2S)-2-amino-3-(1H-indol-3-yl)-propoxy]-pyridin-3-yl}-isoquinoline trifluoroacetic acid salt;

6-{5-[(2S)-2-amino-3-(1H-indol-3-yl)-propoxy]-pyridin-3-yl}-1-chloro-isoquinoline trifluoroacetic acid salt;

(2S)-2-Amino-3-(1H-indol-3-yl)-N-[5-(2-pyridin-4-yl-vinyl)-pyridin-3-yl]-propionamide;

(2S)-2-Amino-3-(naphtha-1-yl)-N-[5-(2-pyridin-4-yl-vinyl)-pyridin-3-yl]-propionamide hydrochloride;

(2S)-2-Amino-3-phenyl-N-[5-(2-pyridin-4-yl-vinyl)-pyridin-3-yl]-propionamide hydrochloride;

S-2-Amino-3-(imidazol-4-yl)-N-[5-(2-pyridin-4-yl-vinyl)-pyridin-3-yl]-propionamide hydrochloride;

(1R)-2-(1H-indol-3-yl)-1-{[[(5-isoquinolin-6-ylpyridin-3-yl)oxy]methyl}ethylamine;

(1S)-5-{5-[2-Amino-3-(1H-indol-3-yl)-propoxy]-pyridin-3-yl}-1H-indazol-3-ylamine;

(1S)-6-{5-[2-Amino-3-(1H-indol-3-yl)-propoxy]-pyridin-3-yl}-1H-indazol-3-ylamine;

2-Amino-N-[(1S)-1-(1H-indol-3-ylmethyl)-2-(5-isoquinolin-6-yl-pyridin-3-yloxy)-ethyl]-acetamide;

(2S)-2-Amino-N-[(1S)-1-(1H-indol-3-ylmethyl)-2-(5-isoquinolin-6-yl-pyridin-3-yloxy)-ethyl]-propionamide;

2-Dimethylamino-N-[(1S)-1-(1H-indol-3-ylmethyl)-2-(5-isoquinolin-6-yl-pyridin-3-yloxy)-ethyl]-acetamide;

(1S)-1-(1H-Indol-3-ylmethyl)-2-[5-(3-methyl-1H-indazol-5-yl)-pyridin-3-yloxy]-ethylamine;

(1S)-1-(1H-Indol-3-ylmethyl)-2-{5-[3-(1H-pyrrol-2-yl)-1H-indazol-5-yl]-pyridin-3-yloxy}-ethylamine;

(1S)-1-(1H-Indol-3-ylmethyl)-2-[5-(3-phenyl-1H-indazol-5-yl)-pyridin-3-yloxy]-ethylamine;

(1S)-2-[5-(3-Cyclopropyl-1H-indazol-5-yl)-pyridin-3-yloxy]-1-(1H-indol-3-ylmethyl)-ethylamine;

(1S)-2-[5-(3-Ethyl-1H-indazol-5-yl)-pyridin-3-yloxy]-1-(1H-indol-3-ylmethyl)-ethylamine;

(1S)-1-(1H-Indol-3-ylmethyl)-2-{5-[3-(1-methyl-1H-imidazol-2-yl)-1H-indazol-5-yl]-pyridin-3-yloxy}-ethylamine;

(1S)-1-(1H-Indol-3-ylmethyl)-2-[5-(3-thiazol-2-yl-1H-indazol-5-yl)-pyridin-3-yloxy]-ethylamine;

(1S)-2-{5-1H-(1H-Imidazol-2-yl)-1H-indazol-5-yl]-pyridin-3-yloxy}-1-(1H-indol-3-ylmethyl)-ethylamine;

(1S)-1-(1H-Indol-3-ylmethyl)-2-[5-(3-thiophen-2-yl-1H-indazol-5-yl)-pyridin-3-yloxy]-ethylamine;

(1S)-1-(1H-Indol-3-ylmethyl)-2-[5-(3-morpholin-4-yl-1H-indazol-5-yl)-pyridin-3-yloxy]-ethylamine;

(1S)-2-[5-(1,3-Dimethyl-1H-indazol-5-yl)-pyridin-3-yloxy]-1-(1H-indol-3-ylmethyl)-ethylamine;

(1S)-1-(1H-Indol-3-ylmethyl)-2-[3-(3-methyl-1H-indazol-5-yl)-phenoxy]-ethylamine;

(1S)-1-(1H-Indol-3-ylmethyl)-2-{5-[3-(4-methyl-piperazin-1-yl)-1H-indazol-5-yl]-pyridin-3-yloxy}-ethylamine;

(1S)-(5-{5-[2-Amino-3-(1H-indol-3-yl)-propoxy]-pyridin-3-yl}-1H-indazol-3-yl)-dimethyl-amine;

(1S)-(4-(5-(2-Amino-3-(1H-indol-3-yl)-propoxy)-pyridin-3-yl)-benzyl)-phenyl-amine;

(1S)-(4-(5-(2-Amino-3-(1H-indol-3-yl)-propoxy)-pyridin-3-yl)-phenyl)-methanol;

(1S)-2-(5-(4-Fluoro-phenyl)-pyridin-3-yloxy)-1-(1H-indol-3-ylmethyl)-ethylamine;

(1S)-4-(5-(2-Amino-3-(1H-indol-3-yl)-propoxy)-pyridin-3-yl)-benzoic acid;

(1S)-2-(3-Bromo-5-isoquinolin-6-yl-phenoxyoxy)-1-(1H-indol-3-ylmethyl)-ethylamine;

N4-(3-(5-(2-Amino-3-(1H-indol-3-yl)-propoxy)-pyridin-3-yl)-phenyl)-pyrimidine-2,4-diamine;

(1S)-3-(2-Amino-3-(1H-indol-3-yl)-propoxy)-5-isoquinolin-6-yl-phenylamine;

((2S)-2-Amino-5-(5-(2-amino-3-(1H-indol-3-yl)-propoxy)-pyridin-3-yl)-phenyl-(3-chloro-phenyl-methanone;

(1S)-N6-(3-(5-(2-Amino-3-(1H-indol-3-yl)-propoxy)-pyridin-3-yl)-phenyl)-9H-purine-2,6-diamine;

(3-(5-((2S)-2-Amino-3-(1H-indol-3-yl)-propoxy)-pyridin-3-yl)-phenyl)-pyrimidin-2yl-amine;

(3-(5-((2S)-2-Amino-3-(1H-indol-3-yl)-propoxy)-pyridin-3-yl)-phenyl)-thiazol-2yl-amine;

N-(3-(5-((2S)-2-Amino-3-(1H-indol-3-yl)-propoxy)-pyridin-3-yl)-phenyl)-acetamide;

6-(5-(4-(1H-Indol-3-ylmethyl)-piperazin-1-yl)-pyridin-3-yl)-isoquinoline;

3-((2S)-2-Amino-3-(1H-indol-3-yl)-propoxy)-5-isoquinolin-6-yl-benzoic acid;

4-(5-((2S)-2-Amino-3-(1H-indol-3-yl)-propoxy)-pyridin-3-yl)-phenylamine;

N-(4-(5-((2S)-2-Amino-3-(1H-indol-3-yl)-propoxy)-pyridin-3-yl)-phenyl)-acetamide;

N6-(4-(5-((2S)-2-Amino-3-(1H-indol-3-yl)-propoxy)-pyridin-3-yl)-phenyl)-9H-purine-2,6-diamine;

N4-(4-(5-((2S)-2-Amino-3-(1H-indol-3-yl)-propoxy)-pyridin-3-yl)-phenyl)-pyrimidine-2,4-diamine;

(4-(5-((2S)-2-Amino-3-(1H-indol-3-yl)-propoxy)-pyridin-3-yl)-phenyl)-pyrimidin-2-yl-amine;

3-((2S)-2-Amino-3-(1H-indol-3-yl)-propoxy)-5-isoquinolin-6-yl-benzonitrile;

5'-Benzyloxy-5-isoquinolin-6-yl-(3,3')bipyridinyl;

(7-(5-((2S)-2-Amino-3-(1H-indol-3-yl)-propoxy)-pyridin-3-yl)-pyrido(2,3-d)pyrimidin-4-yl)-phenyl-amine;

(7-(5-((2S)-2-Amino-3-(1H-indol-3-yl)-propoxy)-pyridin-3-yl)-pyrido(2,3-d)pyrimidin-4-yl)-ethyl-amine;

(7-(5-((2S)-2-Amino-3-(1H-indol-3-yl)-propoxy)-pyridin-3-yl)-pyrido(2,3-d)pyrimidin-4-yl)-benzyl-amine;

(1S)-1-(1H-Indol-3-ylmethyl)-2-(6-isoquinolin-6-yl-pyridin-2-yloxy)-ethylamine;

(1S)-2-(5-isoquinolin-6-yl-pyridin-3-yloxy)-1-phenyl-ethylamine;

(1S)-1-(1H-Indol-3-ylmethyl)-2-(6-(3-methyl-1H-indazol-5-yl)-pyridin-2-yloxy)-ethylamine;

(1S)-1-Cyclohexylmethyl-2-(5-isoquinolin-6-yl-pyridin-3-yloxy)-ethylamine;

(1S)-1-Benzyl-2-(5-(3-methyl-1H-indazol-5-yl)-pyridin-3-yloxy)-ethylamine;

(1S)-2-(5-(3-Methyl-1H-indazol-5-yl)-pyridin-3-yloxy)-1-phenyl-ethylamine;

(1S)-2-(5-(3-Methyl-1H-indazol-5-yl)-pyridin-3-yloxy)-1-phenyl-ethylamine;

4-((2S)-2-Amino-3-(5-(3-methyl-1H-indazol-5-yl)-pyridin-3-yloxy)propyl)-benzonitrile;

(1S)-2-(5-(3-Methyl-1H-indazol-5-yl)-pyridin-3-yloxy)-1-napthalen-2-ylmethyl-ethylamine;

4-((2S)-2-Amino-3-(5-isoquinolin-6-yl-pyridin-3-yloxy-propyl)-benzonitrile;

(1S)-2-(5-Isoquinolin-6-yl-pyridin-3-yloxy)-1-napthalen-2-ylmethyl)-ethylamine;

(1S)-1-Benzyl-2-(5-isoquinolin-6-yl-pyridin-3-yloxy)-ethylamine;

(1S)-1-(4-Fluoro-benzyl)-2-(5-(3-methyl-1H-indazol-5-yl)-pyridin-3-yloxy)-ethylamine;

(1S)-1-(4-Fluoro-benzyl)-2-(5-isoquinolin-6-yl-pyridin-3-yloxy)-ethylamine;

2-((2S)-2-Amino-3-(5-(3-methyl-1H-indazol-5-yl)-pyridin-3-yloxy)-propyl)-benzonitrile;

2-((2S)-2-Amino-3-(5-isoquinolin-6-yl)-pyridin-3-yloxy)-propyl)-benzonitrile;

(1S)-2-5-(3-methyl-1H-indazol-5-yl)-pyridin-3-yloxy)-1-pyridin-4-ylmethyl-ethylamine;

(1S)-2-(5-isoquinolin-6-yl-pyridin-3-yloxy)-1-pyridin-4-ylmethyl-ethylamine;

(1S)-1-(4-Methyl-benzyl)-2-(5-(3-methyl-1H-indazol-5-yl)-pyridin-3-yloxy)-ethylamine;

(1S)-2-(5-Isoquinolin-6-yl-pyridin-3-yloxy)-1-(4-methyl-benzyl)-ethylamine;

(1S)-2-(5-(3-methyl-1H-indazol-5-yl)-pyridin-3-yloxy)-1-quinolin-3-ylmethyl-ethylamine;

(1S)-2-(5-Isoquinolin-6-yl-pyridin-3-yloxy)-1-quinolin-3-ylmethyl-ethylamine;

(1R)-1-Benzyl-2-(5-(3-methyl-1H-indazol-5-yl)-pyridin-3-yloxy)-ethylamine;

(1R)-1-Benzyl-2-(5-isoquinolin-6-yl-pyridin-3-yloxy)-ethylamine;

4-((2S)-2-Amino-3-(5-(3-methyl-1H-indazol-5-yl)-pyridin-3-yloxy)-propyl)-phenol;

(1S)-1-(4-Benzyloxy-benzyl)-2-(5-(3-methyl-1H-indazol-5-yl)-pyridin-3-yloxy)-ethylamine;

(1S)-1-(3-Methyl-benzyl)-2-(5-(3-methyl-1H-indazol-5-yl)-pyridin-3-yloxy)-ethylamine;

(1S)-1-(2-Methyl-benzyl)-2-(5-(3-methyl-1H-indazol-5-yl)-pyridin-3-yloxy)-ethylamine;

(1S)-2-(5-(3-methyl-1H-indazol-5-yl)-pyridin-3-yloxy)-1-(4-nitro-benzyl)-ethylamine;

(1S)-1-(4-Methoxy-benzyl)-2-(5-(3-methyl-1H-indazol-5-yl)-pyridin-3-yloxy)-ethylamine;

(1S)-1-Biphenyl-4-ylmethyl-2-(5-(3-methyl-1H-indazol-5-yl)-pyridin-3-yloxy)-ethylamine;

(1S)-2-(5-(3-Methyl-1H-indazol-5-yl)-pyridin-3-yloxy)-1-napthalen-1-ylmethyl-ethylamine;

(1S)-1-(3-Chloro-benzyl)-2-(5-(3-methyl-1H-indazol-5-yl)-pyridin-3-yloxy)-ethylamine;

3-((2S)-2-Amino-3-(5-(3-methyl-1H-indazol-5-yl)-pyridin-3-yloxy)-propyl)-benzonitrile;

(1S)-1-(3,4-Difluoro-benzyl)-2-(5-(3-methyl-1H-indazol-5-yl)-pyridin-3-yloxy)-ethylamine;

(1S)-1-(3,4-Dimethoxy-benzyl)-2-(5-(3-methyl-1H-indazol-5-yl)-pyridin-3-yloxy)-ethylamine;

(1S)-1-(3-Fluoro-benzyl)-2-(5-(3-methyl-1H-indazol-5-yl)-pyridin-3-yloxy)-ethylamine;

(1S)-2-(5-(3-methyl-1H-indazol-5-yl)-pyridin-3-yloxy)-1-(3-trifluoromethyl-benzyl)-ethylamine;

(1S)-1-(4-Ethoxy-benzyl)-2-[5-(3-methyl-1H-indazol-5-yl)-pyridin-3-yloxy]-ethylamine;

(1S)-1-(4-tert-Butyl-benzyl)-2-(5-(3-methyl-1H-indazol-5-yl)-pyridin-3-yloxy)-ethylamine;

(1S)-1-(4-Methoxy-3-methyl-benzyl)-2-(5-(3-methyl-1H-indazol-5-yl)-pyridin-3-yloxy)-ethylamine;

2-((2S)-2-Amino-3-(5-(3-methyl-1H-indazol-5-yl)-pyridin-3-yloxy)-propyl)-4-methyl-phenol;

(1S)-1-Methyl-2-[5-(3-methyl-1H-indazol-5-yl)-pyridin-3-yloxy]-ethylamine;

(±)-1-(1H-Benzoimidazol-2-ylmethyl)-2-(5-isoquinolin-6-yl-pyridin-3-yloxy)-ethylamine;

(±)-1-(1H-Indazol-3-ylmethyl)-2-(5-isoquinolin-6-yl-pyridin-3-yloxy)-ethylamine;

(1S)-1-(2-Fluoro-benzyl)-2-[5-(3-methyl-1H-indazol-5-yl)-pyridin-3-yloxy]-ethylamine;

(1S)-1-(2-Chloro-benzyl)-2-[5-(3-methyl-1H-indazol-5-yl)-pyridin-3-yloxy]-ethylamine;

(1S)-2-[5-(3-Methyl-1H-indazol-5-yl)-pyridin-3-yloxy]-1-thiophen-2-ylmethyl-ethylamine;

(1R)-1-(1H-Indol-3-ylmethyl)-2-[5-(3-methyl-1H-indazol-5-yl)-pyridin-3-yloxy]-ethylamine;

1-(4-Chloro-benzyl)-2-[5-(3-methyl-1H-indazol-5-yl)-pyridin-3-yloxy]-ethylamine;

(1S)-2-[5-(3-Methyl-1H-indazol-5-yl)-pyridin-3-yloxy]-1-(4-pyrrol-1-yl-benzyl)-ethylamine;

(1S)-1-(4-Methyl-benzylsulfanylmethyl)-2-[5-(3-methyl-1H-indazol-5-yl)-pyridin-3-yloxy]-ethylamine;

(1S)-2-[5-(3-Methyl-1H-indazol-5-yl)-pyridin-3-yloxy]-1-(2-trifluoromethyl-benzyl])-ethylamine;

(1R)-1-Benzyl-3-[5-(3-methyl-1H-indazol-5-yl)-pyridin-3-yloxy]-propylamine;

(1R)-1-Benzyl-4-[5-(3-methyl-1H-indazol-5-yl)-pyridin-3-yloxy]-butylamine;

(1S)-1-[5-(3-Methyl-1H-indazol-5-yl)-pyridin-3-yloxymethyl]-3-phenyl-propylamine;

(1S)-2-(5-Isoquinolin-6-yl-pyridin-3-yloxy)-1-(1-methyl-1H-indol-3-ylmethyl)-ethylamine trifloroacetic acid salt;

(1S)-[1-(1H-Indol-3-ylmethyl)-2-(5-isoquinolin-6-y1-pyridin-3-yloxy)-ethyl]-dimethyl-amine;

(1S)-1-Benzo[b]thiophen-3-ylmethyl-2-[5-(3-methyl-1H-indazol-5-yl)-pyridin-3-yloxy]-ethylamine;

(1S)-2-[5-(3-Methyl-1H-indazol-5-yl)-pyridin-3-yloxy]-1-thiophen-3-ylmethyl-ethylamine;

(1S)-1-Benzyloxymethyl-2-(5-isoquinolin-6-yl-pyridin-3-yloxy)-ethylamine;

(1S)-1-Benzyloxymethyl-2-[5-(3-methyl-1H-indazol-5-yl)-pyridin-3-yloxy]-ethylamine;

(1S)-2-(5-Isoquinolin-6-yl-pyridin-3-yloxy)-1-(naphthalen-2-yloxymethyl)-ethylamine;

(1S)-2-(5-Isoquinolin-6-yl-pyridin-3-yloxy)-1-(pyridin-3-yloxymethyl)-ethylamine;

(1S)-2-(5-Isoquinolin-6-yl-pyridin-3-yloxy)-1-(quinolin-7-yloxymethyl)-ethylamine;

(2S)-4-[2-Amino-3-(5-isoquinolin-6-yl-pyridin-3-yloxy)-propoxy]-benzonitrile;

(2S)-N'-(5-(3-methyl-1H-indazol-5-yl)-pyridin-3-yl)-3-phenyl-propane-1,2-diamine;

(2S)-N-(2-Amino-3-phenyl-propyl)-N-[5-(3-methyl-1H-indazol-5-yl)-pyridin-3-yl]-methanesulfonamide;

(2S)-N-(2-Amino-3-phenyl-propyl)-N-[5-(3-methyl-1H-indazol-5-yl)-pyridin-3-yl]-benzenesulfonamide;

(2S)-N-(2-Amino-3-phenyl-propyl)-N-[5-(3-methyl-1H-indazol-5-yl)-pyridin-3-yl]-benzamide;

(2S)-N-(2-Amino-3-phenyl-propyl)-N-[5-(3-methyl-1H-indazol-5-yl)-pyridin-3-yl]-acetamide;

(2S)-3-[2-Amino-3-(1H-indol-3-yl)-propylidene]-5-isoquinolin-6-yl-1,3-dihydro-indol-2-one;

(1S)-2-(5-Isoquinolin-6-yl-pyridin-3-yloxy)-1-(1-methyl-1H-indol-3-ylmethyl)-ethylamine;

(1S)-1-(1H-Indol-3-ylmethyl)-2-[5-(1H-pyrrolo[2,3-b]pyridin-5-yl)-pyridin-3-yloxy]-ethylamine;

(1S)-2-{5-[2-(2-Fluoro-pyridin-4-yl)-vinyl]-pyridin-3-yloxy}-1-(1H-indol-3-ylmethyl)-ethylamine;

(1S)-1-(1H-Indol-3-ylmethyl)-2-{5-[2-(2-methoxy-pyridin-4-yl)-vinyl]-pyridin-3-yloxy}-ethylamine;

(1S)-1-(1H-Indol-3-ylmethyl)-2-{5-[2-(2-phenoxy-pyridin-4-yl)-vinyl]-pyridin-3-yloxy}-ethylamine;

(1S)-2-{5-[2-(2-Benzylsulfanyl-pyridin-4-yl)-vinyl]-pyridin-3-yloxy}-1-(1H-indol-3-ylmethyl)-ethylamine;

[4-(2-{5-[(2S)-2-Amino-3-(1H-indol-3-yl)-propoxy]-pyridin-3-yl}-vinyl)-pyridin-2-yl]-cyclopropyl-amine;

[4-(2-{5-[(2S)-2-Amino-3-(1H-indol-3-yl)-propoxy]-pyridin-3-yl}-vinyl)-pyridin-2-yl]-benzyl-amine;

[4-(2-{5-[(2S)-2-Amino-3-(1H-indol-3-yl)-propoxy]-pyridin-3-yl}-vinyl)-pyridin-2-yl]-ethyl-amine;

[4-(2-{5-[(2S)-2-Amino-3-(1H-indol-3-yl)-propoxy]-pyridin-3-yl}-vinyl)-pyridin-2-yl]-methyl-amine;

(1S)-1-(1H-Indol-3-ylmethyl)-2-{5-[2-(2-indol-1-yl-pyridin-4-yl)-vinyl]-pyridin-3-yloxy}-ethylamine;

(±)-2-[5-(3-Methyl-1H-indazol-5-yl)-pyridin-3-yloxy]-1-(2-methyl-1H-indol-3-ylmethyl)-ethylamine;

7-{5-[(2S)-2-Amino-3-(1H-indol-3-yl)-propoxy]-pyridin-3-yl}-quinazolin-2-ylamine;

2-Phenyl-2-(3-pyridin-4-yl-1H-pyrazolo[3,4-b]pyridin-6-yl)-ethylamine;

Naphthalen-2-yl-(3-pyridin-4-yl-1H-pyrazolo[3,4-b]pyridin-6-yl)-acetonitrile;

2-Naphthalen-2-yl-2-(3-pyridin-4-yl-1H-pyrazolo[3,4-b]pyridin-6-yl)-ethylamine;

(3-Isoquinolin-6-yl-1H-pyrazolo[3,4-b]pyridin-6-yl)-phenyl-acetonitrile;

2-(3-Isoquinolin-6-yl-1H-pyrazolo[3,4-b]pyridin-6-yl)-2-phenyl-ethylamine;

(1S)-1-Benzyl-2-(3-pyridin-4-yl-1H-pyrazolo[3,4-b]pyridin-5-yloxy)-ethylamine;

2-Benzyl-3-[5-(3-methyl-1H-indazol-5-yl)-pyridin-3-yloxy]-propylamine;

(1S)-1-(1H-idol-3-ylmethyl)-2-(2-pyridin-4-yl-[1,7]naphthyridin-5-yloxy)-ethylamine;

(1R)-1-(1H-Indol-3-ylmethyl)-2-(2-pyridin-4-yl-[1,7]naphthyridin-5-yloxy)-ethylamine;

(1S)-1-(1H-Indol-3-ylmethyl)-2-(5-isoquinolin-6-yl-pyridin-3-ylsulfanyl)-ethylamine;

(1S)-1-(1H-Indol-3-ylmethyl)-2-[5-(3-methyl-1H-indazol-5-yl)-pyridin-3-ylsulfanyl]-ethylamine;

(1S)-1-(4-Bromo-benzyl)-2-[5-(3-methyl-1H-indazol-5-yl)-pyridin-3-yloxy]-ethylamine;

(1S)-1-(1H-Indol-3-ylmethyl)-2-[5-(2-methyl-quinazolin-7-yl)-pyridin-3-yloxy]-ethylamine;

(1S)-1-(1H-Indol-3-ylmethyl)-2-[5-(1H-indol-5-yl)-pyridin-3-yloxy]-ethylamine;

(1S)-1-(1H-Indol-3-ylmethyl)-2-{5-[4-(1H-tetrazol-5-yl)-phenyl]-pyridin-3-yloxy}-ethylamine;

(1S)-1-Benzyl-2-[3-(3-methyl-1H-indazol-5-yl)-phenoxy]-ethylamine;

(1S)-1-Benzyl-2-[6-(3-methyl-1H-indazol-5-yl)-pyridin-2-yloxy]-ethylamine;

(1S)-2-[5-(3-Methyl-1H-indazol-5-yl)-pyridin-3-yloxy]-1-(4-thiophen-3-yl-benzyl)-ethylamine;

(1S)-1-(4-Iodo-benzyl)-2-[5-(3-methyl-1H-indazol-5-yl)-pyridin-3-yloxy]-ethylamine;

[4-((2S)-2-Amino-3-phenyl-propoxy)-2-(3-methyl-1H-indazol-5-yl)-phenyl]-methanol;

(1S)-2-[5-(1H-Benzotriazol-5-yl)-pyridin-3-yloxyl]-1-(1H-indol-3-ylmethyl)-ethylamine;

(1S)-2-[5-(1H-Benzotriazol-5-yl)-pyridin-3-yloxy]-1-benzyl-ethylamine;

(1S)-1-Benzyl-2-[5-(3-morpholin-4-yl-1H-indazol-5-yl)-pyridin-3-yloxy]-ethylamine;

(1S)-1-Benzyl-2-{5-[3-(4-methyl-piperazin-1-yl)-1H-indazol-5-yl]-pyridin-3-yloxy}-ethylamine;

(1S)-{5-[5-(2-Amino-3-phenyl-propoxy)-pyridin-3-yl]-1H-indazol-3-yl}-dimethyl-amine;

(1S)-{5-[5-(2-Amino-3-phenyl-propoxy)-pyridin-3-yl]-1H-indazol-3-yl}-(2-methoxy-ethyl)-amine;

{5-[5-((2S)-2-Amino-3-phenyl-propoxy)-pyridin-3-yl]-1H-indazol-3-yl}-(2-morpholin-4-yl-ethyl)-amine;

5-[5-((2S)-2-Amino-3-phenyl-propoxy)-pyridin-3-yl]-1H-indazol-3-ylamine;

N-{5-[5-((2S)-2-Amino-3-phenyl-propoxy)-pyridin-3-yl]-1H-indazol-3-yl}-2,2,2-trifluoro-acetamide;

(2S)-2-Amino-N-[5-(3-methyl-1H-indazol-5-yl)-pyridin-3-yl]-3-phenyl-propionamide;

(1S)-2-[5-(3-Benzyl-1H-indazol-5-yl)-pyridin-3-yloxy]-1-(1H-indol-3-ylmethyl)-ethylamine;

(1S)-1-Benzyl-2-[5-(3-benzyl-1H-indazol-5-yl)-pyridin-3-yloxy]-ethylamine;
(1S)-2-[5-(3-Benzyl-1H-indazol-5-yl)-pyridin-3-yloxy]-1-methyl-ethylamine;
(6-{5-[(2S)-2-Amino-3-(1H-indol-3-yl)-propoxy]-pyridin-3-yl}-cinnolin-4-yl)-phenyl-amine;
(1S)-2-[5-(1H-Indazol-6-yl)-pyridin-3-yloxy]-1-(1H-indol-3-ylmethyl)-ethylamine;
5-{5-[(2S)-2-Amino-3-(1H-indol-3-yl)-propoxy]-pyridin-3-yl}-2,3-dihydro-isoindol-1-one;
6-{5-[(2S)-2-Amino-3-(1H-indol-3-yl)-propoxy]-pyridin-3-yl}-1H-cinnolin-4-one;
(1S)-1-(1H-Indol-3-ylmethyl)-2-[5-(4-phenyl-cinnolin-6-yl)-pyridin-3-yloxy]-ethylamine;
(6-{5-[(2S)-2-Amino-3-(1H-indol-3-yl)-propoxy]-pyridin-3-yl}-cinnolin-4-yl)-benzyl-amine;
(6-{5-[(2S)-2-Amino-3-(1H-indol-3-yl)-propoxy]-pyridin-3-yl}-cinnolin-4-yl)-methyl-amine;
6-{5-[(2S)-2-Amino-3-(1H-indol-3-yl)-propoxy]-pyridin-3-yl}-cinnolin-4-ylamine;
[(3S)-3-(5-Isoquinolin-6-yl-pyridin-3-yloxymethyl)-1,2,3,4-tetrahydro-b-carboline-9-yl]-methanol;
3-(5-Isoquinolin-6-yl-pyridin-3-yloxymethyl)-2,3,4,9-tetrahydro-1H-□-carboline;
5-{5-[(2S)-2-Amino-3-(1H-indol-3-yl)-propoxy]-pyridin-3-yl}-1H-indazole-3-carboxylic acid;
5-[5-((2S)-2-tert-Butoxycarbonylamino-3-hydroxy-propoxy)-pyridin-3-yl]-3-methyl-indazole-1-carboxylic acid tert-butyl ester;
5-[5-((2S)-Aziridin-2-ylmethoxy)-pyridin-3-yl]-3-methyl-1H-indazole;
(1S)-2-[5-(3-Methyl-1H-indazol-5-yl)-pyridin-3-yloxy]-1-(3-trifluoromethoxy-benzyl)-ethylamine;
(1S)-1-(3,5-Dichloro-benzyl)-2-[5-(3-methyl-1H-indazol-5-yl)-pyridin-3-yloxy]-ethylamine;
(1S)-1-(2,3-Dichloro-benzyl)-2-[5-(3-methyl-1H-indazol-5-yl)-pyridin-3-yloxy]-ethylamine;
(1S)-1-Biphenyl-3-ylmethyl-2-[5-(3-methyl-1H-indazol-5-yl)-pyridin-3-yloxy]-ethylamine;
(1S)-1-(3-Chloro-4-fluoro-benzyl)-2-[5-(3-methyl-1H-indazol-5-yl)-pyridin-3-yloxy]-ethylamine;
(1S)-1-(4-Chloro-3-fluoro-benzyl)-2-[5-(3-methyl-1H-indazol-5-yl)-pyridin-3-yloxy]-ethylamine;
(1S)-2-[5-(3-Methyl-1H-indazol-5-yl)-pyridin-3-yloxy]-1-(4-trifluoromethoxy-benzyl)-ethylamine;
(1S)-1-(2-Fluoro-4-trifluoromethyl-benzyl)-2-[5-(3-methyl-1H-indazol-5-yl)-pyridin-3-yloxy]-ethylamine;
(1S)-1-(3-Fluoro-5-trifluoromethyl-benzyl)-2-[5-(3-methyl-1H-indazol-5-yl)-pyridin-3-yloxy]-ethylamine;
(1S)-1-(2-Methoxy-benzyl)-2-[5-(3-methyl-1H-indazol-5-yl)-pyridin-3-yloxy]-ethylamine;
(3-{(2S)-2-Amino-3-[5-(3-methyl-1H-indazol-5-yl)-pyridin-3-yloxy]-propyl}-phenyl)-dimethyl-amine;
(1S)-1-(4-Chloro-2-methyl-benzyl)-2-[5-(3-methyl-1H-indazol-5-yl)-pyridin-3-yloxy]-ethylamine;
(1S)-1-(3-Iodo-benzyl)-2-[5-(3-methyl-1H-indazol-5-yl)-pyridin-3-yloxyl]-ethylamine;
(1S)-(1S)-1-(3-Fluoro-4-methyl-benzyl)-2-[5-(3-methyl-1H-indazol-5-yl)-pyridin-3-yloxy]-ethylamine;
(1S)-1-(3-Fluoro-4-methoxy-benzyl)-2-[5-(3-methyl-1H-indazol-5-yl)-pyridin-3-yloxy]-ethylamine;
(1S)-2-[6-Chloro-5-(3-methyl-1H-indazol-5-yl)-pyridin-3-yloxy]-1-(3,4-dichloro-benzyl)-ethylamine;
(1S)-1-(2-Fluoro-6-trifluoromethyl-benzyl)-2-[5-(3-methyl-1H-indazol-5-yl)-pyridin-3-yloxy]-ethylamine;
(1S)-1-(4-Fluoro-3-trifluoromethyl-benzyl)-2-[5-(3-methyl-1H-indazol-5-yl)-pyridin-3-yloxy]-ethylamine;
(1S)-1-Furan-2-ylmethyl-2-[5-(3-methyl-1H-indazol-5-yl)-pyridin-3-yloxy]-ethylamine;
(1S)-1-Benzofuran-2-ylmethyl-2-[5-(3-methyl-1H-indazol-5-yl)-pyridin-3-yloxy]-ethylamine;
(1S)-1-(3-Fluoro-4-trifluoromethyl-benzyl)-2-[5-(3-methyl-1H-indazol-5-yl)-pyridin-3-yloxy]-ethylamine;
(1S)-1-(4-Chloro-3-methyl-benzyl)-2-[5-(3-methyl-1H-indazol-5-yl)-pyridin-3-yloxy]-ethylamine;
(1S)-1-Furan-3-ylmethyl-2-[5-(3-methyl-1H-indazol-5-yl)-pyridin-3-yloxy]-ethylamine;
(1S)-1-(2-Fluoro-5-methyl-benzyl)-2-[5-(3-methyl-1H-indazol-5-yl)-pyridin-3-yloxy]-ethylamine;
(1S)-1-(3-Chloro-5-fluoro-benzyl)-2-[5-(3-methyl-1H-indazol-5-yl)-pyridin-3-yloxy]-ethylamine;
(1S)-2-[5-(3-Methyl-1H-indazol-5-yl)-pyridin-3-yloxy]-1-(3,4,5-trifluoro-benzyl)-ethylamine;
(1S)-1-(4-Fluoro-3-methyl-benzyl)-2-[5-(3-methyl-1H-indazol-5-yl)-pyridin-3-yloxy]-ethylamine;
(1S)-1-(2,4-Dichloro-benzyl)-2-[5-(3-methyl-1H-indazol-5-yl)-pyridin-3-yloxy]-ethylamine;
(1S)-1-(4-Chloro-3-trifluoromethyl-benzyl)-2-[5-(3-methyl-1H-indazol-5-yl)-pyridin-3-yloxyl]-ethylamine;
(1S)-2-[5-(3-Methyl-1H-indazol-5-yl)-pyridin-3-yloxy]-1-(2-trifluoromethoxy-benzyl)-ethylamine;
(1S)-1-(2,5-Dimethoxy-benzyl)-2-[5-(3-methyl-1H-indazol-5-yl)-pyridin-3-yloxy]-ethylamine;
(1S)-2-[5-(3-Methyl-1H-indazol-5-yl)-pyridin-3-yloxy]-1-(4-methylsulfanyl-benzyl)-ethylamine;
(1S)-1-(2-Cyclohexyl-benzyl)-2-[5-(3-methyl-1H-indazol-5-yl)-pyridin-3-yloxy]-ethylamine;
(1S)-1-(2,5-Dichloro-benzyl)-2-[5-(3-methyl-1H-indazol-5-yl)-pyridin-3-yloxy]-ethylamine;
(1S)-1-(2,5-Dimethyl-benzyl)-2-[5-(3-methyl-1H-indazol-5-yl)-pyridin-3-yloxy]-ethylamine;
(1S)-1-(2,3-Dimethyl-benzyl)-2-[5-(3-methyl-1H-indazol-5-yl)-pyridin-3-yloxy]-ethylamine;
(1S)-1-(3,4-Dichloro-benzyl)-2-[5-(3-methyl-1H-indazol-5-yl)-pyridin-3-yloxy]-ethylamine;
(1S)-1-(2,4-Dimethyl-benzyl)-2-[5-(3-methyl-1H-indazol-5-yl)-pyridin-3-yloxy]-ethylamine;
(1S)-1-(3-Fluoro-4-trifluoromethyl-benzyl)-2-[5-(3-methyl-1H-indazol-5-yl)-pyridin-3-yloxy]-ethylamine;
(1S)-1-(3,5-Dimethyl-benzyl)-2-[5-(3-methyl-1H-indazol-5-yl)-pyridin-3-yloxy]-ethylamine;
(1S)-1-Biphenyl-2-ylmethyl-2-[5-(3-methyl-1H-indazol-5-yl)-pyridin-3-yloxy]-ethylamine;
(1S)-1-(3,4-Dimethyl-benzyl)-2-[5-(3-methyl-1H-indazol-5-yl)-pyridin-3-yloxy]-ethylamine;
(1S)-1-(2,3-Difluoro-benzyl)-2-[5-(3-methyl-1H-indazol-5-yl)-pyridin-3-yloxy]-ethylamine;
(1S)-1-(2,5-Difluoro-benzyl)-2-[5-(3-methyl-1H-indazol-5-yl)-pyridin-3-yloxy]-ethylamine;
(1S)-1-(2,6-Dichloro-benzyl)-2-[5-(3-methyl-1H-indazol-5-yl)-pyridin-3-yloxy]-ethylamine;
(1S)-1-(2,4-Difluoro-benzyl)-2-[5-(3-methyl-1H-indazol-5-yl)-pyridin-3-yloxy]-ethylamine;
(1S)-1-(2,6-Dimethyl-benzyl)-2-[5-(3-methyl-1H-indazol-5-yl)-pyridin-3-yloxy]-ethylamine;

(1S)-1-(2,3-Dihydro-benzo[1,4]dioxin-6-ylmethyl)-2-[5-(3-methyl-1H-indazol-5-yl)-pyridin-3-yloxy]-ethylamine;
(1S)-1-(3,5-Difluoro-benzyl)-2-[5-(3-methyl-1H-indazol-5-yl)-pyridin-3-yloxy]-ethylamine;
(1S)-1-(2,6-Difluoro-benzyl)-2-[5-(3-methyl-1H-indazol-5-yl)-pyridin-3-yloxy]-ethylamine;
(1S)-1-Benzo[1,3]dioxol-5-ylmethyl-2-[5-(3-methyl-1H-indazol-5-yl)-pyridin-3-yloxy]-ethylamine;
(1S)-1-(4-Fluoro-3-methyl-benzyl)-2-[5-(3-methyl-1H-indazol-5-yl)-pyridin-3-yloxy]-ethylamine;
(1S)-2-[5-(3-Methyl-1H-indazol-5-yl)-pyridin-3-yloxy]-1-(2,4,6-trimethyl-benzyl)-ethylamine;
(1S)-1-(2,4-Dimethoxy-benzyl)-2-[5-(3-methyl-1H-indazol-5-yl)-pyridin-3-yloxy]-ethylamine;
(1S)-2-[5-(3-Methyl-1H-indazol-5-yl)-pyridin-3-yloxy]-1-(4-trifluoromethyl-benzyl)-ethylamine;
(1S)-1-(5-Fluoro-2-methyl-benzyl)-2-[5-(3-methyl-1H-indazol-5-yl)-pyridin-3-yloxy]-ethylamine;
(1S)-1-(3,5-Bis-trifluoromethyl-benzyl)-2-[5-(3-methyl-1H-indazol-5-yl)-pyridin-3-yloxy]-ethylamine;
(1S)-1-(4-Fluoro-2-methyl-benzyl)-2-[5-(3-methyl-1H-indazol-5-yl)-pyridin-3-yloxy]-ethylamine;
(1S)-1-(5-Fluoro-2-methoxy-benzyl)-2-[5-(3-methyl-1H-indazol-5-yl)-pyridin-3-yloxy]-ethylamine;
(1S)-2-[5-(3-Methyl-1H-indazol-5-yl)-pyridin-3-yloxy]-1-(2-methyl-naphthalen-1-ylmethyl)-ethylamine;
(1S)-1-(2,2-Difluoro-benzo[1,3]dioxol-4-ylmethyl)-2-[5-(3-methyl-1H-indazol-5-yl)-pyridin-3-yloxy]-ethylamine;
(1S)-1-(4-Fluoro-naphthalen-1-ylmethyl)-2-[5-(3-methyl-1H-indazol-5-yl)-pyridin-3-yloxy]-ethylamine;
(1S)-2-[5-(3-Methyl-1H-indazol-5-yl)-pyridin-3-yloxy]-1-(2,2,3,3-tetrafluoro-2,3-dihydro-benzo[1,4]dioxin-6-ylmethyl)-ethylamine;
(1S)-2-[5-(3-Methyl-1H-indazol-5-yl)-pyridin-3-yloxy]-1-(4-methyl-naphthalen-1-ylmethyl)-ethylamine;
(1S)-2-[5-(3-Methyl-1H-indazol-5-yl)-pyridin-3-yloxy]-1-(2,4,6-trifluoro-benzyl)-ethylamine; (1S)-2-[5-(3-Methyl-1H-indazol-5-yl)-pyridin-3-yloxy]-1-(2,3,4-trifluoro-benzyl)-ethylamine;
(1S)-1-(4-Bromo-2-fluoro-benzyl)-2-[5-(3-methyl-1H-indazol-5-yl)-pyridin-3-yloxy]-ethylamine;
(1S)-1-(4-Bromo-3-fluoro-benzyl)-2-[5-(3-methyl-1H-indazol-5-yl)-pyridin-3-yloxy]-ethylamine;
(1S)-1-(2-Bromo-4,6-difluoro-benzyl)-2-[5-(3-methyl-1H-indazol-5-yl)-pyridin-3-yloxy]-ethylamine;
(1S)-1-(4-Bromo-3-methyl-benzyl)-2-[5-(3-methyl-1H-indazol-5-yl)-pyridin-3-yloxy]-ethylamine;
(1S)-Bromo-benzyl)-2-[5-(3-methyl-1H-indazol-5-yl)-pyridin-3-yloxy]-ethylamine;
(1S)-1-(3-Methoxy-benzyl)-2-[5-(3-methyl-1H-indazol-5-yl)-pyridin-3-yloxy]-ethylamine;
(1S)-1-(3-Bromo-benzyl)-2-[5-(3-methyl-1H-indazol-5-yl)-pyridin-3-yloxy]-ethylamine;
(1S)-1-(2-Methoxy-naphthalen-1-ylmethyl)-2-[5-(3-methyl-1H-indazol-5-yl)-pyridin-3-yloxy]-ethylamine;
(1R)-1-(4-Chloro-benzyl)-2-[5-(3-methyl-1H-indazol-5-yl)-pyridin-3-yloxy]-ethylamine;
(1R)-1-Benzo[1,3]dioxol-5-ylmethyl-2-[5-(3-methyl-1H-indazol-5-yl)-pyridin-3-yloxy]-ethylamine;
(1R)-1-(3-Fluoro-4-methyl-benzyl)-2-[5-(3-methyl-1H-indazol-5-yl)-pyridin-3-yloxy]-ethylamine;
(1S)-1-Benzyl-2-[6-chloro-5-(3-methyl-1H-indazol-5-yl)-pyridin-3-yloxy]-ethylamine;
(1S)-1-(4-Bromo-benzyl)-2-[6-chloro-5-(3-methyl-1H-indazol-5-yl)-pyridin-3-yloxy]-ethylamine;
(1S)-1-(4-Chloro-benzyl)-2-[6-chloro-5-(3-methyl-1H-indazol-5-yl)-pyridin-3-yloxy]-ethylamine;
(1S)-2-[6-Chloro-5-(3-methyl-1H-indazol-5-yl)-pyridin-3-yloxy]-1-cyclohexylmethyl-ethylamine;
(1S)-2-[6-Chloro-5-(3-methyl-1H-indazol-5-yl)-pyridin-3-yloxy]-1-(2,6-dimethyl-benzyl)-ethylamine;
(1S)-1-[6-Chloro-5-(3-methyl-1H-indazol-5-yl)-pyridin-3-yloxymethyl]-2-phenyl-propylamine;
(1S)-1-[6-Chloro-5-(3-methyl-1H-indazol-5-yl)-pyridin-3-yloxymethyl]-2,2-diphenyl-ethylamine;
(1S)-1-[5-(3-Methyl-1H-indazol-5-yl)-pyridin-3-yloxymethyl]-2-phenyl-propylamine;
(1S)-1-[5-(3-Methyl-1H-indazol-5-yl)-pyridin-3-yloxymethyl]-2,2-diphenyl-ethylamine;
(1S)-3-Methyl-1-[5-(3-methyl-1H-indazol-5-yl)-pyridin-3-yloxymethyl]-butylamine;
(1S)-2-[6-Chloro-5-(3-methyl-1H-indazol-5-yl)-pyridin-3-yloxy]-1-(1H-indol-3-ylmethyl)-ethylamine;
(1S)-2-(6-Chloro-5-thieno[2,3-c]pyridin-2-yl-pyridin-3-yloxy)-1-(1H-indol-3-ylmethyl)-ethylamine;
5-[(2S)-2-Amino-3-(1H-indol-3-yl)-propoxyl-3-isoquinolin-6-yl-pyridine-2-carbonitrile;
(1S)-1-(1H-Indol-3-ylmethyl)-2-[5-(3-phenyl-isoquinolin-6-yl)-pyridin-3-yloxy]-ethylamine;
(1S)-2-[5-(3-Ethyl-isoquinolin-6-yl)-pyridin-3-yloxy]-1-(1H-indol-3-ylmethyl)-ethylamine;
(1S)-1-(1H-Indol-3-ylmethyl)-2-[5-(3-pyridin-4-yl-isoquinolin-6-yl)-pyridin-3-yloxy]-ethylamine;
(1S)-2-[5-(3-Furan-2-yl-isoquinolin-6-yl)-pyridin-3-yloxy]-1-(1H-indol-3-ylmethyl)-ethylamine;
(1S)-1-(1H-Indol-3-ylmethyl)-2-[5-(3-phenylethynyl-isoquinolin-6-yl)-pyridin-3-yloxy]-ethylamine;
(1S)-1-(1H-Indol-3-ylmethyl)-2-[5-(3-prop-1-ynyl-isoquinolin-6-yl)-pyridin-3-yloxy]-ethylamine;
(1S)-1-(1H-Indol-3-ylmethyl)-2-[5-(3-vinyl-isoquinolin-6-yl)-pyridin-3-yloxy]-ethylamine;
(1S)-6-{5-[2-Amino-3-(1H-indol-3-yl)-propoxy]-pyridin-3-yl}-isoquinoline-3-carbonitrile;
(1S)-1-(1H-Indol-3-ylmethyl)-2-(5-isoquinolin-6-yl-6-vinyl-pyridin-3-yloxy)-ethylamine;
(1S)-2-(6-Ethynyl-5-isoquinolin-6-yl-pyridin-3-yloxy)-1-(1H-indol-3-ylmethyl)-ethylamine;
(1S)-2-(6-Furan-2-yl-5-isoquinolin-6-yl-pyridin-3-yloxy)-1-(1H-indol-3-ylmethyl)-ethylamine;
(1S)-1-(1H-Indol-3-ylmethyl)-2-(5-isoquinolin-6-yl-6-phenylethynyl-pyridin-3-yloxy)-ethylamine;
6-{5-[(2S)-2-Amino-3-(1H-indol-3-yl)-propoxy]-pyridin-3-yl}-isoquinolin-5-ylamine;
(1S)-1-(1H-Indol-3-ylmethyl)-2-[5-(8-methyl-isoquinolin-6-yl)pyridin-3-yloxy]-ethylamine;
(1S)-2-[5-(4-Chloro-thieno[2,3-c]pyridin-2-yl)-pyridin-3-yloxy]-(1H-indol-3-ylmethyl)-ethylamine;
(1S)-1-(1H-Indol-3-ylmethyl)-2-[5-(4-phenyl-thieno[2,3-c]pyridin-2-yl)-pyridin-3-yloxy]-ethylamine;
(1S)-1-(1H-Indol-3-ylmethyl)-2-[5-(4-phenoxy-thieno[2,3-c]pyridin-2-yl)-pyridin-3-yloxy]-ethylamine;
(1S)-1-(1H-Indol-3-ylmethyl)-2-[5-(4-vinyl-thieno[2,3-c]pyridin-2-yl)-pyridin-3-yloxy]-ethylamine;

(1S)-2-[5-(4-Ethyl-thieno[2,3-c]pyridin-2-yl)-pyridin-3-yloxy]-1-(1H-indol-3-ylmethyl)-ethylamine;

(1S)-(2-{5-(2-Amino-3-(1H-indol-3-yl)-propoxy]-pyridin-3-yl}-thieno[2,3-c]pyridin-4-yl)-phenyl-amine;

5-{5-[(2S)-2-Amino-3-(1H-indol-3-yl)-propoxy]-pyridin-3-yl}-3,3-difluoro-1,3-dihydro-indol-2-one;

6-{5-[(2S)-2-Amino-3-(1H-indol-3-yl)-propoxy]-pyridin-3-yl}-3H-oxazolo[4,5-b]pyridin-2-one;

N1-(5-Isoquinolin-6-yl-pyridin-3-yl)-ethane-1,2-diamine;

Naphthalene-2-sulfonic acid (2-amino-ethyl)-(5-isoquinolin-6-yl-pyridin-3-yl)-amide;

Naphthalene-1-sulfonic acid (2-amino-ethyl)-(5-isoquinolin-6-yl-pyridin-3-yl)-amide;

5-Dimethylamino-naphthalene-1-sulfonic acid (2-amino-ethyl)-(5-isoquinolin-6-yl-pyridin-3-yl)-amide;

Quinoline-5-sulfonic acid (2-amino-ethyl)-(5-isoquinolin-6-yl-pyridin-3-yl)-amide;

Biphenyl-4-sulfonic acid (2-amino-ethyl)-(5-isoquinolin-6-yl-pyridin-3-yl)-amide;

1-Methyl-1H-imidazole-4-sulfonic acid (2-amino-ethyl)-(5-isoquinolin-6-yl-pyridin-3-yl)-amide;

3-Amino-2-[5-(3-methyl-1H-indazol-5-yl)-pyridin-3-yloxy]-propan-1-ol;

2-[5-(3-Methyl-1H-indazol-5-yl)-pyridin-3-yloxy]-3-phenoxy-propylamine;

2-[5-(3-Methyl-1H-indazol-5-yl)-pyridin-3-yloxy]-3-(naphthalen-2-yloxy)-propylamine;

3-(Biphenyl-4-yloxy)-2-[5-(3-methyl-1H-indazol-5-yl)-pyridin-3-yloxy]-propylamine;

2-[5-(3-Methyl-1H-indazol-5-yl)-pyridin-3-yloxy]-3-(quinolin-7-yloxy)-propylamine;

2-[5-(3-Methyl-1H-indazol-5-yl)-pyridin-3-yloxy]-3-(pyridin-4-yloxy)-propylamine;

2-[5-(3-Methyl-1H-indazol-5-yl)-pyridin-3-yloxy]-3-(naphthalen-1-yloxy)-propylamine;

3-{(2S)-2-Amino-3-[5-(3-methyl-1H-indazol-5-yl)-pyridin-3-yloxy]-propyl}-1H-indol-5-ol;

(1S)-1-(5-Methoxy-1H-indol-3-ylmethyl)-2-[5-(3-methyl-1H-indazol-5-yl)-pyridin-3-yloxy]-ethylamine;

(1S)-1-(5-Ethoxy-1H-indol-3-ylmethyl)-2-[5-(3-methyl-1H-indazol-5-yl)-pyridin-3-yloxy]-ethylamine;

(1S)-1-(5-Butoxy-1H-indol-3-ylmethyl)-2-[5-(3-methyl-1H-indazol-5-yl)-pyridin-3-yloxy]-ethylamine;

(1S)-1-(5-Isopropoxy-1H-indol-3-ylmethyl)-2-[5-(3-methyl-1H-indazol-5-yl)-pyridin-3-yloxy]-ethylamine;

3-(1H-Indol-3-yl)-2-[5-(3-methyl-1H-indazol-5-yl)-pyridin-3-yloxy]-propan-1-ol;

3-(1H-Indol-3-yl)-2-[5-(3-methyl-1H-indazol-5-yl)-pyridin-3-yloxy]-propylamine;

Naphthalene-2-sulfonic acid (2-amino-ethyl)-[5-(3-methyl-1H-indazol-5-yl)-pyridin-3-yl]-amide;

Biphenyl-4-sulfonic acid (2-amino-ethyl)-[5-(3-methyl-1H-indazol-5-yl)-pyridin-3-yl]-amide;

5-{5-[(2S)-2-Amino-3-(1H-indol-3-yl)-propoxy]-pyridin-3-yl}-3-isopropylidene-1,3-dihydro-indol-2-one;

5-{5-[(2S)-2-Amino-3-(1H-indol-3-yl)-propoxy]-pyridin-3-yl}-3-(1H-imidazol-2-ylmethylene)-1,3-dihydro-indol-2-one;

5-{5-[2-Amino-3-(1H-indol-3-yl)-propoxy]-pyridin-3-yl}-3-pyridin-2-ylmethylene-1,3-dihydro-indol-2-one;

5-{5-[(2S)-2-Amino-3-(1H-indol-3-yl)-propoxy]-pyridin-3-yl }-3-furan-2-ylmethylene-1,3-dihydro-indol-2-one;

5-{5-[(2S)-2-Amino-3-(1H-indol-3-yl)-propoxy]-pyridin-3-yl}-3-(5-methyl-furan-2-ylmethylene)-1,3-dihydro-indol-2-one;

5-{5-[(2S)-2-Amino-3-(1H-indol-3-yl)-propoxy]-pyridin-3-yl}-3-(4,5-dimethyl-furan-2-ylmethylene)-1,3-dihydro-indol-2-one;

5-{5-[(2S)-2-Amino-3-(1H-indol-3-yl)-propoxy]-pyridin-3-yl}-3-thiophen-2-ylmethylene-1,3-dihydro-indol-2-one;

5-{5-[(2S)-2-Amino-3-(1H-indol-3-yl)-propoxy]-pyridin-3-yl}-3-(1-methyl-1H-pyrrol-2-ylmethylene)-1,3-dihydro-indol-2-one;

5-{5-[(2S)-2-Amino-3-(1H-indol-3-yl)-propoxy]-pyridin-3-yl}-3-(1H-indol-3-ylmethylene)-1,3-dihydro-indol-2-one;

5-{5-[(2S)-2-Amino-3-(1H-indol-3-yl)-propoxy]-pyridin-3-yl}-3-(1-phenyl-1H-pyrrol-3-ylmethylene)-1,3-dihydro-indol-2-one;

5-{5-[(2S)-2-Amino-3-(1H-indol-3-yl)-propoxy]-pyridin-3-yl}-3-pyridin-3-ylmethylene-1,3-dihydro-indol-2-one;

5-{5-[(2S)-2-Amino-3-(1H-indol-3-yl)-propoxy]-pyridin-3-yl}-3-(1H-pyrrol-3-ylmethylene)-1,3-dihydro-indol-2-one;

5-{5-[(2S)-2-Amino-3-(1H-indol-3-yl)-propoxy]-pyridin-3-yl}-3-(tetrahydro-pyran-4-ylidene)-1,3-dihydro-indol-2-one;

5-{5-[(2S)-2-Amino-3-(1H-indol-3-yl)-propoxy]-pyridin-3-yl}-3-(4-ethyl-3,5-dimethyl-1H-pyrrol-2-ylmethylene)-1,3-dihydro-indol-2-one;

5-{5-[(2S)-2-Amino-3-(1H-indol-3-yl)-propoxy]-pyridin-3-yl}-3-cyclopropylmethylene-1,3-dihydro-indol-2-one;

5-{5-[(2S)-2-Amino-3-(1H-indol-3-yl)-propoxy]-pyridin-3-yl}-3-pyrrolidin-2-ylmethylene-1,3-dihydro-indol-2-one;

5-(5-{5-[(2S)-2-Amino-3-(1H-indol-3-yl)-propoxy]-pyridin-3-yl}-2-oxo-1,2-dihydro-indol-3-ylidenemethyl)-furan-2-carboxylic acid;

5-{5-[(2S)-2-Amino-3-(1H-indol-3-yl)-propoxy]-pyridin-3-yl}-3-benzylidene-1,3-dihydro-indol-2-one;

5-{5-[(2S)-2-Amino-3-(1H-indol-3-yl)-propoxy]-pyridin-3-yl}-1H-indole-2,3-dione 3-oxime;

(1S)-2-(5-Benzo[b]thiophen-2-yl-6-furan-2-yl-pyridin-3-yloxy)-1-(1H-indol-3-ylmethyl)-ethylamine;

(1S)-2-(5-Benzo[b]thiophen-2-yl-6-vinyl-pyridin-3-yloxy)-1-(1H-indol-3-ylmethyl)-ethylamine;

(1S)-2-(5-Benzo[b]thiophen-2-yl-6-thiophen-2-yl-pyridin-3-yloxy)-1-(1H-indol-3-ylmethyl)-ethylamine;

(1S)-2-(5-Benzo[b]thiophen-2-yl-6-thiazol-2-yl-pyridin-3-yloxy)-1-(1H-indol-3-ylmethyl)-ethylamine;

(1S)-2-(5-Benzo[b]thiophen-2-yl-6-pyridin-2-yl-pyridin-3-yloxy)-1-(1H-indol-3-ylmethyl)-ethylamine;

{5-[(2S)-2-Amino-3-(1H-indol-3-yl)-propoxyl]-3-benzo[b]thiophen-2-yl-pyridin-2-yl}-phenyl-amine;

{5-[(2S)-2-Amino-3-(1H-indol-3-yl)-propoxy]-3-benzo[b]thiophen-2-yl-pyridin-2-yl}-pyridin-3-yl-amine;

6-{5-[(2S)-2-Amino-3-(1H-indol-3-yl)-propoxy]-pyridin-3-yl}-3H-benzooxazol-2-one;

1-Benzoimidazol-1-ylmethyl-2-[5-(3-methyl-1H-indazol-5-yl)-pyridin-3-yloxy]-ethylamine;

2-[5-(3-Methyl-1H-indazol-5-yl)-pyridin-3-yloxyl]-1-morpholin-4-ylmethyl-ethylamine;

5-[5-((2S)-2-Amino-3-phenyl-propoxy)-pyridin-3-yl]-1,3-dihydro-indol-2-one;

5-[5-((2S)-2-Amino-3-phenyl-propoxy)-pyridin-3-yl]-3-(1H-pyrrol-2-ylmethylene)-1,3-dihydro-indol-2-one;

5-[5-((2S)-2-Amino-3-phenyl-propoxy)-pyridin-3-yl]-3-furan-2-ylmethylene-1,3-dihydro-indol-2-one;

(1S)-1-Benzoimidazol-1-ylmethyl-2-[5-(3-methyl-1H-indazol-5-yl)-pyridin-3-yloxy]-ethylamine;

3-{3-[(2S)-2-Amino-3-(1H-indol-3-yl)-propoxy]-5-isoquinolin-6-yl-pyridin-4-yl}-acrylonitrile;

(1S)-1-(1H-Indol-3-ylmethyl)-2-(5-isoquinolin-6-yl-4-methyl-pyridin-3-yloxy)-ethylamine;

5-{5-[(2S)-2-Amino-3-(1H-indol-3-yl)-propoxy]-pyridin-3-yl}-3-methyl-1,3-dihydro-indol-2-one;

5-{5-[(2S)-2-Amino-3-(1H-indol-3-yl)-propoxy]-pyridin-3-yl}-3,3-dimethyl-1,3-dihydro-indol-2-one;

5-{5-[(2S)-2-Amino-3-(1H-indol-3-yl)-propoxy]-pyridin-3-yl}-1,3,3-trimethyl-1,3-dihydro-indol-2-one;

5-{5-[(2S)-2-Amino-3-(1H-indol-3-yl)-propoxy]-pyridin-3-yl}-3-ethyl-1,3-dihydro-indol-2-one; and 5-{5-[(2S)-2-Amino-3-(1H-indol-3-yl)-propoxy]-pyridin-3-yl }-3-benzyl-1,3-dihydro-indol-2-one.

21. A pharmaceutical composition comprising a compound of claim 1 or claim 2, or a therapeutically acceptable salt of both the forgoing, in combination with a pharmaceutically acceptable carrier.

* * * * *